United States Patent
Zhi et al.

(10) Patent No.: US 9,622,991 B2
(45) Date of Patent: Apr. 18, 2017

(54) HEMATOPOIETIC GROWTH FACTOR MIMETIC SMALL MOLECULE COMPOUNDS AND THEIR USES

(71) Applicant: LIGAND PHARMACEUTICALS INC., La Jolla, CA (US)

(72) Inventors: Lin Zhi, San Diego, CA (US); Andrew R. Hudson, San Diego, CA (US); Cornelis A. Van Oeveren, San Diego, CA (US); Steven L. Roach, San Diego, CA (US); Bijan Pedram, San Diego, CA (US); Yixing Shen, Encinitas, CA (US); Lino J. Valdez, San Diego, CA (US); Jillian Basinger, San Diego, CA (US); Virginia Heather Sharron Grant, San Diego, CA (US); Jason C. Pickens, Chula Vista, CA (US)

(73) Assignee: Ligand Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 14/713,930

(22) Filed: May 15, 2015

(65) Prior Publication Data
US 2015/0252043 A1   Sep. 10, 2015

Related U.S. Application Data

(62) Division of application No. 13/501,622, filed as application No. PCT/US2010/052359 on Oct. 12, 2010, now Pat. No. 9,144,557.
(Continued)

(51) Int. Cl.
*A61K 31/15* (2006.01)
*A61K 31/167* (2006.01)
(Continued)

(52) U.S. Cl.
CPC ............ *A61K 31/15* (2013.01); *A61K 31/167* (2013.01); *A61K 31/18* (2013.01); *A61K 31/245* (2013.01); *A61K 31/343* (2013.01); *A61K 31/36* (2013.01); *A61K 31/381* (2013.01); *A61K 31/402* (2013.01); *A61K 31/404* (2013.01); *A61K 31/405* (2013.01); *A61K 31/4015* (2013.01); *A61K 31/4025* (2013.01); *A61K 31/4045* (2013.01); *A61K 31/41* (2013.01); *A61K 31/415* (2013.01); *A61K 31/416* (2013.01); *A61K 31/4155* (2013.01); *A61K 31/4164* (2013.01); *A61K 31/4184* (2013.01); *A61K 31/4192* (2013.01); *A61K 31/421* (2013.01); *A61K 31/423* (2013.01); *A61K 31/4245* (2013.01); *A61K 31/437* (2013.01); *A61K 31/438* (2013.01); *A61K 31/4409* (2013.01); *A61K 31/4418* (2013.01); *A61K 31/4439* (2013.01); *A61K 31/4468* (2013.01); *A61K 31/454* (2013.01); *A61K 31/4535* (2013.01); *A61K 31/4747* (2013.01); *A61K 31/495* (2013.01); *A61K 31/4985* (2013.01); *A61K 31/501* (2013.01); *A61K 31/506* (2013.01); *A61K 31/538* (2013.01); *A61K 31/5375* (2013.01); *A61K 31/5377* (2013.01); *A61K 31/541* (2013.01); *C07C 233/78* (2013.01); *C07C 233/80* (2013.01); *C07C 235/56* (2013.01); *C07C 237/40* (2013.01); *C07C 237/42* (2013.01); *C07C 243/38* (2013.01); *C07C 247/18* (2013.01); *C07C 251/48* (2013.01); *C07C 251/66* (2013.01); *C07C 251/68* (2013.01); *C07C 251/86* (2013.01); *C07C 271/28* (2013.01); *C07C 311/08* (2013.01); *C07D 207/12* (2013.01); *C07D 207/27* (2013.01); *C07D 207/273* (2013.01); *C07D 207/32* (2013.01); *C07D 207/327* (2013.01); *C07D 207/34* (2013.01); *C07D 207/416* (2013.01); *C07D 209/08* (2013.01); *C07D 209/12* (2013.01); *C07D 209/14* (2013.01); *C07D 209/16* (2013.01); *C07D 209/24* (2013.01); *C07D 209/34* (2013.01);
(Continued)

(58) Field of Classification Search
None
See application file for complete search history.

(56) References Cited

U.S. PATENT DOCUMENTS

| 2,777,855 | A | 1/1957 | Scalera et al. |
| 3,245,995 | A | 4/1966 | Demler |

(Continued)

FOREIGN PATENT DOCUMENTS

| CH | 101215379 | 7/2008 |
| GB | 1 236 282 | 6/1971 |

(Continued)

OTHER PUBLICATIONS

Schreivogel, Alina. Synthesis and Electrochemical Properties of Tetrasubstituted Tetraphenylethenes. Eur. J. Org. Chem. 2006, 3395-3404.*

(Continued)

*Primary Examiner* — Samantha Shterengarts
(74) *Attorney, Agent, or Firm* — Knobbe Martens Olson & Bear LLP

(57) ABSTRACT

The present embodiments relate to compounds with physiological effects, such as the activation of hematopoietic growth factor receptors. The present embodiments also relate to use of the compounds to treat a variety of conditions, diseases and ailments such as hematopoietic conditions and disorders.

23 Claims, No Drawings

Related U.S. Application Data

(60) Provisional application No. 61/251,259, filed on Oct. 13, 2009.

(51) Int. Cl.

| | |
|---|---|
| *A61K 31/18* | (2006.01) |
| *A61K 31/245* | (2006.01) |
| *A61K 31/343* | (2006.01) |
| *A61K 31/36* | (2006.01) |
| *A61K 31/381* | (2006.01) |
| *A61K 31/4015* | (2006.01) |
| *A61K 31/402* | (2006.01) |
| *A61K 31/4025* | (2006.01) |
| *A61K 31/404* | (2006.01) |
| *A61K 31/4045* | (2006.01) |
| *A61K 31/41* | (2006.01) |
| *A61K 31/415* | (2006.01) |
| *A61K 31/4155* | (2006.01) |
| *A61K 31/405* | (2006.01) |
| *A61K 31/416* | (2006.01) |
| *A61K 31/4164* | (2006.01) |
| *A61K 31/4184* | (2006.01) |
| *A61K 31/4192* | (2006.01) |
| *A61K 31/421* | (2006.01) |
| *A61K 31/423* | (2006.01) |
| *A61K 31/4245* | (2006.01) |
| *A61K 31/437* | (2006.01) |
| *A61K 31/438* | (2006.01) |
| *A61K 31/4409* | (2006.01) |
| *A61K 31/4418* | (2006.01) |
| *A61K 31/4439* | (2006.01) |
| *A61K 31/4468* | (2006.01) |
| *A61K 31/4535* | (2006.01) |
| *A61K 31/454* | (2006.01) |
| *A61K 31/4747* | (2006.01) |
| *A61K 31/495* | (2006.01) |
| *A61K 31/4985* | (2006.01) |
| *A61K 31/501* | (2006.01) |
| *A61K 31/506* | (2006.01) |
| *A61K 31/5375* | (2006.01) |
| *A61K 31/5377* | (2006.01) |
| *A61K 31/538* | (2006.01) |
| *A61K 31/541* | (2006.01) |
| *C07C 233/78* | (2006.01) |
| *C07C 233/80* | (2006.01) |
| *C07C 235/56* | (2006.01) |
| *C07C 237/40* | (2006.01) |
| *C07C 237/42* | (2006.01) |
| *C07C 243/38* | (2006.01) |
| *C07C 247/18* | (2006.01) |
| *C07C 251/48* | (2006.01) |
| *C07C 251/66* | (2006.01) |
| *C07C 251/68* | (2006.01) |
| *C07C 251/86* | (2006.01) |
| *C07C 271/28* | (2006.01) |
| *C07C 311/08* | (2006.01) |
| *C07D 207/12* | (2006.01) |
| *C07D 207/27* | (2006.01) |
| *C07D 207/273* | (2006.01) |
| *C07D 207/32* | (2006.01) |
| *C07D 207/327* | (2006.01) |
| *C07D 207/34* | (2006.01) |
| *C07D 207/416* | (2006.01) |
| *C07D 209/08* | (2006.01) |
| *C07D 209/12* | (2006.01) |
| *C07D 209/14* | (2006.01) |
| *C07D 209/16* | (2006.01) |
| *C07D 209/24* | (2006.01) |
| *C07D 209/34* | (2006.01) |
| *C07D 209/42* | (2006.01) |
| *C07D 211/46* | (2006.01) |
| *C07D 211/58* | (2006.01) |
| *C07D 213/12* | (2006.01) |
| *C07D 213/53* | (2006.01) |
| *C07D 213/79* | (2006.01) |
| *C07D 213/80* | (2006.01) |
| *C07D 213/81* | (2006.01) |
| *C07D 213/82* | (2006.01) |
| *C07D 231/14* | (2006.01) |
| *C07D 231/26* | (2006.01) |
| *C07D 231/40* | (2006.01) |
| *C07D 231/56* | (2006.01) |
| *C07D 233/60* | (2006.01) |
| *C07D 233/61* | (2006.01) |
| *C07D 233/90* | (2006.01) |
| *C07D 235/06* | (2006.01) |
| *C07D 235/14* | (2006.01) |
| *C07D 235/20* | (2006.01) |
| *C07D 235/24* | (2006.01) |
| *C07D 235/30* | (2006.01) |
| *C07D 237/24* | (2006.01) |
| *C07D 239/28* | (2006.01) |
| *C07D 241/04* | (2006.01) |
| *C07D 241/24* | (2006.01) |
| *C07D 249/04* | (2006.01) |
| *C07D 261/18* | (2006.01) |
| *C07D 263/04* | (2006.01) |
| *C07D 263/16* | (2006.01) |
| *C07D 263/57* | (2006.01) |
| *C07D 265/36* | (2006.01) |
| *C07D 277/56* | (2006.01) |
| *C07D 285/06* | (2006.01) |
| *C07D 295/135* | (2006.01) |
| *C07D 295/155* | (2006.01) |
| *C07D 295/185* | (2006.01) |
| *C07D 307/68* | (2006.01) |
| *C07D 317/62* | (2006.01) |
| *C07D 317/68* | (2006.01) |
| *C07D 333/24* | (2006.01) |
| *C07D 333/38* | (2006.01) |
| *C07D 401/04* | (2006.01) |
| *C07D 401/10* | (2006.01) |
| *C07D 401/12* | (2006.01) |
| *C07D 401/14* | (2006.01) |
| *C07D 403/10* | (2006.01) |
| *C07D 403/12* | (2006.01) |
| *C07D 405/04* | (2006.01) |
| *C07D 405/10* | (2006.01) |
| *C07D 409/04* | (2006.01) |
| *C07D 409/12* | (2006.01) |
| *C07D 413/10* | (2006.01) |
| *C07D 413/12* | (2006.01) |
| *C07D 413/14* | (2006.01) |
| *C07D 417/10* | (2006.01) |
| *C07D 417/12* | (2006.01) |
| *C07D 471/04* | (2006.01) |
| *C07D 491/113* | (2006.01) |
| *C07D 409/14* | (2006.01) |
| *C07D 417/14* | (2006.01) |

(52) U.S. Cl.
CPC .......... *C07D 209/42* (2013.01); *C07D 211/46* (2013.01); *C07D 211/58* (2013.01); *C07D 213/12* (2013.01); *C07D 213/53* (2013.01); *C07D 213/79* (2013.01); *C07D 213/80* (2013.01); *C07D 213/81* (2013.01); *C07D 213/82* (2013.01); *C07D 231/14* (2013.01); *C07D 231/26* (2013.01); *C07D 231/40* (2013.01); *C07D 231/56* (2013.01); *C07D 233/60* (2013.01); *C07D 233/61* (2013.01); *C07D 233/90* (2013.01); *C07D 235/06* (2013.01); *C07D 235/14* (2013.01); *C07D 235/20* (2013.01); *C07D 235/24* (2013.01); *C07D 235/30* (2013.01); *C07D 237/24* (2013.01); *C07D 239/28* (2013.01); *C07D 241/04* (2013.01); *C07D 241/24* (2013.01); *C07D 249/04* (2013.01); *C07D 261/18* (2013.01); *C07D 263/04* (2013.01); *C07D 263/16* (2013.01); *C07D 263/57* (2013.01); *C07D 265/36* (2013.01); *C07D 277/56* (2013.01); *C07D 285/06* (2013.01); *C07D 295/135* (2013.01); *C07D 295/155* (2013.01); *C07D 295/185* (2013.01); *C07D 307/68* (2013.01); *C07D 317/62* (2013.01); *C07D 317/68* (2013.01); *C07D 333/24* (2013.01); *C07D 333/38* (2013.01); *C07D 401/04* (2013.01); *C07D 401/10* (2013.01); *C07D 401/12* (2013.01); *C07D 401/14* (2013.01); *C07D 403/10* (2013.01); *C07D 403/12* (2013.01); *C07D 405/04* (2013.01); *C07D 405/10* (2013.01); *C07D 409/04* (2013.01); *C07D 409/12* (2013.01); *C07D 409/14* (2013.01); *C07D 413/10* (2013.01); *C07D 413/12* (2013.01); *C07D 413/14* (2013.01); *C07D 417/10* (2013.01); *C07D 417/12* (2013.01); *C07D 417/14* (2013.01); *C07D 471/04* (2013.01); *C07D 491/113* (2013.01)

(56) References Cited

U.S. PATENT DOCUMENTS

| | | | |
|---|---|---|---|
| 6,388,045 | B1 | 5/2002 | Ueno et al. |
| 2007/0270422 | A1 | 11/2007 | Fukushima et al. |
| 2009/0239876 | A1 | 9/2009 | Clements et al. |

FOREIGN PATENT DOCUMENTS

| | | | | |
|---|---|---|---|---|
| GB | 1 430 004 | * | 3/1976 | .......... C07C 103/76 |
| JP | 49-042799 | | 2/1975 | |
| JP | H4-297446 | | 10/1992 | |
| JP | 2000-500464 A | | 1/2000 | |
| JP | 2002-527438 A | | 8/2002 | |
| JP | 2006-298893 A | | 11/2006 | |
| JP | 2008-533166 A | | 8/2008 | |
| JP | 2008-539180 A | | 11/2008 | |
| JP | 2009-530409 A | | 8/2009 | |
| KR | 2010 0047998 A | | 5/2010 | |
| WO | WO 97/17958 A1 | | 5/1997 | |
| WO | WO 1998/16498 | | 4/1998 | |
| WO | WO 00/21959 A1 | | 4/2000 | |
| WO | WO 00/63180 A1 | | 10/2000 | |
| WO | WO 00/68291 A1 | | 11/2000 | |
| WO | WO 01/55093 A1 | | 8/2001 | |
| WO | WO 2004/101495 A1 | | 11/2004 | |
| WO | WO 2005/023242 A1 | | 3/2005 | |
| WO | WO 2006/101977 A2 | | 9/2006 | |
| WO | WO 2007/109362 A2 | | 9/2007 | |
| WO | WO 2007/112093 A2 | | 10/2007 | |
| WO | WO 2008/008234 A1 | | 1/2008 | |
| WO | WO 2009/030887 A2 | | 3/2009 | |
| WO | WO 2009/087238 A2 | | 7/2009 | |
| WO | WO 2009/155362 A1 | | 12/2009 | |
| WO | WO 2010/059606 A2 | | 5/2010 | |

OTHER PUBLICATIONS

Adams, et al., "Quinone Imides. XLV. Structures of Aromatic Amine Adducts of p-Benzoquinonedibenzimide," Journal of Organic Chemistry, 1957, 22(11): 1287-1291.
CAPlus Accession No. 1970-122893. 1970.
CAPlus Accession No. 1994-323289. 1994.
CAS Registry No. 26705-18-0. Nov. 16, 1984.
CAS Registry No. 155085-04-4. May 17, 1994.
CAS Registry No. 155085-05-5. May 17, 1994.
Heerding, et al., "Novel Peptidomimetic Hematoregulatory Compounds," *Bioorg. Med. Chem. Lett.*, 2000, 10, 531-534.
Kim, et al., "Synthesis and antiproliferative activity of pyrrolo[3,2-b]pyridine derivatives against melanoma," Bioorganic & Medicinal Chemistry Letters, 2010, 20(1): 413-417.
Kuroda, et al., "Utilization of 3-hydroxy-2-naphthoic acid. III. Synthesis and utilization of some 3-hydroxy-2-naphthoic acid derivatives," *Kogyo Kagaku Zasshi*, 1969, 72(6): 1331-1336.
Perugini, et al., "Hematopoietic growth factor mimetics: From concept to clinic," Cytokine & Growth Factor Reviews, 2009, 20, 87-94.
Science IP, Chemical Structure Search Report. 2010.
Sek, D. et al., "New semiladder polymers. Part II: Synthesis and properties of new poly (amideimidazopyrrolones)," *Polymer*, 1999, 40(9): 2419-2428.
Sellarajah, S. et al., "Synthesis of Analogues of Congo Red and Evaluation of Their Anti-Prion Activity," *J. Med. Chem.*, 2004, 47(22): 5515-5534.
Srivastava, et al., "Studies in antiparastic agents. Part 20. Synthesis of probenzimidazoles, benzimidazoles and pyrimido[1,2-a]benzimidazoles as possible anthelmintics," *Indian Journal of Chemistry, Section B : Organic Chemistry Including Medicinal Chemistry*, 1993, 32B(10): 1035-1044.
International Search Report and Written Opinion mailed Dec. 24, 2010 in PCT Application No. PCT/US2010/052359, filed Oct. 10, 2010.
International Preliminary Report on Patentability Issued on Apr. 17, 2012 in PCT Application No. PCT/US2010/052359, filed Oct. 10, 2010.
Supplementary Search Report mailed Feb. 28, 2013 in EP 10823959.1, filed Oct. 12, 2010.
Office Action dated Oct. 9, 2014 in corresponding Japanese Application No. 2012-534288.
CAS Registry No. 177155-72-5, Entered STN: Jun. 7, 1996.
Office Action dated Jul. 12, 2016 in corresponding Australian Application No. 2010307006.
Barashkov, N. N., Vysokomolekulyarnye Soedineniya, Seriya B: Kratkie Soobshcheniya, 1984, 26(5), 356-361.
Trostyanskay, et al., Plasticheskie Massy, 1968, 9, 20-23.

* cited by examiner

HEMATOPOIETIC GROWTH FACTOR MIMETIC SMALL MOLECULE COMPOUNDS AND THEIR USES

RELATED APPLICATIONS

This application is a division of U.S. application Ser. No. 13/501,622, filed Apr. 12, 2012, which is the U.S. National Phase of International Application No. PCT/US2010/052359, filed Oct. 12, 2010, which claims the benefit of U.S. Provisional Application No. 61/251,259, filed Oct. 13, 2009, each of which is incorporated herein by reference in its entirety.

FIELD OF THE INVENTION

The present embodiments relate to compounds with physiological effects, such as the activation of hematopoietic growth factor receptors. The present embodiments also relate to use of the compounds to treat a variety of conditions, diseases and ailments such as hematopoietic conditions and disorders.

BACKGROUND

Hematopoietic growth factor (HGF) represents a family of biological molecules such as glycoproteins with important regulatory functions in the processes of proliferation, differentiation, and functional activation of hematopoietic progenitors and mature blood cells. HGF compounds can be potent regulators of blood cell proliferation and development in the bone marrow. They are able to augment hematopoiesis when bone marrow dysfunction exists. Recombinant DNA technology has made it possible to clone the genes responsible for many of these factors.

One example of an HGF is the glycoprotein hormone erythropoietin (EPO). EPO is an essential viability and growth factor for the erythrocytic progenitors. EPO is a member of the family of class I cytokines which fold into a compact globular structure consisting of 4 α-helical bundles. Its molecular mass is 30.4 kDa, although it migrates with an apparent size of 34-38 kDa on SDS-polyacrylamide gels. The peptide core of 165 amino acids suffices for receptor-binding and in vitro stimulation of erythropoiesis, while the carbohydrate portion (40% of the total molecule) is required for the in vivo survival of the hormone. The 4 carbohydrate chains of EPO have been analyzed in detail. The 3 complex-type N-linked oligosaccharides at asparagines 24, 38 and 83 appear involved in stabilizing EPO in circulation. EPO is mainly produced by hepatocytes during the fetal stage. After birth, almost all circulating EPO originates from peritubular fibroblast-like cells located in the cortex of the kidneys. Transcription factors of the GATA-family may be important in the control of the time-specific and tissue-specific expression of the EPO gene. In adults, minor amounts of EPO mRNA are expressed in liver parenchyma, spleen, lung, testis and brain. In brain, EPO exerts neurotrophic and neuroprotective effects, which are separate from the action of circulating EPO on erythropoietic tissues. See e.g., Jelkmann, W., *Internal Medicine* Vol. 43, No. 8 (August 2004).

SUMMARY OF THE INVENTION

Some embodiments disclosed herein provide a compound of Formula VIII:

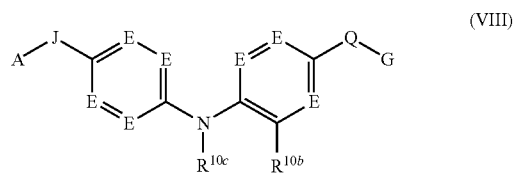

(VIII)

and pharmaceutically acceptable salts thereof;
wherein:
A-J is

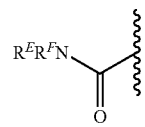

and Q-G is

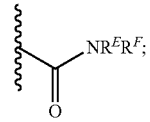

or A-J is

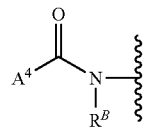

and Q-G is

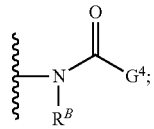

or A-J is

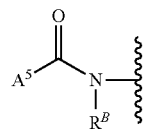

and Q-G is

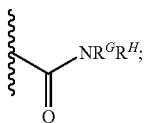

or A-J is

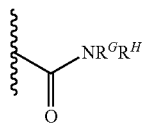

and Q-G is

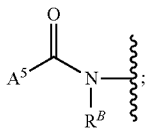

each E is separately selected from the group consisting of —$CR^{10a}$— and N (nitrogen);

each $R^{10a}$ is separately selected from the group consisting of H (hydrogen), halogen, cyano, $C_1$-$C_6$ alkyl optionally substituted with up to five fluoro, $C_1$-$C_6$ alkoxy optionally substituted with up to five fluoro, $C_2$-$C_6$ alkenyl optionally substituted with up to five fluoro, $C_2$-$C_6$ alkynyl optionally substituted with up to five fluoro, $C_3$-$C_7$ cycloalkyl optionally substituted with up to five fluoro, and $C_3$-$C_7$ cycloalkenyl optionally substituted with up to five fluoro;

$R^{10b}$ is selected from the group consisting of $R^{10bb}$, H (hydrogen), halogen, cyano, $C_1$-$C_6$ alkyl optionally substituted with up to five fluoro, $C_1$-$C_6$ alkoxy optionally substituted with up to five fluoro, $C_2$-$C_6$ alkenyl optionally substituted with up to five fluoro, $C_2$-$C_6$ alkynyl optionally substituted with up to five fluoro, $C_3$-$C_7$ cycloalkyl optionally substituted with up to five fluoro, and $C_3$-$C_7$ cycloalkenyl optionally substituted with up to five fluoro;

$R^{10c}$ is selected from the group consisting of H (hydrogen), $R^U SO_2$—, $R^U C(=O)$—, $C_1$-$C_6$ alkyl optionally substituted with up to five fluoro, and $C_3$-$C_7$ cycloalkyl optionally substituted with up to five fluoro, or 0 is $R^{10cc}$ when $R^{10b}$ is $R^{10bb}$;

$R^{10cc}$ and $R^{10bb}$ together with the atoms to which they are attached is a five-membered heteroaryl optionally substituted with one or more substituents each separately selected from the group consisting of halogen, cyano, $C_1$-$C_6$ alkyl optionally substituted with up to five fluoro, $C_1$-$C_6$ alkoxy optionally substituted with up to five fluoro, $C_1$-$C_6$ alkylC(=O)— and $C_3$-$C_7$ cycloalkylC(=O)—;

$A^4$ is selected from the group consisting of $C_3$-$C_7$ cycloalkenyl, $C_3$-$C_7$ cycloalkyl, $C_1$-$C_6$ alkyl, $C_1$-$C_6$ heteroalkyl, $C_2$-$C_6$ alkenyl, $C_1$-$C_6$ alkoxy, —$(CH_2)_m NR^P R^L$, heterocycle, polycyclic heterocyclyl, aryl, and heteroaryl, said $C_3$-$C_7$ cycloalkenyl, $C_3$-$C_7$ cycloalkyl, $C_1$-$C_6$ alkyl, $C_1$-$C_6$ heteroalkyl, $C_2$-$C_6$ alkenyl, heterocycle, polycyclic heterocyclyl, aryl, and heteroaryl, each optionally substituted with one or more substituents selected from the group consisting of $R^1$, $R^2$, and $R^3$;

$G^4$ is selected from the group consisting of polycyclic heterocyclyl, aryl, and heteroaryl, each optionally substituted with one or more substituents selected from the group consisting of $R^4$, $R^5$, and $R^6$;

$A^5$ is selected from the group consisting of polycyclic heterocyclyl, aryl and heteroaryl, each optionally substituted with one or more substituents selected from the group consisting of $R^1$, $R^2$, and $R^3$;

each $R^B$ is separately selected from the group consisting of hydrogen, an optionally substituted $C_1$-$C_6$ alkyl, an optionally substituted $C_2$-$C_6$ alkenyl, and an optionally substituted $C_3$-$C_7$ cycloalkyl;

each —$NR^E R^F$ is separately selected, wherein each $R^E$ is independently selected from the group consisting of hydrogen and an optionally $C_1$-$C_6$ alkyl, and each $R^F$ is independently selected from the group consisting of aryl and heteroaryl, said aryl and heteroaryl in the definition of $R^F$ are each optionally substituted with halogen, cyano, $C_1$-$C_6$ alkyl, $C_1$-$C_6$ alkoxy, $C_3$-$C_7$ cycloalkyl, $C_3$-$C_7$ cycloalkenyl, —C(=O)$NR^N R^O$, —OC(=O)$NR^N R^O$, —NHC(=O)$NR^N R^O$, —O($CH_2$)$_q NR^N R^O$, —NH($CH_2$)$_p NR^N R^O$ —($CH_2$)$_p NR^N R^O$, an optionally substituted aryl and an optionally substituted heteroaryl, and said aryl and heteroaryl in the definition of $R^F$ are each further optionally fused with an optionally substituted nonaromatic heterocycle or an optionally substituted nonaromatic carbocycle;

$R^G$ is selected from the group consisting of $C_1$-$C_6$ alkyl, $C_3$-$C_6$ cycloalkyl, $C_3$-$C_8$ cycloalkenyl, $C_1$-$C_6$ heteroalkyl, $C_1$-$C_6$ heteroalkenyl, $C_1$-$C_6$ heteroalkynyl, heterocycle, aryl, and heteroaryl, each optionally substituted with one or more substituents selected from the group consisting of $R^4$, $R^5$, and $R^6$, said aryl and heteroaryl in the definition of $R^G$ are each further optionally fused with an optionally substituted nonaromatic heterocycle or an optionally substituted nonaromatic carbocycle, or $R^G$ is —$OR^L$ or —$NR^P R^L$;

$R^H$ is selected from the group consisting of hydrogen, $C_1$-$C_6$ alkyl, $C_2$-$C_6$ alkenyl, $C_3$-$C_7$ cycloalkyl, and $C_1$-$C_3$ haloalkyl, or —$NR^G R^H$ is an optionally substituted nonaromatic heterocycle linked through a ring nitrogen atom;

each $R^1$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, optionally substituted $C_3$-$C_7$ cycloalkenyl, an optionally substituted $C_1$-$C_6$ haloalkyl, an optionally substituted $C_1$-$C_6$ heteroalkyl, an optionally substituted aryl, and an optionally substituted heteroaryl;

each $R^2$ is separately selected from the group consisting of halogen, —O($CH_2$)$_m OR^I$, —($CH_2$)$_m OR^I$, —$NR^J R^K$, —($CH_2$)$_m SR^I$, —C(=O)$R^L$, —($CH_2$)$_m R^L$, an optionally substituted $C_1$-$C_6$ alkyl, an optionally substituted $C_1$-$C_6$ alkoxy, an optionally substituted $C_2$-$C_6$ alkenyl, an optionally substituted $C_1$-$C_6$ haloalkyl, an optionally substituted $C_1$-$C_6$ heteroalkyl, and an optionally substituted $C_3$-$C_7$ cycloalkyl where said $C_3$-$C_7$ cycloalkyl is further optionally fused with aryl or heteroaryl;

each $R^3$ is separately selected from the group consisting of halogen, —($CH_2$)$_m OR^G$, —$NR^L C(=O)R^M$, —$NR^L C(=O)OR^M$, —$NR^L C(=O)NR^N R^O$, —$NR^N R^O$, —($CH_2$)$_m S(O)_{0-2} R^M$, —($CH_2$)$_m NHS(O)_{0-2} R^M$, —($CH_2$)$_m NO_2$, —($CH_2$)$_m CN$, —($CH_2$)$_m R^P$, $C_1$-$C_6$ alkyl $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$;

each R$^4$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, an optionally substituted $C_1$-$C_6$ heteroalkyl, an optionally substituted aryl, and an optionally substituted heteroaryl;

each R$^5$ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —(CH$_2$)$_m$C(=O)R$^L$, —(CH$_2$)$_m$R$^L$, an optionally substituted $C_1$-$C_6$ alkyl, an optionally substituted $C_1$-$C_6$ alkoxy, an optionally substituted $C_2$-$C_6$ alkenyl, an optionally substituted $C_3$-$C_7$ cycloalkyl, an optionally substituted $C_1$-$C_6$ haloalkyl, and an optionally substituted $C_1$-$C_6$ heteroalkyl;

each R$^6$ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$NO$_2$, —(CH$_2$)$_m$CN, —(CH$_2$)$_m$R$^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, $C_1$-$C_6$ heteroalkyl, heterocycle, aryl, polycyclic heterocyclyl, and heteroaryl, said heterocycle, aryl, polycyclic heterocyclyl, and heteroaryl in the definition of R$^6$ are each optionally substituted with halogen, cyano, $C_1$-$C_6$ alkyl, $C_1$-$C_6$ haloalkyl, $C_1$-$C_6$ alkoxy, —C(=O)OR$^M$, or —NR$^J$R$^K$;

each R$^I$ is separately selected from the group consisting of hydrogen, $C_1$-$C_6$ alkyl, $C_2$-$C_4$ alkenyl, $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl;

each —NR$^J$R$^K$ is separately selected, wherein R$^J$ and R$^K$ are each independently selected from the group consisting of hydrogen, $C_1$-$C_6$ alkyl optionally substituted with up to 5 fluoro, —(CH$_2$)$_m$OR$^{JA}$, —(CH$_2$)$_m$NR$^{JB}$R$^{JC}$, —(CH$_2$)$_m$R$^R$, $C_3$-$C_7$ cycloalkyl, heterocycle, aryl and heteroaryl, said $C_3$-$C_7$ cycloalkyl, heterocycle, aryl and heteroaryl in the definition of R$^J$ and R$^K$ are each independently optionally substituted with one or more substituents selected from the group consisting of halo, $C_1$-$C_6$ alkyl, $C_1$-$C_6$ haloalkyl, $C_1$-$C_6$ alkoxy, aryl and heteroaryl, said aryl and heteroaryl substituent off of R$^J$ and R$^K$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{KA}$R$^{KB}$; or —NR$^J$R$^K$ is an optionally substituted non-aromatic heterocycle linked through a ring nitrogen atom;

each R$^{JA}$ is independently selected from the group consisting of hydrogen, $C_1$-$C_6$ alkyl, and $C_1$-$C_6$ haloalkyl;

each —NR$^{JB}$R$^{JC}$ is separately selected, wherein R$^{JB}$ and R$^{JC}$ are each independently selected from the group consisting of hydrogen, $C_1$-$C_6$ alkyl, and $C_1$-$C_6$ haloalkyl;

each —NR$^{KA}$R$^{KB}$ is separately selected, wherein R$^{KA}$ and R$^{KB}$ are each independently selected from the group consisting of hydrogen, $C_1$-$C_6$ alkyl, and $C_1$-$C_6$ haloalkyl;

each R$^M$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_3$-$C_7$ cycloalkenyl, and —(CH$_2$)$_m$R$^P$;

each —NR$^N$R$^O$ is separately selected, wherein R$^N$ and R$^O$ are each independently selected from the group consisting of hydrogen, —(CH$_2$)$_m$NR$^{NA}$R$^{NB}$, aryl and heteroaryl, said aryl and heteroaryl in the definition of R$^N$ and R$^O$ are each independently optionally substituted with one or more substituents selected from the group consisting of —(CH$_2$)$_m$NR$^{OA}$R$^{OB}$, halo, $C_1$-$C_6$ alkyl, $C_1$-$C_6$ haloalkyl, $C_1$-$C_6$ alkoxy, aryl and heteroaryl, said aryl and heteroaryl substituent off of R$^N$ and R$^O$ are each optionally substituted with one or more halo, $C_1$-$C_6$ alkyl, $C_1$-$C_6$ haloalkyl, $C_1$-$C_6$ alkoxy, or —NR$^{NA}$R$^{NB}$, each —NR$^{NA}$R$^{NB}$ is separately selected, wherein R$^{NA}$ and R$^{NB}$ are each independently selected from the group consisting of hydrogen, $C_1$-$C_6$ alkyl, and $C_1$-$C_6$ haloalkyl;

each —NR$^{OA}$R$^{OB}$ is separately selected, wherein R$^{OA}$ and R$^{OB}$ are each independently selected from the group consisting of hydrogen, $C_1$-$C_6$ alkyl, and $C_1$-$C_6$ haloalkyl;

each R$^P$ is independently selected from the group consisting of hydrogen and $C_1$-$C_6$ alkyl;

each R$^L$ is independently selected from the group consisting of $C_3$-$C_7$ cycloalkyl, optionally substituted $C_1$-$C_6$ alkyl, optionally substituted $C_1$-$C_6$ alkoxy, —(CH$_2$)$_m$OR$^{LA}$, —(CH$_2$)$_m$NR$^{LB}$R$^{LC}$, aryl and heteroaryl, said aryl and heteroaryl in the definition of R$^L$ are each independently optionally substituted with one or more substituents selected from the group consisting of halo, $C_1$-$C_6$ alkyl, $C_1$-$C_6$ haloalkyl, $C_1$-$C_6$ alkoxy, —(CH$_2$)$_m$NR$^{LD}$R$^{LE}$, aryl and heteroaryl, said aryl and heteroaryl substituent off of R$^L$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{LF}$R$^{LG}$;

each R$^{LA}$ is independently selected from the group consisting of hydrogen, $C_1$-$C_6$ alkyl, and $C_1$-$C_6$ haloalkyl;

R$^{LB}$ and R$^{LC}$ are each independently selected from the group consisting of hydrogen, $C_1$-$C_6$ alkyl, $C_1$-$C_6$ haloalkyl, and $C_1$-$C_6$ heteroalkenyl, said $C_1$-$C_6$ alkyl, $C_1$-$C_6$ haloalkyl, and $C_1$-$C_6$ heteroalkenyl each optionally substituted with one or more halogen, cyano, or —(CH$_2$)$_m$C(=O)OH; or —NR$^{LB}$R$^{LC}$ is an optionally substituted non-aromatic heterocycle linked through a ring nitrogen atom;

each —NR$^{LD}$R$^{LE}$ is separately selected, wherein R$^{LD}$ and R$^{LE}$ are each independently selected from the group consisting of hydrogen, aryl, heteroaryl, and optionally substituted $C_1$-$C_6$ alkyl, said aryl and heteroaryl in the definition of R$^{LD}$ and R$^{LE}$ are each optionally substituted with $C_1$-$C_6$ alkyl or $C_1$-$C_6$ alkoxy; or —NR$^{LD}$R$^{LE}$ is an optionally substituted non-aromatic heterocycle linked through a ring nitrogen atom;

each —NR$^{LF}$R$^{LG}$ is separately selected, wherein R$^{LF}$ and R$^{LG}$ are each independently selected from the group consisting of hydrogen, and $C_1$-$C_6$ alkyl; or —NR$^{LF}$R$^{LG}$ is an optionally substituted non-aromatic heterocycle linked through a ring nitrogen atom;

R$^R$ is selected from the group consisting of $C_1$-$C_6$ alkyl, an optionally substituted aryl, and an optionally substituted heteroaryl;

R$^U$ is selected from the group consisting of $C_3$-$C_7$ cycloalkyl $C_1$-$C_6$ alkyl optionally substituted with up to 5 fluoro, and an optionally substituted heteroaryl;

each m is independently 0, 1, 2, or 3;

each p is independently 0, 1, 2, 3, 4, 5, or 6; and each q is independently 1, 2, 3, 4, 5, or 6.

Some embodiments disclosed herein provide a compound of Formula VIII having the formula VIIIa:

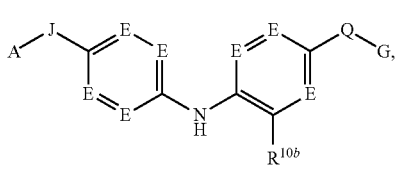
(VIIIa)

and pharmaceutically acceptable salts thereof.

Some embodiments disclosed herein provide a compound of Formula VIIIa having the formula VIIIaa:

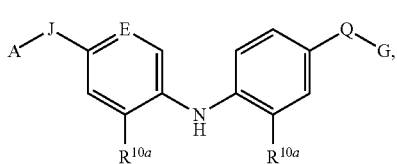
(VIIIaa)

and pharmaceutically acceptable salts thereof, and having the formula VIIIab:

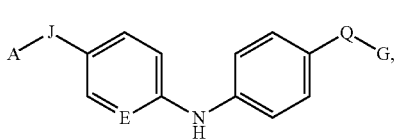
(VIIIab)

and pharmaceutically acceptable salts thereof.

Some embodiments disclosed herein provide a compound of Formula VIIIaa, wherein A-J is

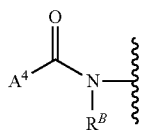

and Q-G is

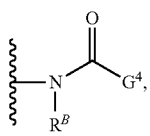

$A^4$ is selected from the group consisting of aryl and heteroaryl, where at least one atom forming the heteroaryl aromatic ring is a N (nitrogen), and said aryl and heteroaryl are each optionally substituted with one or more substituents selected from the group consisting of $R^1$, $R^2$, and $R^3$, and $G^4$ is selected from the group consisting of aryl and heteroaryl, where at least one atom forming the heteroaryl aromatic ring is a N (nitrogen), and said aryl and heteroaryl are each optionally substituted with one or more substituents selected from the group consisting of $R^4$, $R^5$, and $R^6$.

Some embodiments disclosed herein provide a compound of Formula VIII having the formula VIIIb:

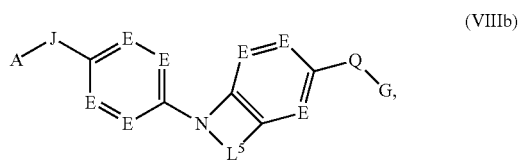
(VIIIb)

and pharmaceutically acceptable salts thereof, wherein $L^5$ is $E^1=E^1$ or $E^2$-$E^2$, each $E^1$ is separately selected from the group consisting of —$CR^{10dd}$— and N (nitrogen), each $R^{10dd}$ is separately selected from the group consisting of H (hydrogen), halogen, cyano, $C_1$-$C_6$ alkyl optionally substituted with up to five fluoro, $C_1$-$C_6$ alkoxy optionally substituted with up to five fluoro, $C_1$-$C_6$ alkylC(=O)— and $C_3$-$C_7$ cycloalkylC(=O)—, each $E^2$ is separately selected from the group consisting of —$CR^7R^8$— and $NR^9$, $R^7$ and $R^8$ are each independently selected from the group consisting of hydrogen, —OH, and $C_1$-$C_6$ alkyl optionally substituted with up to five fluoro, or optionally $CR^7R^8$ is —C(=O)—, and, $R^9$ is selected from the group consisting of hydrogen, $C_3$-$C_7$cycloalkylC(O)— and $C_1$-$C_6$ alkylC(O)—, and $C_1$-$C_6$ alkyl optionally substituted with up to five fluoro.

Some embodiments disclosed herein provide a compound of Formula VIIIb having the formula VIIIbb:

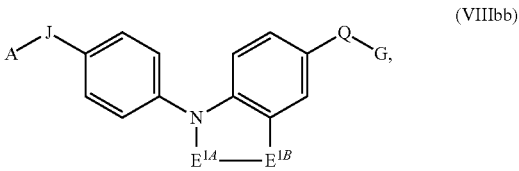
(VIIIbb)

and pharmaceutically acceptable salts thereof, wherein $E^{1A}$ is N (nitrogen) and $E^{1B}$ is —CH—, or $E^{1A}$ is —CH— and $E^{1B}$ is —CH—, or $E^{1A}$ is —CH— and $E^{1B}$ is N (nitrogen); and A-J is

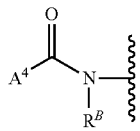

and Q-G is

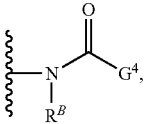

or A-J is

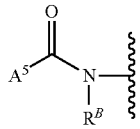

and Q-G is

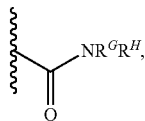

or A-J is

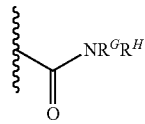

and Q-G is

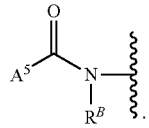

Some embodiments disclosed herein provide a compound of Formula VIIIbb having the formula VIIIbbb:

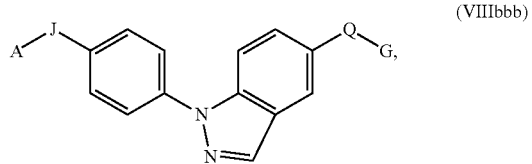

(VIIIbbb)

and pharmaceutically acceptable salts thereof, wherein A-J is

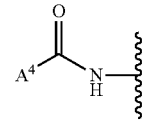

and Q-G is

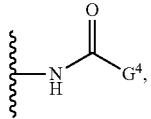

or A-J is

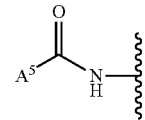

and Q-G is

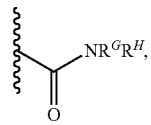

or A-J is

and Q-G is

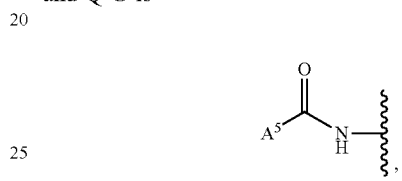

$A^4$ is selected from the group consisting of $C_5$-$C_7$ cycloalkenyl, $C_3$-$C_6$ cycloalkyl, $C_1$-$C_6$ alkyl, $C_1$-$C_6$ heteroalkyl, $C_2$-$C_6$ alkenyl, —$NR^PR^L$, heterocycle, aryl, and heteroaryl, said $C_5$-$C_7$ cycloalkenyl, $C_3$-$C_6$ cycloalkyl, $C_1$-$C_6$ alkyl, $C_1$-$C_6$ heteroalkyl, $C_2$-$C_6$ alkenyl, heterocycle, aryl, and heteroaryl, each optionally substituted with one or more substituents selected from the group consisting of $R^1$, $R^2$, and $R^3$, each $R^1$ is separately selected from the group consisting of halogen, cyano, an optionally substituted $C_1$-$C_6$ alkyl, an optionally substituted $C_1$-$C_6$ alkoxy, an optionally substituted $C_1$-$C_6$ heteroalkyl, an optionally substituted aryl, and an optionally substituted heteroaryl, each $R^2$ is separately selected from the group consisting of —O(CH$_2$)$_m$OR$^I$, —(CH$_2$)$_m$OR$^I$, —NR$^J$R$^K$, —(CH$_2$)$_m$SR$^I$, —C(=O)R$^L$, and —(CH$_2$)$_m$R$^L$, each $R^3$ is separately selected from the group of —(CH$_2$)$_m$OR$^G$, —NR$^L$C(=O)R$^M$, —NR$^L$C(=O)OR$^M$, —NR$^L$C(=O) NR$^N$R$^O$, —NR$^N$R$^O$, —(CH$_2$)$_m$S(O)$_{0-2}$R$^M$, —(CH$_2$)$_m$NHS (O)$_{0-2}$R$^M$, —(CH$_2$)$_m$NO$_2$, —(CH$_2$)$_m$CN, —(CH$_2$)$_m$R$^P$, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$, $G^4$ is selected from the group consisting of aryl, and heteroaryl, each optionally substituted with one or more substituents selected from the group consisting of $R^4$, $R^5$, and $R^6$, each $R^4$ is separately selected from the group consisting of halogen, cyano, an optionally substituted $C_1$-$C_6$ alkyl, and an optionally substituted $C_1$-$C_6$ heteroalkyl, each $R^5$ is separately selected from the group consisting of halogen, —(CH$_2$)$_m$OH, —NR$^J$R$^K$, and —(CH$_2$)$_m$C(=O)R$^L$, each $R^L$ is independently selected from the group consisting of —OH, $C_1$-$C_6$ alkyl, and $C_1$-$C_6$ alkoxy, each $R^6$ is separately selected from the group consisting of —NR$^L$C(=O)R$^M$, —NR$^L$C(=O)OR$^M$, —NR$^L$C(=O)NR$^N$R$^O$, —NR$^N$R$^O$, —(CH$_2$)$_m$R$^P$, heterocycle, aryl, polycyclic heterocyclyl, and heteroaryl, said heterocycle, aryl, polycyclic heterocyclyl, and heteroaryl in the definition of $R^6$ are each optionally substituted with halogen, cyano, $C_1$-$C_6$ alkyl, $C_1$-$C_6$ haloalkyl, $C_1$-$C_6$ alkoxy, —C(=O)OR$^M$, or —NR$^J$R$^K$, R$^G$ within the definition of —NR$^G$R$^H$ is heteroaryl optionally substituted with one or more substituents selected from the group consisting of R$^4$, R$^5$, and R$^6$, and R$^H$ within the definition of —NR$^G$R$^H$ is hydrogen.

Some embodiments disclosed herein provide a compound of Formula IX:

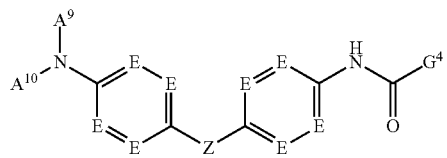

(IX)

and pharmaceutically acceptable salts thereof;
wherein:
Z is

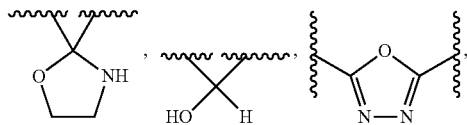

or —C(=E$^3$)-;

each E is separately selected from the group consisting of —CR$^{10a}$— and N (nitrogen);

each R$^{10a}$ is separately selected from the group consisting of H (hydrogen), halogen, $C_1$-$C_6$ alkyl optionally substituted with up to five fluoro, and $C_1$-$C_6$ alkoxy optionally substituted with up to five fluoro;

E$^3$ is O (oxygen), N—NHR$^Q$ or N—OR$^Q$ where R$^Q$ in the definition of E$^3$ is selected from the group consisting of hydrogen, $C_1$-$C_6$ alkyl, $C_2$-$C_6$ alkenyl, —(CH$_2$)$_m$R$^{RA}$, and —C(=O)(CH$_2$)$_m$R$^{RA}$;

R$^{RA}$ is selected from the group consisting of $C_1$-$C_6$ alkyl, aryl, and heteroaryl;

A$^9$ is hydrogen or $C_1$-$C_6$ alkyl;

A$^{10}$ is selected from the group consisting of $C_1$-$C_6$ alkyl, $C_2$-$C_6$ alkenyl, —C(=O)R$^A$, —C(=O)C(=O)R$^A$, —(CH$_2$)R$^B$, —(CH$_2$)OR$^B$;

R$^A$ is selected from the group consisting of $C_1$-$C_6$ alkyl, $C_3$-$C_7$ cycloalkyl, heterocycle, polycyclic heterocyclyl, aryl and heteroaryl, each optionally substituted with one or more substituents selected from the group consisting of R$^1$, R$^2$, and R$^3$;

R$^B$ is selected from the group consisting of hydrogen, $C_1$-$C_6$ alkyl, $C_1$-$C_6$ alkoxy, $C_2$-$C_6$ alkenyl, $C_3$-$C_7$ cycloalkyl, and heteroaryl;

G$^4$ is selected from the group consisting of polycyclic heterocyclyl, aryl, and heteroaryl, each optionally substituted with one or more substituents selected from the group consisting of R$^4$, R$^5$, and R$^6$;

each R$^1$ is separately selected from the group consisting of halogen, cyano, $C_1$-$C_6$ heteroalkyl, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, optionally substituted $C_3$-$C_7$ cycloalkenyl, an optionally substituted $C_1$-$C_6$ haloalkyl, an optionally substituted aryl, and an optionally substituted heteroaryl;

each R$^2$ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —C(=O)R$^L$, —(CH$_2$)$_m$R$^L$, $C_1$-$C_6$ heteroalkyl, an optionally substituted $C_1$-$C_6$ alkyl, an optionally substituted $C_1$-$C_6$ alkoxy, an optionally substituted $C_2$-$C_6$ alkenyl, an optionally substituted $C_1$-$C_6$ haloalkyl, and an optionally substituted $C_3$-$C_7$ cycloalkyl where said $C_3$-$C_7$ cycloalkyl is further optionally fused with aryl or heteroaryl;

each R$^3$ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$CN, —(CH$_2$)$_m$R$^P$, $C_1$-$C_6$ alkyl $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, heterocycle, aryl, polycyclic heterocyclyl, and heteroaryl, said heterocycle, aryl polycyclic heterocyclyl, and heteroaryl in the definition of R$^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$;

each R$^4$ is separately selected from the group consisting of halogen, cyano, $C_1$-$C_6$ heteroalkyl, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, an optionally substituted aryl, and an optionally substituted heteroaryl;

each R$^5$ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —(CH$_2$)$_m$C(=O)R$^L$, —(CH$_2$)$_m$R$^L$, $C_1$-$C_6$ heteroalkyl, an optionally substituted $C_1$-$C_6$ alkyl, an optionally substituted $C_1$-$C_6$ alkoxy, an optionally substituted $C_2$-$C_6$ alkenyl, an optionally substituted $C_3$-$C_7$ cycloalkyl, and an optionally substituted $C_1$-$C_6$ haloalkyl;

each R$^6$ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$CN, —(CH$_2$)$_m$R$^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, $C_1$-$C_6$ heteroalkyl, heterocycle, aryl, polycyclic heterocyclyl, and heteroaryl, said heterocycle, aryl, polycyclic heterocyclyl, and heteroaryl in the definition of R$^6$ are each optionally substituted with halogen, cyano, $C_1$-$C_6$ alkyl, $C_1$-$C_6$ haloalkyl, $C_1$-$C_6$ alkoxy, —C(=O)OR$^M$, or —NR$^J$R$^K$;

R$^G$ is selected from the group consisting of $C_1$-$C_6$ alkyl, $C_3$-$C_6$ cycloalkyl, $C_3$-$C_8$ cycloalkenyl, $C_1$-$C_6$ heteroalkyl, $C_1$-$C_6$ heteroalkenyl, $C_1$-$C_6$ heteroalkynyl, heterocycle, aryl, and heteroaryl, each optionally substituted with one or more substituents selected from the group consisting of R$^4$, R$^5$, and R$^6$, said aryl and heteroaryl in the definition of R$^G$ are each further optionally fused with an optionally substituted nonaromatic heterocycle or an optionally substituted nonaromatic carbocycle, or R$^G$ is —OR$^L$ or —NR$^P$R$^L$;

each R$^I$ is separately selected from the group consisting of hydrogen, $C_1$-$C_6$ alkyl, $C_2$-$C_4$ alkenyl, $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl;

each —NR$^J$R$^K$ is separately selected, wherein R$^J$ and R$^K$ are each independently selected from the group consisting of hydrogen, $C_1$-$C_6$ alkyl optionally substituted with up to 5 fluoro, —(CH$_2$)$_m$OR$^{JA}$, —(CH$_2$)$_m$NR$^{JB}$R$^{JC}$, —(CH$_2$)$_m$R$^R$, $C_3$-$C_7$ cycloalkyl, heterocycle, aryl and heteroaryl, said $C_3$-$C_7$ cycloalkyl, heterocycle, aryl and heteroaryl in the definition of R$^J$ and R$^K$ are each independently optionally substituted with one or more substituents selected from the group consisting of halo, $C_1$-$C_6$ alkyl, $C_1$-$C_6$ haloalkyl, $C_1$-$C_6$ alkoxy, aryl and heteroaryl, said aryl and heteroaryl substituent off of R$^J$ and R$^K$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{KA}$R$^{KB}$; or —NR$^J$R$^K$ is an optionally substituted non-aromatic heterocycle linked through a ring nitrogen atom;

each R$^{JA}$ is independently selected from the group consisting of hydrogen, $C_1$-$C_6$ alkyl, and $C_1$-$C_6$ haloalkyl;

each —NR$^{JB}$R$^{JC}$ is separately selected, wherein R$^{JB}$ and R$^{JC}$ are each independently selected from the group consisting of hydrogen, $C_1$-$C_6$ alkyl, and $C_1$-$C_6$ haloalkyl;

each —NR$^{KA}$R$^{KB}$ is separately selected, wherein R$^{KA}$ and R$^{KB}$ are each independently selected from the group consisting of hydrogen, $C_1$-$C_6$ alkyl, and $C_1$-$C_6$ haloalkyl;

each R$^M$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_3$-$C_7$ cycloalkenyl, and —(CH$_2$)$_m$R$^P$;

each —NR$^N$R$^O$ is separately selected, wherein R$^N$ and R$^O$ are each independently selected from the group consisting of hydrogen, —(CH$_2$)$_m$NR$^{NA}$R$^{NB}$, aryl and heteroaryl, said aryl and heteroaryl in the definition of R$^N$ and R$^O$ are each independently optionally substituted with one or more substituents selected from the group consisting of —(CH$_2$)$_m$NR$^{OA}$R$^{OB}$, halo, $C_1$-$C_6$ alkyl, $C_1$-$C_6$ haloalkyl, $C_1$-$C_6$ alkoxy, aryl and heteroaryl, said aryl and heteroaryl substituent off of R$^N$ and R$^O$ are each optionally substituted with one or more halo, $C_1$-$C_6$ alkyl, $C_1$-$C_6$ haloalkyl, $C_1$-$C_6$ alkoxy, or —NR$^{NA}$R$^{NB}$, each —NR$^{NA}$R$^{NB}$ is separately selected, wherein R$^{NA}$ and R$^{NB}$ are each independently selected from the group consisting of hydrogen, $C_1$-$C_6$ alkyl, and $C_1$-$C_6$ haloalkyl;

each —NR$^{OA}$R$^{OB}$ is separately selected, wherein R$^{OA}$ and R$^{OB}$ are each independently selected from the group consisting of hydrogen, $C_1$-$C_6$ alkyl, and $C_1$-$C_6$ haloalkyl;

R$^P$ is selected from the group consisting of hydrogen and $C_1$-$C_6$ alkyl;

each R$^L$ is independently selected from the group consisting of $C_3$-$C_7$ cycloalkyl, optionally substituted $C_1$-$C_6$ alkyl, optionally substituted $C_1$-$C_6$ alkoxy, —(CH$_2$)$_m$OR$^{LA}$, —(CH$_2$)$_m$NR$^{LB}$R$^{LC}$, aryl and heteroaryl, said aryl and heteroaryl in the definition of R$^L$ are each independently optionally substituted with one or more substituents selected from the group consisting of halo, $C_1$-$C_6$ alkyl, $C_1$-$C_6$ haloalkyl, $C_1$-$C_6$ alkoxy, —(CH$_2$)$_m$NR$^{LD}$R$^{LE}$, aryl and heteroaryl, said aryl and heteroaryl substituent off of R$^L$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{LF}$R$^{LG}$;

each R$^{LA}$ is independently selected from the group consisting of hydrogen, $C_1$-$C_6$ alkyl, and $C_1$-$C_6$ haloalkyl;

R$^{LB}$ and R$^{LC}$ are each independently selected from the group consisting of hydrogen, $C_1$-$C_6$ alkyl, $C_1$-$C_6$ haloalkyl, and $C_1$-$C_6$ heteroalkenyl, said $C_1$-$C_6$ alkyl, $C_1$-$C_6$ haloalkyl, and $C_1$-$C_6$ heteroalkenyl each optionally substituted with one or more halogen, cyano, or —(CH$_2$)$_m$C(=O)OH; or —NR$^{LB}$R$^{LC}$ is an optionally substituted non-aromatic heterocycle linked through a ring nitrogen atom;

each —NR$^{LD}$R$^{LE}$ is separately selected, wherein R$^{LD}$ and R$^{LE}$ are each independently selected from the group consisting of hydrogen, aryl, heteroaryl, and optionally substituted $C_1$-$C_6$ alkyl, said aryl and heteroaryl in the definition of R$^{LD}$ and R$^{LE}$ are each optionally substituted with $C_1$-$C_6$ alkyl or $C_1$-$C_6$ alkoxy; or —NR$^{LD}$R$^{LE}$ is an optionally substituted non-aromatic heterocycle linked through a ring nitrogen atom;

each —NR$^{LF}$R$^{LG}$ is separately selected, wherein R$^{LF}$ and R$^{LG}$ are each independently selected from the group consisting of hydrogen, and $C_1$-$C_6$ alkyl; or —NR$^{LF}$R$^{LG}$ is an optionally substituted non-aromatic heterocycle linked through a ring nitrogen atom;

R$^R$ is selected from the group consisting of $C_1$-$C_6$ alkyl, an optionally substituted aryl, and an optionally substituted heteroaryl; and each m is independently 0, 1, 2, or 3, having the proviso that a compound of Formula IX is not selected from the group consisting of:

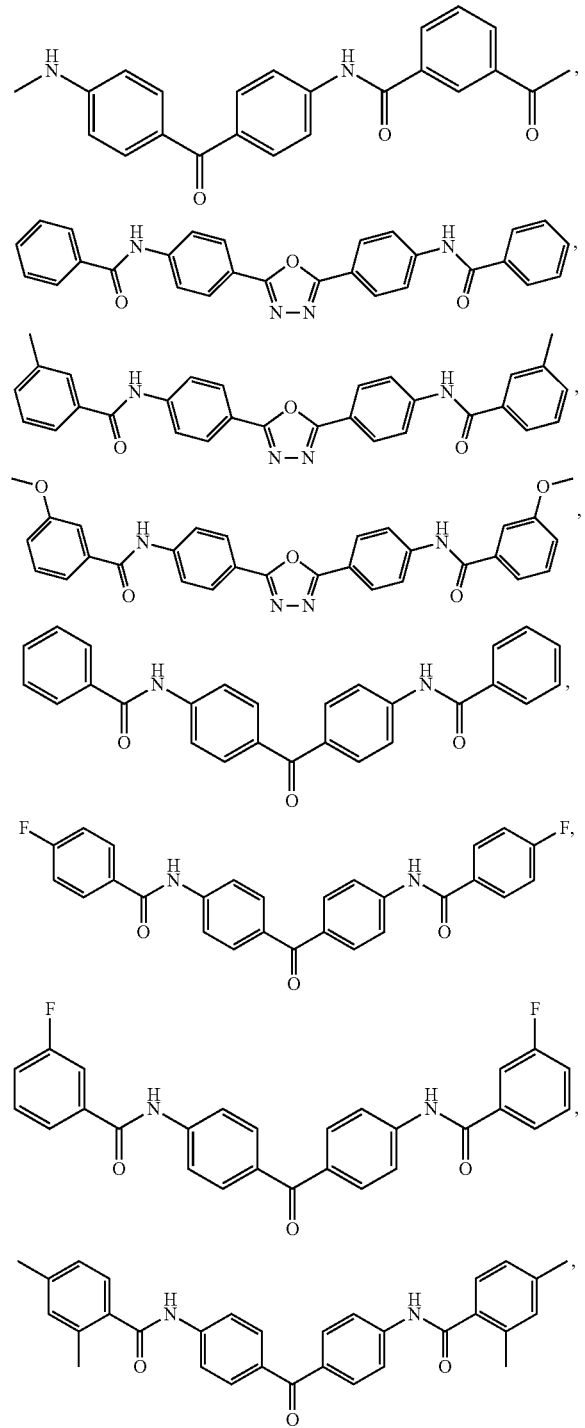

-continued

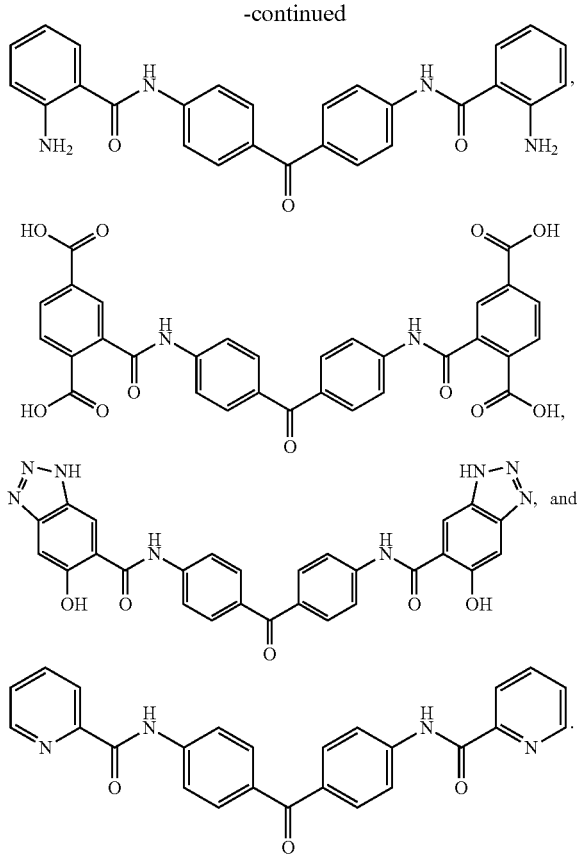

Some embodiments disclosed herein provide a compound of Formula IX having the formula IXa:

(IXa)

and pharmaceutically acceptable salts thereof, wherein Z is

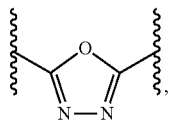 [SMILES: *c1nnc(*)o1]

or —C(=O)—, $R^A$ is selected from the group consisting of heterocycle, polycyclic heterocyclyl, aryl and heteroaryl, each substituted with one or more substituents selected from the group consisting of $R^1$, $R^2$, and $R^3$, each $R^1$ is separately selected from the group consisting of chloro, cyano, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_3$-$C_7$ cycloalkenyl, and $C_1$-$C_6$ haloalkyl, each $R^2$ is separately selected from the group consisting of —O(CH$_2$)$_m$OR$^I$, —(CH$_2$)$_m$OR$^I$, —NR$^J$R$^K$, —(CH$_2$)$_m$SR$^I$, —C(=O)R$^L$, and —(CH$_2$)$_m$R$^L$, and each $R^3$ is separately selected from the group consisting of —(CH$_2$)$_m$OR$^G$, —NR$^L$C(=O)R$^M$, —NR$^L$C(=O)OR$^M$, —NR$^L$C(=O) NR$^N$R$^O$, —NR$^N$R$^O$, —(CH$_2$)$_m$S(O)$_{0-2}$R$^M$, —(CH$_2$)$_m$NHS (O)$_{0-2}$R$^M$, —(CH$_2$)$_m$CN, —(CH$_2$)$_m$R$^P$, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$.

Some embodiments disclosed herein provide a compound of Formula IXa having the formula IXaa:

(IXaa)

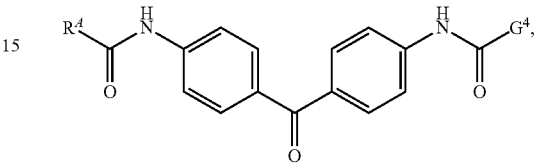

and pharmaceutically acceptable salts thereof, wherein $G^4$ is selected from the group consisting of polycyclic heterocyclyl, aryl, and heteroaryl, each substituted with one or more substituents selected from the group consisting of $R^4$, $R^5$, and $R^6$, each $R^4$ is separately selected from the group consisting of chloro, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, an optionally substituted $C_1$-$C_6$ heteroalkyl, an optionally substituted aryl, and an optionally substituted heteroaryl, each $R^5$ is separately selected from the group consisting of —O(CH$_2$)$_m$OR$^I$, —(CH$_2$)$_m$OR$^I$, —NR$^J$R$^K$, —(CH$_2$)$_m$SR$^I$, —(CH$_2$)$_m$C(=O) R$^L$, —(CH$_2$)$_m$R$^L$, an optionally substituted $C_1$-$C_6$ alkyl, an optionally substituted $C_1$-$C_6$ alkoxy, an optionally substituted $C_2$-$C_6$ alkenyl, an optionally substituted $C_3$-$C_7$ cycloalkyl, an optionally substituted $C_1$-$C_6$ haloalkyl, and an optionally substituted $C_1$-$C_6$ heteroalkyl, each $R^6$ is separately selected from the group consisting of —(CH$_2$)$_m$OR$^G$, —NR$^L$C(=O)R$^M$, —NR$^L$C(=O)OR$^M$, —NR$^L$C(=O) NR$^N$R$^O$, —NR$^N$R$^O$, —(CH$_2$)$_m$S(O)$_{0-2}$R$^M$, —(CH$_2$)$_m$NHS (O)$_{0-2}$R$^M$, —(CH$_2$)$_m$NO$_2$, —(CH$_2$)$_m$CN, —(CH$_2$)$_m$R$^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, $C_1$-$C_6$ heteroalkyl, heterocycle, aryl, polycyclic heterocyclyl, and heteroaryl, said heterocycle, aryl, polycyclic heterocyclyl, and heteroaryl in the definition of $R^6$ are each optionally substituted with halogen, cyano, $C_1$-$C_6$ alkyl, $C_1$-$C_6$ haloalkyl, $C_1$-$C_6$ alkoxy, —C(=O)OR$^M$, or —NR$^J$R$^K$.

Some embodiments disclosed herein provide a compound of Formula IXa, wherein each $R^1$ is separately selected from the group consisting of cyano, an optionally substituted $C_1$-$C_6$ alkyl, an optionally substituted $C_1$-$C_6$ alkoxy, an optionally substituted $C_1$-$C_6$ heteroalkyl, an optionally substituted aryl, and an optionally substituted heteroaryl, each $R^2$ is separately selected from the group consisting of —O(CH$_2$)$_m$OR$^I$, —(CH$_2$)$_m$OR$^I$, —NR$^J$R$^K$, —(CH$_2$)$_m$SR$^I$, —C(=O)R$^L$, and —(CH$_2$)$_m$R$^L$, each $R^3$ is separately selected from the group consisting of —(CH$_2$)$_m$OR$^G$, —NR$^L$C(=O)R$^M$, —NR$^L$C(=O)OR$^M$, —NR$^L$C(=O) NR$^N$R$^O$, —NR$^N$R$^O$, —(CH$_2$)$_m$S(O)$_{0-2}$R$^M$, —(CH$_2$)$_m$NHS (O)$_{0-2}$R$^M$, —(CH$_2$)$_m$NO$_2$, —(CH$_2$)$_m$CN, —(CH$_2$)$_m$R$^P$, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$, each R$^4$ is separately selected from the group consisting of cyano, an optionally substituted $C_1$-$C_6$ alkyl, and an optionally substituted $C_1$-$C_6$ heteroalkyl, each R$^5$ is separately selected from the group consisting of —(CH$_2$)$_m$OH, —NR$^J$R$^K$, and —(CH$_2$)$_m$C(=O)R$^L$, each R$^L$ is independently selected from the group consisting of —OH, $C_1$-$C_6$ alkyl, and $C_1$-$C_6$ alkoxy, and each R$^6$ is separately selected from the group consisting of —NR$^L$C(=O)R$^M$, —NR$^L$C(=O)OR$^M$, —NR$^L$C(=O)NR$^N$R$^O$, —NR$^N$R$^O$, —(CH$_2$)$_m$R$^P$, heterocycle, aryl, polycyclic heterocyclyl, and heteroaryl, said heterocycle, aryl, polycyclic heterocyclyl, and heteroaryl in the definition of R$^6$ are each optionally substituted with halogen, cyano, $C_1$-$C_6$ alkyl, $C_1$-$C_6$ haloalkyl, $C_1$-$C_6$ alkoxy, —C(=O)OR$^M$, or —NR$^J$R$^K$.

Some embodiments disclosed herein provide a compound of Formula I:

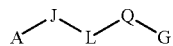

(I)

and pharmaceutically acceptable salts, esters, stereoisomers, tautomers or prodrugs thereof;

wherein:

A-J is

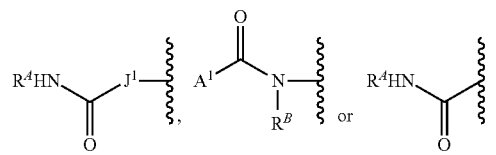

and Q-G is

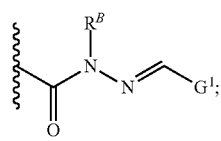

or A-J is

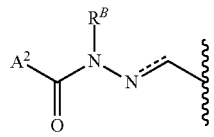

and Q-G is

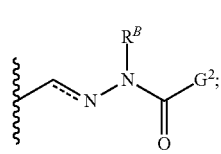

or A-J is

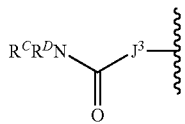

and Q-G is

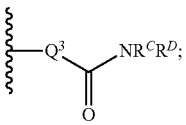

or A-J is

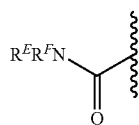

and Q-G is

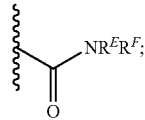

or A-J is

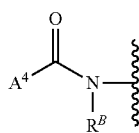

and Q-G is

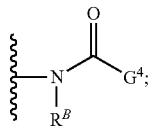

or A-J is

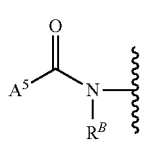

and Q-G is

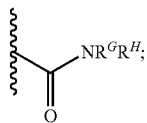

$A^1$ is selected from the group consisting of $C_3$-$C_7$ cycloalkenyl, $C_3$-$C_7$ cycloalkyl, $C_1$-$C_6$ alkyl, $C_2$-$C_6$ alkenyl, $C_1$-$C_6$ alkoxy, —(CH$_2$)$_m$NR$^P$R$^L$, heterocycle, aryl, and heteroaryl, said $C_3$-$C_7$ cycloalkenyl, $C_3$-$C_7$ cycloalkyl, heterocycle, aryl, and heteroaryl, each optionally substituted with one or more substituents selected from the group consisting of R$^1$, R$^2$, and R$^3$, said aryl and heteroaryl in the definition of $A^1$ are each further optionally fused with an optionally substituted nonaromatic heterocycle or an optionally substituted nonaromatic carbocycle;

$J^1$ is selected from the group consisting of —(CH$_2$)$_r$NR$^B$C(=O)(CH$_2$)$_m$— and —(CH$_2$)$_r$NR$^B$(CH$_2$)$_m$—, and —(CH$_2$)$_r$—;

$G^1$ is selected from the group consisting of aryl and heteroaryl, each optionally substituted with one or more substituents selected from the group consisting of R$^4$, R$^5$, and R$^6$, said aryl and heteroaryl in the definition of $G^1$ are each further optionally fused with an optionally substituted nonaromatic heterocycle or an optionally substituted nonaromatic carbocycle;

$A^2$ is selected from the group consisting of aryl and heteroaryl, each optionally substituted with one or more substituents selected from the group consisting of R$^1$, R$^2$, and R$^3$, said aryl and heteroaryl in the definition of $A^2$ are each further optionally fused with an optionally substituted nonaromatic heterocycle or an optionally substituted nonaromatic carbocycle;

$G^2$ is selected from the group consisting of aryl and heteroaryl, each optionally substituted with one or more substituents selected from the group consisting of R$^4$, R$^5$, and R$^6$, said aryl and heteroaryl in the definition of $G^2$ are each further optionally fused with an optionally substituted nonaromatic heterocycle or an optionally substituted nonaromatic carbocycle;

$J^3$ is selected from the group consisting of an optionally substituted aryl, —(CH$_2$)$_m$NR$^B$C(=O)(CH$_2$)$_m$—, —(CH$_2$)$_r$O(CH$_2$)$_m$—, —(CH$_2$)$_r$NR$^B$(CH$_2$)$_m$—, and —(CH=CH)$_m$—;

$Q^3$ is selected from the group consisting of an optionally substituted aryl, —(CH$_2$)$_p$NR$^B$C(=O)(CH$_2$)$_m$—, —(CH$_2$)$_r$O(CH$_2$)$_m$—, —(CH$_2$)$_r$NR$^B$(CH$_2$)$_m$—, and —(CH=CH)$_r$—;

$A^4$ is selected from the group consisting of $C_3$-$C_7$ cycloalkenyl, $C_3$-$C_7$ cycloalkyl, $C_1$-$C_6$ alkyl, $C_1$-$C_6$ heteroalkyl, $C_2$-$C_6$ alkenyl, $C_1$-$C_6$ alkoxy, —(CH$_2$)$_m$NR$^P$R$^L$, heterocycle, aryl, and heteroaryl, said $C_3$-$C_7$ cycloalkenyl, $C_3$-$C_7$ cycloalkyl, $C_1$-$C_6$ alkyl, $C_1$-$C_6$ heteroalkyl, $C_2$-$C_6$ alkenyl, heterocycle, aryl, and heteroaryl, each optionally substituted with one or more substituents selected from the group consisting of R$^1$, R$^2$, and R$^3$, and said aryl and heteroaryl in the definition of $A^4$ are each further optionally fused with an optionally substituted nonaromatic heterocycle or an optionally substituted nonaromatic carbocycle;

$G^4$ is selected from the group consisting of $C_3$-$C_7$ cycloalkenyl, aryl, and heteroaryl, each optionally substituted with one or more substituents selected from the group consisting of R$^4$, R$^5$, and R$^6$, said aryl and heteroaryl in the definition of $G^4$ are each further optionally fused with an optionally substituted nonaromatic heterocycle or an optionally substituted nonaromatic carbocycle;

$A^5$ is selected from the group consisting of aryl and heteroaryl, each optionally substituted with one or more substituents selected from the group consisting of R$^1$, R$^2$, and R$^3$, said aryl and heteroaryl in the definition of $A^5$ are each further optionally fused with an optionally substituted nonaromatic heterocycle or an optionally substituted nonaromatic carbocycle;

$R^A$ is selected from the group consisting of —(CH$_2$)$_p$R$^L$, —(CH$_2$)$_p$OR$^L$, —SO$_2$R$^L$, —C(=O)R$^L$, —C(=O)NR$^N$R$^O$, —(CH$_2$)$_p$NR$^N$R$^O$, an aryl and an heteroaryl, said aryl and heteroaryl in the definition of $R^A$ are each optionally substituted with halogen, cyano, $C_1$-$C_6$ haloalkyl, $C_1$-$C_6$ alkyl, $C_1$-$C_6$ alkoxy, $C_3$-$C_7$ cycloalkyl, $C_3$-$C_7$ cycloalkenyl, —C(=O)NR$^N$R$^O$, —OC(=O)NR$^N$R$^O$, —NHC(=O)NR$^N$R$^O$, —O(CH$_2$)$_q$NR$^N$R$^O$, —NH(CH$_2$)$_q$NR$^N$R$^O$, —(CH$_2$)$_p$NR$^N$R$^O$, an optionally substituted aryl and an optionally substituted heteroaryl, and said aryl and heteroaryl in the definition of $R^A$ are each further optionally fused with an optionally substituted nonaromatic heterocycle or an optionally substituted nonaromatic carbocycle;

each $R^B$ is separately selected from the group consisting of hydrogen, an optionally substituted $C_1$-$C_6$ alkyl, an optionally substituted $C_2$-$C_6$ alkenyl, and an optionally substituted $C_3$-$C_7$ cycloalkyl;

each —NR$^C$R$^D$ is separately selected, wherein each R$^C$ is independently selected from the group consisting of hydrogen and an optionally $C_1$-$C_6$ alkyl, and each R$^D$ is independently selected from the group consisting of aryl and heteroaryl, said aryl and heteroaryl in the definition of R$^D$ are each optionally substituted with halogen, cyano, $C_1$-$C_6$ alkyl, $C_1$-$C_6$ alkoxy, $C_3$-$C_7$ cycloalkyl, $C_3$-$C_7$ cycloalkenyl, —C(=O)NR$^N$R$^O$, —OC(=O)NR$^N$R$^O$, —NHC(=O)NR$^N$R$^O$, —O(CH$_2$)$_q$NR$^N$R$^O$, —NH(CH$_2$)$_q$NR$^N$R$^O$, —(CH$_2$)$_p$NR$^N$R$^O$, an optionally substituted aryl and an optionally substituted heteroaryl, and said aryl and heteroaryl in the definition of R$^D$ are each further optionally fused with an optionally substituted nonaromatic heterocycle or an optionally substituted nonaromatic carbocycle;

each —NR$^E$R$^F$ is separately selected, wherein each R$^E$ is independently selected from the group consisting of hydrogen and an optionally $C_1$-$C_6$ alkyl, and each R$^F$ is independently selected from the group consisting of aryl and heteroaryl, said aryl and heteroaryl in the definition of R$^F$ are each optionally substituted with halogen, cyano, $C_1$-$C_6$ alkyl, $C_1$-$C_6$ alkoxy, $C_3$-$C_7$ cycloalkyl, $C_3$-$C_7$ cycloalkenyl, —C(=O)NR$^N$R$^O$, —OC(=O)NR$^N$R$^O$, —NHC(=O)NR$^N$R$^O$, —O(CH$_2$)$_q$NR$^N$R$^O$, —NH(CH$_2$)$_q$NR$^N$R$^O$, —(CH$_2$)$_p$NR$^N$R$^O$, an optionally substituted aryl and an optionally substituted heteroaryl, and said aryl and heteroaryl in the definition of R$^F$ are each further optionally fused with an optionally substituted nonaromatic heterocycle or an optionally substituted nonaromatic carbocycle;

$R^G$ within the definition of —NR$^G$R$^H$ is selected from the group consisting of $C_1$-$C_6$ alkyl, $C_3$-$C_6$ cycloalkyl, $C_3$-$C_8$ cycloalkenyl, $C_1$-$C_6$ heteroalkyl, $C_1$-$C_6$ heteroalkenyl, $C_1$-$C_6$ heteroalkynyl, heterocycle, aryl, and heteroaryl, each optionally substituted with one or more substituents selected from the group consisting of R$^4$, R$^5$, and R$^6$, said aryl and heteroaryl in the definition of R$^G$ are each further optionally fused with an optionally substituted nonaromatic heterocycle or an optionally substituted nonaromatic carbocycle, or R$^G$ is —OR$^L$ or —NR$^P$R$^L$;

$R^H$ within the definition of —NR$^G$R$^H$ is selected from the group consisting of hydrogen, $C_1$-$C_6$ alkyl, $C_2$-$C_6$ alkenyl, $C_3$-$C_7$ cycloalkyl, and $C_1$-$C_3$ haloalkyl, or —NR$^G$R$^H$ is an optionally substituted non-aromatic heterocycle linked through a ring nitrogen atom;

each $R^1$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, optionally substituted $C_3$-$C_7$ cycloalkenyl, an optionally substituted $C_1$-$C_6$ haloalkyl, an optionally substituted $C_1$-$C_6$ heteroalkyl, an optionally substituted aryl, and an optionally substituted heteroaryl;

each $R^2$ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —C(=O)R$^L$, —(CH$_2$)$_m$R$^L$, an optionally substituted $C_1$-$C_6$ alkyl, an optionally substituted $C_1$-$C_6$ alkoxy, an optionally substituted $C_2$-$C_6$ alkenyl, an optionally substituted $C_1$-$C_6$ haloalkyl, an optionally substituted $C_1$-$C_6$ heteroalkyl, and an optionally substituted $C_3$-$C_7$ cycloalkyl where said $C_3$-$C_7$ cycloalkyl is further optionally fused with aryl or heteroaryl;

each $R^3$ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0\text{-}2}$R$^M$, —(CH$_2$)$_m$NHS(O)$_{0\text{-}2}$R$^M$, —(CH$_2$)$_m$NO$_2$, —(CH$_2$)$_m$CN, —(CH$_2$)$_m$R$^P$, $C_1$-$C_6$ alkyl $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, heterocycle, aryl, and heteroaryl, said heterocycle, aryl and heteroaryl in the definition of $R^3$ are each optionally substituted with halogen, cyano, $C_1$-$C_6$ alkyl, $C_1$-$C_6$ haloalkyl, $C_1$-$C_6$ alkoxy, or —NR$^J$R$^K$;

each $R^4$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, an optionally substituted $C_1$-$C_6$ heteroalkyl, an optionally substituted aryl, and an optionally substituted heteroaryl;

each $R^5$ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —C(=O)R$^L$, —(CH$_2$)$_m$R$^L$, an optionally substituted $C_1$-$C_6$ alkyl, an optionally substituted $C_1$-$C_6$ alkoxy, an optionally substituted $C_2$-$C_6$ alkenyl, an optionally substituted $C_3$-$C_7$ cycloalkyl, an optionally substituted $C_1$-$C_6$ haloalkyl, and an optionally substituted $C_1$-$C_6$ heteroalkyl;

each $R^6$ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0\text{-}2}$R$^M$, —(CH$_2$)$_m$NHS(O)$_{0\text{-}2}$R$^M$, —(CH$_2$)$_m$NO$_2$, —(CH$_2$)$_m$CN, —(CH$_2$)$_m$R$^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, $C_1$-$C_6$ heteroalkyl, heterocycle, aryl, and heteroaryl, said heterocycle, aryl and heteroaryl in the definition of $R^6$ are each optionally substituted with halogen, cyano, $C_1$-$C_6$ alkyl, $C_1$-$C_6$ haloalkyl, $C_1$-$C_6$ alkoxy, or —NR$^J$R$^K$;

each $R^I$ is separately selected from the group consisting of hydrogen, $C_1$-$C_6$ alkyl, $C_2$-$C_4$ alkenyl, $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl;

each —NR$^J$R$^K$ is separately selected, wherein $R^J$ and $R^K$ are each independently selected from the group consisting of hydrogen, $C_1$-$C_6$ alkyl optionally substituted with up to 5 fluoro, —(CH$_2$)$_m$OR$^{JA}$, —(CH$_2$)$_m$NR$^{JB}$R$^{JC}$, —(CH$_2$)$_m$R$^R$, $C_3$-$C_7$ cycloalkyl, heterocycle, aryl and heteroaryl, said $C_3$-$C_7$ cycloalkyl, heterocycle, aryl and heteroaryl in the definition of $R^J$ and $R^K$ are each independently optionally substituted with one or more substituents selected from the group consisting of halo, $C_1$-$C_6$ alkyl, $C_1$-$C_6$ haloalkyl, $C_1$-$C_6$ alkoxy, aryl and heteroaryl, said aryl and heteroaryl substituent off of $R^J$ and $R^K$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{KA}$R$^{KB}$; or —NR$^J$R$^K$ is an optionally substituted non-aromatic heterocycle linked through a ring nitrogen atom; or —NR$^J$R$^K$ is an optionally substituted $C_1$-$C_6$ alkylideneamino;

each $R^{JA}$ is independently selected from the group consisting of hydrogen, $C_1$-$C_6$ alkyl, and $C_1$-$C_6$ haloalkyl;

each —NR$^{JB}$R$^{JC}$ is separately selected, wherein $R^{JB}$ and $R^{JC}$ are each independently selected from the group consisting of hydrogen, $C_1$-$C_6$ alkyl, and $C_1$-$C_6$ haloalkyl;

each —NR$^{KA}$R$^{KB}$ is separately selected, wherein $R^{KA}$ and $R^{KB}$ are each independently selected from the group consisting of hydrogen, $C_1$-$C_6$ alkyl, and $C_1$-$C_6$ haloalkyl;

each $R^M$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_3$-$C_7$ cycloalkenyl, and —(CH$_2$)$_m$R$^P$;

each —NR$^N$R$^O$ is separately selected, wherein $R^N$ and $R^O$ are each independently selected from the group consisting of hydrogen, —(CH$_2$)$_m$NR$^{NA}$R$^{NB}$, aryl and heteroaryl, said aryl and heteroaryl in the definition of $R^N$ and $R^O$ are each independently optionally substituted with one or more substituents selected from the group consisting of —(CH$_2$)$_m$NR$^{OA}$R$^{OB}$, halo, $C_1$-$C_6$ alkyl, $C_1$-$C_6$ haloalkyl, $C_1$-$C_6$ alkoxy, aryl and heteroaryl, said aryl and heteroaryl substituent off of $R^N$ and $R^O$ are each optionally substituted with one or more halo, $C_1$-$C_6$ alkyl, $C_1$-$C_6$ haloalkyl, $C_1$-$C_6$ alkoxy, or —NR$^{NA}$R$^{NB}$, each —NR$^{NA}$R$^{NB}$ is separately selected, wherein $R^{NA}$ and $R^{NB}$ are each independently selected from the group consisting of hydrogen, $C_1$-$C_6$ alkyl, and $C_1$-$C_6$ haloalkyl;

each —NR$^{OA}$R$^{OB}$ is separately selected, wherein $R^{OA}$ and $R^{OB}$ are each independently selected from the group consisting of hydrogen, $C_1$-$C_6$ alkyl, and $C_1$-$C_6$ haloalkyl;

$R^P$ is selected from the group consisting of hydrogen and $C_1$-$C_6$ alkyl;

$R^L$ is selected from the group consisting of $C_3$-$C_7$ cycloalkyl, optionally substituted $C_1$-$C_6$ alkyl, optionally substituted $C_1$-$C_6$ alkoxy, —(CH$_2$)$_m$OR$^{LA}$, —(CH$_2$)$_m$NR$^{LB}$R$^{LC}$, aryl and heteroaryl, said aryl and heteroaryl in the definition of $R^L$ are each independently optionally substituted with one or more substituents selected from the group consisting of halo, $C_1$-$C_6$ alkyl, $C_1$-$C_6$ haloalkyl, $C_1$-$C_6$ alkoxy, —(CH$_2$)$_m$NR$^{LD}$R$^{LE}$, aryl and heteroaryl, said aryl and heteroaryl substituent off of $R^L$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{LF}$R$^{LG}$;

$R^{LA}$ is selected from the group consisting of hydrogen, $C_1$-$C_6$ alkyl, and $C_1$-$C_6$ haloalkyl;

$R^{LB}$ and $R^{LC}$ are each independently selected from the group consisting of hydrogen, $C_1$-$C_6$ alkyl, $C_1$-$C_6$ haloalkyl, and $C_1$-$C_6$ heteroalkenyl; or —NR$^{LB}$R$^{LC}$ is an optionally substituted non-aromatic heterocycle linked through a ring nitrogen atom;

each —NR$^{LD}$R$^{LE}$ is separately selected, wherein $R^{LD}$ and $R^{LE}$ are each independently selected from the group consisting of hydrogen, aryl, heteroaryl, and optionally substituted $C_1$-$C_6$ alkyl, said aryl and heteroaryl in the definition of $R^{LD}$ and $R^{LE}$ are each optionally substituted with $C_1$-$C_6$ alkyl or C$_1$-C$_6$ alkoxy; or —NR$^{LD}$R$^{LE}$ is an optionally substituted non-aromatic heterocycle linked through a ring nitrogen atom;

each —NR$^{LF}$R$^{LG}$ is separately selected, wherein R$^{LF}$ and R$^{LG}$ are each independently selected from the group consisting of hydrogen, and C$_1$-C$_6$ alkyl; or —NR$^{LF}$R$^{LG}$ is an optionally substituted non-aromatic heterocycle linked through a ring nitrogen atom;

L is selected from the group consisting of —O(CH$_2$)$_p$O—, C$_1$-C$_7$ alkyl, C$_1$-C$_7$ heteroalkyl, C$_3$-C$_7$ cycloalkyl, C$_3$-C$_7$ cycloalkenyl, an optionally substituted heterocycle, an optionally substituted aryl, and an optionally substituted heteroaryl, or L is selected from the group consisting of L$^1$-L$^2$, L$^1$-O-L$^2$, L$^1$-S-L$^2$, L$^1$-NR$^9$-L$^2$, L$^1$-L$^2$-L$^3$, L$^1$-L$^2$-L$^3$-L$^4$, L$^1$-C(=E)-L$^2$, and L$^1$-CR$^7$R$^8$-L$^2$;

L$^1$ is selected from the group consisting of an optionally substituted aryl, an optionally substituted heteroaryl, and an optionally substituted heterocycle;

L$^2$ is selected from the group consisting of an optionally substituted aryl, an optionally substituted heteroaryl, and an optionally substituted heterocycle;

L$^3$ is selected from the group consisting of an optionally substituted aryl, an optionally substituted heteroaryl, and an optionally substituted heterocycle;

L$^4$ is an optionally substituted aryl;

E is O (oxygen), N—NHR$^Q$ or N—OR$^Q$ where R$^Q$ in the definition of E is selected from the group consisting of hydrogen, an optionally substituted C$_1$-C$_6$ alkyl, an optionally substituted C$_2$-C$_6$ alkenyl, —(CH$_2$)$_m$R$^R$, and —C(=O)(CH$_2$)$_m$R$^R$;

R$^R$ is selected from the group consisting of C$_1$-C$_6$ alkyl, an optionally substituted aryl, and an optionally substituted heteroaryl;

R$^7$ and R$^8$ are each independently selected from the group consisting of hydrogen, C$_1$-C$_6$ alkyl, C$_1$-C$_6$ heteroalkyl, and —OH; or CR$^7$R$^8$ is a three- to eight-membered optionally substituted carbocycle, which optionally has one to three additional hetero atoms incorporated in the ring;

R$^9$ is selected from the group consisting of hydrogen, C$_1$-C$_6$ alkyl, C$_1$-C$_6$ haloalkyl, C$_1$-C$_6$ heteroalkyl, C$_3$-C$_7$cycloalkylC(O)— and C$_1$-C$_6$ alkylC(O)—;

each m is independently 0, 1, 2, or 3;
each p is independently 0, 1, 2, 3, 4, 5, or 6;
each q is independently 1, 2, 3, 4, 5, or 6;
each r is independently 1, 2, 3, or 4; and any bond represented by a dashed and solid line represents a bond selected from the group consisting of a single bond and a double bond.

Some embodiments disclosed herein provide a compound of Formula I, wherein R$^1$ can be selected from the group consisting of fluorine, chlorine, and methyl; R$^2$ can be selected from the group consisting of —(CH$_2$)$_m$OR$^I$, —NR$^J$R$^K$, and —(CH$_2$)$_m$SR$^I$; R$^3$ can be selected from the group consisting of —(CH$_2$)$_m$R$^P$, —(CH$_2$)$_m$OR$^M$, and —NR$^N$R$^O$; R$^4$ can be selected from the group consisting of fluorine, chlorine, and methyl; R$^5$ can be selected from the group consisting of —(CH$_2$)$_m$OR$^I$, —NR$^J$R$^K$, and —(CH$_2$)$_m$SR$^I$; R$^6$ can be selected from the group consisting of —(CH$_2$)$_m$R$^P$, —(CH$_2$)$_m$OR$^M$, and —NR$^N$R$^O$; R$^I$ can be selected from the group consisting of hydrogen, C$_1$-C$_6$ alkyl, C$_1$-C$_6$ haloalkyl, and C$_1$-C$_6$ heteroalkyl; each —NR$^J$R$^K$ can be separately selected, wherein R$^J$ and R$^K$ can each be independently selected from the group consisting of hydrogen, C$_1$-C$_6$ alkyl, C$_1$-C$_6$ haloalkyl, and C$_1$-C$_6$ heteroalkyl; or —NR$^J$R$^K$ can be an optionally substituted non-aromatic heterocycle linked through a ring nitrogen atom; or —NR$^J$R$^K$ can be an optionally substituted C$_1$-C$_6$ alkylideneamino; each R$^M$ can be independently selected from the group consisting of hydrogen, an optionally substituted C$_1$-C$_6$ alkyl, an optionally substituted C$_1$-C$_6$ haloalkyl, an optionally substituted C$_1$-C$_6$ heteroalkyl, and —(CH$_2$)$_m$R$^P$; R$^L$ can be selected from the group consisting of hydrogen, C$_1$-C$_3$ alkyl, C$_1$-C$_3$ haloalkyl, and an optionally substituted aryl or an optionally substituted heteroaryl; and m can be 0, 1, or 2.

Some embodiments disclosed herein provide a compound of Formula I, wherein G$^1$ can be selected from the group consisting of aryl and heteroaryl, each substituted with one or more substituents selected from the group consisting of R$^4$, R$^5$, and R$^6$, said aryl and heteroaryl in the definition of G$^1$ can each be further optionally fused with a nonaromatic heterocycle or nonaromatic carbocycle; A$^2$ can be selected from the group consisting of aryl and heteroaryl, each substituted with one or more substituents selected from the group consisting of R$^1$, R$^2$, and R$^3$, said aryl and heteroaryl in the definition of A$^2$ can each be further optionally fused with a nonaromatic heterocycle or nonaromatic carbocycle; G$^2$ can be selected from the group consisting of aryl and heteroaryl, each substituted with one or more substituents selected from the group consisting of R$^4$, R$^5$, and R$^6$, said aryl and heteroaryl in the definition of G$^2$ can each be further optionally fused with a nonaromatic heterocycle or nonaromatic carbocycle; A$^4$ can be selected from the group consisting of C$_3$-C$_7$ cycloalkenyl, C$_3$-C$_7$ cycloalkyl, C$_1$-C$_6$ alkyl, C$_1$-C$_6$ heteroalkyl, C$_2$-C$_6$ alkenyl, C$_1$-C$_6$ alkoxy, —(CH$_2$)$_m$NR$^P$R$^L$, heterocycle, aryl, and heteroaryl, said C$_3$-C$_7$ cycloalkenyl, C$_3$-C$_7$ cycloalkyl, C$_1$-C$_6$ alkyl, C$_1$-C$_6$ heteroalkyl, C$_2$-C$_6$ alkenyl, heterocycle, aryl, and heteroaryl, each substituted with one or more substituents selected from the group consisting of R$^1$, R$^2$, and R$^3$, said aryl and heteroaryl in the definition of A$^4$ can each be further optionally fused with a nonaromatic heterocycle or nonaromatic carbocycle; G$^4$ can be selected from the group consisting of C$_3$-C$_7$ cycloalkenyl, aryl, and heteroaryl, each substituted with one or more substituents selected from the group consisting of R$^4$, R$^5$, and R$^6$, said aryl and heteroaryl in the definition of G$^4$ can each be further optionally fused with a nonaromatic heterocycle or nonaromatic carbocycle; A$^5$ can be selected from the group consisting of aryl and heteroaryl, each substituted with one or more substituents selected from the group consisting of R$^1$, R$^2$, and R$^3$, said aryl and heteroaryl in the definition of A$^5$ can each be further optionally fused with a nonaromatic heterocycle or nonaromatic carbocycle; R$^1$ can be selected from the group consisting of fluorine, chlorine, and methyl; R$^2$ can be selected from the group consisting of —(CH$_2$)$_m$OR$^I$ and —NR$^J$R$^K$; R$^3$ can be —R$^P$; R$^4$ can be selected from the group consisting of fluorine, chlorine, and methyl; R$^5$ can be selected from the group consisting of —(CH$_2$)$_m$OR$^I$ and —NR$^J$R$^K$; R$^6$ can be —R$^P$; and R$^L$ can be selected from the group consisting of C$_1$-C$_3$ alkyl, C$_1$-C$_3$ haloalkyl, an optionally substituted aryl and an optionally substituted heteroaryl.

Some embodiments disclosed herein provide a compound of Formula I, wherein L can be selected from the group consisting of an optionally substituted

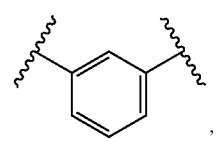 [SMILES: *c1cccc(*)c1]

, an optionally substituted

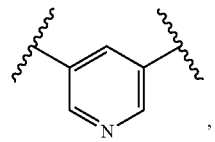 [SMILES: *c1cncc(*)c1], an optionally substituted

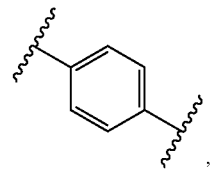 [SMILES: *c1ccc(*)cc1], an optionally substituted

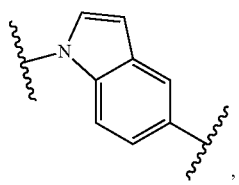,

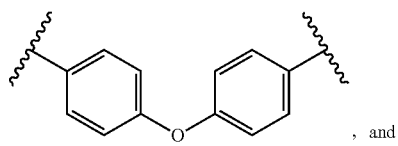, and

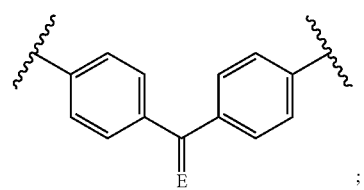;

and E can be O (oxygen), N—NHR$^Q$ or N—OR$^Q$ where R$^Q$ in the definition of E can be selected from the group consisting of hydrogen, an optionally substituted C$_1$-C$_6$ alkyl, an optionally substituted C$_2$-C$_4$ alkenyl, —R$^R$, and —C(=O)R$^R$. In some embodiments, L can be selected from the group consisting of an optionally substituted

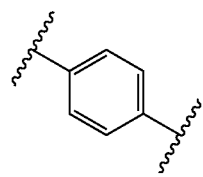 [SMILES: *c1ccc(*)cc1]

and an optionally substituted

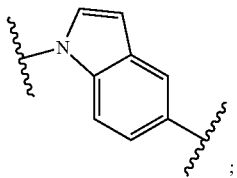 [SMILES: *c1ccc2c(ccn2*)c1];

each R$^1$ can be separately selected from the group consisting of an optionally substituted aryl and an optionally substituted heteroaryl; each R$^2$ can be separately selected from the group consisting of halogen, —(CH$_2$)$_m$OR, and —NR$^B$R$^C$, where R$^I$ in the definition of can be R$^2$ selected from the group consisting of hydrogen, and C$_1$-C$_6$ alkyl; each R$^3$ can be fluoro; each —NR$^J$R$^K$ can be separately selected, wherein R$^J$ and R$^K$ can each be independently selected from the group consisting of hydrogen and C$_1$-C$_6$ alkyl; or —NR$^J$R$^K$ can be an optionally substituted non-aromatic heterocycle linked through a ring nitrogen atom; each R$^4$ can be separately selected from the group consisting of chloro, fluoro, and an optionally substituted C$_1$-C$_6$ alkyl; each R$^5$ can be separately selected from the group consisting of —OCH$_2$CH$_2$OR$^I$, —(CH$_2$)$_m$OR$^I$, and —NR$^J$R$^K$, where R$^I$ in the definition of can be R$^5$ selected from the group consisting of hydrogen, and C$_1$-C$_6$ alkyl; and each R$^6$ can be separately selected from the group consisting an optionally substituted aryl and an optionally substituted heteroaryl.

Some embodiments disclosed herein provide a compound of Formula I, wherein A$^1$, A$^2$, A$^4$, and A$^5$ can each be selected from the group consisting of phenyl, naphthyl, benz[d][1,3]dioxolyl, indolyl, and benz[d]imidazolyl, each substituted with one or more substituents selected from the group consisting of R$^1$ and R$^2$; each R$^1$ can be separately selected from the group consisting of phenyl, pyrrolyl, and imidazolyl, each optionally substituted with a substituent selected from C$_1$-C$_6$ alkyl, C$_1$-C$_6$ alkoxy, C$_1$-C$_6$ alkylHN— and (C$_1$-C$_6$ alkyl)$_2$N—; each R$^2$ can be separately selected from the group consisting of bromo, chloro, fluoro, —(CH$_2$)$_m$OR$^I$, —(CH$_2$)$_m$R$^L$, and —NR$^J$R$^K$, where each R$^I$ in the definition of R$^2$ can be separately selected from the group consisting of hydrogen and C$_1$-C$_6$ alkyl; each —NR$^J$R$^K$ can be separately selected, wherein R$^J$ and R$^K$ can each be independently selected from the group consisting of hydrogen, and C$_1$-C$_6$ alkyl optionally substituted with up to 3 fluoro; or —NR$^J$R$^K$ can be a morpholinyl, piperazinyl, pyrrolidinyl, and piperidinyl, each optionally substituted with one or more oxo; each R$^L$ can be separately selected from the group consisting aryl and heteroaryl, each optionally substituted with one or more substituents each separately selected from the group consisting of halogen, C$_1$-C$_6$ alkyl optionally substituted with up to 5 fluoro, and C$_1$-C$_6$ alkoxy optionally substituted with up to 5 fluoro; G$^1$, G$^2$, and G$^4$ can each be selected from the group consisting of: phenyl, naphthyl, benz[d][1,3]dioxolyl, indolyl, and benz[d]imidazolyl, each substituted with one or more substituents selected from the group consisting of R$^4$ and R$^5$; each R$^4$ can be separately selected from the group consisting of phenyl, pyrrolyl, and imidazolyl, each optionally substituted with a substituent selected from C$_1$-C$_6$ alkyl, C$_1$-C$_6$ alkoxy, C$_1$-C$_6$ alkylHN— and (C$_1$-C$_6$ alkyl)$_2$N—; and each R$^5$ can be separately selected from the group consisting of bromo, chloro, fluoro, —(CH$_2$)$_m$OR$^I$, and —NR$^J$R$^K$, where each R$^I$ in the definition of R$^5$ can be separately selected from the group consisting of hydrogen and C$_1$-C$_6$ alkyl.

Some embodiments disclosed herein provide a compound of Formula I, wherein $A^2$ can be selected from the group consisting of phenyl, naphthyl, and, indolyl, each substituted with one or more substituents selected from the group consisting of $R^1$ and $R^2$; each $R^1$ can be separately selected from the group consisting of phenyl, pyrrolyl, and imidazolyl, each optionally substituted with a substituent selected from $C_1$-$C_6$ alkyl, $C_1$-$C_6$ alkoxy, $C_1$-$C_6$ alkylHN— and $(C_1$-$C_6$ alkyl$)_2$N—; each $R^2$ can be separately selected from the group consisting of bromo, chloro, fluoro, —$(CH_2)_mOR^I$, —$(CH_2)_mR^L$, and —$NR^JR^K$, where each $R^I$ in the definition of $R^2$ can be separately selected from the group consisting of hydrogen and $C_1$-$C_6$ alkyl; each —$NR^JR^K$ can be separately selected, wherein $R^J$ and $R^K$ can each be independently selected from the group consisting of hydrogen, and $C_1$-$C_6$ alkyl optionally substituted with up to 3 fluoro; or —$NR^JR^K$ can be a morpholinyl, piperazinyl, pyrrolidinyl, and piperidinyl, each optionally substituted with one or more oxo; each $R^L$ can be separately selected from the group consisting aryl and heteroaryl, each optionally substituted with one or more substituents each separately selected from the group consisting of halogen, $C_1$-$C_6$ alkyl optionally substituted with up to 5 fluoro, and $C_1$-$C_6$ alkoxy optionally substituted with up to 5 fluoro; $G^2$ can be selected from the group consisting of: phenyl, naphthyl, and, indolyl, each substituted with one or more substituents selected from the group consisting of $R^4$ and $R^5$; each $R^4$ can be separately selected from the group consisting of phenyl, pyrrolyl, and imidazolyl, each optionally substituted with a substituent selected from $C_1$-$C_6$ alkyl, $C_1$-$C_6$ alkoxy, $C_1$-$C_6$ alkylHN— and $(C_1$-$C_6$ alkyl$)_2$N—; and each $R^5$ can be separately selected from the group consisting of bromo, chloro, fluoro, —$(CH_2)_mOR^I$, and —$NR^JR^K$, where each $R^I$ in the definition of $R^5$ can be separately selected from the group consisting of hydrogen and $C_1$-$C_6$ alkyl.

Some embodiments disclosed herein provide a compound of Formula I, wherein $A^1$, $A^2$, $A^4$, and $A^5$ can each be selected from the group consisting of selected from the group consisting of a phenyl, naphthyl, benz[d][1,3]dioxolyl, each substituted with one or more substituents selected from the group consisting of $R^1$, $R^2$, and $R^3$; and $G^1$, $G^2$, and $G^4$ can each be selected from the group consisting of aryl and heteroaryl, each substituted with one or more substituents selected from the group consisting of $R^4$, $R^5$, and $R^6$ and each optionally fused with a nonaromatic heterocycle or carbocycle.

Some embodiments disclosed herein provide a compound of Formula I, wherein L can be selected from the group consisting of aryl, and heteroaryl, each substituted with one or more substituents each individually selected from the group consisting of alkyl, cycloalkyl, alkoxy, alkenylO—, arylC(=O)—, arylC(=O)NH—, arylNHC(=O)—, aryl$(CH_2)_{0-3}$O$(CH_2)_{0-3}$—, aryl$(CH_2)_{0-3}$NH$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, and amino.

Some embodiments disclosed herein provide a compound of Formula I, wherein L can be $L^1$-$L^2$, or $L^1$-O-$L^2$, or $L^1$-$NR^9$-$L^2$, or $L^1$-$L^2$-$L^3$, or $L^1$-$L^2$-$L^3$-$L^4$, or $L^1$-C(=E)-$L^2$.

Some embodiments disclosed herein provide a compound of Formula I, wherein $L^1$ can be selected from the group consisting of aryl and heteroaryl, each substituted with one or more substituents each individually selected from the group consisting of alkyl, cycloalkyl, alkoxy, alkenylO—, arylC(=O)—, arylC(=O)NH—, arylNHC(=O)—, aryl$(CH_2)_{0-3}$O$(CH_2)_{0-3}$—, aryl$(CH_2)_{0-3}$NH$(CH_2)_{0-3}$—, HO$(CH_2)_{1-3}$NH—, HO$(CH_2)_{1-3}$O, HO$(CH_2)_{1-3}$—, HO$(CH_2)_{1-3}$O$(CH_2)_{1-3}$—, and amino.

Some embodiments disclosed herein provide a compound of Formula I, wherein $L^2$ can be selected from the group consisting of aryl, heteroaryl, and heterocyclyl, each substituted with one or more substituents each individually selected from the group consisting of alkyl, cycloalkyl, alkoxy, alkenylO—, arylC(=O)—, arylC(=O)NH—, arylNHC(=O)—, aryl$(CH_2)_{0-3}$O$(CH_2)_{0-3}$—, aryl$(CH_2)_{0-3}$NH$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, and amino.

Some embodiments disclosed herein provide a compound of Formula I, wherein $L^3$ can be selected from the group consisting of aryl, heteroaryl, and heterocyclyl, each substituted with one or more substituents each individually selected from the group consisting of alkyl, cycloalkyl, alkoxy, alkenylO—, arylC(=O)—, arylC(=O)NH—, arylNHC(=O)—, aryl$(CH_2)_{0-3}$O$(CH_2)_{0-3}$—, aryl$(CH_2)_{0-3}$NH$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, and amino.

Some embodiments disclosed herein provide a compound of Formula I, wherein $L^4$ can be aryl substituted with one or more substituents each individually selected from the group consisting of alkyl, cycloalkyl, alkoxy, alkenylO—, arylC(=O)—, arylC(=O)NH—, arylNHC(=O)—, aryl$(CH_2)_{0-3}$O$(CH_2)_{0-3}$—, aryl$(CH_2)_{0-3}$NH$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, and amino.

Some embodiments disclosed herein provide a compound of Formula I, having the proviso that a compound for Formula I is not selected from the group consisting of:

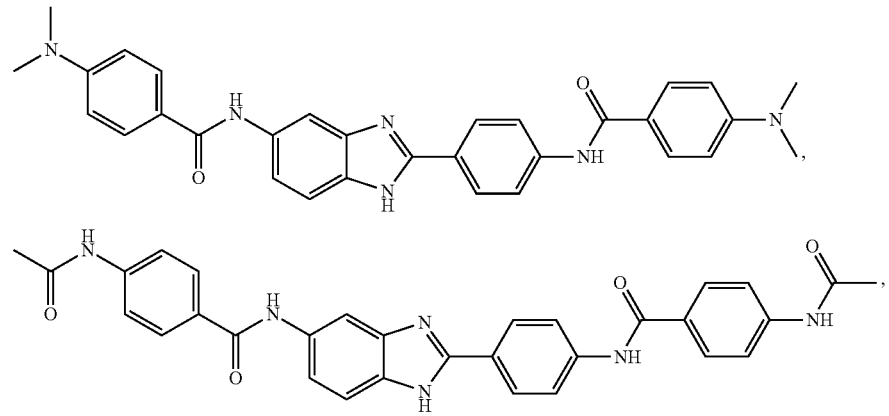

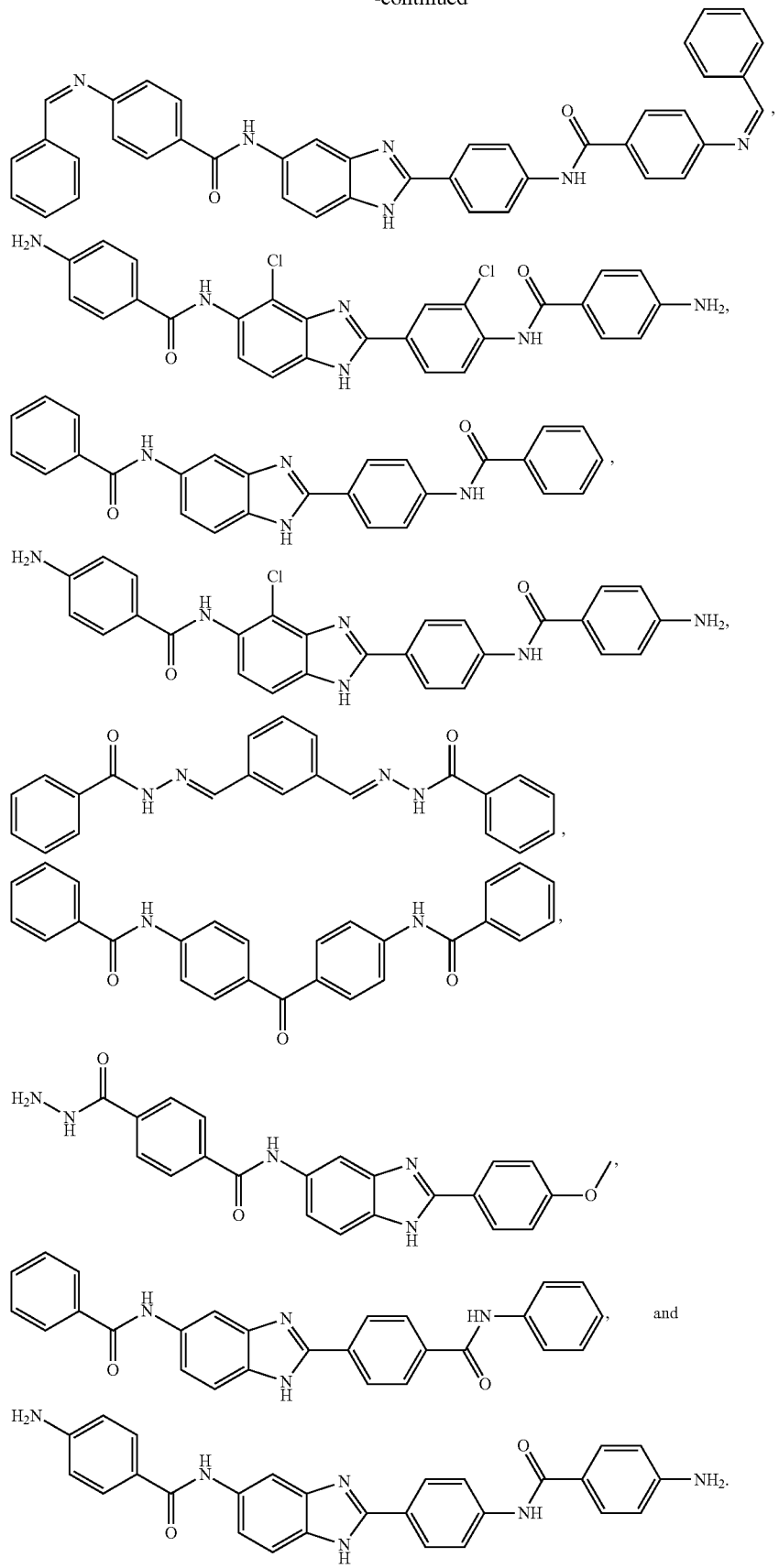

Some embodiments disclosed herein provide a compound of Formula I having the formula Ia:

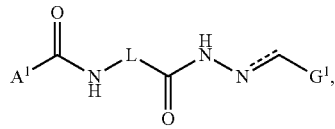

and pharmaceutically acceptable salts thereof, having the formula Ib:

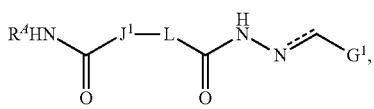

and pharmaceutically acceptable salts thereof, or having the formula Ic:

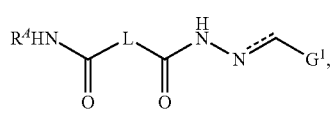

and pharmaceutically acceptable salts thereof.

Some embodiments disclosed herein provide a compound of Formula Ia, Ib, Ic, or Id, wherein L can be selected from the group consisting of an optionally substituted aryl, and an optionally substituted heteroaryl.

Some embodiments disclosed herein provide a compound of Formula I having the formula Id:

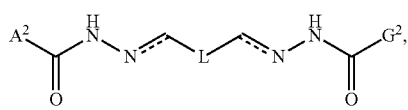

and pharmaceutically acceptable salts thereof.

Some embodiments disclosed herein provide a compound of Formula I having the structure of Formula Ie:

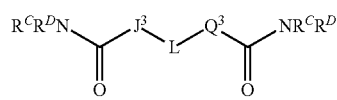

and pharmaceutically acceptable salts thereof.

Some embodiments disclosed herein provide a compound of Formula Ie, wherein L can be selected from the group consisting of —O(CH$_2$)$_p$O—, an optionally substituted aryl, and an optionally substituted heteroaryl, or L is L$^1$-L$^2$; J$^3$ can be selected from the group consisting of an optionally substituted aryl, —(CH$_2$)$_m$NR$^B$C(=O)—, —(CH$_2$)$_r$O—, and —(CH=CH)$_m$; Q$^3$ can be selected from the group consisting of an optionally substituted aryl, —(CH$_2$)$_r$NR$^B$C(=O)—, —(CH$_2$)$_r$O—, and —(CH=CH)$_r$—; L$^1$ can be selected from the group consisting of an optionally substituted aryl, and an optionally substituted heteroaryl; and L$^2$ can be selected from the group consisting of an optionally substituted aryl, and an optionally substituted heteroaryl. In some embodiments, L can be —O(CH$_2$)$_p$O—.

Some embodiments disclosed herein provide a compound of Formula I having the structure of Formula If:

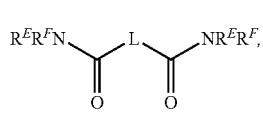

and pharmaceutically acceptable salts thereof.

Some embodiments disclosed herein provide a compound of Formula If, wherein L can be selected from the group consisting of C$_4$-C$_6$ cycloalkyl, an optionally substituted aryl, and an optionally substituted heteroaryl, or L is L$^1$-L$^2$; L$^1$ can be selected from the group consisting of an optionally substituted aryl, and an optionally substituted heteroaryl; and L$^2$ can be selected from the group consisting of an optionally substituted aryl, and an optionally substituted heteroaryl.

Some embodiments disclosed herein provide a compound of Formula I having the structure of Formula Ig:

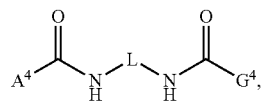

and pharmaceutically acceptable salts thereof.

Some embodiments disclosed herein provide a compound of Formula Ig, wherein L can be selected from the group consisting of an optionally substituted aryl, and an optionally substituted heteroaryl, or L can be selected from the group consisting of L$^1$-L$^2$, L$^1$-O-L$^2$, L$^1$-S-L$^2$, L$^1$-NR$^9$-L$^2$, L$^1$-L$^2$-L$^3$, L$^1$-L$^2$-L$^3$-L$^4$, L$^1$-C(=E)-L$^2$, and L-CR$^7$R$^8$-L$^2$; L$^1$ can be selected from the group consisting of an optionally substituted aryl, and an optionally substituted heteroaryl; L$^2$ can be selected from the group consisting of an optionally substituted aryl, an optionally substituted heteroaryl, and an optionally substituted heterocycle; L$^3$ can be selected from the group consisting of an optionally substituted aryl, and an optionally substituted heteroaryl; and L$^4$ is an optionally substituted aryl.

Some embodiments disclosed herein provide a compound of Formula I having the structure of Formula Ih:

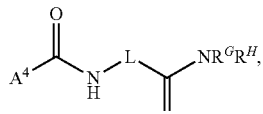

and pharmaceutically acceptable salts thereof.

Some embodiments disclosed herein provide a compound of Formula Ih, wherein L can be selected from the group consisting of an optionally substituted aryl or L can be selected from the group consisting of L$^1$-L$^2$, and L$^1$-L$^2$-L$^3$; L$^1$ can be an optionally substituted heteroaryl; L$^2$ can be selected from the group consisting of an optionally substituted aryl, an optionally substituted heteroaryl, and an optionally substituted heterocycle; and $L^3$ can be an optionally substituted heterocycle.

Some embodiments disclosed herein provide a compound of Formula II:

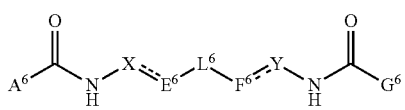

and pharmaceutically acceptable salts, esters, stereoisomers, tautomers or prodrugs thereof;
wherein:

$A^6$ is selected from the group consisting of aryl and heteroaryl, each optionally substituted with one or more substituents selected from the group consisting of $R^{11}$, $R^{12}$, and $R^{13}$, said aryl and heteroaryl in the definition of $A^6$ are each further optionally fused with an optionally substituted nonaromatic heterocycle or an optionally substituted nonaromatic carbocycle;

$G^6$ is selected from the group consisting of aryl and heteroaryl, each optionally substituted with one or more substituents selected from the group consisting of $R^{14}$, $R^{15}$, and $R^{16}$, said aryl and heteroaryl in the definition of $G^6$ are each further optionally fused with an optionally substituted nonaromatic heterocycle or an optionally substituted nonaromatic carbocycle;

$L^6$ is an optionally substituted aryl, or an optionally substituted heteroaryl; where the aryl and heteroaryl in the definition of $L^6$ are optionally fused with a nonaromatic heterocycle or a nonaromatic carbocycle; or $L^6$ is selected from the group consisting of an optionally substituted

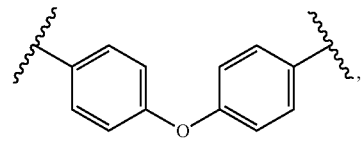 [SMILES: *c1ccc(Oc2ccc(*)cc2)cc1]

and an optionally substituted

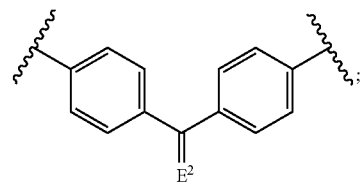

$E^2$ is O (oxygen) or N—$OR^D$ where $R^D$ in the definition of $E^2$ is selected from the group consisting of hydrogen and an optionally substituted $C_1$-$C_6$ alkyl;

each $R^{11}$ is separately selected from the group consisting of halogen, an optionally substituted $C_1$-$C_6$ alkyl, an optionally substituted $C_1$-$C_6$ alkoxy, an optionally substituted $C_2$-$C_4$ alkenyl, an optionally substituted $C_2$-$C_4$ alkynyl, an optionally substituted $C_3$-$C_7$ cycloalkyl, an optionally substituted $C_1$-$C_6$ haloalkyl, and an optionally substituted $C_1$-$C_6$ heteroalkyl, an optionally substituted aryl, and an optionally substituted heteroaryl;

each $R^{12}$ is separately selected from the group consisting of —O(CH$_2$)$_m$OR$^A$, —(CH$_2$)$_m$OR$^A$, —NR$^B$R$^C$, and —(CH$_2$)$_m$SR$^A$;

each $R^{13}$ is separately selected from the group consisting of —(CH$_2$)$_m$OR$^D$, —NR$^E$R$^F$, —S(O)$_{0-2}$R$^D$, —(CH$_2$)$_m$NO$_2$, —(CH$_2$)$_m$CN, and —(CH$_2$)$_m$R$^G$;

each $R^{14}$ is separately selected from the group consisting of halogen, an optionally substituted $C_1$-$C_6$ alkyl, an optionally substituted $C_1$-$C_6$ alkoxy, an optionally substituted $C_2$-$C_4$ alkenyl, an optionally substituted $C_2$-$C_4$ alkynyl, an optionally substituted $C_3$-$C_7$ cycloalkyl, an optionally substituted $C_1$-$C_6$ haloalkyl, an optionally substituted $C_1$-$C_6$ heteroalkyl, an optionally substituted aryl, and an optionally substituted heteroaryl;

each $R^{15}$ is separately selected from the group consisting of —O(CH$_2$)$_m$OR$^A$, —(CH$_2$)$_m$OR$^A$, —NR$^B$R$^C$, and —(CH$_2$)$_m$SR$^A$;

each $R^{16}$ is separately selected from the group consisting of —(CH$_2$)$_m$OR$^D$, —NR$^E$R$^F$, —(CH$_2$)$_m$S(O)$_{0-2}$R$^D$, —(CH$_2$)$_m$NO$_2$, —(CH$_2$)$_m$CN, and —(CH$_2$)$_m$R$^G$;

$E^6$ is $CR^{17}$ when the dashed line between $E^6$ and X represents a double bond; or $E^6$ is $CR^{17}R^{17}$ when the dashed line between $E^6$ and X represents a single bond;

$F^6$ is $CR^{18}$ when the dashed line between $F^6$ and Y represents a double bond; or $F^6$ is $CR^{18}R^{18}$ when the dashed line between $F^6$ and Y represents a single bond;

each $R^{17}$ is independently selected from the group consisting of hydrogen, halogen, an optionally substituted $C_1$-$C_4$ alkoxy, an optionally substituted $C_3$-$C_7$ cycloalkyl, and an optionally substituted $C_1$-$C_4$ alkyl;

each $R^{18}$ is independently selected from the group consisting of hydrogen, halogen, an optionally substituted $C_1$-$C_4$ alkoxy, an optionally substituted $C_3$-$C_7$ cycloalkyl, and an optionally substituted $C_1$-$C_4$ alkyl;

$R^A$ is selected from the group consisting of hydrogen, $C_1$-$C_6$ alkyl, $C_2$-$C_4$ alkenyl, $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl;

each —NR$^B$R$^C$ is separately selected, wherein $R^B$ and $R^C$ are each independently selected from the group consisting of hydrogen, —SO$_2$R$^H$, —C(=O)R$^H$, —C(=O)NR$^E$R$^F$, heterocycle, $C_1$-$C_6$ alkyl, $C_2$-$C_4$ alkenyl, an optionally substituted $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl, where the $C_1$-$C_6$ alkyl in the definition of $R^B$ and $R^C$ is optionally substituted with an optionally substituted aryl or an optionally substituted heteroaryl and where the $C_3$-$C_7$ cycloalkyl and the heterocycle in the definition of $R^B$ and $R^C$ are optionally fused with an aryl or heteroaryl; or —NR$^B$R$^C$ is an optionally substituted non-aromatic heterocycle linked through a ring nitrogen atom; or —NR$^B$R$^C$ is an optionally substituted $C_1$-$C_6$ alkylideneamino;

each $R^D$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_1$-$C_6$ haloalkyl, an optionally substituted $C_1$-$C_6$ heteroalkyl, and —(CH$_2$)$_m$R$^G$;

each —NR$^E$R$^F$ is separately selected, wherein $R^E$ and $R^F$ are each independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_1$-$C_6$ haloalkyl, an optionally substituted $C_1$-$C_6$ heteroalkyl, and —(CH$_2$)$_m$R$^G$; or —NR$^E$R$^F$ is an optionally substituted $C_1$-$C_6$ alkylideneamino; or —NR$^E$R$^F$ is an optionally substituted nonaromatic heterocycle linked through a ring nitrogen atom; $R^G$ is selected from an optionally substituted aryl and an optionally substituted heteroaryl;

$R^H$ is selected from the group consisting of hydrogen, $C_1$-$C_3$ alkyl, an optionally substituted $C_1$-$C_3$ alkoxy, an optionally substituted $C_2$-$C_4$ alkenyl, an optionally substituted $C_2$-$C_4$ alkynyl, an optionally substituted $C_3$-$C_7$ cycloalkyl, $C_2$-$C_4$ alkenyl, $C_2$-$C_4$ alkynyl, $C_3$-$C_7$ cycloalkyl, $C_1$-$C_3$ haloalkyl, and an optionally substituted aryl or heteroaryl;

X and Y are independently selected from N (nitrogen), NH, $CR^{19}$, and $CR^{19}R^{20}$;

each $R^{19}$ and $R^{20}$ are independently selected from the group consisting of hydrogen and an optionally substituted $C_1$-$C_4$ alkyl;

each m is independently 0, 1, or 2; and any bond represented by a dashed and solid line represents a bond selected from the group consisting of a single bond and a double bond.

Some embodiments disclosed herein provide a compound of Formula II, wherein $A^6$ can be selected from the group consisting of aryl and heteroaryl, each optionally substituted with one or more substituents selected from the group consisting of $R^{11}$, $R^{12}$, and $R^{13}$, said aryl and heteroaryl in the definition of $A^6$ can each be further optionally fused with a nonaromatic heterocycle or carbocycle; $L^6$ can be selected from the group consisting of

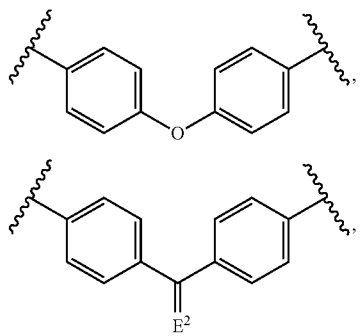

an optionally substituted

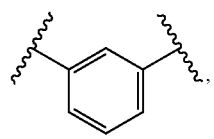

an optionally substituted

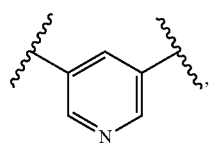 [SMILES: *c1cncc(*)c1]

an optionally substituted

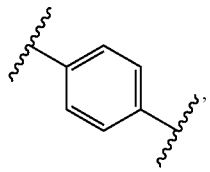 [SMILES: *c1ccc(*)cc1]

and an optionally substituted

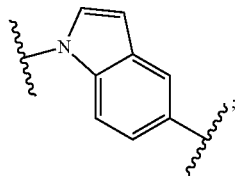 [SMILES: *c1ccc2c(ccn2*)c1]

$E^2$ can be O (oxygen) or N—$OR^D$ where $R^D$ in the definition of $E^2$ can be selected from the group consisting of hydrogen and an optionally substituted $C_1$-$C_6$ alkyl; $G^6$ can be selected from the group consisting of aryl and heteroaryl, each optionally substituted with one or more substituents selected from the group consisting of $R^{14}$, $R^{15}$, and $R^{16}$, said aryl and heteroaryl in the definition of $G^6$ can each be further optionally fused with a nonaromatic heterocycle or carbocycle; each $R^{11}$ can be separately selected from the group consisting of fluoro, an optionally substituted aryl and an optionally substituted heteroaryl; each $R^{12}$ can be separately selected from the group consisting of —$O(CH_2)_mOR^A$, —$(CH_2)_mOR^A$, and —$NR^BR^C$, where $R^A$ in the definition of can be $R^{12}$ selected from the group consisting of hydrogen, and $C_1$-$C_6$ alkyl; each $R^{13}$ can be separately selected from the group consisting of —$OR^D$, —$NR^ER^F$, —$S(O)_2R^D$, —CN, and —$R^G$; each —$NR^BR^C$ can be separately selected, wherein $R^B$ and $R^C$ can each be independently selected from the group consisting of hydrogen, $C_3$-$C_7$ cycloalkyl, $C_1$-$C_6$ alkyl, and $C_1$-$C_6$ haloalkyl, where the $C_1$-$C_6$ alkyl in the definition of $R^B$ and $R^C$ can be optionally substituted with an optionally substituted aryl or an optionally substituted heteroaryl, and where the $C_3$-$C_7$ cycloalkyl in the definition of $R^B$ and $R^C$ can be optionally fused with an optionally substituted aryl; or —$NR^BR^C$ can be an optionally substituted non-aromatic heterocycle linked through a ring nitrogen atom; $R^H$ can be selected from the group consisting of hydrogen, $C_1$-$C_3$ alkyl, an optionally substituted aryl and an optionally substituted heteroaryl; each $R^{14}$ can be separately selected from the group consisting of chloro, fluoro, an optionally substituted $C_1$-$C_6$ alkyl, an optionally substituted aryl, and an optionally substituted heteroaryl; each $R^{15}$ can be separately selected from the group consisting of —$O(CH_2)_mOR^A$, —$(CH_2)_mOR^A$, and —$NR^BR^C$, where $R^A$ in the definition of $R^{15}$ can be selected from the group consisting of hydrogen, and $C_1$-$C_6$ alkyl; and each $R^{16}$ can be separately selected from the group consisting of —$OR^D$, —$NR^ER^F$, —$S(O)_2R^D$, —CN, and —$R^G$. In some embodiments, $A^6$ can be selected from the group consisting of aryl and heteroaryl, each substituted with one or more substituents selected from the group consisting of $R^{11}$, $R^{12}$, and $R^{13}$, said aryl in the definition of $A^6$ can each be further optionally fused with a nonaromatic heterocycle or nonaromatic carbocycle; $G^6$ can be selected from the group consisting of aryl and heteroaryl, each substituted with one or more substituents selected from the group consisting of $R^{14}$, $R^{15}$, and $R^{16}$, said aryl and heteroaryl in the definition of $G^6$ can each be further optionally fused with a nonaromatic heterocycle or carbocycle; each $R^{11}$ can be separately selected from the group consisting of an optionally substituted aryl and an optionally substituted heteroaryl; each $R^{12}$ can be separately selected from the group consisting of —$(CH_2)_mOR^A$, and —$NR^BR^C$, where $R^A$ in the definition of $R^{12}$ can be selected from the group consisting of hydrogen, and $C_1$-$C_6$ alkyl; each $R^{13}$ can be fluoro; each —$NR^BR^C$ can be separately selected, wherein $R^B$ and $R^C$ can each be independently selected from the group consisting of hydrogen, —$C(=O)R^H$, and $C_1$-$C_6$ alkyl; or —$NR^BR^C$ can be an optionally substituted non-aromatic heterocycle linked through a ring nitrogen atom; each $R^{14}$ can be separately selected from the group consisting of chloro, fluoro, an optionally substituted $C_1$-$C_6$ alkyl, an optionally substituted aryl and an optionally substituted heteroaryl; each $R^{15}$ can be separately selected from the group consisting of —$OCH_2CH_2OR^A$, —$(CH_2)_mOR^A$, and —$NR^BR^C$, where $R^A$ in the definition of can be $R^{15}$ selected from the group consisting of hydrogen, and $C_1$-$C_6$ alkyl; and each $R^{16}$ can be fluoro.

Some embodiments disclosed herein provide a compound of Formula II, wherein

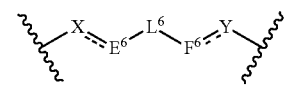

is selected from the group consisting of:

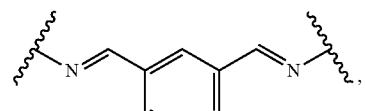

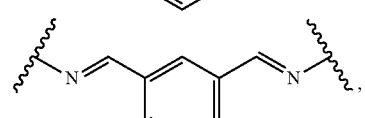

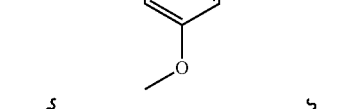

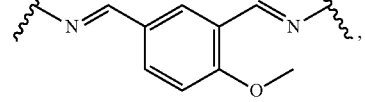

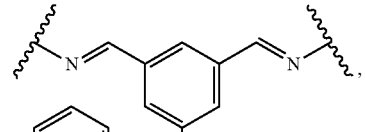

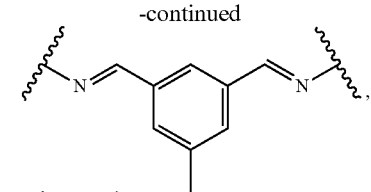

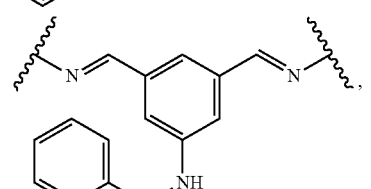

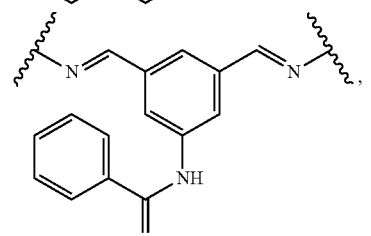

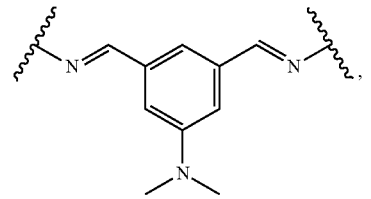

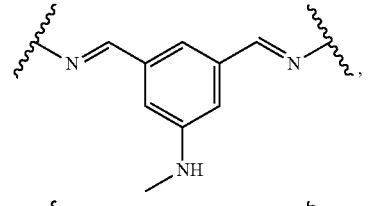

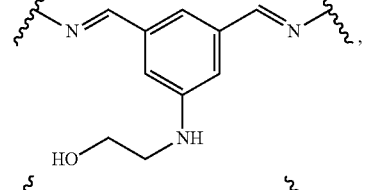

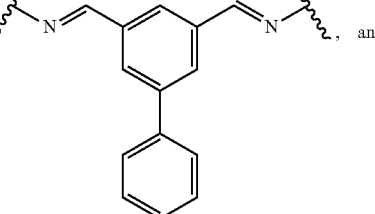, and

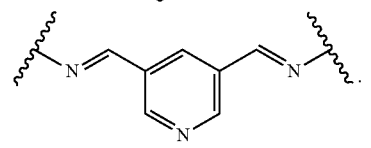.

Some embodiments disclosed herein provide a compound of Formula II, wherein $A^6$ can be selected from the group consisting of phenyl, naphthyl, benz[d][1,3]dioxolyl, indolyl, and benz[d]imidazolyl, each optionally substituted with one or more substituents selected from the group consisting of $R^{11}$ and $R^{12}$; each $R^{11}$ can be separately selected from the group consisting of phenyl, pyrrolyl, and imidazolyl, each optionally substituted with a substituent selected from $C_1$-$C_6$ alkyl, $C_1$-$C_6$ alkoxy, $C_1$-$C_6$ alkylHN— and $(C_1$-$C_6$ alkyl$)_2$N—; each $R^{12}$ can be separately selected from the group consisting of bromo, chloro, fluoro, —$(CH_2)_mOR^A$, and —$NR^BR^C$, where each $R^A$ in the definition of $R^{12}$ can be separately selected from the group consisting of hydrogen and $C_1$-$C_6$ alkyl; each —$NR^BR^C$ can be separately selected, wherein $R^B$ and $R^C$ can each be independently selected from the group consisting of hydrogen, —C(=O)$R^H$, $C_1$-$C_6$ alkyl optionally substituted with up to 5 fluoro, and an optionally substituted $C_3$-$C_7$ cycloalkyl further optionally fused with phenyl; or —$NR^BR^C$ can be a morpholinyl, piperazinyl, pyrrolidinyl, and piperidinyl, each optionally substituted with one or more oxo; each $R^H$ can be separately selected from the group consisting aryl and heteroaryl, each optionally substituted with one or more substituents each separately selected from the group consisting of halogen, $C_1$-$C_6$ alkyl optionally substituted with up to 5 fluoro, and $C_1$-$C_6$ alkoxy optionally substituted with up to 5 fluoro; $G^6$ can be selected from the group consisting of: phenyl, naphthyl, benz[d][1,3]dioxolyl, indolyl, and benz[d]imidazolyl, each optionally substituted with one or more substituents selected from the group consisting of $R^{14}$ and $R^{15}$ each $R^{14}$ can be separately selected from the group consisting of phenyl, pyrrolyl, and imidazolyl, each optionally substituted with a substituent selected from $C_1$-$C_6$ alkyl, $C_1$-$C_6$ alkoxy, $C_1$-$C_6$ alkylHN— and $(C_1$-$C_6$ alkyl$)_2$N—; and each $R^{15}$ can be separately selected from the group consisting of bromo, chloro, fluoro, —$(CH_2)_mOR^A$, and —$NR^BR^C$, where each $R^A$ in the definition of $R^{15}$ can be separately selected from the group consisting of hydrogen and $C_1$-$C_6$ alkyl.

Some embodiments disclosed herein provide a compound of Formula III:

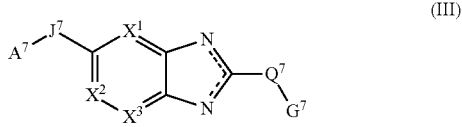

(III)

and pharmaceutically acceptable salts, esters stereoisomers, tautomers or prodrugs thereof;

wherein:

$A^7$ is selected from the group consisting of aryl, heteroaryl, isoindolinyl, indenyl, dihydroindenyl, tetrahydroisoquinolinyl, and tetrahydronaphthalenyl, each optionally substituted with one or more substituents selected from the group consisting of $R^{21}$, $R^{22}$, and $R^{23}$, said aryl and heteroaryl in the definition of $A^7$ are each further optionally fused with an optionally substituted nonaromatic heterocycle or an optionally substituted nonaromatic carbocycle; or $A^7$ is $C_3$-$C_7$ cycloalkyl optionally substituted with one or more substituents selected from the group consisting of $R^{21}$, $R^{22}$, and $R^{23}$, said $C_3$-$C_7$ cycloalkyl in the definition of $A^7$ is fused with an optionally substituted aryl or optionally substituted heteroaryl;

each $R^{21}$ is independently selected from the group consisting of halogen, cyano, an optionally substituted $C_1$-$C_6$ alkyl, an optionally substituted $C_1$-$C_6$ alkoxy, an optionally substituted $C_2$-$C_4$ alkenyl, an optionally substituted $C_2$-$C_4$ alkynyl, an optionally substituted $C_3$-$C_7$ cycloalkyl, an optionally substituted aryl, an optionally substituted heteroaryl, and an optionally substituted heterocycle;

each $R^{22}$ is independently selected from the group consisting of —$(CH_2)_mOR^A$, —$O(CH_2)_mOR^A$, —C(=O)$OR^A$, —$O(CH_2)_oNR^BR^C$, —$(CH_2)_mNR^BR^C$, —C(=O)$NR^BR^C$, and —$(CH_2)_mSR^A$;

each $R^{23}$ is independently selected from the group consisting of phenyl, —NHC(=NH)$NH_2$, —$(CH_2)_mOR^D$, —C(=NN$R^BR^C$)H, —$NR^LC$(=O)$NR^BR^C$, —C(=O)$NR^DN$(=CH$R^G$), —$(CH_2)_mS(O)_{0-2}R^D$, —$(CH_2)_mNO_2$, —$(CH_2)_mCN$, and —$(CH_2)_mR^G$, said phenyl in the definition of $R^{23}$ is substituted with one or more substituents selected from the group consisting of halogen, cyano, $C_1$-$C_3$ alkyl, an optionally substituted $C_1$-$C_3$ alkoxy, —$O(CH_2)_mOR^A$, —$(CH_2)_mNR^BR^C$;

$J^7$ is selected from the group consisting of —$(CH_2)_n$[NHC(=O)]$(CH_2)_o$[NHC(=O)]$(CH_2)_p$—, —$(CH_2)_n$[NHC(=O)]$(CH_2)_o$[NH]$_q$—, —N[C(=O)][C(=O)]NH— and

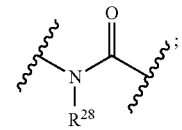

$Q^7$ is selected from the group consisting of O (oxygen), —$NR^{28}$—, aryl, and arylamido; or $Q^7$ is null;

each $R^{28}$ is independently selected from the group consisting of hydrogen and an optionally substituted $C_1$-$C_4$ alkyl;

$G^7$ is selected from the group consisting aryl, heteroaryl, and heterocycle, each optionally substituted with one or more substituents selected from the group consisting of $R^{24}$, $R^{25}$, and $R^{26}$, said aryl and heteroaryl in the definition of $G^7$ are each further optionally fused with an optionally substituted nonaromatic heterocycle or an optionally substituted nonaromatic carbocycle;

each $R^{24}$ is independently selected from the group consisting of halogen, cyano, an optionally substituted $C_1$-$C_6$ alkyl, an optionally substituted $C_1$-$C_6$ alkoxy, an optionally substituted $C_2$-$C_4$ alkenyl, an optionally substituted $C_2$-$C_4$ alkynyl, an optionally substituted $C_3$-$C_7$ cycloalkyl, an optionally substituted aryl, an optionally substituted heteroaryl, and an optionally substituted heterocycle;

each $R^{25}$ is independently selected from the group consisting of —$(CH_2)_mOR^A$, —$O(CH_2)_mOR^A$, —C(=O)$OR^A$, —$O(CH_2)_oNR^BR^C$, —$(CH_2)_mNR^BR^C$, —$(CH_2)_mC$(=O)$NR^BR^C$, —C(=NN$R^BR^C$)H, and —$(CH_2)_mSR^A$;

each $R^{26}$ is independently selected from the group consisting of phenyl, —NHC(=NH)$NH_2$, —$(CH_2)_mOR^D$, —C(=NN$R^BR^C$)H, —$NR^LC$(=O)$NR^BR^C$, —C(=O)$NR^DN$(=CH)$R^G$, —$(CH_2)_mS(O)_{0-2}R^D$, —$(CH_2)_mNO_2$, —$(CH_2)_mCN$, —$(CH_2)_mR^G$, said phenyl in the definition of $R^{23}$ is substituted with —$(CH_2)_mNR^BR^C$;

$X^1$, $X^2$, and $X^3$ are each independently selected from N (nitrogen) and $CR^{27}$;

$R^{27}$ is selected from the group consisting of hydrogen, halogen, and an optionally substituted $C_1$-$C_4$ alkyl;

$R^A$ is selected from the group consisting of hydrogen, $C_1$-$C_6$ alkyl, $C_2$-$C_4$ alkenyl, $C_2$-$C_4$ alkynyl, $C_3$-$C_7$ cycloalkyl, and $C_1$-$C_6$ haloalkyl;

each —NR$^B$R$^C$ is separately selected, wherein R$^B$ and R$^C$ are each independently selected from the group consisting of hydrogen, —SO$_2$R$^H$, —C(=O)R$^H$, —(CH$_2$)$_n$OR$^H$, —(CH$_2$)$_m$R$^I$, —(CH$_2$)$_m$R$^J$, —(CH$_2$)$_n$C(=O)NR$^E$R$^F$, —(CH$_2$)$_n$NR$^E$R$^F$, —SO$_2$NR$^E$R$^F$, heterocycle, C$_1$-C$_6$ alkyl, C$_1$-C$_6$ haloalkyl, C$_1$-C$_6$ heteroalkyl, C$_3$-C$_7$ cycloalkyl, and C$_1$-C$_6$ heterohaloalkyl where the C$_3$-C$_7$ cycloalkyl and the heterocycle are each optionally fused with an optionally substituted aryl or optionally substituted heteroaryl; or —NR$^B$R$^C$ is an optionally substituted non-aromatic heterocycle linked through a ring nitrogen atom, said optionally substituted non-aromatic heterocycle is optionally fused with an optionally substituted aryl or optionally substituted heteroaryl;

each R$^D$ is independently selected from the group consisting of hydrogen, an optionally substituted C$_1$-C$_6$ alkyl, an optionally substituted C$_1$-C$_6$ haloalkyl, an optionally substituted C$_1$-C$_6$ heteroalkyl, and —(CH$_2$)$_m$R$^I$;

each —NR$^E$R$^F$ is separately selected, wherein R$^E$ and R$^F$ are each independently selected from the group consisting of hydrogen, an optionally substituted C$_1$-C$_6$ alkyl, an optionally substituted C$_1$-C$_6$ haloalkyl, an optionally substituted C$_1$-C$_6$ heteroalkyl, an optionally substituted C$_3$-C$_7$ cycloalkyl, an optionally substituted heterocycle, and —(CH$_2$)$_m$R$^G$; or —NR$^E$R$^F$ is an optionally substituted non-aromatic heterocycle linked through a ring nitrogen atom; or —NR$^E$R$^F$ is C$_1$-C$_6$ alkylideneamino substituted with an optionally substituted aryl;

each R$^G$ is independently selected from an optionally substituted aryl and an optionally substituted heteroaryl;

each R$^H$ is independently selected from the group consisting of hydrogen, C$_1$-C$_3$ alkoxy, C$_1$-C$_3$ alkyl, C$_1$-C$_3$ haloalkyl, an optionally substituted aryl and an optionally substituted heteroaryl;

each R$^I$ is independently selected from the group consisting of an optionally substituted aryl and an optionally substituted heteroaryl;

each R$^J$ is independently selected from the group consisting of aryl and heteroaryl, each substituted with one or more —NR$^E$R$^F$;

each R$^L$ is independently selected from the group consisting of C$_3$-C$_7$ cycloalkyl, optionally substituted C$_1$-C$_6$ alkyl, optionally substituted C$_1$-C$_6$ alkoxy, —(CH$_2$)$_m$OR$^{LA}$, —(CH$_2$)$_m$NR$^{LB}$R$^{LC}$, aryl and heteroaryl, said aryl and heteroaryl in the definition of R$^L$ are each independently optionally substituted with one or more substituents selected from the group consisting of halo, C$_1$-C$_6$ alkyl, C$_1$-C$_6$ haloalkyl, C$_1$-C$_6$ alkoxy, —(CH$_2$)$_m$NR$^{LD}$R$^{LE}$, aryl and heteroaryl, said aryl and heteroaryl substituent off of R$^L$ are each optionally substituted with one or more halo, C$_1$-C$_6$ alkyl, C$_1$-C$_6$ haloalkyl, C$_1$-C$_6$ alkoxy, or —(CH$_2$)$_m$NR$^{LF}$R$^{LG}$;

each R$^{LA}$ is independently selected from the group consisting of hydrogen, C$_1$-C$_6$ alkyl, and C$_1$-C$_6$ haloalkyl;

R$^{LB}$ and R$^{LC}$ are each independently selected from the group consisting of hydrogen, C$_1$-C$_6$ alkyl, C$_1$-C$_6$ haloalkyl, and C$_1$-C$_6$ heteroalkenyl; or —NR$^{LB}$R$^{LC}$ is an optionally substituted non-aromatic heterocycle linked through a ring nitrogen atom;

each —NR$^{LD}$R$^{LE}$ is separately selected, wherein R$^{LD}$ and R$^{LE}$ are each independently selected from the group consisting of hydrogen, aryl, heteroaryl, and optionally substituted C$_1$-C$_6$ alkyl, said aryl and heteroaryl in the definition of R$^{LD}$ and R$^{LE}$ are each optionally substituted with C$_1$-C$_6$ alkyl or C$_1$-C$_6$ alkoxy; or —NR$^{LD}$R$^{LE}$ is an optionally substituted non-aromatic heterocycle linked through a ring nitrogen atom;

each —NR$^{LF}$R$^{LG}$ is separately selected, wherein R$^{LF}$ and R$^{LG}$ are each independently selected from the group consisting of hydrogen, and C$_1$-C$_6$ alkyl; or —NR$^{LF}$R$^{LG}$ is an optionally substituted non-aromatic heterocycle linked through a ring nitrogen atom;

each m is independently 0, 1, or 2;
each n is independently 0, 1, 2, 3, or 4;
each o is independently 1, 2, or 3;
each p is independently 0, 1, 2, or 3;
each q is independently 0 or 1; and any bond represented by a dashed and solid line represents a bond selected from the group consisting of a single bond and a double bond.

Some embodiments disclosed herein provide a compound of Formula III, wherein A$^7$ can be selected from the group consisting of phenyl, pyridinyl, pyrimidinyl, imidazolyl, isoxazolyl, thienyl, indolyl, and benzimidazolyl, each substituted with one or more substituents selected from the group consisting of R$^{21}$, R$^{22}$, and R$^{23}$, said aryl and heteroaryl in the definition of A$^7$ can each be further optionally fused with an optionally substituted nonaromatic heterocycle or an optionally substituted nonaromatic carbocycle; G$^7$ can be selected from the group consisting aryl, heteroaryl, and heterocycle, each substituted with one or more substituents selected from the group consisting of R$^{24}$, R$^{25}$, and R$^{26}$, said aryl and heteroaryl in the definition of G$^7$ can each be further optionally fused with an optionally substituted nonaromatic heterocycle or an optionally substituted nonaromatic carbocycle; R$^{21}$ can be selected from the group consisting of fluorine and chlorine; R$^{22}$ can be selected from the group consisting of —(CH$_2$)$_m$OR$^A$, —C(=O)NR$^B$R$^C$, —NR$^B$R$^C$, and —(CH$_2$)$_m$SR$^A$; R$^{23}$ can be selected from the group consisting of —(CH$_2$)$_m$OR$^D$, and —C(=O)NR$^D$N(=CHR$^G$); R$^{25}$ can be selected from the group consisting of —(CH$_2$)$_m$OR$^A$, —C(=O)NR$^B$R$^C$, —NR$^B$R$^C$; each R$^A$ can be independently selected from the group consisting of hydrogen, C$_1$-C$_6$ alkyl, C$_1$-C$_6$ haloalkyl, and C$_1$-C$_6$ heteroalkyl; each —NR$^B$R$^C$ can be separately selected, wherein R$^B$ and R$^C$ can each be independently selected from the group consisting of C$_1$-C$_6$ alkyl, C$_1$-C$_6$ haloalkyl, C$_1$-C$_6$ heteroalkyl, and C$_1$-C$_6$ heterohaloalkyl; or —NR$^B$R$^C$ can be an optionally substituted non-aromatic heterocycle linked through a ring nitrogen atom; or —NR$^B$R$^C$ is an optionally substituted C$_1$-C$_6$ alkylideneamino; J$^7$ can be

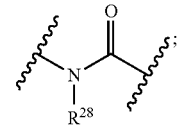

each R$^{28}$ can be independently selected from the group consisting of hydrogen and an optionally substituted C$_1$-C$_3$ alkyl, with the proviso when A$^7$ and G$^7$ are a phenyl then at least one of R$^{22}$, R$^{23}$, R$^{25}$, and R$^{26}$ can be selected from the group consisting of —(CH$_2$)$_m$OR$^A$, —(CH$_2$)$_m$OR$^D$, —NR$^B$R$^C$, —C(=O)NR$^D$N(=CHR$^G$), —NR$^E$R$^F$, —C(=O)NR$^B$R$^C$, and an optionally substituted phenyl.

Some embodiments disclosed herein provide a compound of Formula III, wherein A$^7$ can be selected from the group consisting of phenyl, pyridinyl, pyrimidinyl, imidazolyl, isoxazolyl, thienyl, indolyl, and benzimidazolyl, each substituted with one or more substituents selected from the group consisting of R$^{21}$, R$^{22}$, and R$^{23}$, said aryl and heteroaryl in the definition of A$^7$ can each be further optionally fused with an optionally substituted nonaromatic heterocycle or an optionally substituted nonaromatic carbocycle;

$G^7$ can be selected from the group consisting aryl, heteroaryl, and heterocycle, each substituted with one or more substituents selected from the group consisting of $R^{24}$, $R^{25}$, and $R^{26}$, said aryl and heteroaryl in the definition of $G^7$ can each be further optionally fused with an optionally substituted nonaromatic heterocycle or an optionally substituted nonaromatic carbocycle; $R^{21}$ can be selected from the group consisting of $C_1$-$C_6$ alkyl, fluorine, and chlorine; $R^{22}$ can be selected from the group consisting of —NHC(=O)$R^E R^F$, —(CH$_2$)$_m$OR$^A$, and —NR$^B R^C$; $R^{23}$ can be selected from the group consisting of —(CH$_2$)$_m$OR$^D$, and —C(=O)NR$^D$N(=CHR$^G$); $R^A$ can be selected from the group consisting of hydrogen, $C_1$-$C_6$ alkyl, and $C_1$-$C_6$ haloalkyl; each —NR$^B R^C$ can be separately selected, wherein $R^B$ and $R^C$ can each be independently selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl; or —NR$^B R^C$ can be an optionally substituted non-aromatic heterocycle linked through a ring nitrogen atom; or —NR$^B R^C$ can be an optionally substituted $C_1$-$C_6$ alkylideneaminyl; and $J^7$ can be

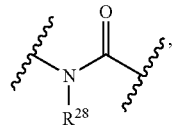

with the proviso when $A^7$ and $G^7$ are a phenyl then at least one of $R^{22}$, $R^{23}$, $R^{25}$, and $R^{26}$ can be selected from the group consisting of —(CH$_2$)$_m$OR$^A$, —(CH$_2$)$_m$OR$^D$, —NR$^B R^C$, —NHC(=O)$R^E R^F$, —C(=O)NR$^D$N(=CHR$^G$), and an optionally substituted phenyl.

Some embodiments disclosed herein provide a compound of Formula III having the structure of Formula IIIaa:

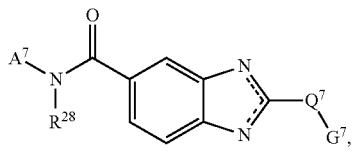

(IIIaa)

and pharmaceutically acceptable salts, esters, stereoisomers, tautomers or prodrugs thereof, or having the formula IIIab:

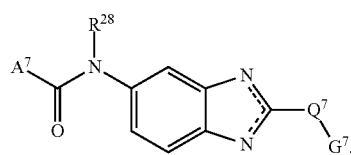

(Ib)

and pharmaceutically acceptable salts, esters, stereoisomers, tautomers or prodrugs thereof.

Some embodiments disclosed herein provide a compound of Formula IIIab having the structure of Formula IIIabb:

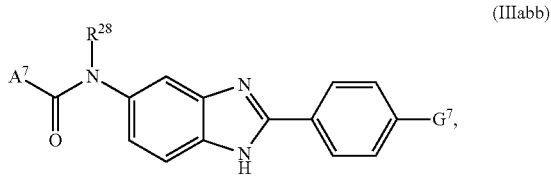

(IIIabb)

and pharmaceutically acceptable salts, esters, stereoisomers, tautomers or prodrugs thereof, wherein $A^7$ can be aryl substituted with one or more substituents selected from the group consisting of $R^{21}$, $R^{22}$, and $R^{23}$; each $R^{21}$ can be independently selected from the group consisting of halogen, cyano, $C_1$-$C_6$ alkyl, and $C_1$-$C_6$ alkoxy; each $R^{22}$ can be independently selected from the group consisting of —(CH$_2$)$_m$OR$^A$, —O(CH$_2$)$_m$OR$^A$ and —(CH$_2$)$_m$NR$^B R^C$; each $R^{23}$ can be phenyl substituted with —(CH$_2$)$_m$NR$^B R^C$; $G^7$ can be heterocycle substituted with one or more substituents selected from the group consisting of $R^{24}$, $R^{25}$, and $R^{26}$; each $R^{24}$ can be independently selected from the group consisting of halogen, cyano, $C_1$-$C_6$ alkyl, and $C_1$-$C_6$ alkoxy; each $R^{25}$ can be independently selected from the group consisting of —(CH$_2$)$_m$OR$^A$, —O(CH$_2$)$_m$OR$^A$; each $R^{26}$ can be phenyl substituted with one or more —(CH$_2$)$_m$NR$^B R^C$; $R^B$ can be hydrogen; $R^C$ can be —C(=O)$R^H$; and $R^H$ can be an optionally substituted aryl.

Some embodiments disclosed herein provide a compound of Formula IIIabb, wherein $A^7$ can be phenyl substituted with one or more substituents selected from the group consisting of $R^{22}$; each $R^{22}$ can be independently selected from the group consisting of —(CH$_2$)$_m$OR$^A$, and —O(CH$_2$)$_m$OR$^A$; each $R^A$ can be independently selected from the group consisting of hydrogen, $C_1$-$C_3$ alkyl, and $C_1$-$C_3$ haloalkyl; $G^7$ can be piperidinyl substituted with one or more substituents selected from the group consisting of $R^{26}$; each $R^{26}$ can be phenyl substituted with —NHC(=O)$R^H$; and $R^H$ can be an optionally substituted phenyl.

Some embodiments disclosed herein provide a compound of Formula III having the structure of Formula IIIb:

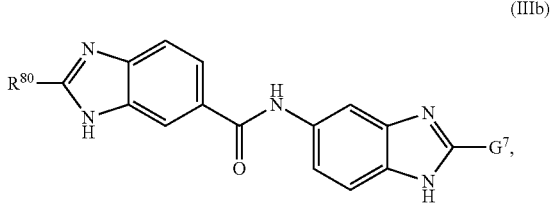

(IIIb)

and pharmaceutically acceptable salts thereof, wherein $R^{80}$ can be selected from the group consisting of hydrogen, $R^{21}$, $R^{22}$, and $R^{23}$.

Some embodiments disclosed herein provide a compound of Formula III having the structure of Formula IIIc:

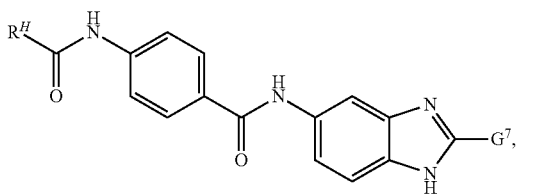

and pharmaceutically acceptable salts thereof.

Some embodiments disclosed herein provide a compound of Formula III having the structure of Formula IIId:

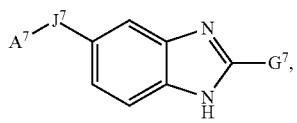

and pharmaceutically acceptable salts thereof, wherein $A^7$ can be selected from the group consisting of aryl and heteroaryl, each substituted with one or more substituents selected from the group consisting of $R^{21}$, $R^{22}$, and $R^{23}$, said aryl and heteroaryl in the definition of $A^7$ can each be further optionally fused with an optionally substituted nonaromatic heterocycle or an optionally substituted nonaromatic carbocycle; or $A^7$ can be $C_3$-$C_7$ cycloalkyl optionally substituted with one or more substituents selected from the group consisting of $R^{21}$, $R^{22}$, and $R^{23}$, said $C_3$-$C_7$ cycloalkyl in the definition of $A^7$ can be fused with an optionally substituted aryl or optionally substituted heteroaryl; $J^7$ can be selected from the group consisting of $—(CH_2)_n[NHC(=O)](CH_2)_oNHC(=O)(CH_2)_p—$, $—(CH_2)_n[NHC(=O)](CH_2)_o[NH]_q—$, and

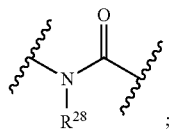

and $G^7$ can be selected from the group consisting of a aryl and heteroaryl, each substituted with one or more substituents selected from the group consisting of $R^{24}$, $R^{25}$, and $R^{26}$, said aryl and heteroaryl in the definition of $G^7$ can each be further optionally fused with an optionally substituted nonaromatic heterocycle or an optionally substituted nonaromatic carbocycle.

Some embodiments disclosed herein provide a compound of Formula IIId having the structure of Formula IIIda:

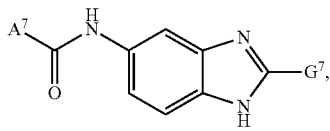

and pharmaceutically acceptable salts, esters, or prodrugs thereof, wherein $A^7$ can be selected from the group consisting of phenyl, indolyl, pyridinyl, pyrimidinyl, thienyl, benzothiofuranyl, naphthalenyl, and tetrahydronaphthalenyl, each substituted with one or more substituents selected from the group consisting of $R^{21}$, $R^{22}$, and $R^{23}$; and $G^7$ can be selected from the group consisting of a aryl and heteroaryl, each optionally substituted with one or more substituents selected from the group consisting of $R^{24}$, $R^{25}$, and $R^{26}$, said aryl and heteroaryl in the definition of $G^7$ can each be further optionally fused with an optionally substituted nonaromatic heterocycle or an optionally substituted nonaromatic carbocycle.

Some embodiments disclosed herein provide a compound of Formula IIId having the structure of Formula IIIdb:

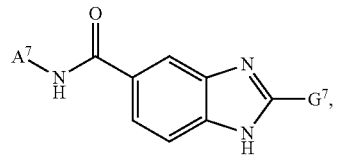

and pharmaceutically acceptable salts, esters, or prodrugs thereof, wherein $A^7$ can be selected from the group consisting of phenyl, indolyl, pyridinyl, pyrimidinyl, thienyl, benzothiofuranyl, naphthalenyl, and tetrahydronaphthalenyl, each substituted with one or more substituents selected from the group consisting of $R^{21}$, $R^{22}$, and $R^{23}$; and $G^7$ can be selected from the group consisting of a aryl and heteroaryl, each optionally substituted with one or more substituents selected from the group consisting of $R^{24}$, $R^{25}$, and $R^{26}$, said aryl and heteroaryl in the definition of $G^7$ can each be further optionally fused with an optionally substituted nonaromatic heterocycle or an optionally substituted nonaromatic carbocycle.

Some embodiments disclosed herein provide a compound of Formula IIIda or Formula IIIdb, wherein $G^7$ can be selected from the group consisting of phenyl, naphthyl, indolyl, dihydrobenzofuranyl, 1,4-benzodioxanyl, benzotriazolyl, benzimidazolyl, benzofuranyl, and 2,1,3-benzoxadiazolyl, each optionally substituted with one or more substituents selected from the group consisting of $R^{24}$, $R^{25}$, and $R^{26}$. In some embodiments, $R^{21}$ can be selected from the group consisting of halogen, an optionally substituted $C_1$-$C_6$ alkyl, an optionally substituted $C_1$-$C_6$ alkoxy, and an optionally substituted $C_3$-$C_7$ cycloalkyl; $R^{22}$ can be selected from the group consisting of $—(CH_2)_mOR^A$, $—O(CH_2)_mOR^A$, and $—NR^BR^C$; $R^{23}$ can be selected from the group consisting of $—(CH_2)_mOR^D$, $—(CH_2)_mS(O)_{0-2}R^D$, and $—(CH_2)_mR^G$; $R^{24}$ can be selected from the group consisting of halogen, an optionally substituted $C_1$-$C_6$ alkyl, an optionally substituted $C_1$-$C_6$ alkoxy, an optionally substituted $C_3$-$C_7$ cycloalkyl; $R^{25}$ can be selected from the group consisting of $—(CH_2)_mOR^A$, $—O(CH_2)_mOR^A$, $—C(=O)NR^BR^C$, $—C(=NNR^BR^C)H$, $—NR^BR^C$; $R^{26}$ can be selected from the group consisting of $—(CH_2)_mOR^D$, $—(CH_2)_mR^G$; $R^A$ can be selected from the group consisting of hydrogen, $C_1$-$C_6$ alkyl, $C_3$-$C_7$ cycloalkyl, and $C_1$-$C_6$ haloalkyl; each $—NR^BR^C$ can be separately selected, wherein $R^B$ and $R^C$ can each be independently selected from the group consisting of hydrogen, $—SO_2R^H$, $—C(=O)R^H$, $—(CH_2)_nOR^H$, $—(CH_2)_mR^I$, $—(CH_2)_mR^J$, $—(CH_2)_nC(=O)NR^ER^F$, $—(CH_2)_nNR^ER^F$, $—SO_2NR^ER^F$, $C_1$-$C_6$ alkyl, $C_1$-$C_6$ haloalkyl, $C_1$-$C_6$ heteroalkyl, $C_3$-$C_7$ cycloalkyl, and $C_1$-$C_6$ heterohaloalkyl where the alkyl and the heteroalkyl are optionally fused with an aryl or heteroaryl; or —NR$^B$R$^C$ can be an optionally substituted heterocycle; each R$^D$ can be independently selected from the group consisting of hydrogen, an optionally substituted C$_1$-C$_6$ alkyl, and —(CH$_2$)$_m$R$^I$; each —NR$^E$R$^F$ can be separately selected, wherein R$^E$ and R$^F$ can each be independently selected from the group consisting of hydrogen, an optionally substituted C$_1$-C$_6$ alkyl, and —(CH$_2$)$_m$R$^G$; or —NR$^E$R$^F$ can be an optionally substituted C$_1$-C$_6$ alkylideneamino; or —NR$^E$R$^F$ can be an optionally substituted heterocycle; each R$^G$ can be independently selected from the group consisting of an optionally substituted aryl and an optionally substituted heteroaryl; each R$^H$ can be independently selected from the group consisting of hydrogen, C$_1$-C$_3$ alkoxy, C$_1$-C$_3$ alkyl, C$_1$-C$_3$ haloalkyl, an optionally substituted aryl and optionally substituted heteroaryl; each R$^I$ can be independently selected from the group consisting of an optionally substituted aryl and an optionally substituted heteroaryl; each R$^J$ can be independently selected from the group consisting of aryl and heteroaryl, each substituted with one or more —NR$^E$R$^F$; each m can be independently 0, 1, or 2; and each n can be independently 0, 1, 2, 3, or 4.

Some embodiments disclosed herein provide a compound of Formula III having the proviso that a compound of Formula III is not selected from the group consisting of:

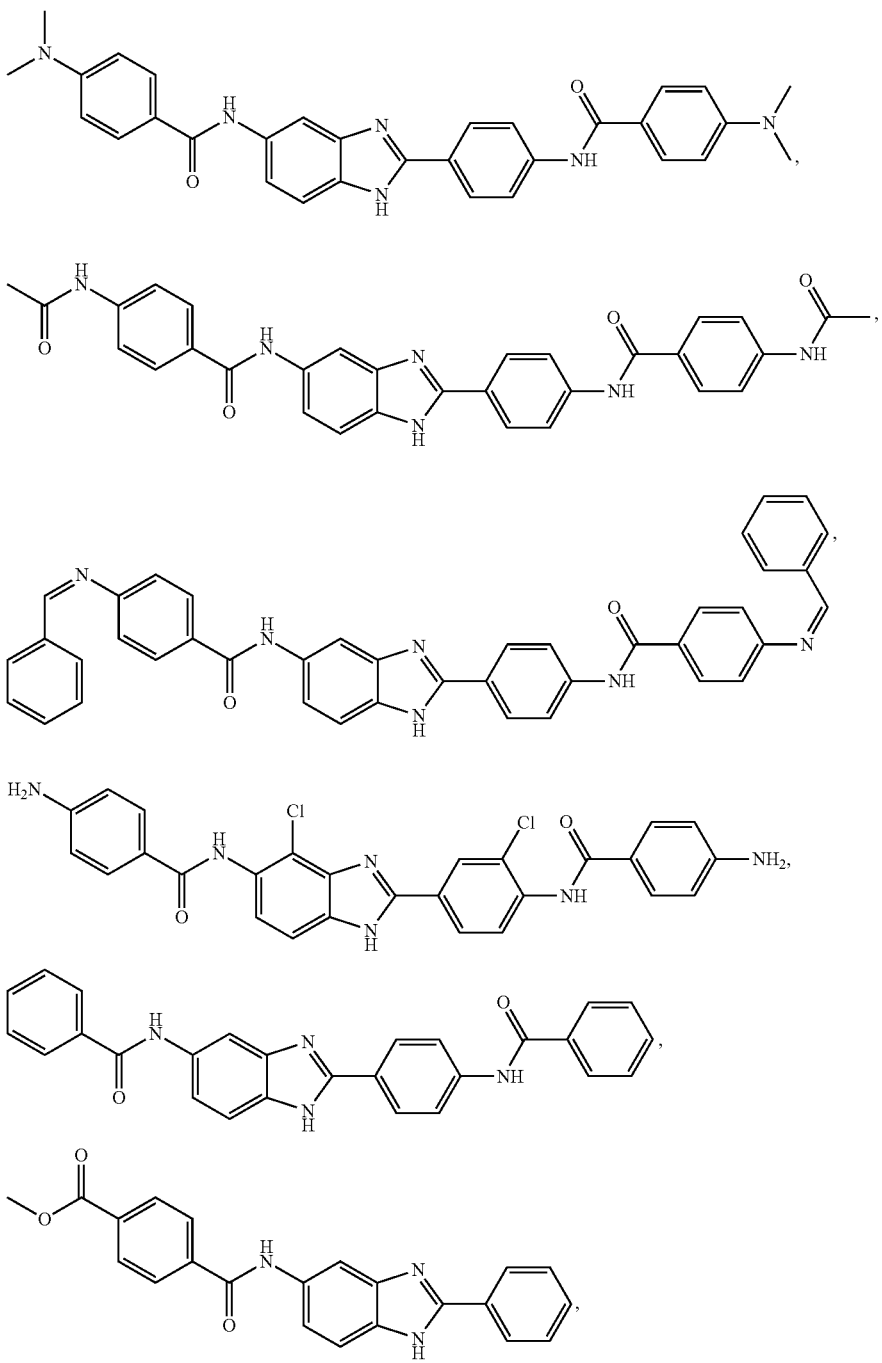

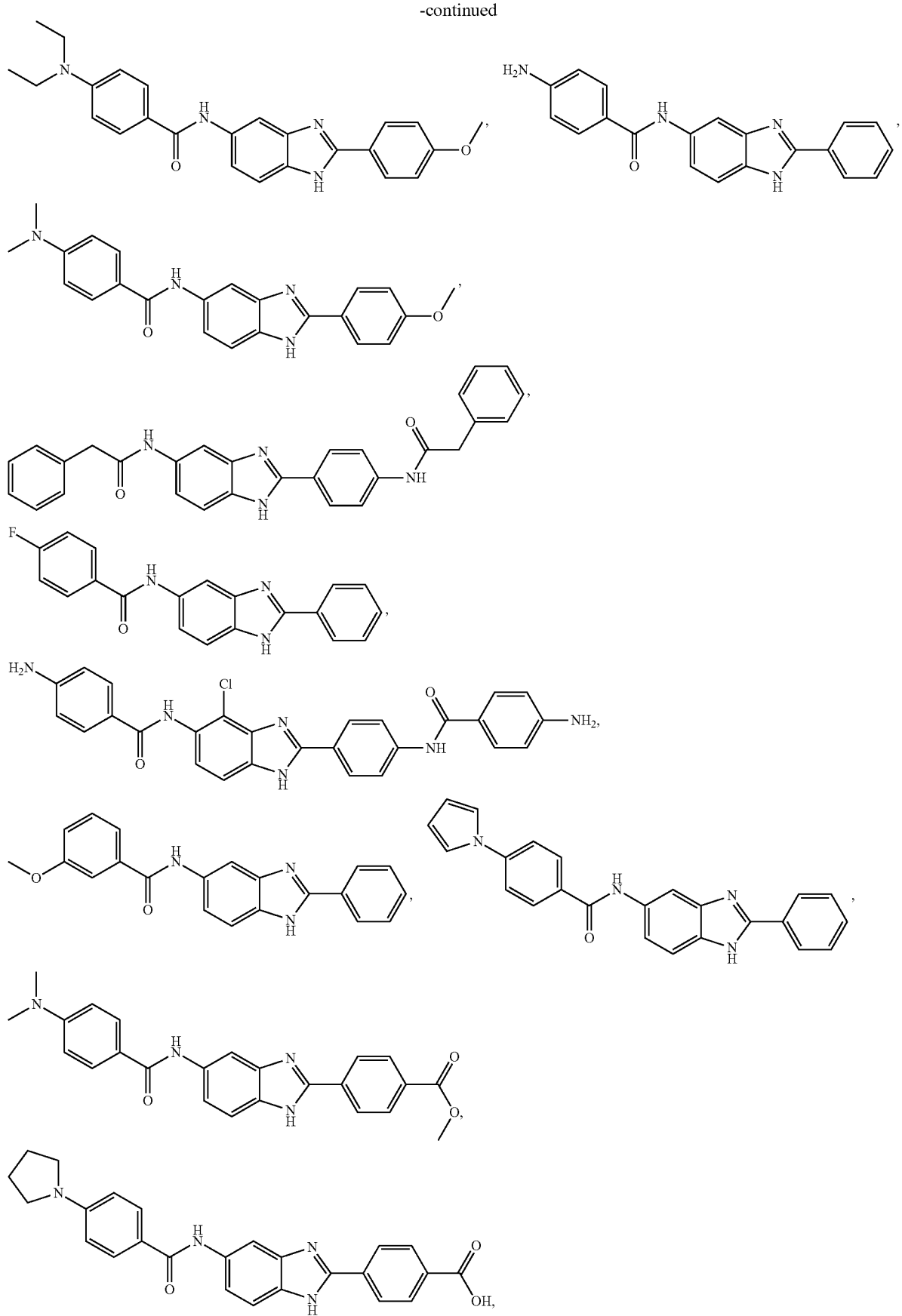

-continued
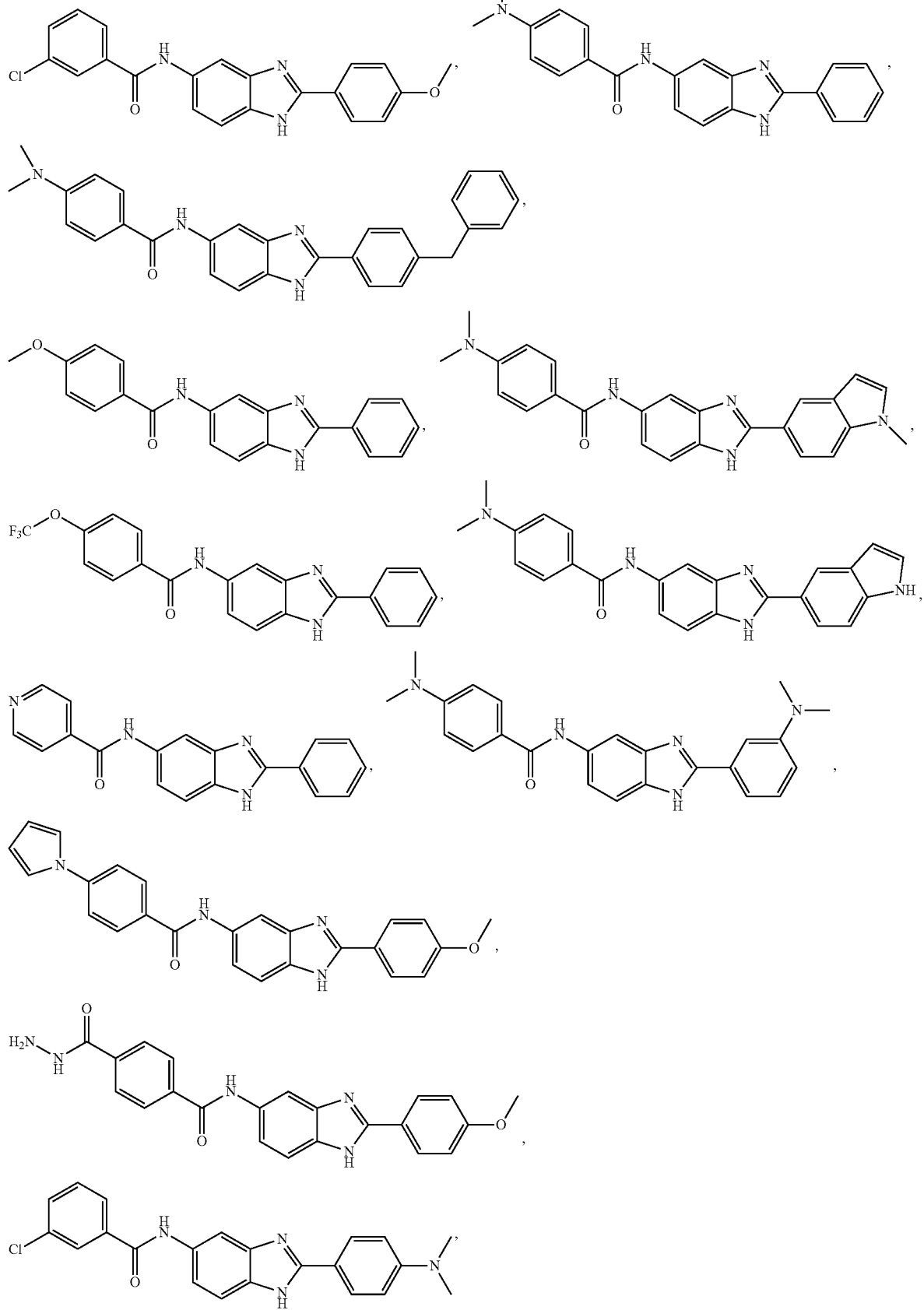

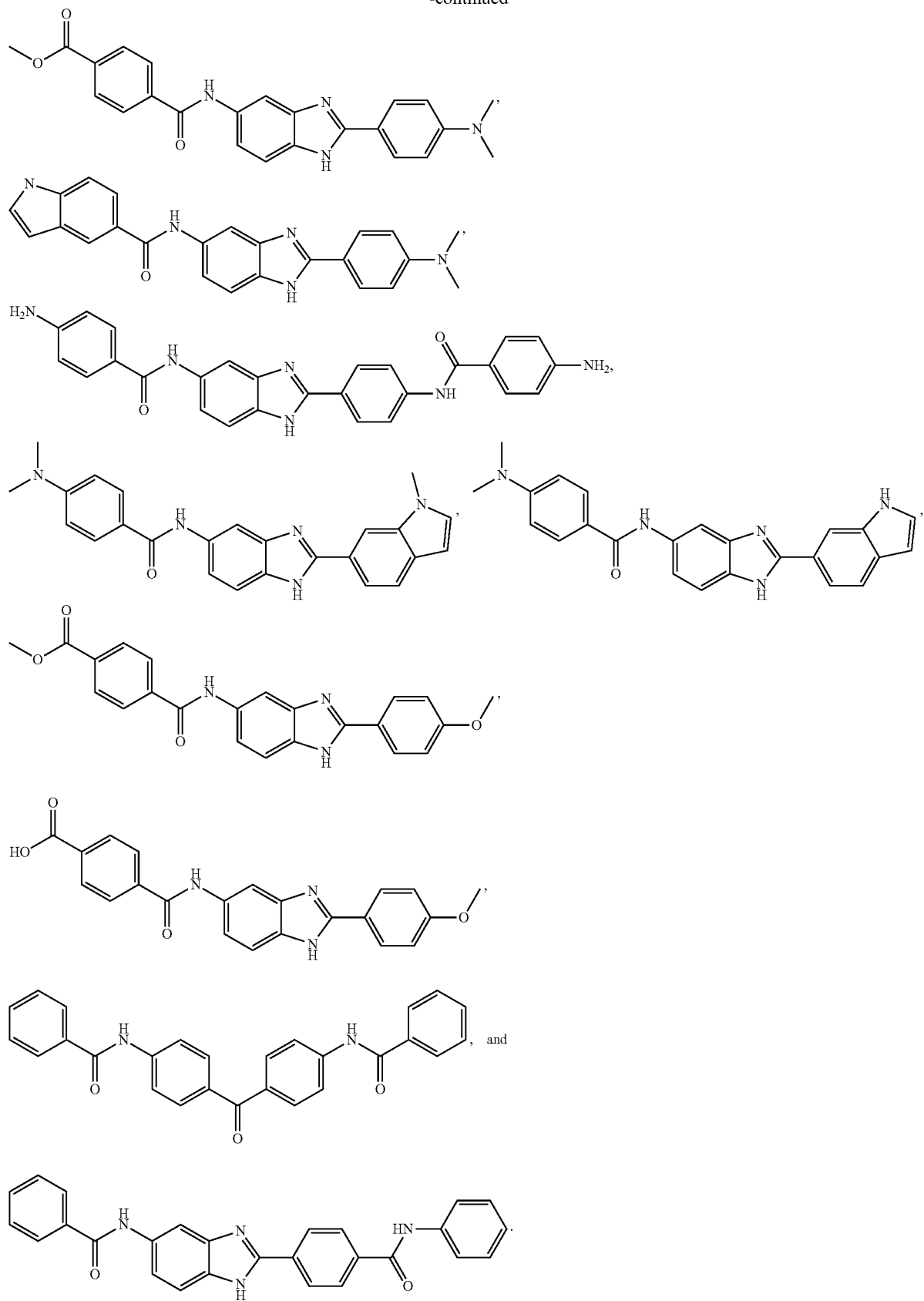

Some embodiments disclosed herein provide a compound of Formula IV:

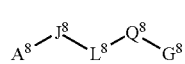 (IV)

and pharmaceutically acceptable salts, esters stereoisomers, tautomers or prodrugs thereof;

wherein:

$A^8$ is selected from the group consisting of heterocycle, aryl and heteroaryl, each optionally substituted with one or more substituents selected from the group consisting of $R^{31}$, $R^{32}$, and $R^{33}$, said aryl and heteroaryl in the definition of $A^8$ are each further optionally fused with an optionally substituted nonaromatic heterocycle or an optionally substituted nonaromatic carbocycle;

$G^8$ is selected from the group consisting of aryl and heteroaryl, each optionally substituted with one or more substituents selected from the group consisting of $R^{34}$, $R^{35}$, and $R^{36}$, said aryl and heteroaryl in the definition of $G^8$ are each further optionally fused with an optionally substituted nonaromatic heterocycle or an optionally substituted nonaromatic carbocycle;

$J^8$ is selected from the group consisting of aryl, heteroaryl, heterocycle, —C(=O)—, —(CH=CH)—, —OC(=O)—, —NHC(=O)NH—, —NHC(=S)NH—, —S(=O)$_2$—NH$_2$—, —OC(=S)—, —NHC(=S)—, —(CH$_2$)$_n$NH—, —(CH$_2$)$_n$[NHC(=O)](CH$_2$)$_o$NHC(=O)(CH$_2$)$_p$—, —(CH$_2$)$_n$[NHC(=O)](CH$_2$)$_o$[NH]$_q$—,

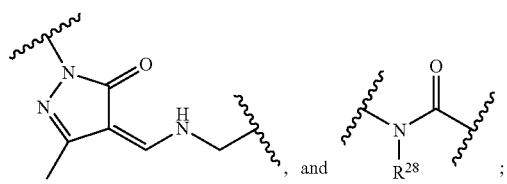, and or $J^8$ is null;

$Q^8$ is selected from the group consisting of aryl, heteroaryl, heterocycle, —C(=O)—, —(CH=CH)—, —OC(=O)—, —NHC(=O)NH—, —NHC(=S)NH—, —S(=O)$_2$—NH$_2$—, —OC(=S)—, —NHC(=S)—, —(CH$_2$)$_n$NH—, —(CH$_2$)$_n$[NHC(=O)](CH$_2$)$_o$NHC(=O)(CH$_2$)$_p$—, —(CH$_2$)$_n$[NHC(=O)](CH$_2$)$_o$[NH]$_q$—,

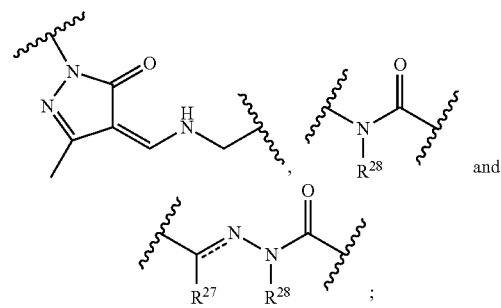

or $Q^8$ is null;

$L^8$ is selected from the group consisting of

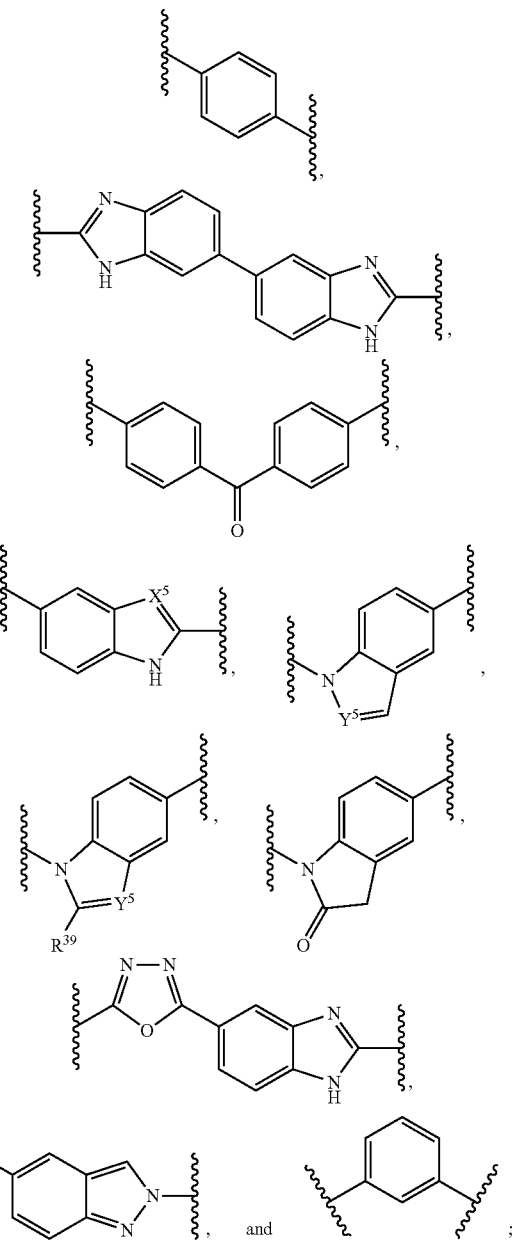

$X^5$ is selected from the group consisting of N (nitrogen) and $CR^{39}$;

$Y^5$ is selected from the group consisting of N (nitrogen) and $CR^{40}$;

each $R^{27}$ is independently selected from the group consisting of hydrogen, halogen, and an optionally substituted $C_1$-$C_4$ alkyl;

each $R^{28}$ is independently selected from the group consisting of hydrogen and an optionally substituted $C_1$-$C_4$ alkyl;

each $R^{31}$ is independently selected from the group consisting of halogen, cyano, an optionally substituted $C_1$-$C_6$ alkyl, an optionally substituted $C_1$-$C_6$ alkoxy, an optionally substituted $C_2$-$C_4$ alkenyl, an optionally substituted $C_2$-$C_4$ alkynyl, an optionally substituted $C_3$-$C_7$ cycloalkyl, an optionally substituted $C_1$-$C_6$ haloalkyl, and an optionally substituted $C_1$-$C_6$ heteroalkyl;

each $R^{32}$ is independently selected from the group consisting of halogen, —$(CH_2)_mOR^A$, —$NR^BR^C$, and —$(CH_2)_mSR^A$;

each $R^{33}$ is independently selected from the group consisting of halogen, —C(=O)OH, —$(CH_2)_mOR^D$, —$NR^ER^F$, —$NR^LC(=O)NR^BR^C$, —$(CH_2)_mS(O)_{0-2}R^D$, —$(CH_2)_mNO_2$, —$(CH_2)_mCN$, and —$(CH_2)_mR^G$;

each $R^{34}$ is independently selected from the group consisting of halogen, cyano, an optionally substituted $C_1$-$C_6$ alkyl, an optionally substituted $C_1$-$C_6$ alkoxy, an optionally substituted $C_2$-$C_4$ alkenyl, an optionally substituted $C_2$-$C_4$ alkynyl, an optionally substituted $C_3$-$C_7$ cycloalkyl, an optionally substituted $C_1$-$C_6$ haloalkyl, and an optionally substituted $C_1$-$C_6$ heteroalkyl;

each $R^{35}$ is independently selected from the group consisting of halogen, —C(=O)OH, —$(CH_2)_mOR^A$, —$NR^BR^C$, —C(=O)$NR^BR^C$, and —$(CH_2)_mSR^A$;

each $R^{36}$ is independently selected from the group consisting of halogen, —$(CH_2)_mOR^D$, —$NR^ER^F$, —$NR^LC(=O)NR^BR^C$, —$(CH_2)_mS(O)_{0-2}R^D$, —$(CH_2)_mNO_2$, —$(CH_2)_mCN$, and —$(CH_2)_mR^G$;

each $R^{39}$ and $R^{40}$ are independently selected from the group consisting of hydrogen, halogen, —OH, —$NHR^B$, and an optionally substituted $C_1$-$C_4$ alkyl;

each $R^A$ is independently selected from the group consisting of hydrogen, $C_1$-$C_6$ alkyl, $C_1$-$C_6$ haloalkyl, $C_1$-$C_6$ heteroalkyl, and $C_1$-$C_6$ heterohaloalkyl;

each —$NR^BR^C$ is separately selected, wherein $R^B$ and $R^C$ are each independently selected from the group consisting of hydrogen, —$SO_2R^H$, —C(=O)$R^H$, —C(=O)C(=O)$R^H$, —$(CH_2)_mC(=O)OR^H$, —C(=O)$NR^ER^F$, —$(CH_2)_mR^G$, —$(CH_2)_mOR^H$, —$(CH_2)_mR^H$, $C_1$-$C_6$ alkyl, $C_3$-$C_7$ cycloalkyl, $C_2$-$C_6$ alkenyl, non-aromatic heterocycle, $C_1$-$C_6$ haloalkyl, $C_1$-$C_6$ heteroalkyl, and $C_1$-$C_6$ heterohaloalkyl where the $C_3$-$C_7$ cycloalkyl and the non-aromatic heterocycle are optionally fused with an optionally substituted aryl or an optionally substituted heteroaryl; or —$NR^BR^C$ is an optionally substituted non-aromatic heterocycle linked through a ring nitrogen atom; or —$NR^BR^C$ is an optionally substituted $C_1$-$C_6$ alkylideneamino;

each $R^D$ is independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and —$(CH_2)_mR^G$ each —$NR^ER^F$ is separately selected, wherein $R^E$ and $R^F$ are each independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and —$(CH_2)_mR^G$; or —$NR^ER^F$ is an optionally substituted $C_1$-$C_6$ alkylideneaminyl; or —$NR^ER^F$ is an optionally substituted non-aromatic heterocycle linked through a ring nitrogen atom;

each $R^G$ is independently selected from an optionally substituted aryl and an optionally substituted heteroaryl;

$R^H$ is selected from the group consisting of hydrogen, $C_1$-$C_3$ alkyl, $C_1$-$C_3$ haloalkyl, $C_3$-$C_7$ cycloalkyl, and an optionally substituted aryl or an optionally substituted heteroaryl;

each $R^L$ is independently selected from the group consisting of $C_3$-$C_7$ cycloalkyl, optionally substituted $C_1$-$C_6$ alkyl, optionally substituted $C_1$-$C_6$ alkoxy, —$(CH_2)_mOR^{LA}$, —$(CH_2)_mNR^{LB}R^{LC}$, aryl and heteroaryl, said aryl and heteroaryl in the definition of $R^L$ are each independently optionally substituted with one or more substituents selected from the group consisting of halo, $C_1$-$C_6$ alkyl, $C_1$-$C_6$ haloalkyl, $C_1$-$C_6$ alkoxy, —$(CH_2)_mNR^{LD}R^{LE}$, aryl and heteroaryl, said aryl and heteroaryl substituent off of $R^L$ are each optionally substituted with one or more halo, $C_1$-$C_6$ alkyl, $C_1$-$C_6$ haloalkyl, $C_1$-$C_6$ alkoxy, or —$(CH_2)_mNR^{LF}R^{LG}$;

each $R^{LA}$ is independently selected from the group consisting of hydrogen, $C_1$-$C_6$ alkyl, and $C_1$-$C_6$ haloalkyl;

$R^{LB}$ and $R^{LC}$ are each independently selected from the group consisting of hydrogen, $C_1$-$C_6$ alkyl, $C_1$-$C_6$ haloalkyl, and $C_1$-$C_6$ heteroalkenyl; or —$NR^{LB}R^{LC}$ is an optionally substituted non-aromatic heterocycle linked through a ring nitrogen atom;

each —$NR^{LD}R^{LE}$ is separately selected, wherein $R^{LD}$ and $R^{LE}$ are each independently selected from the group consisting of hydrogen, aryl, heteroaryl, and optionally substituted $C_1$-$C_6$ alkyl, said aryl and heteroaryl in the definition of $R^{LD}$ and $R^{LE}$ are each optionally substituted with $C_1$-$C_6$ alkyl or $C_1$-$C_6$ alkoxy; or —$NR^{LD}R^{LE}$ is an optionally substituted non-aromatic heterocycle linked through a ring nitrogen atom;

each —$NR^{LF}R^{LG}$ is separately selected, wherein $R^{LF}$ and $R^{LG}$ are each independently selected from the group consisting of hydrogen, and $C_1$-$C_6$ alkyl; or —$NR^{LF}R^{LG}$ is an optionally substituted non-aromatic heterocycle linked through a ring nitrogen atom;

each —$NR^{LF}R^{LG}$ is separately selected, wherein $R^{LF}$ and $R^{LG}$ are each independently selected from the group consisting of hydrogen, and $C_1$-$C_6$ alkyl; or —$NR^{LF}R^{LG}$ is an optionally substituted non-aromatic heterocycle linked through a ring nitrogen atom;

each m is independently 0, 1, or 2;

each n is independently 0, 1, 2, 3, or 4;

each o is independently 1, 2, or 3;

each p is independently 0, 1, 2, or 3;

each q is independently 0 or 1; and any bond represented by a dashed and solid line represents a bond selected from the group consisting of a single bond and a double bond.

Some embodiments disclosed herein provide a compound of Formula IV, wherein $J^8$ and $Q^8$ can each be null. Some embodiments disclosed herein provide a compound of Formula IV, wherein $A^8$ can be aryl substituted with one or more substituents selected from the group consisting of $R^{31}$, $R^{32}$, and $R^{33}$; $J^8$ can be —NHC(=O)—; $L^8$ can be

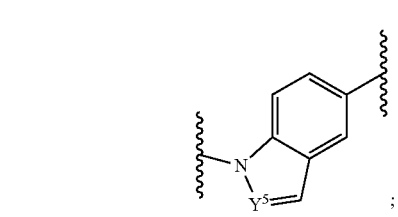

$Q^8$ can be null; and $G^8$ can be aryl substituted with one or more substituents selected from the group consisting of $R^{34}$, $R^{35}$, and $R^{36}$. Some embodiments disclosed herein provide a compound of Formula IV, wherein $A^8$ can be aryl substituted with one or more $R^{32}$; $J^8$ can be —C(=O)—; $L^8$ can be

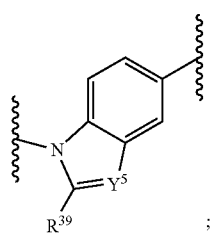

$Q^8$ can be

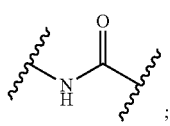 [SMILES: *NC(*)=O]

and $G^8$ can be aryl substituted with one or more $R^{35}$. Some embodiments disclosed herein provide a compound of Formula IV, wherein $A^8$ can be heteroaryl substituted with one or more substituents selected from the group consisting of $R^{31}$, $R^{32}$, and $R^{33}$; $G^8$ can be heteroaryl substituted with one or more substituents selected from the group consisting of $R^{34}$, $R^{35}$, and $R^{36}$; $J^8$ can be

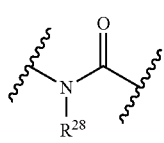

and $Q^8$ can be

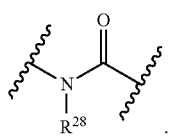

Some embodiments disclosed herein provide a compound of Formula IV, wherein $L^8$ can be

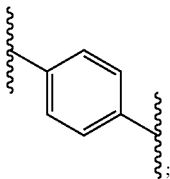 [SMILES: *c1ccc(*)cc1]

$J^8$ can be —C(=O)—; $Q^8$ can be —C(=O)NH—; $A^8$ can be aryl substituted with $R^{32}$; $G^8$ can be aryl substituted with $R^{35}$; $R^{32}$ can be —NR$^B$R$^C$, and $R^{35}$ can be —NR$^B$R$^C$.

Some embodiments disclosed herein provide a compound of Formula IV having the structure of Formula IVa:

and pharmaceutically acceptable salts thereof, wherein $J^8$ can be selected from the group consisting —OC(=O)—, —S(=O)$_2$—NH$_2$—, —(CH$_2$)$_n$NH—, and

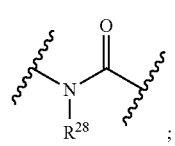

and $Q^8$ can be selected from the group consisting —OC(=O)—, —S(=O)$_2$—NH$_2$—, —(CH$_2$)$_n$NH—, and

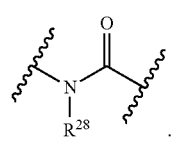

Some embodiments disclosed herein provide a compound of Formula IVa, wherein $J^8$ can be selected from the group consisting of —S(=O)$_2$—NH$_2$— and

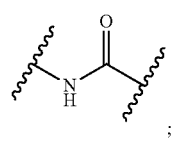 [SMILES: *NC(*)=O]

and $Q^8$ can be selected from the group consisting —S(=O)$_2$—NH$_2$—, and

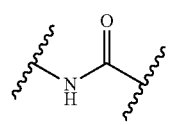

Some embodiments disclosed herein provide a compound of Formula IV having the structure of Formula IVb:

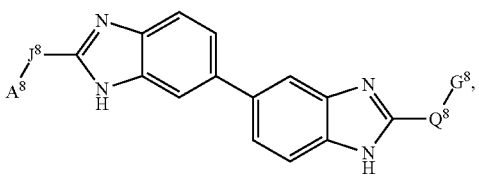

and pharmaceutically acceptable salts thereof, wherein $J^8$ can be —CH=CH—; or $J^8$ can be null; and $Q^8$ can be —CH=CH—; or $Q^8$ can be null.

Some embodiments disclosed herein provide a compound of Formula IVb having the structure of Formula IVba:

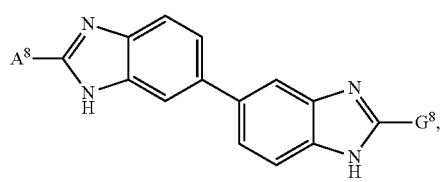
(IVba)

and pharmaceutically acceptable salts thereof.

Some embodiments disclosed herein provide a compound of Formula IVb having the structure of Formula IVbc:

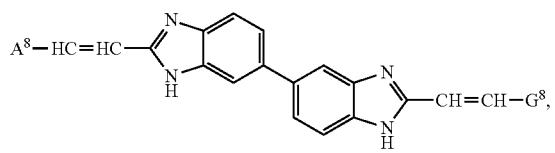
(IVba)

and pharmaceutically acceptable salts thereof.

Some embodiments disclosed herein provide a compound of Formula IV having the structure of Formula IVc:

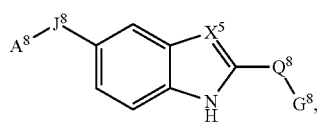
(IVc)

and pharmaceutically acceptable salts thereof, wherein $J^8$ can be selected from the group consisting of —OC(=O)—, —NHC(=O)NH—, —S(=O)$_2$—NH$_2$—, and

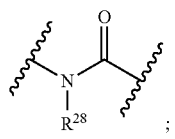
;

or $J^8$ can be null; $Q^8$ can be selected from the group consisting of —OC(=O)—, —NHC(=O)NH—, —S(=O)$_2$—NH$_2$—, and

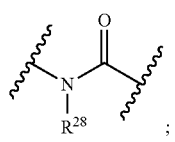
;

or Q can be null.

Some embodiments disclosed herein provide a compound of Formula IVc having the structure of Formula IVca:

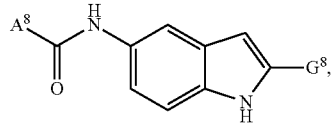
(IVca)

and pharmaceutically acceptable salts thereof, or having the structure of Formula IVcb:

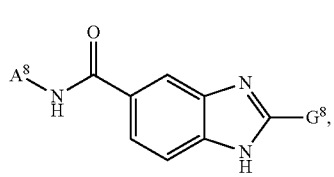
(IVcb)

and pharmaceutically acceptable salts thereof, or having the structure of Formula IVcc:

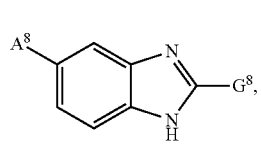
(IVcc)

and pharmaceutically acceptable salts thereof.

Some embodiments disclosed herein provide a compound of Formula IV having the structure of Formula IVd:

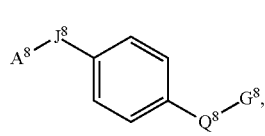
(IVd)

and pharmaceutically acceptable salts thereof, wherein $J^8$ can be selected from the group consisting of —C(=O)—, —(CH$_2$)NH—, —NHC(=S)NH—, and

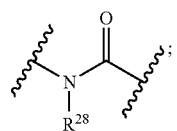
;

or $J^8$ can be null; $Q^8$ can be selected from the group consisting of —C(=O)—, —NHC(=S)NH—, and

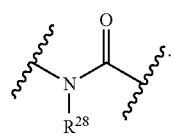
.

Some embodiments disclosed herein provide a compound of Formula IVd having the structure of Formula IVda:

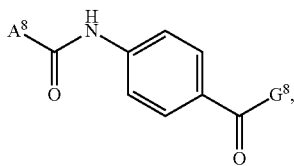

(IVda)

and pharmaceutically acceptable salts thereof, or having the structure of Formula IVdb:

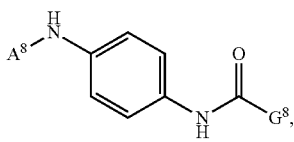

(IVdb)

and pharmaceutically acceptable salts thereof, or having the structure of Formula IVdc:

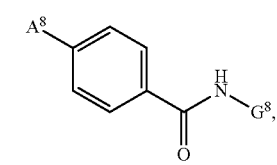

(IVdc)

and pharmaceutically acceptable salts thereof, or having the structure of Formula IVde:

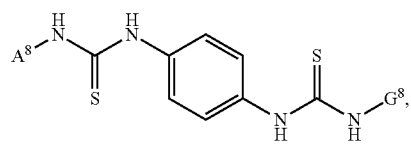

(IVde)

and pharmaceutically acceptable salts thereof.

Some embodiments disclosed herein provide a compound of Formula IV having the structure of Formula IVe:

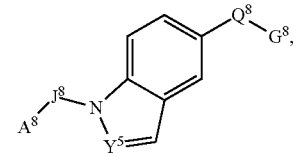

(IVe)

and pharmaceutically acceptable salts thereof, wherein $J^8$ can be null; and $Q^8$ can be

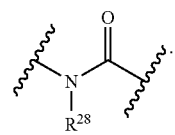

Some embodiments disclosed herein provide a compound of Formula IVe having the structure of Formula IVea:

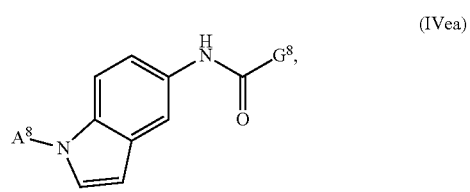

(IVea)

and pharmaceutically acceptable salts thereof, or having the structure of Formula IVeb:

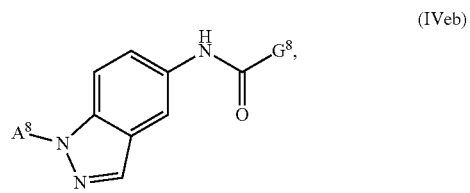

(IVeb)

and pharmaceutically acceptable salts thereof, or having the structure of Formula IVec:

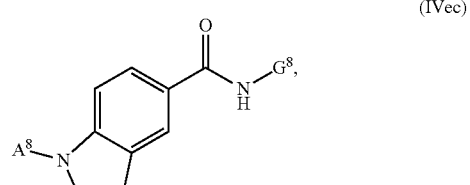

(IVec)

and pharmaceutically acceptable salts thereof.

Some embodiments disclosed herein provide a compound of Formula IV having the structure of Formula IVf:

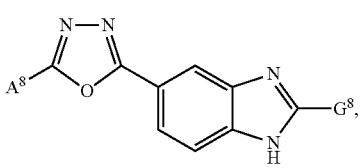

(IVf)

and pharmaceutically acceptable salts thereof.

Some embodiments disclosed herein provide a compound of Formula IV having the structure of Formula IVg:

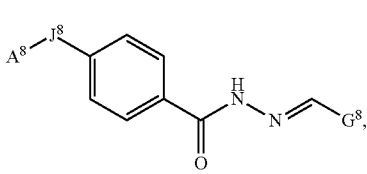

(IVg)

and pharmaceutically acceptable salts thereof, wherein $J^8$ can be selected from the group consisting of —(CH$_2$)$_n$[NHC(=O)](CH$_2$)$_o$NHC(=O)(CH$_2$)$_p$— and —(CH$_2$)$_n$[NHC(=O)](CH$_2$)$_o$[NH]$_q$—.

Some embodiments disclosed herein provide a compound of Formula IV having the structure of Formula IVh:

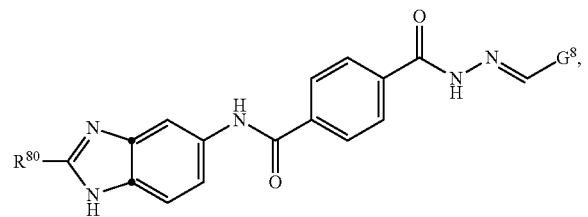

(IVh)

and pharmaceutically acceptable salts thereof, wherein $R^{80}$ can be selected from the group consisting of hydrogen, $R^{31}$, $R^{32}$, and $R^{33}$.

Some embodiments disclosed herein provide a compound of Formula IV having the structure of Formula IVi:

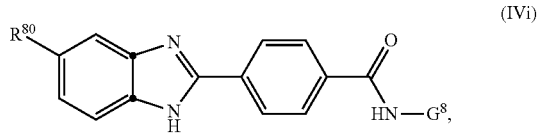

(IVi)

and pharmaceutically acceptable salts thereof, wherein $R^{80}$ can be selected from the group consisting of hydrogen, $R^{31}$, $R^{32}$, and $R^{33}$. Some embodiments disclosed herein provide a compound of Formula IVi, wherein $G^8$ can be phenyl optionally substituted with one or more substituents selected from the group consisting of $R^{34}$, $R^{35}$, and $R^{36}$.

Some embodiments disclosed herein provide a compound of Formula IV having the proviso that a compound of Formula IV is not selected from the group consisting of:

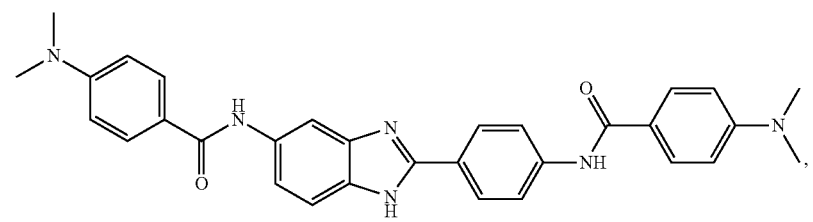

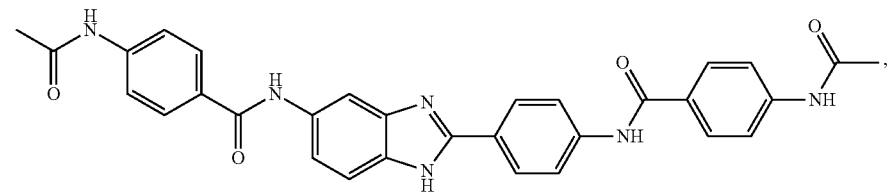

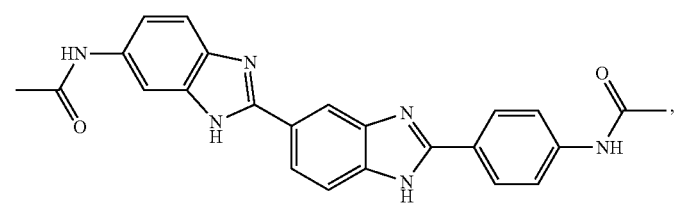

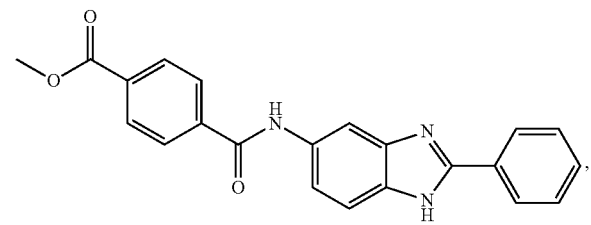

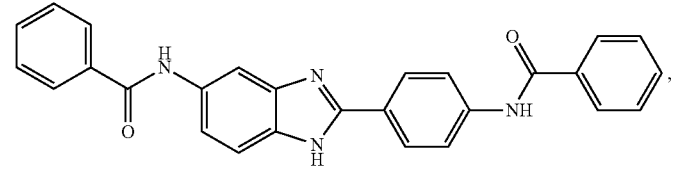

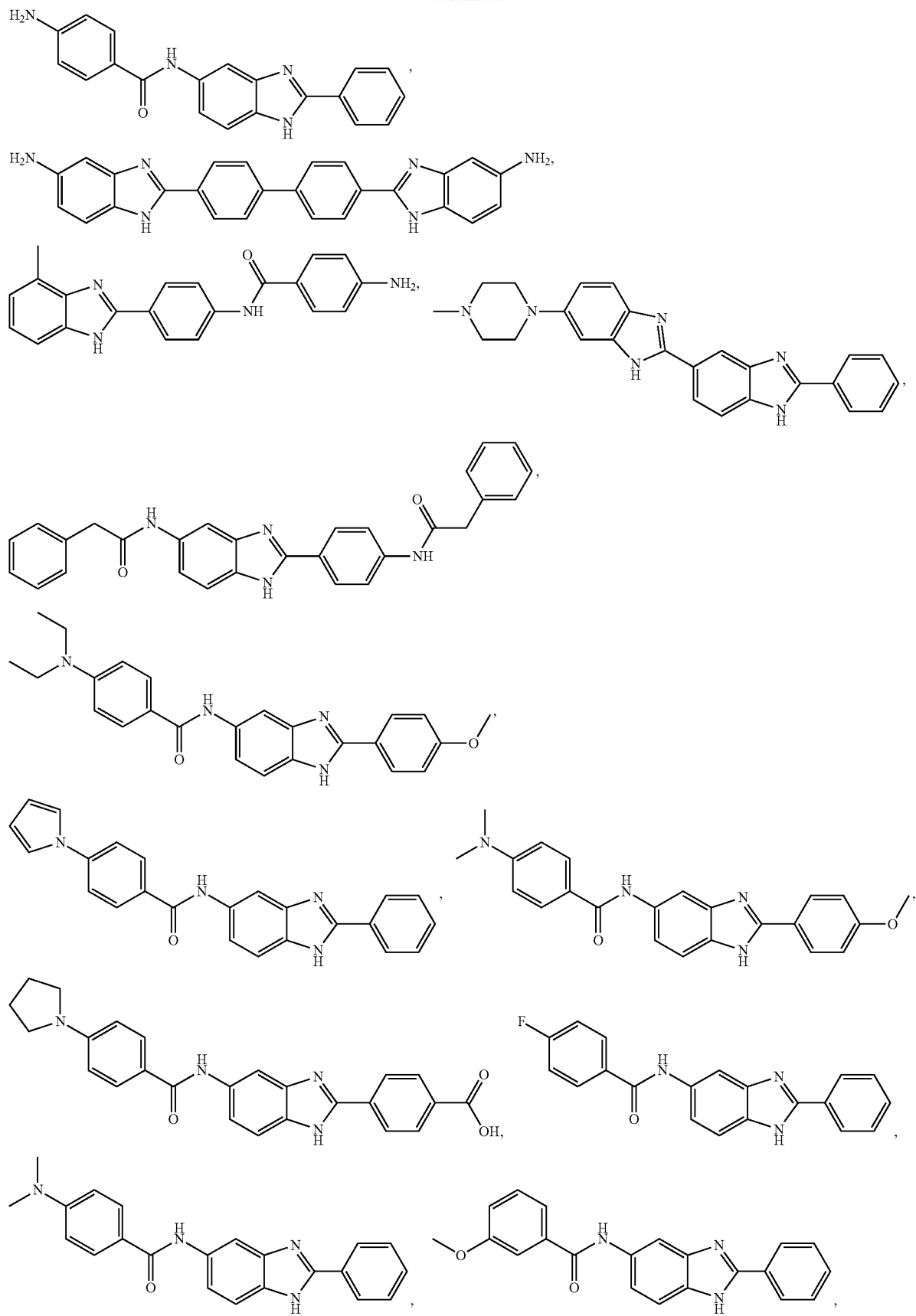

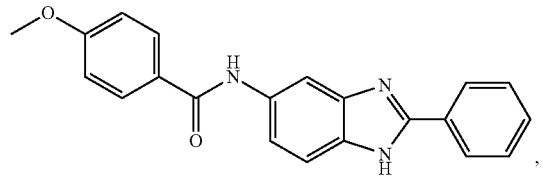
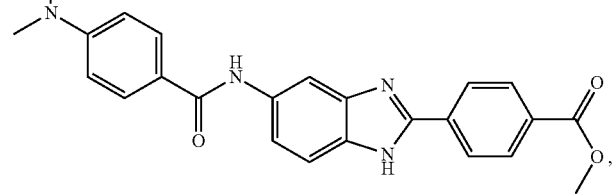
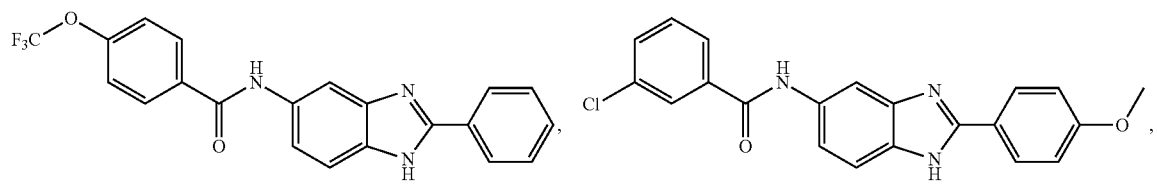
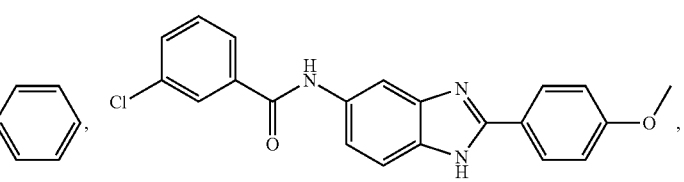
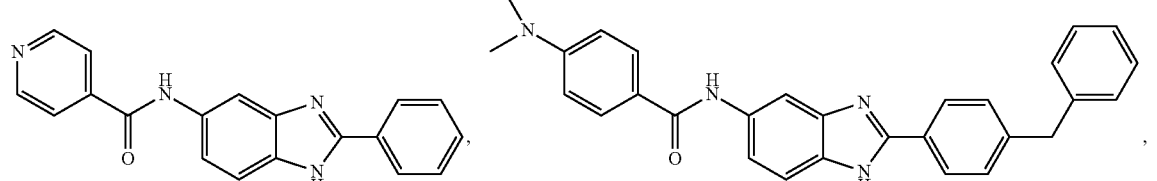
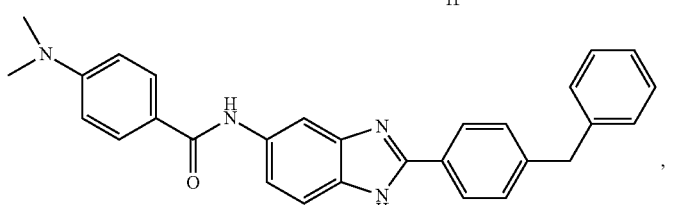
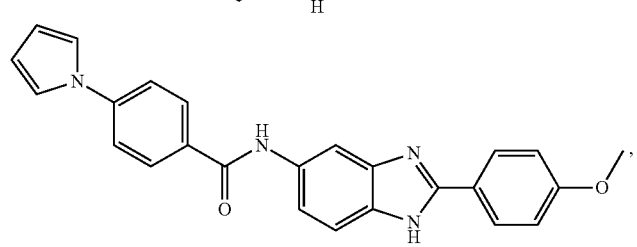
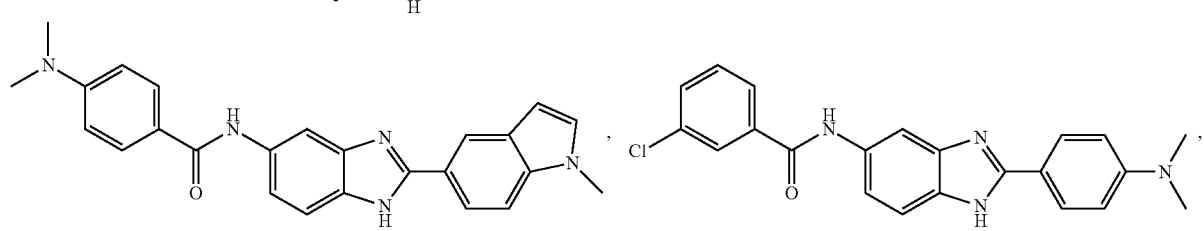
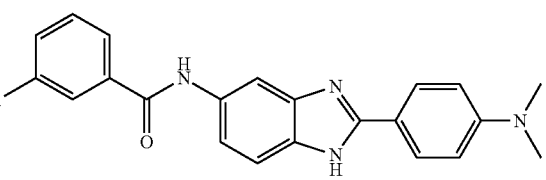
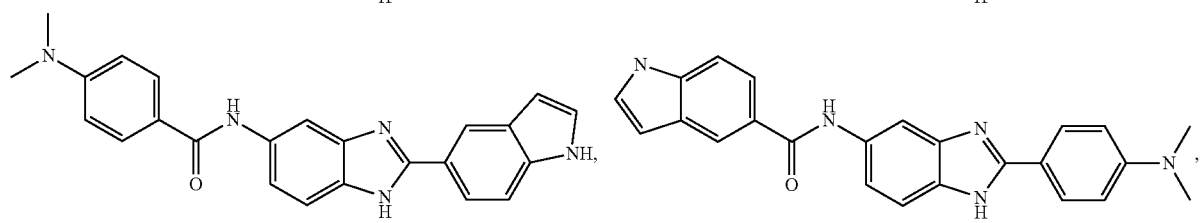
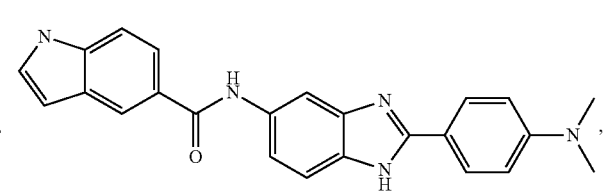
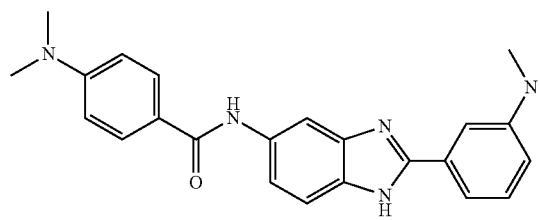
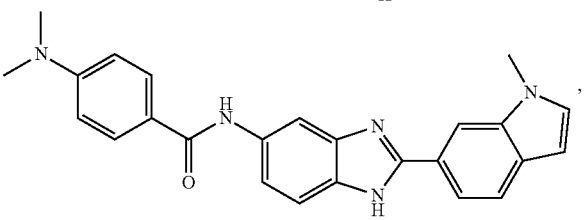
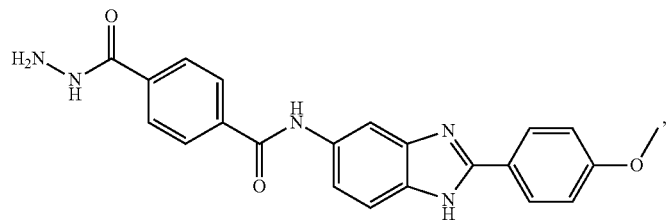

-continued
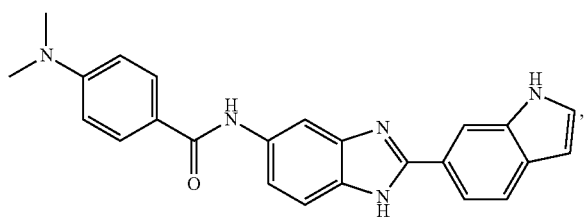
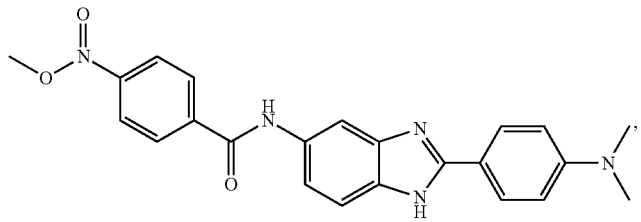
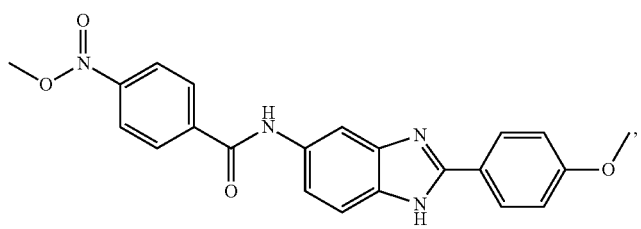
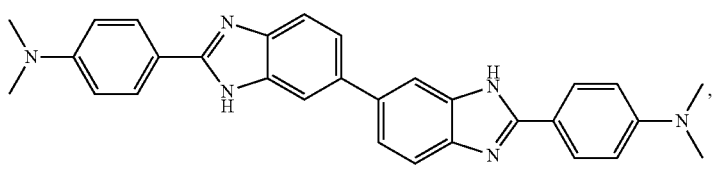
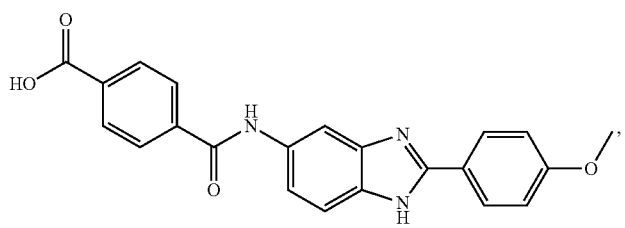
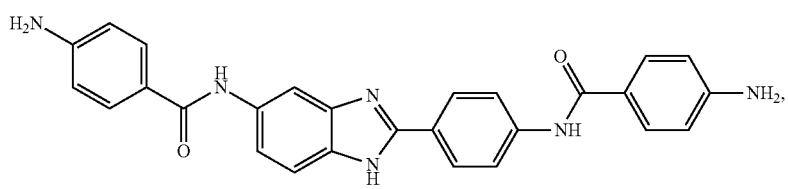
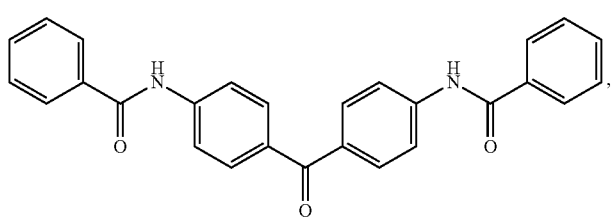
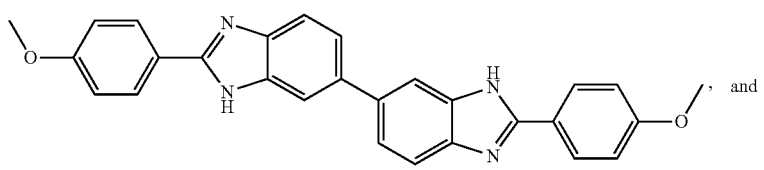

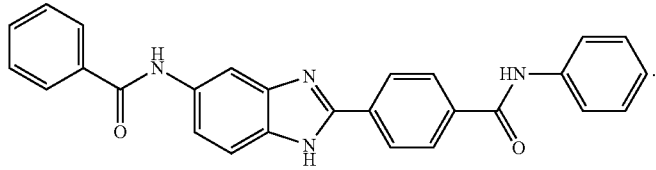

Some embodiments disclosed herein provide a compound of Formula V:

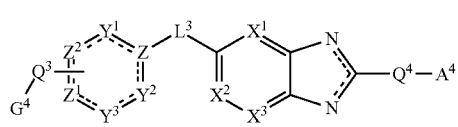

and pharmaceutically acceptable salts, esters, stereoisomers, tautomers or prodrugs thereof;

wherein:

$G^4$ is selected from the group consisting of is selected from the group consisting of aryl and heteroaryl, each optionally substituted with one or more substituents selected from the group consisting of $R^{43}$ and $R^{44}$, said aryl and heteroaryl in the definition of $G^4$ are each further optionally fused with an optionally substituted nonaromatic heterocycle or an optionally substituted nonaromatic carbocycle;

$Q^3$ is selected from the group consisting of an ester, an amide, a urea, a carbamide, a thioamide, a sulfonamide; or $Q^3$ is selected from the group consisting of —C(=O)O—, —C(=O)NR$^{45}$—, —C(=O)NHN=CH—, —NR$^{45}$C(=O)NR$^{45}$—, —NR$^{45}$C(=O)(CH$_2$)$_m$O—, —OC(=O)NR$^{45}$—, —C(=S)NR$^{45}$—, —NR$^{45}$S(O)$_{1-2}$—, C$_1$-C$_6$ alkylideneamino, and

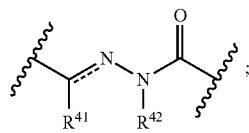

or when $Y^3$ is C (carbon) substituted with -Q$^3$-G$^4$ then $Q^3$ is optionally fused with $Z^1$ to form a five-member ring heterocycle;

$L^3$ is selected from the group consisting of —C(=O)NR$^{45}$—, —O—C$_1$-C$_8$ alkyl, —C(=NR$^{45}$)—, —NR$^{45}$C(=O)—(CH$_2$)$_m$C(=O)NR$^{45}$—, and —NR$^{45}$C(=O)—(CH$_2$)$_m$NR$^{45}$C(=O)—;

$Q^4$ is selected from the group consisting of NR$^{48}$, and O (oxygen); or $Q^4$ is null;

$A^4$ is selected from the group consisting of C$_1$-C$_6$ alkyl, C$_2$-C$_6$ alkenyl, C$_2$-C$_6$ alkynyl, C$_3$-C$_7$ cycloalkyl, C$_3$-C$_7$ cycloalkenyl, a C$_1$-C$_6$ heteroalkyl, phenyl, pyridinyl, imidazolyl, and thienyl, each optionally substituted with one or more substituents selected from the group consisting of R$^{41}$ and R$^{42}$;

$X^1$, $X^2$, and $X^3$ are each independently selected from N (nitrogen) and CR$^{46}$;

$Y^1$, $Y^2$, and $Y^3$ are each independently selected from N (nitrogen) and CR$^{47}$;

Z, $Z^1$, and $Z^2$ are each independently selected from C (carbon), CH, and N (nitrogen);

$R^{41}$ is independently selected from the group consisting of halogen, cyano, an optionally substituted C$_1$-C$_6$ alkyl, an optionally substituted C$_1$-C$_6$ alkoxy, an optionally substituted C$_2$-C$_4$ alkenyl, an optionally substituted C$_2$-C$_4$ alkynyl, an optionally substituted C$_3$-C$_7$ cycloalkyl, an optionally substituted C$_1$-C$_6$ haloalkyl, an optionally substituted C$_1$-C$_6$ heteroalkyl;

each $R^{42}$ is independently selected from the group consisting of —(CH$_2$)$_m$OR$^A$, —O(CH$_2$)$_m$OR$^A$, —NR$^B$R$^C$, —C(=O)NR$^B$R$^C$, —C(=NNR$^B$R$^C$)H, —(CH$_2$)$_m$SR$^A$, —(CH$_2$)$_m$R$^K$, —O(CH$_2$)$_m$R$^K$;

or $R^{41}$ and $R^{42}$ are linked to form an optionally substituted ring;

each $R^{43}$ is independently selected from the group consisting of halogen, cyano, an optionally substituted C$_1$-C$_6$ alkyl, an optionally substituted C$_1$-C$_6$ alkoxy, an optionally substituted C$_2$-C$_4$ alkenyl, an optionally substituted C$_2$-C$_4$ alkynyl, an optionally substituted C$_3$-C$_7$ cycloalkyl, an optionally substituted C$_1$-C$_6$ haloalkyl, an optionally substituted C$_1$-C$_6$ heteroalkyl;

each $R^{44}$ is independently selected from the group consisting of —(CH$_2$)$_m$OR$^A$, —O(CH$_2$)$_m$OR$^A$, —NR$^B$R$^C$, —C(=O)NR$^B$R$^C$, —C(=NNR$^B$R$^C$)H, —(CH$_2$)$_m$SR$^A$, —(CH$_2$)$_m$R$^K$, —O(CH$_2$)$_m$R$^K$;

each $R^{45}$ is independently selected from the group consisting of hydrogen, an optionally substituted C$_1$-C$_4$ alkyl, and an optionally substituted C$_1$-C$_6$ heteroalkyl;

each $R^{46}$ and $R^{47}$ is independently selected from the group consisting of hydrogen, halogen, an optionally substituted C$_1$-C$_6$ alkyl, and an optionally substituted C$_1$-C$_6$ heteroalkyl;

$R^{48}$ is selected from the group consisting of hydrogen, an optionally substituted C$_1$-C$_6$ alkyl, an optionally substituted C$_1$-C$_6$ alkoxy, an optionally substituted C$_2$-C$_4$ alkenyl, an optionally substituted C$_2$-C$_4$ alkynyl, an optionally substituted C$_3$-C$_7$ cycloalkyl, an optionally substituted C$_3$-C$_7$ cycloalkenyl, and an optionally substituted C$_1$-C$_6$ heteroalkyl;

each $R^A$ is independently selected from the group consisting of hydrogen, C$_1$-C$_6$ alkyl, C$_1$-C$_6$ haloalkyl, C$_1$-C$_6$ heteroalkyl, and C$_1$-C$_6$ heterohaloalkyl;

each —NR$^B$R$^C$ is separately selected, wherein R$^B$ and R$^C$ are each independently selected from the group consisting of hydrogen, —SO$_2$R$^F$, —C(=O)R$^F$, —(CH$_2$)$_m$R$^F$, —SO$_2$NR$^D$R$^E$, —C(=O)NR$^D$R$^E$, —(CH$_2$)$_m$NR$^D$R$^E$, C$_1$-C$_6$ alkyl, C$_3$-C$_7$ cycloalkyl, C$_3$-C$_7$ cycloalkenyl, C$_1$-C$_6$ haloalkyl, C$_1$-C$_6$ heteroalkyl, and C$_1$-C$_6$ heterohaloalkyl where the alkyl and the heteroalkyl are optionally fused with an aryl or heteroaryl; or —NR$^B$R$^C$ is an optionally substituted non-aromatic heterocycle linked through a ring nitrogen atom; or —NR$^B$R$^C$ is an optionally substituted C$_1$-C$_6$ alkylideneamino;

each —NR$^D$R$^E$ is separately selected, wherein R$^D$ and R$^E$ are each independently selected from the group consisting of hydrogen, an optionally substituted C$_1$-C$_6$ alkyl, an optionally substituted C$_3$-C$_7$ cycloalkyl, an optionally substituted C$_3$-C$_7$ cycloalkenyl, an optionally substituted C$_1$-C$_6$ haloalkyl, an optionally substituted C$_1$-C$_6$ heteroalkyl, and —(CH$_2$)$_m$R$^G$; or —NR$^D$R$^E$ is an optionally substituted C$_1$-C$_6$ alkylideneaminyl; or —NR$^D$R$^E$ is an optionally substituted non-aromatic heterocycle linked through a ring nitrogen atom;

each R$^F$ is independently selected from the group consisting of hydrogen, an optionally substituted C$_1$-C$_4$ alkyl, an optionally substituted C$_1$-C$_4$ haloalkyl, an optionally substituted C$_3$-C$_7$ cycloalkyl, an optionally substituted C$_3$-C$_7$ cycloalkenyl, aryl and heteroaryl, where the aryl and heteroaryl in the definition of R$^F$ are each optionally substituted with —C(=O)NR$^D$R$^E$ or —NR$^D$R$^E$;

each R$^G$ is independently selected from the group consisting of an optionally substituted aryl and an optionally substituted heteroaryl;

each R$^K$ is independently selected from the group consisting of —C(=O)NR$^D$R$^E$, —NR$^D$R$^E$, an optionally substituted aryl and an optionally substituted heteroaryl;

each m is independently 0, 1, or 2; and each dashed line represents an optional double bond.

Some embodiments disclosed herein provide a compound of Formula V having the structure of Formula Va:

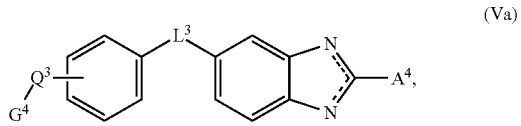
(Va)

and pharmaceutically acceptable salts, esters, or prodrugs thereof, wherein G$^4$ can be selected from the group consisting of hydrogen, halogen, —(CH$_2$)$_m$OR$^A$, —O(CH$_2$)$_m$OR$^A$, —NR$^B$R$^C$, an optionally substituted C$_1$-C$_6$ alkyl, an optionally substituted phenyl, an optionally substituted pyridinyl, an optionally substituted tetrazolyl, and an optionally substituted imidazolyl; Q$^3$ can be selected from the group consisting of —C(=O)O—, —C(=O)NH—, —C(=O)NHNH—, —NR$^{45}$C(=O)NR$^{45}$—, —OC(=O)NR$^{45}$—, —C(=S)NR$^{45}$—, —NR$^{45}$S(O)$_{1-2}$—, C$_1$-C$_6$ alkylideneaminyl, and

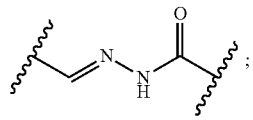 [SMILES: */C=N/NC(*)=O]

or Q$^3$ can be null; A$^4$ can be selected from the group consisting of a aryl and heteroaryl, each substituted with one or more substituents selected from the group consisting of R$^{41}$ and R$^{42}$, said aryl and heteroaryl in the definition of A$^4$ can each be further optionally fused with an optionally substituted nonaromatic heterocycle or an optionally substituted nonaromatic carbocycle; L$^3$ can be selected from —O— (oxygen), —S(O)$_{0-2}$—, —NR$^{45}$S(O)$_{1-2}$—, —NR$^{45}$C(=O)—(CH$_2$)$_m$C(=O)NR$^{45}$—, —NR$^{45}$C(=O)—(CH$_2$)$_m$NR$^{45}$C(=O)—, —NR$^{45}$—, —C(=O)—, —C(=S)—, —C(=O)NR$^{45}$—, —C(=NR$^{45}$)—, an optionally substituted C$_1$-C$_8$ alkyl, an optionally substituted C$_1$-C$_8$ heteroalkyl, an optionally substituted heterocycle, an optionally substituted aryl, and an optionally substituted heteroaryl; or L$^3$ can be null; each R$^{41}$ can be independently selected from the group consisting of hydrogen, halogen, and an optionally substituted C$_1$-C$_3$ alkyl; each R$^{42}$ can be independently selected from the group consisting of hydrogen and an optionally substituted C$_1$-C$_3$ alkyl; each R$^{43}$ can be independently selected from the group consisting of halogen, an optionally substituted C$_1$-C$_6$ alkyl, an optionally substituted C$_1$-C$_6$ alkoxy, an optionally substituted C$_3$-C$_7$ cycloalkyl, an optionally substituted C$_1$-C$_6$ haloalkyl, an optionally substituted C$_1$-C$_6$ heteroalkyl; each R$^{44}$ can be independently selected from the group consisting of halogen, —(CH$_2$)$_m$OR$^A$, —O(CH$_2$)$_m$OR$^A$, —NR$^B$R$^C$, —C(=O)NR$^B$R$^C$, —C(=NNR$^B$R$^C$)H, —(CH$_2$)$_m$R$^K$, —O(CH$_2$)$_m$R$^K$, an optionally substituted C$_1$-C$_6$ alkyl, an optionally substituted C$_1$-C$_6$ alkoxy, an optionally substituted C$_3$-C$_7$ cycloalkyl, an optionally substituted C$_3$-C$_7$ cycloalkenyl, an optionally substituted C$_1$-C$_6$ haloalkyl, and an optionally substituted C$_1$-C$_6$ heteroalkyl; each R$^{45}$ can be independently selected from the group consisting of hydrogen, and an optionally substituted C$_1$-C$_4$ alkyl; each R$^A$ can be independently selected from the group consisting of hydrogen, C$_1$-C$_6$ alkyl, and C$_1$-C$_6$ haloalkyl; each —NR$^B$R$^C$ can be separately selected, wherein R$^B$ and R$^C$ can each be independently selected from the group consisting of hydrogen, —SO$_2$R$^F$, —C(=O)R$^F$, —(CH$_2$)$_m$R$^F$, —(CH$_2$)$_m$OR$^F$, —SO$_2$NR$^D$R$^E$, —C(=O)NR$^D$R$^E$, —C(=NH)NR$^D$R$^E$, —(CH$_2$)$_m$NR$^D$R$^E$, C$_1$-C$_6$ alkyl, C$_3$-C$_7$ cycloalkyl, C$_3$-C$_7$ cycloalkenyl, C$_1$-C$_6$ haloalkyl, C$_1$-C$_6$ heteroalkyl, and C$_1$-C$_6$ heterohaloalkyl where the alkyl and the heteroalkyl are optionally fused with an aryl or heteroaryl; or —NR$^B$R$^C$ can be an optionally substituted non-aromatic heterocycle linked through a ring nitrogen atom; or —NR$^B$R$^C$ can be an optionally substituted C$_1$-C$_6$ alkylideneamino; each —NR$^D$R$^E$ can be separately selected, wherein R$^D$ and R$^E$ can each be independently selected from the group consisting of hydrogen, an optionally substituted C$_1$-C$_6$ alkyl, an optionally substituted C$_3$-C$_7$ cycloalkyl, an optionally substituted C$_3$-C$_7$ cycloalkenyl, an optionally substituted C$_1$-C$_6$ haloalkyl, an optionally substituted C$_1$-C$_6$ heteroalkyl, and —(CH$_2$)$_m$R$^G$; or —NR$^D$R$^E$ can be an optionally substituted C$_1$-C$_6$ alkylideneamino; or —NR$^D$R$^E$ can be an optionally substituted non-aromatic heterocycle linked through a ring nitrogen atom; each R$^F$ can be independently selected from the group consisting of hydrogen, an optionally substituted C$_1$-C$_3$ alkyl, an optionally substituted C$_1$-C$_3$ haloalkyl, an optionally substituted C$_3$-C$_7$ cycloalkyl, an optionally substituted C$_3$-C$_7$ cycloalkenyl, aryl and heteroaryl, where the aryl and heteroaryl in the definition of R$^F$ can each be optionally substituted with —C(=O)NR$^D$R$^E$ or —NR$^D$R$^E$; each R$^G$ can be independently selected from an optionally substituted aryl and an optionally substituted heteroaryl; each R$^K$ can be independently selected from the group consisting of —C(=O)NR$^D$R$^E$, —NR$^D$R$^E$, an optionally substituted aryl and an optionally substituted heteroaryl; each m can be independently 0, 1, or 2; and each dashed line represents an optionally double bond.

Some embodiments disclosed herein provide a compound of Formula Va, wherein G$^4$ can be selected from the group consisting of hydrogen, halogen, —(CH$_2$)$_m$OR$^A$, —O(CH$_2$)$_m$OR$^A$, —NR$^B$R$^C$, an optionally substituted C$_1$-C$_6$ alkyl, an optionally substituted phenyl, an optionally substituted pyridinyl, an optionally substituted tetrazolyl, and an optionally substituted imidazolyl; Q$^3$ can be selected from the group consisting of —C(=O)NH—, and

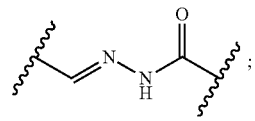 [SMILES: */C=N/NC(*)=O]

or $Q^3$ can be null: $A^4$ can be selected from the group consisting of phenyl, naphthyl, dihydrobenzofuranyl, 1,4-benzodioxanyl, benzotriazolyl, benzimidazolyl, benzofuranyl, and 2,1,3-benzoxadiazolyl, each optionally substituted with one or more substituents selected from the group consisting of, each optionally substituted with one or more substituents selected from the group consisting of $R^{41}$ and $R^{42}$; $L^3$ can be a 1-6 atom long linker comprising one or more groups selected from —$NR^{45}$—, —C(=O)—, —C(=S)—, and —C(=O)$NR^{45}$—; or L can be null; each $R^{41}$ can be independently selected from the group consisting of halogen, an optionally substituted $C_1$-$C_6$ alkyl, and an optionally substituted $C_1$-$C_6$ alkoxy; each $R^{42}$ can be independently selected from the group consisting of —$(CH_2)_mOR^A$, —$O(CH_2)_mOR^A$, —$NR^BR^C$, —C(=O)$NR^BR^C$, —C(=$NNR^BR^C$)H, —$(CH_2)_mR^K$, and —$O(CH_2)_mR^K$; each $R^{45}$ can be independently selected from the group consisting of hydrogen, and methyl; each $R^A$ can be independently selected from the group consisting of hydrogen, $C_1$-$C_4$ alkyl, and $C_1$-$C_4$ haloalkyl; each —$NR^BR^C$ can be separately selected, wherein $R^B$ and $R^C$ can each be independently selected from the group consisting of hydrogen, —C(=O)$R^F$, —$(CH_2)_mR^F$, —$SO_2NR^DR^E$, —C(=O)$NR^DR^E$, —C(=NH)$NR^DR^E$, $C_1$-$C_6$ alkyl, $C_3$-$C_7$ cycloalkyl, $C_3$-$C_7$ cycloalkenyl, and $C_1$-$C_6$ haloalkyl; or —$NR^BR^C$ can be an optionally substituted non-aromatic heterocycle linked through a ring nitrogen atom; or —$NR^BR^C$ can be an optionally substituted $C_1$-$C_6$ alkylideneamino; each —$NR^DR^E$ can be separately selected, wherein $R^D$ and $R^E$ can each be independently selected from the group consisting of hydrogen, an optionally substituted $C_1$-$C_6$ alkyl, an optionally substituted $C_3$-$C_7$ cycloalkyl, an optionally substituted $C_3$-$C_7$ cycloalkenyl, an optionally substituted $C_1$-$C_6$ haloalkyl, and —$(CH_2)_mR^G$; or —$NR^DR^E$ can be an optionally substituted $C_1$-$C_6$ alkylideneaminyl; or —$NR^DR^E$ can be an optionally substituted non-aromatic heterocycle linked through a ring nitrogen atom; each $R^F$ can be independently selected from the group consisting of hydrogen, an optionally substituted $C_1$-$C_3$ alkyl, an optionally substituted $C_3$-$C_6$ cycloalkyl, an optionally substituted $C_3$-$C_6$ cycloalkenyl, an optionally substituted $C_1$-$C_3$ haloalkyl, aryl and heteroaryl, where the aryl and heteroaryl in the definition of $R^F$ can each be optionally substituted with —C(=O)$NR^DR^E$ or —$NR^DR^E$; each $R^G$ can be independently selected from an optionally substituted aryl and an optionally substituted heteroaryl; each m can be independently 0, 1, or 2; and each dashed line represents an optional double bond.

Some embodiments disclosed herein provide a compound of Formula V, wherein $G^4$ can be selected from the group consisting of hydrogen, halogen, —$(CH_2)_mOR^A$, —$O(CH_2)_mOR^A$, —$NR^BR^C$, an optionally substituted $C_1$-$C_6$ alkyl, an optionally substituted phenyl, an optionally substituted pyridinyl, an optionally substituted tetrazolyl, and an optionally substituted imidazolyl; $Q^3$ can be selected from the group consisting of an ester, an amide, a urea, a carbamide, a thioamide, an imidamide, a sulfonamide, and a hydrazide derivative; or $Q^3$ is selected from the group consisting of —C(=O)O—, —C(=O)NH—, —$NR^{45}$C(=O)$NR^{45}$—, —OC(=O)$NR^{45}$—, —C(=S)$NR^{45}$—, —$NR^{45}S(O)_{1-2}$—, $C_1$-$C_6$ alkylideneaminyl, and

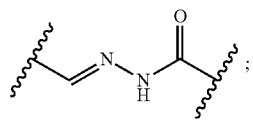 [SMILES: */C=N/NC(*)=O]
;

$Q^3$ can be null; $A^4$ can be selected from the group consisting of a aryl and heteroaryl, each substituted with one or more substituents selected from the group consisting of $R^{41}$ and $R^{42}$, said aryl and heteroaryl in the definition of $A^4$ can each be further optionally fused with an optionally substituted nonaromatic heterocycle or an optionally substituted non-aromatic carbocycle; $L^3$ can be selected from —O— (oxygen), —$S(O)_{0-2}$—, —$NR^{45}S(O)_{1-2}$—, —$NR^{45}$—, —C(=O)—, —C(=S)—, —C(=O)$NR^{45}$—, —C(=$NR^{45}$)—, —$NR^{45}$C(=O)—$(CH_2)_mC$(=O)$NR^{45}$—, —$NR^{45}$C(=O)—$(CH_2)_mNR^{45}C$(=O)—, an optionally substituted $C_1$-$C_8$ alkyl, an optionally substituted $C_1$-$C_8$ heteroalkyl, an optionally substituted heterocycle, an optionally substituted aryl, and an optionally substituted heteroaryl; or $L^3$ can be null; each $R^{41}$ can be independently selected from the group consisting of halogen, cyano, an optionally substituted $C_1$-$C_6$ alkyl, an optionally substituted $C_1$-$C_6$ alkoxy, an optionally substituted $C_1$-$C_6$ haloalkyl, an optionally substituted $C_1$-$C_6$ heteroalkyl, and null; each $R^{42}$ can be independently selected from the group consisting of —$(CH_2)_mOR^A$, —$NR^BR^C$, —C(=O)$NR^BR^C$, —C(=$NNR^BR^C$)H, —$(CH_2)_mR^K$, —$O(CH_2)_mR^K$, an optionally substituted $C_1$-$C_6$ alkyl, an optionally substituted $C_1$-$C_6$ alkoxy, an optionally substituted $C_1$-$C_6$ haloalkyl, and an optionally substituted $C_1$-$C_6$ heteroalkyl; each $R^{45}$ can be independently selected from the group consisting of hydrogen, and an optionally substituted $C_1$-$C_4$ alkyl; each $R^A$ can be independently selected from the group consisting of hydrogen, $C_1$-$C_6$ alkyl, and $C_1$-$C_6$ haloalkyl; each —$NR^BR^C$ can be separately selected, wherein $R^B$ and $R^C$ can each be independently selected from the group consisting of hydrogen, —$SO_2R^F$, —C(=O)$R^F$, —$(CH_2)_mR^F$, —$(CH_2)_mOR^F$, —$SO_2NR^DR^E$, —C(=O)$NR^DR^E$, —C(=NH)$NR^DR^E$, $C_1$-$C_6$ alkyl, $C_1$-$C_6$ haloalkyl, $C_1$-$C_6$ heteroalkyl, and $C_1$-$C_6$ heterohaloalkyl where the alkyl and the heteroalkyl are optionally fused with an aryl or heteroaryl; or —$NR^BR^C$ can be an optionally substituted non-aromatic heterocycle linked through a ring nitrogen atom; or —$NR^BR^C$ can be an optionally substituted $C_1$-$C_6$ alkylideneamino; each —$NR^DR^E$ can be separately selected, wherein $R^D$ and $R^E$ can each be independently selected from the group consisting of hydrogen, an optionally substituted $C_1$-$C_6$ alkyl, an optionally substituted $C_1$-$C_6$ haloalkyl, an optionally substituted $C_1$-$C_6$ heteroalkyl, and —$(CH_2)_mR^G$; or —$NR^DR^E$ can be an optionally substituted $C_1$-$C_6$ alkylideneaminyl; or —$NR^DR^E$ can be an optionally substituted non-aromatic heterocycle linked through a ring nitrogen atom; each $R^F$ can be independently selected from the group consisting of hydrogen, $C_1$-$C_3$ alkyl, $C_1$-$C_3$ haloalkyl, aryl and heteroaryl, where the aryl and heteroaryl in the definition of $R^F$ can each be optionally substituted with —C(=O)$NR^DR^E$ or —$NR^DR^E$; each $R^G$ can be independently selected from an optionally substituted aryl and an optionally substituted heteroaryl; each m can be independently 0, 1, or 2; and one dashed line represents a double bond.

Some embodiments disclosed herein provide a compound of Formula Va having the structure of Formula Vb:

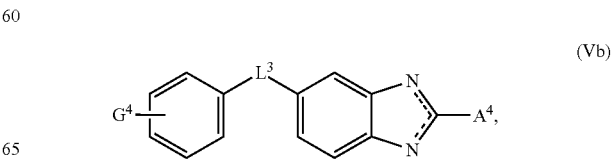

(Vb)

and pharmaceutically acceptable salts, wherein $G^4$ can be selected from the group consisting of hydrogen, halogen, fluoro, chloro, bromo, —$OR^A$, —$O(CH_2)_mOR^A$, —$NR^BR^C$, an optionally substituted $C_1$-$C_6$ alkyl, an optionally substituted phenyl, an optionally substituted pyridinyl, an optionally substituted tetrazolyl, and an optionally substituted imidazolyl; $A^4$ can be phenyl optionally substituted with one or more substituents selected from the group consisting of $R^{41}$ and $R^{42}$, where the phenyl in the definition of $A^4$ can be further optionally fused with an optionally substituted nonaromatic heterocycle or an optionally substituted nonaromatic carbocycle; $L^3$ can be selected from —C(=O)$NR^{45}$—, —$NR^{45}$C(=O)—$(CH_2)_m$C(=O)$NR^{45}$—, —$NR^{45}$C(=O)—$(CH_2)_mNR^{45}$C(=O)—, and an optionally substituted heteroaryl; or $L^3$ can be null; each $R^{41}$ can be independently selected from the group consisting of halogen, an optionally substituted $C_1$-$C_6$ alkyl, an optionally substituted $C_1$-$C_6$ alkoxy; each $R^{42}$ can be independently selected from the group consisting of —$(CH_2)_mOR^A$, —$O(CH_2)_mOR^A$, —$NR^BR^C$, —$C(=O)NR^BR^C$, —$C(=NNR^BR^C)H$, —$(CH_2)_mR^K$, —$O(CH_2)_mR^K$; each $R^{45}$ can be independently selected from the group consisting of hydrogen, and an optionally substituted $C_1$-$C_4$ alkyl; each $R^A$ is independently selected from the group consisting of hydrogen, $C_1$-$C_6$ alkyl, and $C_1$-$C_6$ haloalkyl; each —$NR^BR^C$ can be separately selected, wherein $R^B$ and $R^C$ can each be independently selected from the group consisting of hydrogen, —$SO_2R^F$, —$C(=O)R^F$, —$(CH_2)_mR^F$, —$(CH_2)_mOR^F$, —$SO_2NR^DR^E$, —$C(=O)NR^DR^E$, —$C(=NH)NR^DR^E$, —$(CH_2)_mNR^DR^E$, $C_1$-$C_6$ alkyl, $C_3$-$C_7$ cycloalkyl, $C_3$-$C_7$ cycloalkenyl, $C_1$-$C_6$ haloalkyl, $C_1$-$C_6$ heteroalkyl, and $C_1$-$C_6$ heterohaloalkyl where the alkyl and the heteroalkyl are optionally fused with an aryl or heteroaryl; or —$NR^BR^C$ can be an optionally substituted non-aromatic heterocycle linked through a ring nitrogen atom; each —$NR^DR^E$ can be separately selected, wherein $R^D$ and $R^E$ can each be independently selected from the group consisting of hydrogen, an optionally substituted $C_1$-$C_6$ alkyl, an optionally substituted $C_3$-$C_7$ cycloalkyl, an optionally substituted $C_3$-$C_7$ cycloalkenyl, an optionally substituted $C_1$-$C_6$ haloalkyl, an optionally substituted $C_1$-$C_6$ heteroalkyl, and —$(CH_2)_mR^G$; or —$NR^DR^E$ can be an optionally substituted $C_1$-$C_6$ alkylideneaminyl; or —$NR^DR^E$ can be an optionally substituted non-aromatic heterocycle linked through a ring nitrogen atom; each $R^F$ can be independently selected from the group consisting of hydrogen, an optionally substituted $C_1$-$C_3$ alkyl, an optionally substituted $C_3$-$C_7$ cycloalkyl, aryl and heteroaryl, where the aryl and heteroaryl in the definition of $R^F$ can each be optionally substituted with —$C(=O)NR^DR^E$ or —$NR^DR^E$; each $R^G$ can be independently selected from an optionally substituted aryl and an optionally substituted heteroaryl; each $R^K$ can be independently selected from the group consisting of —$C(=O)NR^DR^E$, —$NR^DR^E$, an optionally substituted aryl and an optionally substituted heteroaryl; each m can be independently 0, 1, or 2; and, each dashed line represents an optionally double bond.

Some embodiments disclosed herein provide a compound of Formula Vb, wherein $G^4$ can be selected from the group consisting of hydrogen, fluoro, chloro, bromo, imidazolyl, tetrazolyl, N-methyl-N-(2-hydroxyethyl)aminyl, methylaminosulfonamido, 2-hydroxyethyloxy, —$(CH_2)_mOR^A$, —$O(CH_2)_mOR^A$, and —$NR^BR^C$; $A^4$ can be phenyl optionally substituted with one or more substituents selected from the group consisting of $R^{41}$ and $R^{42}$, where the phenyl in the definition of $G^4$ can be further optionally fused with an optionally substituted nonaromatic heterocycle or an optionally substituted nonaromatic carbocycle; $L^3$ can be selected from the group consisting of —C(=O)NH—, —NHC(=O)—C(=O)NH— and an optionally substituted heteroaryl; or $L^3$ can be null; each $R^{41}$ can be an optionally substituted $C_1$-$C_6$ alkoxy; each $R^{42}$ can be independently selected from the group consisting of —$(CH_2)_mOR^A$, —$O(CH_2)_mOR^A$, —$NR^BR^C$, —$C(=O)NR^BR^C$, —$C(=NNR^BR^C)H$, —$(CH_2)_mR^K$, and —$O(CH_2)_mR^K$; each $R^A$ can be independently selected from the group consisting of hydrogen, and $C_1$-$C_6$ alkyl; each —$NR^BR^C$ can be separately selected, wherein $R^B$ and $R^C$ can each be independently selected from the group consisting of hydrogen, —$SO_2R^F$, —$C(=O)R^F$, —$(CH_2)_mR^F$, —$OR^F$, —$SO_2NR^DR^E$, —$(CH_2)_mNR^DR^E$, $C_1$-$C_6$ alkyl, and $C_3$-$C_7$ cycloalkyl; or —$NR^BR^C$ can be selected from the group consisting of pyrrolidinyl, morpholinyl, 4-methylpiperazinyl, piperazinyl, piperidinyl, 3-hydroxypyrrolidinyl, and 4-hydroxypiperidinyl, each optionally substituted with oxo; each —$NR^DR^E$ can be separately selected, wherein $R^D$ and $R^E$ can each be independently selected from the group consisting of hydrogen, an optionally substituted $C_1$-$C_6$ alkyl, an optionally substituted $C_3$-$C_6$ cycloalkyl, and —$(CH_2)_mR^G$; or —$NR^DR^E$ can be selected from the group consisting of pyrrolidinyl, morpholinyl, 4-methylpiperazinyl, piperazinyl, piperidinyl, 3-hydroxypyrrolidinyl, and 4-hydroxypiperidinyl, each optionally substituted with oxo; each $R^F$ can be independently selected from the group consisting of hydrogen, an optionally substituted $C_1$-$C_3$ alkyl, an optionally substituted $C_3$-$C_6$ cycloalkyl, aryl and heteroaryl, where the aryl and heteroaryl in the definition of $R^F$ can each be optionally substituted with —$NR^DR^E$; each $R^G$ can be independently selected from an optionally substituted aryl and an optionally substituted heteroaryl; each $R^K$ can be independently selected from the group consisting of an optionally substituted aryl and an optionally substituted heteroaryl; each m can be independently 0, 1, or 2; and each dashed line represents an optionally double bond.

Some embodiments disclosed herein provide a compound of Formula V, having the proviso that a compound of Formula V is not selected from the group consisting of:

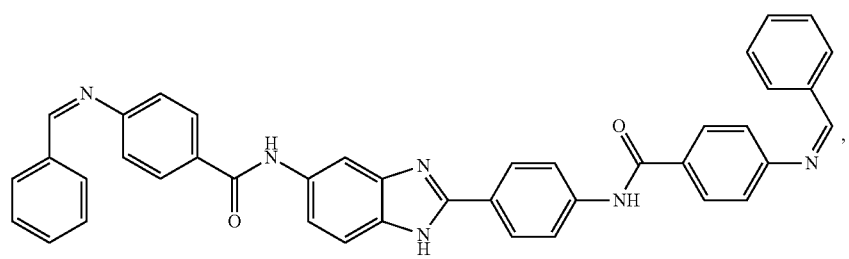

-continued

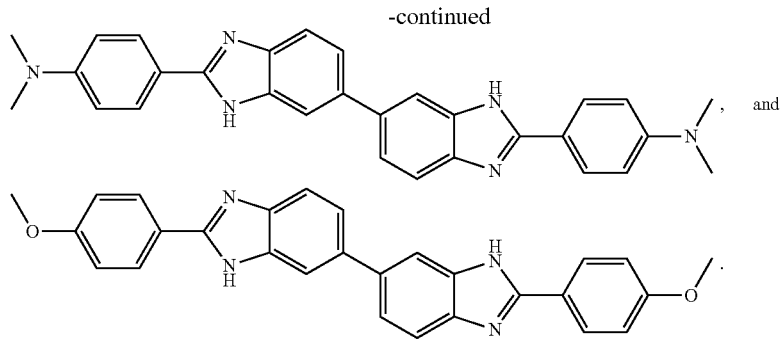

Some embodiments disclosed herein provide a compound of Formula VI:

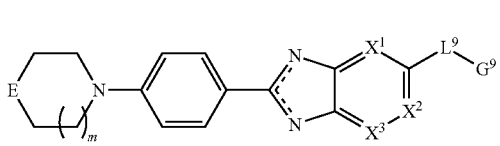

and pharmaceutically acceptable salts, esters, stereoisomers, tautomers or prodrugs thereof;
wherein:
E is selected from the group consisting of O (oxygen), S (sulfur), $NR^{41}$ and $CR^{42}R^{43}$;

$R^{41}$ is selected from the group consisting of hydrogen, halogen, cyano, —C(=O)$R^C$, $C_1$-$C_6$ haloalkyl, $C_1$-$C_6$ heteroalkyl, and an optionally substituted $C_1$-$C_6$ alkyl;

$R^{42}$ and $R^{43}$ are each independently selected from the group consisting of hydrogen, halogen, —$OR^{AA}$, —$OR^{CC}$, —$NR^AR^B$, —$NR^CR^D$, —$SR^{AA}$, —$(CH_2)_mR^E$, —$CONR^CR^D$, an optionally substituted $C_1$-$C_6$ alkyl, an optionally substituted $C_1$-$C_6$ haloalkyl, and an optionally substituted $C_1$-$C_6$ heteroalkyl; or $CR^{42}R^{43}$ is an optionally substituted $C_3$-$C_7$ cycloalkyl;

$X^1$, $X^2$, and $X^3$ are each independently selected from the group consisting of N (nitrogen) and $CR^{41}$;

$G^9$ is selected from the group consisting of aryl and heteroaryl, each optionally substituted with one or more substituents selected from the group consisting of $R^{44}$ and $R^{45}$, said aryl and heteroaryl in the definition of $G^9$ are each further optionally fused with an optionally substituted non-aromatic heterocycle or an optionally substituted nonaromatic carbocycle;

each $R^{44}$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, and an optionally substituted $C_1$-$C_6$ heteroalkyl;

each $R^{45}$ is separately selected from the group consisting of hydrogen, halogen, —$OR^{AA}$, —$OR^{CC}$, —$NR^AR^B$, —$NR^CR^D$, —$SR^{AA}$, —$(CH_2)_mR^E$, $C_1$-$C_6$ haloalkyl, $C_1$-$C_6$ heteroalkyl, and an optionally substituted $C_1$-$C_6$ alkyl;

each $R^{AA}$ is independently selected from the group consisting of hydrogen, —$(CH_2)_mSO_2R^F$, —$(CH_2)_mC(=O)R^F$, —$(CH_2)_mC(=O)NR^CR^D$, an optionally substituted $C_1$-$C_8$ alkyl, an optionally substituted $C_1$-$C_8$ alkoxy, an optionally substituted $C_2$-$C_8$ alkenyl, an optionally substituted $C_2$-$C_8$ alkynyl, and an optionally substituted $C_3$-$C_7$ cycloalkyl, where said $C_3$-$C_7$ cycloalkyl is optionally fused with an aryl or heteroaryl;

each $R^{BB}$ is independently selected from the group consisting of hydrogen, an optionally substituted $C_1$-$C_8$ alkyl, an optionally substituted $C_1$-$C_8$ alkoxy, an optionally substituted $C_2$-$C_8$ alkenyl, an optionally substituted $C_2$-$C_8$ alkynyl, an optionally substituted $C_3$-$C_7$ cycloalkyl, and $(CH_2)_mR^E$;

each —$NR^AR^B$ is separately selected, wherein $R^A$ and $R^B$ are each independently selected from the group consisting of hydrogen, —$(CH_2)_mSO_2R^F$, —$(CH_2)_mC(=O)R^F$, —$(CH_2)_mC(=O)NR^CR^B$, an optionally substituted $C_1$-$C_8$ alkyl, an optionally substituted $C_1$-$C_8$ alkoxy, an optionally substituted $C_2$-$C_8$ alkenyl, an optionally substituted $C_2$-$C_8$ alkynyl, and an optionally substituted $C_3$-$C_7$ cycloalkyl, where said $C_3$-$C_7$ cycloalkyl is optionally fused with an aryl or heteroaryl; or —$NR^AR^B$ is an optionally substituted non-aromatic heterocycle linked through a ring nitrogen atom optionally fused with an aryl or heteroaryl; or —$NR^AR^B$ is an optionally substituted $C_1$-$C_6$ alkylideneamino;

each —$NR^CR^D$ is separately selected, wherein $R^C$ and $R^D$ are each independently selected from the group consisting of hydrogen, an optionally substituted $C_1$-$C_8$ alkyl, an optionally substituted $C_1$-$C_8$ alkoxy, an optionally substituted $C_2$-$C_8$ alkenyl, an optionally substituted $C_2$-$C_8$ alkynyl, an optionally substituted $C_3$-$C_7$ cycloalkyl, and $(CH_2)_mR^E$; or —$NR^CR^D$ is an optionally substituted $C_1$-$C_8$ alkylideneamino; or —$NR^CR^D$ is an optionally substituted non-aromatic heterocycle linked through a ring nitrogen atom;

each $R^E$ is separately selected from the group consisting of an optionally substituted aryl and an optionally substituted heteroaryl;

each $R^F$ is separately selected from the group consisting of hydrogen, a an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted aryl and an optionally substituted heteroaryl;

$L^9$ is selected from the group consisting of —$(CH_2)_mC(=O)NR^{46}(CH_2)_q$—, —$(CH_2)_mC(=O)NR^{46}(CH_2)_qC(=O)NR^{46}$—, —$S(O)_2NH$—, O (oxygen), —$NR^{46}$—, —$OC(=O)O$—, —$OC(=O)NH$—, —$NHC(=O)NH$—, —$NHC=SNH$—, —$C(=NR^{46})$—, —$C(=O)NR^{46}$—, —$C(=S)NR^{46}$—; or $L^9$ is null;

each $R^{46}$ is independently selected from the group consisting of hydrogen, $C_1$-$C_6$ haloalkyl, and an optionally substituted $C_1$-$C_6$ alkyl;

each m is independently 0, 1, or 2;
each q is independently 1, 2, 3, 4, 5, or 6; and
any bond represented by a dashed and solid line represents a bond selected from the group consisting of a single bond and a double bond.

Some embodiments disclosed herein provide a compound of Formula VI having the structure of Formula VIa:

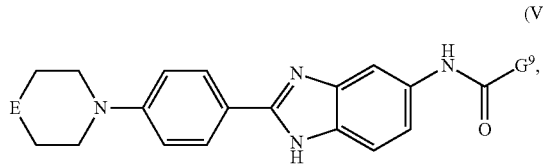

(VIa)

and pharmaceutically acceptable salts.

Some embodiments disclosed herein provide a compound of Formula VII:

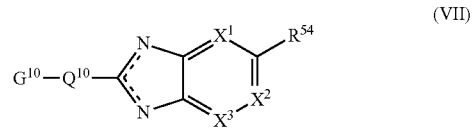

(VII)

and pharmaceutically acceptable salts, esters, stereoisomers, tautomers or prodrugs thereof;
wherein:

$G^{10}$ is selected from the group consisting of $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ haloalkyl, $C_1$-$C_6$ heteroalkyl, heterocycle, aryl and heteroaryl, each optionally substituted with one or more substituents selected from the group consisting of $R^{51}$, $R^{52}$, and $R^{53}$, said aryl and heteroaryl in the definition of $G^{10}$ are each further optionally fused with an optionally substituted nonaromatic heterocycle or an optionally substituted nonaromatic carbocycle;

$Q^{10}$ is selected from the group consisting of $Q^{11}$, $Q^{11}$-$Q^{12}$, and $Q^{11}$-$Q^{12}$-$Q^{13}$;

$Q^{11}$ and $Q^{13}$ are each independently selected from the group consisting of piperazinyl, —C(=O)O—, —C(=O)NR$^{51}$—, —NR$^{51}$C(=O)NR$^{51}$—, —OC(=O)NR$^{51}$—, —C(=S)NR$^{51}$—, —NR$^{51}$S(O)$_{1-2}$—, —(CH$_2$)$_m$C(=O)NR$^{51}$(CH$_2$)$_q$—, and —(CH$_2$)$_m$C(=O)NR$^{51}$(CH$_2$)$_q$C(=O)NR$^{51}$;

$Q^{12}$ is selected from the group consisting of an optionally substituted aryl, an optionally substituted heteroaryl and an optionally substituted heterocycle;

each $R^{51}$ is separately selected from the group consisting of hydrogen, halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_3$-$C_7$ cycloalkenyl, an optionally substituted $C_1$-$C_6$ haloalkyl, and an optionally substituted $C_1$-$C_6$ heteroalkyl;

each $R^{52}$ is separately selected from the group consisting of —(CH$_2$)$_m$OR$^A$, —(CH$_2$)$_m$NR$^B$R$^C$, —(CH$_2$)$_m$SO$_2$NR$^B$R$^C$, and —(CH$_2$)$_m$SR$^A$;

each $R^{53}$ is separately selected from the group consisting of —(CH$_2$)$_m$OR$^D$, —(CH$_2$)$_m$NR$^E$R$^F$, —(CH$_2$)$_m$S(O)$_{0-2}$R$^D$, —(CH$_2$)$_m$NO$_2$, —(CH$_2$)$_m$CN, and —(CH$_2$)$_m$R$^G$;

each $R^{54}$ is separately selected from the group consisting of hydrogen, —(CH$_2$)$_m$OR$^A$, —(CH$_2$)$_m$NR$^B$R$^C$, —O(CH$_2$)$_m$NR$^B$R$^C$, —C(=O)NR$^B$R$^C$, —(CH$_2$)$_m$SR$^A$, —(CH$_2$)$_m$R$^G$, —O(CH$_2$)$_m$R$^G$, —(CH$_2$)$_m$SO$_2$NR$^B$R$^C$, —(CH$_2$)$_m$CN, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_3$-$C_7$ cycloalkenyl, an optionally substituted $C_1$-$C_6$ haloalkyl, and an optionally substituted $C_1$-$C_6$ heteroalkyl;

each $R^A$ is separately selected from the group consisting of hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_3$-$C_7$ cycloalkyl, an optionally substituted $C_3$-$C_7$ cycloalkenyl, an optionally substituted $C_1$-$C_6$ haloalkyl, and an optionally substituted $C_1$-$C_6$ heteroalkyl;

each —NR$^B$R$^C$ is separately selected, wherein R$^B$ and R$^C$ are each independently selected from the group consisting of hydrogen, —(CH$_2$)$_m$SO$_2$R$^H$, —(CH$_2$)$_m$COR$^H$, —(CH$_2$)$_m$CONR$^E$R$^F$, an optionally substituted $C_1$-$C_8$ alkyl, an optionally substituted $C_1$-$C_8$ alkoxy, an optionally substituted $C_2$-$C_8$ alkenyl, an optionally substituted $C_2$-$C_8$ alkynyl, an optionally substituted $C_3$-$C_7$ cycloalkyl, and —(CH$_2$)$_m$R$^G$, where said $C_3$-$C_7$ cycloalkyl is optionally fused with an aryl or heteroaryl; or —NR$^B$R$^C$ or is an optionally substituted non-aromatic heterocycle linked through a ring nitrogen atom optionally fused with an aryl or heteroaryl; or —NR$^B$R$^C$ is an optionally substituted $C_1$-$C_8$ alkylideneamino;

each $R^D$ is separately selected from the group consisting of hydrogen, an optionally substituted $C_1$-$C_8$ alkyl, an optionally substituted $C_2$-$C_8$ alkenyl, an optionally substituted $C_2$-$C_8$ alkynyl, an optionally substituted $C_3$-$C_8$ cycloalkyl, an optionally substituted $C_3$-$C_8$ cycloalkenyl, an optionally substituted $C_1$-$C_8$ haloalkyl, and an optionally substituted $C_1$-$C_8$ heteroalkyl;

each —NR$^E$R$^F$ is separately selected, wherein R$^E$ and R$^F$ are each independently selected from the group consisting of hydrogen, an optionally substituted $C_1$-$C_8$ alkyl, an optionally substituted $C_1$-$C_8$ alkoxy, an optionally substituted $C_2$-$C_8$ alkenyl, an optionally substituted $C_2$-$C_8$ alkynyl, an optionally substituted $C_3$-$C_7$ cycloalkyl, and (CH$_2$)$_m$R$^G$; or —NR$^E$R$^F$ or is an optionally substituted non-aromatic heterocycle linked through a ring nitrogen atom; or —NR$^C$R$^D$ is an optionally substituted $C_1$-$C_8$ alkylideneamino;

each $R^G$ is separately selected from a substituted or unsubstituted aryl and a substituted or unsubstituted heteroaryl;

each $R^H$ is separately selected from the group consisting of hydrogen, a $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ haloalkyl, $C_1$-$C_6$ heteroalkyl, an optionally substituted heterocycle, an optionally substituted aryl, and an optionally substituted heteroaryl;

$X^1$, $X^2$, and $X^3$ are each independently selected from the group consisting of N (nitrogen) and CR$^{47}$;

each $R^{47}$ is separately selected from the group consisting of hydrogen, halogen, an optionally substituted $C_1$-$C_6$ alkyl, and an optionally substituted $C_1$-$C_6$ heteroalkyl each m is independently 0, 1, 2, or 3; and any bond represented by a dashed and solid line represents a bond selected from the group consisting of a single bond and a double bond.

Some embodiments disclosed herein provide a compound of Formula VII having the structure of Formula VIIa:

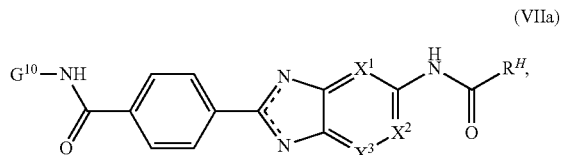

(VIIa)

and pharmaceutically acceptable salts.

Some embodiments disclosed herein provide a compound of Formula VII, having the proviso that a compound of Formula VII is not selected from the group consisting of:
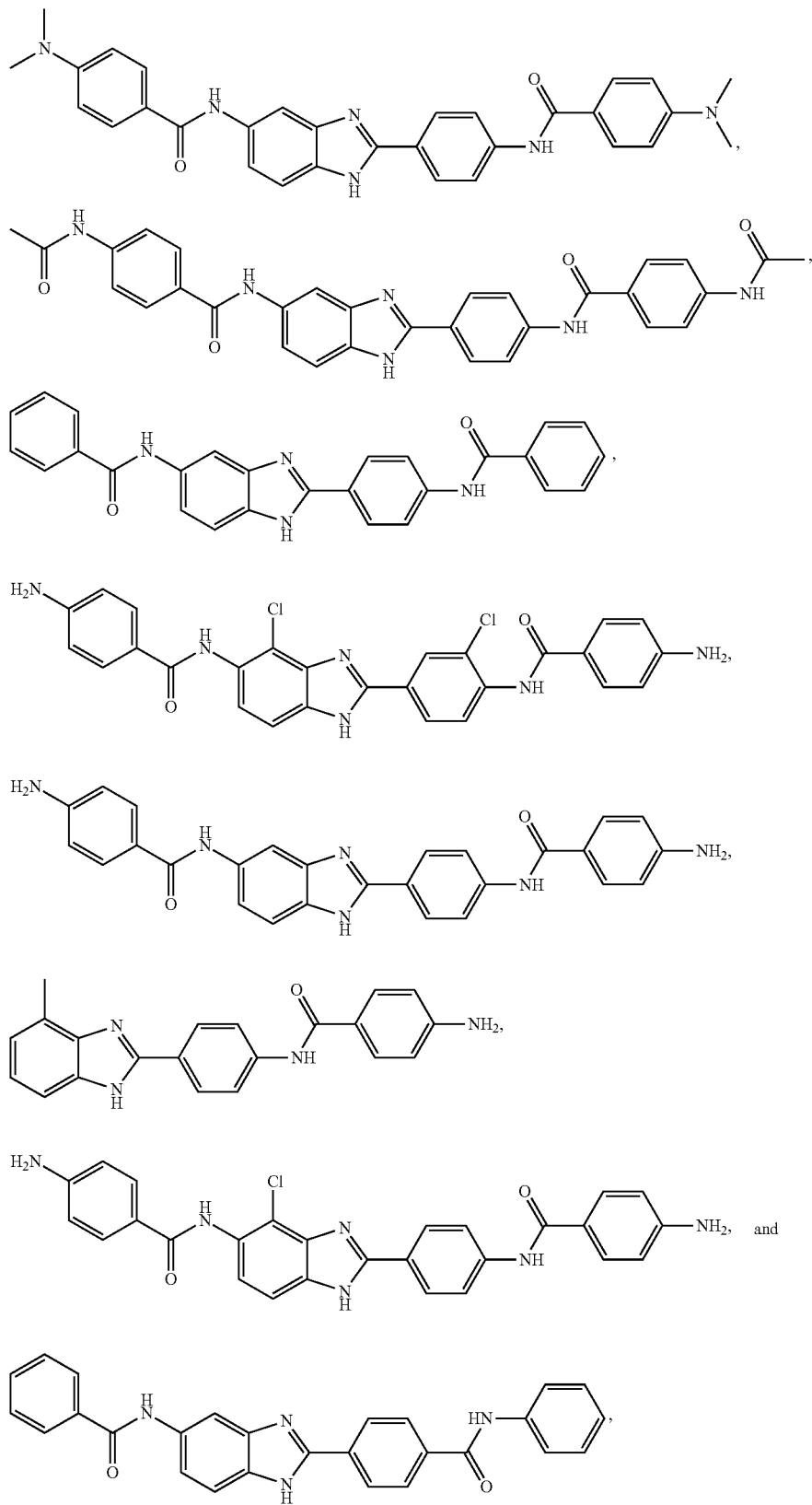

-continued

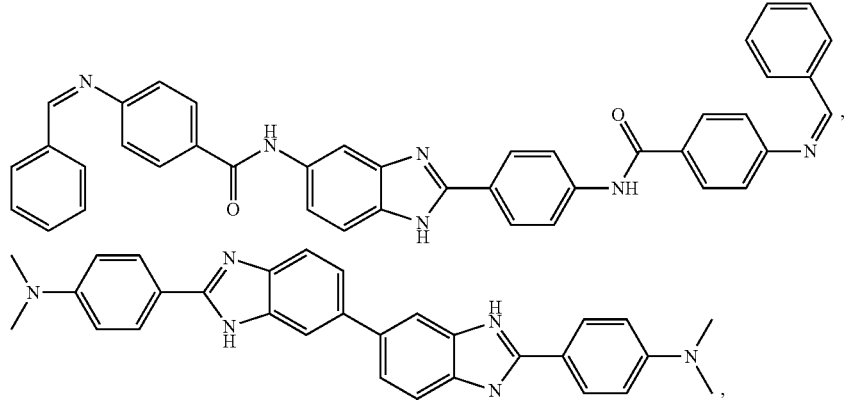

Some embodiments disclosed herein provide a compound of any of Formulae I to IX, or any compound specifically disclosed herein, that is a HGF mimetic, an HGF receptor agonist or an HGF receptor antagonist.

Some embodiments disclosed herein provide a compound of any of Formulae I to IX, or any compound specifically disclosed herein, that is a hematopoietic growth factor mimetic, a hematopoietic growth factor receptor agonist or a hematopoietic growth factor receptor antagonist.

Some embodiments disclosed herein provide a compound of any of Formulae I to IX, or any compound specifically disclosed herein, that is an EPO mimic.

Some embodiments disclosed herein provide a compound of any of Formulae I to IX, or any compound specifically disclosed herein, that is a selective EPO receptor agonist.

Some embodiments disclosed herein provide a compound of any of Formulae I to IX, or any compound specifically disclosed herein, that is a selective EPO receptor partial agonist.

Some embodiments disclosed herein provide a compound of any of Formulae I to IX, or any compound specifically disclosed herein, that is a selective EPO receptor antagonist.

Some embodiments disclosed herein provide a compound of any of Formulae I to IX, or any compound specifically disclosed herein, that is a selective EPO receptor binding compound.

Some embodiments disclosed herein provide a method for modulating an EPO activity in a cell comprising contacting a cell with a compound of any of Formulae I to IX, or any compound specifically disclosed herein.

Some embodiments disclosed herein provide a method for identifying a compound that modulates an EPO activity, comprising contacting a cell that expresses an EPO receptor with a compound of any of Formulae I to IX, or any compound specifically disclosed herein; and monitoring an effect of the compound on the cell.

Some embodiments disclosed herein provide a method of treating a patient, comprising administering to the patient a therapeutically effective amount of a compound of any of Formulae I to IX, or any compound specifically disclosed herein.

Some embodiments disclosed herein provide a method of treating a patient, comprising administering to the patient a therapeutically effective amount of a compound having Formula X:

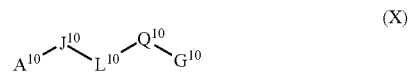

(X)

and pharmaceutically acceptable salts, esters, stereoisomers, tautomers or prodrugs thereof;

wherein:

$A^{10}$ is selected from the group consisting of $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ haloalkyl, $C_1$-$C_6$ heteroalkyl, heterocycle, aryl, and heteroaryl, each optionally substituted with one or more substituents selected from the group consisting of $R^1$, $R^2$, and $R^3$, said aryl and heteroaryl in the definition of $A^{10}$ are each further optionally fused with an optionally substituted nonaromatic heterocycle or an optionally substituted nonaromatic carbocycle;

$G^{10}$ is selected from the group consisting of $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ haloalkyl, $C_1$-$C_6$ heteroalkyl, heterocycle, aryl, and heteroaryl, each optionally substituted with one or more substituents selected from the group consisting of $R^4$, $R^5$, and $R^6$, said aryl and heteroaryl in the definition of $G^{10}$ are each further optionally fused with an optionally substituted nonaromatic heterocycle or an optionally substituted nonaromatic carbocycle;

$J^{10}$ is a 1-8 atom long spacer containing at least 2 heteroatoms separated by 2 bonds and comprising one or more groups selected from —S(O)$_2$NR$^4$—, an optionally substituted $C_1$-$C_6$ heteroalkyl, an optionally substituted heterocycle, and an optionally substituted heteroalkylheterocycle; including the proviso that $J^{10}$ is not a 1-8 atom spacer containing at least 2 heteroatoms separated by 3 or 4 bonds and comprising one or more groups selected from an optionally substituted $C_1$-$C_6$ heteroalkyl, an optionally substituted heterocycle, and an optionally substituted heteroalkylheterocycle;

$Q^{10}$ is a 1-8 atom long spacer containing at least 2 heteroatoms separated by 2 bonds and comprising one or more groups selected from —S(O)$_2$NR$^4$—, an optionally substituted $C_1$-$C_6$ heteroalkyl, an optionally substituted heterocycle, and an optionally substituted heteroalkylheterocycle;

$L^{10}$ is a 2-14 atom long linker comprising one or more groups selected from —O— (oxygen), —C(=O)—, —C(=S)—, —NR$^4$—, —S(O)$_{0-2}$—, —NR$^4$S(O)$_{1-2}$NR$^4$—, and —NR$^4$S(O)$_{1-2}$O—, and one or more groups selected from —O— (oxygen), —C(=O)—, —C(=S)—, —NR$^A$—, —S(O)$_{0-2}$—, —NR$^A$S(O)$_{1-2}$NR$^A$—, and —NR$^A$S(O)$_{1-2}$O—, an optionally substituted C$_1$-C$_{10}$ alkyl, an optionally substituted aryl, and an optionally substituted heteroaryl; where the an optionally substituted aryl and an optionally substituted heteroaryl in the definition of L$^{10}$ are each further optionally fused with an optionally substituted nonaromatic heterocycle or an optionally substituted nonaromatic carbocycle;

R$^1$ is selected from the group consisting of halogen, optionally substituted C$_1$-C$_6$ alkyl, an optionally substituted C$_1$-C$_6$ alkoxy, an optionally substituted C$_2$-C$_6$ alkenyl, an optionally substituted C$_2$-C$_6$ alkynyl, an optionally substituted C$_3$-C$_7$ cycloalkyl, optionally substituted C$_3$-C$_7$ cycloalkenyl, and an optionally substituted C$_1$-C$_6$ heteroalkyl;

R$^2$ is selected from the group consisting of halogen, —OR$^A$, —NR$^B$R$^C$, —SR$^A$;

R$^3$ is selected from the group consisting of —OR$^D$, —NR$^E$R$^F$, —S(O)$_{0-2}$R$^D$, —NO$_2$, —CN, and —(CH$_2$)$_m$R$^G$;

R$^4$ is selected from the group consisting of halogen, optionally substituted C$_1$-C$_6$ alkyl, an optionally substituted C$_1$-C$_6$ alkoxy, an optionally substituted C$_2$-C$_6$ alkenyl, an optionally substituted C$_2$-C$_6$ alkynyl, an optionally substituted C$_3$-C$_7$ cycloalkyl, optionally substituted C$_3$-C$_7$ cycloalkenyl, an optionally substituted C$_1$-C$_6$ heteroalkyl;

R$^5$ is selected from the group consisting of —OR$^A$, —NR$^B$R$^C$, —SR$^A$;

R$^6$ is selected from the group consisting of —OR$^D$, —NR$^E$R$^F$, —S(O)$_{0-2}$R$^D$, —NO$_2$, —CN, and —(CH$_2$)$_m$R$^G$;

each R$^A$ is separately selected from the group consisting of hydrogen, —SO$_2$R$^F$, —C(=O)R$^F$, —C(=O)NR$^C$R$^D$, C$_1$-C$_6$ alkyl, C$_2$-C$_6$ alkenyl, C$_2$-C$_6$ alkynyl, C$_3$-C$_7$ cycloalkyl, C$_3$-C$_7$ cycloalkenyl, C$_1$-C$_6$ haloalkyl, C$_1$-C$_6$ heteroalkyl, and C$_1$-C$_6$ heterohaloalkyl, where the C$_1$-C$_6$ alkyl, C$_3$-C$_7$ cycloalkyl, C$_1$-C$_6$ heteroalkyl, and C$_1$-C$_6$ heterohaloalkyl in the definition of R$^A$ are optionally substituted;

each —NR$^B$R$^C$ is separately selected, wherein R$^B$ and R$^C$ are each independently selected from the group consisting of hydrogen, —SO$_2$R$^H$, —C(=O)R$^H$, —C(=O)NR$^E$R$^F$, C$_1$-C$_6$ alkyl, C$_2$-C$_4$ alkenyl, an optionally substituted C$_2$-C$_4$ alkynyl, C$_3$-C$_7$ cycloalkyl, C$_1$-C$_6$ haloalkyl, C$_1$-C$_6$ heteroalkyl, heterocycle, and C$_1$-C$_6$ heterohaloalkyl where the cycloalkyl and the heterocycle are optionally fused with an aryl or heteroaryl; or —NR$^B$R$^C$ is an optionally substituted non-aromatic heterocycle linked through a ring nitrogen atom; or —NR$^B$R$^C$ is an optionally substituted C$_1$-C$_6$ alkylideneamino;

each R$^D$ is independently selected from the group consisting of hydrogen, an optionally substituted C$_1$-C$_6$ alkyl, an optionally substituted C$_2$-C$_4$ alkenyl, an optionally substituted C$_2$-C$_4$ alkynyl, an optionally substituted C$_3$-C$_7$ cycloalkyl, an optionally substituted C$_1$-C$_6$ haloalkyl, an optionally substituted C$_1$-C$_6$ heteroalkyl, an optionally substituted heterocyle, and —(CH$_2$)$_m$R$^G$;

each —NR$^E$R$^F$ is separately selected, wherein R$^E$ and R$^F$ are each independently selected from the group consisting of hydrogen, an optionally substituted C$_1$-C$_6$ alkyl, an optionally substituted C$_2$-C$_4$ alkenyl, an optionally substituted C$_2$-C$_4$ alkynyl, an optionally substituted C$_3$-C$_7$ cycloalkyl, an optionally substituted C$_1$-C$_6$ haloalkyl, an optionally substituted C$_1$-C$_6$ heteroalkyl, an optionally substituted heterocycle, and —(CH$_2$)$_m$R$^G$; or —NR$^E$R$^F$ is an optionally substituted non-aromatic heterocycle linked through a ring nitrogen atom;

each R$^G$ is separately selected from an optionally substituted aryl and an optionally substituted heteroaryl;

each R$^H$ is separately selected from the group consisting of hydrogen, a C$_1$-C$_6$ alkyl, a C$_1$-C$_6$ haloalkyl, a C$_1$-C$_6$ heteroalkyl, a C$_3$-C$_6$ cycloalkyl, an optionally substituted heterocycle, and an optionally substituted aryl or an optionally substituted heteroaryl; and each m is independently 0, 1, or 2.

Some embodiments disclosed herein provide a method of treating a patient, comprising administering to the patient a therapeutically effective amount of a compound having Formula X having the structure of Formula Xa:

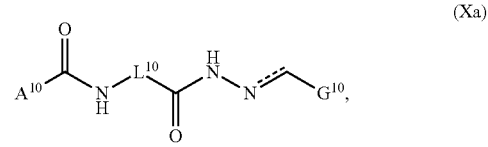

(Xa)

and pharmaceutically acceptable salts thereof, wherein A$^{10}$ can be selected from the group consisting of aryl and heteroaryl, each optionally substituted with one or more substituents selected from the group consisting of R$^1$, R$^2$, and R$^3$, said aryl and heteroaryl in the definition of A$^{10}$ can each be further optionally fused with a nonaromatic heterocycle or nonaromatic carbocycle; and G$^{10}$ can be selected from the group consisting of aryl and heteroaryl, each optionally substituted with one or more substituents selected from the group consisting of R$^4$, R$^5$, and R$^6$, said aryl and heteroaryl in the definition of G$^{10}$ can each be further optionally fused with a nonaromatic heterocycle or nonaromatic carbocycle.

Some embodiments disclosed herein provide a method of treating a patient, comprising administering to the patient a therapeutically effective amount of a compound having Formula X having the structure of Formula Xb:

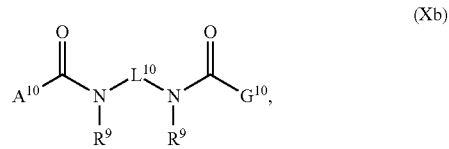

(Xb)

and pharmaceutically acceptable salts thereof, wherein A$^{10}$ can be selected from the group consisting of aryl and heteroaryl, each optionally substituted with one or more substituents selected from the group consisting of R$^1$, R$^2$, and R$^3$, said aryl and heteroaryl in the definition of A$^{10}$ can each be further optionally fused with a nonaromatic heterocycle or nonaromatic carbocycle; and G$^{10}$ can be selected from the group consisting of aryl and heteroaryl, each optionally substituted with one or more substituents selected from the group consisting of R$^4$, R$^5$, and R$^6$, said aryl and heteroaryl in the definition of G$^{10}$ can each be further optionally fused with a nonaromatic heterocycle or nonaromatic carbocycle.

Some embodiments disclosed herein provide a method of treating a patient, comprising administering to the patient a therapeutically effective amount of a compound having Formula X, wherein A$^{10}$ can be selected from the group consisting of C$_1$-C$_6$ alkyl, C$_3$-C$_7$ cycloalkyl, C$_1$-C$_6$ heteroalkyl, heterocycle, aryl, and heteroaryl, each substituted with one or more substituents selected from the group consisting of R$^1$, R$^2$, and R$^3$, said aryl and heteroaryl in the definition of A$^{10}$ can each be further optionally fused with a nonaromatic heterocycle or nonaromatic carbocycle; $G^{10}$ can be selected from the group consisting of $C_1$-$C_6$ alkyl, $C_3$-$C_7$ cycloalkyl, $C_1$-$C_6$ heteroalkyl, heterocycle, aryl, and heteroaryl, each substituted with one or more substituents selected from the group consisting of $R^4$, $R^5$, and $R^6$, said aryl and heteroaryl in the definition of $G^{10}$ can each be further optionally fused with a nonaromatic heterocycle or nonaromatic carbocycle; $R^1$ can be selected from the group consisting of fluorine, chlorine, and methyl; $R^2$ can be selected from the group consisting of —$OR^A$, —$NR^BR^C$, and —$SR^A$; $R^3$ can be selected from the group consisting of —$(CH_2)_mR^G$, —$OR^D$, and —$NR^ER^F$; $R^4$ can be selected from the group consisting of fluorine, chlorine, and methyl; $R^5$ can be selected from the group consisting of —$OR^A$, —$NR^BR^C$, and —$SR^A$; $R^6$ can be selected from the group consisting of —$(CH_2)_mR^G$, —$OR^D$, and —$NR^ER^F$; $J^{10}$ and $Q^{10}$ can each be independently selected from the group consisting of an ester, an amide, a urea, a carbamide, —$S(O)_2NR^4$—, a thioamide, a thioester, and an imidamide; $L^{10}$ can be a 3-13 atom long linker comprising one or more groups selected from —O— (oxygen), —$NR^4$—, —$S(O)_{0-2}$—, and —$NR^4S(O)_{1-2}O$—, and one or more groups selected from —O— (oxygen), —$NR^4$—, —$S(O)_{0-2}$—, and —$NR^4S(O)_{1-2}O$—, an optionally substituted $C_1$-$C_8$ alkyl, an optionally substituted aryl, and an optionally substituted heteroaryl; where the an optionally substituted aryl and an optionally substituted heteroaryl in the definition of $L^{10}$ can each be further optionally fused with a nonaromatic heterocycle or a nonaromatic carbocycle; and each m can be independently 0, 1, or 2.

Some embodiments disclosed herein provide a method of treating a patient, comprising administering to the patient a therapeutically effective amount of a compound having Formula X, wherein $A^{10}$ can be selected from the group consisting of a $C_2$-$C_6$ alkyl, a $C_2$-$C_7$ cycloalkyl, a $C_1$-$C_6$ heteroalkyl, a heterocycle, phenyl, pyridinyl, pyrrolyl, pyrimidinyl, imidazolyl, isoxazolyl, thiazolyl, thienyl, indolyl, benzoxazolyl, benzthiazolyl, benzimidazolyl, and purinyl, each substituted with one or more substituents selected from the group consisting of $R^1$, $R^2$, and $R^3$; $G^{10}$ can be selected from the group consisting of a $C_2$-$C_6$ alkyl, a $C_2$-$C_7$ cycloalkyl, a $C_1$-$C_6$ heteroalkyl, a heterocycle, phenyl, pyridinyl, pyrrolyl, pyrimidinyl, imidazolyl, isoxazolyl, thiazolyl, thienyl, indolyl, benzoxazolyl, benzthiazolyl, benzimidazolyl, and purinyl, each substituted with one or more substituents selected from the group consisting of $R^4$, $R^5$, and $R^6$; $R^1$ can be selected from the group consisting of fluorine, chlorine, and methyl; $R^2$ can be selected from the group consisting of —$OR^A$ and —$NR^BR^C$; $R^3$ can be $R^G$; $R^4$ can be selected from the group consisting of fluorine, chlorine, and methyl; $R^5$ can be selected from the group consisting of —$OR^A$ and —$NR^AR^B$; $R^6$ can be $R^G$; $J^{10}$ and $Q^{10}$ can each be independently selected from the group consisting of an amide, a urea, a carbamide, —$S(O)_2NR^4$—, a thioamide, and an imidamide; $L^{10}$ can be a 3-13 atom long linker comprising one or more groups selected from —O— (oxygen), —$C(=O)$—, —$NR^4$—, —$S(O)_{0-2}$—, —$NR^4S(O)_{1-2}NR^4$—, and one or more groups selected from an optionally substituted aryl, and an optionally substituted heteroaryl; where the an optionally substituted aryl and an optionally substituted heteroaryl in the definition of $L^{10}$ can each be further optionally fused with a nonaromatic heterocycle or a nonaromatic carbocycle.

Some embodiments disclosed herein provide a method of treating a patient, comprising administering to the patient a therapeutically effective amount of a compound having the structure:

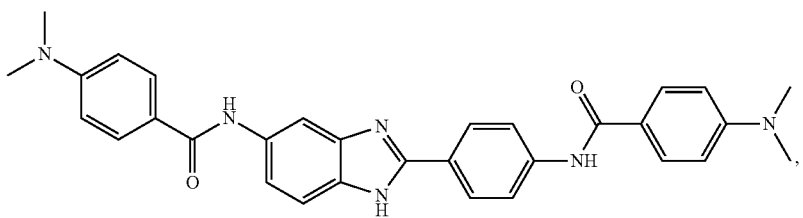

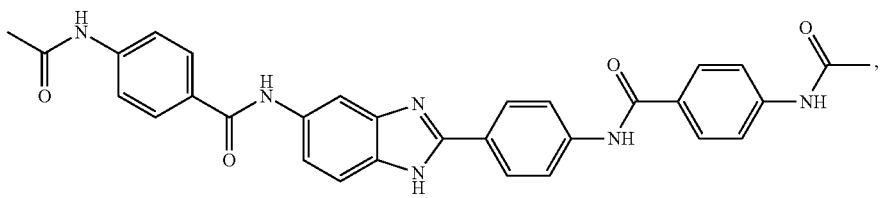

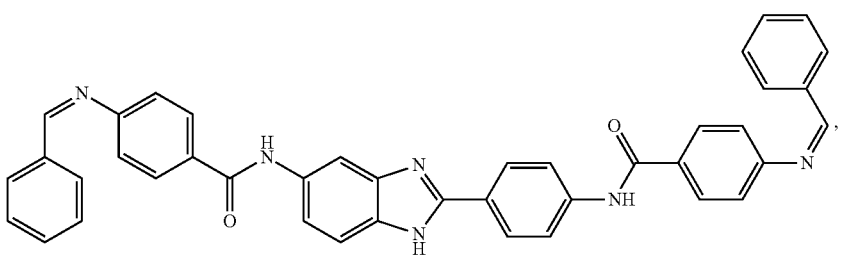

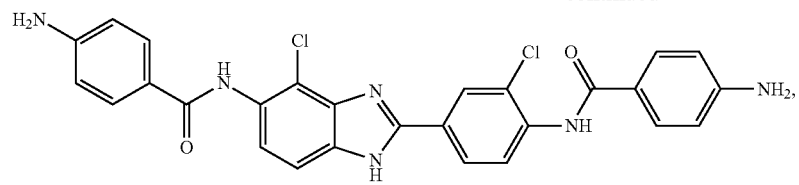
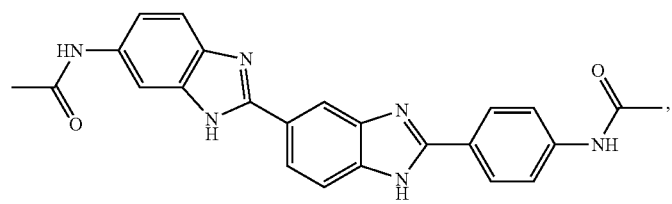
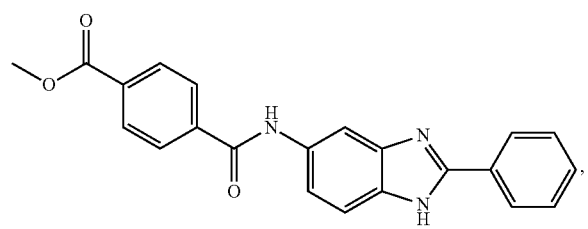
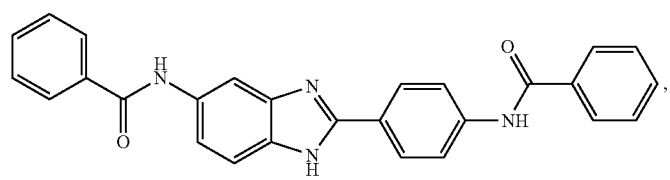
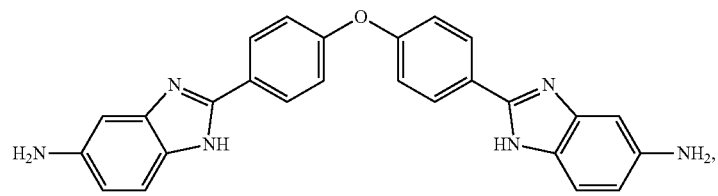
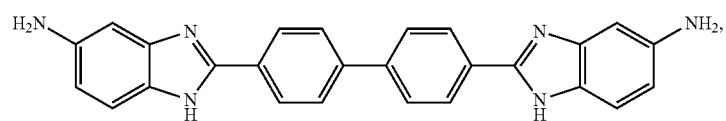
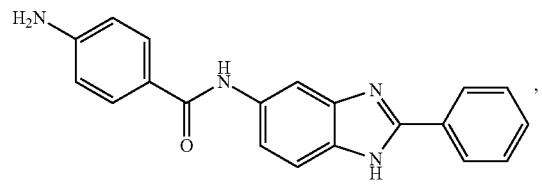
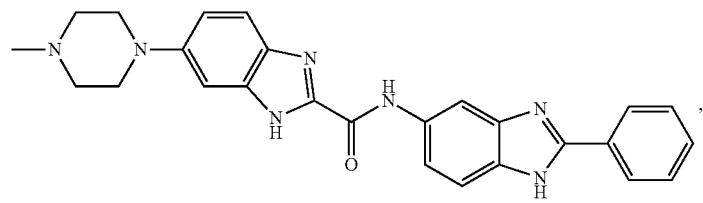
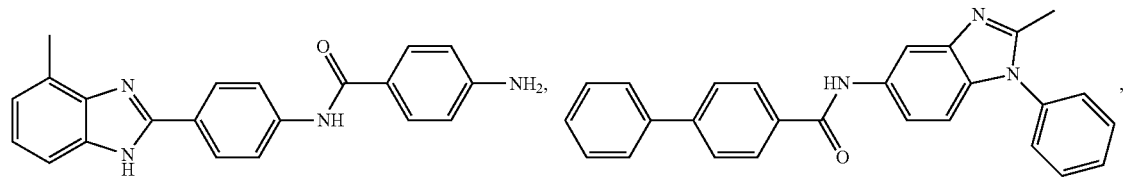

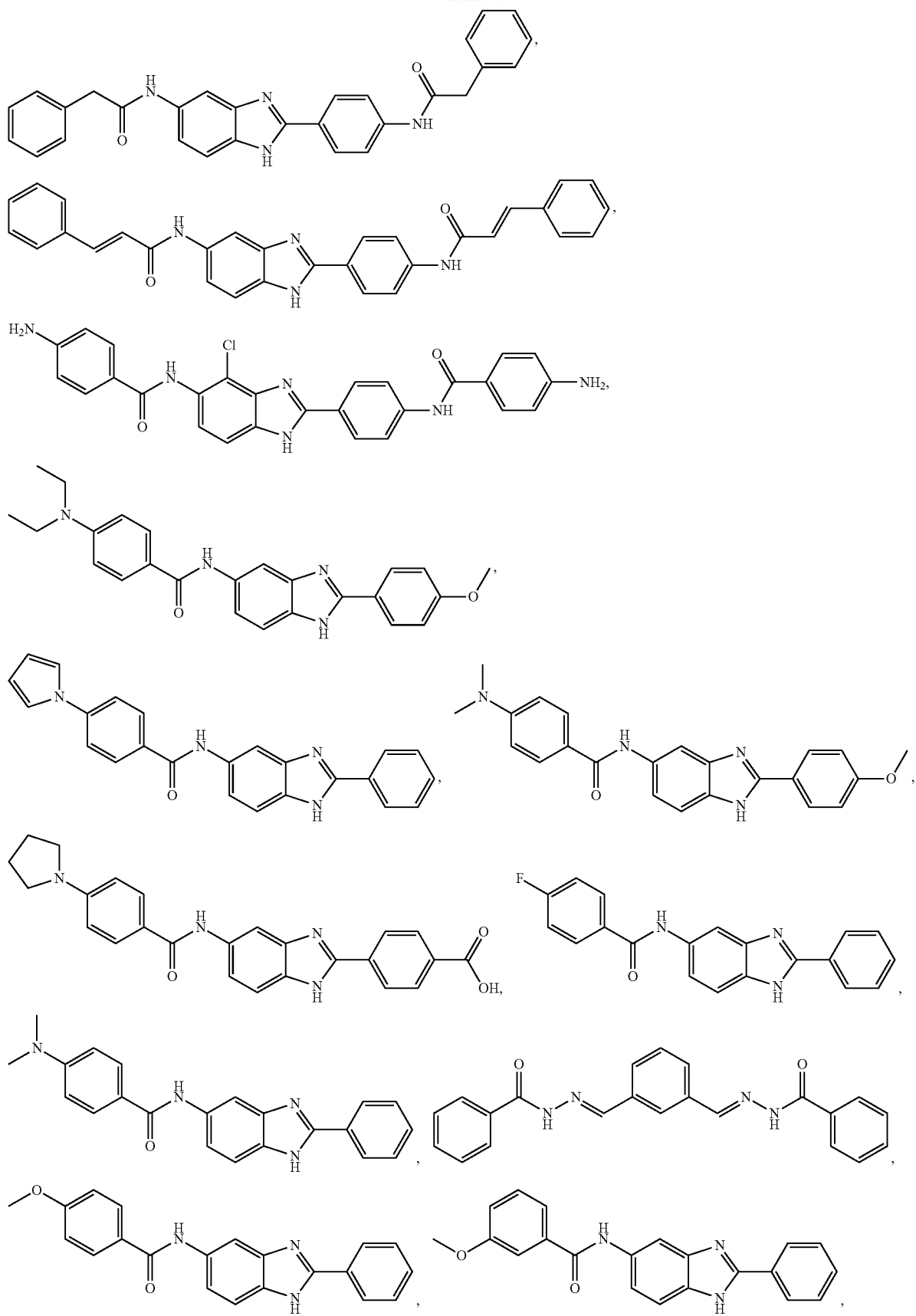

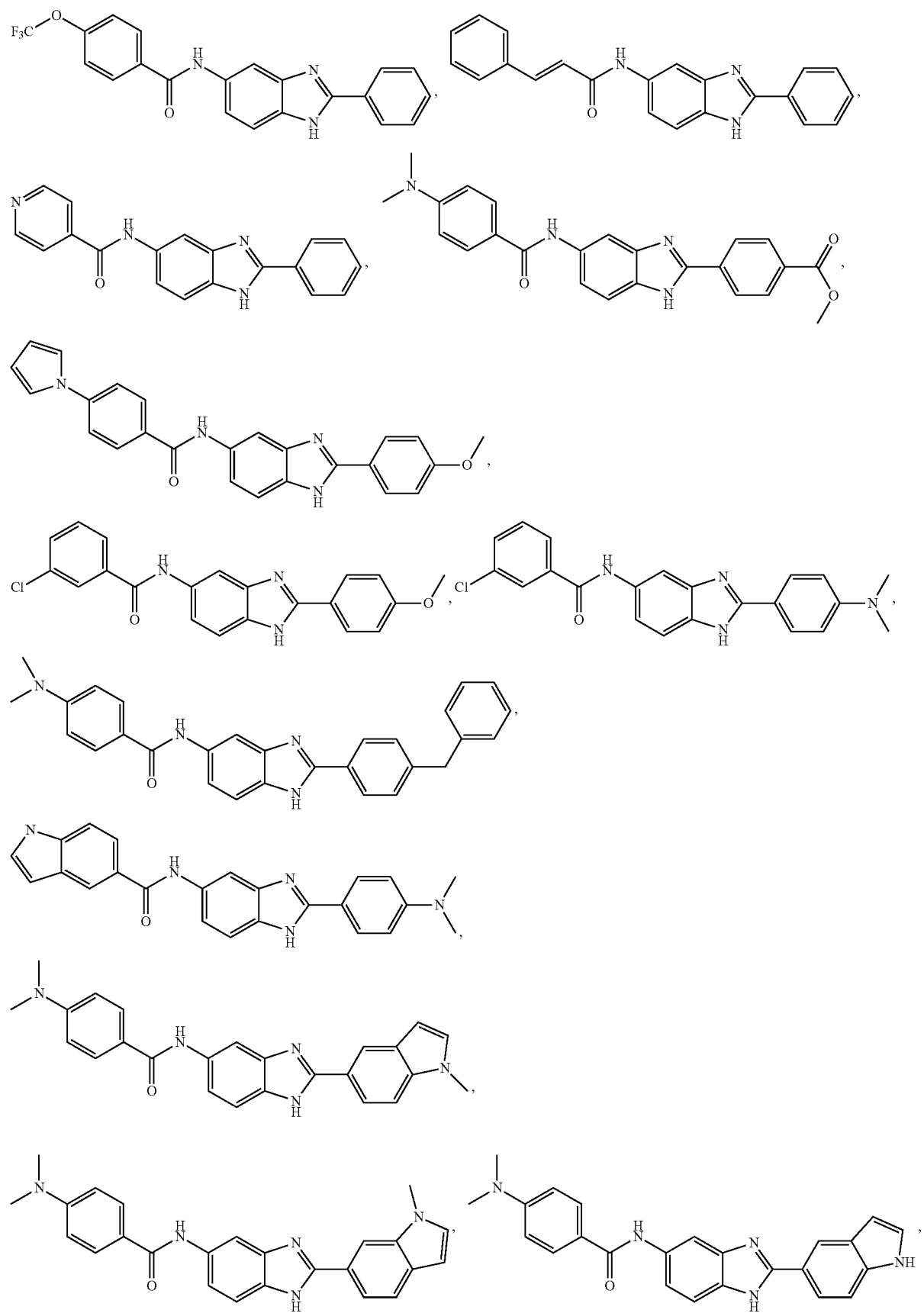

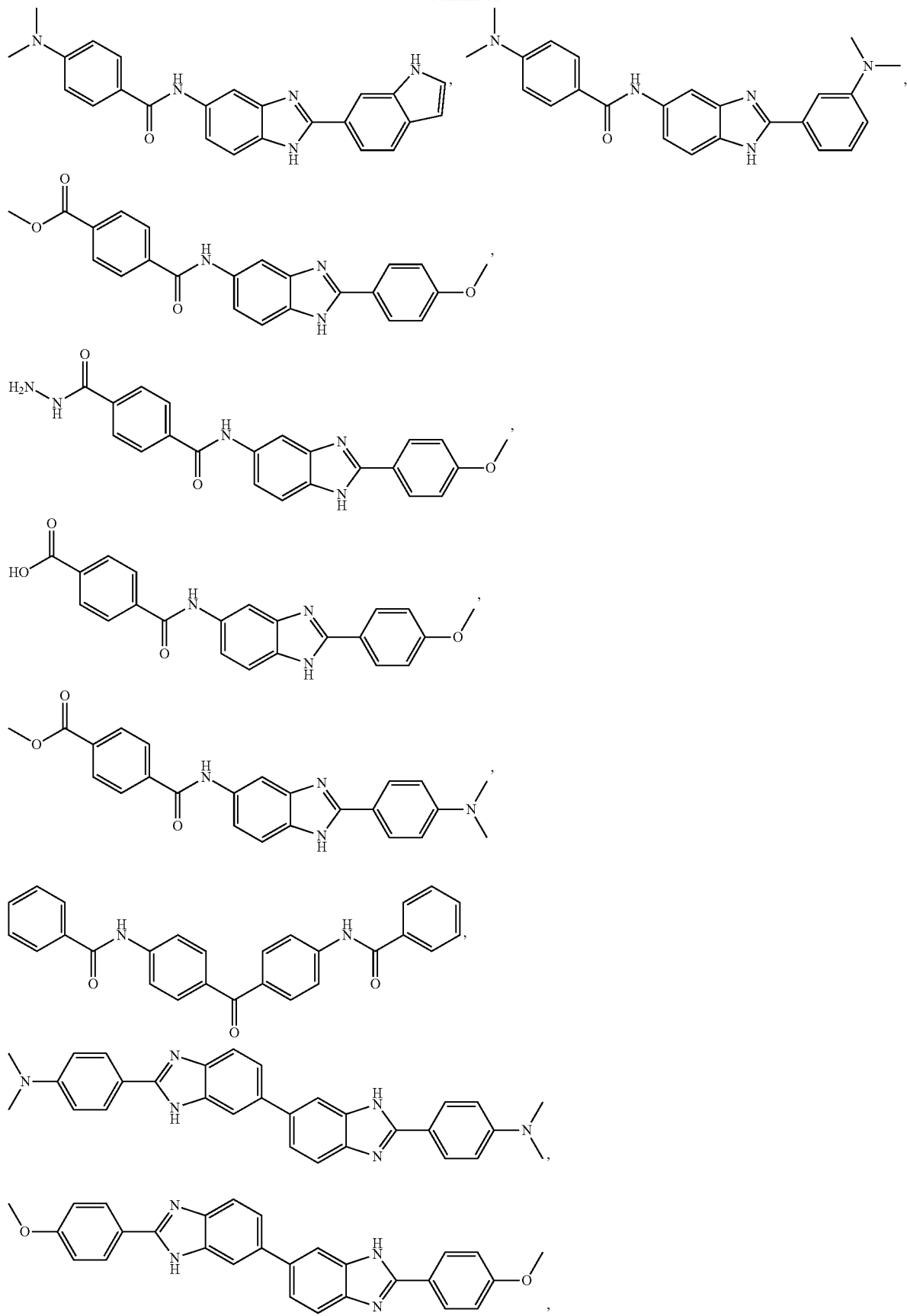

-continued

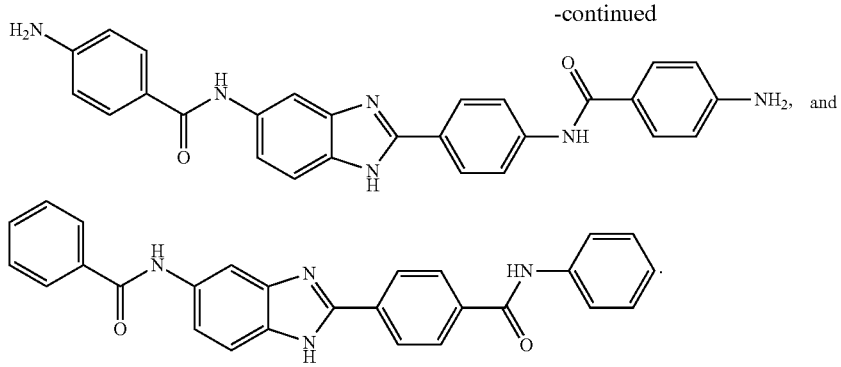

Some embodiments disclosed herein provide a pharmaceutical composition comprising a physiologically acceptable carrier, diluent, or excipient; and a compound of any of Formulae I to IX, or any compound specifically disclosed herein.

A pharmaceutical composition comprising a physiologically acceptable carrier, diluent, or excipient; and a compound of any of Formulae I to IX, or any compound specifically disclosed herein.

In certain embodiments, a compound of Formula I, II, III, IV, V, VI, VII, VIII, or IX, is a hematopoietic growth factor mimetic.

In certain embodiments, provided are methods for modulating activity of HGF receptors. Such methods comprise contacting a cell with one or more compounds of the present embodiments. Such methods include, but are not limited to, contacting HGF and/or HGF receptors with one or more compounds of the present embodiments.

In certain embodiments, the embodiments provide a method for identifying a compound that is capable of modulating HGF activity comprising: a) contacting a cell capable of a HGF activity with a compound of the present embodiments; and b) monitoring an effect on the cell. In certain such embodiments, the cell expresses a HGF receptor.

In certain embodiments, provided are methods of treating a patient comprising administering to the patient a compound of the present embodiments. In certain embodiments, such a patient suffers from thrombocytopenia. In certain embodiments, one or more compounds of the present embodiments are administered to a patient before, during or after chemotherapy, bone marrow transplantation, and/or radiation therapy. In certain embodiments, one or more compounds of the embodiments are administered to a patient suffering from aplastic anemia, bone marrow failure, and/or idiopathic thrombocytopenia. In certain embodiments, one or more compounds of the present embodiments are administered to a patient suffering from a disease of the nervous system. In certain embodiments, one or more compounds of the present embodiments are administered to a patient suffering from amyotrophic lateral sclerosis, multiple sclerosis, or multiple dystrophy. In certain embodiments, one or more compounds of the present embodiments are administered to a patient with a nerve injury, including, but not limited to, a spinal cord injury.

In certain embodiments, provided are pharmaceutical compositions comprising: i) a physiologically acceptable carrier, diluent, or excipient, or a combination thereof; and ii) one or more compounds of the present embodiments.

Certain embodiments provide a selective HGF modulator. Certain embodiments provide a selective HGF receptor agonist. Certain embodiments provide a selective HGF receptor antagonist. Certain embodiments provide a selective HGF partial agonist. Certain embodiments provide a selective HGF receptor binding compound. Certain embodiments provide a HGF mimic.

DETAILED DESCRIPTION

It is to be understood that both the foregoing general description and the following detailed description are exemplary and explanatory only and are not restrictive of the embodiments claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

DEFINITIONS

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference in its entirety for any purpose.

As used herein, the following terms are defined with the following meanings, unless expressly stated otherwise.

The term "selective binding compound" refers to a compound that selectively binds to any portion of one or more target.

The term "selective HGF receptor binding compound" refers to a compound that selectively binds to any portion of a HGF receptor.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a HGF receptor.

The term "modulator" refers to a compound that alters an activity. For example, a modulator may cause an increase or decrease in the magnitude of a certain activity compared to the magnitude of the activity in the absence of the modulator. In certain embodiments, a modulator is an inhibitor, which decreases the magnitude of one or more activities. In certain embodiments, an inhibitor completely prevents one or more biological activities. In certain embodiments, a modulator is an activator, which increases the magnitude of at least one activity. In certain embodiments the presence of a modulator results in a activity that does not occur in the absence of the modulator.

The term "selective modulator" refers to a compound that selectively modulates a target activity.

The term "selective HGF modulator" refers to a compound that selectively modulates at least one HGF activity. The term selective HGF modulator includes, but is not limited to "HGF mimic" which refers to a compound, the presence of which results in at least one HGF activity.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity, signal transduction, enzymatic activity, the proliferation and/or differentiation of progenitor cells, generation of platelets, and alleviation of symptoms of a disease or condition.

The term "HGF activity" refers to a biological activity that results, either directly or indirectly from the presence of HGF. Exemplary HGF activities include, but are not limited to, proliferation and or differentiation of progenitor cells to produce platelets; hematopoiesis; growth and/or development of glial cells; repair of nerve cells; and alleviation of thrombocytopenia.

The term "receptor mediated activity" refers to any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound, the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "alkyl" refers to a branched or unbranched fully saturated acyclic aliphatic hydrocarbon group. An alkyl may be branched or straight chain. Alkyls may be substituted or unsubstituted. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "alkenyl" used herein refers to a monovalent straight or branched chain aliphatic hydrocarbon radical of from two to twenty carbon atoms containing at least one carbon-carbon double bond including, but not limited to, 1-propenyl, 2-propenyl, 2-methyl-1-propenyl, 1-butenyl, 2-butenyl, and the like. In certain embodiments, an alkenyl comprises 2 to 20 carbon atoms (whenever it appears herein, a numerical range such as "2 to 20" refers to each integer in the given range; e.g., "2 to 20 carbon atoms" means that an alkenyl group may comprise only 2 carbon atoms, 3 carbon atoms, etc., up to and including 20 carbon atoms, although the term "alkenyl" also includes instances where no numerical range of carbon atoms is designated). An alkenyl may be designated as "$C_2$-$C_6$ alkenyl" or similar designations. By way of example only, "$C_2$-$C_4$ alkenyl" indicates an alkenyl having two, three, or four carbon atoms, e.g., the alkenyl is selected from ethenyl, propenyl, and butenyl.

The term "alkynyl" used herein refers to a monovalent straight or branched chain aliphatic hydrocarbon radical of from two to twenty carbon atoms containing at least one carbon-carbon triple bond including, but not limited to, 1-propynyl, 1-butynyl, 2-butynyl, and the like. In certain embodiments, an alkynyl comprises 2 to 20 carbon atoms (whenever it appears herein, a numerical range such as "2 to 20" refers to each integer in the given range; e.g., "2 to 20 carbon atoms" means that an alkynyl group may comprise only 2 carbon atoms, 3 carbon atoms, etc., up to and including 20 carbon atoms, although the term "alkynyl" also includes instances where no numerical range of carbon atoms is designated). An alkynyl may be designated as "$C_2$-$C_6$ alkynyl" or similar designations. By way of example only, "$C_2$-$C_4$ alkynyl" indicates an alkenyl having two, three, or four carbon atoms, e.g., the alkenyl is selected from ethynyl, propynyl, and butynyl.

The term "cycloalkyl" used herein refers to saturated aliphatic ring system radical having three to twenty carbon atoms. A cycloalkyl refers to monocyclic and polycyclic saturated aliphatic ring system including, but not limited to, cyclopropyl, cyclopentyl, cyclohexyl, cycloheptyl, bicyclo[4.4.0]decanyl, bicyclo[2.2.1]heptanyl, adamantyl, norbornyl, and the like. In certain embodiments, a cycloalkyl comprises 3 to 20 carbon atoms (whenever it appears herein, a numerical range such as "3 to 20" refers to each integer in the given range; e.g., "3 to 20 carbon atoms" means that a cycloalkyl group may comprise only 3 carbon atoms, etc., up to and including 20 carbon atoms, although the term "cycloalkyl" also includes instances where no numerical range of carbon atoms is designated). A cycloalkyl may be designated as "$C_3$-$C_7$ cycloalkyl" or similar designations. By way of example only, "$C_3$-$C_6$ cycloalkyl" indicates an alkenyl having two, three, four, five or six carbon atoms, e.g., the cycloalkyl is selected from cyclopropyl, cyclobutyl, cyclopentyl, and cyclohexyl.

The term "cycloalkenyl" used herein refers to aliphatic ring system radical having three to twenty carbon atoms having at least one carbon-carbon double bond in the ring. A cycloalkenyl refers to monocyclic and polycyclic unsaturated aliphatic ring system including, but are not limited to, cyclopropenyl, cyclopentenyl, cyclohexenyl, cycloheptenyl, bicyclo[3.1.0]hexyl, norbornylenyl, 1,1'-bicyclopentenyl, and the like. In certain embodiments, a cycloalkenyl comprises 3 to 20 carbon atoms (whenever it appears herein, a numerical range such as "3 to 20" refers to each integer in the given range; e.g., "3 to 20 carbon atoms" means that a cycloalkenyl group may comprise only 3 carbon atoms, etc., up to and including 20 carbon atoms, although the term "cycloalkenyl" also includes instances where no numerical range of carbon atoms is designated). A cycloalkenyl may be designated as "$C_3$-$C_7$ cycloalkenyl" or similar designations. By way of example only, "$C_3$-$C_6$ cycloalkenyl" indicates an alkenyl having two, three, four, five or six carbon atoms, e.g., the cycloalkyl is selected from cyclopropenyl, cyclobutenyl, cyclopentenyl, and cyclohexenyl.

The term "haloalkyl" refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another.

The term "heteroalkyl" refers to a group comprising an alkyl and one or more heteroatoms. Certain heteroalkyls are acylalkyls, in which the one or more heteroatoms are within an alkyl chain. Examples of heteroalkyls include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, $CH_3NHC(=O)CH_2-$, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like. An alkoxy may be designated as "$C_1$-$C_6$ alkoxy" or similar designations. By way of example only, "$C_1$-$C_4$ alkoxy" indicates an alkyl having one, two, three, or four carbon atoms, e.g., the alkoxy is selected from methoxy, ethoxy, propoxy, iso-propoxy, butoxy, iso-butoxy, sec-butoxy, and tert-butoxy.

The term "olefin" refers to a C=C bond.

The term "alkylideneamino" used herein refers to a moiety of from one to twenty carbon atoms containing at least one carbon-nitrogen double bond where the moiety is connected to the main group through the nitrogen, including, but not limited to, methylideneamino, ethylideneamino, methylethylideneamino, propylideneamino, 1-methylpropylideneaminyl, 2-methylpropylideneamino, butylideneamino, 1-methylbutylideneamino, 2-methylbutylideneamino, cyclopropylideneamino, cyclobutylideneamino, cyclopentylideneamino, cyclohexylideneamino and the like.

The term "carbocycle" refers to a group comprising a covalently closed ring, wherein each of the atoms forming the ring is a carbon atom. Carbocylic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

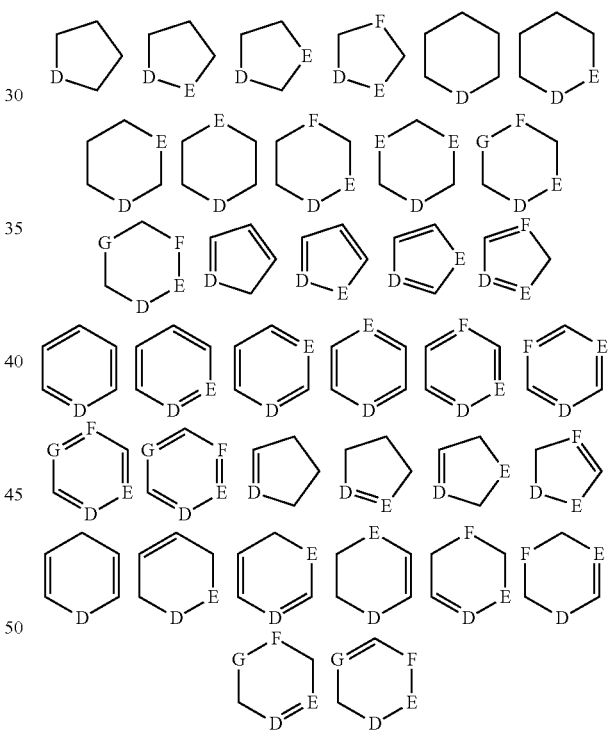

wherein D, E, F, and G independently represent a heteroatom. Each of D, E, F, and G may be the same or different from one another. Heterocycles may be aromatic heterocycles (i.e., heteroaryls) or non-aromatic heterocycles. In some embodiments, a non-aromatic heterocycle is a fully saturated covalently closed ring (for example, piperidine, pyrrolidine, morpholine, piperazine, and the like).

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic mono-, bi- or tricyclic ring system wherein at least one atom forming the aromatic ring system is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline.

The term "non-aromatic ring" refers to a group comprising a covalently closed ring that does not have a delocalized π-electron system.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "polycyclic heterocyclyl" used herein refers a bicyclic moiety or tricyclic moiety optionally containing one or more heteroatoms wherein at least one of the rings is an aryl or heteroaryl ring and at least one of the rings is non-aromatic. The bicyclic moiety contains two rings wherein the rings are fused. The bicyclic moiety can be appended at any position of the two rings. For example, bicyclic moiety may refer to a radical including but not limited to:

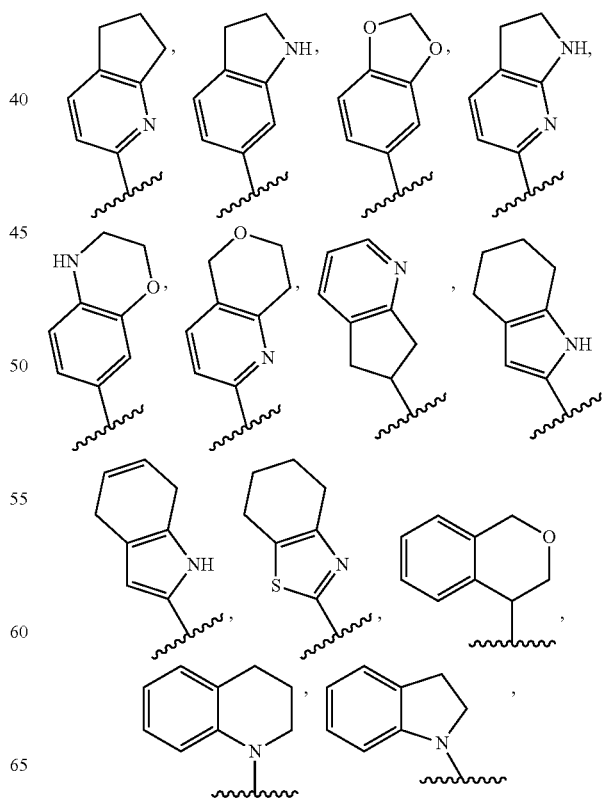

-continued

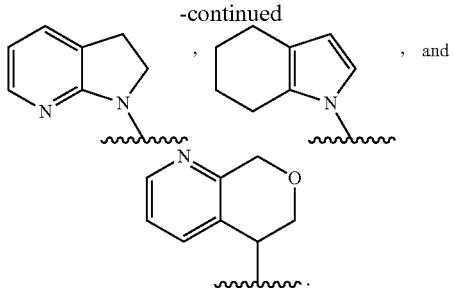

, and

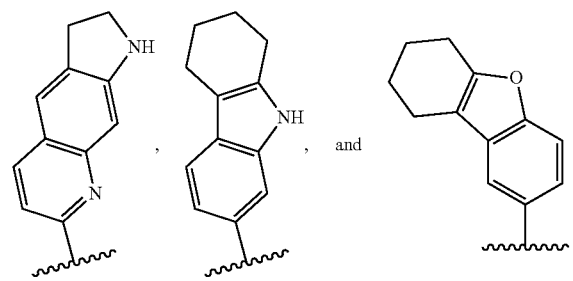

The tricyclic moiety contains a bicyclic moiety with an additional fused ring. The tricyclic moiety can be appended at any position of the three rings. For example, tricyclic moiety may refer to a radical including but not limited to:

The term "arylalkyl" refers to a group comprising an aryl group bound to an alkyl group.

The term "carbocycloalkyl" refers to a group comprising a carbocyclic cycloalkyl ring. Carbocycloalkyl rings may be formed by three, four, five, six, seven, eight, nine, or more than nine carbon atoms. Carbocycloalkyl groups may be optionally substituted.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings may be optionally substituted. Rings may form part of a ring system.

The term "ring system" refers to a either a single ring or two or more rings, wherein, if two or more rings are present, the two or more of the rings are fused. The term "fused" refers to structures in which two or more rings share one or more bonds.

The term "spacer" refers to an atom or group of atoms that separate two or more groups from one another by a desired number of atoms. For example, in certain embodiments, it may be desirable to separate two or more groups by one, two, three, four, five, six, or more than six atoms. In such embodiments, any atom or group of atoms may be used to separate those groups by the desired number of atoms. Spacers are optionally substituted. In certain embodiments, a spacer comprises saturated or unsaturated alkyls, heteroalkyls and/or haloalkyls. In certain embodiments, a spacer comprises atoms that are part of a ring.

Solely for the purposes of illustration, and without limiting the above definition, some examples of spacers are provided. Examples of 1 atom spacers include, but are not limited to, the following:

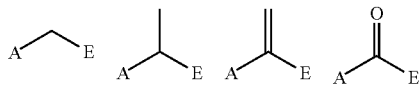

where A and E represent groups which are separated by the desired number of atoms. Examples of 2 atom spacers include, but are not limited to, the following:

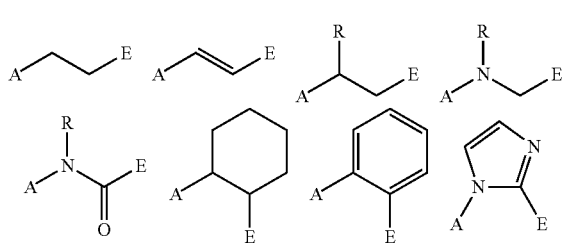

where A and E represent groups which are separated by the desired number of atoms. Examples of 3 atom spacers include, but are not limited to, the following:

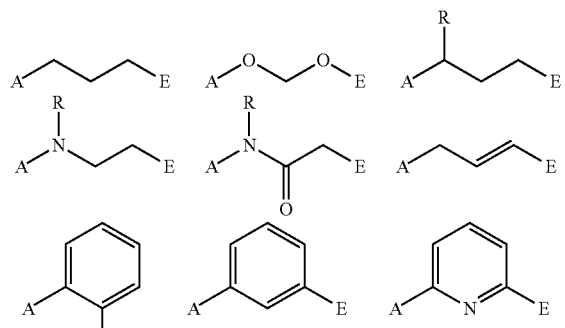

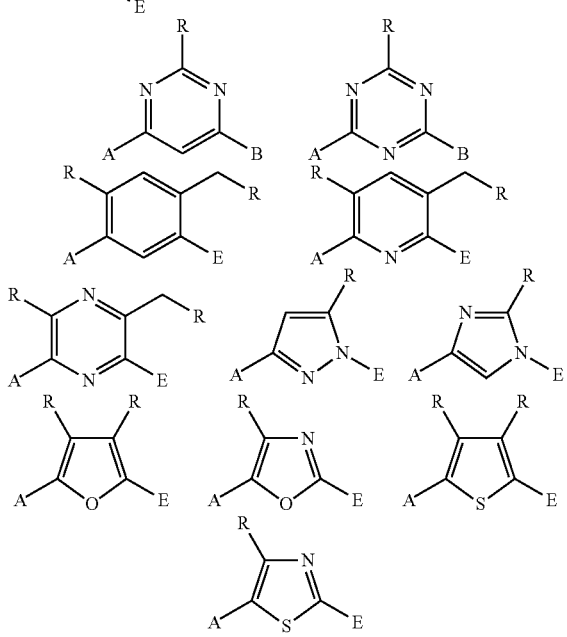

where A and E represent groups which are separated by the desired number of atoms. Examples of 4 atom spacers include, but are not limited to, the following:

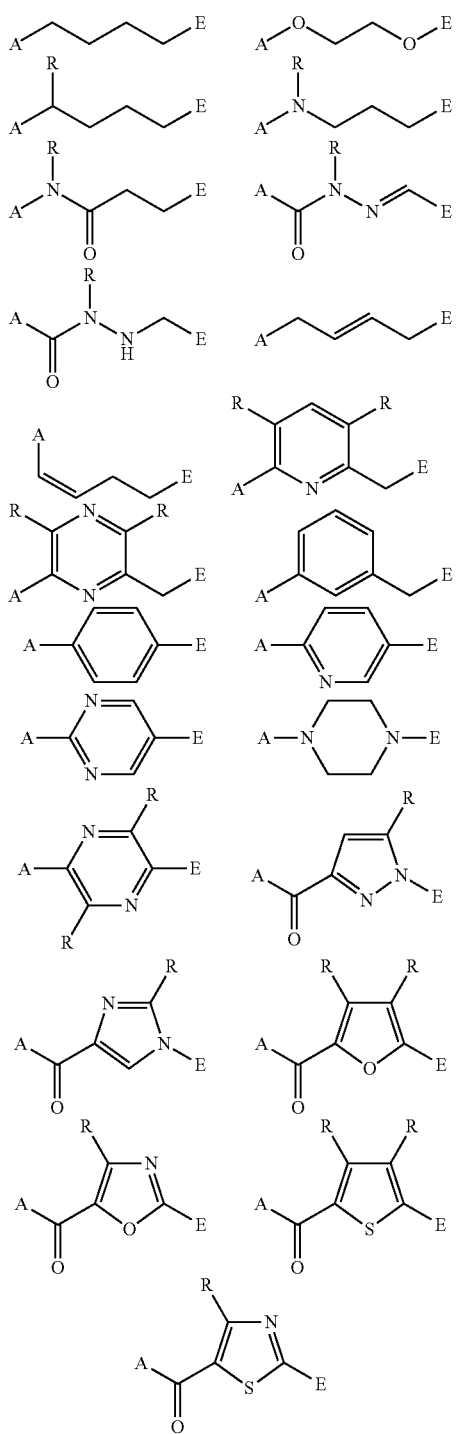

where A and E represent groups which are separated by the desired number of atoms. As is evident from the above examples, the atoms that create the desired separation may themselves be part of a group. That group may be, for example, an alkyl, heteroalkyl, haloalkyl, heterohaloalkyl, cycloalkyl, aryl, arylalkyl, heteroaryl, non-aromatic heterocycle, or substituted alkyl all of which are optionally substituted. Thus the term "1-5 atom spacer" refers to a spacer that separates two groups by 1, 2, 3, 4, or 5 atoms and does not indicate the total size of the group that constitutes the spacer.

As used herein, the term "linked to form a ring" refers to instances where two atoms that are bound either to a single atom or to atoms that are themselves ultimately bound, are each bound to a linking group, such that the resulting structure forms a ring. That resulting ring comprises the two atoms that are linked to form a ring, the atom (or atoms) that previously linked those atoms, and the linker. For example, if A and E below are "linked to form a ring"

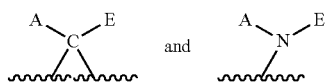

the resulting ring includes A, E, the C (carbon) or N (nitrogen) to which they are attached, and a linking group. Unless otherwise indicated, that linking group may be of any length and may be optionally substituted. Referring to the above example, resulting structures include, but are not limited to:

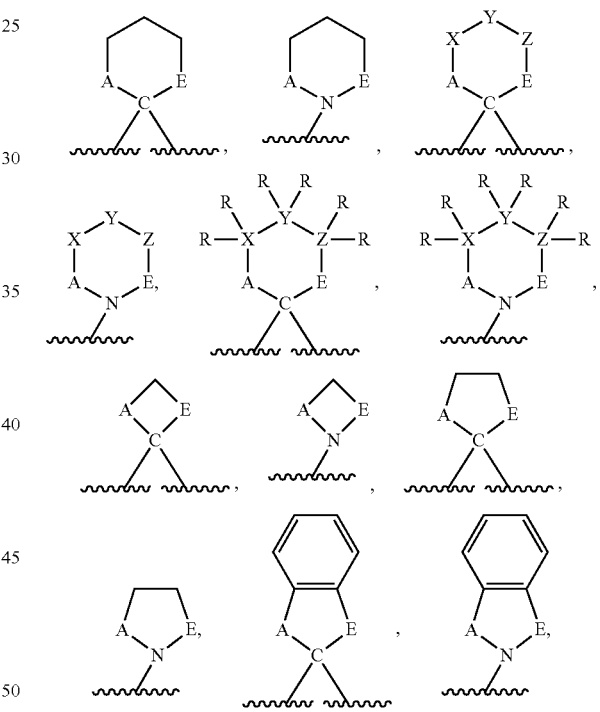

and the like.

In certain embodiments, the two substituents that together form a ring are not immediately bound to the same atom. For example, if A and E, below, are linked to form a ring:

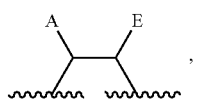

the resulting ring comprises A, E, the two atoms that already link A and E and a linking group. Examples of resulting structures include, but are not limited to:

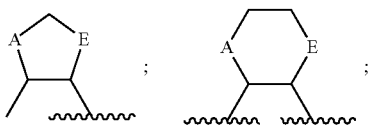

and the like.

In certain embodiments, the atoms that together form a ring are separated by three or more atoms. For example, if A and E, below, are linked to form a ring:

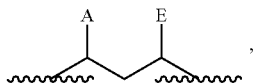

the resulting ring comprises A, E, the 3 atoms that already link A and E, and a linking group. Examples of resulting structures include, but are not limited to:

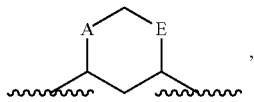

and the like.

As used herein, the term "together form a bond" refers to the instance in which two substituents to neighboring atoms are null the bond between the neighboring atoms becomes a double bond. For example, if A and E below "together form a bond"

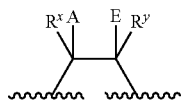

the resulting structure is:

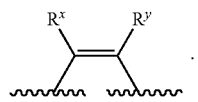

The term "null" refers to a group being absent from a structure. For example, in the structure

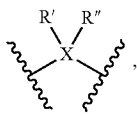

where in certain instances X is N (nitrogen), if X is N (nitrogen), one of R' or R" is null, meaning that only three groups are bound to the N (nitrogen).

The substituent "R" appearing by itself and without a number designation refers to a substituent selected from alkyl, cycloalkyl, aryl, heteroaryl (bonded through a ring carbon) and non-aromatic heterocycle (bonded through a ring carbon).

The term "O-carboxy" refers to the group consisting of formula RC(=O)O—.

The term "C-carboxy" refers to the group consisting of formula —C(=O)OR.

The term "acetyl" refers to the group consisting of formula —C(=O)CH$_3$.

The term "trihalomethanesulfonyl" refers to the group consisting of formula X$_3$CS(=O)$_2$— where X is a halogen.

The term "cyano" refers to the group consisting of formula —CN.

The term "isocyanato" refers to the group consisting of formula —NCO.

The term "thiocyanato" refers to the group consisting of formula —CNS.

The term "isothiocyanato" refers to the group consisting of formula —NCS.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "trihalomethanesulfonamido" refers to the group consisting of formula X$_3$CS(=O)$_2$NR—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "keto" and "carbonyl" used herein refers to C=O.

The term "thiocarbonyl" used herein refers to C=S.

The term "ester" refers to a chemical moiety with formula —(R)$_n$—C(=O)OR', where R and R' are independently selected from alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(=O)NHR' or —(R)$_n$—NHC(=O)R', where R is selected from alkyl, cycloalkyl, aryl, heteroaryl (bonded through a ring carbon) and heteroalicyclic (bonded through a ring carbon), where n is 0 or 1 and R' is selected from hydrogen, alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The term "amino" refers to a chemical moiety with formula —NHR'R", where R' and R" are each independently selected from hydrogen, alkyl, cycloalkyl, aryl, heteroaryl (bonded through a ring carbon) and heteroalicyclic (bonded through a ring carbon).

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) individually and independently selected from: alkyl, alkenyl, cycloalkenyl, alkynyl, heteroalkyl, haloalkyl, cycloalkyl, aryl, arylalkyl, alkenylO—, arylalkylO—, arylalkylNH—, alkenylO—, cycloalkylC(=O)—, arylC(=O)—, arylC(=O)NH—, arylNHC(=O)—, aryl(CH$_2$)$_{0-3}$O(CH$_2$)$_{0-3}$—, HO(CH$_2$)$_{1-3}$NH—, HO(CH$_2$)$_{1-3}$O—, HO(CH$_2$)$_{1-3}$—, HO(CH$_2$)$_{1-3}$O(CH$_2$)$_{1-3}$—, —C(=O)NHNH$_2$, heteroaryl, heterocycle, hydroxy, alkoxy, aryloxy, mercapto, alkylthio, arylthio, cyano, halo, carbonyl, oxo, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives of amino groups. Such protective derivatives (and protecting groups that may form such protective derivatives) are known to those of skill in the art and may be found in references such as Greene and Wuts, above. When the group contains a nitrogen, or a sulfur, an oxo as a substituent also includes oxides, for example pyridine-N-oxide, thiopyran sulfoxide and thiopyran-S,S-dioxide. In embodiments in which two or more hydrogen atoms have been substituted, the substituent groups may together form a ring.

The term "stereoisomers" as used herein means isomers that possess identical constitution, but which differ in the arrangement of their atoms in space. Including, for example, all enantiomers, diastereomers, geometric isomers, and atropisomers.

Wherever a substituent as depicted as a di-radical (i.e., has two points of attachment to the rest of the molecule), it is to be understood that the substituent can be attached in any directional configuration unless otherwise indicated. Thus, for example, a substituent depicted as -AE- or

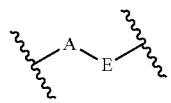

includes the substituent being oriented such that the A is attached at the leftmost attachment point of the molecule as well as attached at the rightmost attachment point of the molecule.

It is to be understood that certain radical naming conventions can include either a mono-radical or a di-radical, depending on the context. For example, where a substituent requires two points of attachment to the rest of the molecule, it is understood that the substituent is a di-radical. A substituent identified as alkyl, that requires two points of attachment, includes di-radicals such as —CH$_2$—, —CH$_2$CH$_2$—, —CH$_2$CH(CH$_3$)CH$_2$—, and the like; a substituent depicted as alkoxy that requires two points of attachment, includes di-radicals such as —OCH$_2$—, —OCH$_2$CH$_2$—, —OCH$_2$CH(CH$_3$)CH$_2$—, and the like: and a substituent depicted as arylC(=O)— that requires two points of attachment, includes di-radicals such as

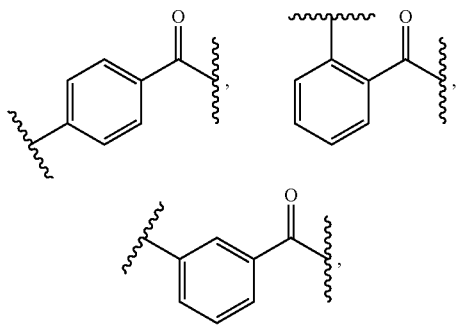

and the like.

Throughout the specification, groups and substituents thereof can be chosen by one skilled in the field to provide stable moieties and compounds.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to an pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate receptor mediated biological activity in one tissue and fail to modulate, or modulate to a lesser degree, receptor mediated biological activity in another tissue type.

The term "monitoring" refers to observing an effect or absence of any effect. In certain embodiments, one monitors cells after contacting those cells with a compound of the present embodiments. Examples of effects that may be monitored include, but are not limited to, changes in cell phenotype, cell proliferation, receptor activity, or the interaction between a receptor and a compound known to bind to the receptor.

The term "cell phenotype" refers to physical or biological characteristics. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. In certain embodiments, cells are in situ in an organism. In certain embodiments, cell are grown in vitro in a vessel. The number of cells growing in a vessel can be quantified by a person skilled in the art (e.g., by counting cells in a defined area using a microscope or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may be dead. Cells may or may not be intact.

Certain Compounds

Certain compounds that modulate one or more HGF activity and/or bind to HGF receptors play a role in health. In certain embodiments, compounds are useful for treating any of a variety of diseases or conditions.

Certain embodiments provide selective HGF modulators. Certain embodiments provide selective HGF receptor binding agents. Certain embodiments provide methods of making and methods of using selective HGF modulators and/or selective HGF receptor binding agents. In certain embodiments, selective HGF modulators are agonists, partial agonists, and/or antagonists for the HGF receptor.

The compounds disclosed herein can be used alone or in combination with other agents, for example, to modulate hematopoiesis, erythropoiesis, granulopoiesis, thrombopoiesis, and myelopoiesis. The instant compounds can also be used alone or in combination with other agents in treatment or prevention of a disease or condition caused by abnormal function of hematopoiesis, erythropoiesis, granulopoiesis, thrombopoiesis, and myelopoiesis. Some non-limiting examples of diseases include anemia, neutropenia, thrombocytopenia, cardiovascular disorders, immune/autoimmune disorders, cancers, infectious disorders or diseases, and neurologic disorders.

One of skill in the art will recognize that analogous synthesis schemes may be used to synthesize similar compounds. One of skill will recognize that compounds of the present embodiments may be synthesized using other synthesis schemes. In certain embodiments, a salt corresponding to any of the compounds provided herein is provided.

In certain embodiments, a salt corresponding to a selective HGF modulator is provided. In certain embodiments, a salt corresponding to a selective HGF receptor binding agent is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a selective HGF modulator or selective HGF binding agent with multiple molar equivalents of a base, such as bis-sodium, bis-ethanolamine, and the like.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subacetate, succinate, sulfate, tannate, tartrate, teoclate, tosylate, triethiodide, tromethamine, trimethylammonium, and valerate salts.

In certain embodiments, one or more carbon atoms of a compound of the present embodiments are replaced with silicon. See e.g., WO 03/037905A1; Tacke and Zilch, Endeavour, New Series, 10, 191-197 (1986); Bains and Tacke, Curr. Opin. Drug Discov Devel. July: 6(4):526-43 (2003), all of which are incorporated herein by reference in their entirety. In certain embodiments, compounds comprising one or more silicon atoms possess certain desired properties, including, but not limited to, greater stability and/or longer half-life in a patient, when compared to the same compound in which none of the carbon atoms have been replaced with a silicon atom.

Certain Assays

In certain embodiments, assays may be used to determine the level of HGF modulating activity of the compounds of the present embodiments.

Proliferation Assay

In some embodiments, compounds are tested in an in vitro proliferation assay using the cell lines that express EPO, GCSF or other cytokine receptors that may be dependant upon these cytokines for their growth.

Luciferase Assay

In some embodiments, compounds are tested in a reporter assay using the cell lines that express EPO, GCSF or other cytokine receptors. These cells are transfected with the STAT responsive reporter (such as luciferase) and the activity of the compounds is determined by a reporter assay.

Differentiation Assay

In some embodiments, compounds are tested in purified human CD34+ progenitor cells. After addition of the compounds to the cells, the number of cells expressing markers of hematopoiesis, erythropoiesis, granulopoiesis, thrombopoiesis, or myelopoiesis is measured by flow cytometry or by analyzing expression of genes associated with these pathways.

Certain Pharmaceutical Agents

In certain embodiments, at least one selective HGF modulator, or pharmaceutically acceptable salt, ester, amide, and/or prodrug thereof, either alone or combined with one or more pharmaceutically acceptable carriers, forms a pharmaceutical agent. Techniques for formulation and administration of compounds of the present embodiments may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semi-permeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present embodiments is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a selective HGF modulator in a dose from about 1 µg/kg of body weight to about 50 mg/kg of body weight. In certain embodiments, such dosage units comprise a selective HGF modulator in a dose from about 2 µg/kg of body weight to about 25 mg/kg of body weight. In certain embodiments, such dosage units comprise a selective HGF modulator in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present embodiments can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses.

In certain embodiments, a pharmaceutical agent of the present embodiments is administered by continuous intravenous infusion. In certain of such embodiments, from 0.1 mg to 500 mg of a composition of the present embodiments is administered per day.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Combination Therapies

In certain embodiments, one or more pharmaceutical agents of the present embodiments are co-administered with one or more other pharmaceutical agents. In certain embodiments, such one or more other pharmaceutical agents are designed to treat the same disease or condition as the one or more pharmaceutical agents of the present embodiments. In certain embodiments, such one or more other pharmaceutical agents are designed to treat a different disease or condition as the one or more pharmaceutical agents of the present embodiments. In certain embodiments, such one or more other pharmaceutical agents are designed to treat an undesired effect of one or more pharmaceutical agents of the present embodiments. In certain embodiments, one or more pharmaceutical agents of the present embodiments are co-administered with another pharmaceutical agent to treat an undesired effect of that other pharmaceutical agent. In certain embodiments, one or more pharmaceutical agents of the present embodiments and one or more other pharmaceutical agents are administered at the same time. In certain embodiments, one or more pharmaceutical agents of the present embodiments and one or more other pharmaceutical agents are administered at the different times. In certain embodiments, one or more pharmaceutical agents of the present embodiments and one or more other pharmaceutical agents are prepared together in a single formulation. In certain embodiments, one or more pharmaceutical agents of the present embodiments and one or more other pharmaceutical agents are prepared separately.

Examples of pharmaceutical agents that may be co-administered with a pharmaceutical agent of the present embodiments include, but are not limited to, anti-cancer treatments, including, but not limited to, chemotherapy and radiation treatment; corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Indications

In certain embodiments, provided are methods of treating a patient comprising administering one or more compounds of the present embodiments. In certain embodiments, such patient suffers from thrombocytopenia. In certain such embodiments, thrombocytopenia results from chemotherapy and/or radiation treatment. In certain embodiments, thrombocytopenia results bone marrow failure resulting from bone marrow transplantation and/or aplastic anemia. In certain embodiments thrombocytopenia is idiopathic. In certain embodiments, one or more compounds of the present embodiments are administered to a patient to in conjunction with harvesting peripheral blood progenitor cells and/or in conjunction with platelet apheresis. Such administration may be done before, during, and/or after such harvesting.

In certain embodiments, one or more compounds of the present embodiments are administered to a patient who suffers from a condition affecting the nervous system, including, but are not limited to, diseases affecting the nervous system and injuries to the nervous system. Such diseases, include, but not limited to, amyotrophic lateral sclerosis, multiple sclerosis, and multiple dystrophy. Injury to the nervous system include, but are not limited to spinal cord injury or peripheral nerve damage, including, but not limited to, injury resulting from trauma or from stroke. In certain embodiments, one or more compounds of the present embodiments are used to promote growth and/or development of glial cells. Such glial cells may repair nerve cells. In certain embodiments, compounds of the present embodiments are used to treat psychological disorders, including, but not limited to, cognitive disorders.

Certain Synthesis Methods

Scheme I

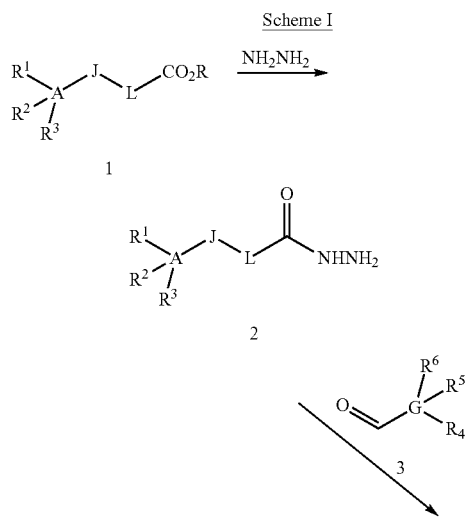

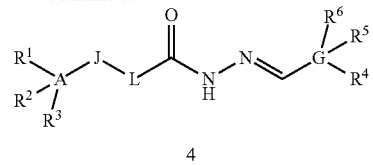

The process of Scheme I describes the general synthesis of compounds of general structure 4 described in Formula I, wherein R can be $C_{1-6}$ alkyl, aryl and the like. Treatment of the ester derivatives of general structure 1 with hydrazine affords hydrazide derivatives of general structure 2. The intermediates of general structure 2 are condensed with an aldehyde of general structure 3 to generate the compounds of general structure 4.

Scheme II

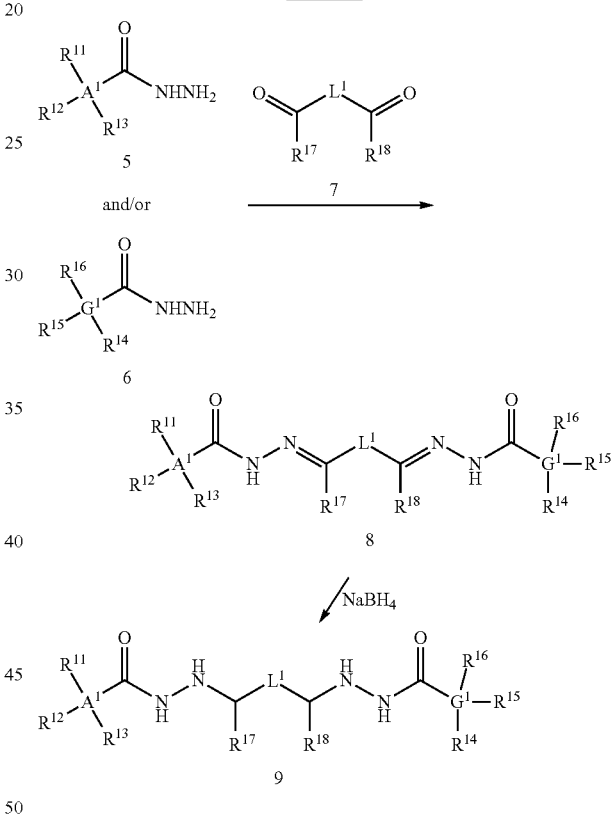

The process of Scheme II describes general synthesis of the compounds of Formula II. Condensation reactions of the biscarbonyl compounds of general structure 7 and substituted hydrazides of general structures 5 or 6 under standard conditions provide the pseudo-symmetric compounds of structure 8. Alternatively, when the hydrazides of general structures 5 and 6 are different, the condensation reactions can be run sequentially to provide compounds of general structure 8. Compounds of general structure 9 can be obtained by a standard reduction of compounds of general structure 8. For example, reducing agents such sodium borohydride, lithium borohydride, sodium cyanoborohydride, potassium trisiamylborohydride, potassium tri-sec-butylborohydride, lithium trisiamylborohydride, lithium tri-sec-butylborohydride, diisobutylaluminum hydride, lithium triethoxyaluminum hydride and the like can be used in the reduction.

Scheme III

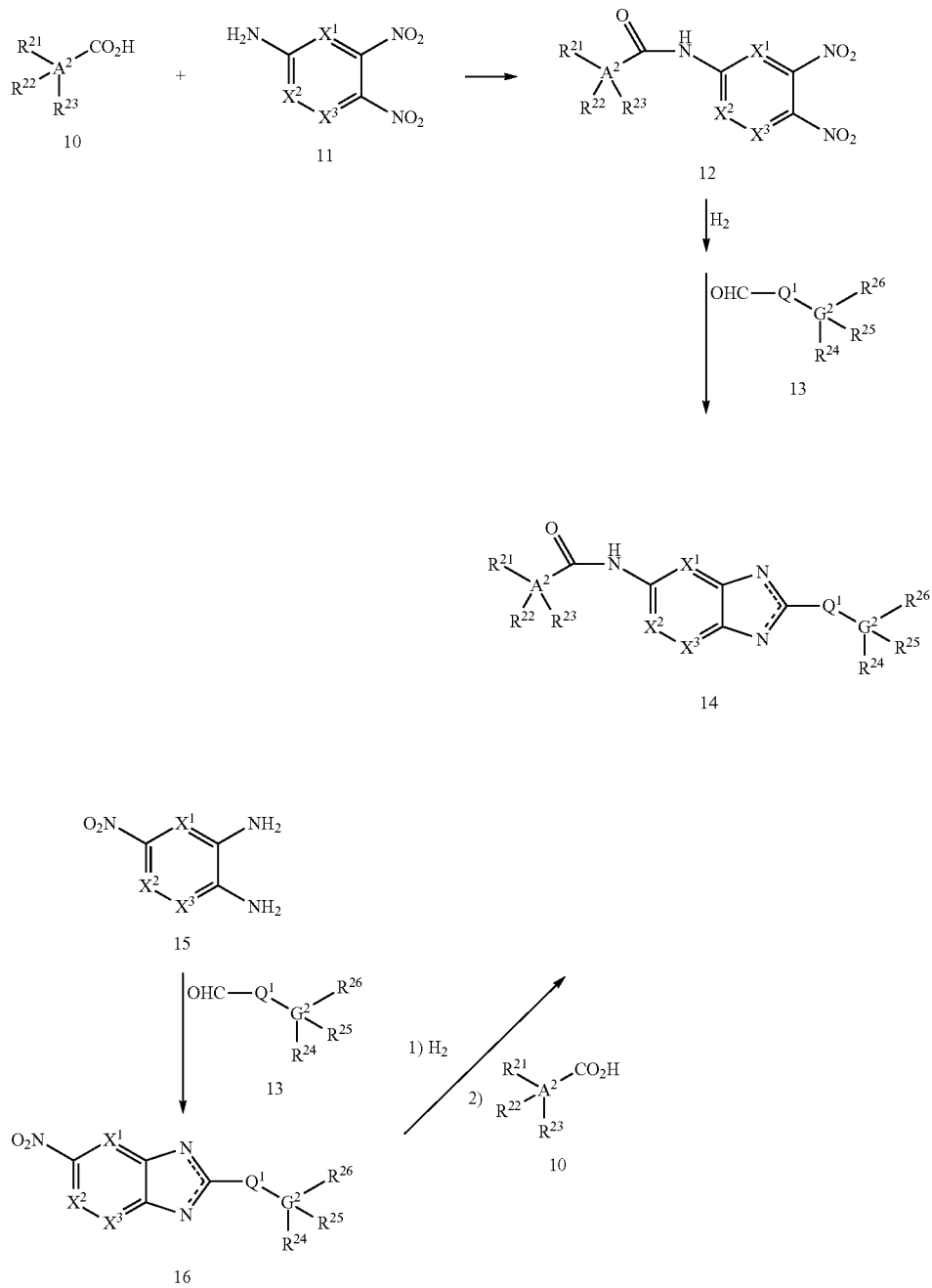

The process of Scheme III describes general synthesis of the compounds of Formula III. Coupling of an acid derivative of structure 10 with an amino derivative of structure 11 under standard conditions provides the amide intermediate of structure 12. The two nitro groups of structure 12 are reduced under a typical reduction condition such as a metal catalyzed hydrogenation to give the diamino intermediate and then the intermediate is condensed with an aldehyde of structure 13 under an oxidative condition to afford desired compounds of structure 14. Alternatively, compounds of structure 10 can be prepared from diamino derivatives of structure 15. Condensation reaction of compounds of structure 15 with compounds of structure 13 under an oxidative condition provides the intermediate of structure 16. A nitro reduction of intermediates 16 followed by an amide formation reaction under similar conditions described previously generate the compounds of structure 14.

Scheme IV

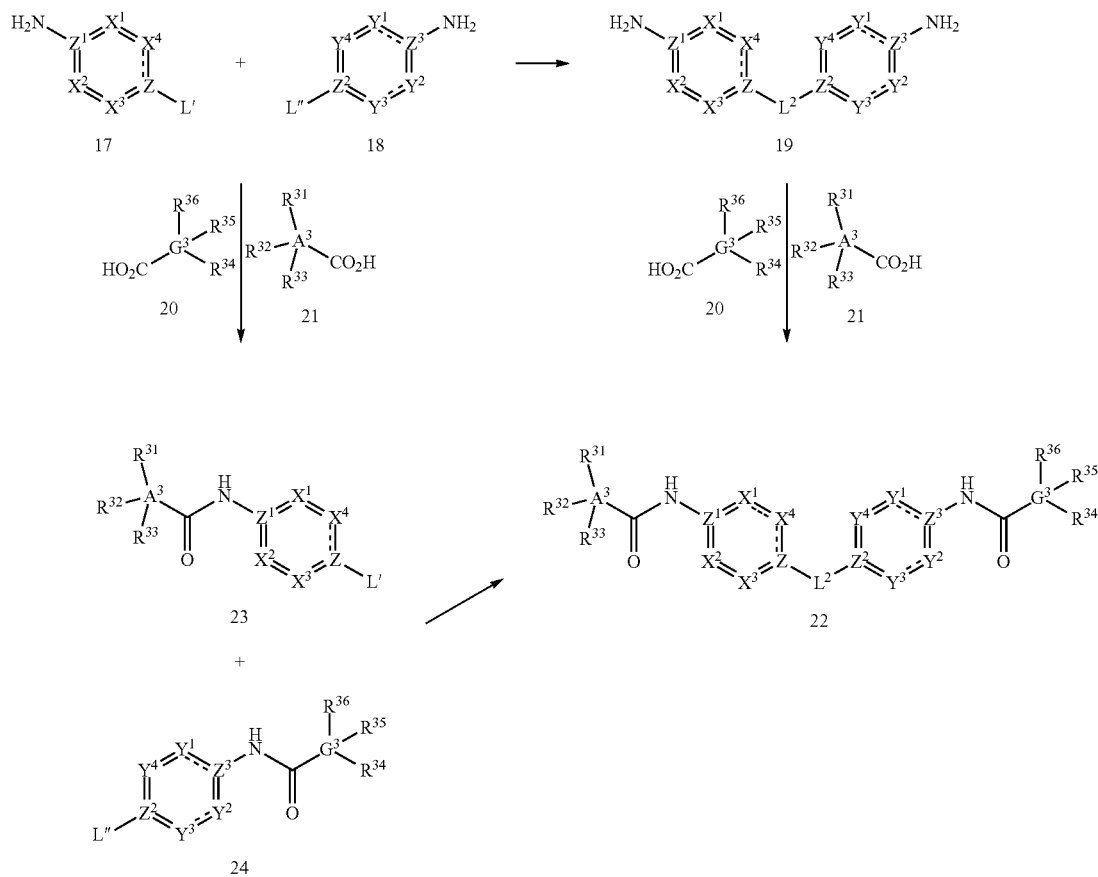

The process of Scheme IV describes general synthesis of the compounds of Formula IV. Coupling reaction of compounds of structure 17 and compounds of structure 18 under the standard condition based on the nature of substituents L' and L" provides intermediates of structure 19. Amide formation reaction of compounds of structures 20 and 21 and intermediates of structure 19 affords the products of structure 22. Alternatively, especially for compounds of structure 22 that have different rings or side chains, compounds of structure 22 can be prepared with different coupling strategy. Amide coupling reactions between compounds of structures 17 and 21 and between compounds of structures 18 and 20 generate separate intermediates of structures 23 and 24. The intermediates of structures 23 and 24 are then coupled to form final compounds of structure 22.

Scheme V

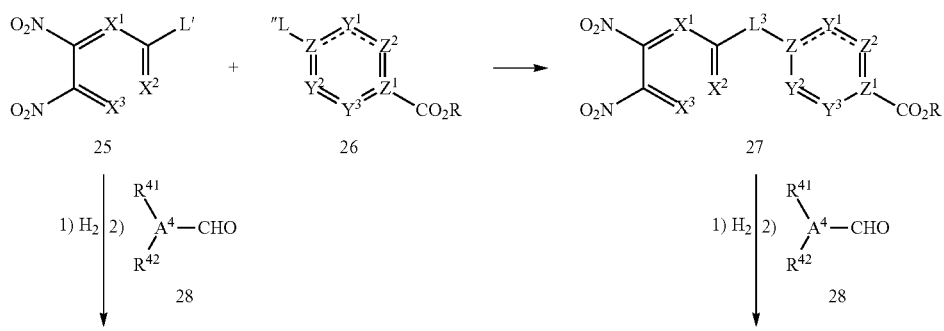

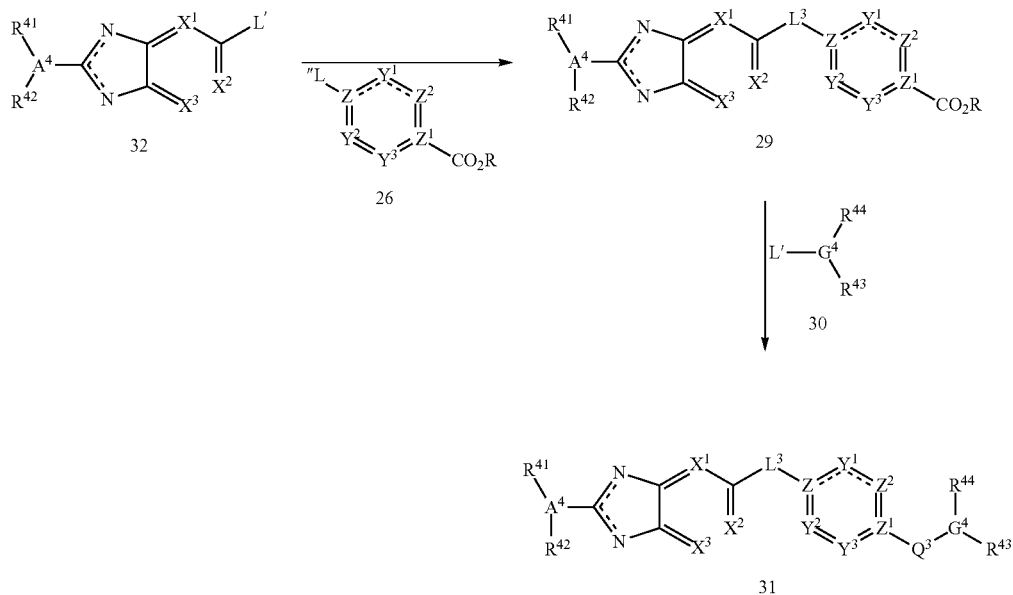

The process of Scheme V describes general synthesis of the compounds of Formula V. General coupling reaction of compounds of structures 25 and 26 affords the intermediates of structure 27. A reduction of intermediate of structure 27 by a reducing agent such as metal catalyzed hydrogenation followed by an oxidative condensation with compounds of structure 28 give intermediates of structure 29. The acid derivatives of structure 29 are coupled with compounds of structure 30 to provide the final products of structure 31. Alternatively, compounds of structure 25 can be reduced and coupled with aldehydes 28 to provide bicyclic imidazole derivatives of structure 32. Coupling reaction between compounds of structures 32 and 26 affords the same intermediates of structure 29.

EXAMPLES

The following examples are set forth merely to assist in understanding the embodiments and should not be construed as limiting the embodiments described and claimed herein in any way. Variations of the invention, including the substitution of all equivalents now known or later developed, which would be within the purview of those skilled in the art, and changes in formulation or minor changes in experimental design, are to be considered to fall within the scope of the invention incorporated herein.

Example 1

(N',N'''E,N',N'''E)-N',N'''-((Oxybis(4,1-phenylene))bis(methanylylidene))bis(4-(dimethylamino)benzohydrazide) (Compound 101)

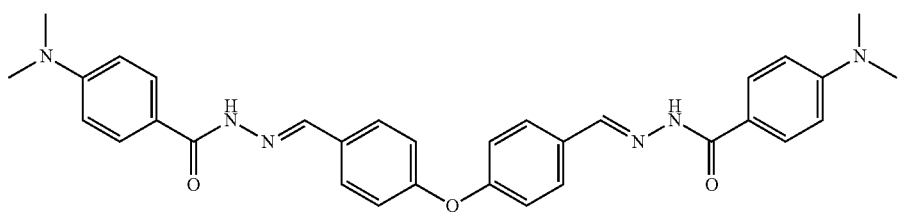

Compound 101 was prepared according to the procedure described in Scheme II. To a solution of 4,4'-oxybisbenzaldehyde (Aldrich, 42 mg, 0.186 mmol) and 4-dimethylaminobenzyhydrazide (Alfa Aesar, 73 mg, 0.408 mmol) in 3 mL of ethanol was added 3 drops of acetic acid. The reaction was heated to 60° C. for 12 h, cooled to room temperature and filtered. The white precipitate was washed with water (5 mL) followed by methanol (5 mL) and dried under vacuum to yield 55 mg of compound 101 as a white powder. $[M+H]^+$ calcd for $C_{32}H_{33}N_6O_3$: 549.2. found: 549.05.

Example 2

(N',N'''E,N',N'''E)-N',N'''-((oxybis(4,1-phenylene))bis(methanylylidene))bis(3-methoxybenzohydrazide) (Compound 102)

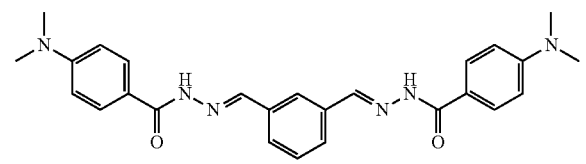

Compound 102 was prepared according to the procedure described in Scheme II from 4,4'-oxybisbenzaldehyde and 3-methoxybenzoate. $[M+H]^+$ calcd for $C_{30}H_{26}N_4O_5$: 523.2. found: 513.15.

Example 3

(N',N'''E,N',N'''E)-N',N'''-(1,3-phenylenebis(methanylylidene))bis(4-(dimethylamino)benzohydrazide) (Compound 103)

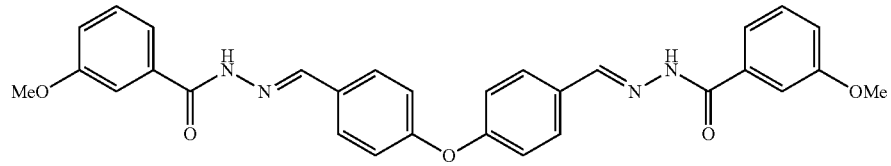 [SMILES: COc1cccc(C(=O)N/N=C/c2ccc(Oc3ccc(/C=N/NC(=O)c4cccc(OC)c4)cc3)cc2)c1]

Compound 103 was prepared according to the procedure described in Scheme II from benzene-1,3-dicarboxaldehyde and 4-dimethylaminobenzoate. $[M+H]^+$ calcd for $C_{26}H_{28}N_6O_2$: 457.2. found: 457.01.

Example 4

(N',N'''E,N',N'''E)-N',N'''-((5-methoxy-1,3-phenylene)bis(methanylylidene))bis(4-(dimethylamino)benzohydrazide) (Compound 104)

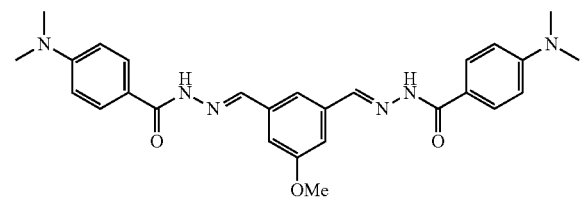

Compound 104 was prepared according to the procedure described in Scheme II from 5-5-methoxybenzene-1,3-dicarboxaldehyde and 4-dimethylaminobenzoate. $^1$H NMR (300 MHz, DMSO-$d_6$) δ 11.62 (s, 2H), 8.41 (s, 2H), 7.81 (d, J=7.5 Hz, 4H), 7.60 (s, 1H), 7.26 (d, J=3 Hz, 2H), 6.76 (d, J=7.5 Hz, 4H), 3.84 (s, 3H), 2.99 (s, 12H).

Example 5

(N',N'''E,N',N'''E)-N',N'''-((5-methoxy-1,3-phenylene)bis(methanylylidene))bis(4-methoxybenzohydrazide) (Compound 105)

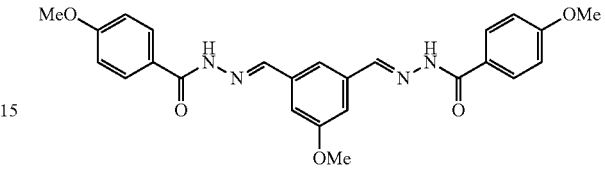

Compound 105 was prepared according to the procedure described in Scheme II from 5-5-methoxybenzene-1,3-dicarboxaldehyde and 4-methoxybenzoate. $[M+H]^+$ calcd for $C_{25}H_{24}N_4O_5$: 461.1. found: 461.00.

Example 6

(N',N'''E,N',N'''E)-N',N'''-((4-methoxy-1,3-phenylene)bis(methanylylidene))bis(4-(dimethylamino)benzohydrazide) (Compound 106)

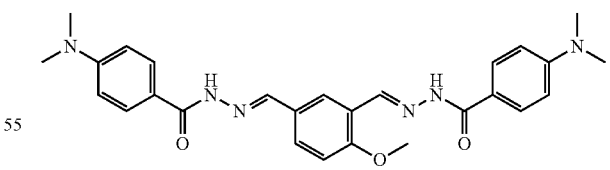

Compound 106 was prepared according to the procedure described in Scheme II from 4-4-methoxybenzene-1,3-dicarboxaldehyde and 4-dimethylaminobenzoate. $^1$H NMR (500 MHz, DMSO-$d_6$) δ 11.72 (s, 1H), 11.58 (s, 1H), 8.88 (s, 1H), 8.51 (s, 1H), 8.33 (s, 1H), 7.94 (dd, J=7.5, 15 Hz, 4H), 7.80 (d, J=7.5 Hz, 1H), 7.29 (d, J=7.5 Hz, 1H), 6.86 (d, J=7.5 Hz, 4H), 4.10 (s, 3H), 3.10 (s, 12H).

Example 7

(N',N'''E,N',N'''E)-N',N'''-((5-(benzyloxy)-1,3-phenylene)bis(methanylylidene))bis(4-(dimethylamino)benzohydrazide) (Compound 107)

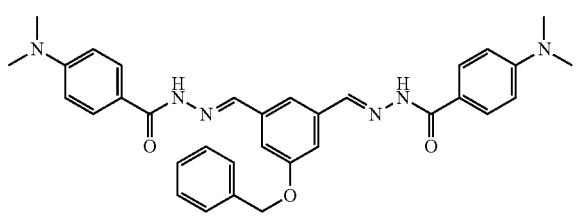

Compound 107 was prepared according to the procedure described in Scheme II from 5-5-benzyloxybenzene-1,3-dicarboxaldehyde and 4-dimethylaminobenzoate. [M+H]⁺ calcd for $C_{33}H_{35}N_6O_3$: 563.2. found: 563.08.

Example 8

2(N',N'''E,N',N'''E)-N',N'''-([1,1'-biphenyl]-3,5-diyl-bis(methanylylidene))bis(4-(dimethylamino)benzohydrazide) (Compound 108)

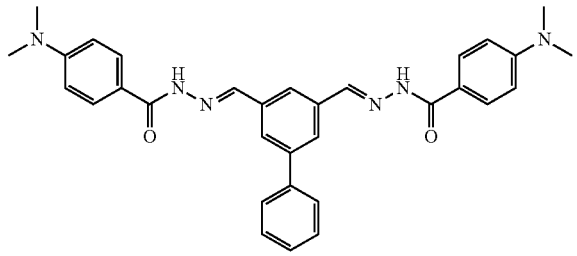

Compound 108 was prepared according to the procedure described in Scheme II from 5-phenylbenzene-1,3-dicarboxaldehyde and 4-dimethylaminobenzoate. [M+H]⁺ calcd for $C_{32}H_{32}N_6O_2$: 533.2. found: 533.08.

Example 9

(N',N'''E,N',N'''E)-N',N'''-(1,3-phenylenebis(methanylylidene))bis(benzo[d][1,3]dioxole-5-carbohydrazide) (Compound 109)

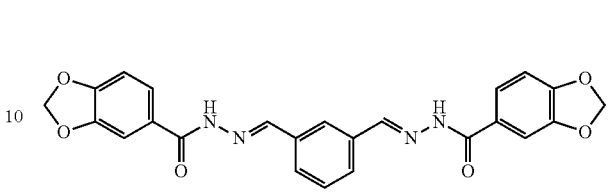

Compound 109 was prepared according to the procedure described in Scheme II from benzene-1,3-dicarboxaldehyde and 5-(1,3-dioxolano)benzoate. ¹H NMR (500 MHz, DMSO-d₆) δ 11.88 (s, 2H), 8.58 (s, 2H), 8.19 (s, 1H), 7.85 (d, J=6.3 Hz, 2H), 7.64 (m, 3H), 7.56 (s, 2H), 7.17 (d, J=6 Hz, 2H), 6.22 (s, 4H).

Example 10

(N',N'''E,N',N'''E)-N',N'''-(1,3-phenylenebis(methanylylidene))bis(4-(1H-pyrrol-1-yl)benzohydrazide) (Compound 110)

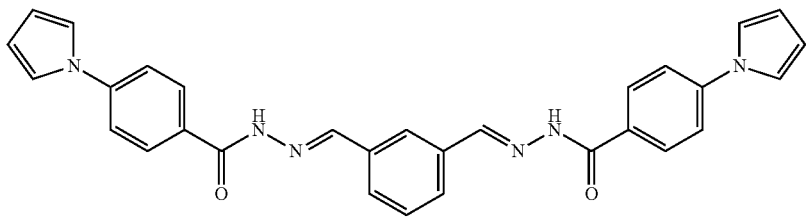 [SMILES: O=C(N/N=C/c1cccc(/C=N/NC(=O)c2ccc(-n3cccc3)cc2)c1)c1ccc(-n2cccc2)cc1]

Compound 110 was prepared according to the procedure described in Scheme II from benzene-1,3-dicarboxaldehyde and 4-pyrrolebenzoate. ¹H NMR (500 MHz, DMSO-d₆) δ 12.15 (s, 2H), 8.63 (s, 2H), 8.24 (s, 1H), 8.13 (d, J=7.5 Hz, 4H), 7.89 (d, J=7.5 Hz, 6H), 7.64 (m, 5H), 6.43 (s, 4H).

Example 11

(N',N'''E,N',N'''E)-N',N'''-((5-(dimethylamino)-1,3-phenylene)bis(methanylylidene))bis(4-(dimethylamino)benzohydrazide) (Compound 111)

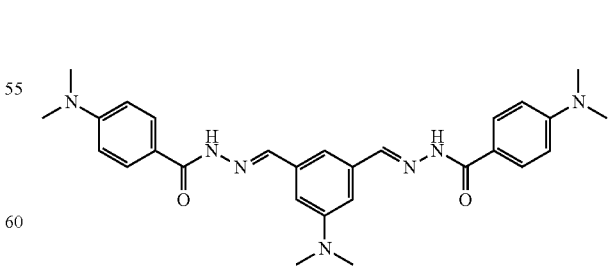

Compound 111 was prepared according to the procedure described in Scheme II from 5-dimethylaminobenzene-1,3-dicarboxaldehyde and 4-dimethylaminobenzoate. [M+H]⁺ calcd for $C_{28}H_{33}N_7O_2$: 500.2. found: 500.07.

Example 12

(N',N'''E,N',N'''E)-N',N'''-(1,3-phenylenebis(methanylylidene))bis(4-isopropylbenzohydrazide) (Compound 112)

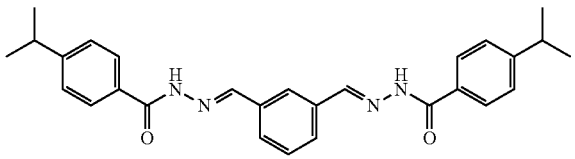

Compound 112 was prepared according to the procedure described in Scheme II from benzene-1,3-dicarboxaldehyde and 4-isopropylbenzoate. $^1$H NMR (500 MHz, DMSO-$d_6$) δ 11.9 (s, 2H), 8.51 (s, 2H), 8.12 (s, 1H), 7.87 (d, J=8.1 Hz, 4H), 7.77 (d, J=7.3 Hz, 2H), 7.56 (dd, J=7.3, 7.3 Hz, 1H), 7.42 (d, J=8.1 Hz, 4H), 3.01-2.96 (m, 2H), 1.25 (d, J=6.8 Hz, 12H).

Example 13

(N',N'''E,N',N'''E)-N',N'''-((5-(allyloxy)-1,3-phenylene)bis(methanylylidene))bis(4-(dimethylamino)benzohydrazide) (Compound 113)

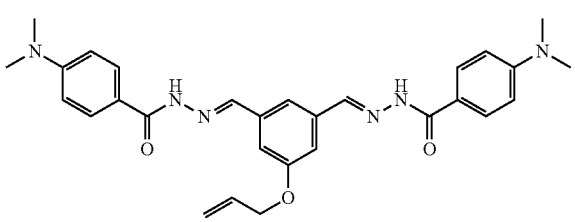

Compound 113 was prepared according to the procedure described in Scheme II from 5-allyloxybenzene-1,3-dicarboxaldehyde and 4-dimethylaminobenzoate. [M+H]$^+$ calcd for $C_{29}H_{32}N_6O_3$: 513.2. found: 513.10.

Example 14

(N',N'''E,N',N'''E)-N',N'''-((5-(benzylamino)-1,3-phenylene)bis(methanylylidene))bis(4-(dimethylamino)benzohydrazide) (Compound 114)

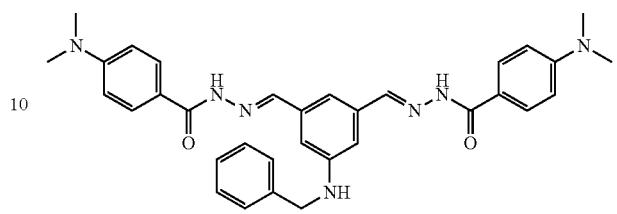

Compound 114 was prepared according to the procedure described in Scheme II from 5-benzylaminobenzene-1,3-dicarboxaldehyde and 4-dimethylaminobenzoate. [M+H]$^+$ calcd for $C_{33}H_{35}N_7O_2$: 562.2. found: 562.17.

Example 15

(N',N'''E,N',N'''E)-N',N'''-(1,3-phenylenebis(methanylylidene))bis(4-(bis(2,2,2-trifluoroethyl)amino)benzohydrazide) (Compound 115)

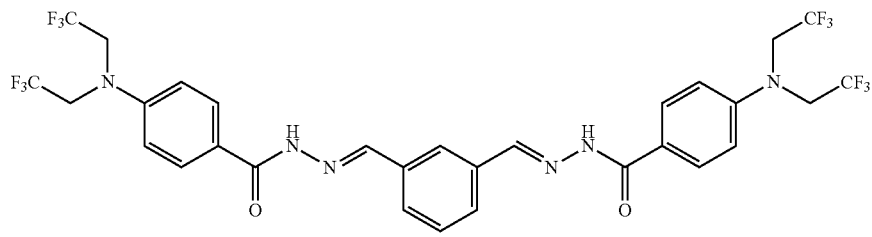 [SMILES: O=C(N/N=C/c1cccc(/C=N/NC(=O)c2ccc(N(CC(F)(F)F)CC(F)(F)F)cc2)c1)c1ccc(N(CC(F)(F)F)CC(F)(F)F)cc1]

Compound 115 was prepared according to the procedure described in Scheme II from benzene-1,3-dicarboxaldehyde and 4-di(2,2,2-trifluoroethyl)aminobenzoate. $^1$H NMR (500 MHz, DMSO-$d_6$) δ 11.7 (s, 2H), 8.47 (s, 2H), 8.08 (s, 1H), 7.83 (d, J=8.3 Hz, 4H), 7.72 (m, 2H), 7.53 (t, J=7.8 Hz, 1H), 7.19 (d, J=7.8 Hz, 4H), 4.49 (q, $J_{H-F}$=8.3 Hz, 8H).

Example 16

N-(3,5-bis((E)-(2-(4-(dimethylamino)benzoyl)hydrazono)methyl)phenyl)benzamide (Compound 116)

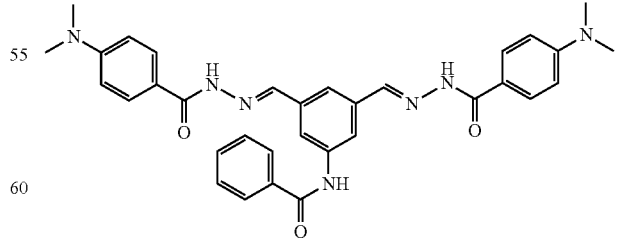

Compound 116 was prepared according to the procedure described in Scheme II from 5-benzoylaminobenzene-1,3-dicarboxaldehyde and 4-dimethylaminobenzoate. [M+H]$^+$ calcd for $C_{35}H_{38}N_8O_3$: 619.3. found: 619.16.

Example 17

(N',N'''E,N',N'''E)-N',N'''-(1,3-phenylenebis(methanylylidene))bis(4-(isopropylamino)benzohydrazide) (Compound 117)

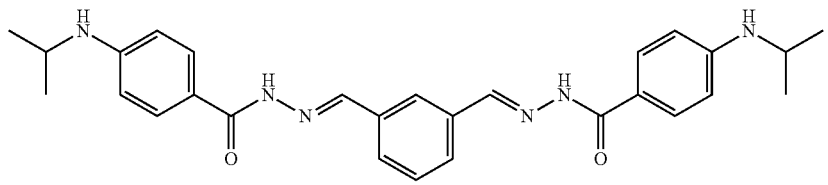 [SMILES: CC(C)Nc1ccc(C(=O)N/N=C/c2cccc(/C=N/NC(=O)c3ccc(NC(C)C)cc3)c2)cc1]

Compound 117 was prepared according to the procedure described in Scheme II from benzene-1,3-dicarboxaldehyde and 4-isopropylaminobenzoate. $^1$H NMR (500 MHz, DMSO-$d_6$) δ 11.52 (s, 2H), 8.45 (s, 2H), 8.04 (s, 1H), 7.74-7.69 (m, 6H), 7.52 (t, J=7.8 Hz, 1H), 6.61 (d, J=8.8 Hz, 4H), 6.16 (d, J=7.8 Hz, 2H), 3.68-3.61 (m, 2H), 1.16 (d, J=6.3 Hz, 12H).

Example 18

(N',N'''E,N',N'''E)-N',N'''-(1,3-phenylenebis(methanylylidene))bis(4-(cyclopentylamino)benzohydrazide) (Compound 118)

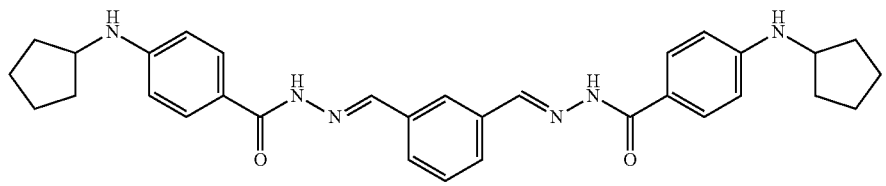 [SMILES: O=C(N/N=C/c1cccc(/C=N/NC(=O)c2ccc(NC3CCCC3)cc2)c1)c1ccc(NC2CCCC2)cc1]

Compound 118 was prepared according to the procedure described in Scheme II from benzene-1,3-dicarboxaldehyde and 4-cyclopentylaminobenzoate. $^1$H NMR (500 MHz, DMSO-$d_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 19

(N',N'''E,N',N'''E)-N',N'''-(1,3-phenylenebis(methanylylidene))bis(([1,1'-biphenyl]-4-carbohydrazide)) (Compound 119)

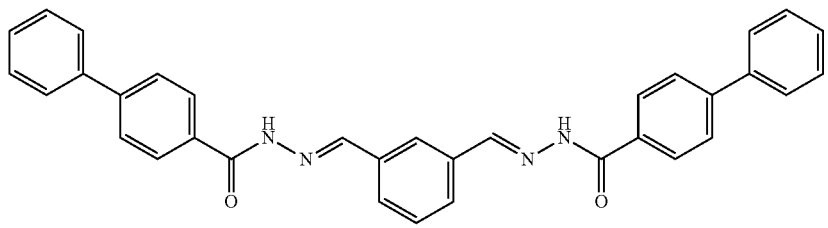 [SMILES: O=C(N/N=C/c1cccc(/C=N/NC(=O)c2ccc(-c3ccccc3)cc2)c1)c1ccc(-c2ccccc2)cc1]

Compound 119 was prepared according to the procedure described in Scheme II from benzene-1,3-dicarboxaldehyde and 4-phenylbenzoate. $^1$H NMR (500 MHz, DMSO-d$_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 20

(N',N'''E,N',N'''E)-N',N'''-(1,3-phenylenebis(methanylylidene))bis(4-(diethylamino)benzohydrazide) (Compound 120)

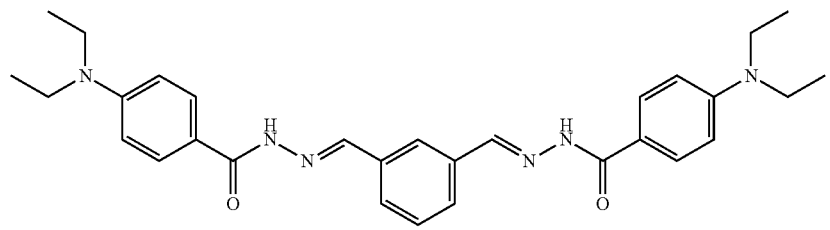 [SMILES: CCN(CC)c1ccc(C(=O)N/N=C/c2cccc(/C=N/NC(=O)c3ccc(N(CC)CC)cc3)c2)cc1]

Compound 120 was prepared according to the procedure described in Scheme II from benzene-1,3-dicarboxaldehyde and 4-diethylaminobenzoate. $^1$H NMR (500 MHz, DMSO-d$_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 21

(N',N'''E,N',N'''E)-N',N'''-(1,3-phenylenebis(methanylylidene))bis(2-naphthohydrazide) (Compound 121)

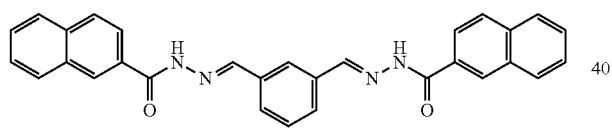

Compound 121 was prepared according to the procedure described in Scheme II from benzene-1,3-dicarboxaldehyde and 4-dimethylaminobenzoate. $^1$H NMR (500 MHz, DMSO-d$_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 22

(N',N'''E,N',N'''E)-N',N'''-(1,3-phenylenebis(methanylylidene))bis(4-(1H-imidazol-1-yl)benzohydrazide) (Compound 122)

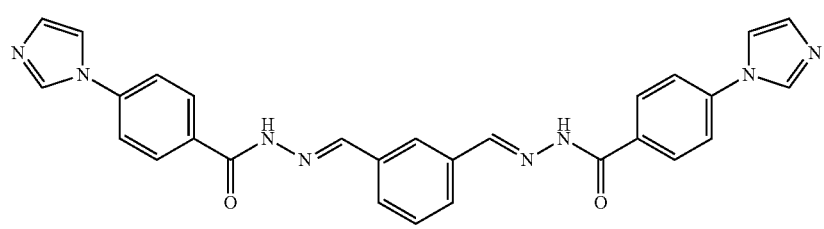 [SMILES: O=C(N/N=C/c1cccc(/C=N/NC(=O)c2ccc(-n3ccnc3)cc2)c1)c1ccc(-n2ccnc2)cc1]

Compound 122 was prepared according to the procedure described in Scheme II from benzene-1,3-dicarboxaldehyde and 4-imidazolebenzoate. $^1$H NMR (500 MHz, DMSO-$d_6$) δ 12.0 (s, 2H), 8.55 (s, 2H), 8.49 (s, 2H), 8.16 (s, 1H), 8.09 (d, J=8.3 Hz, 4H), 7.93 (s, 2H), 7.89 (d, J=7.5 Hz, 4H), 7.81 (d, J=7.5 Hz, 2H), 7.58 (t, J=7.6 Hz, 1H), 7.21 (bs, 2H).

Example 23

(N',N'''E,N',N'''E)-N',N'''-(1,3-phenylenebis(methanylylidene))bis(4-((4-fluorobenzyl)amino)benzohydrazide) (Compound 123)

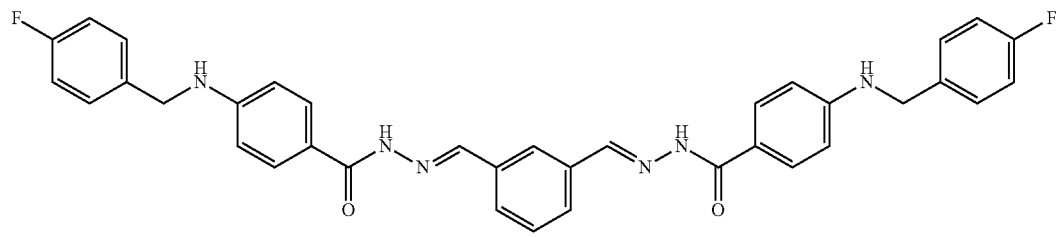 [SMILES: O=C(N/N=C/c1cccc(/C=N/NC(=O)c2ccc(NCc3ccc(F)cc3)cc2)c1)c1ccc(NCc2ccc(F)cc2)cc1]

Compound 123 was prepared according to the procedure described in Scheme II from benzene-1,3-dicarboxaldehyde and 4-(4-fluorobenzylamino)benzoate. $^1$H NMR (500 MHz, DMSO-$d_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 24

(N',N'''E,N',N'''E)-N',N'''-(1,3-phenylenebis(methanylylidene))bis(4-((2,3-dihydro-1H-inden-2-yl)amino)benzohydrazide) (Compound 124)

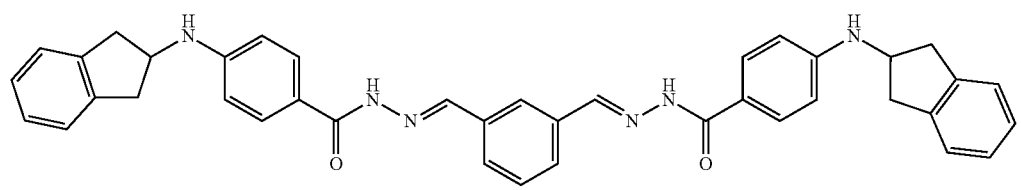 [SMILES: O=C(N/N=C/c1cccc(/C=N/NC(=O)c2ccc(NC3Cc4ccccc4C3)cc2)c1)c1ccc(NC2Cc3ccccc3C2)cc1]

Compound 124 was prepared according to the procedure described in Scheme II from benzene-1,3-dicarboxaldehyde and 4-(2-indanylamino)benzoate. $^1$H NMR (500 MHz, DMSO-$d_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 25

(N',N'''E,N',N'''E)-N',N'''-(1,3-phenylenebis(methanylylidene))bis(1-methyl-1H-indole-5-carbohydrazide) (Compound 125)

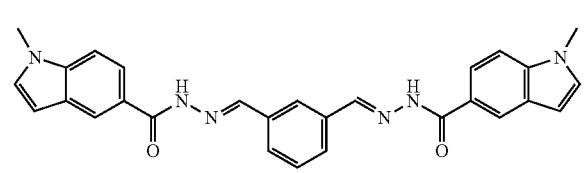 [SMILES: Cn1ccc2cc(C(=O)N/N=C/c3cccc(/C=N/NC(=O)c4ccc5c(ccn5C)c4)c3)ccc21]

Compound 125 was prepared according to the procedure described in Scheme II from benzene-1,3-dicarboxaldehyde and 1-methyl-5-indolecarboxylate. [M+H]$^+$ calcd for $C_{28}H_{24}N_6O_2$: 477.2. found: 477.06.

Example 26

(N',N'''E,N',N'''E)-N',N'''-((5-(methylamino)-1,3-phenylene)bis(methanylylidene))bis(4-(dimethylamino)benzohydrazide) (Compound 126)

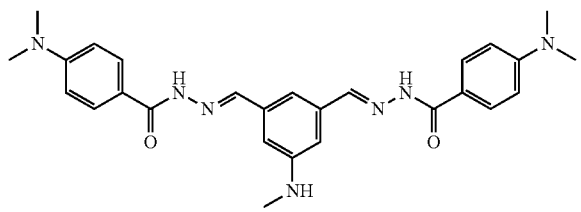

Compound 126 was prepared according to the procedure described in Scheme II from 5-methylaminobenzene-1,3-dicarboxaldehyde and 4-dimethylaminobenzoate. [M+H]$^+$ calcd for $C_{27}H_{31}N_7O_2$: 486.2. found: 486.03.

Example 27

(N',N'''E,N',N'''E)-N',N'''-(1,3-phenylenebis(methanylylidene))bis(4-(pyrrolidin-1-yl)benzohydrazide) (Compound 127)

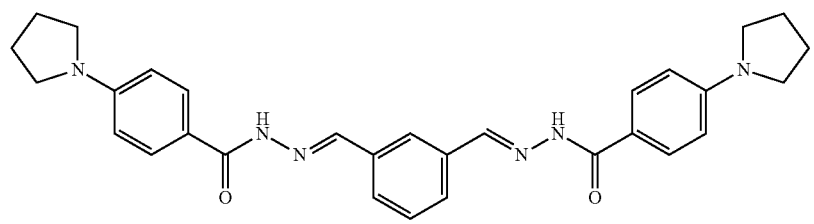 [SMILES: O=C(N/N=C/c1cccc(/C=N/NC(=O)c2ccc(N3CCCC3)cc2)c1)c1ccc(N2CCCC2)cc1]

Compound 127 was prepared according to the procedure described in Scheme II from benzene-1,3-dicarboxaldehyde and 4-pyrrolidinebenzoate. $^1$H NMR (500 MHz, DMSO-d$_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 28

(N',N'''E,N',N'''E)-N',N'''-((5-(((benzyloxy)methyl)-1,3-phenylene)bis(methanylylidene))bis(4-(dimethylamino)benzohydrazide) (Compound 128)

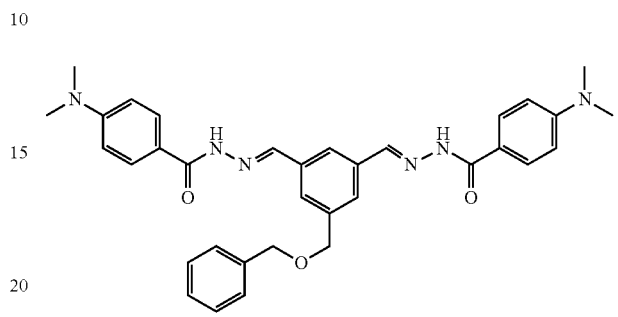

Compound 128 was prepared according to the procedure described in Scheme II from 5-benzyloxymethylbenzene-1,3-dicarboxaldehyde and 4-dimethylaminobenzoate. [M+H]$^+$ calcd for $C_{34}H_{36}N_6O_3$: 577.2. found: 577.10.

Example 29

(N',N'''E,N',N'''E)-N',N'''-(1,3-phenylenebis(methanylylidene))bis(4-(methylamino)benzohydrazide) (Compound 129)

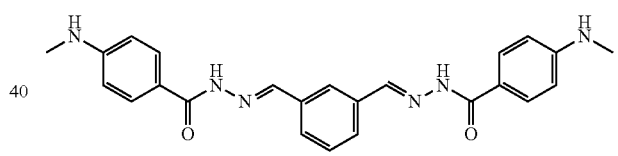

Compound 129 was prepared according to the procedure described in Scheme II from benzene-1,3-dicarboxaldehyde and 4-methylaminobenzoate. $^1$H NMR (500 MHz, DMSO-d$_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 30

(N',N'''E,N',N'''E)-N',N'''-(1,3-phenylenebis(methanylylidene))bis(4-((2-hydroxyethyl)amino)benzohydrazide) (Compound 130)

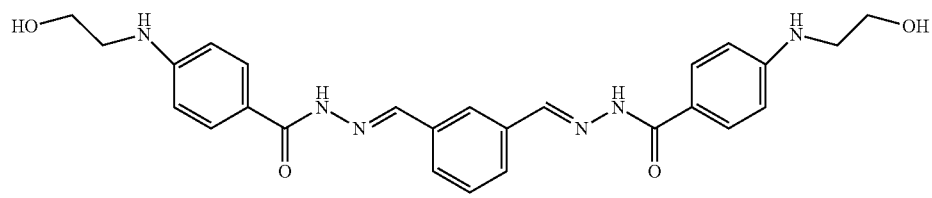 [SMILES: O=C(N/N=C/c1cccc(/C=N/NC(=O)c2ccc(NCCO)cc2)c1)c1ccc(NCCO)cc1]

Compound 130 was prepared according to the procedure described in Scheme II from benzene-1,3-dicarboxaldehyde and 4-(2-hydroxyethylamino)benzoate. $^1$H NMR (500 MHz, DMSO-$d_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 31

(N',N'''E,N',N'''E)-N',N'''-(1,3-phenylenebis(methanylylidene))bis(3-(dimethylamino)benzohydrazide) (Compound 131)

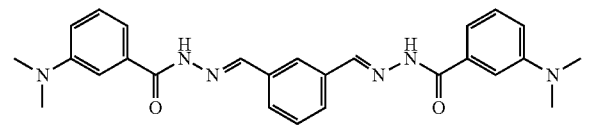

Compound 131 was prepared according to the procedure described in Scheme II from benzene-1,3-dicarboxaldehyde and 3-dimethylaminobenzoate. $^1$H NMR (500 MHz, DMSO-$d_6$) δ 11.82 (s, 2H), 8.52 (s, 2H), 8.11 (s, 1H), 7.76 (d, J=7.5 Hz, 2H), 7.56 (t, J=7.5 Hz, 1H), 7.33 (t, J=8.0 Hz, 2H), 7.19 (d, J=7.0 Hz, 4H), 6.94 (d, J=2.2 Hz, 2H), 2.97 (s, 12H).

Example 32

(N',N'''E,N',N'''E)-N',N'''-(1,3-phenylenebis(methanylylidene))bis(4-morpholinobenzohydrazide) (Compound 132)

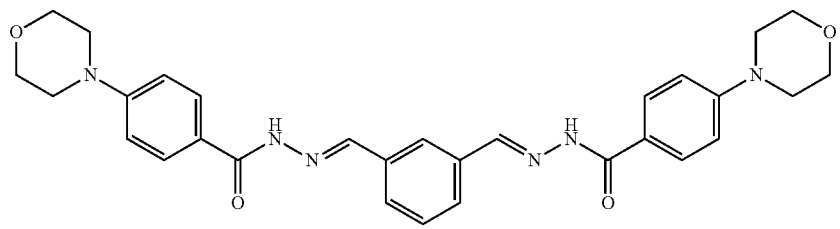 [SMILES: O=C(N/N=C/c1cccc(/C=N/NC(=O)c2ccc(N3CCOCC3)cc2)c1)c1ccc(N2CCOCC2)cc1]

Compound 132 was prepared according to the procedure described in Scheme II from benzene-1,3-dicarboxaldehyde and 4-morpholinobenzoate. [M+H]$^+$ calcd for $C_{30}H_{33}N_6O_4$: 541.2. found: 541.05.

Example 33

(N',N'''E,N',N'''E)-N',N'''-(1,3-phenylenebis(methanylylidene))bis(4-(2-oxopyrrolidin-1-yl)benzohydrazide) (Compound 133)

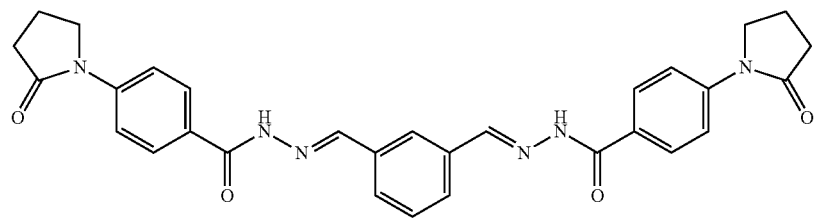 [SMILES: O=C(N/N=C/c1cccc(/C=N/NC(=O)c2ccc(N3CCCC3=O)cc2)c1)c1ccc(N2CCCC2=O)cc1]

Compound 133 was prepared according to the procedure described in Scheme II from benzene-1,3-dicarboxaldehyde and 4-pyrrolidonobenzoate. $^1$H NMR (500 MHz, DMSO-d$_6$) δ 11.93 (s, 2H), 8.47 (s, 2H), 8.17 (s, 1H), 7.95 (d, J=13.7 Hz, 4H), 7.81 (d, J=10 Hz, 4H), 7.77 (d, J=10 Hz, 2H), 7.55 (t, J=10, 12.5 Hz, 1H), 4.28 (m, 4H), 2.53 (m, 4H), 2.07 (m, 4H).

Example 34

(N',N'''E,N',N'''E)-N',N'''-(1,3-phenylenebis(methanylylidene))bis(4-(piperazin-1-yl)benzohydrazide) (Compound 134)

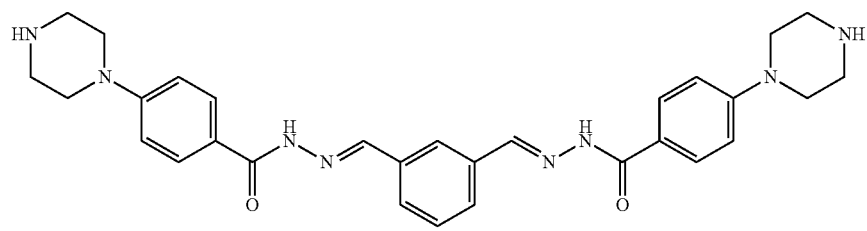 [SMILES: O=C(N/N=C/c1cccc(/C=N/NC(=O)c2ccc(N3CCNCC3)cc2)c1)c1ccc(N2CCNCC2)cc1]

Compound 134 was prepared according to the procedure described in Scheme II from benzene-1,3-dicarboxaldehyde and 4-piperizinylbenzoate. $^1$H NMR (500 MHz, DMSO-d$_6$) δ 11.54 (s, 2H), 10.15 (s, 2H), 8.47 (s, 2H), 8.25 (s, 1H), 7.86 (d, J=12 Hz, 4H), 7.71 (m, 3H), 7.02 (d, J=12 Hz, 4H), 3.17 (m, 8H), 2.86 (m, 8H).

Example 35

(N',N'''E,N',N'''E)-N',N'''-((5-((2-hydroxyethyl)amino)-1,3-phenylene)bis(methanylylidene))bis(4-(dimethylamino)benzohydrazide) (Compound 135)

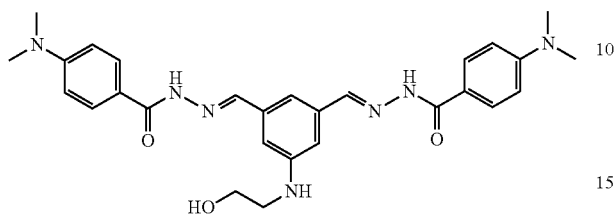

Compound 135 was prepared according to the procedure described in Scheme II from 5-(2-hydroxyethyl)aminobenzene-1,3-dicarboxaldehyde and 4-dimethylaminobenzoate. [M+H]$^+$ calcd for $C_{28}H_{33}N_7O_3$: 516.2. found: 516.00.

Example 36

(N',N'''E,N',N'''E)-N',N'''-(pyridine-3,5-diylbis(methanylylidene))bis(4-morpholinobenzohydrazide) (Compound 136)

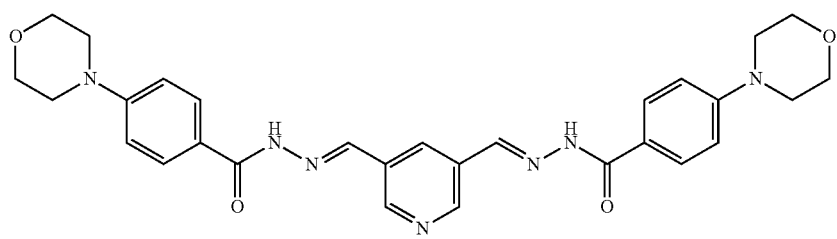 [SMILES: O=C(N/N=C/c1cncc(/C=N/NC(=O)c2ccc(N3CCOCC3)cc2)c1)c1ccc(N2CCOCC2)cc1]

Compound 136 was prepared according to the procedure described in Scheme II from pyridine-3,5-dicarboxaldehyde and 4-morpholinobenzoate. [M+H]$^+$ calcd for $C_{29}H_{31}N_7O_4$: 542.2. found: 541.99.

Example 37

(N',N'''E,N',N'''E)-N',N'''-(pyridine-3,5-diylbis(methanylylidene))bis(4-(dimethylamino)benzohydrazide) (Compound 137)

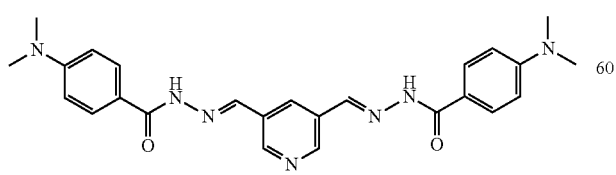

Compound 137 was prepared according to the procedure described in Scheme II from pyridine-3,5-dicarboxaldehyde and 4-dimethylaminobenzoate. $^1$H NMR (500 MHz, DMSO-d$_6$) δ 11.79 (s, 2H), 8.81 (d, J=3.75 Hz, 2H), 8.51 (s, 2H), 8.45 (s, 1H), 7.83 (d, J=15 Hz, 4H), 6.77 (d, J=11.2 Hz, 4H), 3.01 (s, 12H).

Example 38

N',N'''-((5-(benzyloxy)-1,3-phenylene)bis(methylene))bis(4-(dimethylamino)benzohydrazide) (Compound 138)

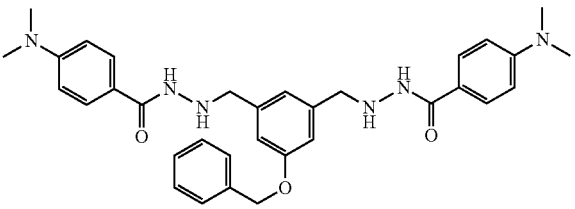

Compound 138 was prepared according to the procedure described in Scheme II from 5-5-benzyloxybenzene-1,3-dicarboxaldehyde and 4-dimethylaminobenzoate. [M+H]$^+$ calcd for $C_{33}H_{28}N_6O_3$: 567.3. found: 567.17.

Example 39

(E)-4-(2-(3-Methoxybenzylidene)hydrazinecarbonyl)-N-(3-(3-methoxyphenethyl)amino)-3-oxopropyl)benzamide (Compound 139)

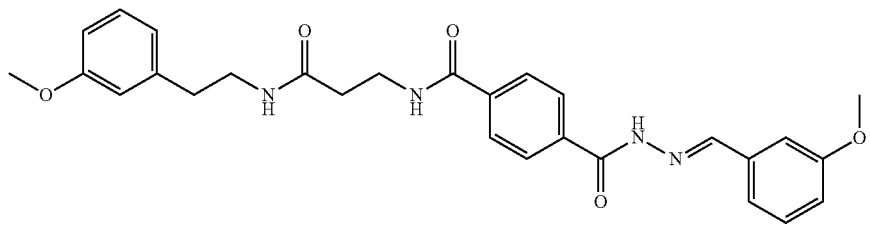

Compound 139 was prepared according to the general procedure described in Scheme I. Preparation of 3-((tert-butoxycarbonyl)amino)propanoic acid: 13-Alanine (Sigma-Aldrich, 1.0 g, 11.2 mmol) and $K_2CO_3$ (3.1 g, 22.4 mmol) were dissolved in a mixture of dioxane (25 mL) and water (12.5 mL) then the solution was cooled to 0° C. in an ice bath. Di-tert-butyl dicarbonate (2.7 g, 12.3 mmol) was added then the solution was warmed slowly to room temperature and allowed to stir overnight. Upon completion, the solution was acidified with $KHSO_4$ until pH 3 then extracted with ethyl acetate. The organic layer was washed with brine, dried over $Na_2SO_4$ then the solvent was removed under reduced pressure to give crude product which was taken forward without further purification.

Preparation of tert-butyl (3-((3-methoxyphenethyl)amino)-3-oxopropyl)carbamate: 3-methoxyphenethylamine (Aldrich, 100 mg, 0.66 mmol), 3-((tert-butoxycarbonyl)amino)-propanoic acid (125 mg, 0.66 mmol), hydroxybenzotriazole (8.9 mg, 0.066 mmol), triethylamine (102 µL, 0.73 mmol) and dimethylformamide (6.6 mL) were combined, then 1-ethyl-3-(3-dimethylaminopropyl) carbodiimide (139 mg, 0.73 mmol) was added. The solution was allowed to stir at room temperature overnight. Upon completion, ethyl acetate and water were added and the layers were separated. The aqueous phase was extracted with ethyl acetate then the combined organic layers were washed with brine and dried over $Na_2SO_4$. Solvent was removed under reduced pressure to give crude product which was purified by flash chromatography using 0-80% ethyl acetate/hexane as the eluent to give the product as a pure white solid (140 mg, 66%).

Preparation of 3-amino-N-(3-methoxyphenethyl)propanamide: tert-butyl (3-((3-methoxyphenethyl)amino)-3-oxopropyl)carbamate was dissolved in dichloromethane (0.5 mL) then the solution was cooled to 0° C. in an ice bath. Trifluoroacetic acid (300 µL) was added then the solution was allowed to warm slowly to room temperature with stirring. Upon completion of the reaction the solvent is removed under reduced pressure to give crude product which is used without further purification.

Preparation of methyl 4-((3-((3-methoxyphenethyl)amino)-3-oxopropyl)carbamoyl)benzoate: To 3-amino-N-(3-methoxyphenethyl)propanamide (60 mg, 0.27 mmol) was added 4-(methoxycarbonyl)benzoic acid (49 mg, 0.27 mmol), hydroxybenzotriazole (3.7 mg, 0.027 mmol), triethylamine (42 µL, 0.30 mmol) and dimethylformamide (2.7 mL). Lastly, 1-ethyl-3-(3-dimethylaminopropyl) carbodiimide (57 mg, 0.30 mmol) was added and the solution was allowed to stir overnight at room temperature in a capped vial. Upon completion of the reaction an aqueous workup is performed to give the crude product which was purified using flash chromatography.

Preparation of 4-(hydrazinecarbonyl)-N-(3-((3-methoxyphenethyl)amino)-3-oxopropyl)benzamide: Methyl 4-((3-((3-methoxyphenethyl)amino)-3-oxopropyl)carbamoyl)benzoate was treated with methanol (3 mL) and hydrazine hydrate (300 µL), heated to 65° C., then allowed to stir overnight. The reaction is monitored by TLC and upon completion the solvent is removed under reduced pressure to give crude product which is used without purification.

Preparation of Compound 139: To the above crude product (15.0 mg, 0.039 mmol) was added 3-anisaldehyde (9.5 µL, 0.078 mmol), acetic acid (several drops) and ethanol (1 mL). The reaction was allowed to stir overnight at room temperature. The solid product that has formed is isolated by centrifugation then analyzed by LCMS. MS [M+H]+ calcd for $C_{28}H_{30}N_4O_5$: 503.2. found: 503.04.

Example 40

(E)-N-(3-((2-(1H-indol-3-yl)ethyl)amino)-3-oxopropyl)-4-(2-(3-methoxybenzylidene) hydrazinecarbonyl)benzamide (Compound 140)

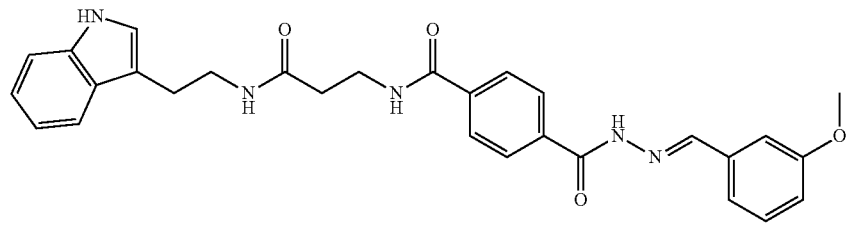 [SMILES: COc1cccc(/C=N/NC(=O)c2ccc(C(=O)NCCC(=O)NCCc3c[nH]c4ccccc34)cc2)c1]

Compound 140 was prepared according to the procedure described in Scheme I from 4-(2-(3-indolylethyl)aminocarbonyl)ethylaminocarbonyl)benzoate and 3-methoxybenzaldehyde. [M+H]+ calcd for $C_{29}H_{29}N_5O_4$: 512.2. found: 512.03.

Example 41

(E)-N-(3-((2-hydroxyethyl)amino)-3-oxopropyl)-4-(2-(3-methoxybenzylidene) hydrazinecarbonyl)benzamide (Compound 141)

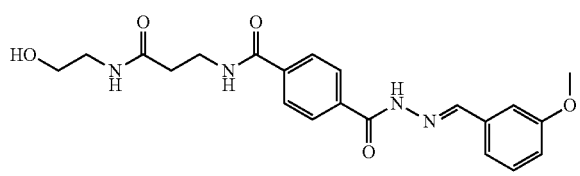 [SMILES: COc1cccc(/C=N/NC(=O)c2ccc(C(=O)NCCC(=O)NCCO)cc2)c1]

Compound 141 was prepared according to the procedure described in Scheme I from 4-(2-(2-hydroxyethylaminocarbonyl)ethylaminocarbonyl)benzoate and 3-methoxybenzaldehyde. $[M+H]^+$ calcd for $C_{21}H_{24}N_4O_5$: 413.1. found: 413.00.

Example 42

4-((E)-2-(3-((E)-2-chlorostyryl)benzylidene)hydrazinecarbonyl)-N-(3-((2-hydroxyethyl)amino)-3-oxopropyl)benzamide (Compound 142)

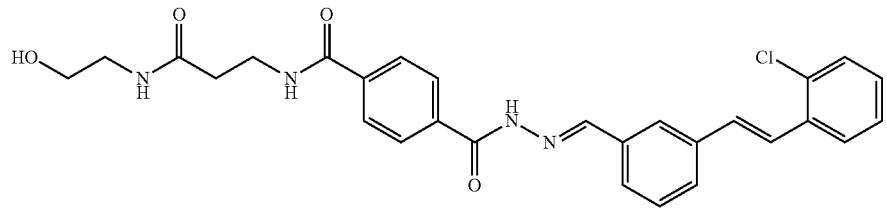 [SMILES: O=C(CCNC(=O)c1ccc(C(=O)N/N=C/c2cccc(/C=C/c3ccccc3Cl)c2)cc1)NCCO]

Compound 142 was prepared according to the procedure described in Scheme I from 4-(2-(2-hydroxyethylaminocarbonyl)ethylaminocarbonyl)benzoate and 3-(2E-(2-chlorophenyl)ethenyl)benzaldehyde. $[M+H]^+$ calcd for $C_{28}H_{27}ClN_4O_4$: 519.17. found: 519.00.

Example 43

(E)-4-(2-(4-fluoro-3-methoxybenzylidene)hydrazinecarbonyl)-N-(3-((2-hydroxyethyl)amino)-3-oxopropyl)benzamide (Compound 143)

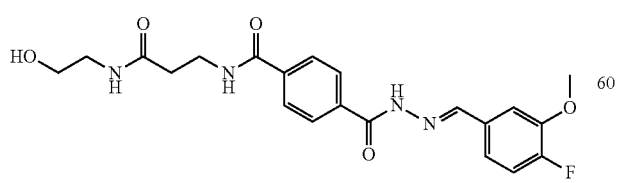

Compound 143 was prepared according to the procedure described in Scheme I from 4-(2-(2-hydroxyethylaminocarbonyl)ethylaminocarbonyl)benzoate and 4-fluoro-3-methoxybenzaldehyde. $[M+H]^+$ calcd for $C_{21}H_{23}FN_4O_5$: 431.1. found: 431.00.

Example 44

(E)-4-(2-(2-hydroxy-5-methoxybenzylidene)hydrazinecarbonyl)-N-(3-((2-hydroxyethyl)amino)-3-oxopropyl)benzamide (Compound 144)

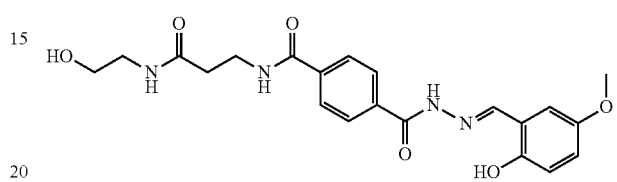

Compound 144 was prepared according to the procedure described in Scheme I from 4-(2-(2-hydroxyethylaminocarbonyl)ethylaminocarbonyl)benzoate and 2-hydroxy-5-methoxybenzaldehyde. $[M+H]^+$ calcd for $C_{21}H_{24}N_4O_6$: 429.1. found: 429.00.

Example 45

(E)-4-(2-(3,5-dimethoxybenzylidene)hydrazinecarbonyl)-N-(3-((2-hydroxyethyl)amino)-3-oxopropyl) benzamide (Compound 145)

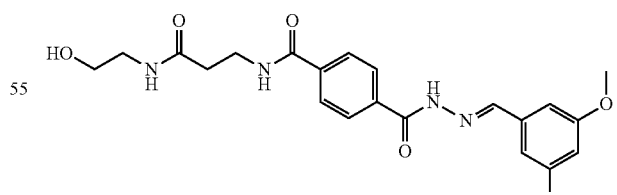

Compound 145 was prepared according to the procedure described in Scheme I from 4-(2-(2-hydroxyethylaminocarbonyl)ethylaminocarbonyl)benzoate and 3,5-dimethoxybenzaldehyde. $[M+H]^+$ calcd for $C_{22}H_{26}N_4O_6$: 443.1. found: 442.91.

Example 46

(E)-4-(2-(4-hydroxy-3-methoxybenzylidene)hydrazinecarbonyl)-N-(3-((2-hydroxyethyl)amino)-3-oxopropyl)benzamide (Compound 146)

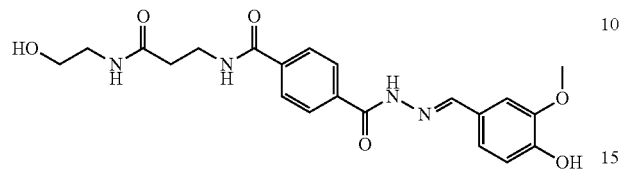

Compound 146 was prepared according to the procedure described in Scheme I from 4-(2-(2-hydroxyethylaminocarbonyl)ethylaminocarbonyl)benzoate and 4-hydroxy-5-methoxybenzaldehyde. [M+H]$^+$ calcd for $C_{21}H_{24}N_4O_6$: 429.1. found: 428.88.

Example 47

(E)-N-(3-((2-hydroxyethyl)amino)-3-oxopropyl)-4-(2-(3-methoxy-4-methylbenzylidene) hydrazinecarbonyl)benzamide (Compound 147)

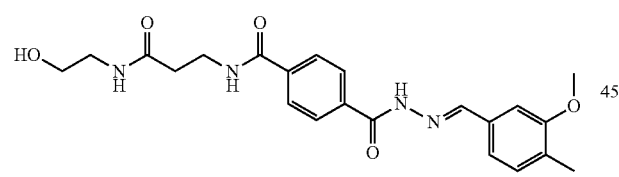

Compound 147 was prepared according to the procedure described in Scheme I from 4-(2-(2-hydroxyethylaminocarbonyl)ethylaminocarbonyl)benzoate and 3-methoxy-4-methylbenzaldehyde. [M+H]$^+$ calcd for $C_{22}H_{26}N_4O_5$: 427.1. found: 426.92.

Example 48

(E)-N-(2-hydroxyethyl)-4-((4-(2-(3-methoxybenzylidene)hydrazinecarbonyl)phenyl)amino) butanamide (Compound 148)

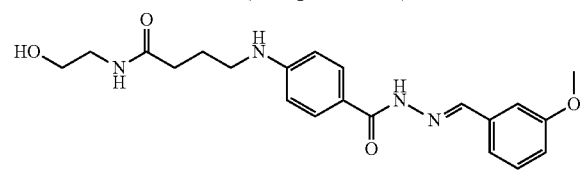

Compound 148 was prepared according to the procedure described in Scheme I from 4-(3-(2-hydroxyethylaminocarbonyl)propylamino)benzoate and 3-methoxybenzaldehyde. [M+H]$^+$ calcd for $C_{21}H_{26}N_4O_4$: 399.2. found: 399.47.

Example 49

(E)-4-(2-(3-(dimethylamino)benzylidene)hydrazinecarbonyl)-N-(3-((2-hydroxyethyl)amino)-3-oxopropyl)benzamide (Compound 149)

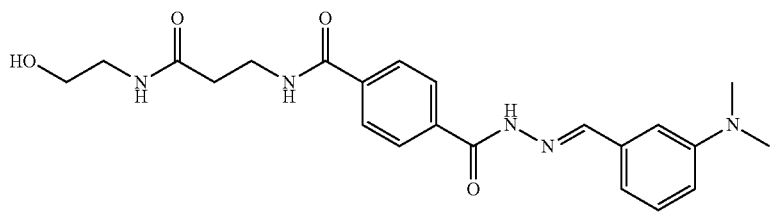 [SMILES: CN(C)c1cccc(/C=N/NC(=O)c2ccc(C(=O)NCCC(=O)NCCO)cc2)c1]

Compound 149 was prepared according to the procedure described in Scheme I from 4-(2-(2-hydroxyethylaminocarbonyl)ethylaminocarbonyl)benzoate and 3-dimethylaminobenzaldehyde. [M+H]$^+$ calcd for $C_{22}H_{27}N_5O_4$: 426.2. found: 426.53.

Example 50

(E)-4-((4-(2-(2-hydroxy-5-methoxybenzylidene)hydrazinecarbonyl)phenyl)amino)-N-(2-hydroxyethyl)butanamide (Compound 150)

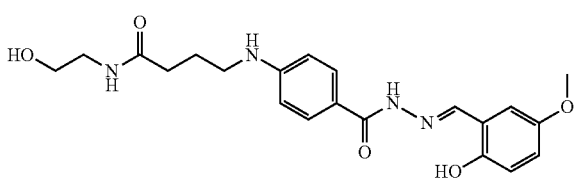 [SMILES: COc1ccc(O)c(/C=N/NC(=O)c2ccc(NCCCC(=O)NCCO)cc2)c1]

Compound 150 was prepared according to the procedure described in Scheme I from 4-(3-(2-hydroxyethylaminocarbonyl)propylamino)benzoate and 2-hydroxy-5-methoxybenzaldehyde. [M+H]$^+$ calcd for $C_{21}H_{26}N_4O_5$: 415.1. found: 415.53.

Example 51

(E)-4-((4-(2-(3-(dimethylamino)benzylidene)hydrazinecarbonyl)phenyl)amino)-N-(2-hydroxyethyl)butanamide (Compound 151)

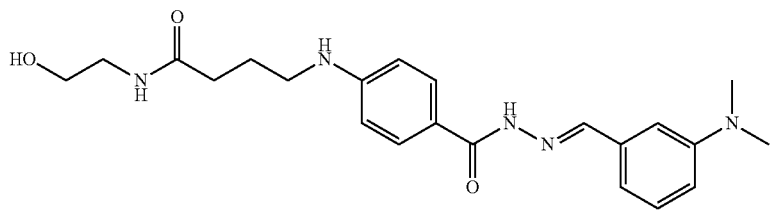 [SMILES: CN(C)c1cccc(/C=N/NC(=O)c2ccc(NCCCC(=O)NCCO)cc2)c1]

Compound 151 was prepared according to the procedure described in Scheme I from 4-(3-(2-hydroxyethylaminocarbonyl)propylamino)benzoate and 3-dimethylaminobenzaldehyde. [M+H]$^+$ calcd for $C_{22}H_{29}N_5O_3$: 412.2. found: 412.56.

Example 52

(E)-4-((4-(2-(3-(2-hydroxyethoxy)benzylidene)hydrazinecarbonyl)phenyl)amino)-N-(2-hydroxyethyl)butanamide (Compound 152)

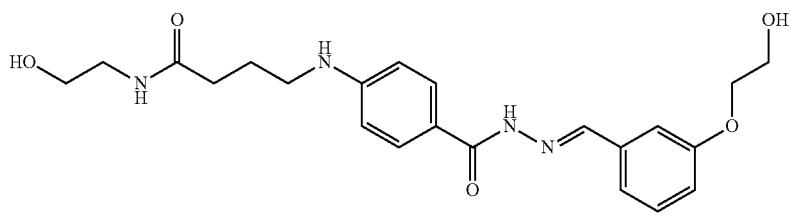 [SMILES: O=C(CCCNc1ccc(C(=O)N/N=C/c2cccc(OCCO)c2)cc1)NCCO]

Compound 152 was prepared according to the procedure described in Scheme I from 4-(3-(2-hydroxyethylaminocarbonyl)propylamino)benzoate and 3-(2-hydroxyethoxy)benzaldehyde. [M+H]$^+$ calcd for $C_{22}H_{28}N_4O_5$: 429.2. found: 429.50.

Example 53

(E)-4-((4-(2-(3,5-dimethoxybenzylidene)hydrazinecarbonyl)phenyl)amino)-N-(2-hydroxyethyl)butanamide (Compound 153)

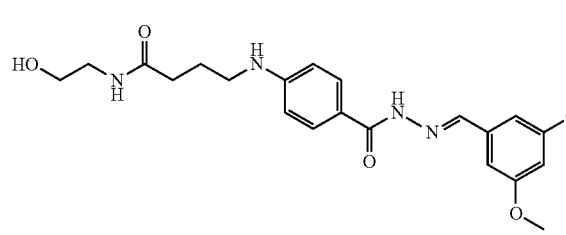

Compound 153 was prepared according to the procedure described in Scheme I from 4-(3-(2-hydroxyethylaminocarbonyl)propylamino)benzoate and 3,5-dimethoxybenzaldehyde. [M+H]$^+$ calcd for $C_{22}H_{28}N_4O_5$: 429.2. found: 429.50.

Example 54

(E)-4-((4-(2-((1H-indol-6-yl)methylene)hydrazinecarbonyl)phenyl)amino)-N-(2-hydroxyethyl)butanamide (Compound 154)

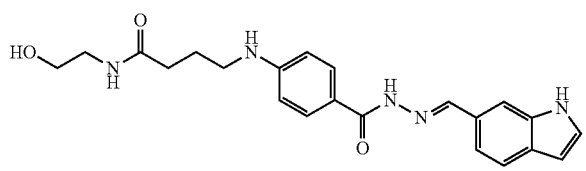 [SMILES: O=C(CCCNc1ccc(C(=O)N/N=C/c2ccc3cc[nH]c3c2)cc1)NCCO]

Compound 154 was prepared according to the procedure described in Scheme I from 4-(3-(2-hydroxyethylaminocarbonyl)propylamino)benzoate and 6-indolecarboxaldehyde. [M+H]$^+$ calcd for $C_{22}H_{25}N_5O_3$: 408.2. found: 408.51.

Example 55

(E)-4-(5-(2-(3-methoxybenzylidene)hydrazinecarbonyl)-1H-indol-1-yl)-N-(2-methoxyethyl)butanamide (Compound 155)

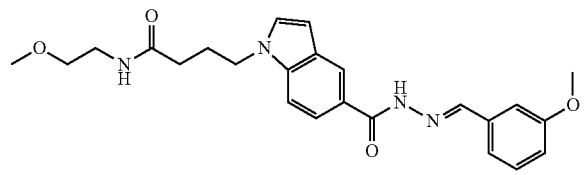

Compound 155 was prepared according to the procedure described in Scheme I from 1-(3-(2-methoxyethyl)aminocarbonylpropyl)indole-5-carboxylate and 3-methoxybenzaldehyde. $^1$H NMR (500 MHz, DMSO-d$_6$) δ 11.77 (s, 1H), 8.43 (s, 1H), 8.20 (d, J=1.5 Hz, 1H), 7.89 (t, J=5.5 Hz, 1H), 7.72 (dd, J=2, 9 Hz, 1H), 7.57 (d, J=9 Hz, 1H), 7.46 (d, J=3 Hz, 1H), 7.36 (t, J=8 Hz, 1H), 7.27 (s, 2H), 6.99 (d, J=8 Hz, 1H), 6.58 (d, J=2.5 Hz, 1H), 4.20 (t, J=6.5 Hz, 2H), 3.80 (s, 3H), 3.32-3.29 (m, 2H), 3.20-3.14 (m, 5H), 2.05 (t, J=8 Hz, 2H), 1.96 (p, J=7 Hz, 2H).

Example 56

(E)-N-(3-(dimethylamino)phenyl)-4-(5-(2-(3-methoxybenzylidene)hydrazinecarbonyl)-1H-indol-1-yl)butanamide (Compound 156)

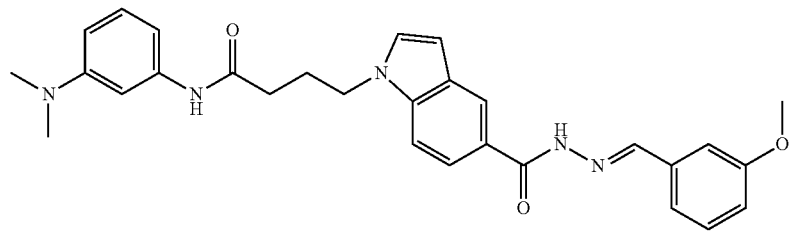

Compound 156 was prepared according to the procedure described in Scheme I from 1-(3-(3-dimethylaminophenyl)aminocarbonylpropyl)indole-5-carboxylate and 3-methoxybenzaldehyde. [M+H]$^+$ calcd for C$_{29}$H$_{31}$N$_5$O$_3$: 498.2. found: 497.98.

Example 57

(E)-N-(4-(dimethylamino)phenyl)-4-(5-(2-(3-methoxybenzylidene)hydrazinecarbonyl)-1H-indol-1-yl)butanamide (Compound 157)

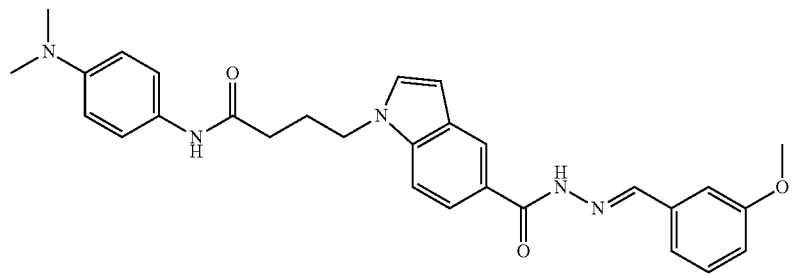

Compound 157 was prepared according to the procedure described in Scheme I from 1-(3-(4-dimethylaminophenyl)aminocarbonylpropyl)indole-5-carboxylate and 3-methoxybenzaldehyde. $^1$H NMR (500 MHz, DMSO-$d_6$) δ 11.77 (s, 1H), 9.58 (s, 1H), 8.43 (bs, 1H), 8.21 (d, J=1.0 Hz, 1H), 7.73 (dd, J=1.5, 8.5 Hz, 1H), 7.60 (d, J=8.5 Hz, 1H), 7.50 (d, J=2.5 Hz, 1H), 7.44 (m, 1H), 7.36 (d, J=9 Hz, 2H), 7.26 (m, 2H), 6.99 (d, J=8 Hz, 1H), 6.75 (d, J=9 Hz, 1H), 6.65 (d, J=9 Hz, 2H), 6.60 (d, J=2.5 Hz, 1H), 4.27 (t, J=7 Hz, 2H), 3.80 (s, 3H), 2.81 (s, 6H), 2.23 (t, J=7.5 Hz, 2H), 2.06 (p, J=7.5 Hz, 2H).

Example 58

(E)-4-(5-(2-(3-(1H-pyrazol-1-yl)benzylidene)hydrazinecarbonyl)-1H-indol-1-yl)-N-(3-(dimethylamino)phenyl)butanamide (Compound 158)

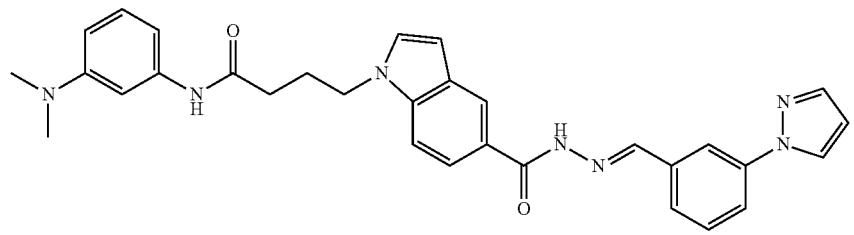 [SMILES: CN(C)c1cccc(NC(=O)CCCn2ccc3cc(C(=O)N/N=C/c4cccc(-n5cccn5)c4)ccc32)c1]

Compound 158 was prepared according to the procedure described in Scheme I from 1-(3-(3-dimethylaminophenyl)aminocarbonylpropyl)indole-5-carboxylate and 3-(pyrazol-1-yl)benzaldehyde. [M+H]$^+$ calcd for $C_{31}H_{31}N_7O_2$: 534.2. found: 534.00.

Example 59

(E)-4-(5-(2-(3-(1H-pyrazol-1-yl)benzylidene)hydrazinecarbonyl)-1H-indol-1-yl)-N-(4-(dimethylamino)phenyl)butanamide (Compound 159)

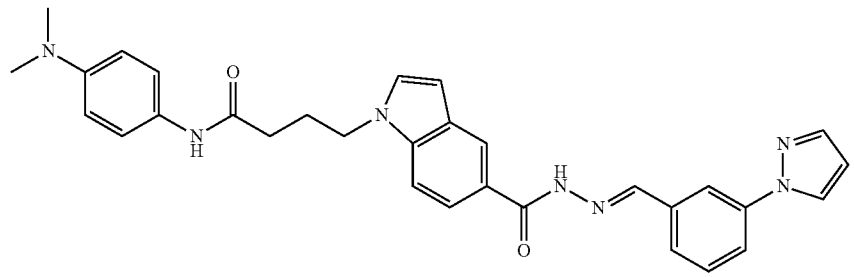 [SMILES: CN(C)c1ccc(NC(=O)CCCn2ccc3cc(C(=O)N/N=C/c4cccc(-n5cccn5)c4)ccc32)cc1]

Compound 159 was prepared according to the procedure described in Scheme I from 1-(3-(4-dimethylaminophenyl)aminocarbonylpropyl)indole-5-carboxylate and 3-(pyrazol-1-yl)benzaldehyde. [M+H]$^+$ calcd for $C_{31}H_{31}N_7O_2$: 534.2. found: 533.97.

Example 60

(E)-4-(5-(2-(3-(1H-pyrazol-1-yl)benzylidene)hydrazinecarbonyl)-1H-indol-1-yl)-N-(2-methoxyethyl)butanamide (Compound 160)

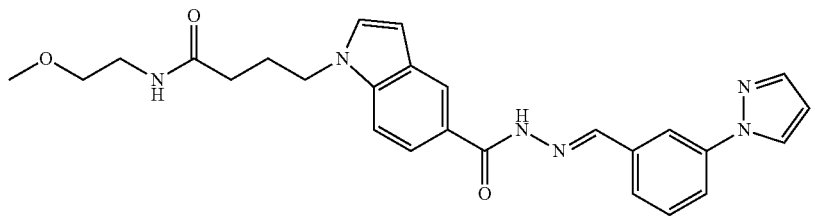 [SMILES: COCCNC(=O)CCCn1ccc2cc(C(=O)N/N=C/c3cccc(-n4cccn4)c3)ccc21]

Compound 160 was prepared according to the procedure described in Scheme I from 1-(3-(2-methoxyethyl)aminocarbonylpropyl)indole-5-carboxylate and 3-(pyrazol-1-yl)benzaldehyde. [M+H]$^+$ calcd for $C_{26}H_{28}N_6O_3$: 473.2. found: 472.94.

Example 61

(E)-4-(5-(2-(3-(1H-pyrazol-1-yl)benzylidene)hydrazinecarbonyl)-1H-indol-1-yl)-N-(2-acetamidoethyl)butanamide (Compound 161)

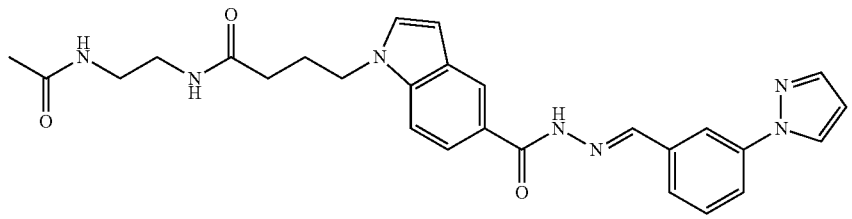 [SMILES: CC(=O)NCCNC(=O)CCCn1ccc2cc(C(=O)N/N=C/c3cccc(-n4cccn4)c3)ccc21]

Compound 161 was prepared according to the procedure described in Scheme I from 1-(3-(2-acetylamidoethyl)aminocarbonylpropyl)indole-5-carboxylate and 3-(pyrazol-1-yl)benzaldehyde. [M+H]$^+$ calcd for $C_{27}H_{29}N_7O_3$: 500.2. found: 499.94.

Example 62

(E)-N-(2-acetamidoethyl)-4-(5-(2-(3-methoxybenzylidene)hydrazinecarbonyl)-1H-indol-1-yl)butanamide (Compound 162)

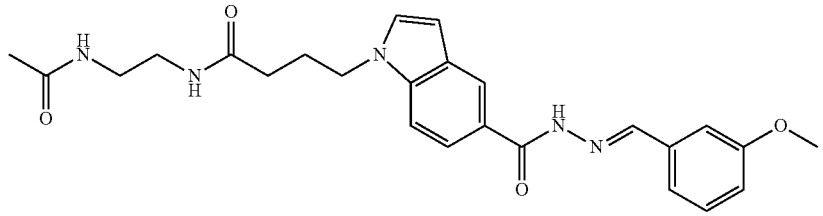 [SMILES: COc1cccc(/C=N/NC(=O)c2ccc3c(ccn3CCCC(=O)NCCNC(C)=O)c2)c1]

Compound 162 was prepared according to the procedure described in Scheme I from 1-(3-(2-acetylamidoethyl)aminocarbonylpropyl)indole-5-carboxylate and 3-methoxybenzaldehyde. [M+H]$^+$ calcd for $C_{25}H_{29}N_5O_4$: 464.2. found: 463.93.

167

Example 63

(E)-4-(5-(2-(3-methoxybenzylidene)hydrazinecarbonyl)-1H-indol-1-yl)-N-(2,2,2-trifluoroethyl)butanamide (Compound 163)

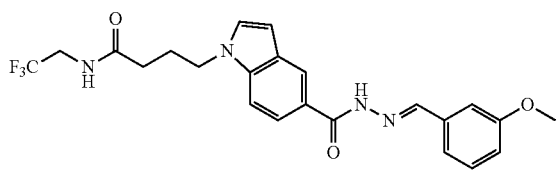 [SMILES: COc1cccc(/C=N/NC(=O)c2ccc3c(ccn3CCCC(=O)NCC(F)(F)F)c2)c1]

Compound 163 was prepared according to the procedure described in Scheme I from 1-(3-(2,2,2-trifluoroethyl)aminocarbonylpropyl)indole-5-carboxylate and 3-methoxybenzaldehyde. [M+H]$^+$ calcd for $C_{23}H_{23}F_3N_4O_3$: 461.1. found: 460.92.

168

Example 64

(E)-N-(2-hydroxyethyl)-4-(5-(2-(3-methoxybenzylidene)hydrazinecarbonyl)-1H-indol-1-yl)butanamide (Compound 164)

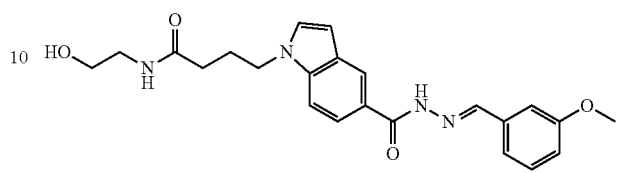

Compound 164 was prepared according to the procedure described in Scheme I from 1-(3-(2-hydroxyethyl)aminocarbonylpropyl)indole-5-carboxylate and 3-methoxybenzaldehyde. [M+H]$^+$ calcd for $C_{23}H_{26}N_4O_4$: 423.2. found: 422.88.

Example 65

(E)-N-(3-((4-hydroxybutyl)amino)-3-oxopropyl)-4-(2-(3-methoxybenzylidene) hydrazinecarbonyl)benzamide (Compound 165)

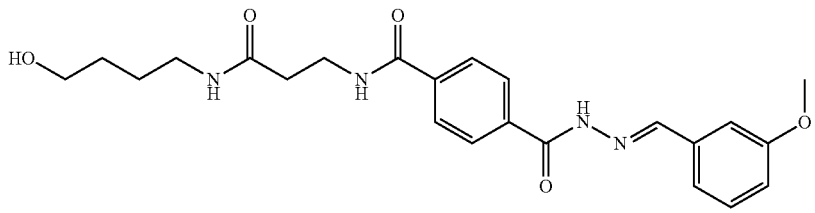 [SMILES: COc1cccc(/C=N/NC(=O)c2ccc(C(=O)NCCC(=O)NCCCCO)cc2)c1]

Compound 165 was prepared according to the procedure described in Scheme I from 4-(2-(4-hydroxybutylaminocarbonyl)ethylaminocarbonyl)benzoate and 3-methoxybenzaldehyde. [M+H]$^+$ calcd for $C_{23}H_{28}N_4O_5$: 441.2. found: 441.01.

Example 66

(E)-N-(2-(dimethylamino)ethyl)-4-(5-(2-(3-methoxybenzylidene)hydrazinecarbonyl)-1H-indol-1-yl)butanamide (Compound 166)

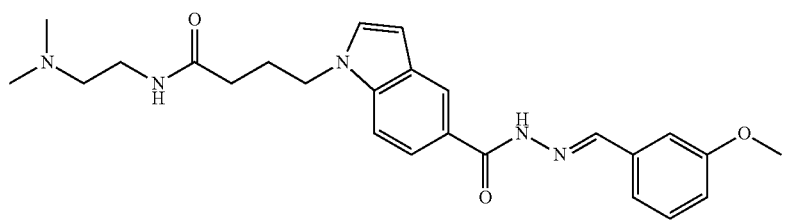

Compound 166 was prepared according to the procedure described in Scheme I from 1-(3-(2-dimethylaminoethyl) aminocarbonylpropyl)indole-5-carboxylate and 3-methoxybenzaldehyde. ¹H NMR (500 MHz, Acetone-d₆) δ 11.09 (bs, 1H), 8.51 (bs, 1H), 8.26 (d, J=19 Hz, 2H), 7.83 (dd, J=1.5, 8.5 Hz, 1H), 7.39 (bs, 1H), 7.35 (t, J=7.5 Hz, 1H), 7.30 (m, 1H), 7.08 (s, 1H), 6.99-6.97 (m, 1H), 6.58 (d, J=3 Hz, 1H), 4.31 (t, J=7 Hz, 2H), 3.85 (s, 3H), 3.39 (q, J=6 Hz, 2H), 2.67 (t, J=6 Hz, 2H), 2.41 (s, 6H), 2.18-2.11 (m, 4H).

Example 67

Methyl 4-(2-(4-morpholinophenyl)-1H-benzo[d]imidazole-5-carboxamido)benzoate (Compound 167)

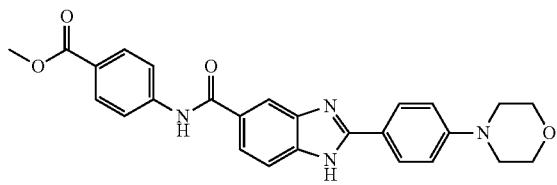 [SMILES: COC(=O)c1ccc(NC(=O)c2ccc3[nH]c(-c4ccc(N5CCOCC5)cc4)nc3c2)cc1]

Compound 167 was prepared according to the general procedure similar to that described in Scheme III. Preparation of 2-(4-morpholinophenyl)-1H-benzo[d]imidazole-5-carboxylic acid: 4-Morpholinobenzaldehyde (475 mg, 2.5 mmole), sodium metabisulfite (85 mg) and 3,4-diaminobenzoic acid (152 mg, 2.7 mmole) were placed in a 10-mL microwave tube and 5.0 mL HPLC grade 2-propanol added. The reaction mixture was microwaved at 170° C. for 55 minutes. The reaction mixture was added dropwise to 25 mL water and stirred at room temperature for 30 min. then it was filtered and washed with plenty of water, ethyl acetate and hexanes and dried to provide the pure intermediate acid (323 mg, 40% yield). This compound was used for next step without any further purification.

Preparation of Compound 167: 2-(4-Morpholinophenyl)-1H-benzo[d]imidazole-5-carboxylic acid (32 mg, 0.1 mmol) and N-(3-dimethylaminopropyl)-N'-ethylcarbodiimide hydrochloride (EDC) (40 mg, 0.2 mmole) were place in a 20 mL vial and pyridine (1.0 mL) added and capped tightly. The reaction mixture was stirred at room temperature for overnight. The reaction mixture was evaporated to dryness and the residue was washed thoroughly with plenty of water, hexanes and EtOAc then dried. Crystallization out of methanol/water provided compound 167 in 25% yield (11.4 mg). [M+H]⁺ calcd for $C_{26}H_{24}N_4O_4$: 457.1. found: 456.94.

Example 68

2-(4-Morpholinophenyl)-N-(3-((4-morpholinophenyl)amino)-3-oxopropyl)-1H-benzo[d]imidazole-5-carboxamide (Compound 168)

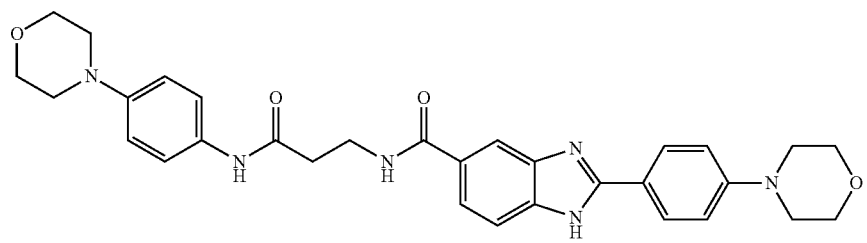 [SMILES: O=C(CCNC(=O)c1ccc2[nH]c(-c3ccc(N4CCOCC4)cc3)nc2c1)Nc1ccc(N2CCOCC2)cc1]

Compound 168 was prepared according to the procedure similar to that described in Scheme III from the 3,4-dinitrobenzamide and 4-morpholinobenzaldehyde. [M+H]$^+$ calcd for $C_{31}H_{34}N_6O_4$: 555.2. found: 555.03.

Example 69

N-(2-(4-Methyl-3,4-dihydro-2H-benzo[b][1,4]oxazin-7-yl)-1H-benzimidazol-5-yl)-4-morpholinobenzamide (Compound 169)

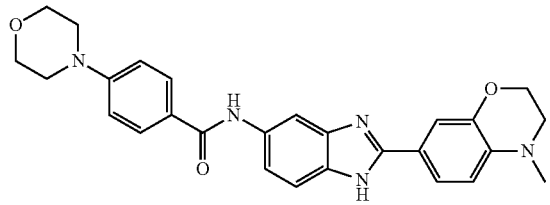 [SMILES: CN1CCOc2cc(-c3nc4cc(NC(=O)c5ccc(N6CCOCC6)cc5)ccc4[nH]3)ccc21]

Compound 169 was prepared according to the procedure similar to that described in Scheme III from 5-amino-2-(4-methyl-3,4-dihydrobenzoxazin-7-yl)benzimidazole and 4-morpholinobenzoic acid. [M+H]$^+$ calcd for $C_{27}H_{27}N_5O_3$: 470.21. found: 496.96.

Example 70

N-(2-(4-Phenoxyphenyl)-1H-benzo[d]imidazol-5-yl)benzamide (Compound 170)

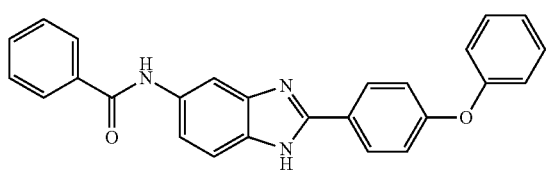 [SMILES: O=C(Nc1ccc2[nH]c(-c3ccc(Oc4ccccc4)cc3)nc2c1)c1ccccc1]

Compound 170 was prepared according to the procedure similar to that described in Scheme III from 3,4-dinitro-N-benzoaniline and 4-phenoxybenzaldehyde. [M+H]$^+$ calcd for $C_{26}H_{19}N_3O_2$: 406.1. found: 406.08.

Example 71

N-(2-(6-Methoxynaphthalen-2-yl)-1H-benzo[d]imidazol-5-yl)benzamide (Compound 171)

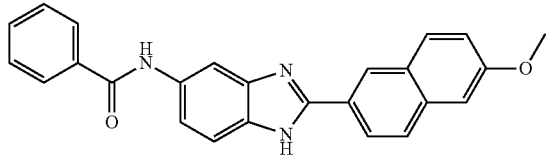 [SMILES: COc1ccc2cc(-c3nc4cc(NC(=O)c5ccccc5)ccc4[nH]3)ccc2c1]

Compound 171 was prepared according to the procedure similar to that described in Scheme III from 3,4-dinitro-N-benzoaniline and 6-methoxynaphthalene-2-carboxaldehyde. [M+H]$^+$ calcd for $C_{25}H_{19}N_3O_2$: 394.1. found: 394.10.

Example 72

N-(2-Phenyl-1H-benzo[d]imidazol-5-yl)-[1,1'-biphenyl]-4-carboxamide (Compound 172)

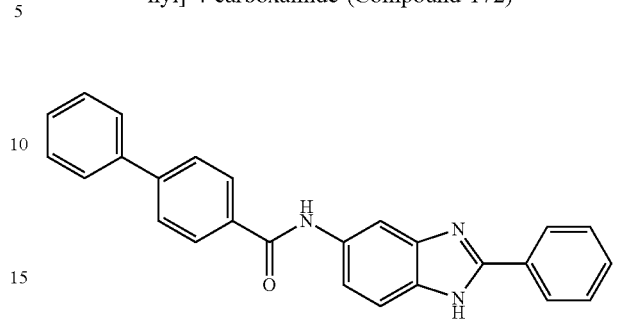

Compound 172 was prepared according to the procedure similar to that described in Scheme III from 3,4-dinitro-N-(4-phenylbenzo)aniline and benzaldehyde. $^1$H NMR (500 MHz, DMSO-d$_6$) δ 10.62 (s, 1H), 8.83 (m, 1H), 8.52 (d, J=1.5 Hz, 1H), 8.23 (m, 2H), 8.13 (d, J=8.5 Hz, 2H), 7.82 (d, J=9 Hz, 3H), 7.79 (dd, J=1.5, 9 Hz, 1H), 7.70 (dd, J=1.5, 9 Hz, 2H), 7.73 (m, 3H), 7.53 (t, J=7.5 Hz, 2H), 7.44 (dt, J=1, 7.5 Hz, 1H).

Example 73

N-(2-(4-(pyrimidin-5-yl)phenyl)-1H-benzo[d]imidazol-5-yl)benzamide (Compound 173)

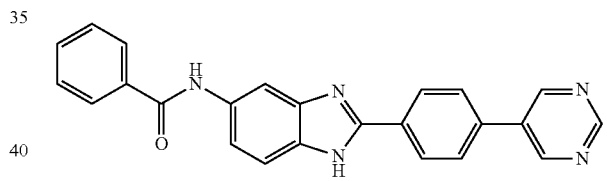

Compound 173 was prepared according to the procedure similar to that described in Scheme III from 3,4-dinitro-N-benzoaniline and 4-(pyrimidin-5-yl)benzaldehyde. [M+H]$^+$ calcd for $C_{24}H_{17}N_5O$: 392.1. found: 391.91.

Example 74

N-(2-(4-(pyridin-3-yl)phenyl)-1H-benzo[d]imidazol-5-yl)benzamide (Compound 174)

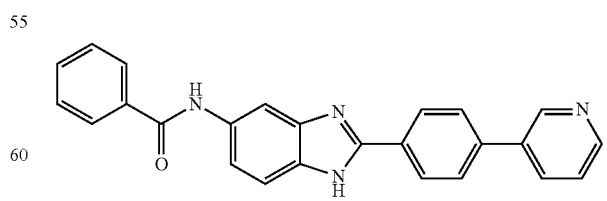

Compound 174 was prepared according to the procedure similar to that described in Scheme III from 3,4-dinitro-N-benzoaniline and 4-(pyridyl-3-)benzaldehyde. [M+H]$^+$ calcd for $C_{25}H_{18}N_4O$: 391.1. found: 390.90.

Example 75

2'-(4-Ethoxyphenyl)-5-(4-methylpiperazin-1-yl)-1H,1'H-2,5'-bibenzo[d]imidazole (Compound 175)

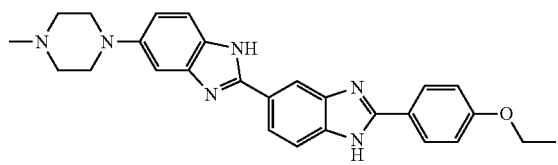 [SMILES: CCOc1ccc(-c2nc3cc(-c4nc5cc(N6CCN(C)CC6)ccc5[nH]4)ccc3[nH]2)cc1]

Compound 175 was prepared according to the procedure similar to that described in Scheme III from 5-(N-methylpiperizinyl)-2-(3,4-diaminophenyl)benzimidazole and 4-ethoxybenzaldehyde.

Example 76

3-Bromo-N-(2-phenyl-1H-benzo[d]imidazol-5-yl)benzamide (Compound 176)

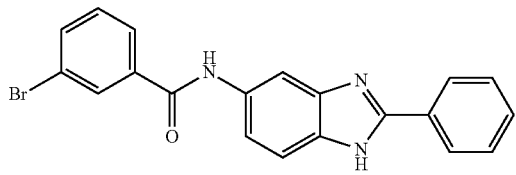 [SMILES: O=C(Nc1ccc2[nH]c(-c3ccccc3)nc2c1)c1cccc(Br)c1]

Compound 176 was prepared according to the procedure similar to that described in Scheme III from 3,4-dinitro-N-(3-bromobenzo)aniline and benzaldehyde. $^1$H NMR (300 MHz, Acetone-d$_6$) δ 9.77 (bs, 1H), 8.37 (s, 1H), 8.23 (d, J=7 Hz, 2H), 8.18 (s, 1H), 8.04 (m, 1H), 7.75 (d, J=8.5 Hz, 1H), 7.62-7.46 (m, 7H).

Example 77

4-Methoxy-N-(2-(4-(pyrrolidin-1-yl)phenyl)-1H-benzo[d]imidazol-5-yl)benzamide (Compound 177)

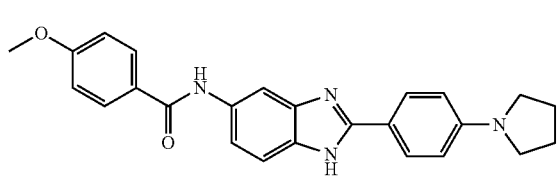 [SMILES: COc1ccc(C(=O)Nc2ccc3[nH]c(-c4ccc(N5CCCC5)cc4)nc3c2)cc1]

Compound 177 was prepared according to the procedure similar to that described in Scheme III from 3,4-dinitro-N-(4-methoxybenzo)aniline and 4-(pyrrolidin-1-yl)benzaldehyde. [M+H]$^+$ calcd for C$_{25}$H$_{24}$N$_4$O$_2$: 413.2. found: 413.51.

Example 78

4-Guanidino-N-(2-(4-(pyrrolidin-1-yl)phenyl)-1H-benzo[d]imidazol-5-yl)benzamide (Compound 178)

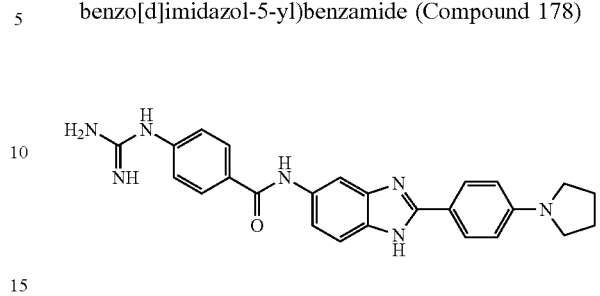

Compound 178 was prepared according to the procedure similar to that described in Scheme III from 3,4-dinitro-N-(4-amidinoaminobenzo)aniline and 4-(pyrrolidin-1-yl)benzaldehyde. [M+H]$^+$ calcd for C$_{25}$H$_{25}$N$_7$O: 440.2. found: 440.57.

Example 79

4-(Dimethylamino)-N-(2-(4-(2-oxopyrrolidin-1-yl)phenyl)-1H-benzo[d]imidazol-5-yl)benzamide (Compound 179)


Compound 179 was prepared according to the procedure similar to that described in Scheme III from 3,4-dinitro-N-(4-dimethylaminobenzo)aniline and 4-(pyrolidon-1-yl)benzaldehyde. [M+H]$^+$ calcd for C$_{26}$H$_{25}$N$_5$O$_2$: 440.2. found: 440.50.

Example 80

4-(Dimethylamino)-N-(2-(phenylamino)-1H-benzo[d]imidazol-5-yl)benzamide (Compound 180)

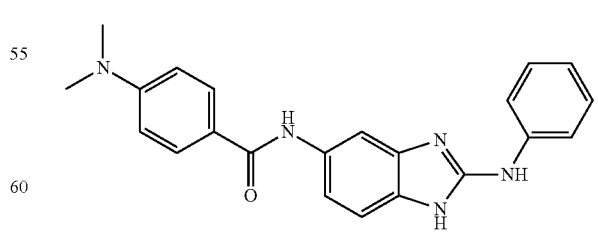

Compound 180 was prepared according to the procedure similar to that described in Scheme III from 4-dimethylaminobenzoic acid and 5-amino-2-phenylaminobenzimidazole. [M+H]$^+$ calcd for C$_{22}$H$_{22}$N$_5$O: 372.1. found: 371.95.

Example 81

4-(Dimethylamino)-N-(2-(4-methyl-3,4-dihydro-2H-benzo[b][1,4]oxazin-7-yl)-1H-benzo[d]imidazol-5-yl)benzamide (Compound 181)

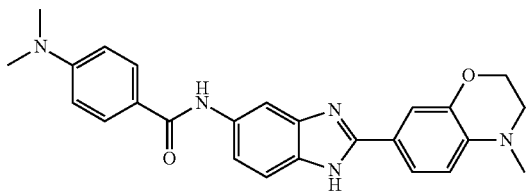

Compound 181 was prepared according to the procedure similar to that described in Scheme III from 3,4-dinitro-N-(4-dimethylaminobenzoyl)aniline and 1-methyl-2,3-dihydrobenzo[1,4]oxazine-6-carboxaldehyde. [M+H]$^+$ calcd for C$_{25}$H$_{25}$N$_5$O$_2$: 428.20. found: 428.49.

Example 82

N-(4-(5-(cyclopent-1-enecarboxamido)-1H-benzo[d]imidazol-2-yl)phenyl)cyclopent-1-enecarboxamide (Compound 182)

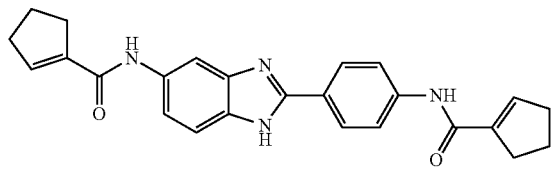 [SMILES: O=C(Nc1ccc(-c2nc3cc(NC(=O)C4=CCCC4)ccc3[nH]2)cc1)C1=CCCC1]

Compound 182 was prepared according to the procedure similar to that described in Scheme III from 5-amino-2-(4-aminophenyl)benzimidazole and 1-cyclohexenecarboxylic acid. [M+H]$^+$ calcd for C$_{25}$H$_{24}$N$_4$O$_2$: 413.2. found: 412.96.

Example 83

N-(2-(2,3-dihydrobenzofuran-5-yl)-1H-benzo[d]imidazol-5-yl)-4-(dimethylamino)benzamide (Compound 183)

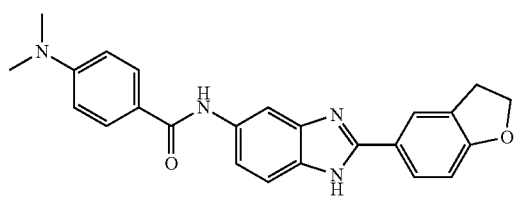 [SMILES: CN(C)c1ccc(C(=O)Nc2ccc3[nH]c(-c4ccc5c(c4)CCO5)nc3c2)cc1]

Compound 183 was prepared according to the procedure similar to that described in Scheme III from 3,4-dinitro-N-(4-dimethylaminobenzoyl)aniline and 2,3-dihydrobenzofuran-5-carboxaldehyde. [M+H]$^+$ calcd for C$_{24}$H$_{24}$N$_4$O$_2$: 399.1. found: 399.47.

Example 84

N-(2-(2,3-dihydrobenzo[b][1,4]dioxin-6-yl)-1H-benzo[d]imidazol-5-yl)-4-(dimethylamino)benzamide (Compound 184)

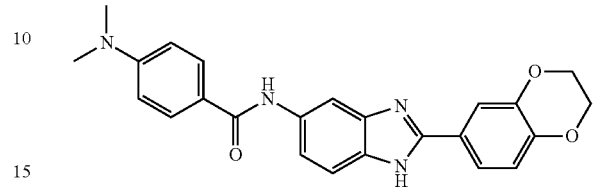

Compound 184 was prepared according to the procedure similar to that described in Scheme III from 3,4-dinitro-N-(4-dimethylaminobenzoyl)aniline and benzo[1,4]dioxane-6-carboxaldehyde. [M+H]$^+$ calcd for C$_{24}$H$_{22}$N$_4$O$_3$: 415.1. found: 415.47.

Example 85

4-(dimethylamino)-N-(2-(1-methyl-1H-benzo[d][1,2,3]triazol-5-yl)-1H-benzo[d]imidazol-5-yl)benzamide (Compound 185)

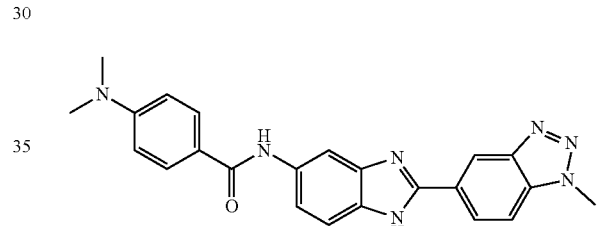

Compound 185 was prepared according to the procedure similar to that described in Scheme III from 3,4-dinitro-N-(4-dimethylaminobenzoyl)aniline and 1-methylbenzotriazole-5-carboxaldehyde. [M+H]$^+$ calcd for C$_{23}$H$_{21}$N$_7$O: 412.18. found: 412.50.

Example 86

N-(2-(benzo[c][1,2,5]oxadiazol-5-yl)-1H-benzo[d]imidazol-5-yl)-4-(dimethylamino)benzamide (Compound 186)

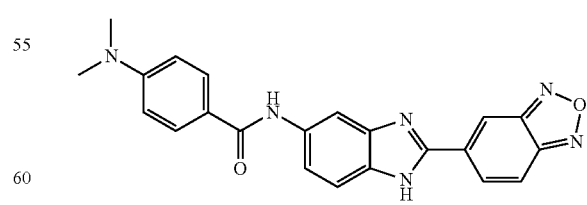

Compound 186 was prepared according to the procedure similar to that described in Scheme III from 3,4-dinitro-N-(4-dimethylaminobenzoyl)aniline and benzofurazan-5-carboxaldehyde. [M+H]$^+$ calcd for C$_{22}$H$_{18}$N$_6$O$_2$: 399.1. found: 399.47.

Example 87

N-(1H,1'H-[2,5'-bibenzo[d]imidazol]-5-yl)-4-(dimethylamino)benzamide (Compound 187)

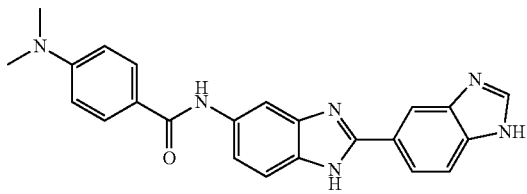 [SMILES: CN(C)c1ccc(C(=O)Nc2ccc3[nH]c(-c4ccc5[nH]cnc5c4)nc3c2)cc1]

Compound 187 was prepared according to the procedure similar to that described in Scheme III from 3,4-dinitro-N-(4-dimethylaminobenzoyl)aniline and benzimidazole-5-carboxaldehyde. [M+H]$^+$ calcd for $C_{23}H_{20}N_6O$: 397.1. found: 397.52.

Example 88

N-(2-(benzofuran-5-yl)-1H-benzo[d]imidazol-5-yl)-4-(dimethylamino)benzamide (Compound 188)

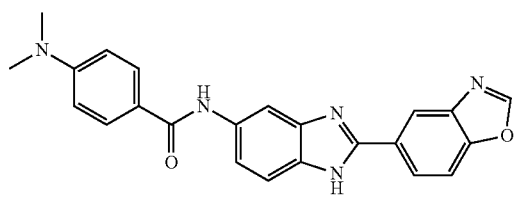 [SMILES: CN(C)c1ccc(C(=O)Nc2ccc3[nH]c(-c4ccc5ocnc5c4)nc3c2)cc1]

Compound 188 was prepared according to the procedure similar to that described in Scheme III from 3,4-dinitro-N-(4-dimethylaminobenzoyl)aniline and benzofuran-5-carboxaldehyde. [M+H]$^+$ calcd for $C_{24}H_{20}N_4O_2$: 397.1. found: 397.52.

Example 89

2N-(2-(4-(1H-imidazol-1-yl)phenyl)-1H-benzo[d]imidazol-5-yl)-4-(pyrrolidin-1-yl)benzamide (Compound 189)

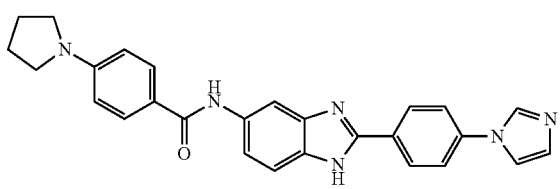 [SMILES: O=C(Nc1ccc2[nH]c(-c3ccc(-n4ccnc4)cc3)nc2c1)c1ccc(N2CCCC2)cc1]

Compound 189 was prepared according to the procedure similar to that described in Scheme III from 3,4-dinitro-N-(4-pyrrolidin-1-ylbenzoyl)aniline and 4-imidazolylbenzaldehyde. [M+H]$^+$ calcd for $C_{27}H_{24}N_6O$: 449.2. found: 449.48.

Example 90

N-(2-(4-(dimethylamino)phenyl)-1H-benzo[d]imidazol-5-yl)-1-methyl-1H-benzo[d][1,2,3]triazole-6-carboxamide (Compound 190)

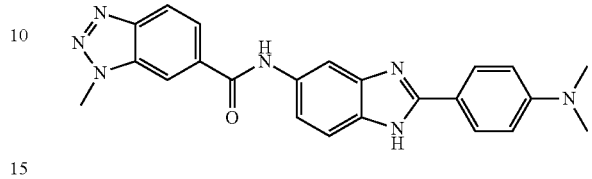

Compound 190 was prepared according to the procedure similar to that described in Scheme III from 3,4-dinitro-N-(1-methyl-6-benzotriazolylcarbonyl)aniline and 4-dimethylaminobenzaldehyde. $^1$H NMR (500 MHz, DMSO-d$_6$) δ 10.74 (s, 1H), 8.78 (s, 1H), 8.43 (d, J=1.5 Hz, 1H), 8.16 (dd, J=1, 8.5 Hz, 1H), 8.10 (d, J=9 Hz, 2H), 8.01 (d, J=8.5 Hz, 2H), 7.84 (dd, J=2, 9 Hz, 1H), 7.72 (d, J=9 Hz, 1H), 6.96 (d, J=9 Hz, 2H), 4.39 (s, 3H), 3.10 (s, 6H).

Example 91

4-(5-benzamido-1H-benzo[d]imidazol-2-yl)-N-(4-(dimethylamino)phenyl)benzamide (Compound 191)

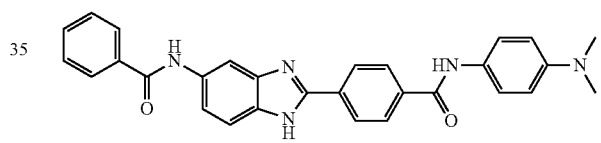

Compound 191 was prepared according to the procedure similar to that described in Scheme III from 3,4-dinitro-N-(4-dimethylaminobenzoyl)aniline and 4-phenylaminocarbonylbenzaldehyde. [M+H]$^+$ calcd for $C_{29}H_{25}N_5O_2$: 476.2. found: 475.98.

Example 92

4-(dimethylamino)-N-(2-(4-(phenylcarbamoyl)phenyl)-1H-benzo[d]imidazol-5-yl)benzamide (Compound 192)

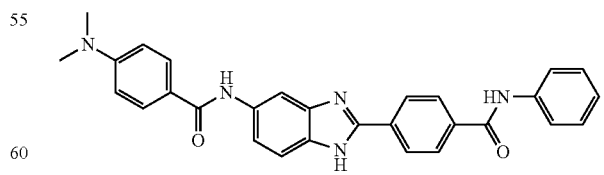

Compound 192 was prepared according to the procedure similar to that described in Scheme III from 3,4-dinitro-N-benzoylaniline and 4-(4-dimethylaminophenyl)aminocarbonylbenzaldehyde. [M+H]$^+$ calcd for $C_{29}H_{25}N_5O_2$: 476.20. found: 475.91.

Example 93

4-(dimethylamino)-N-(2-(4-((4-(dimethylamino)phenyl)carbamoyl)phenyl)-1H-benzo[d]imidazol-5-yl)benzamide (Compound 193)

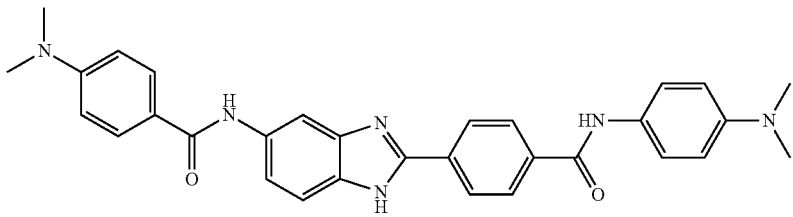

Compound 193 was prepared according to the procedure similar to that described in Scheme III from 3,4-dinitro-N-(4-dimethylaminobenzoyl)aniline and 4-(4-dimethylaminophenyl)aminocarbonylbenzaldehyde. [M+H]$^+$ calcd for $C_{31}H_{30}N_6O_2$: 519.24. found: 519.04.

Example 94

3-chloro-N-(2-(4-(phenylcarbamoyl)phenyl)-1H-benzo[d]imidazol-5-yl)benzamide (Compound 194)

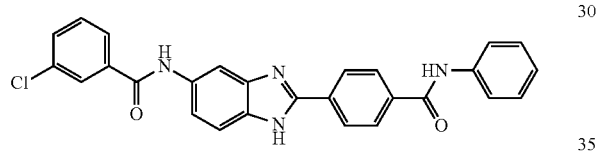

Compound 194 was prepared according to the procedure similar to that described in Scheme III from 3,4-dinitro-N-(4-chlorobenzoyl)aniline and 4-phenylaminocarbonylbenzaldehyde. [M+H]$^+$ calcd for $C_{27}H_{19}ClN_4O_2$: 467.12. found: 466.93.

Example 95

4-morpholino-N-(2-(4-((4-morpholinophenyl)carbamoyl)phenyl)-1H-benzo[d]imidazol-5-yl)benzamide (Compound 195)

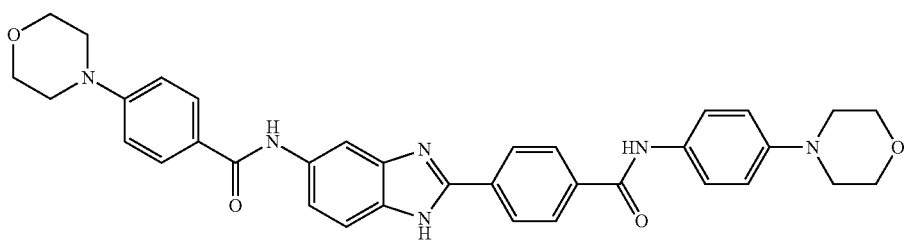 [SMILES: O=C(Nc1ccc(N2CCOCC2)cc1)c1ccc(-c2nc3cc(NC(=O)c4ccc(N5CCOCC5)cc4)ccc3[nH]2)cc1]

Compound 195 was prepared according to the procedure similar to that described in Scheme III from 3,4-dinitro-N-(4-morpholin-4-ylbenzoyl)aniline and 4-(4-morpholinylphenyl)aminocarbonylbenzaldehyde. [M+H]$^+$ calcd for $C_{35}H_{34}N_6O_4$: 603.26. found: 603.36.

Example 96

4-(4-methylpiperazin-1-yl)-N-(2-(4-((4-(4-methyl-piperazin-1-yl)phenyl)carbamoyl)phenyl)-1H-benzo[d]imidazol-5-yl)benzamide (Compound 196)

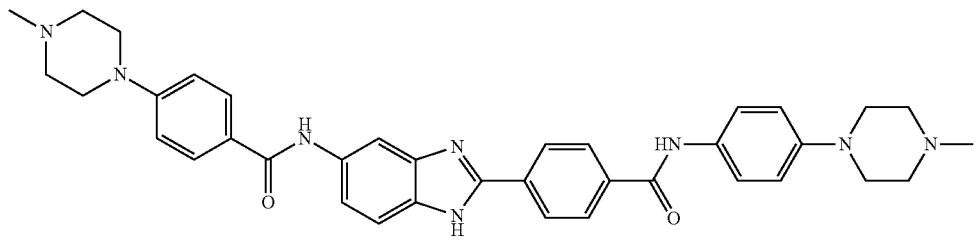

Compound 196 was prepared according to the procedure similar to that described in Scheme III from 3,4-dinitro-N-(4-(4-methylpiperazin-1-yl)benzoyl)aniline and 4-(4-(4-methylpiperazin-1-yl)phenyl)aminocarbonylbenzaldehyde. [M+H]$^+$ calcd for $C_{37}H_{40}N_8O_2$: 629.3. found: 629.16.

Example 97

N-(4-(dimethylamino)phenyl)-2-(4-((4-(dimethyl-amino)phenyl)carbamoyl)phenyl)-1H-benzo[d]imidazole-5-carboxamide (Compound 197)

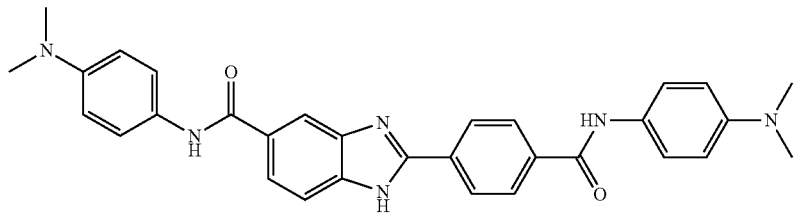

Compound 197 was prepared according to the procedure similar to that described in Scheme III from N-(4-dimethylaminophenyl)-3,4-dinitrobenzamide and 4-(4-dimethylaminophenyl)aminocarbonylbenzaldehyde. [M+H]$^+$ calcd for $C_{31}H_{30}N_6O_2$: 519.24. found: 519.04.

Example 98

2-(4-(4-(dimethylamino)benzamido)phenyl)-N-(4-(dimethylamino)phenyl)-1H-benzo[d]imidazole-5-carboxamide (Compound 198)

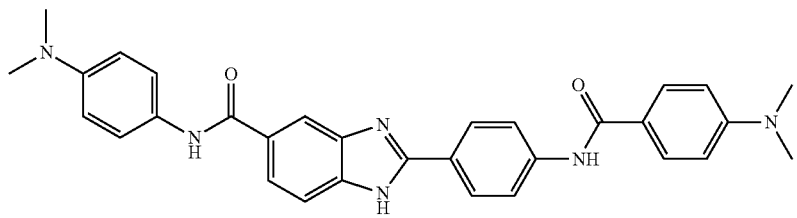

Compound 198 was prepared according to the procedure similar to that described in Scheme III from N-(4-dimethylaminophenyl)-3,4-dinitrobenzamide and 4-(4-dimethylaminobenz)amidobenzaldehyde. [M+H]$^+$ calcd for $C_{31}H_{30}N_6O_2$: 519.24. found: 518.97.

Example 99

N-(2-(4-(1H-pyrazol-1-yl)phenyl)-1H-benzo[d]imidazol-6-yl)-4-(dimethylamino)benzamide (Compound 199)

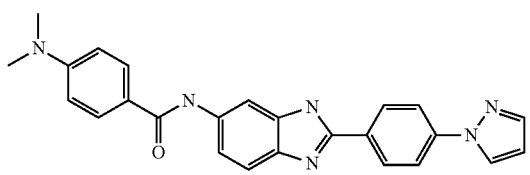 [SMILES: CN(C)c1ccc(C(=O)Nc2ccc3nc(-c4ccc(-n5cccn5)cc4)[nH]c3c2)cc1]

Compound 199 was prepared according to the procedure similar to that described in Scheme III from 3,4-dinitro-N-(4-dimethylaminobenzoyl)aniline and 4-imidazolylbenzaldehyde. [M+H]$^+$ calcd for $C_{25}H_{22}N_6O$: 423.2. found: 423.01.

Example 100

N-(2-(4-(1H-1,2,4-triazol-1-yl)phenyl)-1H-benzo[d]imidazol-5-yl)-4-(dimethylamino)benzamide (Compound 200)

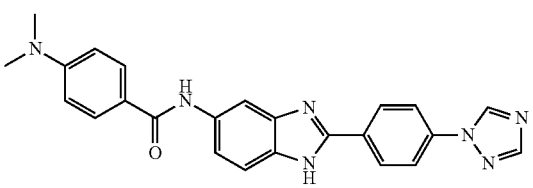 [SMILES: CN(C)c1ccc(C(=O)Nc2ccc3[nH]c(-c4ccc(-n5cncn5)cc4)nc3c2)cc1]

Compound 200 was prepared according to the procedure similar to that described in Scheme III from 3,4-dinitro-N-(4-dimethylaminobenzoyl)aniline and 4-(1,2,4-triazolyl-1-)benzaldehyde. [M+H]$^+$ calcd for $C_{24}H_{21}N_7O$: 424.1. found: 424.02.

Example 101

N-(2-phenyl-1H-benzo[d]imidazol-5-yl)benzo[b]thiophene-2-carboxamide (Compound 201)

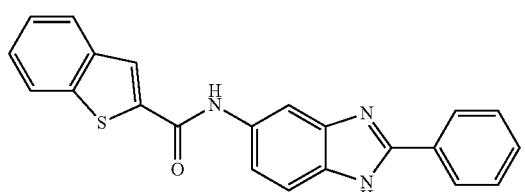

Compound 201 was prepared according to the procedure similar to that described in Scheme III from N-(3,4-dinitrophenyl)benzo[b]thiophene-2-carboxamide and benzaldehyde. $^1$H NMR (500 MHz, CD$_3$OD) δ 8.18 (d, J=2 Hz, 1H), 8.14 (s, 1H), 8.06 (d, J=8 Hz, 2H), 7.91 (m, 2H), 7.85 (d, J=8.5 Hz, 1H), 7.73 (d, J=8.5 Hz, 1H), 7.60 (d, J=8.5 Hz, 1H), 7.53 (m, 3H), 7.44 (m, 3H).

Example 102

N-(2-(4-(2H-tetrazol-5-yl)phenyl)-1H-benzo[d]imidazol-5-yl)-4-(dimethylamino)benzamide (Compound 202)

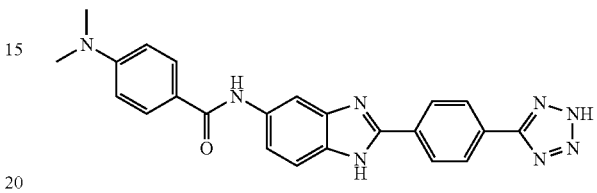

Compound 202 was prepared according to the procedure similar to that described in Scheme III from 3,4-dinitro-N-(4-dimethylaminobenzoyl)aniline and 4-(1,2,3,5-tetrazolyl-5-)benzaldehyde. [M+H]$^+$ calcd for $C_{23}H_{20}N_8O$: 415.1. found: 424.97.

Example 103

N-(2-phenyl-1H-benzo[d]imidazol-5-yl)-1H-indole-2-carboxamide (Compound 203)

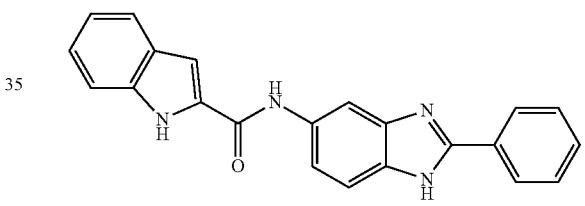

Compound 203 was prepared according to the procedure similar to that described in Scheme III from 3,4-dinitro-N-(indol-2-oyl)aniline and benzaldehyde. $^1$H NMR (500 MHz, CD$_3$OD) δ 8.20 (d, J=1.5 Hz, 1H), 8.09 (dd, J=1.5, 8 Hz, 2H), 7.66 (d, J=8 Hz, 1H), 7.61 (d, J=8.5 Hz, 1H), 7.57-7.52 (m, 4H), 7.48 (dd, J=0.5, 8 Hz, 1H), 7.34 (s, 1H), 7.25 (dt, J=1, 7 Hz, 1H), 7.09 (dt, J=0.5, 8 Hz, 1H).

Example 104

N-(2-phenyl-1H-benzo[d]imidazol-5-yl)-1,2,3,4-tetrahydronaphthalene-2-carboxamide (Compound 204)

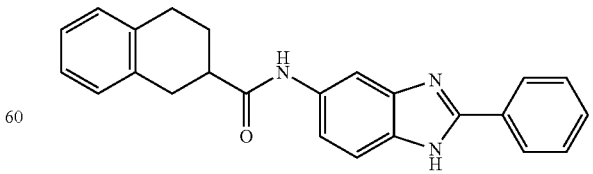

Compound 204 was prepared according to the procedure similar to that described in Scheme III from 3,4-dinitro-N-(1,2,3,4-tetrahydronaphthalen-2-oyl)aniline and benzaldehyde. [M+H]$^+$ calcd for $C_{24}H_{21}N_3O$: 368.1. found: 368.00.

Example 105

N-(2-(4-methoxyphenyl)-1H-benzo[d]imidazol-5-yl)isonicotinamide (Compound 205)

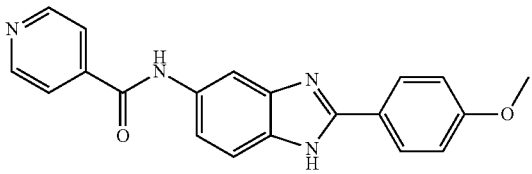 [SMILES: COc1ccc(-c2nc3cc(NC(=O)c4ccncc4)ccc3[nH]2)cc1]

Compound 205 was prepared according to the procedure similar to that described in Scheme III from 3,4-dinitro-N-(pyridin-4-oyl)aniline and 4-methoxybenzaldehyde. [M+H]$^+$ calcd for $C_{20}H_{16}N_4O_2$: 345.1. found: 345.00.

Example 106

4-(dimethylamino)-N-(2-(4-(dimethylamino)phenyl)-1H-benzo[d]imidazol-5-yl)benzamide (Compound 206)

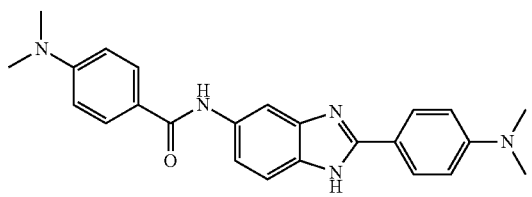

Compound 206 was prepared according to the procedure similar to that described in Scheme III from 3,4-dinitro-N-(4-dimethylaminobenzoyl)aniline and 4-dimethylaminobenzaldehyde. $^1$H NMR (300 MHz, DMSO-d$_6$) δ 10.20 (s, 1H), 8.39 (s, 1H), 8.11 (d, J=8 Hz, 2H), 7.90 (d, J=9 Hz, 2H), 7.81 (d, J=9 Hz, 2H), 7.68 (d, J=9 Hz, 2H), 6.95 (d, J=9 Hz, 2H), 6.78 (d, J=9 Hz, 2H), 3.07 (s, 6H), 2.99 (s, 6H).

Example 107

N-(2-(4-(dimethylamino)phenyl)-1H-benzo[d]imidazol-5-yl)isonicotinamide (Compound 207)

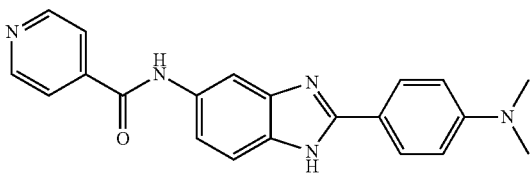 [SMILES: CN(C)c1ccc(-c2nc3cc(NC(=O)c4ccncc4)ccc3[nH]2)cc1]

Compound 207 was prepared according to the procedure similar to that described in Scheme III from 3,4-dinitro-N-(pyridin-4-oyl)aniline and 4-dimethylaminobenzaldehyde. $^1$H NMR (500 MHz, DMSO-d$_6$) δ 10.90 (s, 1H), 8.83 (d, J=6 Hz, 2H), 8.40 (s, 1H), 8.10 (d, J=9 Hz, 2H), 7.98 (d, J=6 Hz, 2H), 7.81 (dd, J=2, 9 Hz, 1H), 7.75 (d, J=9 Hz, 1H), 6.97 (d, J=9 Hz, 2H), 3.09 (s, 6H).

Example 108

N-(2-(4-(dimethylamino)phenyl)-1H-benzo[d]imidazol-5-yl)-4-methoxybenzamide (Compound 208)

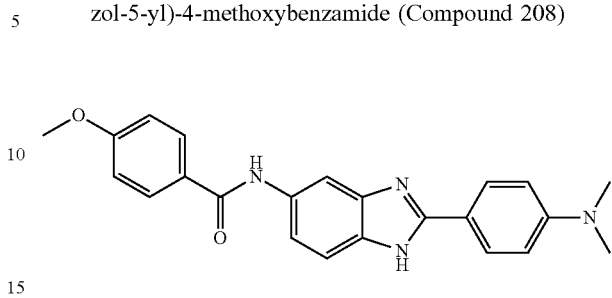

Compound 208 was prepared according to the procedure similar to that described in Scheme III from 3,4-dinitro-N-(4-methoxybenzoyl)aniline and 4-dimethylaminobenzaldehyde. $^1$H NMR (500 MHz, DMSO-d$_6$) δ 10.41 (s, 1H), 8.39 (d, J=1.5 Hz, 1H), 8.08 (d, J=9.5 Hz, 2H), 8.01 (d, J=7 Hz, 2H), 7.79 (dd, J=2, 9 Hz, 1H), 7.67 (d, J=9 Hz, 1H), 7.09 (d, J=9 Hz, 2H), 6.96 (d, J=9 Hz, 2H), 3.82 (s, 3H), 3.08 (s, 6H).

Example 109

4-(1H-imidazol-1-yl)-N-(2-(4-methoxyphenyl)-1H-benzo[d]imidazol-5-yl)benzamide (Compound 209)

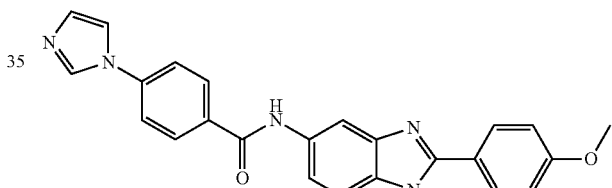

Compound 209 was prepared according to the procedure similar to that described in Scheme III from 3,4-dinitro-N-(4-imidazol-1-ylbenzoyl)aniline and 4-methoxybenzaldehyde. [M+H]$^+$ calcd for $C_{24}H_{19}N_5O_2$: 410.0. found: 410.00.

Example 110

N-(2-(4-methoxyphenyl)-1H-benzo[d]imidazol-5-yl)thiophene-2-carboxamide (Compound 210)

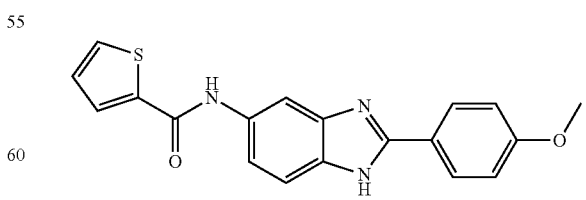

Compound 210 was prepared according to the procedure similar to that described in Scheme III from 3,4-dinitro-N-(thien-2-oyl)aniline and 4-methoxybenzaldehyde. [M+H]$^+$ calcd for $C_{19}H_{15}N_3O_2S$: 350.0. found: 349.89.

Example 111

N,2-bis(4-morpholinophenyl)-1H-benzo[d]imidazole-5-carboxamide (Compound 211)

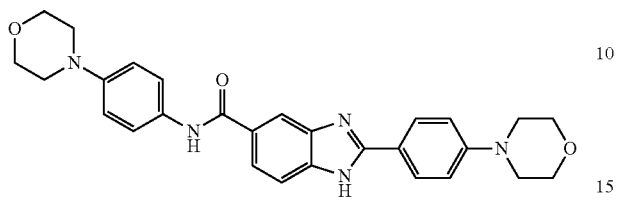

Compound 211 was prepared according to the procedure similar to that described in Scheme III from N-(4-morpholinylphenyl)-3,4-dinitrobenzamide and 4-morpholinylbenzaldehyde. [M+H]$^+$ calcd for $C_{28}H_{29}N_5O_3$: 484.2. found: 483.92.

Example 112

4-morpholino-N-(2-(4-morpholinophenyl)-1H-benzo[d]imidazol-5-yl)benzamide (Compound 212)

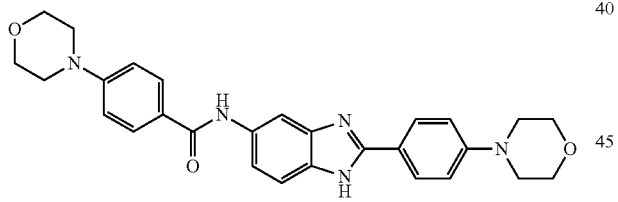

Compound 212 was prepared according to the procedure similar to that described in Scheme III from 3,4-dinitro-N-(4-morpholin-4-ylbenzoyl)aniline and 4-morpholinylbenzaldehyde. [M+H]$^+$ calcd for $C_{28}H_{29}N_5O_3$: 484.2. found: 483.94.

Example 113

N-phenyl-4-(5-(4-(pyrrolidin-1-yl)benzamido)-1H-benzo[d]imidazol-2-yl)benzamide (Compound 213)

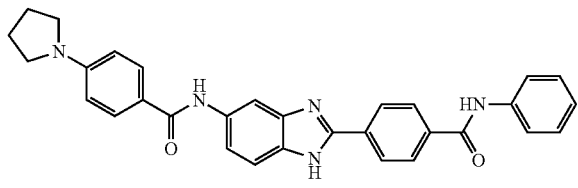 [SMILES: O=C(Nc1ccccc1)c1ccc(-c2nc3cc(NC(=O)c4ccc(N5CCCC5)cc4)ccc3[nH]2)cc1]

Compound 213 was prepared according to the procedure similar to that described in Scheme III from N-(3,4-dinitrophenyl)-4-pyrrolidinylbenzamide and 4-phenylaminocarbonylbenzaldehyde. [M+H]$^+$ calcd for $C_{31}H_{27}N_5O_2$: 502.2. found: 502.03.

Example 114

4-((2-hydroxyethyl)(methyl)amino)-N-(2-(4-(phenylcarbamoyl)phenyl)-1H-benzo[d]imidazol-5-yl)benzamide (Compound 214)

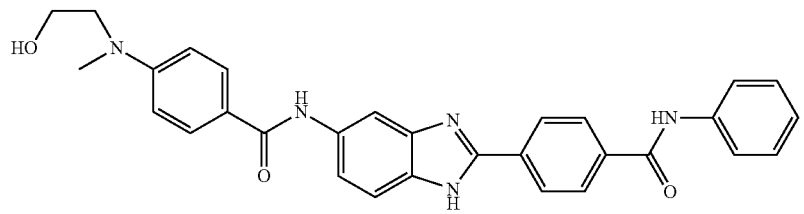 [SMILES: CN(CCO)c1ccc(C(=O)Nc2ccc3[nH]c(-c4ccc(C(=O)Nc5ccccc5)cc4)nc3c2)cc1]

Compound 214 was prepared according to the procedure similar to that described in Scheme III from N-(3,4-dinitrophenyl)-4-(N-methyl-N-2-hydroxyethylamino)benzamide and 4-phenylaminocarbonylbenzaldehyde. [M+H]$^+$ calcd for $C_{30}H_{27}N_5O_3$: 506.2. found: 506.01.

Example 115

N-phenyl-4-(5-(4-(piperidin-1-yl)benzamido)-1H-benzo[d]imidazol-2-yl)benzamide (Compound 215)

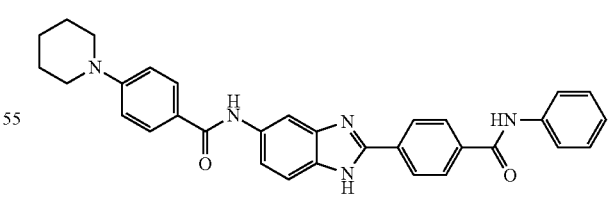

Compound 215 was prepared according to the procedure similar to that described in Scheme III from N-(3,4-dinitrophenyl)-4-piperidinylbenzamide and 4-phenylaminocarbonylbenzaldehyde. [M+H]$^+$ calcd for $C_{32}H_{29}N_5O_2$: 516.2. found: 516.07.

Example 116

4-(4-methylpiperazin-1-yl)-N-(2-(4-(phenylcarbamoyl)phenyl)-1H-benzo[d]imidazol-5-yl)benzamide (Compound 216)

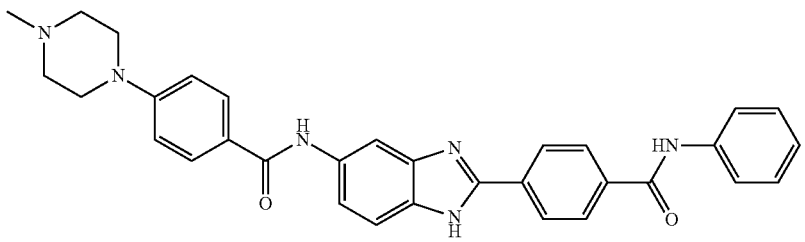 [SMILES: CN1CCN(c2ccc(C(=O)Nc3ccc4[nH]c(-c5ccc(C(=O)Nc6ccccc6)cc5)nc4c3)cc2)CC1]

Compound 216 was prepared according to the procedure similar to that described in Scheme III from N-(3,4-dinitrophenyl)-4-(1-methyl-4-piperazinyl)benzamide and 4-phenylaminocarbonylbenzaldehyde. [M+H]$^+$ calcd for $C_{32}H_{30}N_6O_2$: 531.25. found: 531.05.

Example 117

4-morpholino-N-(2-(4-(phenylcarbamoyl)phenyl)-1H-benzo[d]imidazol-5-yl)benzamide (Compound 217)

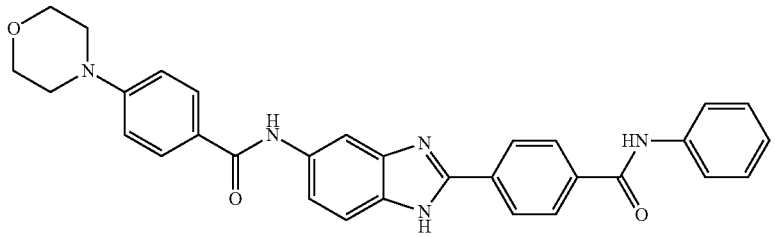 [SMILES: O=C(Nc1ccccc1)c1ccc(-c2nc3cc(NC(=O)c4ccc(N5CCOCC5)cc4)ccc3[nH]2)cc1]

Compound 217 was prepared according to the procedure similar to that described in Scheme III from N-(3,4-dinitrophenyl)-4-morpholinylbenzamide and 4-phenylaminocarbonylbenzaldehyde. [M+H]$^+$ calcd for $C_{31}H_{27}N_5O_3$: 518.2. found: 518.03.

Example 118

4-(dimethylamino)-N-(2-(4-(2-hydroxyethoxy)phenyl)-1H-benzo[d]imidazol-5-yl)benzamide (Compound 218)

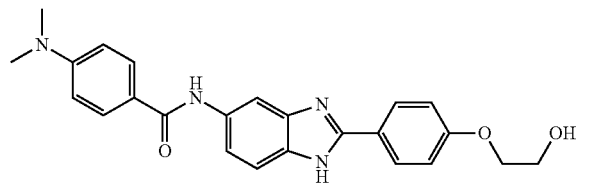 [SMILES: CN(C)c1ccc(C(=O)Nc2ccc3[nH]c(-c4ccc(OCCO)cc4)nc3c2)cc1]

Compound 218 was prepared according to the procedure similar to that described in Scheme III from N-(3,4-dinitrophenyl)-4-dimethylaminobenzamide and 4-(2-hydroxyethyloxy)benzaldehyde. [M+H]$^+$ calcd for $C_{24}H_{24}N_4O_3$: 417.1. found: 417.00.

Example 119

4-(dimethylamino)-N-(2-(3-(2-hydroxyethoxy)phenyl)-1H-benzo[d]imidazol-5-yl)benzamide (Compound 219)

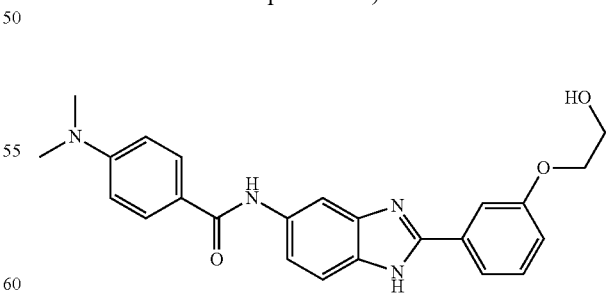

Compound 219 was prepared according to the procedure similar to that described in Scheme III from N-(3,4-dinitrophenyl)-4-dimethylaminobenzamide and 3-(2-hydroxyethyloxy)benzaldehyde. [M+H]$^+$ calcd for $C_{24}H_{24}N_4O_3$: 417.1. found: 416.94.

Example 120

4-(dimethylamino)-N-(2-(4'-(dimethylamino)-[1,1'-biphenyl]-4-yl)-1H-benzo[d]imidazol-5-yl)benzamide (Compound 220)

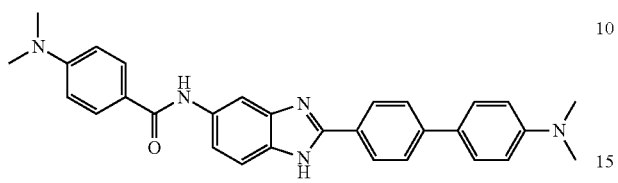

Compound 220 was prepared according to the procedure similar to that described in Scheme III from N-(3,4-dinitrophenyl)-4-dimethylaminobenzamide and 4-(4-dimethylaminophenyl)benzaldehyde. [M+H]$^+$ calcd for $C_{30}H_{29}N_5O$: 476.2. found: 475.98.

Example 121

N-(2-(4-(phenylcarbamoyl)phenyl)-1H-benzo[d]imidazol-5-yl)-2-(pyrrolidin-1-yl)pyrimidine-5-carboxamide (Compound 221)

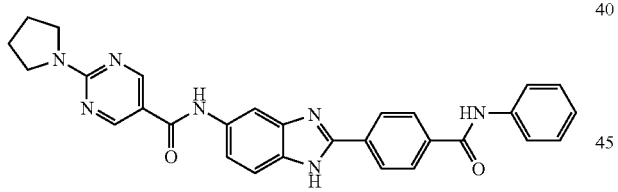

Compound 221 was prepared according to the procedure similar to that described in Scheme III from N-(3,4-dinitrophenyl)-2-(pyrrolidin-1-yl)pyrimidine-5-carboxamide and 4-phenylaminocarbonylbenzaldehyde. [M+H]$^+$ calcd for $C_{29}H_{25}N_7O_2$: 504.2. found: 503.92.

Example 122

4-(5-(4-(1H-tetrazol-1-yl)benzamido)-1H-benzo[d]imidazol-2-yl)-N-phenylbenzamide (Compound 222)

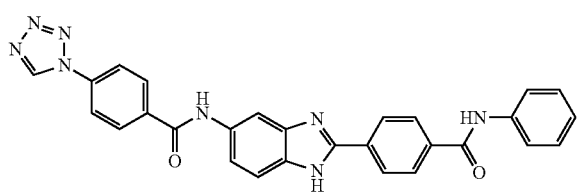 [SMILES: O=C(Nc1ccccc1)c1ccc(-c2nc3cc(NC(=O)c4ccc(-n5cnnn5)cc4)ccc3[nH]2)cc1]

Compound 222 was prepared according to the procedure similar to that described in Scheme III from N-(3,4-dinitrophenyl)-4-tetrazolylbenzamide and 4-phenylaminocarbonylbenzaldehyde. [M+H]$^+$ calcd for $C_{28}H_{20}N_8O_2$: 501.1. found: 500.88.

Example 123

N-(2-(4-(2-hydroxyethoxy)phenyl)-1H-benzo[d]imidazol-5-yl)-4-((2-hydroxyethyl)(methyl)amino)benzamide (Compound 223)

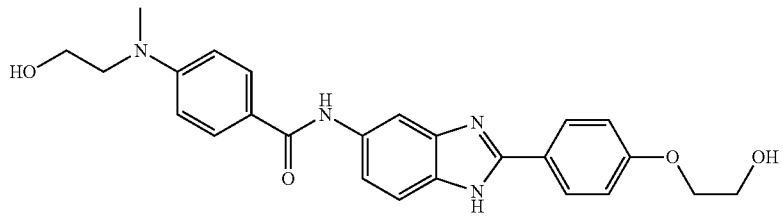 [SMILES: CN(CCO)c1ccc(C(=O)Nc2ccc3[nH]c(-c4ccc(OCCO)cc4)nc3c2)cc1]

Compound 223 was prepared according to the procedure similar to that described in Scheme III from N-(3,4-dinitrophenyl)-4-(N-methyl-N-2-hydroxyethylamino)benzamide and 4-(2-hydroxyethyloxy)benzaldehyde. [M+H]$^+$ calcd for $C_{25}H_{26}N_4O_4$: 447.2. found: 446.89.

Example 124

3-(5-(4-(dimethylamino)benzamido)-1H-benzo[d]imidazol-2-yl)-N-(4-(dimethylamino)phenyl)benzamide (Compound 224)

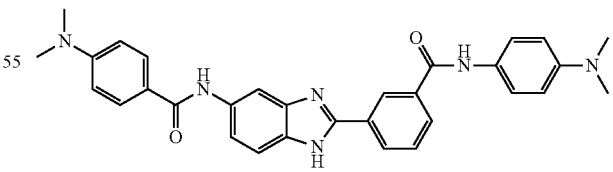

Compound 224 was prepared according to the procedure similar to that described in Scheme III from 3,4-dinitro-N-(4-dimethylaminobenzo)aniline and 3-(4-dimethylaminophenyl)aminocarbonylbenzaldehyde. [M+H]$^+$ calcd for $C_{31}H_{30}N_6O_2$: 519.25. found: 519.04.

Example 125

4-(pyrrolidin-1-yl)-N-(2-(4-(pyrrolidin-1-yl)phenyl)-1H-benzo[d]imidazol-5-yl)benzamide (Compound 225)

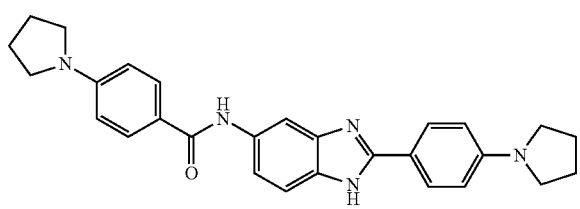 [SMILES: O=C(Nc1ccc2[nH]c(-c3ccc(N4CCCC4)cc3)nc2c1)c1ccc(N2CCCC2)cc1]

Compound 225 was prepared according to the procedure similar to that described in Scheme III from N-(3,4-dinitrophenyl)-4-pyrrolidinylbenzamide and 4-pyrrolidinylbenzaldehyde. [M+H]$^+$ calcd for $C_{28}H_{29}N_5O$: 452.2. found: 451.95.

Example 126

N-(2-(4-(pyrrolidin-1-yl)phenyl)-1H-benzo[d]imidazol-5-yl)-4-(1H-tetrazol-1-yl)benzamide (Compound 226)

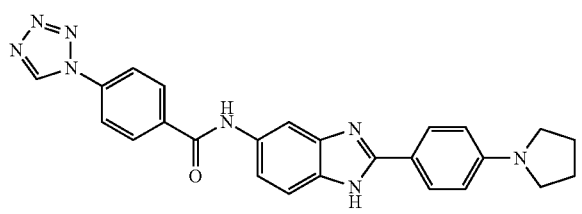 [SMILES: O=C(Nc1ccc2[nH]c(-c3ccc(N4CCCC4)cc3)nc2c1)c1ccc(-n2cnnn2)cc1]

Compound 226 was prepared according to the procedure similar to that described in Scheme III from N-(3,4-dinitrophenyl)-4-tetrazolylbenzamide and 4-pyrrolidinylbenzaldehyde. [M+H]$^+$ calcd for $C_{25}H_{22}N_8O$: 451.2. found: 451.50.

Example 127

N-(2-hydroxyethyl)-4-(5-(4-(pyrrolidin-1-yl)benzamido)-1H-benzo[d]imidazol-2-yl)benzamide (Compound 227)

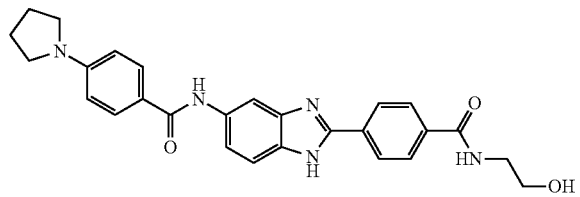 [SMILES: O=C(NCCO)c1ccc(-c2nc3cc(NC(=O)c4ccc(N5CCCC5)cc4)ccc3[nH]2)cc1]

Compound 227 was prepared according to the procedure similar to that described in Scheme III from N-(3,4-dinitrophenyl)-4-pyrrolidinylbenzamide and 4-(2-hydroxyethyl)aminocarbonylbenzaldehyde. [M+H]$^+$ calcd for $C_{27}H_{27}N_5O_3$: 470.22. found: 469.58.

Example 128

N-cyclopropyl-4-(5-(4-(pyrrolidin-1-yl)benzamido)-1H-benzo[d]imidazol-2-yl)benzamide (Compound 228)

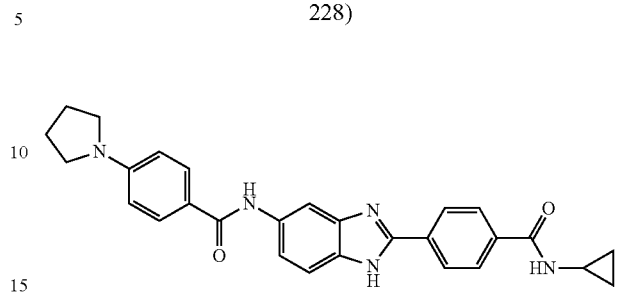

Compound 228 was prepared according to the procedure similar to that described in Scheme III from N-(3,4-dinitrophenyl)-4-pyrrolidinylbenzamide and 4-cyclopropylaminocarbonylbenzaldehyde. [M+H]$^+$ calcd for $C_{28}H_{27}N_5O_2$: 466.23. found: 466.55.

Example 129

N-(2,3-dihydroxypropyl)-4-(5-(4-(pyrrolidin-1-yl)benzamido)-1H-benzo[d]imidazol-2-yl)benzamide (Compound 229)

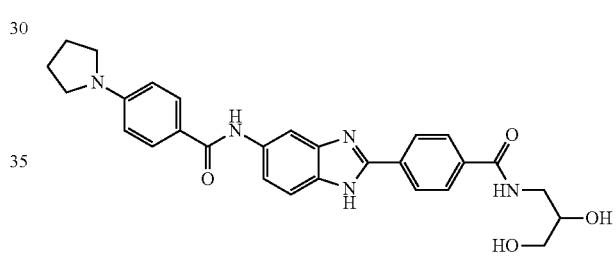

Compound 229 was prepared according to the procedure similar to that described in Scheme III from N-(3,4-dinitrophenyl)-4-pyrrolidinylbenzamide and 4-(2,3-dihydroxypropyl)aminocarbonylbenzaldehyde. [M+H]$^+$ calcd for $C_{28}H_{29}N_5O_4$: 500.23. found: 500.56.

Example 130

N-(2-(4-(hydrazinecarbonyl)phenyl)-1H-benzo[d]imidazol-5-yl)-4-(pyrrolidin-1-yl)benzamide (Compound 230)

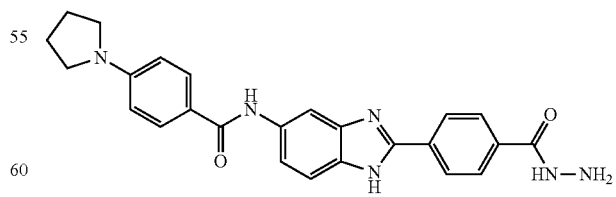

Compound 230 was prepared according to the procedure similar to that described in Scheme III from N-(3,4-dinitrophenyl)-4-pyrrolidinylbenzamide and 4-hydrazinylcarbonylbenzaldehyde. [M+H]$^+$ calcd for $C_{25}H_{24}N_6O_2$: 441.2. found: 441.51.

Example 131

N-(2-morpholinoethyl)-4-(5-(4-(pyrrolidin-1-yl)benzamido)-1H-benzo[d]imidazol-2-yl)benzamide (Compound 231)

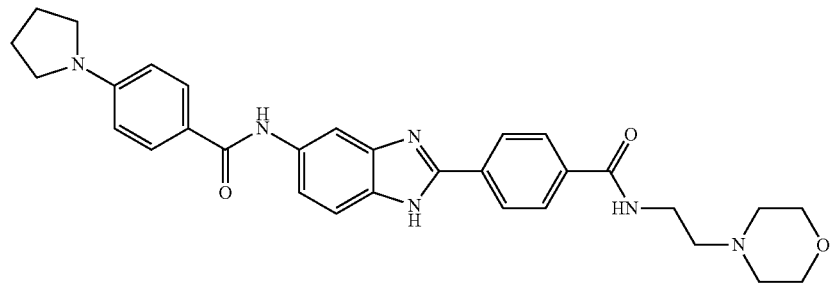 [SMILES: O=C(NCCN1CCOCC1)c1ccc(-c2nc3cc(NC(=O)c4ccc(N5CCCC5)cc4)ccc3[nH]2)cc1]

Compound 231 was prepared according to the procedure similar to that described in Scheme III from N-(3,4-dinitrophenyl)-4-pyrrolidinylbenzamide and 4-(2-morpholinylethyl)aminocarbonylbenzaldehyde. $[M+H]^+$ calcd for $C_{31}H_{34}N_6O_3$: 539.28. found: 539.63.

Example 132

N-(3-methyl-1H-pyrazol-4-yl)-4-(5-(4-(pyrrolidin-1-yl)benzamido)-1H-benzo[d]imidazol-2-yl)benzamide (Compound 232)

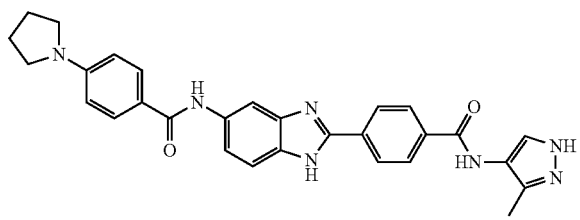 [SMILES: Cc1n[nH]cc1NC(=O)c1ccc(-c2nc3cc(NC(=O)c4ccc(N5CCCC5)cc4)ccc3[nH]2)cc1]

Compound 232 was prepared according to the procedure similar to that described in Scheme III from N-(3,4-dinitrophenyl)-4-pyrrolidinylbenzamide and 4-(3-methyl-4-pyrazolyl)aminocarbonylbenzaldehyde. $[M+H]^+$ calcd for $C_{29}H_{27}N_7O_2$: 506.23. found: 506.25.

Example 133

N-(2-(diethylamino)ethyl)-2-(4-((4-(dimethylamino)phenyl)carbamoyl)phenyl)-1H-benzo[d]imidazole-5-carboxamide (Compound 233)

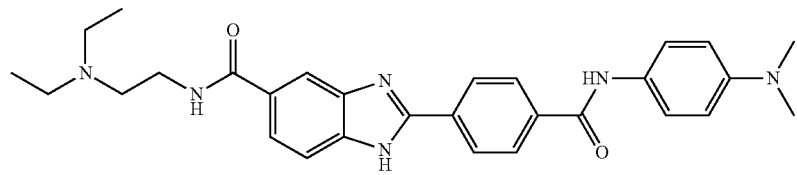 [SMILES: CCN(CC)CCNC(=O)c1ccc2[nH]c(-c3ccc(C(=O)Nc4ccc(N(C)C)cc4)cc3)nc2c1]

Compound 233 was prepared according to the procedure similar to that described in Scheme III from N-(2-N,N-diethylaminoethyl)-dinitrophenyl)-3,4-dinitrobenzamide and 4-(4-dimethylaminophenyl)aminocarbonylbenzaldehyde. $[M+H]^+$ calcd for $C_{29}H_{34}N_6O_2$: 499.2. found: 499.61.

Example 134

N-cyclopropyl-4-(5-(4-fluorobenzamido)-1H-benzo[d]imidazol-2-yl)benzamide (Compound 234)

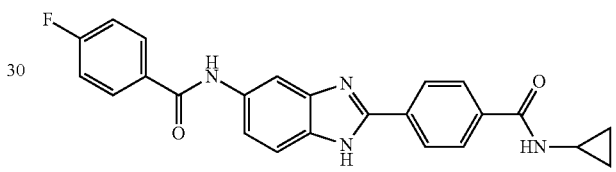

Compound 234 was prepared according to the procedure similar to that described in Scheme III from N-(3,4-dinitrophenyl)-4-fluorobenzamide and 4-cyclopropylaminocarbonylbenzaldehyde. $[M+H]^+$ calcd for $C_{24}H_{19}FN_4O_2$: 415.16. found: 415.53.

Example 135

N-cyclopropyl-4-(5-(4-((2-hydroxyethyl)(methyl)amino)benzamido)-1H-benzo[d]imidazol-2-yl)benzamide (Compound 2351

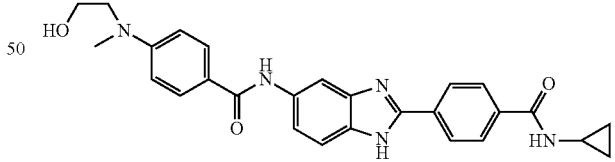

Compound 235 was prepared according to the procedure similar to that described in Scheme III from N-(3,4-dinitrophenyl)-4-(N-2-hydroxyethyl-N-methylamino)benzamide and 4-cyclopropylaminocarbonylbenzaldehyde. [M+H]$^+$ calcd for $C_{27}H_{27}N_5O_3$: 470.2. found: 470.60.

Example 136

N-cyclopropyl-4-(5-(4-((N-methylsulfamoyl)amino)benzamido)-1H-benzo[d]imidazol-2-yl)benzamide (Compound 236)

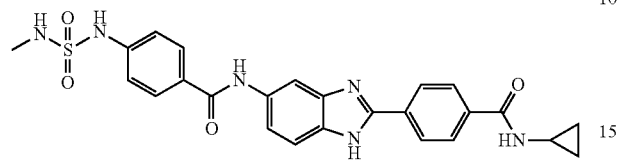

Compound 236 was prepared according to the procedure similar to that described in Scheme III from N-(3,4-dinitrophenyl)-4-methylaminosulfonamido)benzamide and 4-cyclopropylaminocarbonylbenzaldehyde. [M+H]$^+$ calcd for $C_{25}H_{24}N_6O_4S$: 505.17. found: 504.47.

Example 137

N-cyclopropyl-4-(5-(4-(2-hydroxyethoxy)benzamido)-1H-benzo[d]imidazol-2-yl)benzamide (Compound 237)

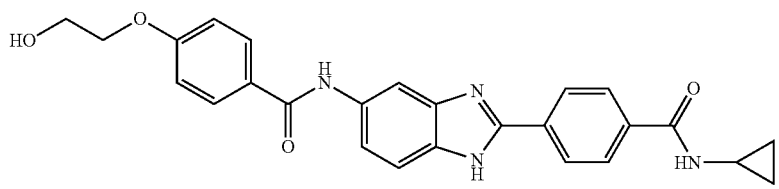 [SMILES: O=C(Nc1ccc2[nH]c(-c3ccc(C(=O)NC4CC4)cc3)nc2c1)c1ccc(OCCO)cc1]

Compound 237 was prepared according to the procedure similar to that described in Scheme III from N-(3,4-dinitrophenyl)-4-(2-hydroxyethoxy)benzamide and 4-cyclopropylaminocarbonylbenzaldehyde. [M+H]$^+$ calcd for $C_{26}H_{24}N_4O_4$: 457.19. found: 457.51.

Example 138

(E)-4-(dimethylamino)-N-(2-(3-((2-(4-(dimethylamino)benzoyl)hydrazono)methyl)phenyl)-1H-benzo[d]imidazol-5-yl)benzamide (Compound 238)

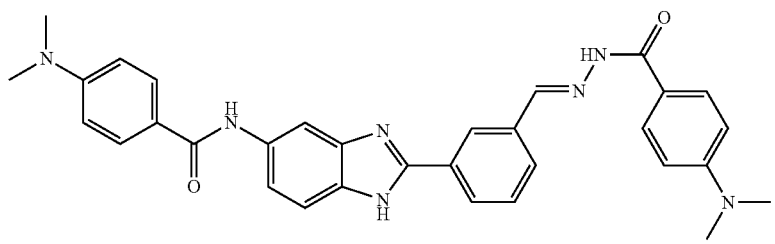

Compound 238 was prepared according to the procedure described in Scheme I from 4-dimethylaminobenzohydrazide and 3-(5-(4-dimethylaminobenzamido)benzimidazolyl-2-)benzaldehyde. [M+H]$^+$ calcd for $C_{32}H_{31}N_7O_2$: 546.2. found: 546.65.

Example 139

N-(2-(4-(morpholine-4-carbonyl)phenyl)-1H-benzo[d]imidazol-5-yl)-4-(pyrrolidin-1-yl)benzamide
(Compound 239)

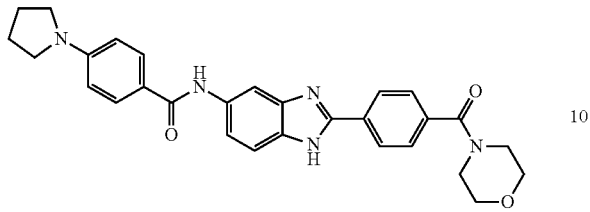

Compound 239 was prepared according to the procedure similar to that described in Scheme III from N-(3,4-dinitrophenyl)-4-pyrrolidinylbenzamide and 4-morpholinylcarbonylbenzaldehyde. [M+H]$^+$ calcd for $C_{29}H_{29}N_5O_3$: 496.2. found: 496.25.

Example 140

N-cyclopropyl-4-(5-(4-(3-hydroxypyrrolidin-1-yl)benzamido)-1H-benzo[d]imidazol-2-yl)benzamide
(Compound 240)

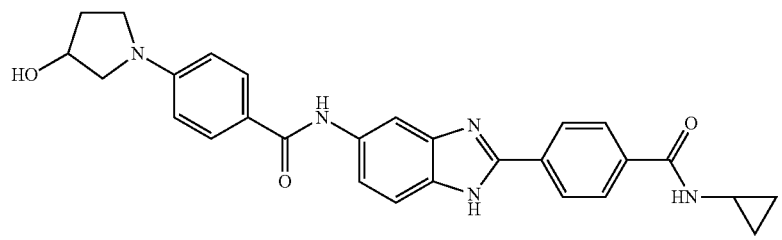 [SMILES: O=C(Nc1ccc2[nH]c(-c3ccc(C(=O)NC4CC4)cc3)nc2c1)c1ccc(N2CCC(O)C2)cc1]

Compound 240 was prepared according to the procedure similar to that described in Scheme III from N-(3,4-dinitrophenyl)-4-(3-hydroxypyrrolidinyl)benzamide and 4-cyclopropyl aminocarbonylbenzaldehyde. [M+H]$^+$ calcd for $C_{28}H_{27}N_5O_3$: 482.22. found: 481.93.

Example 141

N-(pyridin-3-yl)-4-(5-(4-(pyrrolidin-1-yl)benzamido)-1H-benzo[d]imidazol-2-yl)benzamide
(Compound 241)

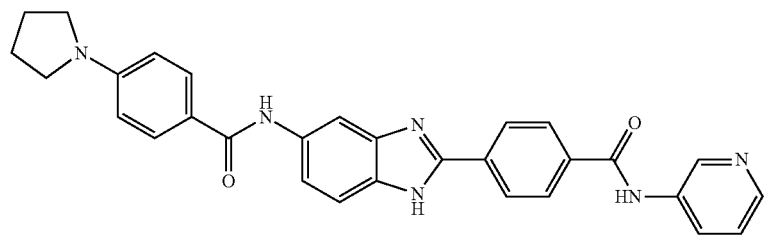 [SMILES: O=C(Nc1cccnc1)c1ccc(-c2nc3cc(NC(=O)c4ccc(N5CCCC5)cc4)ccc3[nH]2)cc1]

Compound 241 was prepared according to the procedure similar to that described in Scheme III from N-(3,4-dinitrophenyl)-4-pyrrolidinylbenzamide and 4-(3-pyridinylaminocarbonyl)benzaldehyde. [M+H]$^+$ calcd for $C_{30}H_{26}N_6O_2$: 503.22. found: 502.97.

Example 142

N-cyclopropyl-4-(5-(4-(4-hydroxypiperidin-1-yl)benzamido)-1H-benzo[d]imidazol-2-yl)benzamide (Compound 242)

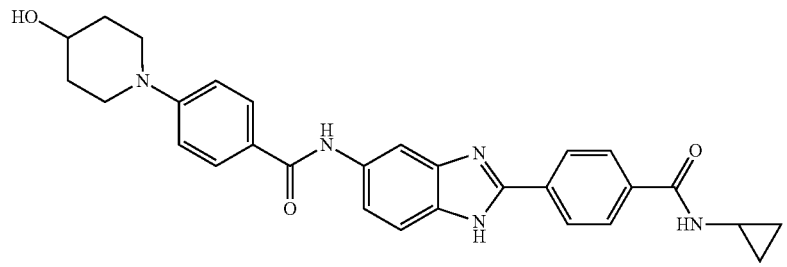 [SMILES: O=C(Nc1ccc2[nH]c(-c3ccc(C(=O)NC4CC4)cc3)nc2c1)c1ccc(N2CCC(O)CC2)cc1]

Compound 242 was prepared according to the procedure similar to that described in Scheme III from N-(3,4-dinitrophenyl)-4-(2-hydroxypiperidinyl)benzamide and 4-cyclopropyl aminocarbonylbenzaldehyde. [M+H]$^+$ calcd for $C_{29}H_{29}N_5O_3$: 496.24. found: 495.95.

Example 143

N-(2-(4-(2-hydroxyethoxy)phenyl)-1H-benzo[d]imidazol-5-yl)-2-(pyrrolidin-1-yl)pyrimidine-5-carboxamide (Compound 243)

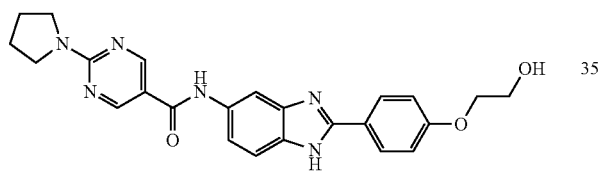

Compound 243 was prepared according to the procedure similar to that described in Scheme III from N-(3,4-dinitrophenyl)-2-(pyrrolidin-1-yl)pyrimidine-5-carboxamide and 4-(2-hydroxyethoxy)benzaldehyde. [M+H]$^+$ calcd for $C_{24}H_{24}N_6O_3$: 445.20. found: 444.87.

Example 144

4-(dimethylamino)-N-(4-(6-(4-(dimethylamino)benzamido)benzo[d]oxazol-2-yl)phenyl)benzamide (Compound 244)

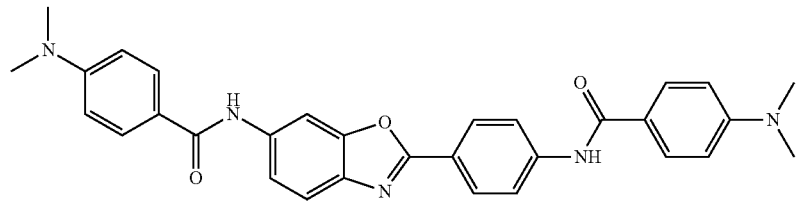

Compound 244 was prepared according to the procedure similar to that described in Scheme III from N-(3-hydoxy-4-nitro)phenyl-4-dimethylaminobenzamide and 4-(4-dimethylaminobenz)amidobenzaldehyde. [M+H]$^+$ calcd for $C_{31}H_{29}N_5O_3$: 520.23. found: 520.60.

Example 145

4-(dimethylamino)-N-(4-(5-(4-(dimethylamino)benzamido)benzo[d]oxazol-2-yl)phenyl)benzamide (Compound 245)

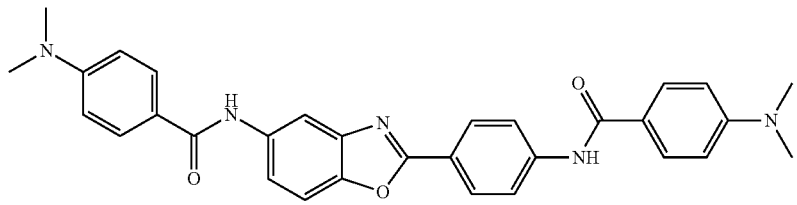

Compound 245 was prepared according to the procedure similar to that described in Scheme III from N-(4-hydoxy-3-nitro)phenyl-4-dimethylaminobenzamide and 4-(4-dimethylaminobenz)amidobenzaldehyde. [M+H]$^+$ calcd for $C_{31}H_{29}N_5O_3$: 520.23. found: 520.60.

Example 146

4-(dimethylamino)-N-(2-(4-((4-(dimethylamino)phenyl)carbamoyl)phenyl)-1H-indol-5-yl)benzamide (Compound 246)

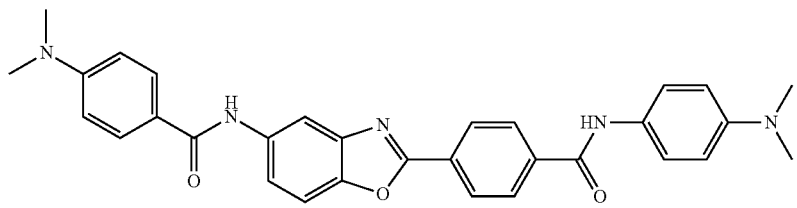

Compound 246 was prepared according to the procedure similar to that described in Scheme III from 5-nitro-2-(4-methoxycarbonylphenyl)indole, 4-dimethylaminoaniline, and 4-dimethylaminobenzoic acid. [M+H]$^+$ calcd for $C_{31}H_{30}N_6O_2$: 519.2. found: 519.59.

Example 147

Methyl 4-(6-(4-(dimethylamino)benzamido)-1H-indol-2-yl)benzoate (Compound 247)

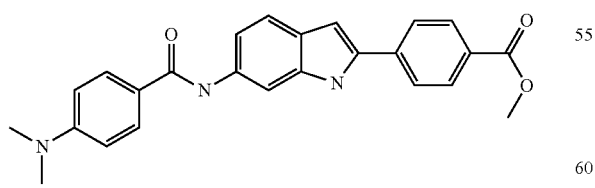

Compound 247 was prepared according to the procedure similar to that described in Scheme III from 5-nitro-2-(4-methoxycarbonylphenyl)indole and 4-dimethylaminobenzoic acid. [M+H]$^+$ calcd for $C_{24}H_{22}N_4O_3$: 415.1. found: 415.60.

Example 148

4-((E)-2-(3-methoxybenzylidene)hydrazinecarbo-
nyl)-N-(4-(6-(4-((E)-2-(3-methoxybenzylidene)
hydrazinecarbonyl)benzamido)benzo[d]oxazol-2-yl)
phenyl)benzamide (Compound 248)

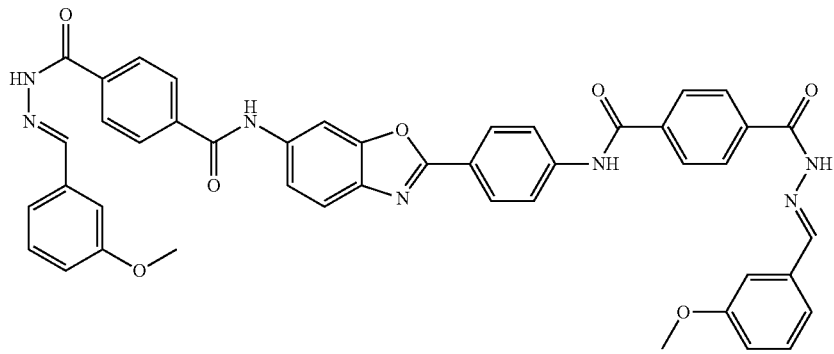 [SMILES: COc1cccc(/C=N/NC(=O)c2ccc(C(=O)Nc3ccc(-c4nc5ccc(NC(=O)c6ccc(C(=O)N/N=C/c7cccc(OC)c7)cc6)cc5o4)cc3)cc2)c1]

Compound 248 was prepared according to the procedure similar to that described in Scheme II from the 2-phenyl-benzoxazole-bis-hydrazide and 3-methoxybenzaldehyde. [M+H]$^+$ calcd for $C_{45}H_{35}N_7O_7$: 786.2. found: 786.23.

Example 149

4-(4-methylpiperazin-1-yl)-N-(2-(4-((4-morpholino-
phenyl)carbamoyl)phenyl)-1H-benzo[d]imidazol-5-
yl)benzamide (Compound 249)

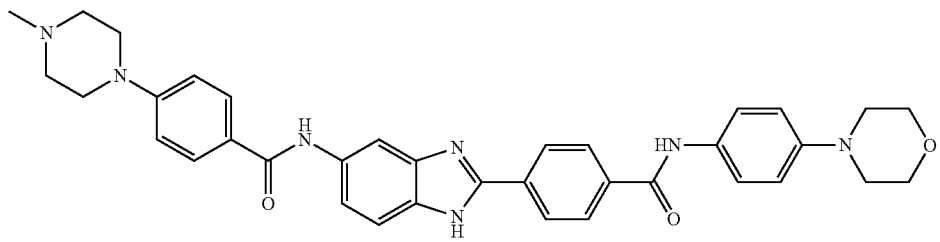 [SMILES: CN1CCN(c2ccc(C(=O)Nc3ccc4[nH]c(-c5ccc(C(=O)Nc6ccc(N7CCOCC7)cc6)cc5)nc4c3)cc2)CC1]

Compound 249 was prepared according to the procedure similar to that described in Scheme III from N-(3,4-dinitro-phenyl)-4-(4-methylpiperazinyl)benzamide and 4-(4-morpholinophenyl)aminocarbonylbenzaldehyde. [M+H]$^+$ calcd for $C_{36}H_{37}N_7O_3$: 616.30. found: 616.09.

Example 150

N-(4-(4-methylpiperazin-1-yl)phenyl)-4-(5-(4-mor-
pholinobenzamido)-1H-benzo[d]imidazol-2-yl)benz-
amide (Compound 250)

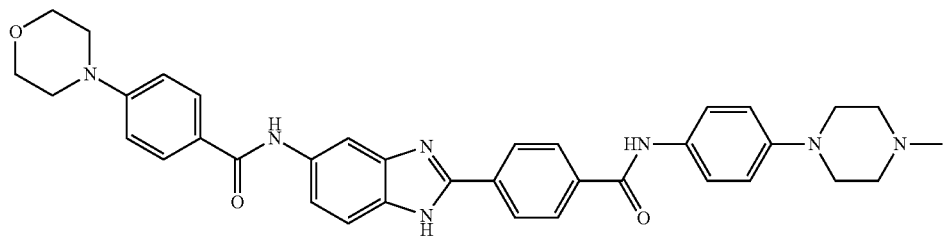 [SMILES: CN1CCN(c2ccc(NC(=O)c3ccc(-c4nc5cc(NC(=O)c6ccc(N7CCOCC7)cc6)ccc5[nH]4)cc3)cc2)CC1]

Compound 250 was prepared according to the procedure similar to that described in Scheme III from N-(3,4-dinitrophenyl)-4-morpholinobenzamide and 4-(4-(4-methylpiperazinyl)phenyl)aminocarbonylbenzaldehyde. [M+H]+ calcd for $C_{36}H_{37}N_7O_3$: 616.3. found: 616.13.

Example 151

4-(piperazin-1-yl)-N-(2-(4-((4-(piperazin-1-yl)phenyl)carbamoyl)phenyl)-1H-benzo[d]imidazol-5-yl)benzamide (Compound 251)

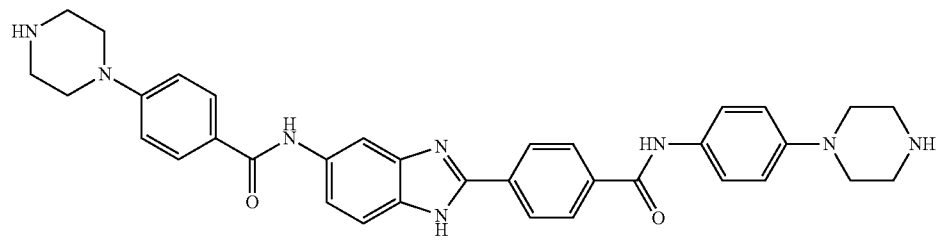 [SMILES: O=C(Nc1ccc(N2CCNCC2)cc1)c1ccc(-c2nc3cc(NC(=O)c4ccc(N5CCNCC5)cc4)ccc3[nH]2)cc1]

Compound 251 was prepared according to the procedure similar to that described in Scheme III from N-(3,4-dinitrophenyl)-4-piperazinylbenzamide and 4-(4-(4-methylpiperazinyl)phenyl)aminocarbonylbenzaldehyde. [M+H]+ calcd for $C_{35}H_{36}N_8O_2$: 601.3. found: 601.19.

Example 152

4-((2-hydroxyethyl)(methyl)amino)-N-(2-(4-((4-morpholinophenyl)carbamoyl)phenyl)-1H-benzo[d]imidazol-5-yl)benzamide (Compound 252)

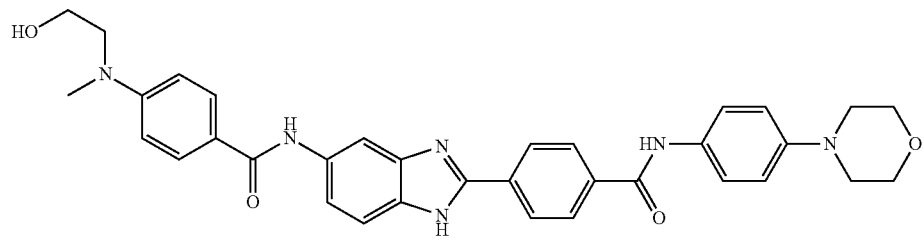 [SMILES: CN(CCO)c1ccc(C(=O)Nc2ccc3[nH]c(-c4ccc(C(=O)Nc5ccc(N6CCOCC6)cc5)cc4)nc3c2)cc1]

Compound 252 was prepared according to the procedure similar to that described in Scheme III from N-(3,4-dinitrophenyl)-4-(N-methyl-N-2-hydroxyethylamino)-benzamide and 4-(4-morpholinophenyl)aminocarbonylbenzaldehyde. [M+H]+ calcd for $C_{34}H_{34}N_6O_4$: 591.2. found: 591.06.

Example 153

6-morpholino-N-(2-(4-((4-morpholinophenyl)carbamoyl)phenyl)-1H-benzo[d]imidazol-5-yl)nicotinamide (Compound 253)

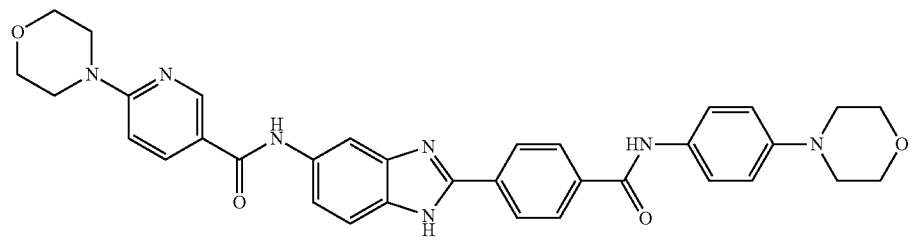 [SMILES: O=C(Nc1ccc(N2CCOCC2)cc1)c1ccc(-c2nc3cc(NC(=O)c4ccc(N5CCOCC5)nc4)ccc3[nH]2)cc1]

Compound 253 was prepared according to the procedure similar to that described in Scheme III from 3,4-dinitro-N-(2-morpholinyl-5-pyridinecarbonyl)aniline and 4-(4-morpholinylphenyl)aminocarbonylbenzaldehyde. [M+H]+ calcd for $C_{34}H_{33}N_7O_4$: 604.26. found: 604.10.

Example 154

4-morpholino-N-(2-(4-thiomorpholinophenyl)-1H-benzo[d]imidazol-5-yl)benzamide (Compound 254)

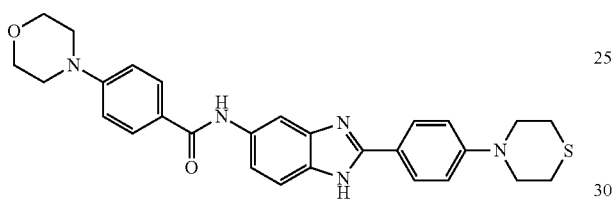

Compound 254 was prepared according to the procedure similar to that described in Scheme III from 3,4-dinitro-N-(4-thiomorpholinylbenzoyl)aniline and 4-morpholinylbenzaldehyde. [M+H]+ calcd for $C_{28}H_{29}N_5O_2S$: 500.2. found: 500.00.

Example 155

N-(2-(4-(4-hydroxypiperidin-1-yl)phenyl)-1H-benzo[d]imidazol-5-yl)-4-morpholinobenzamide (Compound 255)

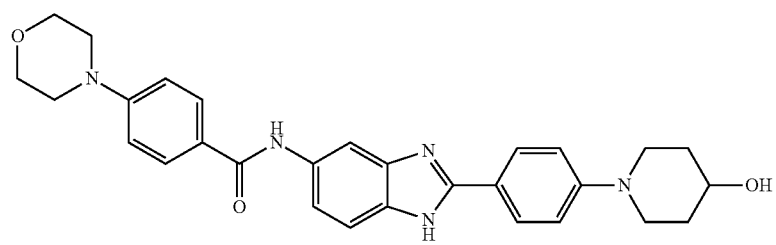 [SMILES: O=C(Nc1ccc2[nH]c(-c3ccc(N4CCC(O)CC4)cc3)nc2c1)c1ccc(N2CCOCC2)cc1]

Compound 255 was prepared according to the procedure similar to that described in Scheme III from 3,4-dinitro-N-(4-morpholinylbenz)aniline and 4-(4-hydroxypiperidinyl)benzaldehyde. [M+H]+ calcd for $C_{29}H_{31}N_5O_3$: 498.2. found: 497.98.

Example 156

4-morpholino-N-(2-(6-morpholinopyridin-3-yl)-1H-benzo[d]imidazol-5-yl)benzamide (Compound 256)

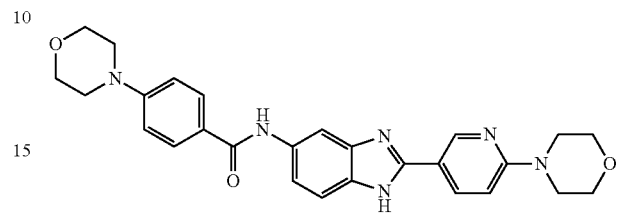

Compound 256 was prepared according to the procedure similar to that described in Scheme III from 3,4-dinitro-N-(4-morpholinylbenz)aniline and 6-morpholinylpyridine-3-carboxaldehyde. [M+H]+ calcd for $C_{27}H_{28}N_6O_3$: 485.22. found: 484.99.

Example 157

4-morpholino-N-(2-(4-(morpholinomethyl)phenyl)-1H-benzo[d]imidazol-5-yl)benzamide (Compound 257)

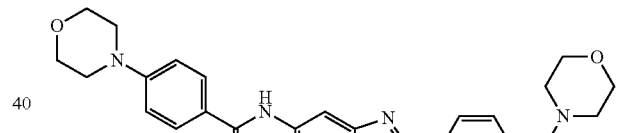

Compound 257 was prepared according to the procedure similar to that described in Scheme III from 3,4-dinitro-N-(4-morpholinylbenz)aniline and 4-morpholinomethylbenzaldehyde. [M+H]+ calcd for $C_{29}H_{31}N_5O_3$: 498.2. found: 498.02.

Example 158

N-(2-(4-(3-(dimethylamino)propoxy)phenyl)-1H-benzo[d]imidazol-5-yl)-4-morpholinobenzamide (Compound 258)

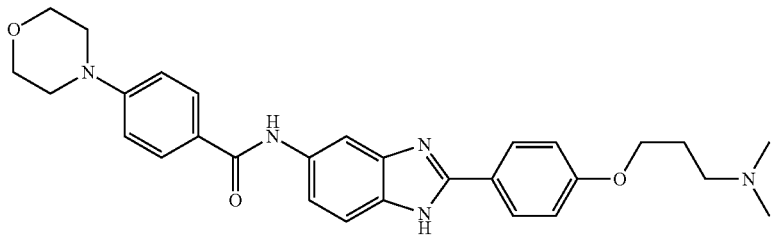 [SMILES: CN(C)CCCOc1ccc(-c2nc3cc(NC(=O)c4ccc(N5CCOCC5)cc4)ccc3[nH]2)cc1]

Compound 258 was prepared according to the procedure similar to that described in Scheme III from 3,4-dinitro-N-(4-morpholinylbenz)aniline and 4-(3-dimethylaminopropyloxy)benzaldehyde. [M+H]$^+$ calcd for $C_{29}H_{33}N_5O_3$: 500.26. found: 500.01.

Example 159

N-(2-(4-morpholinophenyl)-1H-benzo[d]imidazol-5-yl)benzamide (Compound 259)

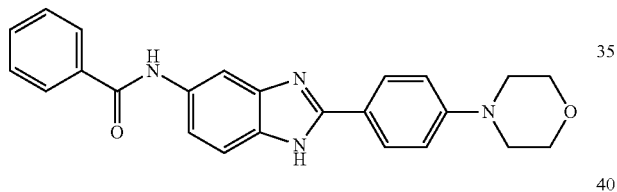

Compound 259 was prepared according to the procedure similar to that described in Scheme III from 3,4-dinitro-N-benzoylaniline and 4-morpholinylbenzaldehyde. [M+H]$^+$ calcd for $C_{24}H_{22}N_4O_2$: 399.1. found: 398.99.

Example 160

2,2'-((1H,3'H-[5,5'-bibenzo[d]imidazole]-2,2'-diylbis(4,1-phenylene))bis(oxy))diethanol (Compound 260)

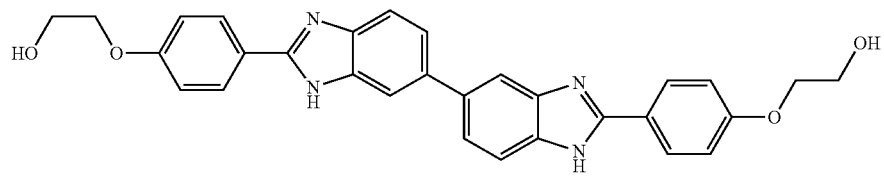 [SMILES: OCCOc1ccc(-c2nc3cc(-c4ccc5nc(-c6ccc(OCCO)cc6)[nH]c5c4)ccc3[nH]2)cc1]

Compound 260 was prepared according to the procedure similar to that described in Scheme III from 3,3'-diaminobenzidine and 4-(2-hydroxyethoxy)benzaldehyde. [M+H]$^+$ calcd for $C_{30}H_{26}N_4O_4$: 507.2. found: 507.00.

Example 161

4,4'-(1H,3'H-[5,5'-bibenzo[d]imidazole]-2,2'-diyl)bis(N-phenylbenzamide) (Compound 261)

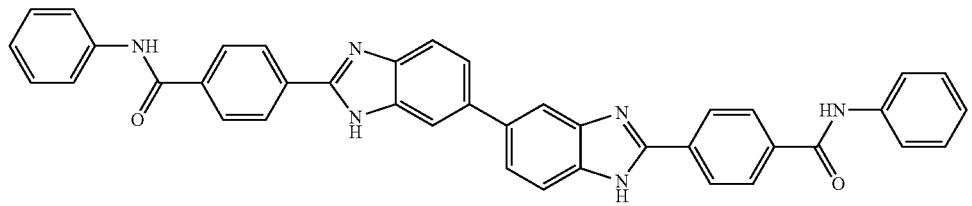 [SMILES: O=C(Nc1ccccc1)c1ccc(-c2nc3cc(-c4ccc5nc(-c6ccc(C(=O)Nc7ccccc7)cc6)[nH]c5c4)ccc3[nH]2)cc1]

Compound 261 was prepared according to the procedure similar to that described in Scheme III from 3,3'-diaminobenzidine and 4-phenylaminocarbonylbenzaldehyde. [M+H]$^+$ calcd for $C_{40}H_{28}N_6O_2$: 625.2. found: 625.53.

Example 162

2,2'-bis((E)-4-methoxystyryl)-1H,3'H-5,5'-bibenzo[d]imidazole (Compound 262)

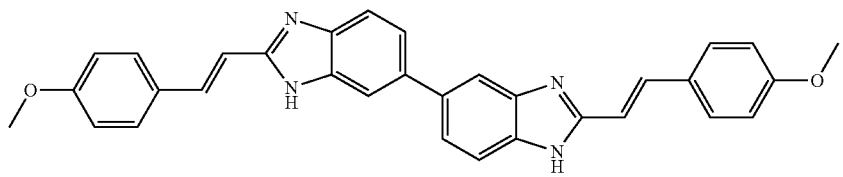

Compound 262 was prepared according to the procedure similar to that described in Scheme III from 3,3'-diaminobenzidine and 3-(4-methoxyphenyl)acrylaldehyde. [M+H]$^+$ calcd for $C_{32}H_{26}N_4O_2$: 499.2. found: 499.00.

Example 163

4,4'-(propane-1,3-diylbis(oxy))bis(N-(2-(4-methoxyphenyl)-1H-benzo[d]imidazol-5-yl)benzamide) (Compound 263)

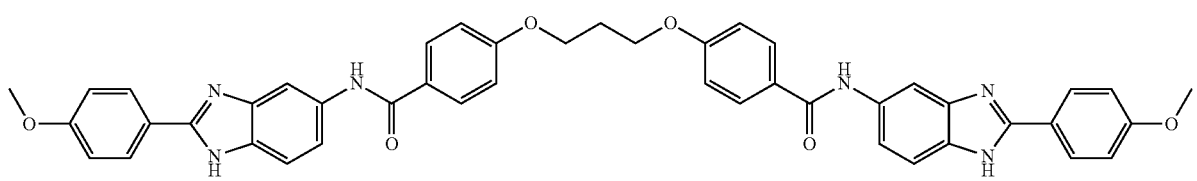

Compound 263 was prepared according to the procedure similar to that described in Scheme III from 1,3-propanedioxybis-(4-benzoic acid) and 5-amino-2-(4-methoxyphenyl)benzimidazole. [M+H]$^+$ calcd for $C_{45}H_{38}N_6O_6$: 759.2. found: 759.54.

Example 164

4,4'-((1E,1'E)-1H,3'H-[5,5'-bibenzo[d]imidazole]-2,2'-diylbis(ethene-2,1-diyl))bis(N,N-dimethylaniline) (Compound 264)

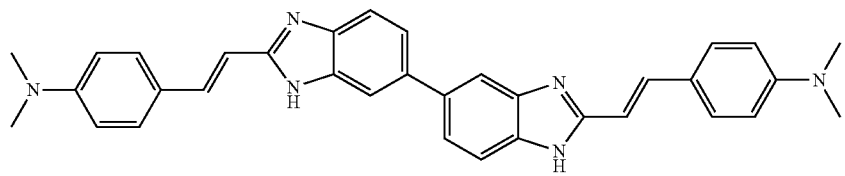

Compound 264 was prepared according to the procedure similar to that described in Scheme III from 3,3'-diaminobenzidine and 3-(4-dimethylaminophenyl)acrylaldehyde. [M+H]$^+$ calcd for $C_{34}H_{32}N_6$: 525.2. found: 525.59.

Example 165

N,N'-(1H,3'H-[5,5'-bibenzo[d]imidazole]-2,2'-diylbis(4,1-phenylene))bis(4-(dimethylamino)benzamide) (Compound 265)

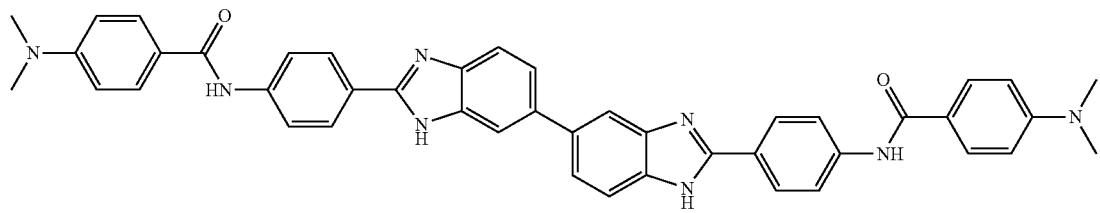

Compound 265 was prepared according to the procedure similar to that described in Scheme III from 3,3'-diaminobenzidine and 4-(4-dimethylaminobenzamido)benzaldehyde. [M+H]$^+$ calcd for $C_{44}H_{38}N_8O_2$: 711.31. found: 711.38.

Example 166

4,4'-(propane-1,3-diylbis(oxy))bis(N-(2-(trifluoromethyl)-1H-benzo[d]imidazol-5-yl)benzamide) (Compound 266)

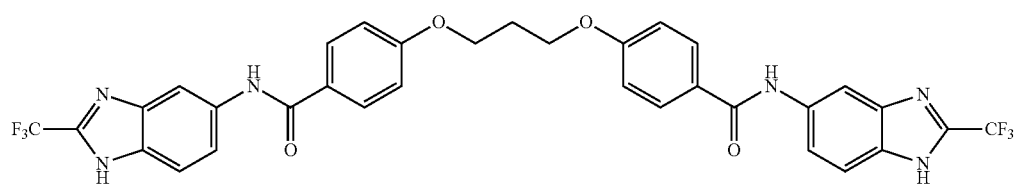 [SMILES: O=C(Nc1ccc2[nH]c(C(F)(F)F)nc2c1)c1ccc(OCCCOc2ccc(C(=O)Nc3ccc4[nH]c(C(F)(F)F)nc4c3)cc2)cc1]

Compound 266 was prepared according to the procedure similar to that described in Scheme III from 1,3-propanedioxybis-(4-benzoic acid) and 5-amino-2-trifluoromethylbenzimidazole. [M+H]$^+$ calcd for $C_{33}H_{24}F_6N_6O_4$: 683.1. found: 683.04.

Example 167

4,4'-(1H,3'H-[5,5'-bibenzo[d]imidazole]-2,2'-diyl)bis(N-(4-(dimethylamino)phenyl)benzamide) (Compound 267)

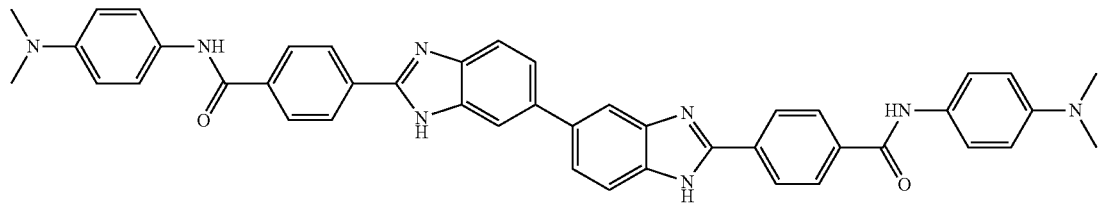

Compound 267 was prepared according to the procedure similar to that described in Scheme III from 3,3'-diaminobenzidine and 4-(4-dimethylaminophenyl)aminocarbonylbenzaldehyde. [M+H]+ calcd for $C_{44}H_{38}N_8O_2$: 711.31. found: 711.38.

Example 168

N,N'-(2,2'-(1,3-phenylene)bis(1H-benzo[d]imidazole-5,2-diyl))bis(4-(pyrrolidin-1-yl)benzamide) (Compound 268)

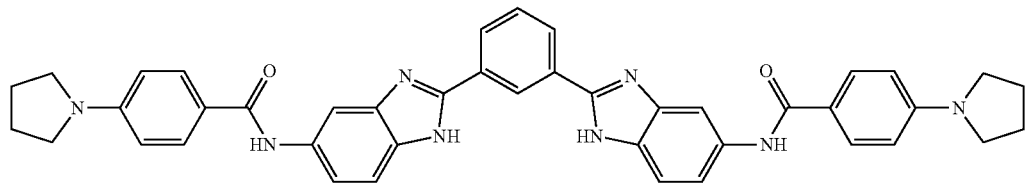 [SMILES: O=C(Nc1ccc2[nH]c(-c3cccc(-c4nc5cc(NC(=O)c6ccc(N7CCCC7)cc6)ccc5[nH]4)c3)nc2c1)c1ccc(N2CCCC2)cc1]

Compound 268 was prepared according to the procedure similar to that described in Scheme III from N-(3,4-dinitrophenyl)-4-pyrrolidinylbenzamide and 1,3-benzbisaldehyde. [M+H]+ calcd for $C_{42}H_{48}N_8O_2$: 687.3. found: 687.19.

Example 169

(E)-4-(2-(3-Methoxybenzylidene)hydrazinecarbonyl)-N-(2-(4-methoxyphenyl)-1H-benzo[d]imidazol-6-yl)benzamide (Compound 269)

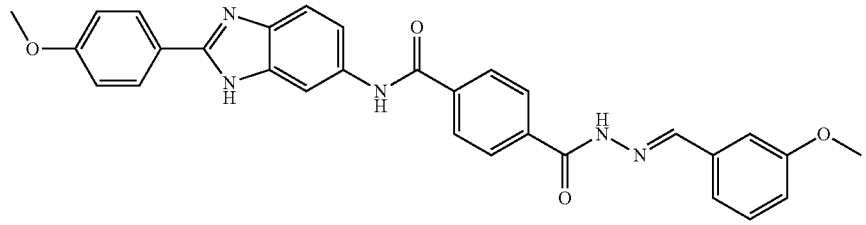

Compound 269 was prepared according to the general procedure described in Scheme V. Preparation of methyl 4-((2-(4-methoxyphenyl)-1H-benzo[d]imidazol-6-yl)carbamoyl)benzoate: 2-(4-Methoxyphenyl)-1H-benzo[d]imidazol-6-amine (120 mg, 0.5 mmol) and methyl 4-(chlorocarbonyl)benzoate (80 mg, 0.4 mmole) were place in a 20 mL vial and pyridine (2.0 mL) added and capped tightly. The reaction mixture was stirred at room temperature for 2 h till a solid precipitated out. To this mixture, 10 mL EtOAC was added and stirred for further 15 minutes then filtered. The filter cake was washed with plenty of water and then with some EtOAc (10 mL) and dried to provide pure title compound (70 mg, 44% yield).

Preparation of 4-(hydrazinecarbonyl)-N-(2-(4-methoxyphenyl)-1H-benzo[d]imidazol-6-yl)benzamide: In a 15-mL sealed tube, methyl 4-((2-(4-methoxyphenyl)-1H-benzo[d]imidazol-6-yl)carbamoyl)benzoate (28 mg, 0.07 mmole) was dissolved in 2 mL absolute ethanol and hydrazine (1 mL) was added. The reaction mixture was heated in an oil bath at 70° C. for overnight. In the morning the reaction mixture was evaporated to dryness to provide the title compound (28 mg, 99%, >95% pure by $^1$H-NMR). This compound was used for next step without any further purification.

Preparation of Compound 269: In a 20-mL sealed tube, 4-(hydrazinecarbonyl)-N-(2-(4-methoxyphenyl)-1H-benzo[d]imidazol-6-yl)benzamide (28 mg, 0.07 mmole) was dissolved in 2 mL absolute ethanol then glacial acetic acid (1.0 mL) and sodium acetate (20 mg) was added. The reaction mixture was heated in an oil bath at 72° C. for overnight. In the morning, water (5.0 mL) added and stirred for 15 min then it was filtered. The filter cake was washed with water, hexanes, ethyl acetate and dried to provide pure compound 269 (10 mg, 27% yield). [M+H]+ calcd for $C_{30}H_{25}N_5O_4$: 520.19. found: 519.98.

Example 170

2,2'-(1,4-phenylenebis(oxy))bis(N-(2-(trifluoromethyl)-1H-benzo[d]imidazol-5-yl)acetamide) (Compound 270)

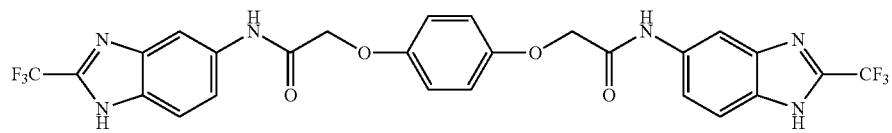 [SMILES: O=C(COc1ccc(OCC(=O)Nc2ccc3[nH]c(C(F)(F)F)nc3c2)cc1)Nc1ccc2[nH]c(C(F)(F)F)nc2c1]

Compound 270 was prepared according to the procedure similar to that described in Scheme V from 1,4-phenyldioxybisacetate and 5-amino-2-trifluoromethylbenzimidazole. [M+H]$^+$ calcd for $C_{26}H_{18}F_6N_6O_4$: 593.1. found: 592.86.

Example 171 methyl 4-((2-(trifluoromethyl)-1H-benzo[d]imidazol-5-yl)carbamoyl)benzoate (Compound 271)

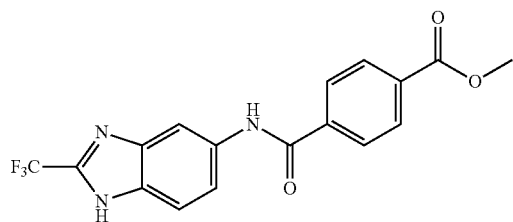 [SMILES: COC(=O)c1ccc(C(=O)Nc2ccc3[nH]c(C(F)(F)F)nc3c2)cc1]

Compound 271 was prepared according to the procedure similar to that described in Scheme V from terephthalic acid mono-ester and 5-amino-2-trifluoromethylbenzimidazole. [M+H]$^+$ calcd for $C_{17}H_{12}F_3N_3O_3$: 364.0. found: 363.86.

Example 172

2-(4-(dimethylamino)phenyl)-N-(2-(4-methoxyphenyl)-1H-benzo[d]imidazol-5-yl)-1H-benzo[d]imidazole-6-carboxamide (Compound 272)

Compound 272 was prepared according to the procedure similar to that described in Scheme V from 2-(4-dimethylaminophenyl)-5-aminobenzimidazole and 2-(4-dimethylaminophenyl)benzimidazole-5-carboxylate. [M+H]$^+$ calcd for $C_{30}H_{26}N_6O_2$: 503.21. found: 503.25.

Example 173

N-(2-(4-(dimethylamino)phenyl)-1H-benzo[d]imidazol-5-yl)-4-(hydrazinecarbonyl)benzamide (Compound 273)

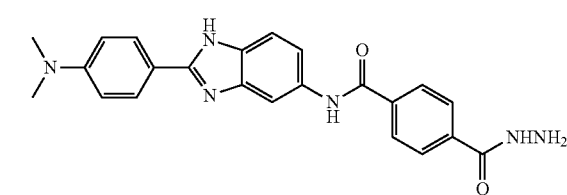

Compound 273 was prepared according to the procedure similar to that described in Scheme V from 2-(4-dimethylaminophenyl)-5-aminobenzimidazole and terephthalic acid. [M+H]$^+$ calcd for $C_{23}H_{22}N_6O_2$: 415.1. found: 414.91.

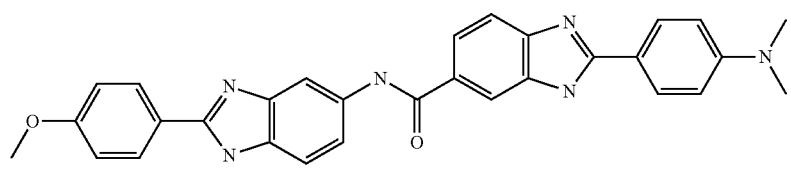

Example 174

N$^1$,N$^4$-bis(2-(4-methoxyphenyl)-1H-benzo[d]imidazol-5-yl) terephthalamide (Compound 274)

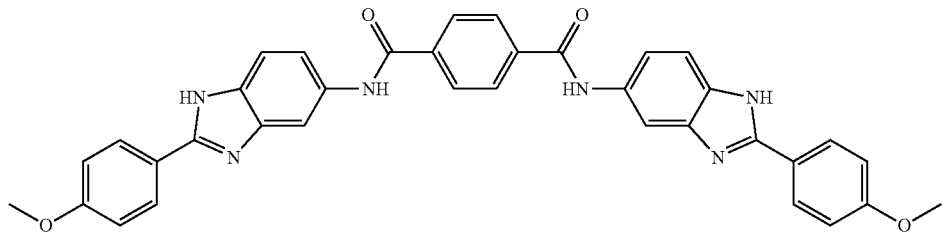

Compound 274 was prepared according to the procedure similar to that described in Scheme V from 2-(4-methoxyphenyl)-5-aminobenzimidazole and terephthalic acid. [M+H]$^+$ calcd for C$_{36}$H$_{28}$N$_6$O$_4$: 609.2. found: 608.99.

Example 175

2-(4-(dimethylamino)phenyl)-N-(4-(hydrazinecarbonyl)phenyl)-1H-benzo[d]imidazole-5-carboxamide (Compound 275)

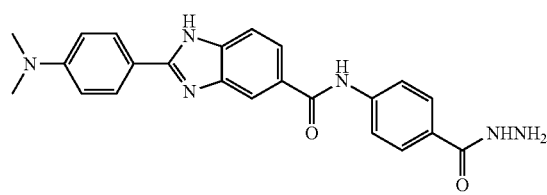 [SMILES: CN(C)c1ccc(-c2nc3cc(C(=O)Nc4ccc(C(=O)NN)cc4)ccc3[nH]2)cc1]

Compound 275 was prepared according to the procedure similar to that described in Scheme V from 2-(4-dimethylaminophenyl)benzimidazole-5-carboxylic acid and 4-aminobenzhydrazide. [M+H]$^+$ calcd for C$_{23}$H$_{22}$N$_6$O$_2$: 415.1. found: 414.91.

Example 176

(E)-4-(2-(3-methoxybenzylidene)hydrazinecarbonyl)-N-(2-(trifluoromethyl)-1H-benzo[d]imidazol-5-yl)benzamide (Compound 276)

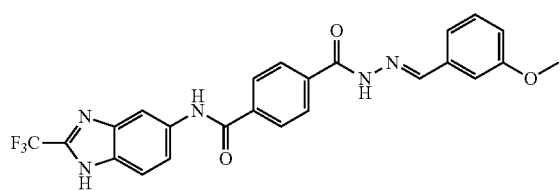 [SMILES: COc1cccc(/C=N/NC(=O)c2ccc(C(=O)Nc3ccc4[nH]c(C(F)(F)F)nc4c3)cc2)c1]

Compound 276 was prepared according to the procedure similar to that described in Scheme V from terephthalic acid mono-ester, 3-methoxybenzaldehyde and 5-amino-2-trifluoromethylbenzimidazole. [M+H]$^+$ calcd for C$_{24}$H$_{18}$F$_3$N$_5$O$_3$: 482.14. found: 481.45.

Example 177

(E)-4-(2-(4-methoxybenzylidene)hydrazinecarbonyl)-N-(2-(trifluoromethyl)-1H-benzo[d]imidazol-5-yl)benzamide (Compound 277)

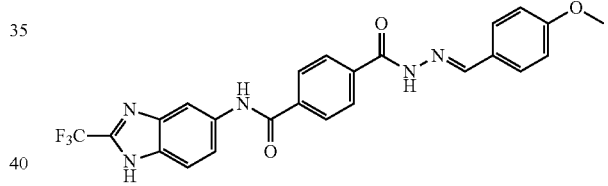

Compound 277 was prepared according to the procedure similar to that described in Scheme V from terephthalic acid mono-ester, 4-methoxybenzaldehyde and 5-amino-2-trifluoromethylbenzimidazole. [M+H]$^+$ calcd for C$_{24}$H$_{18}$F$_3$N$_5$O$_3$: 482.14. found: 481.45.

Example 178

(E)-N-(2-(4-(dimethylamino)phenyl)-1H-benzo[d]imidazol-6-yl)-4-(2-(3-methoxybenzylidene)hydrazinecarbonyl)benzamide (Compound 278)

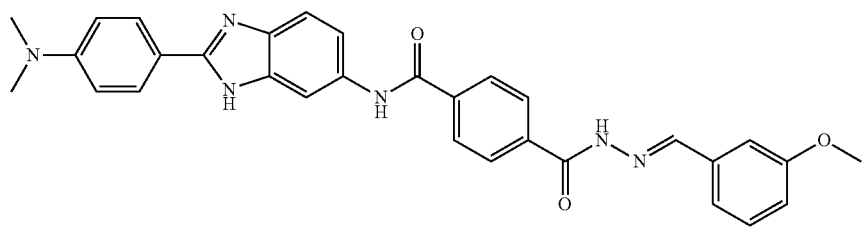

Compound 278 was prepared according to the procedure described in Scheme V from 5-amino-2-(4-dimethylaminophenyl)benzimidazole, terephthalic acid, and 3-methoxybenzaldehyde. [M+H]+ calcd for $C_{31}H_{28}N_6O_3$: 533.2. found: 532.96.

Example 179

(E)-2-(4-(dimethylamino)phenyl)-N-(4-(2-(3-methoxybenzylidene)hydrazinecarbonyl)phenyl)-1H-benzo[d]imidazole-6-carboxamide (Compound 279)

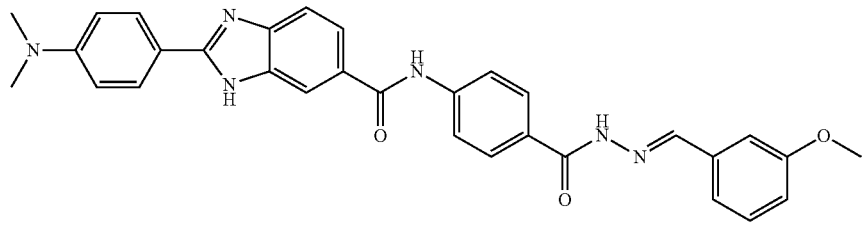

Compound 279 was prepared according to the procedure described in Scheme V from 2-(4-dimethylaminophenyl)benzimidazole-5-carboxylic acid, 4-aminobenzoic acid, and 3-methoxybenzaldehyde. [M+H]+ calcd for $C_{31}H_{28}N_6O_3$: 533.22. found: 532.95.

Example 180

N,N'-(1,4-phenylene)bis(2-(4-morpholinophenyl)-1H-benzo[d]imidazole-5-carboxamide) (Compound 280)

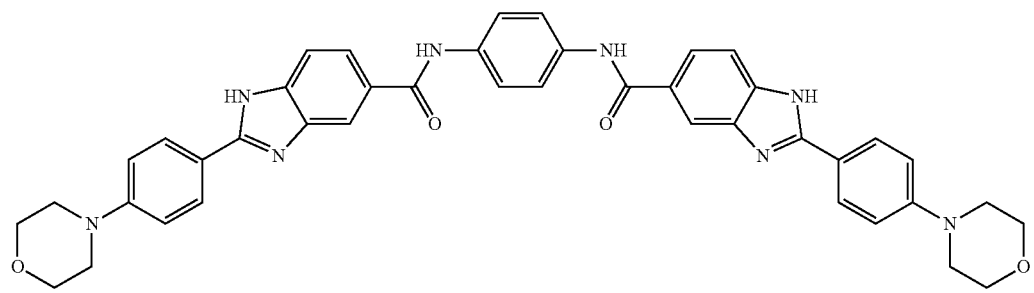 [SMILES: O=C(Nc1ccc(NC(=O)c2ccc3[nH]c(-c4ccc(N5CCOCC5)cc4)nc3c2)cc1)c1ccc2[nH]c(-c3ccc(N4CCOCC4)cc3)nc2c1]

Compound 280 was prepared according to the procedure similar to that described in Scheme V from 2-(4-morpholinylphenyl)benzimidazole-5-carboxylic acid and 1,4-phenylenediamine. [M+H]+ calcd for $C_{42}H_{38}N_8O_4$: 719.3. found: 719.12.

Example 181

N,N'-(1,4-phenylene)bis(2-(4-cyanophenyl)-1H-benzo[d]imidazole-5-carboxamide) (Compound 281)

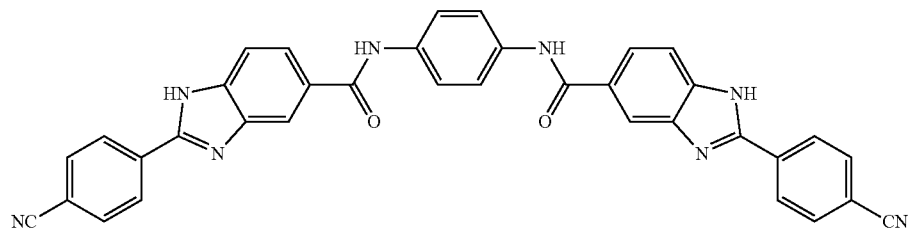 [SMILES: N#Cc1ccc(-c2nc3cc(C(=O)Nc4ccc(NC(=O)c5ccc6[nH]c(-c7ccc(C#N)cc7)nc6c5)cc4)ccc3[nH]2)cc1]

Compound 281 was prepared according to the procedure similar to that described in Scheme V from 2-(4-cyanophenyl)benzimidazole-5-carboxylic acid and 1,4-phenylenediamine. [M+H]$^+$ calcd for $C_{36}H_{22}N_8O_2$: 599.1. found: 598.97.

Example 182

N,N'-(1,4-phenylene)bis(2-(4-(bis(2-hydroxyethyl)amino)phenyl)-1H-benzo[d]imidazole-5-carboxamide) (Compound 282)

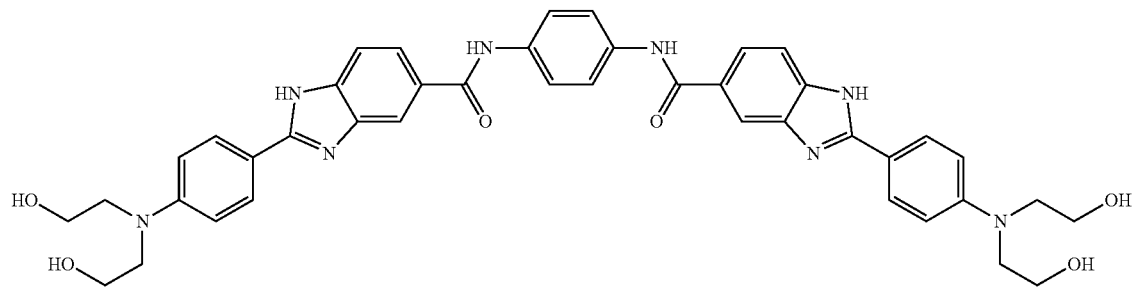 [SMILES: O=C(Nc1ccc(NC(=O)c2ccc3[nH]c(-c4ccc(N(CCO)CCO)cc4)nc3c2)cc1)c1ccc2[nH]c(-c3ccc(N(CCO)CCO)cc3)nc2c1]

Compound 282 was prepared according to the procedure similar to that described in Scheme V from 2-(4-di(2-hydroxyethyl)aminophenyl)benzimidazole-5-carboxylic acid and 1,4-phenylenediamine. [M+H]$^+$ calcd for $C_{42}H_{42}N_8O_6$: 755.32. found: 755.16.

Example 183

N,N'-(1,4-phenylene)bis(2-(4-(dimethylamino)phenyl)-1H-benzo[d]imidazole-5-carboxamide) (Compound 283)

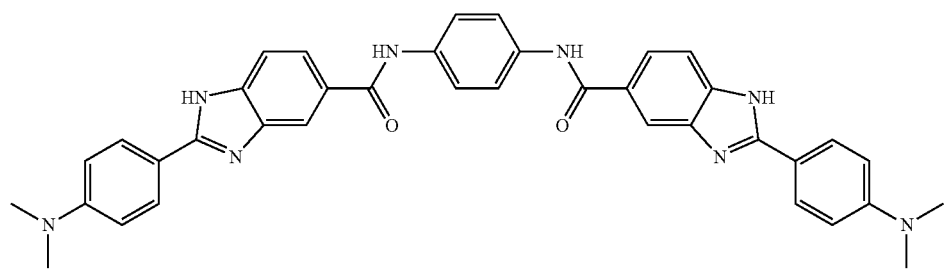

Compound 283 was prepared according to the procedure similar to that described in Scheme V from 2-(4-dimethylaminophenyl)benzimidazole-5-carboxylic acid and 1,4-phenylenediamine. [M+H]$^+$ calcd for $C_{38}H_{34}N_8O_2$: 635.2. found: 635.05.

Example 184

Methyl 4-((2-(4-(2-hydroxyethoxy)phenyl)-1H-benzo[d]imidazol-5-yl)carbamoyl)benzoate (Compound 284)

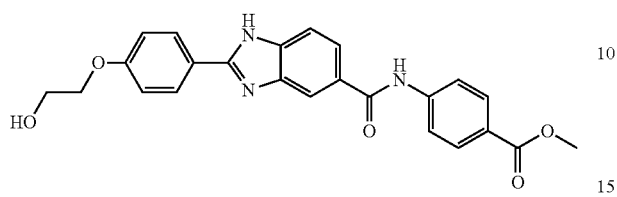

Compound 284 was prepared according to the procedure similar to that described in Scheme V from 2-(4-(2-hydroxyethoxy)phenyl)-5-aminobenzimidazole and terephthalic acid monoester. [M+H]$^+$ calcd for $C_{24}H_{21}N_3O_5$: 432.1. found: 431.86.

Example 185

N$^4$,N$^{4'}$-bis(2-chloro-1H-benzo[d]imidazol-5-yl)-[1,1'-biphenyl]-4,4'-dicarboxamide (Compound 285)

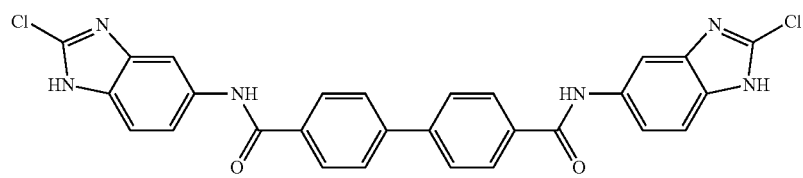 [SMILES: O=C(Nc1ccc2[nH]c(Cl)nc2c1)c1ccc(-c2ccc(C(=O)Nc3ccc4[nH]c(Cl)nc4c3)cc2)cc1]

Compound 285 was prepared according to the procedure similar to that described in Scheme V from 4,4'-bisbenzoic acid and 5-amino-2-chlorobenzimidazole. [M+H]$^+$ calcd for $C_{28}H_{18}N_6O_2$: 541.0. found: 541.91.

Example 186

4,4'-(1H,3'H-[5,5'-bibenzo[d]imidazole]-2,2'-diylbis(4,1-phenylene))dimorpholine (Compound 286)

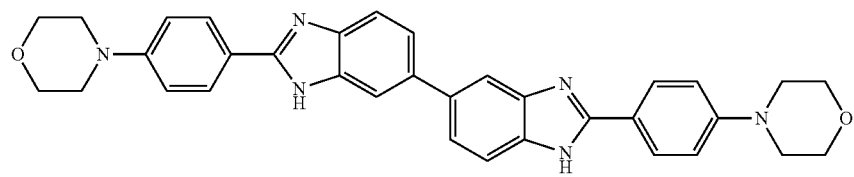 [SMILES: c1cc2[nH]c(-c3ccc(N4CCOCC4)cc3)nc2cc1-c1ccc2nc(-c3ccc(N4CCOCC4)cc3)[nH]c2c1]

Compound 286 was prepared according to the procedure similar to that described in Scheme III from 3,3'-diaminobenzidine and 4-morpholinylbenzaldehyde. [M+H]$^+$ calcd for $C_{34}H_{32}N_6O_2$: 557.2. found: 557.58.

Example 187

(E)-4-(2-(4-(dimethylamino)benzylidene)hydrazin-ecarbonyl)-N-(2-(4-methoxyphenyl)-1H-benzo[d]imidazol-6-yl)benzamide (Compound 287)

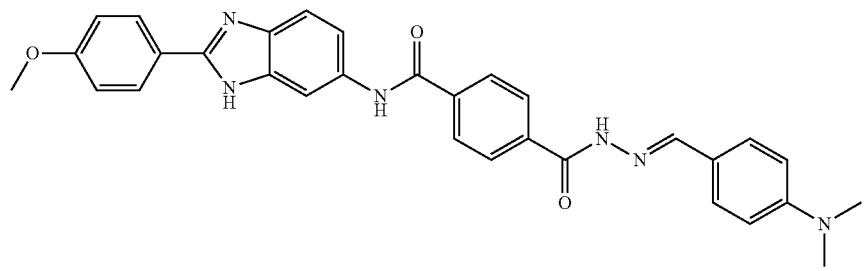

Compound 287 was prepared according to the procedure described in Scheme V from 5-amino-2-(4-methoxyphenyl)benzimidazole, terephthalic acid, and 4-dimethylaminobenzaldehyde. $[M+H]^+$ calcd for $C_{31}H_{28}N_6O_3$: 533.2. found: 532.55.

Example 188

2-(4-(bis(2-hydroxyethyl)amino)phenyl)-N-(2-(4-morpholinophenyl)-1H-benzo[d]imidazol-5-yl)-1H-benzo[d]imidazole-6-carboxamide (Compound 288)

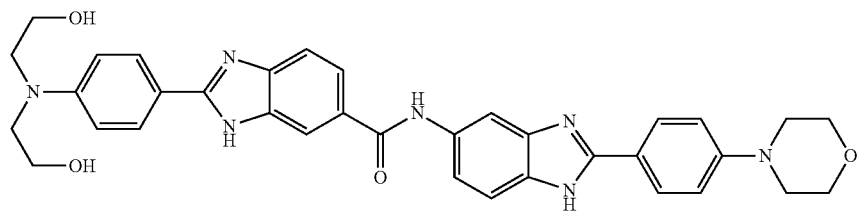 [SMILES: O=C(Nc1ccc2[nH]c(-c3ccc(N4CCOCC4)cc3)nc2c1)c1ccc2nc(-c3ccc(N(CCO)CCO)cc3)[nH]c2c1]

Compound 288 was prepared according to the procedure similar to that described in Scheme V from 2-(4-morpholinophenyl)-5-aminobenzimidazole and 2-(4-N,N-(2-hydroxyethyl)aminophenyl)benzimidazole-5-carboxylate. $[M+H]^+$ calcd for $C_{35}H_{35}N_7O_4$: 618.2. found: 618.03.

Example 189

(2-(4-(bis(2-Hydroxyethyl)amino)phenyl)-N-(2-(4-(bis(2-hydroxyethyl)amino)phenyl)-1H-benzimidazol-5-yl)-1H-benzimidazole-6-carboxamide (Compound 289)

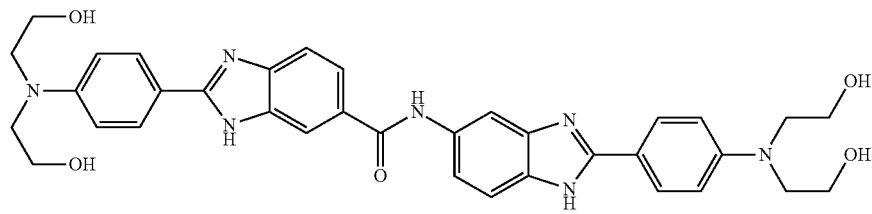 [SMILES: O=C(Nc1ccc2[nH]c(-c3ccc(N(CCO)CCO)cc3)nc2c1)c1ccc2nc(-c3ccc(N(CCO)CCO)cc3)[nH]c2c1]

Compound 289 was prepared according to the procedure similar to that described in Scheme V from 2-(4-(bis(2-hydroxyethyl)amino)phenyl)-5-aminobenzimidazole and 2-(4-(bis(2-hydroxyethyl)amino)phenyl)benzimidazole-5-carboxylate. $[M+H]^+$ calcd for $C_{35}H_{37}N_7O_5$: 636.2. found: 636.06.

Example 190

(2-(4-(bis(2-Hydroxyethyl)amino)phenyl)-N-(2-(4-cyano)phenyl)-1H-benzimidazol-5-yl)-1H-benzimidazole-6-carboxamide (Compound 290)

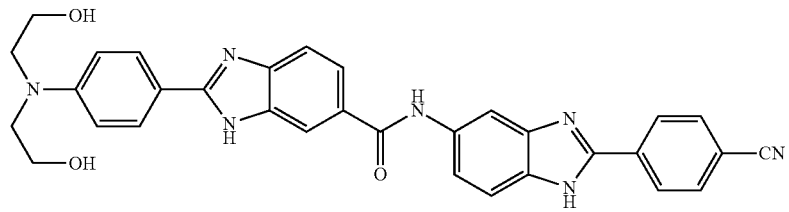 [SMILES: N#Cc1ccc(-c2nc3cc(NC(=O)c4ccc5nc(-c6ccc(N(CCO)CCO)cc6)[nH]c5c4)ccc3[nH]2)cc1]

Compound 290 was prepared according to the procedure similar to that described in Scheme V from 2-(4-cyanophenyl)-5-aminobenzimidazole and 2-(4-(bis(2-hydroxyethyl)amino)phenyl)benzimidazole-5-carboxylate. [M+H]$^+$ calcd for $C_{32}H_{27}N_7O_3$: 558.2. found: 557.95.

Example 191

(2-(4-(bis(2-Hydroxyethyl)amino)phenyl)-N-(2-(4-(2-hydroxyl)ethoxy)phenyl)-1H-benzimidazol-5-yl)-1H-benzimidazole-6-carboxamide (Compound 291)

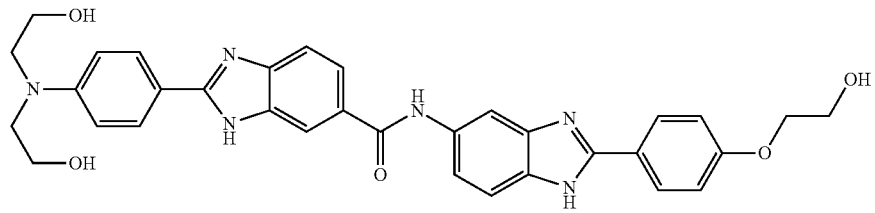 [SMILES: O=C(Nc1ccc2[nH]c(-c3ccc(OCCO)cc3)nc2c1)c1ccc2nc(-c3ccc(N(CCO)CCO)cc3)[nH]c2c1]

Compound 291 was prepared according to the procedure similar to that described in Scheme V from 2-(4-(2-hydroxyl)ethoxyphenyl)-5-aminobenzimidazole and 2-(4-(bis(2-hydroxyethyl)amino)phenyl)benzimidazole-5-carboxylate. [M+H]$^+$ calcd for $C_{33}H_{32}N_6O_5$: 593.2. found: 593.03.

Example 192

2-(4-cyanophenyl)-N-(2-(4-morpholinophenyl)-1H-benzo[d]imidazol-5-yl)-1H-benzo[d]imidazole-6-carboxamide (Compound 292)

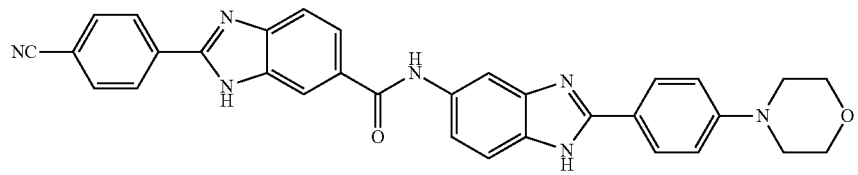 [SMILES: N#Cc1ccc(-c2nc3ccc(C(=O)Nc4ccc5[nH]c(-c6ccc(N7CCOCC7)cc6)nc5c4)cc3[nH]2)cc1]

Compound 292 was prepared according to the procedure similar to that described in Scheme V from 2-(4-morpholinophenyl)-5-aminobenzimidazole and 2-(4-cyanophenyl)benzimidazole-5-carboxylate. [M+H]$^+$ calcd for $C_{32}H_{25}N_7O_2$: 540.21. found: 539.97.

Example 193

N-(2-(4-(bis(2-hydroxyethyl)amino)phenyl)-1H-benzo[d]imidazol-5-yl)-2-(4-cyanophenyl)-1H-benzo[d]imidazole-6-carboxamide (Compound 293)

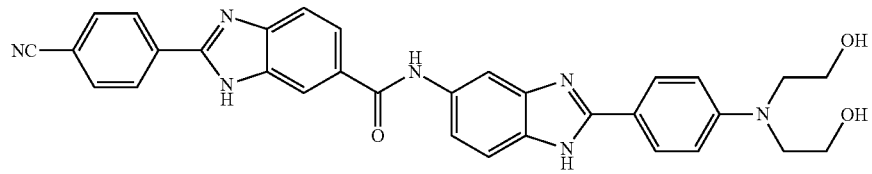 [SMILES: N#Cc1ccc(-c2nc3ccc(C(=O)Nc4ccc5[nH]c(-c6ccc(N(CCO)CCO)cc6)nc5c4)cc3[nH]2)cc1]

Compound 293 was prepared according to the procedure similar to that described in Scheme V from 2-(4-(bis(2-hydroxyethyl)amino)phenyl)-5-aminobenzimidazole and 2-(4-cyanophenyl)benzimidazole-5-carboxylate. $[M+H]^+$ calcd for $C_{32}H_{25}N_7O_3$: 558.22. found: 557.99.

Example 194

2-(4-cyanophenyl)-N-(2-(4-(2-hydroxyethoxy)phenyl)-1H-benzo[d]imidazol-5-yl)-1H-benzo[d]imidazole-6-carboxamide (Compound 294)

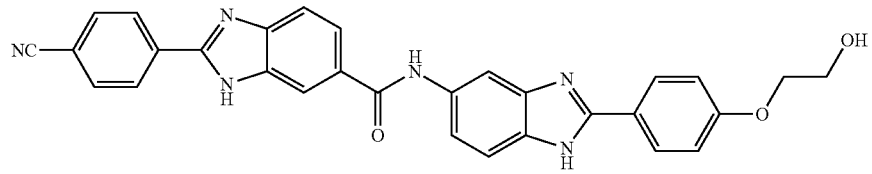 [SMILES: N#Cc1ccc(-c2nc3ccc(C(=O)Nc4ccc5[nH]c(-c6ccc(OCCO)cc6)nc5c4)cc3[nH]2)cc1]

Compound 294 was prepared according to the procedure similar to that described in Scheme V from 2-(4-(2-hydroxyethoxy)amino)phenyl)-5-aminobenzimidazole and 2-(4-cyanophenyl)benzimidazole-5-carboxylate. $[M+H]^+$ calcd for $C_{30}H_{22}N_6O_3$: 515.18. found: 514.92.

Example 195

2-(4-cyanophenyl)-N-(2-(4-cyanophenyl)-1H-benzo[d]imidazol-5-yl)-1H-benzo[d]imidazole-6-carboxamide (Compound 295)

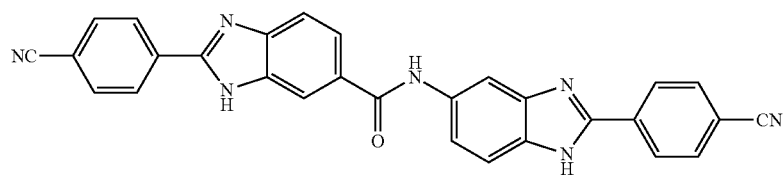 [SMILES: N#Cc1ccc(-c2nc3cc(NC(=O)c4ccc5nc(-c6ccc(C#N)cc6)[nH]c5c4)ccc3[nH]2)cc1]

Compound 295 was prepared according to the procedure similar to that described in Scheme V from 2-(4-cyano)phenyl)-5-aminobenzimidazole and 2-(4-cyanophenyl)benzimidazole-5-carboxylate. $[M+H]^+$ calcd for $C_{29}H_{17}N_7O$: 480.15. found: 479.89.

Example 196

N-(2-(4-(bis(2-hydroxyethyl)amino)phenyl)-1H-benzo[d]imidazol-5-yl)-2-(4-morpholinophenyl)-1H-benzo[d]imidazole-6-carboxamide (Compound 296)

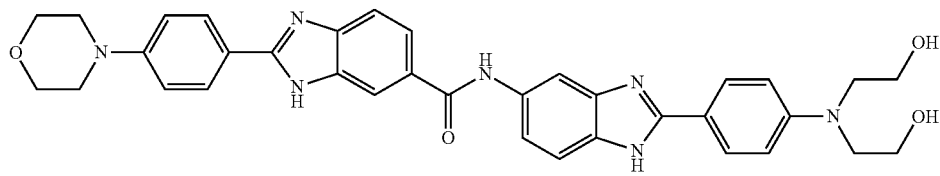

Compound 296 was prepared according to the procedure similar to that described in Scheme V from 2-(4-(bis(2-hydroxyethyl)amino)phenyl)-5-aminobenzimidazole and 2-(4-morpholinophenyl)benzimidazole-5-carboxylate. [M+H]$^+$ calcd for $C_{35}H_{35}N_7O_4$: 618.2. found: 618.03.

Example 197

N-(2-(4-(2-hydroxyethoxy)phenyl)-1H-benzo[d]imidazol-5-yl)-2-(4-morpholinophenyl)-1H-benzo[d]imidazole-6-carboxamide (Compound 297)

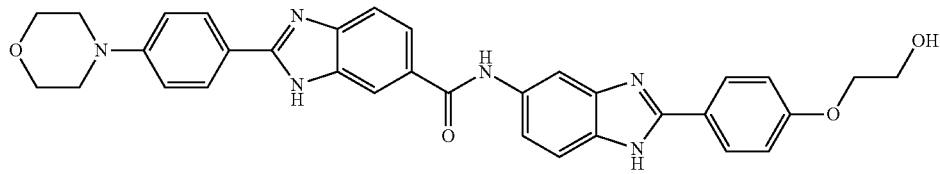 [SMILES: O=C(Nc1ccc2[nH]c(-c3ccc(OCCO)cc3)nc2c1)c1ccc2nc(-c3ccc(N4CCOCC4)cc3)[nH]c2c1]

Compound 297 was prepared according to the procedure similar to that described in Scheme V from 2-(4-(2-hydroxyethoxy)amino)phenyl)-5-aminobenzimidazole and 2-(4-morpholinophenyl)benzimidazole-5-carboxylate. [M+H]$^+$ calcd for $C_{33}H_{30}N_6O_4$: 575.2. found: 575.00.

Example 198

N-(2-(4-cyanophenyl)-1H-benzo[d]imidazol-5-yl)-2-(4-morpholinophenyl)-1H-benzo[d]imidazole-6-carboxamide (Compound 298)

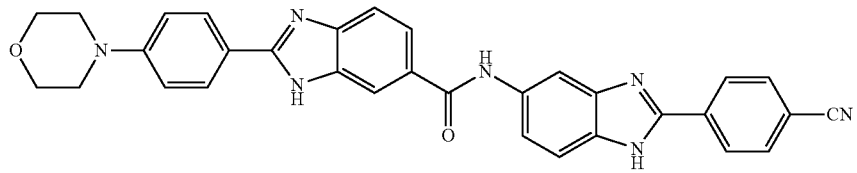 [SMILES: N#Cc1ccc(-c2nc3cc(NC(=O)c4ccc5nc(-c6ccc(N7CCOCC7)cc6)[nH]c5c4)ccc3[nH]2)cc1]

Compound 298 was prepared according to the procedure similar to that described in Scheme V from 2-(4-cyano)phenyl)-5-aminobenzimidazole and 2-(4-morpholinophenyl)benzimidazole-5-carboxylate. [M+H]$^+$ calcd for $C_{32}H_{25}N_7O_2$: 540.21. found: 539.97.

Example 199

2-(4-(2-hydroxyethoxy)phenyl)-N-(2-(4-morpholinophenyl)-1H-benzo[d]imidazol-5-yl)-1H-benzo[d]imidazole-6-carboxamide (Compound 299)

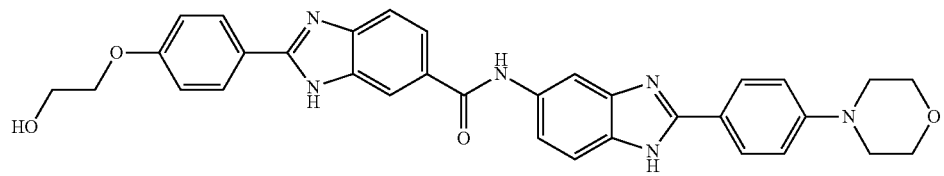 [SMILES: O=C(Nc1ccc2[nH]c(-c3ccc(N4CCOCC4)cc3)nc2c1)c1ccc2nc(-c3ccc(OCCO)cc3)[nH]c2c1]

Compound 299 was prepared according to the procedure similar to that described in Scheme V from 2-(4-morpholinophenyl)-5-aminobenzimidazole and 2-(4-(2-hydroxyethoxy)phenyl)benzimidazole-5-carboxylate. [M+H]$^+$ calcd for $C_{33}H_{30}N_6O_4$: 575.23. found: 575.07.

Example 200

N,N'-(oxybis(4,1-phenylene))bis(4-(dimethylamino)benzamide) (Compound 300)

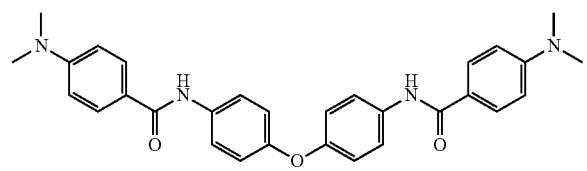

Compound 300 was prepared according to the procedure described in Scheme IV from 4,4'-oxybisphenylamine and 4-dimethylaminobenzoate. [M+H]$^+$ calcd for $C_{30}H_{31}N_4O_3$: 495.2. found: 495.01.

Example 201

N,N'-(carbonylbis(4,1-phenylene))bis(4-(dimethylamino)benzamide) (Compound 301)

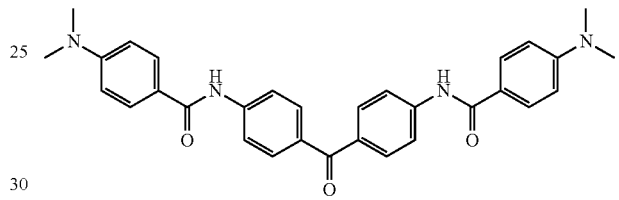

Compound 301 was prepared according to the procedure described in Scheme IV. 4-(Dimethylamino)benzoyl chloride (Aldrich, 151 mg, 0.825 mmol) in 1 mL of methylene chloride was slowly added over 5 min to 4,4'-diaminobenzophenone (Aldrich, 70 mg, 0.330 mmol) in 3 mL of methylene chloride containing 0.3 mL of pyridine. The reaction was allowed to stir at room temperature for 12 h and filtered. The white precipitate was washed with water (5 mL), ethanol (2 mL) and dried under vacuum to yield 165 mg of N,N'-(carbonylbis(4,1-phenylene))bis(4-(dimethylamino)benzamide) as a white powder. $^1$H NMR (500 MHz, DMSO-d$_6$) δ 10.19 (s, 2H), 7.97 (d, J=8.7 Hz, 4H), 7.89 (d, J=8.5 Hz, 4H), 7.77 (d, J=8.5 Hz, 4H), 6.77 (d, J=8.7 Hz, 4H), 3.00 (s, 12H).

Example 202

N,N'-(carbonylbis(4,1-phenylene))bis(4-morpholinobenzamide) (Compound 302)

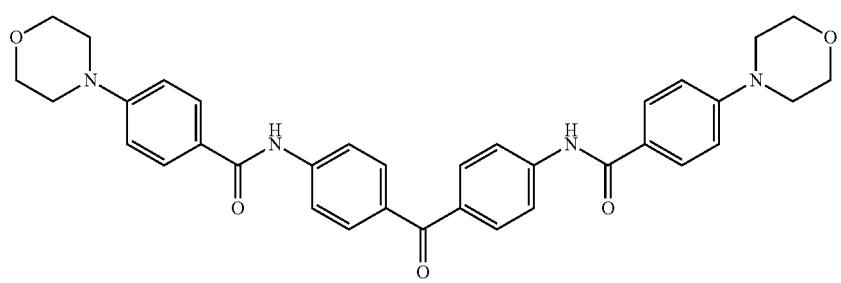 [SMILES: O=C(Nc1ccc(C(=O)c2ccc(NC(=O)c3ccc(N4CCOCC4)cc3)cc2)cc1)c1ccc(N2CCOCC2)cc1]

Compound 302 was prepared according to the procedure described in Scheme IV from 4,4'-diaminobenzophenone and 4-morpholinylbenzoate. [M+H]$^+$ calcd for $C_{35}H_{35}N_4O_5$: 591.2. found: 591.20.

Example 203

N,N'-(((methoxyimino)methylene)bis(4,1-phenylene))bis(4-morpholinobenzamide) (Compound 303)

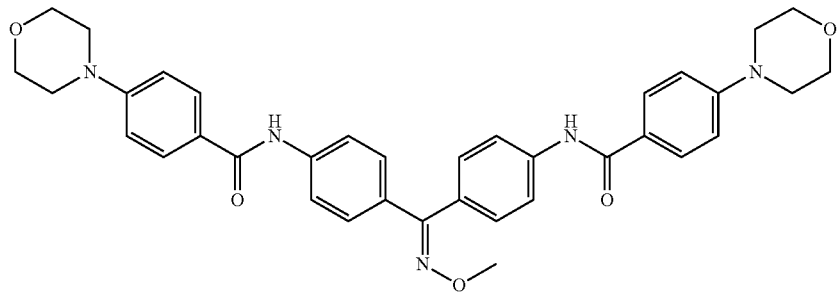 [SMILES: CON=C(c1ccc(NC(=O)c2ccc(N3CCOCC3)cc2)cc1)c1ccc(NC(=O)c2ccc(N3CCOCC3)cc2)cc1]

Compound 303 was prepared from compound 302 by a standard oxime synthesis procedure. [M+H]$^+$ calcd for $C_{36}H_{37}N_5O_5$: 620.2. found: 620.11.

Example 204

N,N'-((hydroxyimino)methylene)bis(4,1-phenylene))bis(4-morpholinobenzamide) (Compound 304)

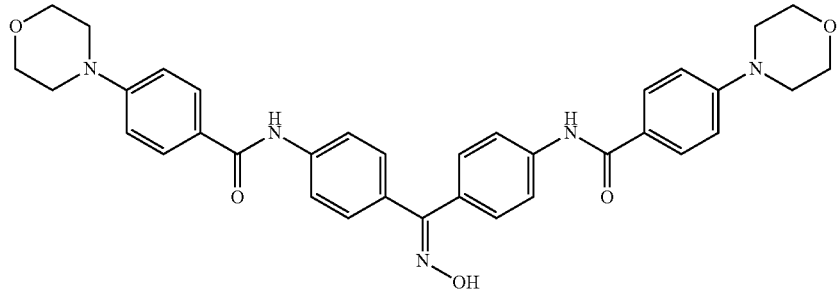 [SMILES: O=C(Nc1ccc(C(=NO)c2ccc(NC(=O)c3ccc(N4CCOCC4)cc3)cc2)cc1)c1ccc(N2CCOCC2)cc1]

Compound 304 was prepared from compound 302 by a standard oxime synthesis procedure. [M+H]$^+$ calcd for $C_{35}H_{35}N_5O_5$: 606.2. found: 606.06.

Example 205

N,N'-((hydroxymethylene)bis(4,1-phenylene))bis(4-(dimethylamino)benzamide) (Compound 305)

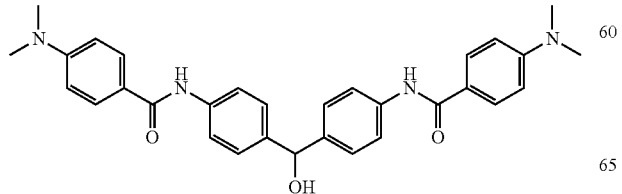

Compound 305 was prepared from compound 301 by a standard reduction condition. [M+H]+ calcd for $C_{31}H_{32}N_4O_3$: 509.1. found: 508.98.

Example 206

N,N'-(((hydroxyimino)methylene)bis(4,1-phenylene))bis(4-(dimethylamino)benzamide) (Compound 306)

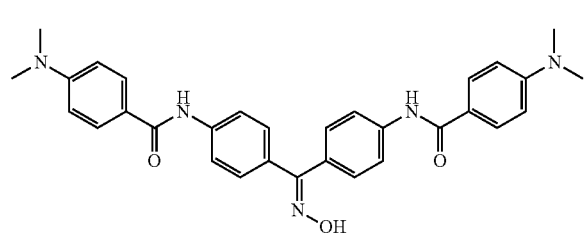

Compound 306 was prepared from compound 301 by a standard oxime synthesis procedure. [M+H]+ calcd for $C_{31}H_{31}N_5O_3$: 522.2. found: 522.01.

Example 207

N,N'-(((ethoxyimino)methylene)bis(4,1-phenylene))bis(4-(dimethylamino)benzamide) (Compound 307)

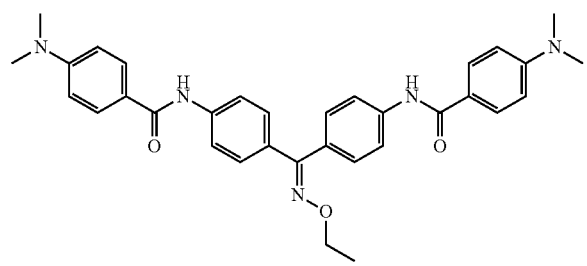

Compound 307 was prepared from compound 301 by a standard oxime synthesis procedure. [M+H]+ calcd for $C_{33}H_{35}N_5O_3$: 550.2. found: 550.02.

Example 208

N,N'-((((benzyloxy)imino)methylene)bis(4,1-phenylene))bis(4-(dimethylamino)benzamide) (Compound 308)

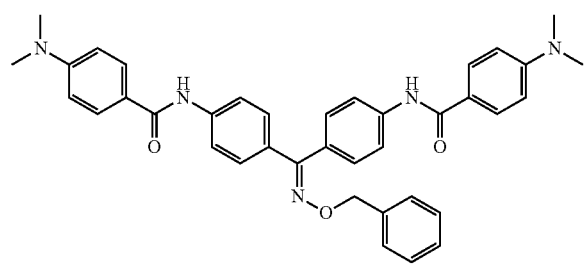

Compound 308 was prepared from compound 301 by a standard oxime synthesis procedure. [M+H]+ calcd for $C_{38}H_{37}N_5O_3$: 612.2. found: 612.07.

Example 209

N,N'-((((allyloxy)imino)methylene)bis(4,1-phenylene))bis(4-(dimethylamino)benzamide) (Compound 309)

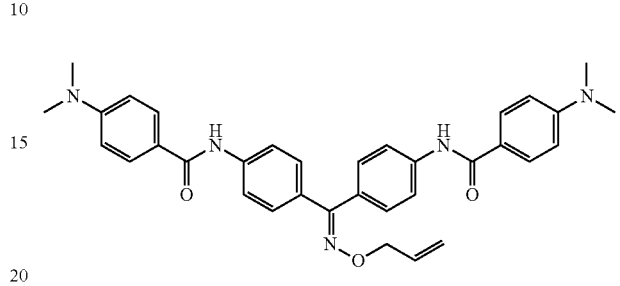

Compound 309 was prepared from compound 301 by a standard oxime synthesis procedure. [M+H]+ calcd for $C_{34}H_{35}N_5O_3$: 562.2. found: 562.04.

Example 210

N,N'-(((((2-phenylacetoxy)imino)methylene)bis(4,1-phenylene))bis(4-(dimethylamino)benzamide) (Compound 310)

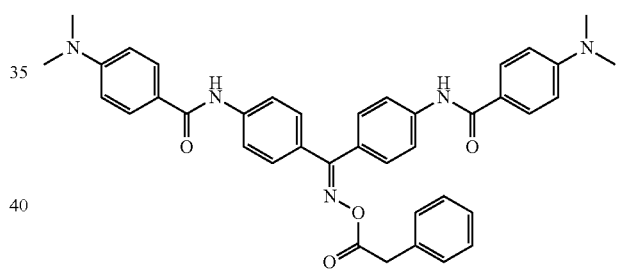

Compound 310 was prepared from compound 301 by a standard oxime synthesis procedure. [M+H]+ calcd for $C_{39}H_{37}N_5O_4$: 640.2. found: 640.23.

Example 211

N,N'-(((acetoxyimino)methylene)bis(4,1-phenylene))bis(4-(dimethylamino)benzamide) (Compound 311)

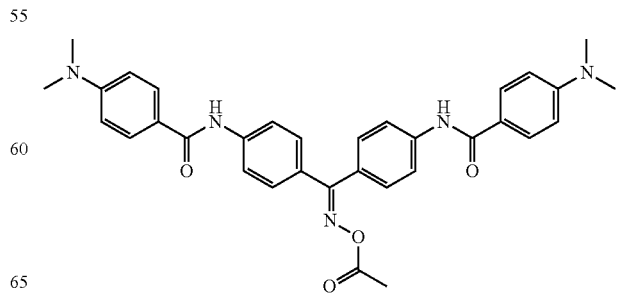

Compound 311 was prepared from compound 301 by a standard oxime synthesis procedure. [M+H]$^+$ calcd for $C_{33}H_{33}N_5O_4$: 564.2. found: 564.00.

Example 212

N,N'-(((((thiophene-2-carbonyl)oxy)imino)methylene)bis(4,1-phenylene))bis(4-(dimethylamino)benzamide) (Compound 312)

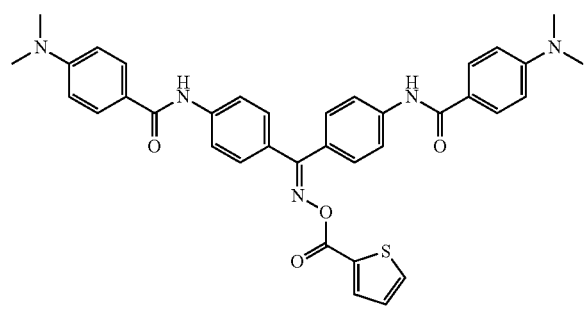

Compound 312 was prepared from compound 301 by a standard oxime synthesis procedure. [M+H]$^+$ calcd for $C_{36}H_{33}N_5O_4S$: 632.7. found: 631.99.

Example 213

N,N'-((((benzoyloxy)imino)methylene)bis(4,1-phenylene))bis(4-(dimethylamino)benzamide) (Compound 313)

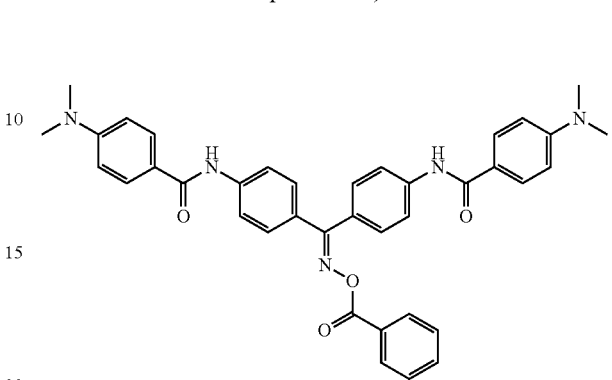

Compound 313 was prepared from compound 301 by a standard oxime synthesis procedure. [M+Na]$^+$ calcd for $C_{38}H_{35}N_5O_4$: 647.7. found: 647.86.

Example 214

N,N'-(carbonylbis(4,1-phenylene))bis(4-(3-hydroxypyrrolidin-1-yl)benzamide) (Compound 314)

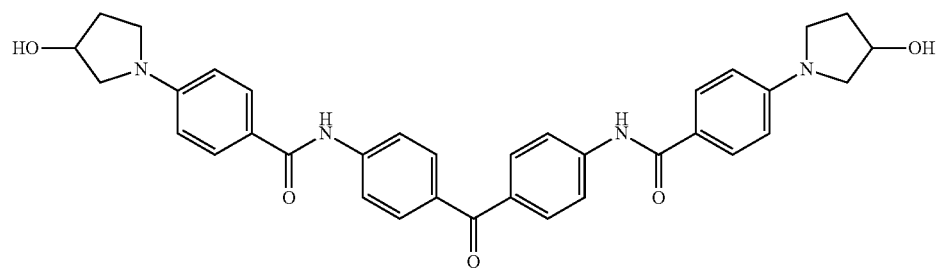 [SMILES: O=C(Nc1ccc(C(=O)c2ccc(NC(=O)c3ccc(N4CCC(O)C4)cc3)cc2)cc1)c1ccc(N2CCC(O)C2)cc1]

Compound 314 was prepared according to the procedure described in Scheme IV from 4,4'-diaminobenzophenone and 4-(2-hydroxypyrrolidino)benzoate. [M+H]$^+$ calcd for $C_{35}H_{35}N_4O_5$: 591.2. found: 591.03.

Example 215

N,N'-(((methoxyimino)methylene)bis(4,1-phenylene))bis(4-(3-hydroxypyrrolidin-1-yl)benzamide) (Compound 315)

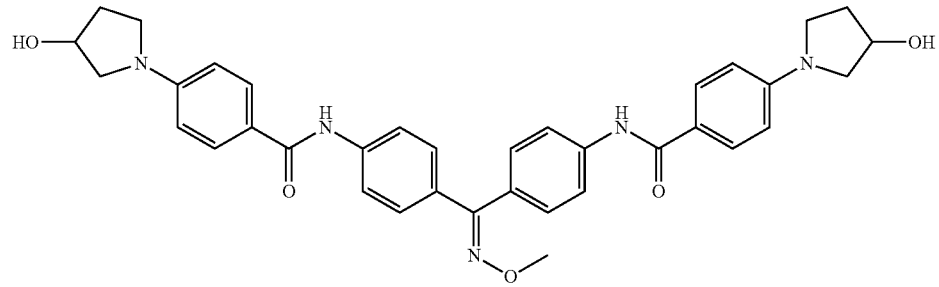 [SMILES: CON=C(c1ccc(NC(=O)c2ccc(N3CCC(O)C3)cc2)cc1)c1ccc(NC(=O)c2ccc(N3CCC(O)C3)cc2)cc1]

Compound 315 was prepared from compound 314 by a standard oxime synthesis procedure. [M+H]$^+$ calcd for $C_{36}H_{37}N_5O_5$: 620.2. found: 620.11.

Example 216

N,N'-(carbonylbis(4,1-phenylene))bis(4-(4-methyl-piperazin-1-yl)benzamide) (Compound 316)

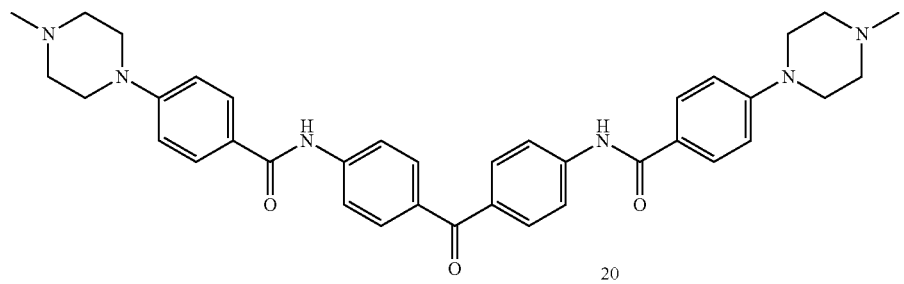

Compound 316 was prepared according to the procedure described in Scheme IV from 4,4'-diaminobenzophenone and 4-(4-methylpiperazino)benzoate. [M+H]$^+$ calcd for $C_{37}H_{41}N_6O_3$: 617.3. found: 617.12.

Example 217

N,N'-(carbonylbis(4,1-phenylene))bis(4-(piperazin-1-yl)benzamide) (Compound 317)

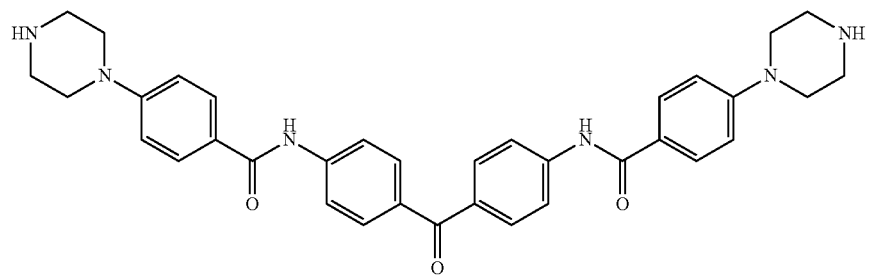 [SMILES: O=C(Nc1ccc(C(=O)c2ccc(NC(=O)c3ccc(N4CCNCC4)cc3)cc2)cc1)c1ccc(N2CCNCC2)cc1]

Compound 317 was prepared according to the procedure described in Scheme IV from 4,4'-diaminobenzophenone and 4-piperazinobenzoate. [M+H]$^+$ calcd for $C_{35}H_{37}N_6O_3$: 589.2. found: 589.07.

Example 218

N,N'-(carbonylbis(4,1-phenylene))bis(4-(4-(3-hydroxypropyl)piperazin-1-yl)benzamide) (Compound 318)

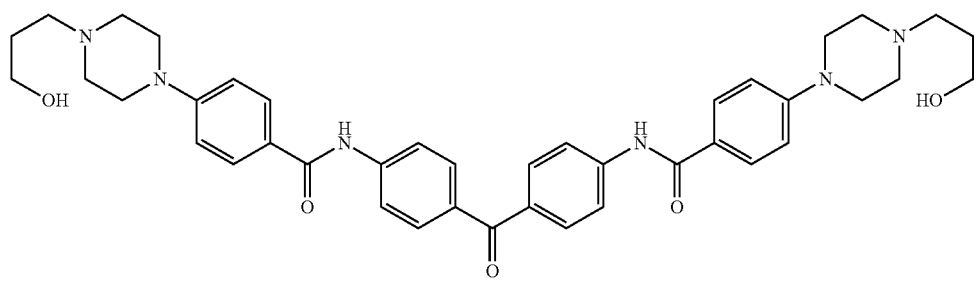 [SMILES: O=C(Nc1ccc(C(=O)c2ccc(NC(=O)c3ccc(N4CCN(CCCO)CC4)cc3)cc2)cc1)c1ccc(N2CCN(CCCO)CC2)cc1]

Compound 318 was prepared according to the procedure described in Scheme IV from 4,4'-diaminobenzophenone and 4-(4-(3-hydroxypropyl)piperazino)benzoate. [M+H]$^+$ calcd for $C_{41}H_{48}N_6O_5$: 705.3. found: 705.19.

Example 219

N,N'-(carbonylbis(4,1-phenylene))bis(4-(3,5-dimethylpiperazin-1-yl)benzamide) (Compound 319)

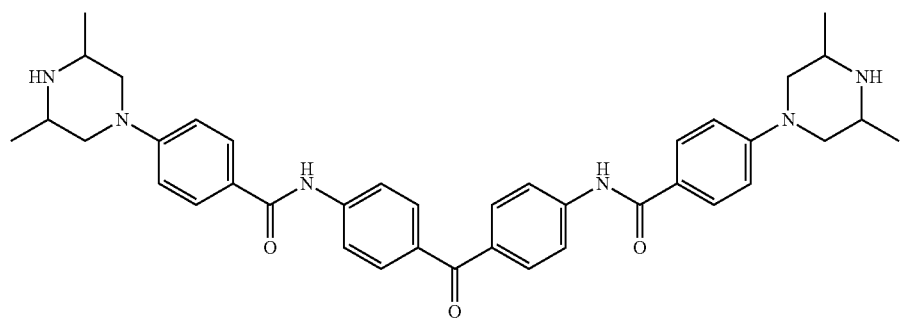

Compound 319 was prepared according to the procedure described in Scheme IV from 4,4'-diaminobenzophenone and 4-(3,5-dimethylpiperazino)benzoate. [M+H]$^+$ calcd for $C_{39}H_{44}N_6O_3$: 645.3. found: 645.16.

Example 220

N,N'-(carbonylbis(4,1-phenylene))bis(4-(4-(2-(2-hydroxyethoxy)ethyl)piperazin-1-yl)benzamide) (Compound 320)

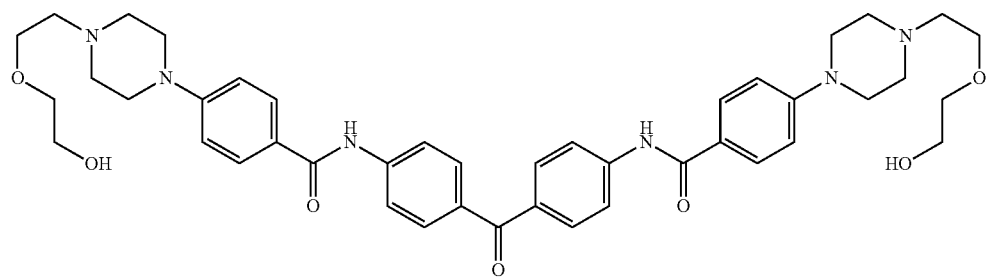 [SMILES: O=C(Nc1ccc(C(=O)c2ccc(NC(=O)c3ccc(N4CCN(CCOCCO)CC4)cc3)cc2)cc1)c1ccc(N2CCN(CCOCCO)CC2)cc1]

Compound 320 was prepared according to the procedure described in Scheme IV from 4,4'-diaminobenzophenone and 4-(4-(2-hydroxyethoxy)ethyl)piperazino)benzoate. [M+H]$^+$ calcd for $C_{43}H_{52}N_6O_7$: 765.39. found: 765.36.

Example 221

N,N'-(carbonylbis(4,1-phenylene))bis(4-(4-(cyclopropanecarbonyl)piperazin-1-yl)benzamide) (Compound 321)

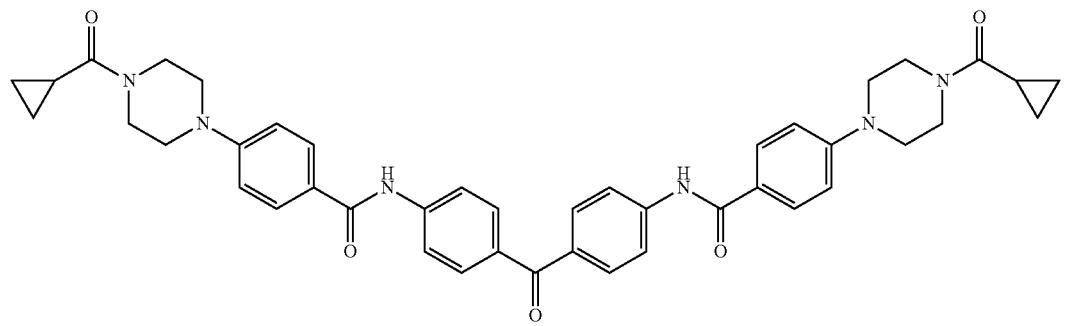 [SMILES: O=C(Nc1ccc(C(=O)c2ccc(NC(=O)c3ccc(N4CCN(C(=O)C5CC5)CC4)cc3)cc2)cc1)c1ccc(N2CCN(C(=O)C3CC3)CC2)cc1]

Compound 321 was prepared according to the procedure described in Scheme IV from 4,4'-diaminobenzophenone and 4-(4-cyclopropylcarbonyl)piperazino)benzoate. [M+H]$^+$ calcd for $C_{43}H_{44}N_6O_5$: 725.34. found: 725.11.

Example 222

N,N'-(carbonylbis(4,1-phenylene))bis(4-(piperidin-1-yl)benzamide) (Compound 322)

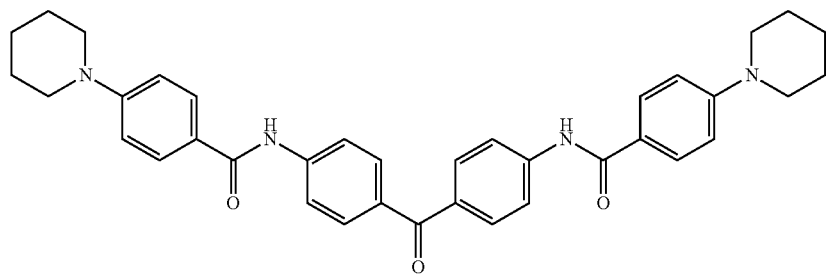 [SMILES: O=C(Nc1ccc(C(=O)c2ccc(NC(=O)c3ccc(N4CCCCC4)cc3)cc2)cc1)c1ccc(N2CCCCC2)cc1]

Compound 322 was prepared according to the procedure described in Scheme IV from 4,4'-diaminobenzophenone and 4-piperidinobenzoate. [M+H]$^+$ calcd for $C_{37}H_{38}N_4O_3$: 587.3. found: 587.02.

Example 223

N,N'-(carbonylbis(4,1-phenylene))bis(4-(4-hydroxypiperidin-1-yl)benzamide) (Compound 323)

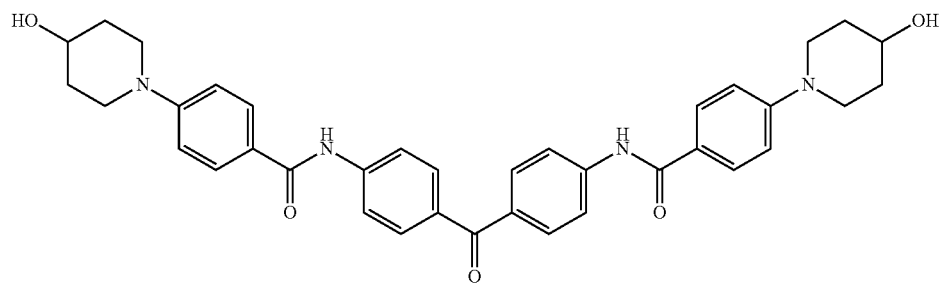 [SMILES: O=C(Nc1ccc(C(=O)c2ccc(NC(=O)c3ccc(N4CCC(O)CC4)cc3)cc2)cc1)c1ccc(N2CCC(O)CC2)cc1]

Compound 323 was prepared according to the procedure described in Scheme IV from 4,4'-diaminobenzophenone and 4-(4-hydroxypiperidino)benzoate. [M+H]$^+$ calcd for $C_{37}H_{39}N_4O_5$: 619.2. found: 619.10.

Example 224

N,N'-(carbonylbis(4,1-phenylene))bis(4-(pyrrolidin-1-yl)benzamide) (Compound 324)

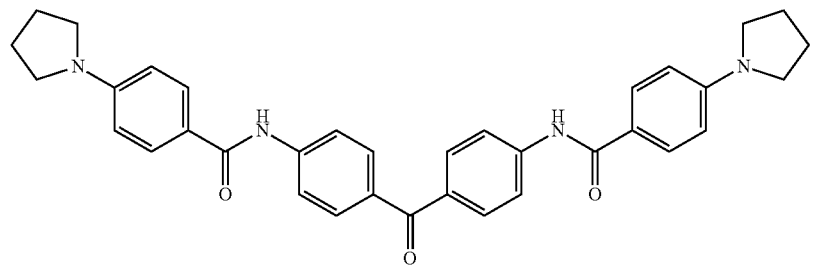 [SMILES: O=C(Nc1ccc(C(=O)c2ccc(NC(=O)c3ccc(N4CCCC4)cc3)cc2)cc1)c1ccc(N2CCCC2)cc1]

Compound 324 was prepared according to the procedure described in Scheme IV from 4,4'-diaminobenzophenone and 4-pyrrolidinobenzoate. [M+H]$^+$ calcd for $C_{35}H_{34}N_4O_3$: 559.2. found: 559.00.

Example 225

N,N'-(carbonylbis(4,1-phenylene))bis(4-(1H-pyrrol-1-yl)benzamide) (Compound 325)

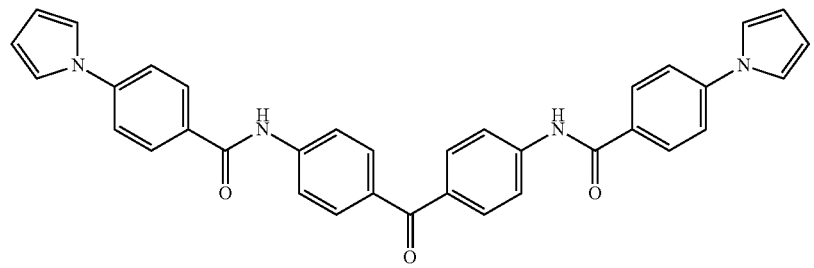 [SMILES: O=C(Nc1ccc(C(=O)c2ccc(NC(=O)c3ccc(-n4cccc4)cc3)cc2)cc1)c1ccc(-n2cccc2)cc1]

Compound 325 was prepared according to the procedure described in Scheme IV from 4,4'-diaminobenzophenone and 4-pyrrolylbenzoate. [M+H]$^+$ calcd for $C_{35}H_{26}N_4O_3$: 551.2. found: 551.04.

Example 226

N,N'-(carbonylbis(4,1-phenylene))bis(4-(1H-imidazol-1-yl)benzamide) (Compound 326)

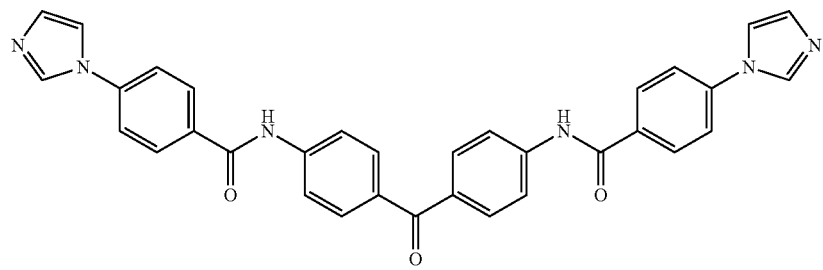 [SMILES: O=C(Nc1ccc(C(=O)c2ccc(NC(=O)c3ccc(-n4ccnc4)cc3)cc2)cc1)c1ccc(-n2ccnc2)cc1]

Compound 326 was prepared according to the procedure described in Scheme IV from 4,4'-diaminobenzophenone and 4-imidazolylbenzoate. [M+H]+ calcd for $C_{33}H_{24}N_6O_3$: 553.1. found: 552.98.

Example 227

N,N'-(carbonylbis(4,1-phenylene))bis(4-(bis(2-hydroxyethyl)amino)benzamide) (Compound 327)

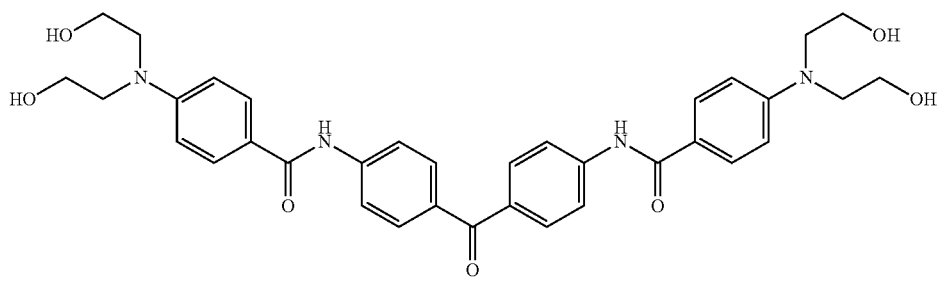 [SMILES: O=C(Nc1ccc(C(=O)c2ccc(NC(=O)c3ccc(N(CCO)CCO)cc3)cc2)cc1)c1ccc(N(CCO)CCO)cc1]

Compound 327 was prepared according to the procedure described in Scheme IV from 4,4'-diaminobenzophenone and 4-bis(2-hydroxylethyl)aminobenzoate. [M+H]+ calcd for $C_{35}H_{38}N_4O_7$: 627.2. found: 627.06.

Example 228

N,N'-(carbonylbis(4,1-phenylene))bis(1-methyl-1H-indole-5-carboxamide) (Compound 328)

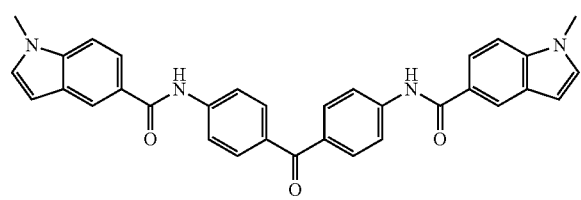 [SMILES: Cn1ccc2cc(C(=O)Nc3ccc(C(=O)c4ccc(NC(=O)c5ccc6c(ccn6C)c5)cc4)cc3)ccc21]

Compound 328 was prepared according to the procedure described in Scheme IV from 4,4'-diaminobenzophenone and 5-(1-methylindole)carboxylate. [M+H]+ calcd for $C_{33}H_{26}N_4O_3$: 527.2. found: 527.00.

Example 229

N,N'-(carbonylbis(4,1-phenylene))bis(4-methyl-3,4-dihydro-2H-benzo[b][1,4]oxazine-7-carboxamide) (Compound 329)

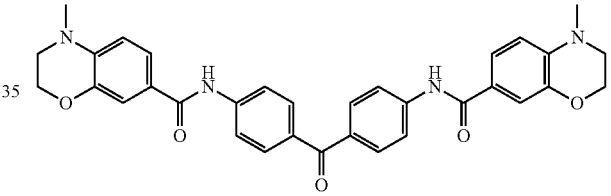

Compound 329 was prepared according to the procedure described in Scheme IV from 4,4'-diaminobenzophenone and 6-(1-methyl-1,4-benzoxazine)carboxylate. [M+H]+ calcd for $C_{33}H_{30}N_4O_5$: 563.2. found: 562.92.

Example 230

N,N'-(carbonylbis(4,1-phenylene))bis(4-((2-hydroxyethyl)(methyl)amino)benzamide) (Compound 330)

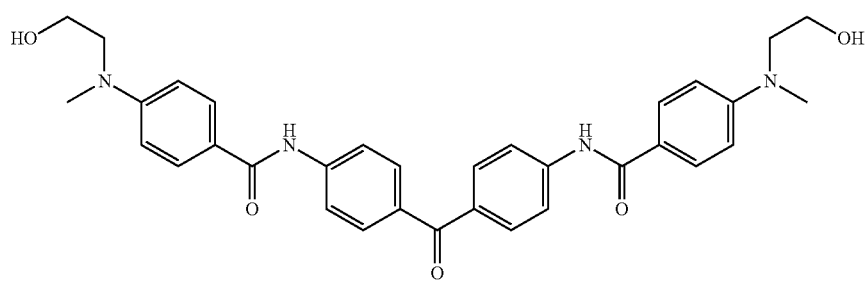 [SMILES: CN(CCO)c1ccc(C(=O)Nc2ccc(C(=O)c3ccc(NC(=O)c4ccc(N(C)CCO)cc4)cc3)cc2)cc1]

Compound 330 was prepared according to the procedure described in Scheme IV from 4,4'-diaminobenzophenone and 4-(N-2-hydroxylethyl-N-methylamino)benzoate. [M+H]⁺ calcd for $C_{33}H_{35}N_4O_5$: 567.2. found: 567.04.

Example 231

N,N'-(((2-phenylhydrazono)methylene)bis(4,1-phenylene))bis(4-(dimethylamino)benzamide) (Compound 331)

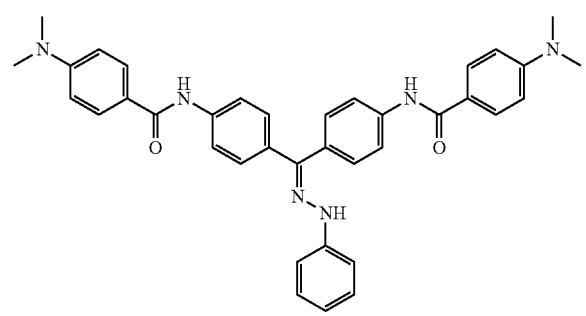

Compound 331 was prepared from compound 301 by a standard hydrazone synthesis procedure. [M+H]⁺ calcd for $C_{37}H_{36}N_6O_2$: 597.2. found: 597.08.

Example 232

N,N'-(((methoxyimino)methylene)bis(4,1-phenylene))bis(4-((2-hydroxyethyl)(methyl)amino)benzamide) (Compound 332)

Compound 332 was prepared from compound 330 by a standard oxime synthesis procedure. [M+H]⁺ calcd for $C_{34}H_{37}N_5O_5$: 596.2. found: 596.07.

Example 233

N,N'-(((methoxyimino)methylene)bis(4,1-phenylene))bis(4-fluorobenzamide) (Compound 333)

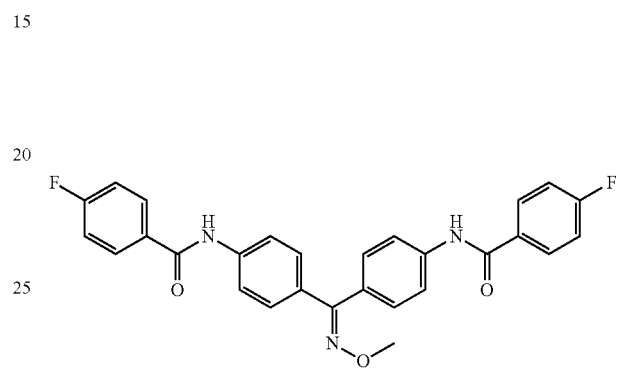

Compound 333 was prepared according to the procedure described in Scheme IV from 4,4'-diaminobenzophenone and 4-fluorobenzoate followed by a standard oxime synthesis procedure. ¹H NMR (500 MHz, DMSO-d₆) δ 11.00 (d, J=12.5 Hz, 1H), 10.41 (d, J=12.5 Hz, 1H), 8.03 (m, 4H), 7.85 (d, J=15 Hz, 2H), 7.79 (d, J=15 Hz, 2H), 7.38 (m, 6H), 7.29 (d, J=15 Hz, 2H), 3.79 (s, 3H).

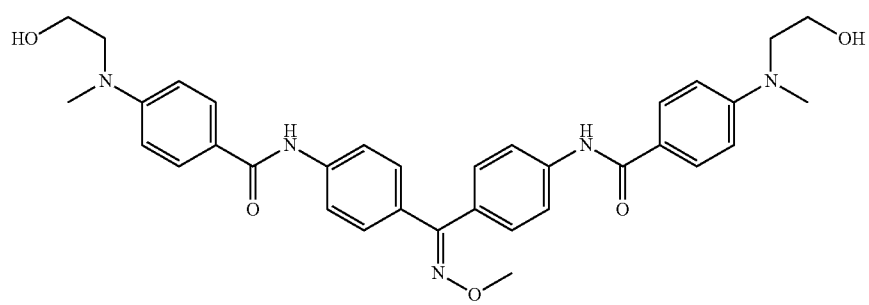 [SMILES: CON=C(c1ccc(NC(=O)c2ccc(N(C)CCO)cc2)cc1)c1ccc(NC(=O)c2ccc(N(C)CCO)cc2)cc1]

Example 234

N,N'-(((methoxyimino)methylene)bis(4,1-phenylene))bis(4-(ethyl(2-hydroxyethyl)amino)benzamide) (Compound 334)

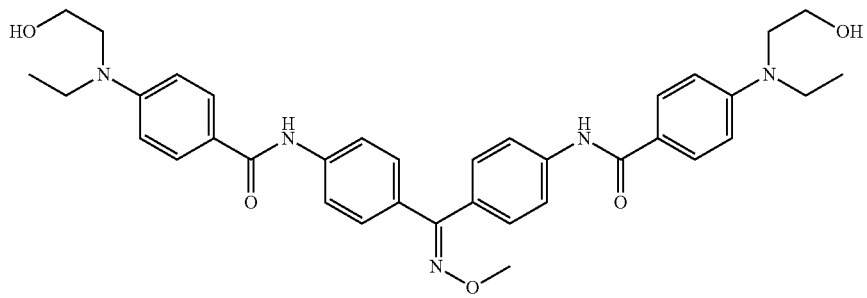 [SMILES: CCN(CCO)c1ccc(C(=O)Nc2ccc(C(=NOC)c3ccc(NC(=O)c4ccc(N(CC)CCO)cc4)cc3)cc2)cc1]

Compound 334 was prepared from compound 333 and N-2-hydroxyethyl-N-ethylamine by a standard procedure. [M+H]$^+$ calcd for $C_{36}H_{41}N_5O_5$: 624.31. found: 624.09.

Example 235

N,N'-(((methoxyimino)methylene)bis(4,1-phenylene))bis(4-((2-hydroxyethyl)amino)benzamide) (Compound 335)

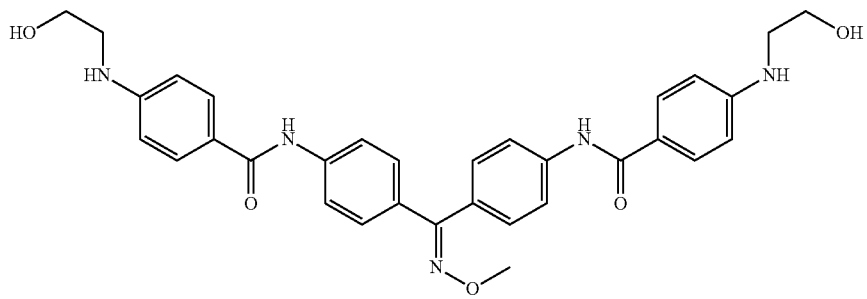 [SMILES: CON=C(c1ccc(NC(=O)c2ccc(NCCO)cc2)cc1)c1ccc(NC(=O)c2ccc(NCCO)cc2)cc1]

Compound 335 was prepared from compound 333 and 2-hydroxyethylamine by a standard procedure. [M+H]$^+$ calcd for $C_{32}H_{33}N_5O_5$: 568.25. found: 567.98.

Example 236

N,N'-(((methoxyimino)methylene)bis(4,1-phenylene))bis(4-(2-hydroxyethoxy)benzamide) (Compound 336)

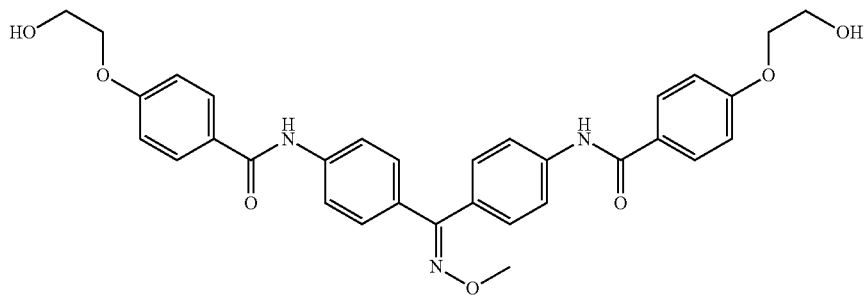 [SMILES: CON=C(c1ccc(NC(=O)c2ccc(OCCO)cc2)cc1)c1ccc(NC(=O)c2ccc(OCCO)cc2)cc1]

Compound 336 was prepared from compound 333 and ethylenediol by a standard procedure. [M+H]$^+$ calcd for $C_{32}H_{31}N_3O_7$: 570.2. found: 570.01.

Example 237

N,N'-(((methoxyimino)methylene)bis(4,1-phenylene))bis(4-(4-(3-hydroxypropyl)piperazin-1-yl)benzamide) (Compound 337)

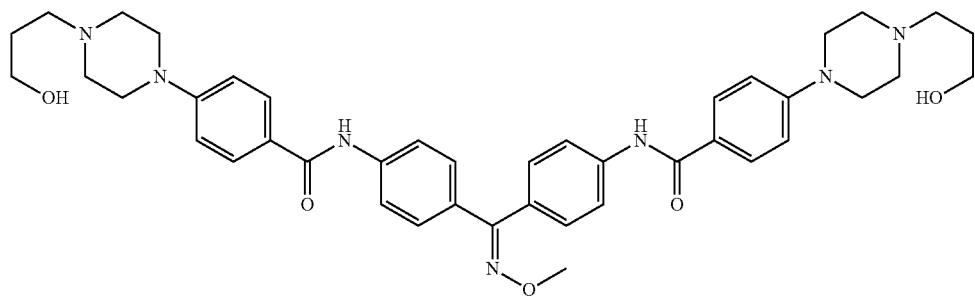 [SMILES: CON=C(c1ccc(NC(=O)c2ccc(N3CCN(CCCO)CC3)cc2)cc1)c1ccc(NC(=O)c2ccc(N3CCN(CCCO)CC3)cc2)cc1]

Compound 337 was prepared from compound 333 and 3-hydroxypropylpiperazine by a standard procedure. [M+H]$^+$ calcd for $C_{42}H_{51}N_7O_5$: 734.93. found: 734.23.

Example 238

N,N'-(((methoxyimino)methylene)bis(4,1-phenylene))bis(4-(4-(cyclopropanecarbonyl)piperazin-1-yl)benzamide) (Compound 338)

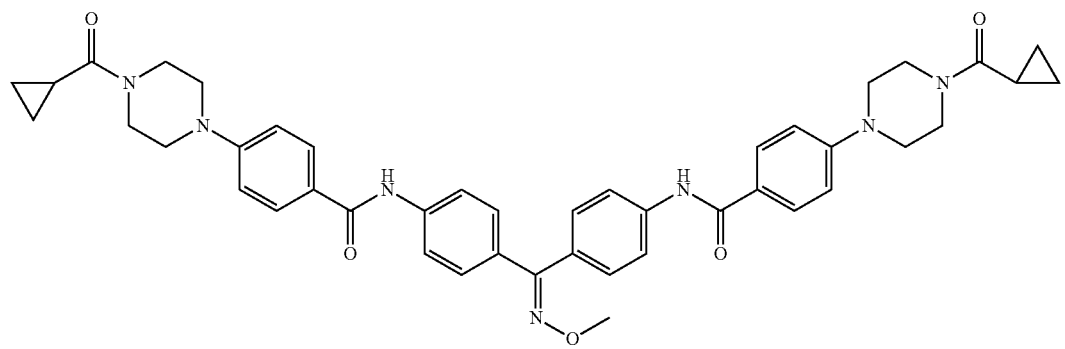 [SMILES: CON=C(c1ccc(NC(=O)c2ccc(N3CCN(C(=O)C4CC4)CC3)cc2)cc1)c1ccc(NC(=O)c2ccc(N3CCN(C(=O)C4CC4)CC3)cc2)cc1]

Compound 338 was prepared from compound 333 and 4-cyclopropylcarbonylpiperazine by a standard procedure. [M+H]$^+$ calcd for $C_{44}H_{47}N_7O_5$: 754.9. found: 754.29.

Example 239

N,N'-(((methoxyimino)methylene)bis(4,1-phenylene))bis(4-(piperidin-1-yl)benzamide) (Compound 339)

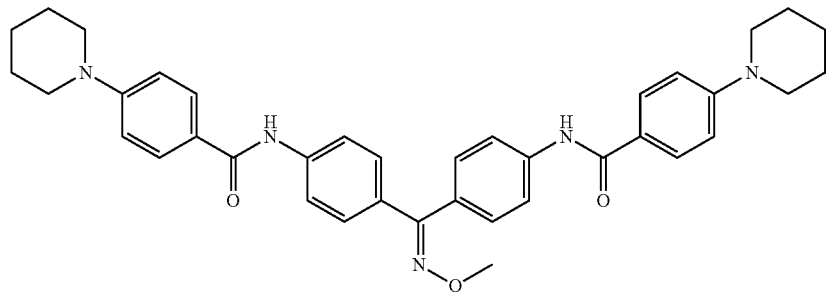 [SMILES: CON=C(c1ccc(NC(=O)c2ccc(N3CCCCC3)cc2)cc1)c1ccc(NC(=O)c2ccc(N3CCCCC3)cc2)cc1]

Compound 339 was prepared from compound 333 and piperidine by a standard procedure. [M+H]$^+$ calcd for $C_{38}H_{41}N_5O_3$: 616.7. found: 616.19.

Example 240

N,N'-(4,4'-(Oxazolidine-2,2-diyl)bis(4,1-phenylene))bis(4-(2-hydroxylethylamino)benzamide) (Compound 340)

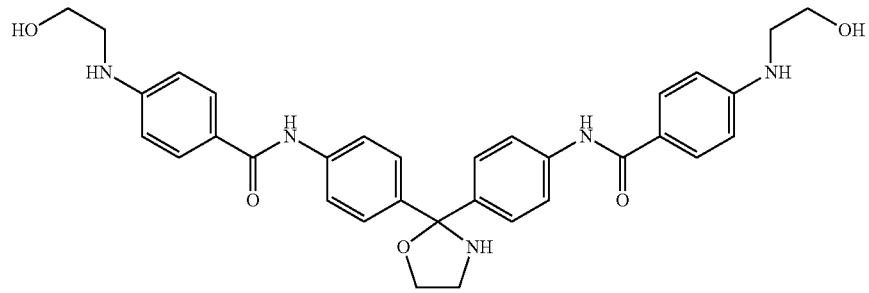 [SMILES: O=C(Nc1ccc(C2(c3ccc(NC(=O)c4ccc(NCCO)cc4)cc3)NCCO2)cc1)c1ccc(NCCO)cc1]

Compound 340 was prepared from N,N'-(4,4'-Benzophenone)bis(4-fluorobenzamide) and 2-hydroxyethylamine by a standard procedure. [M+H]$^+$ calcd for $C_{33}H_{36}N_5O_5$: 582.2. found: 582.07.

Example 241

4,4'-Carbonylbis(4,1-phenylene)bis(4-(dimethylamino)benzoate (Compound 341)

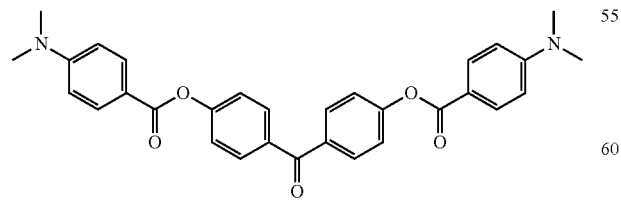

Compound 341 was prepared according to the procedure described in Scheme IV from 4,4'-dihydroxybenzophenone and 4-dimethylaminobenzoic acid. [M+H]$^+$ calcd for $C_{31}H_{28}N_2O_5$: 509.2. found: 509.05.

Example 242

N,N'-(4,4'-Carbonylbis(4,1-phenylene))bis(4-ethoxy-benzamide) (Compound 342)

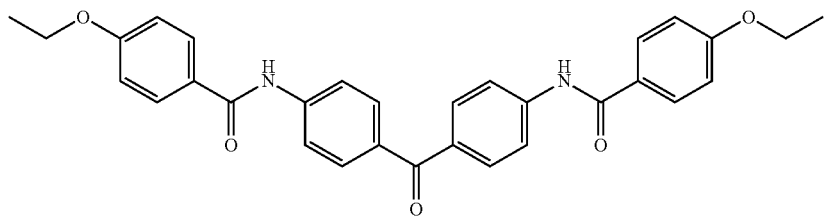 [SMILES: CCOc1ccc(C(=O)Nc2ccc(C(=O)c3ccc(NC(=O)c4ccc(OCC)cc4)cc3)cc2)cc1]

Compound 342 was prepared according to the procedure described in Scheme IV from 4,4'-diaminobenzophenone and 4-ethoxybenzoate. [M+H]$^+$ calcd for $C_{31}H_{28}N_2O_5$: 509.2. found: 508.98.

Example 243

N,N'-(4,4'-Carbonylbis(4,1-phenylene))bis(4-methoxybenzamide) (Compound 343)

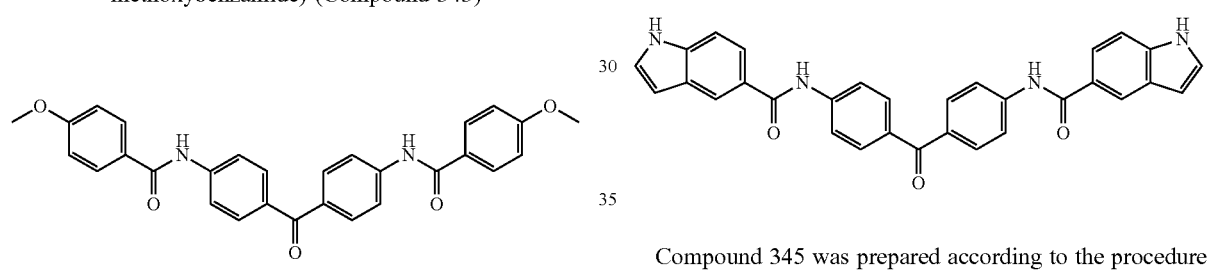

Compound 343 was prepared according to the procedure described in Scheme IV from 4,4'-diaminobenzophenone and 4-methoxybenzoate. [M+H]$^+$ calcd for $C_{29}H_{24}N_2O_5$: 481.1. found: 480.90.

Example 244

N,N'-(4,4'-Carbonylbis(4,1-phenylene))dibenzo[1,3]dioxole-5-carboxamide) (Compound 344)

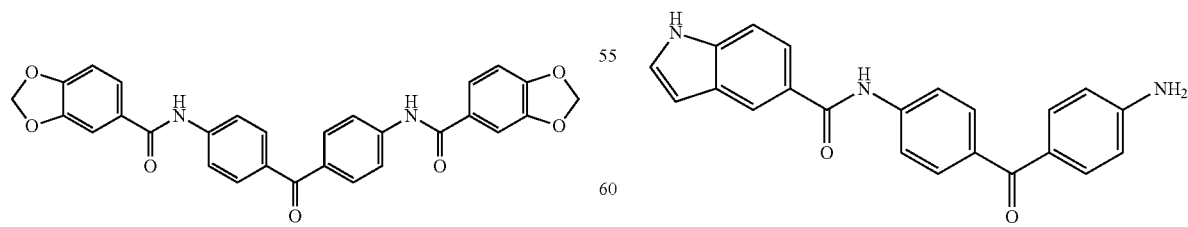

Compound 344 was prepared according to the procedure described in Scheme IV from 4,4'-diaminobenzophenone and benzo[1,3]dioxole-5-carboxylate. [M+H]$^+$ calcd for $C_{29}H_{20}N_2O_7$: 509.1. found: 508.91.

Example 245

N,N'-(4,4'-Carbonylbis(4,1-phenylene))bis(1H-indole-5-carboxamide) (Compound 345)

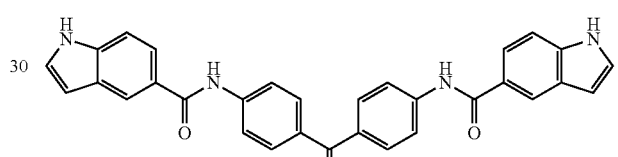

Compound 345 was prepared according to the procedure described in Scheme IV from 4,4'-diaminobenzophenone and 1H-indole-5-carboxylate. [M+H]$^+$ calcd for $C_{31}H_{22}N_4O_3$: 499.1. found: 498.92.

Example 246

N-(4-(4-Aminobenzoyl)phenyl)-1H-indole-5-carboxamide (Compound 346)

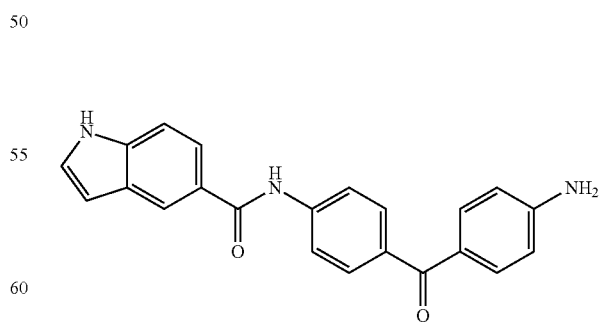

Compound 346 was prepared according to the procedure described in Scheme IV from 4,4'-diaminobenzophenone and 1H-indole-5-carboxylate. [M+H]$^+$ calcd for $C_{22}H_{17}N_3O_2$: 356.1. found: 355.90.

Example 247

N,N'-(4,4'-Carbonylbis(4,1-phenylene))bis(4-(1H-pyrazol-1-yl)benzamide) (Compound 347)

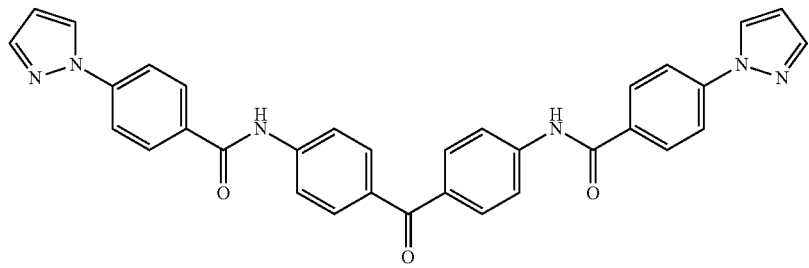 [SMILES: O=C(Nc1ccc(C(=O)c2ccc(NC(=O)c3ccc(-n4cccn4)cc3)cc2)cc1)c1ccc(-n2cccn2)cc1]

Compound 347 was prepared according to the procedure described in Scheme IV from 4,4'-diaminobenzophenone and 4-(pyrazol-1-yl)benzoate. [M+H]$^+$ calcd for $C_{33}H_{24}N_6O_3$: 553.1. found: 552.99.

Example 248

N-(4-(4-(2-phenylacetamido)benzoyl)phenyl)-1H-indole-5-carboxamide (Compound 348)

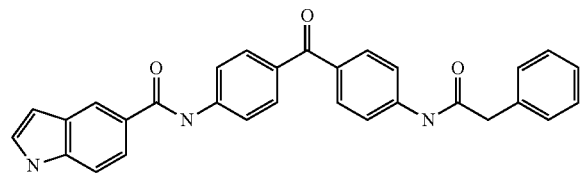 [SMILES: O=C(Cc1ccccc1)Nc1ccc(C(=O)c2ccc(NC(=O)c3ccc4[nH]ccc4c3)cc2)cc1]

Compound 348 was prepared from compound 346 and benzylbromide. [M+H]$^+$ calcd for $C_{30}H_{23}N_3O_3$: 474.0. found: 474.49.

Example 249

4-ethoxy-N-(4-(4-(2-(4-ethoxyphenyl)-2-oxoethyl)benzoyl)phenyl)benzamide (Compound 349)

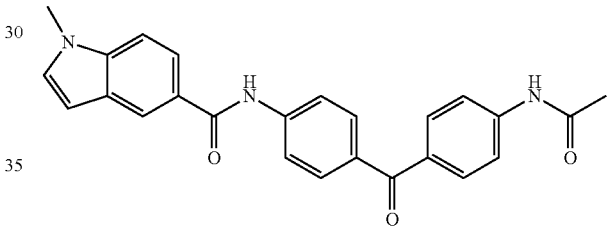

Compound 349 was prepared according to the procedure described in Scheme IV from 4,4'-diaminobenzophenone and 1-methylindole-5-carboxylate. [M+H]$^+$ calcd for $C_{25}H_{21}N_3O_3$: 412.0. found: 411.94.

Example 250

N-(4-(4-(4-Methoxyphenylsulfonamido)benzoyl)phenyl)-4-(pyrrolidin-1-yl)benzamide (Compound 350)

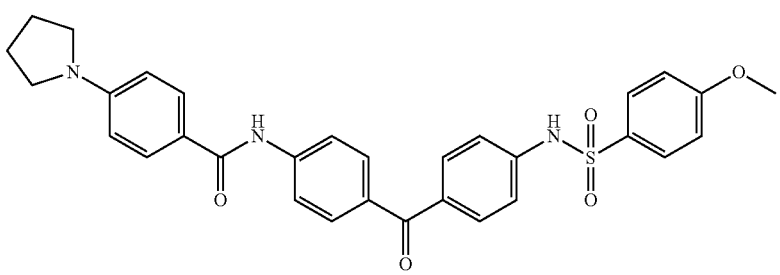 [SMILES: COc1ccc(S(=O)(=O)Nc2ccc(C(=O)c3ccc(NC(=O)c4ccc(N5CCCC5)cc4)cc3)cc2)cc1]

Compound 350 was prepared according to the procedure described in Scheme IV from 4,4'-diaminobenzophenone and 4-pyrrolidinylbenzoate. [M+H]$^+$ calcd for $C_{31}H_{29}N_3O_5S$: 556.1. found: 555.99.

Example 251

N,N'-(4,4'-Carbonylbis(4,1-phenylene))dithiophene-2-carboxamide (Compound 351)

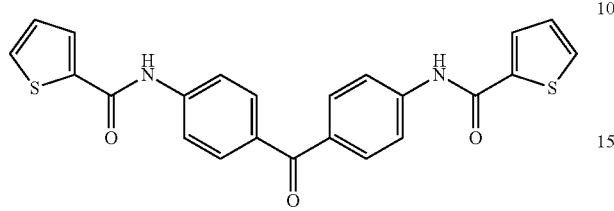

Compound 351 was prepared according to the procedure described in Scheme IV from 4,4'-diaminobenzophenone and 2-thiophenecarboxylate. $^1$H NMR (500 MHz, DMSO-d$_6$) δ 10.54 (s, 2H), 8.09 (d, J=3.75 Hz, 2H), 7.94 (d, J=12.5 Hz, 4H), 7.91 (d, J=3.75 Hz, 2H), 7.88 (d, J=12.5 Hz, 4H), 7.25 (t, J=3.75 Hz, 2H).

Example 252

N,N'-(4,4'-Carbonylbis(4,1-phenylene))bis(4-(2-hydroxyethoxy)benzamide) (Compound 352)

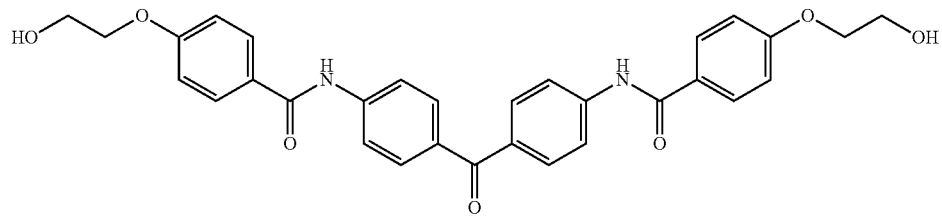 [SMILES: O=C(Nc1ccc(C(=O)c2ccc(NC(=O)c3ccc(OCCO)cc3)cc2)cc1)c1ccc(OCCO)cc1]

Compound 352 was prepared according to the procedure described in Scheme IV from 4,4'-diaminobenzophenone and 4-(2-hydroxyethoxy)benzoate. [M+H]$^+$ calcd for $C_{31}H_{28}N_2O_7$: 541.0. found: 541.05.

Example 253

N-(4-Benzoylphenyl)-4-(4-cyclopropanecarbonylpiperazin-1-yl)benzamide (Compound 353)

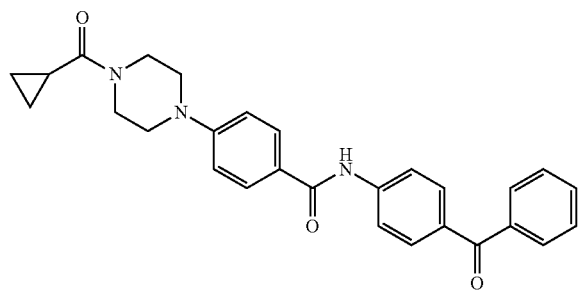 [SMILES: O=C(Nc1ccc(C(=O)c2ccccc2)cc1)c1ccc(N2CCN(C(=O)C3CC3)CC2)cc1]

Compound 353 was prepared according to the procedure described in Scheme IV from 4-aminobenzophenone and 4-piperazinebenzoate. [M+H]$^+$ calcd for $C_{28}H_{28}N_3O_3$: 454.2. found: 454.01.

Example 254

4-(Dimethylamino)-N-(4-(4-(4-fluorobenzamido)benzoyl)phenyl)benzamide (Compound 354)

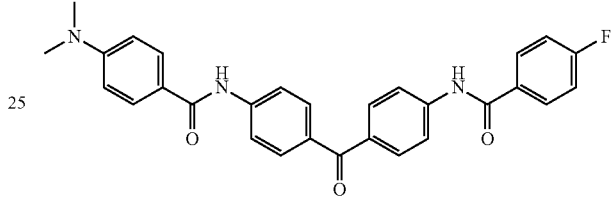

Compound 354 was prepared according to the procedure described in Scheme IV from 4,4'-diaminobenzophenone and the substituted benzoates. [M+H]$^+$ calcd for $C_{29}H_{25}FN_3O_3$: 482.1. found: 482.22.

Example 255

N,N'-(4,4'-Carbonylbis(4,1-phenylene))diisonicotinamide (Compound 355)

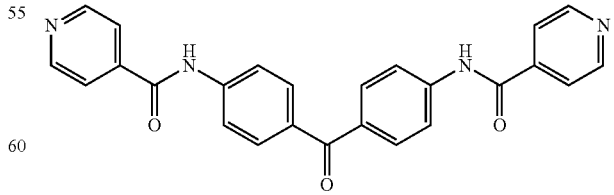

Compound 355 was prepared according to the procedure described in Scheme IV from 4,4'-diaminobenzophenone and 4-picolinic acid. [M+H]$^+$ calcd for $C_{25}H_{19}N_4O_3$: 423.1. found: 422.87.

Example 256

N,N'-(4,4'-Carbonylbis(4,1-phenylene))bis(6-morpholinonicotinamide) (Compound 356)

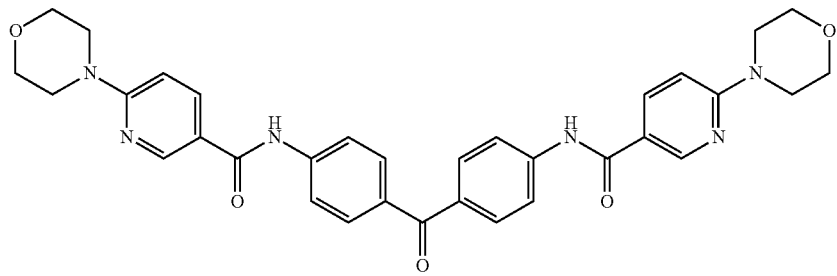 [SMILES: O=C(Nc1ccc(C(=O)c2ccc(NC(=O)c3ccc(N4CCOCC4)nc3)cc2)cc1)c1ccc(N2CCOCC2)nc1]

Compound 356 was prepared according to the procedure described in Scheme IV from 4,4'-diaminobenzophenone and 6-morpholinonicotinic acid. [M+H]$^+$ calcd for $C_{33}H_{33}N_6O_5$: 593.2. found: 593.03.

Example 257

N,N'-(4,4'-Carbonylbis(4,1-phenylene))bis(4-(morpholinomethyl)benzamide) (Compound 357)

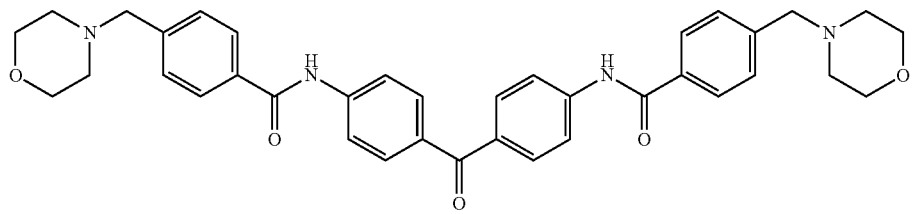 [SMILES: O=C(Nc1ccc(C(=O)c2ccc(NC(=O)c3ccc(CN4CCOCC4)cc3)cc2)cc1)c1ccc(CN2CCOCC2)cc1]

Compound 357 was prepared according to the procedure described in Scheme IV from 4,4'-diaminobenzophenone and 4-morpholinomethylbenzoate. [M+H]$^+$ calcd for $C_{37}H_{39}N_4O_5$: 619.2. found: 619.10.

Example 258

N-(4-(4-(4-Dimethylamino)benzoyl)phenyl)isonicotinamide (Compound 358)

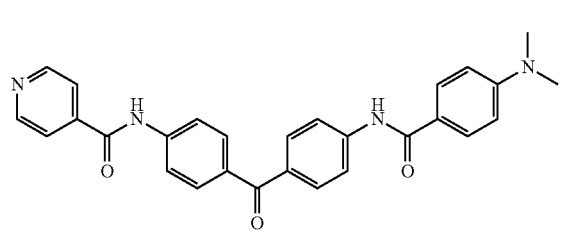 [SMILES: CN(C)c1ccc(C(=O)Nc2ccc(C(=O)c3ccc(NC(=O)c4ccncc4)cc3)cc2)cc1]

Compound 358 was prepared according to the procedure described in Scheme IV from 4,4'-diaminobenzophenone and 4-picolinic acid. [M+H]$^+$ calcd for $C_{28}H_{25}N_4O_3$: 465.1. found: 464.98.

Example 259

N-(4-(4-Cyclopropanecarboxamido)benzoyl)phenyl)-4-morpholinobenzamide (Compound 359)

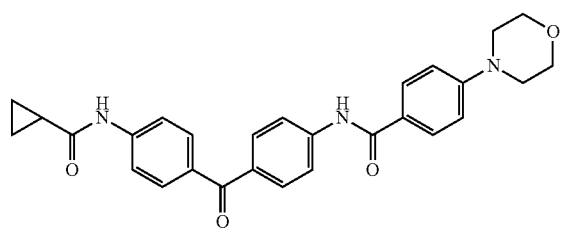 [SMILES: O=C(Nc1ccc(C(=O)c2ccc(NC(=O)C3CC3)cc2)cc1)c1ccc(N2CCOCC2)cc1]

Compound 359 was prepared according to the procedure described in Scheme IV from 4,4'-diaminobenzophenone and 4-morpholinobenzoate. [M+H]$^+$ calcd for $C_{28}H_{28}N_3O_4$: 470.2. found: 469.97.

Example 260

N-(4-(4-(2-Thienyl)carboxamido)benzoyl)phenyl)-4-morpholinobenzamide (Compound 360)

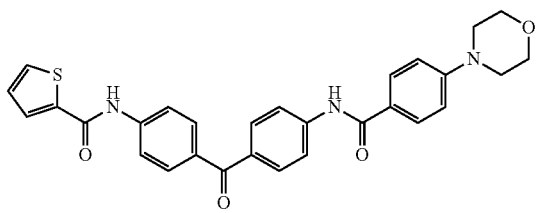 [SMILES: O=C(Nc1ccc(C(=O)c2ccc(NC(=O)c3cccs3)cc2)cc1)c1ccc(N2CCOCC2)cc1]

Compound 360 was prepared according to the procedure described in Scheme IV from 4,4'-diaminobenzophenone and 4-morpholinobenzoate. [M+H]$^+$ calcd for $C_{29}H_{26}N_3O_4S$: 512.1. found: 511.95.

Example 261

N,N'-(4,4'-Azanediylbis(4,1-phenylene))bis(4-(dimethylamino)benzamide) (Compound 361)

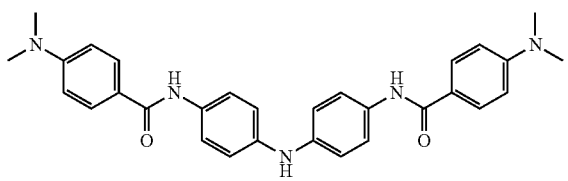

Compound 361 was prepared according to the procedure described in Scheme IV from 4,4'-diaminodiphenylamine and 4-dimethylaminobenzoate. [M+H]$^+$ calcd for $C_{30}H_{31}N_5O_2$: 494.2. found: 494.04.

Example 262

4-(dimethylamino)-N-(4-(N-(4-(4-(dimethylamino)benzamido)phenyl)acetamido)phenyl)benzamide (Compound 362)

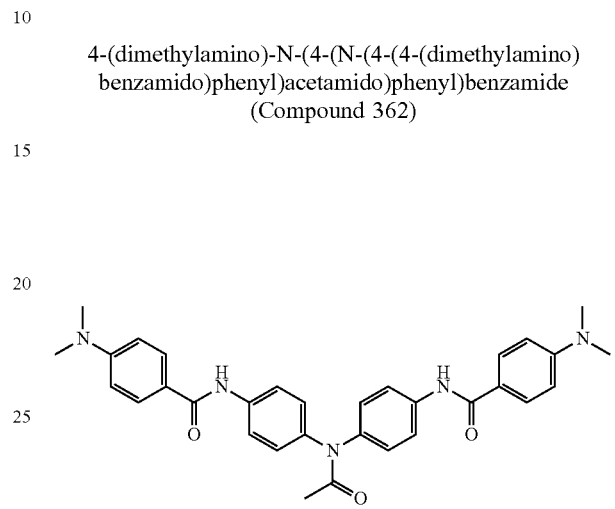

Compound 362 was prepared according to the procedure described in Scheme IV from 4,4'-diaminodiphenylamine and 4-dimethylaminobenzoate. $^1$H NMR (500 MHz, DMSO-d$_6$) δ 9.99 (bs, 1H), 9.89 (bs, 1H), 7.84 (d, J=9 Hz, 6H), 7.70 (bs, 2H), 7.36 (bs, 2H), 7.20 (bs, 2H), 6.73 (d, J=9 Hz, 4H), 2.98 (s, 12H), 1.93 (s, 3H).

Example 263

N,N'-(4,4'-Azanediylbis(4,1-phenylene))bis(4-morpholinobenzamide) (Compound 363)

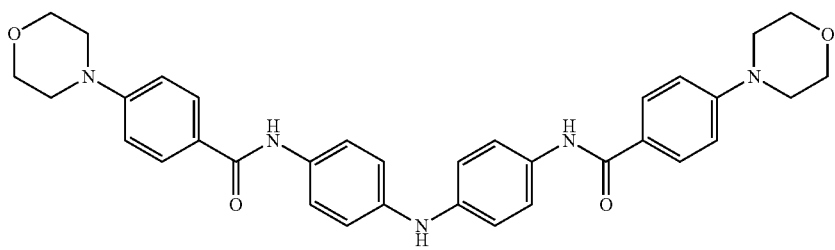 [SMILES: O=C(Nc1ccc(Nc2ccc(NC(=O)c3ccc(N4CCOCC4)cc3)cc2)cc1)c1ccc(N2CCOCC2)cc1]

Compound 363 was prepared according to the procedure described in Scheme IV from 4,4'-diaminodiphenylamine and 4-morpholinobenzoate. [M+H]$^+$ calcd for $C_{34}H_{35}N_5O_4$: 578.2. found: 578.11.

Example 264

N,N'-(4,4'-Azanediylbis(4,1-phenylene))bis(4-(4-hydroxypiperidino)benzamide) (Compound 364)

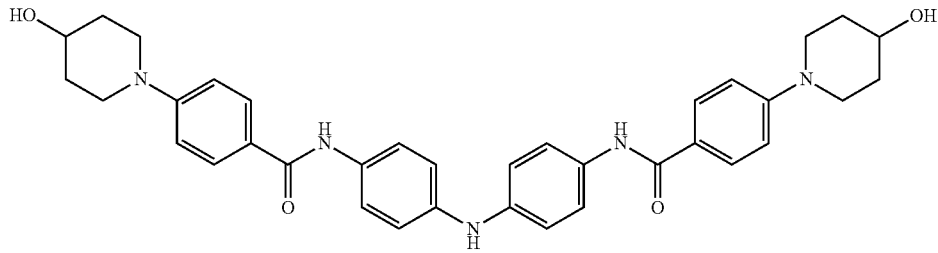 [SMILES: O=C(Nc1ccc(Nc2ccc(NC(=O)c3ccc(N4CCC(O)CC4)cc3)cc2)cc1)c1ccc(N2CCC(O)CC2)cc1]

Compound 364 was prepared according to the procedure described in Scheme IV from 4,4'-diaminodiphenylamine and 4-(4-hydroxypiperidinobenzoate. $^1$H NMR (500 MHz, DMSO-d$_6$) δ 9.75 (s, 2H), 7.94 (s, 1H), 7.82 (d, J=9 Hz, 4H), 7.57 (d, J=9 Hz, 4H), 6.98 (t, J=9 Hz, 8H), 4.71 (d, J=4.5 Hz, 2H), 3.67 (m, 8H), 2.98 (dt, J=3, 10 Hz, 2H), 1.80 (m, 4H), 1.43 (m, 4H).

Example 265

N,N'-(4,4'-Azanediylbis(4,1-phenylene))bis(4-piperazinobenzamide) (Compound 365)

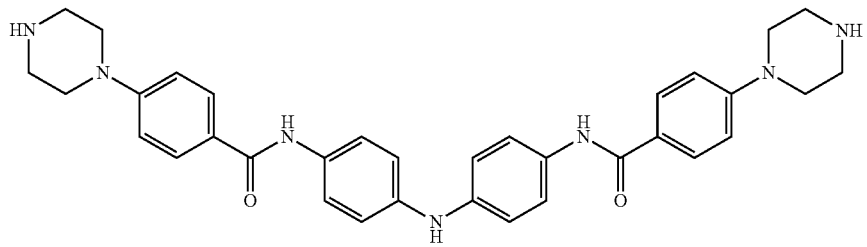 [SMILES: O=C(Nc1ccc(Nc2ccc(NC(=O)c3ccc(N4CCNCC4)cc3)cc2)cc1)c1ccc(N2CCNCC2)cc1]

Compound 365 was prepared according to the procedure described in Scheme IV from 4,4'-diaminodiphenylamine and 4-piperazinobenzoate. [M+H]$^+$ calcd for $C_{34}H_{38}N_7O_2$: 576.3. found: 576.17.

Example 266

4-morpholino-N-(4-((4-(4-(piperazin-1-yl)benzamido)phenyl)amino)phenyl)benzamide (Compound 366)

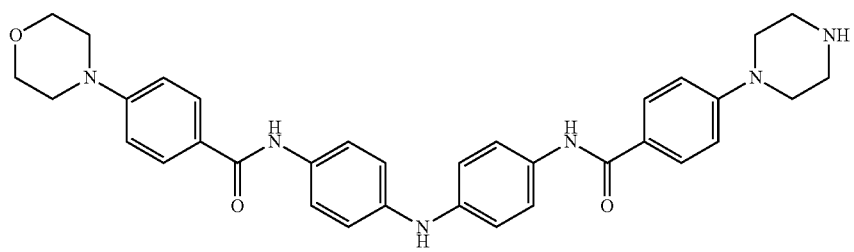 [SMILES: O=C(Nc1ccc(Nc2ccc(NC(=O)c3ccc(N4CCOCC4)cc3)cc2)cc1)c1ccc(N2CCNCC2)cc1]

Compound 366 was prepared according to the procedure described in Scheme IV from 4,4'-diaminodiphenylamine and 4-morpholinobenzoate. [M+H]+ calcd for $C_{34}H_{36}N_6O_3$: 577.2. found: 577.16.

Example 267

4-Fluoro-N-(4-(4-(4-piperazinobenzamido)phenylamino)phenyl)benzamide (Compound 367)

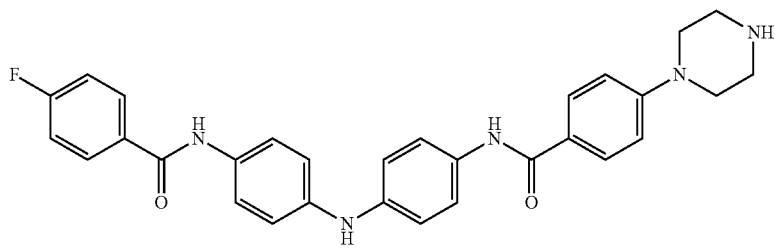 [SMILES: O=C(Nc1ccc(Nc2ccc(NC(=O)c3ccc(N4CCNCC4)cc3)cc2)cc1)c1ccc(F)cc1]

Compound 367 was prepared according to the procedure described in Scheme IV from 4,4'-diaminodiphenylamine and 4-piperazinobenzoate. [M+H]+ calcd for $C_{30}H_{29}FN_5O_2$: 510.2. found: 510.06.

Example 268

N,N'-(4,4'-Azanediylbis(4,1-phenylene))bis(4-fluorobenzamide) (Compound 368)

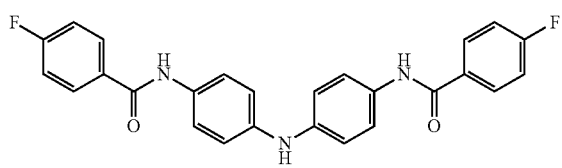 [SMILES: O=C(Nc1ccc(Nc2ccc(NC(=O)c3ccc(F)cc3)cc2)cc1)c1ccc(F)cc1]

Compound 368 was prepared according to the procedure described in Scheme IV from 4,4'-diaminodiphenylamine and 4-fluorobenzoate. [M+H]+ calcd for $C_{26}H_{19}F_2N_3O_2$: 444.1. found: 443.86.

Example 269

N-(1-(4-Aminophenyl)-1H-indol-5-yl)-4-dimethylaminobenzamide (Compound 369)

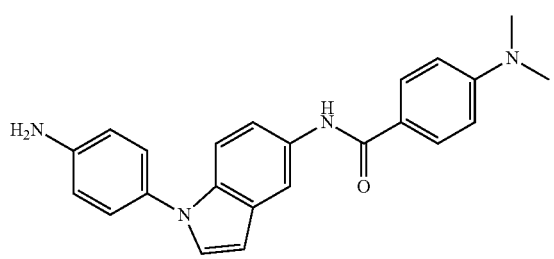 [SMILES: CN(C)c1ccc(C(=O)Nc2ccc3c(ccn3-c3ccc(N)cc3)c2)cc1]

Compound 369 was prepared according to the general procedure described in Scheme IV. Preparation of 4-(dimethylamino)-N-(1H-indol-5-yl)benzamide: 1H-indol-5-amine (200 mg, 1.51 mmol), hydroxybenzotriazole (204 mg, 1.51 mmol), triethylamine (0.23 mL, 1.66 mmol), and 4-(dimethylamino)benzoic acid (275 mg, 1.66 mmol) were taken up in DMF (7.5 mL) and stirred. EDC (319 mg, 1.66 mmol) was added to the solution last. After the addition, the solution was stirred at room temperature for 4 h. Water was then added to the solution and stirred for 10 min. The formed precipitate was filtered and washed well with water, followed by hexanes. The grayish solid was dried under vacuum to give 393 mg (93%) of the product.

Preparation of 4-(dimethylamino)-N-(1-(4-nitrophenyl)-1H-indol-5-yl)benzamide: 4-(Dimethylamino)-N-(1H-indol-5-yl)benzamide (200 mg, 0.71 mmol), 4-fluoronitrobenze (101 mg, 0.71 mmol) and potassium carbonate (99 mg, 0.72 mmol) were taken up in DMSO (7.2 mL). The solution was heated to 100° C. and stirred for 24 h. After the solution was cooled it was diluted with water until a precipitate formed and stirred well for 5 min Filtration gave a yellow solid, which was then washed well with water, followed by hexanes. The solid was dried under vacuum to give 258 mg (90%) product as a yellow solid.

Preparation of Compound 369: 4-(Dimethylamino)-N-(1-(4-nitrophenyl)-1H-indol-5-yl)benzamide (330 mg, 0.82 mmol) was taken up in ethanol (28 mL) under nitrogen. The solution was treated with Pd(OH)$_2$ (35 mg, 0.24 mmol) and placed under a balloon of H$_2$ gas. After stirring at RT for 2 h, the catalyst was removed via filtration through celite. Concentration of the filtrate yielded 260 mg (85%) of compound 369. MS [M+H]+ calcd for $C_{23}H_{22}N_4O$: 371.1. found: 370.94.

Example 270

N-(1-(4-(4-Dimethyl aminobenzamido)phenyl)-1H-indol-5-yl)-4-dimethylaminobenzamide (Compound 370)

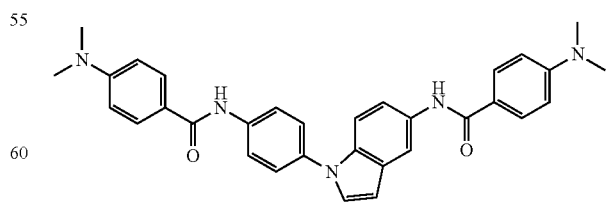

Compound 370 was prepared according to the procedure described in Scheme IV from 5-amino-1-(4-aminophenyl) indole and 4-dimethylaminobenzoate. [M+H]+ calcd for $C_{32}H_{31}N_5O_2$: 518.2. found: 517.95.

Example 271

N-(1-(4-Aminophenyl)-1H-indazol-5-yl)-4-dimethylaminobenzamide (Compound 371)

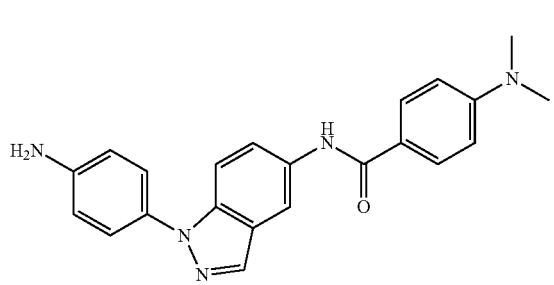 [SMILES: CN(C)c1ccc(C(=O)Nc2ccc3c(cnn3-c3ccc(N)cc3)c2)cc1]

Compound 371 was prepared according to the general procedure described in Scheme IV. Preparation of 4-(dimethylamino)-N-(1H-indazol-5-yl)benzamide: 1H-Indazol-5-amine (200 mg, 1.50 mmol), hydroxybenzotriazole (20 mg, 0.15 mmol), triethylamine (0.23 mL, 1.65 mmol), and 4-(dimethylamino)benzoic acid (273 mg, 1.65 mmol) were taken up in DMF (7.5 mL) and stirred. EDC (317 mg, 1.65 mmol) was added to the solution last. After the addition, the solution was stirred at room temperature for 4 h. Water was then added to the solution and stirred for 10 min. The formed precipitate was filtered and washed well with water, followed by hexanes. The solid was dried under vacuum to give 410 mg (97%) of the product as a brown solid.

Preparation of 4-(dimethylamino)-N-(1-(4-nitrophenyl)-1H-indazol-5-yl)benzamide: 4-(dimethylamino)-N-(1H-indazol-5-yl)benzamide (100 mg, 0.35 mmol), 4-fluoronitrobenze (50 mg, 0.35 mmol) and potassium carbonate (49 mg, 0.35 mmol) were taken up in DMSO (3.6 mL). The solution was heated to 100° C. and stirred for 24 h. After the solution was cooled it was diluted with water until a precipitate formed and stirred well for 5 min Filtration gave a yellow solid, which was then washed well with water, followed by hexanes. The solid was dried under vacuum to give 133 mg (93%) of the product as a yellow solid.

Preparation of Compound 371: 4-(Dimethylamino)-N-(1-(4-nitrophenyl)-1H-indazol-5-yl)benzamide (400 mg, 0.99 mmol) was taken up in ethanol (33 mL) under nitrogen. The solution was treated with Pd(OH)$_2$ (35 mg, 0.25 mmol) and placed under a balloon of H$_2$ gas. After stirring at RT for 2 h, the catalyst was removed via filtration through celite. The filtrate was concentrated onto silica under reduced pressure. Purification via flash chromatography (0-5% MeOH/ CH$_2$Cl$_2$) gave 180 mg (48%) of final compound 371 as a light brown solid. $^1$H NMR (500 MHz, DMSO-d$_6$) 9.95 (s, 1H), 8.29 (s, 1H), 8.18 (s, 1H), 7.89 (d, J=9 Hz, 2H), 7.69 (dd, J=2, 9 Hz, 1H), 7.58 (d, J=9 Hz, 1H), 7.32 (d, J=9 Hz, 2H), 6.76 (d, J=9 Hz, 2H), 6.71 (d, J=9 Hz, 2H), 5.32 (s, 2H), 2.99 (s, 6H).

Example 272

N-(2-Acetyl-1-(4-(4-dimethylaminobenzamido)phenyl)-1H-indol-5-yl)-4-dimethylaminobenzamide (Compound 372)

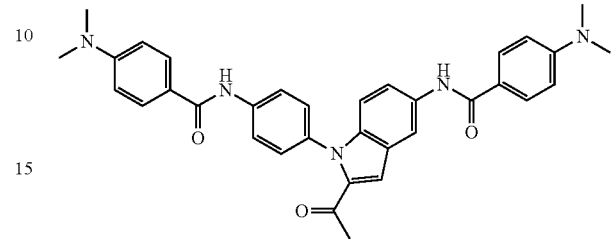

Compound 372 was prepared according to the procedure described in Scheme IV from 2-acetyl-5-amino-1-(4-aminophenyl)indole and 4-dimethylaminobenzoate. [M+H]$^+$ calcd for C$_{34}$H$_{33}$N$_5$O$_3$: 560.2. found: 560.02.

Example 273

N-(1-(4-(4-Dimethyl aminobenzamido)phenyl)-1H-indazol-5-yl)-4-dimethylaminobenzamide (Compound 373)

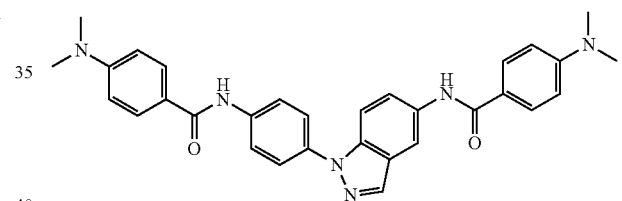

Compound 373 was prepared according to the procedure described in Scheme IV from 5-amino-1-(4-aminophenyl) indazole and 4-dimethylaminobenzoate. $^1$H NMR (500 MHz, Acetone-d$_6$) δ 9.44 (s, 1H), 9.38 (s, 1H), 8.49 (s, 1H), 8.23 (s, 1H), 8.08 (d, J=9 Hz, 2H), 7.95 (d, J=9 Hz, 4H), 7.81 (m, 2H), 7.76 (d, J=9 Hz, 2H), 6.79 (d, J=9 Hz, 4H), 3.06 (s, 6H), 3.05 (s, 6H).

Example 274

N-(1-(4-Acetamidophenyl)-1H-indazol-5-yl)-4-dimethylaminobenzamide (Compound 374)

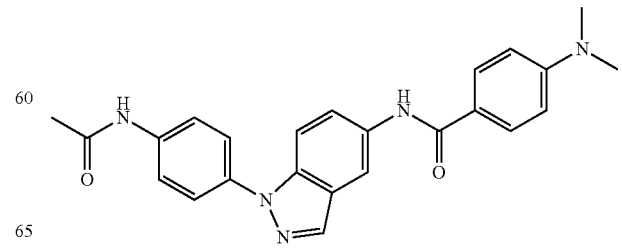

Compound 374 was prepared according to the procedure described in Scheme IV from 5-amino-1-(4-aminophenyl)indazole and 4-dimethylaminobenzoate. [M+H]$^+$ calcd for $C_{24}H_{23}N_5O_2$: 414.1. found: 413.97.

Example 275

N-(1-(4-Benzamidophenyl)-1H-indazol-5-yl)-4-dimethylaminobenzamide (Compound 375)

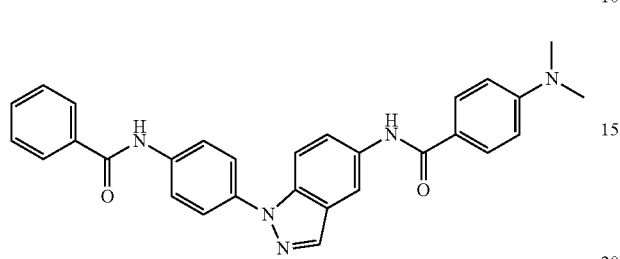

Compound 375 was prepared according to the procedure described in Scheme IV from 5-amino-1-(4-aminophenyl)indazole and 4-dimethylaminobenzoate. $^1$H NMR (500 MHz, DMSO-d$_6$) δ 10.45 (s, 1H), 10.01 (s, 1H), 8.37 (d, J=1.5 Hz, 1H), 8.33 (d, J=1 Hz, 1H), 8.01-7.78 (m, 11H), 7.55 (t, J=8 Hz, 2H), 6.77 (d, J=9 Hz, 2H), 3.00 (s, 6H).

Example 276

4-(dimethylamino)-N-(1-(4-morpholinophenyl)-1H-indol-5-yl)benzamide (Compound 376)

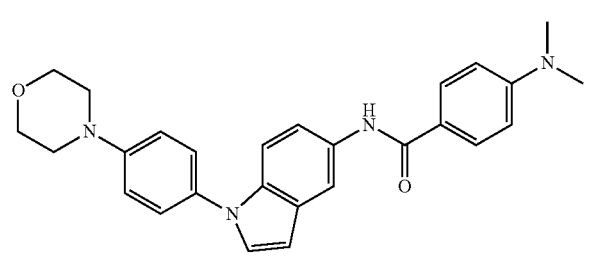 [SMILES: CN(C)c1ccc(C(=O)Nc2ccc3c(ccn3-c3ccc(N4CCOCC4)cc3)c2)cc1]

Compound 376 was prepared according to the procedure described in Scheme IV from 5-amino-1-(4-morpholinophenyl)indole and 4-dimethylaminobenzoate. [M+H]$^+$ calcd for $C_{27}H_{28}N_4O_2$: 441.2. found: 441.02.

Example 277

N-(1-(4-Morpholinocarboxamidophenyl)-1H-indazol-5-yl)-4-dimethylaminobenzamide (Compound 377)

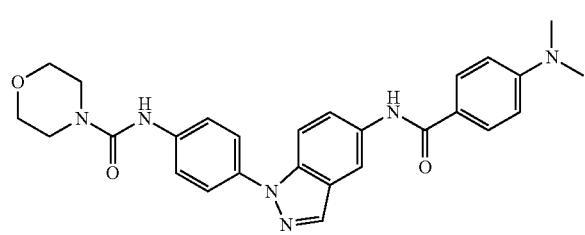 [SMILES: CN(C)c1ccc(C(=O)Nc2ccc3c(cnn3-c3ccc(NC(=O)N4CCOCC4)cc3)c2)cc1]

Compound 377 was prepared according to the procedure described in Scheme IV from 5-amino-1-(4-morpholinocarboxamidophenyl)indazole and 4-dimethylaminobenzoate.

[M+H]$^+$ calcd for $C_{27}H_{28}N_6O_3$: 485.2. found: 485.02.

Example 278

N-(1-(4-Cyclopropanecarboxamidophenyl)-1H-indazol-5-yl)-4-dimethylaminobenzamide (Compound 378)

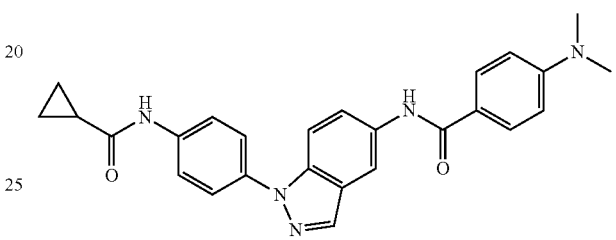

Compound 378 was prepared according to the procedure described in Scheme IV from 5-amino-1-(4-aminophenyl)indazole and 4-dimethylaminobenzoate. $^1$H NMR (500 MHz, DMSO-d$_6$) δ 10.38 (s, 1H), 10.00 (s, 1H), 8.35 (t, J=1 Hz, 1H), 8.30 (d, J=1 Hz, 1H), 7.89 (d, J=7 Hz, 2H), 7.80-7.76 (m, 4H), 7.68 (d, J=9 Hz, 2H), 6.76 (d, J=9 Hz, 2H), 3.00 (s, 6H), 1.80 (m, 1H), 0.82 (m, 4H).

Example 279

N-(2-Acetyl-1-(4-cyclopropanecarboxamidophenyl)-1H-indol-5-yl)-4-dimethylaminobenzamide (Compound 379)

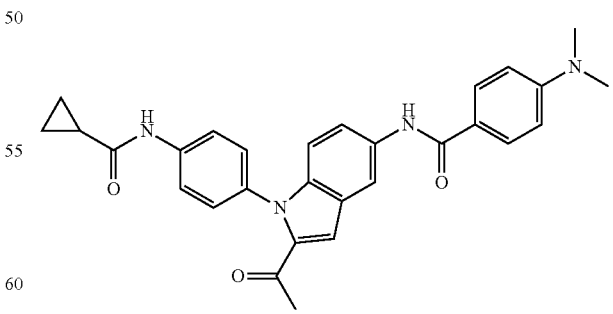

Compound 379 was prepared according to the procedure described in Scheme IV from 2-acetyl-5-amino-1-(4-aminophenyl)indole and 4-dimethylaminobenzoate. [M+H]$^+$ calcd for $C_{29}H_{28}N_4O_3$: 481.2. found: 480.97.

Example 280

N-(1-(4-Cyclopropanecarboxamidophenyl)-1H-indazol-5-yl)-4-morpholinobenzamide (Compound 380)

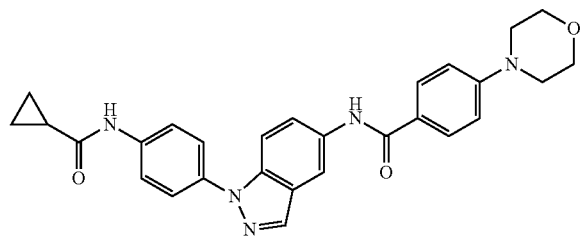 [SMILES: O=C(Nc1ccc2c(cnn2-c2ccc(NC(=O)C3CC3)cc2)c1)c1ccc(N2CCOCC2)cc1]

Compound 380 was prepared according to the procedure described in Scheme IV from 5-amino-1-(4-aminophenyl) indazole and 4-morpholinobenzoate. [M+H]+ calcd for $C_{28}H_{27}N_5O_3$: 482.2. found: 481.98.

Example 281

N-(1-(4-Aminophenyl)-1H-indazol-5-yl)-4-morpholinobenzamide (Compound 381)

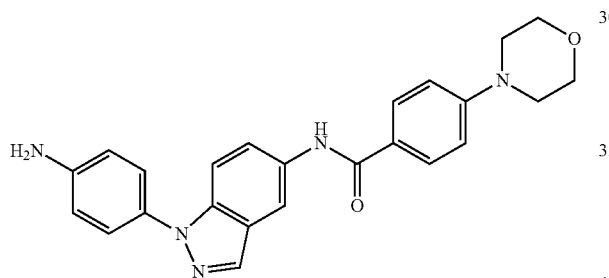

Compound 381 was prepared according to the procedure described in Scheme IV from 5-amino-1-(4-aminophenyl) indazole and 4-morpholinobenzoate. [M+H]+ calcd for $C_{24}H_{23}N_5O_2$: 414.1. found: 414.01.

Example 282

N-(1-(4-Pivaloylaminophenyl)-1H-indazol-5-yl)-4-morpholinobenzamide (Compound 382)

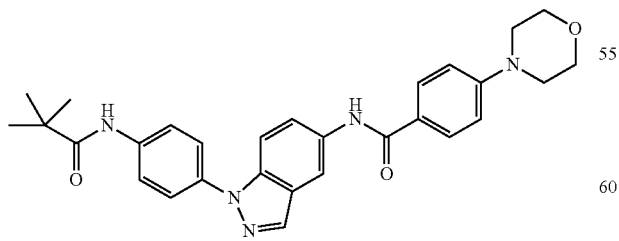

Compound 382 was prepared according to the procedure described in Scheme IV from 5-amino-1-(4-aminophenyl) indazole and 4-morpholinobenzoate. [M+H]+ calcd for $C_{29}H_{31}N_5O_3$: 498.2. found: 498.05.

Example 283 tert-Butyl 1-(4-(4-dimethylaminobenzamido)phenyl)-1H-indazol-5-ylcarbamate (Compound 383)

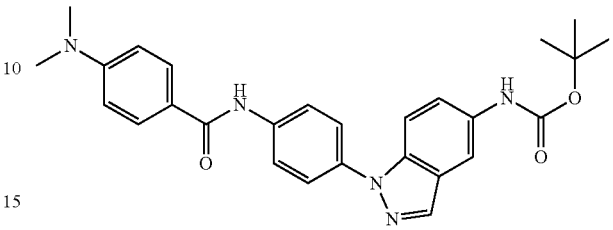

Compound 383 was prepared according to the procedure described in Scheme IV from 5-amino-1-(4-aminophenyl) indazole and 4-dimethylaminobenzoate. [M+H]+ calcd for $C_{27}H_{29}N_5O_3$: 472.2. found: 472.06.

Example 284

N-(4-(5-(cyclopropanecarboxamido)-1H-indazol-1-yl)phenyl)-4-(dimethylamino)benzamide (Compound 384)

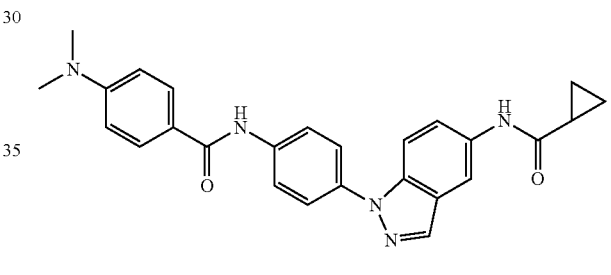

Compound 384 was prepared according to the procedure described in Scheme IV from 5-amino-1-(4-aminophenyl) indazole and 4-dimethylaminobenzoate. 1H NMR (500 MHz, DMSO-d6) δ 10.30 (s, 1H), 10.05 (s, 1H), 8.27 (d, J=1 Hz, 1H), 8.23 (s, 1H), 7.97 (d, J=9 Hz, 2H), 7.89 (d, J=9 Hz, 2H), 7.78 (d, J=9 Hz, 1H), 7.70 (d, J=9 Hz, 1H), 7.55 (dd, J=2, 12 Hz, 1H), 6.77 (d, J=9 Hz, 2H), 3.00 (s, 6H), 1.79 (m, 1H), 0.81 (m, 4H).

Example 285

N-(1-(4-(1-Cyanocyclopropanecarboxamido)phenyl)-1H-indazol-5-yl)-4-morpholinobenzamide (Compound 385)

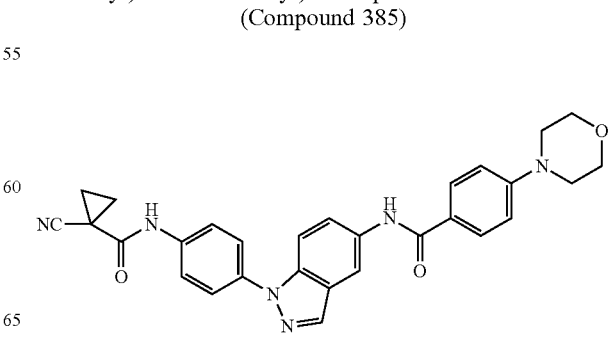

Compound 385 was prepared according to the procedure described in Scheme IV from 5-amino-1-(4-aminophenyl)indazole and 4-morpholinobenzoate. [M+H]$^+$ calcd for $C_{29}H_{26}N_6O_3$: 507.2. found: 507.01.

Example 286

N-(1-(4-Isobutyramidophenyl)-1H-indazol-5-yl)-4-morpholinobenzamide (Compound 386)

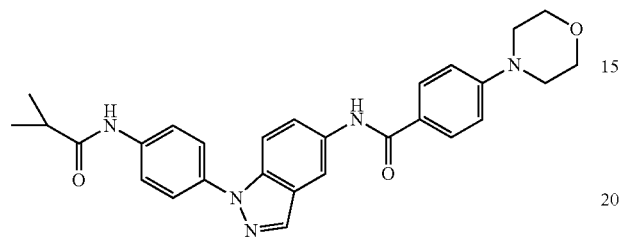

Compound 386 was prepared according to the procedure described in Scheme IV from 5-amino-1-(4-aminophenyl)indazole and 4-morpholinobenzoate. [M+H]$^+$ calcd for $C_{28}H_{29}N_5O_3$: 484.2. found: 484.01.

Example 287

N-(1-(4-(1-Aminomethylcyclopropanecarboxamido)phenyl)-1H-indazol-5-yl)-4-morpholinobenzamide (Compound 387)

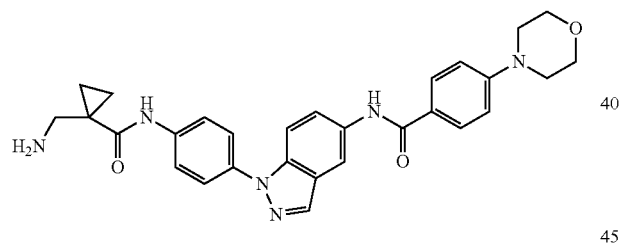

Compound 387 was prepared by reduction of compound 385. [M+H]$^+$ calcd for $C_{29}H_{30}N_6O_3$: 511.2. found: 511.01.

Example 288

N-(1-(4-Amino-2-fluorophenyl)-1H-indazol-5-yl)-4-dimethylaminobenzamide (Compound 388)

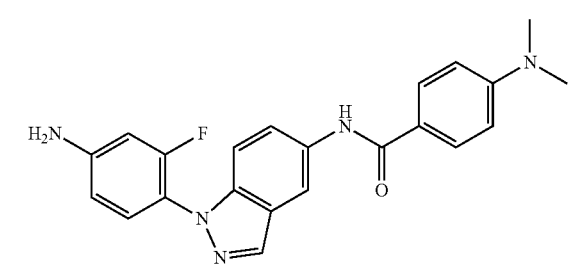 [SMILES: CN(C)c1ccc(C(=O)Nc2ccc3c(cnn3-c3ccc(N)cc3F)c2)cc1]

Compound 388 was prepared according to the procedure described in Scheme IV from 5-amino-1-(4-amino-2-fluorophenyl)indazole and 4-dimethylaminobenzoate. [M+H]$^+$ calcd for $C_{22}H_{20}FN_5O$: 390.1. found: 389.96.

Example 289

N-(1-(4-Cyclopropanecarboxamido-2-fluorophenyl)-1H-indazol-5-yl)-4-dimethylaminobenzamide (Compound 389)

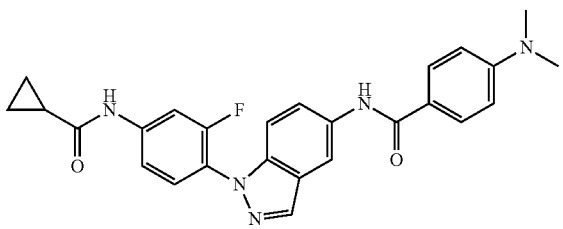 [SMILES: CN(C)c1ccc(C(=O)Nc2ccc3c(cnn3-c3ccc(NC(=O)C4CC4)cc3F)c2)cc1]

Compound 389 was prepared according to the procedure described in Scheme IV from 5-amino-1-(4-amino-2-fluorophenyl)indazole and 4-dimethylaminobenzoate. [M+H]$^+$ calcd for $C_{26}H_{24}FN_5O_2$: 458.1. found: 457.98.

Example 290

N-(1-(4-Acrylamidophenyl)-1H-indazol-5-yl)-4-morpholinobenzamide (Compound 390)

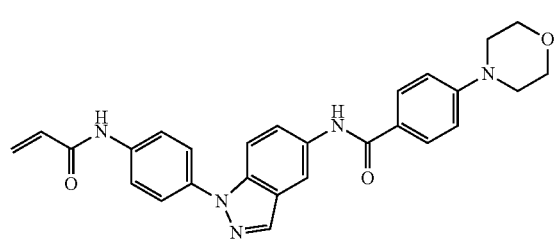 [SMILES: C=CC(=O)Nc1ccc(-n2ncc3cc(NC(=O)c4ccc(N5CCOCC5)cc4)ccc32)cc1]

Compound 390 was prepared according to the procedure described in Scheme IV from 5-amino-1-(4-aminophenyl)indazole and 4-morpholinobenzoate. $^1$H NMR (500 MHz, Acetone-d$_6$) δ 9.59 (s, 1H), 9.47 (s, 1H), 8.49 (s, 1H), 8.24 (s, 1H), 7.98 (dd, J=2, 9 Hz, 4H), 7.81 (m, 2H), 7.77 (d, J=9 Hz, 1H), 7.05 (d, J=9 Hz, 2H), 6.52-6.38 (m, 2H), 5.75 (dd, J=2, 10 Hz, 1H), 3.80 (m, 4H), 3.29 (m, 4H).

Example 291

N-(1-(4-(3-Morpholinopropanamido)phenyl)-1H-indazol-5-yl)-4-morpholinobenzamide (Compound 391)

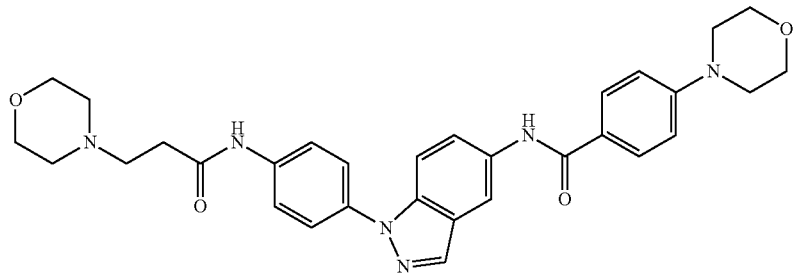 [SMILES: O=C(CCN1CCOCC1)Nc1ccc(-n2ncc3cc(NC(=O)c4ccc(N5CCOCC5)cc4)ccc32)cc1]

Compound 391 was prepared according to the procedure described in Scheme IV from 5-amino-1-(4-aminophenyl)indazole and 4-morpholinobenzoate. [M+H]$^+$ calcd for $C_{31}H_{34}N_6O_4$: 555.2. found: 555.09.

Example 292

N-(1-(4-(4-Dimethylaminobenzamido)-2-fluorophenyl)-1H-indazol-5-yl)-4-dimethylaminobenzamide (Compound 392)

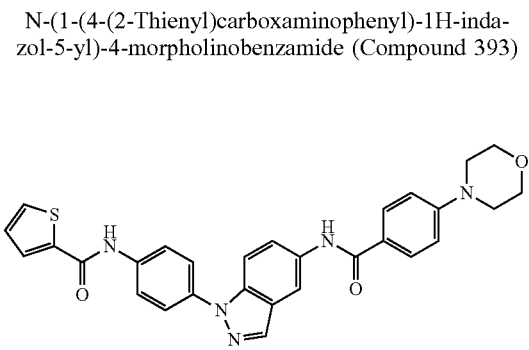

Compound 392 was prepared according to the procedure described in Scheme IV from 5-amino-1-(4-aminophenyl)indazole and 4-dimethylaminobenzoate. $^1$H NMR (500 MHz, DMSO-d$_6$) δ 9.64 (s, 1H), 9.37 (s, 1H), 8.49 (m, 1H), 8.26 (s, 1H), 8.21 (m, 1H), 7.95 (d, J=9 Hz, 4H), 7.79 (dt, J=2, 9 Hz, 1H), 7.76 (m, 1H), 7.61 (t, J=9 Hz, 1H), 7.41 (dd, J=3, 9 Hz, 1H), 6.80 (m, 4H), 3.07 (s, 6H), 3.05 (s, 6H).

Example 293

N-(1-(4-(2-Thienyl)carboxaminophenyl)-1H-indazol-5-yl)-4-morpholinobenzamide (Compound 393)

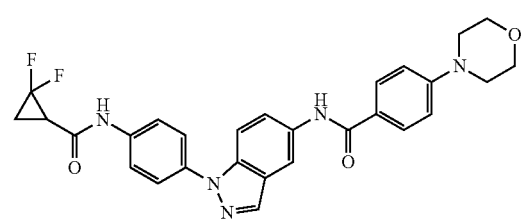

Compound 393 was prepared according to the procedure described in Scheme IV from 5-amino-1-(4-aminophenyl)indazole and 4-morpholinobenzoate. [M+H]$^+$ calcd for $C_{29}H_{25}N_5O_3S$: 524.1. found: 523.97.

Example 294

N-(1-(4-Cyclobutanecarboxaminophenyl)-1H-indazol-5-yl)-4-morpholinobenzamide (Compound 394)

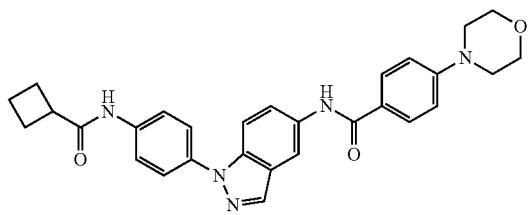 [SMILES: O=C(Nc1ccc2c(cnn2-c2ccc(NC(=O)C3CCC3)cc2)c1)c1ccc(N2CCOCC2)cc1]

Compound 394 was prepared according to the procedure described in Scheme IV from 5-amino-1-(4-aminophenyl)indazole and 4-morpholinobenzoate. [M+H]$^+$ calcd for $C_{29}H_{29}N_5O_3$: 496.2. found: 496.03.

Example 295

(±)-N-(1-(4-(2,2-Difluorocyclopropane)carboxamidophenyl)-1H-indazol-5-yl)-4-morpholinobenzamide (Compound 395)

Compound 395 was prepared according to the procedure described in Scheme IV from 5-amino-1-(4-aminophenyl)indazole and 4-morpholinobenzoate. [M+H]$^+$ calcd for $C_{28}H_{25}F_2N_5O_3$: 518.1. found: 518.03.

Example 296

N-(1-(4-(1-Trifluoromethylcyclopropane)carboxaminophenyl)-1H-indazol-5-yl)-4-morpholinobenzamide (Compound 396)

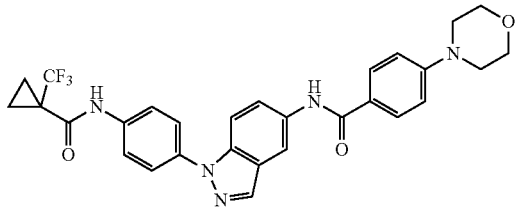 [SMILES: O=C(Nc1ccc2c(cnn2-c2ccc(NC(=O)C3(C(F)(F)F)CC3)cc2)c1)c1ccc(N2CCOCC2)cc1]

Compound 396 was prepared according to the procedure described in Scheme IV from 5-amino-1-(4-aminophenyl)indazole and 4-morpholinobenzoate. $[M+H]^+$ calcd for $C_{29}H_{26}F_3N_5O_3$: 550.2. found: 550.16.

Example 297

N-(1-(4-Cyclopropanecarboxamidophenyl)-1H-indazol-5-yl)-4-(4-hydroxypiperidino)benzamide (Compound 397)

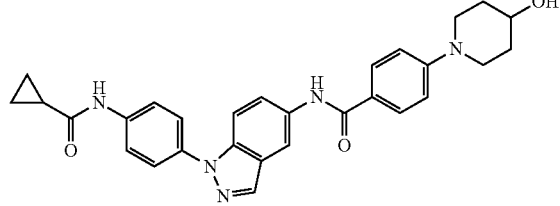

Compound 397 was prepared according to the procedure described in Scheme IV from 5-amino-1-(4-aminophenyl)indazole and 4-(4-hydroxypiperidino)benzoate. $[M+H]^+$ calcd for $C_{29}H_{29}N_5O_3$: 496.2. found: 496.10.

Example 298

N-(1-(4-(3-Methylbut-2-enamido)phenyl)-1H-indazol-5-yl)-4-morpholinobenzamide (Compound 398)

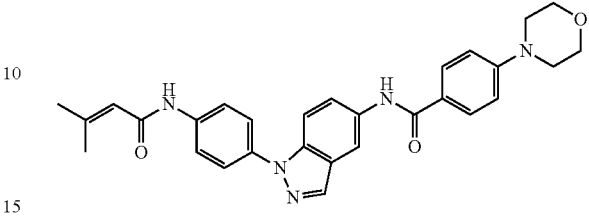

Compound 398 was prepared according to the procedure described in Scheme IV from 5-amino-1-(4-aminophenyl)indazole and 4-morpholinobenzoate. $^1$H NMR (500 MHz, Acetone-d$_6$) δ 9.47 (s, 1H), 9.27 (s, 1H), 8.23 (s, 1H), 7.98 (d, J=8.5 Hz, 2H), 7.94 (d, J=8.5 Hz, 2H), 7.80 (s, 2H), 7.73 (d, J=8.5 Hz, 2H), 7.05 (d, J=8.5 Hz, 2H), 5.92 (s, 1H), 3.80 (t, J=5 Hz, 4H), 3.29 (t, J=5 Hz, 4H), 2.24 (s, 3H), 1.90 (s, 3H).

Example 299

N-(1-(4-Cyclopropanecarboxamidophenyl)-1H-indazol-5-yl)-4-piperazinobenzamide (Compound 399)

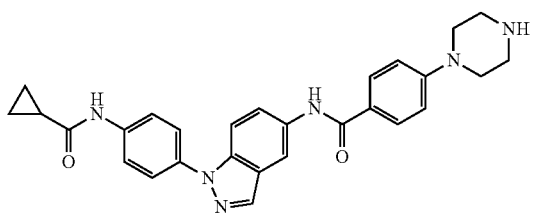 [SMILES: O=C(Nc1ccc2c(cnn2-c2ccc(NC(=O)C3CC3)cc2)c1)c1ccc(N2CCNCC2)cc1]

Compound 399 was prepared according to the procedure described in Scheme IV from 5-amino-1-(4-aminophenyl)indazole and 4-piperazinobenzoate. $[M+H]^+$ calcd for $C_{28}H_{28}N_6O_2$: 481.2. found: 481.04.

Example 300

N-(4-(4-(4-(4-Cyclopropanecarbonyl)piperazin-1-yl)benzamido)benzoyl)phenyl)thiophene-2-carboxamide (Compound 400)

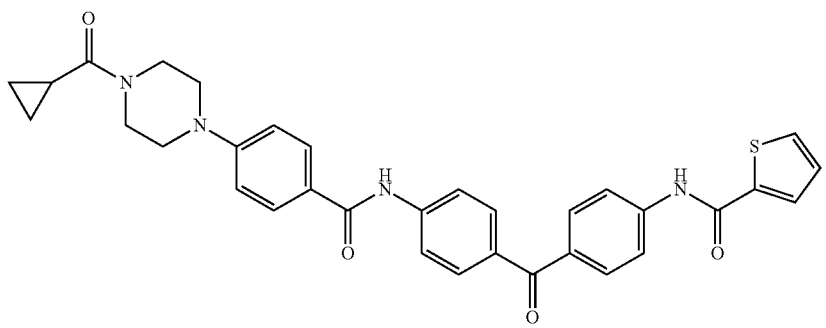 [SMILES: O=C(Nc1ccc(C(=O)c2ccc(NC(=O)c3cccs3)cc2)cc1)c1ccc(N2CCN(C(=O)C3CC3)CC2)cc1]

Compound 400 was prepared according to the procedure described in Scheme IV from 4,4'-diaminobenzophenone and 4-piperazinebenzoate. [M+H]$^+$ calcd for $C_{33}H_{30}N_4O_4S$: 579.5. found: 579.06.

Example 301

N-(4-(4-(4-(4-Cyclopropanecarbonyl)piperazin-1-yl)benzamido)benzoyl)phenyl)cyclopropanecarboxamide (Compound 401)

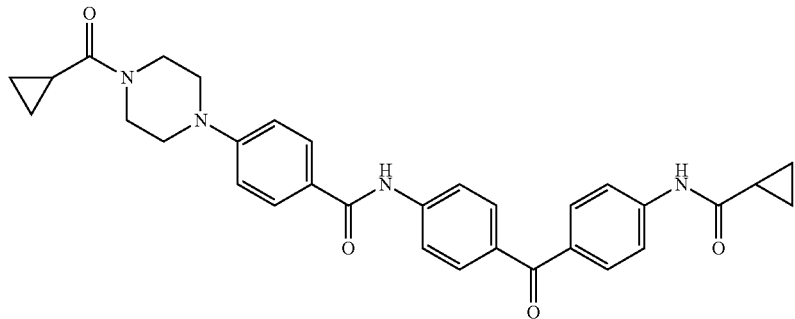 [SMILES: O=C(Nc1ccc(C(=O)c2ccc(NC(=O)C3CC3)cc2)cc1)c1ccc(N2CCN(C(=O)C3CC3)CC2)cc1]

Compound 401 was prepared according to the procedure described in Scheme IV from 4,4'-diaminobenzophenone and 4-piperazinebenzoate. [M+H]$^+$ calcd for $C_{32}H_{32}N_4O_4$: 537.1. found: 537.06.

Example 302

N-(4-(4-(4-Morpholinobenzamido)benzoyl)phenyl)-1H-indole-5-carboxamide (Compound 402)

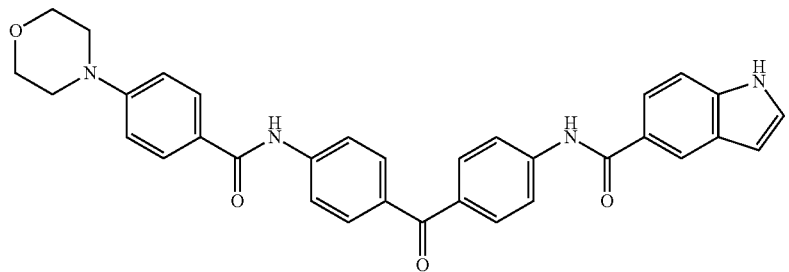 [SMILES: O=C(Nc1ccc(C(=O)c2ccc(NC(=O)c3ccc4[nH]ccc4c3)cc2)cc1)c1ccc(N2CCOCC2)cc1]

Compound 402 was prepared according to the procedure described in Scheme IV from 4,4'-diaminobenzophenone and 4-piperazinebenzoate. [M+H]$^+$ calcd for $C_{33}H_{28}N_4O_4$: 545.1. found: 545.03.

Example 303

N,N'-(carbonylbis(4,1-phenylene))bis(1-methyl-1H-benzo[d][1,2,3]triazole-5-carboxamide) (Compound 403)

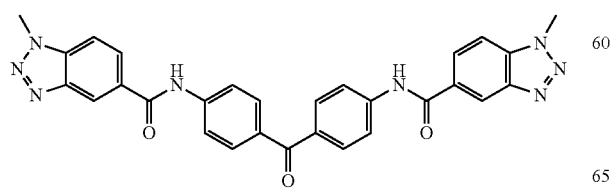

Compound 403 was prepared according to the procedure described in Scheme IV from 4,4'-diaminobenzophenone and 1-methyl-1H-benzotriazole-5-carboxylate. [M+H]+ calcd for $C_{29}H_{22}N_8O_3$: 531.0. found: 531.05.

Example 304

N-(1-(4-Cyanophenyl)-1H-indazol-5-yl)-4-(4-hydroxypiperidino)benzamide (Compound 404)

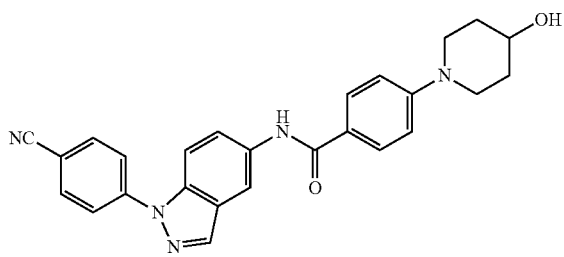 [SMILES: N#Cc1ccc(-n2ncc3cc(NC(=O)c4ccc(N5CCC(O)CC5)cc4)ccc32)cc1]

Compound 404 was prepared according to the procedure described in Scheme IV from 5-amino-1-(4-cyanophenyl)indazole and 4-(4-hydroxypiperidino)benzoate. [M+H]+ calcd for $C_{26}H_{23}N_5O_2$: 438.1. found: 437.99.

Example 305

N-(1-(4-Cyanophenyl)-1H-indazol-5-yl)-4-morpholinobenzamide (Compound 405)

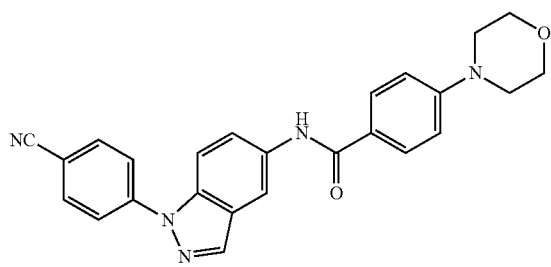 [SMILES: N#Cc1ccc(-n2ncc3cc(NC(=O)c4ccc(N5CCOCC5)cc4)ccc32)cc1]

Compound 405 was prepared according to the procedure described in Scheme IV from 5-amino-1-(4-cyanophenyl)indazole and 4-morpholinobenzoate. [M+H]+ calcd for $C_{25}H_{21}N_5O_2$: 424.1. found: 424.09.

Example 306

1-(4-(4-Dimethylaminobenzamido)phenyl)-N-(4-morpholinophenyl)-1H-indole-5-carboxamide (Compound 406)

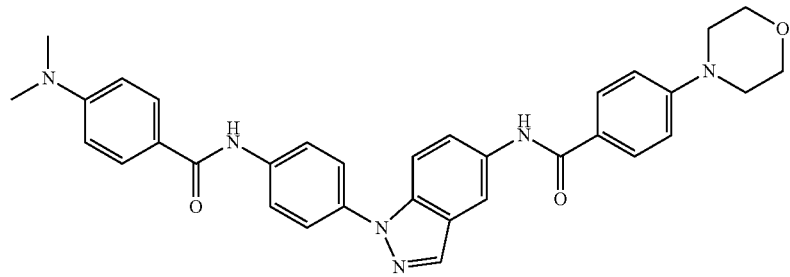 [SMILES: CN(C)c1ccc(C(=O)Nc2ccc(-n3ncc4cc(NC(=O)c5ccc(N6CCOCC6)cc5)ccc43)cc2)cc1]

Compound 406 was prepared according to the procedure described in Scheme IV from 1-(4-dimethylaminophenylbenzamido)indole and 4-morpholinoaniline. 1H NMR (500 MHz, DMSO-$d_6$) δ 10.08 (s, 1H), 10.02 (2, 1H), 8.33 (d, J=2 Hz, 1H), 7.99 (d, J=9 Hz, 2H), 7.89 (d, J=9 Hz, 2H), 7.82 (dd, J=2, 9 Hz, 1H), 7.74 (d, J=3 Hz, 1H), 7.66 (d, J=9 Hz, 2H), 7.60 (d, J=9 Hz, 1H), 7.57 (d, J=5 Hz, 2H), 6.93 (d, J=9 Hz, 2H), 6.83 (d, J=3 Hz, 1H), 6.78 (d, J=9 Hz, 2H), 3.73 (m, 4H), 3.06 (m, 4H), 3.01 (s, 6H).

Example 307

4-Dimethylamino-N-(1-(4-(4-dimethylaminobenzamido)benzoyl)piperidin-4-yl)benzamide (Compound 407)

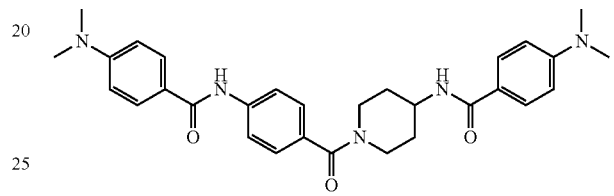

Compound 407 was prepared according to the procedure described in Scheme IV from 4-(4-dimethylaminobenzamido)benzoate and 4-(4-dimethylaminophenyl)piperidine. [M+H]+ calcd for $C_{30}H_{35}N_5O_3$: 514.2. found: 513.98.

Example 308

N,N'-(4,4'-Thiobis(4,1-phenylene))bis(4-(dimethylamino)benzamide) (Compound 408)

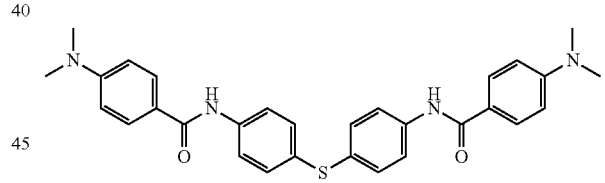

Compound 408 was prepared according to the procedure described in Scheme IV from 4,4'-diaminodiphenylamine and 4-dimethylaminobenzoate. [M+H]+ calcd for $C_{30}H_{30}N_4O_2S$: 511.2. found: 510.94.

Example 309 tert-butyl (4-(4-(4-morpholinobenzamido)piperidine-1-carbonyl)phenyl)carbamate (Compound 409)

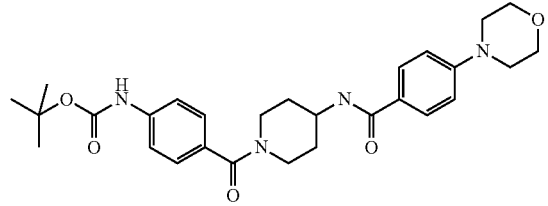 [SMILES: CC(C)(C)OC(=O)Nc1ccc(C(=O)N2CCC(NC(=O)c3ccc(N4CCOCC4)cc3)CC2)cc1]

Compound 409 was prepared according to the procedure described in Scheme IV from 4-aminobenzoate and 4-(4-dimethylaminophenyl)piperidine. [M+H]$^+$ calcd for C$_{28}$H$_{36}$N$_4$O$_5$: 509.2. found: 508.99.

Example 310

N-(4-(4-Morpholinophenylamino)phenyl)-4-dimethylaminobenzamide (Compound 410)

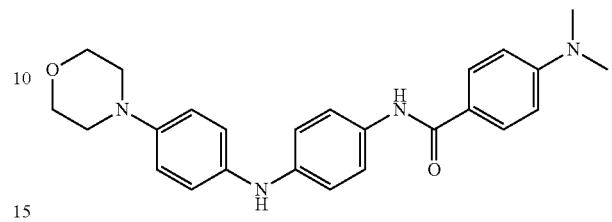

Compound 410 was prepared according to the procedure described in Scheme IV from 4,4'-diaminodiphenylamine and 4-dimethylaminobenzoate. [M+H]$^+$ calcd for C$_{25}$H$_{29}$N$_4$O$_2$: 417.2. found: 417.01.

Example 311

4-Dimethylamino-N-(4-(2-(4-(4-hydroxypiperidinyl)phenyl)-1H-benzimidazol-5-ylcarbamoyl)phenyl)benzamide (Compound 411)

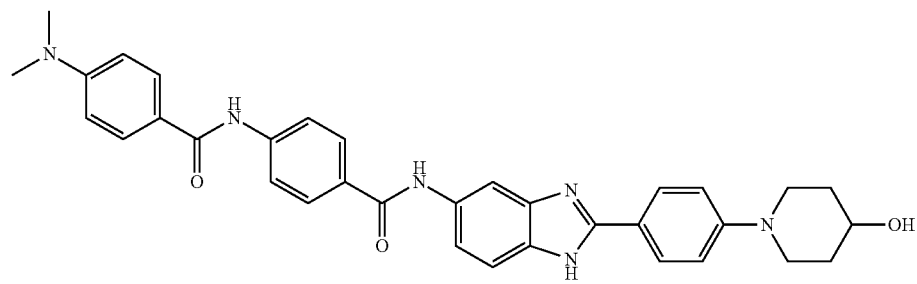 [SMILES: CN(C)c1ccc(C(=O)Nc2ccc(C(=O)Nc3ccc4[nH]c(-c5ccc(N6CCC(O)CC6)cc5)nc4c3)cc2)cc1]

Compound 411 was prepared according to the procedure similar to that described in Scheme III from 3,4-dinitro-N-(4-aminobenzoyl)aniline and 4-(4-hydroxypiperidinyl)benzaldehyde. [M+H]$^+$ calcd for C$_{34}$H$_{34}$N$_6$O$_3$: 575.2. found: 575.07.

Example 312

4-Dimethylamino-N-(4-(2-(4-(bis(2-hydroxyethyl)amino)phenyl)-1H-benzimidazol-5-ylcarbamoyl)phenyl)benzamide (Compound 412)

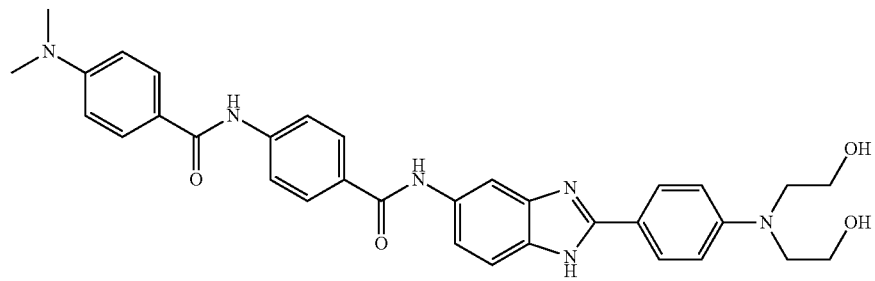 [SMILES: CN(C)c1ccc(C(=O)Nc2ccc(C(=O)Nc3ccc4[nH]c(-c5ccc(N(CCO)CCO)cc5)nc4c3)cc2)cc1]

Compound 412 was prepared according to the procedure similar to that described in Scheme III from 3,4-dinitro-N-(4-aminobenzoyl)aniline and 4-bis(2-hydroxyethyl)aminobenzaldehyde. [M+H]$^+$ calcd for $C_{33}H_{34}N_6O_4$: 579.2. found: 579.06.

Example 313

N-(2-(4-(1,4-Dioxa-8-azaspiro[4,5]decan-8-yl)phenyl)-1H-benzimidazol-5-yl)-4-morpholinobenzamide (Compound 413)

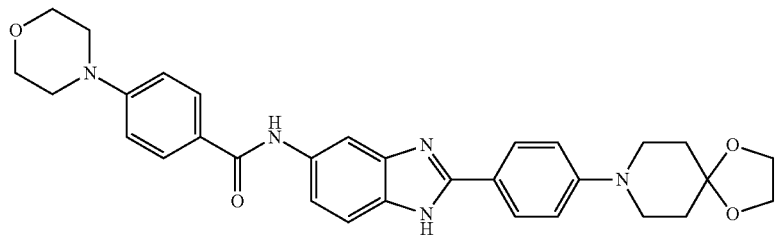 [SMILES: O=C(Nc1ccc2[nH]c(-c3ccc(N4CCC5(CC4)OCCO5)cc3)nc2c1)c1ccc(N2CCOCC2)cc1]

Compound 413 was prepared according to the procedure similar to that described in Scheme III from 3,4-dinitro-N-(4-morpholinobenzoyl)aniline and 4-(1,4-dioxa-8-azaspiro[4,5]decan-8-yl)benzaldehyde. [M+H]$^+$ calcd for $C_{31}H_{33}N_5O_4$: 540.25. found: 540.05.

Example 314

N-(2-(4-(4-(2-Hydroxyethyl)piperidinyl)phenyl)-1H-benzimidazol-5-yl)-4-morpholinobenzamide (Compound 414)

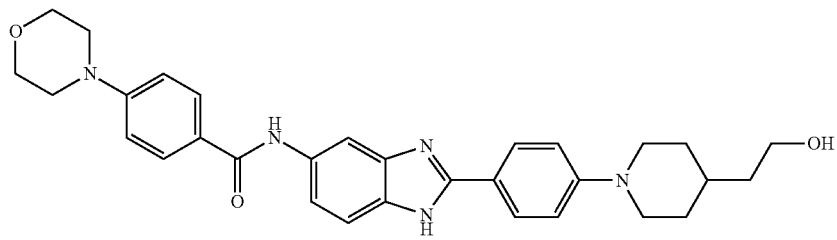 [SMILES: O=C(Nc1ccc2[nH]c(-c3ccc(N4CCC(CCO)CC4)cc3)nc2c1)c1ccc(N2CCOCC2)cc1]

Compound 414 was prepared according to the procedure similar to that described in Scheme III from 3,4-dinitro-N-(4-morpholinobenzoyl)aniline and 4-(2-hydroxyethyl)piperidinylbenzaldehyde. [M+H]$^+$ calcd for $C_{31}H_{35}N_5O_3$: 526.27. found: 526.11.

Example 315

N-(2-(4-(4-Cyclopropanecarbonylpiperazinyl)phenyl)-1H-benzimidazol-5-yl)-4-morpholinobenzamide (Compound 415)

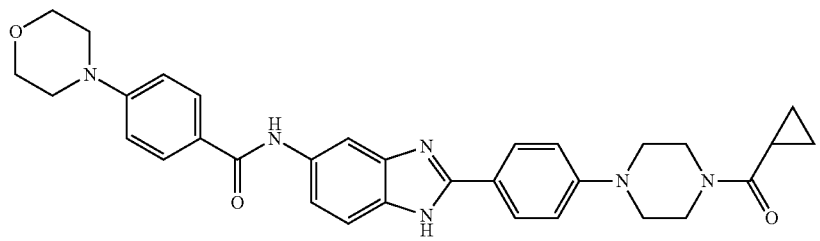 [SMILES: O=C(Nc1ccc2[nH]c(-c3ccc(N4CCN(C(=O)C5CC5)CC4)cc3)nc2c1)c1ccc(N2CCOCC2)cc1]

Compound 415 was prepared according to the procedure similar to that described in Scheme III from 3,4-dinitro-N-(4-morpholinobenzoyl)aniline and 4-(4-cyclopropanecarbonylpiperazinyl)benzaldehyde. [M+H]$^+$ calcd for C$_{32}$H$_{34}$N$_6$O$_3$: 551.27. found: 551.10.

Example 316

N-(2-(4-(4-(2-Hydroxymethyl)piperidinyl)phenyl)-1H-benzimidazol-5-yl)-4-morpholinobenzamide (Compound 416)

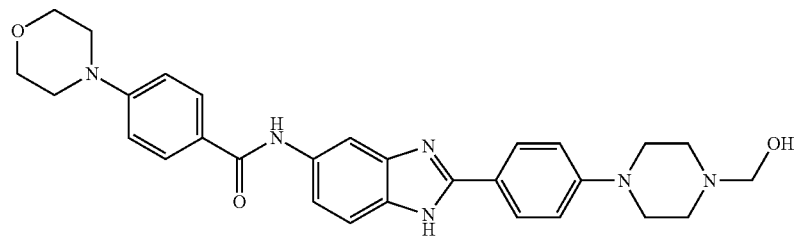 [SMILES: O=C(Nc1ccc2[nH]c(-c3ccc(N4CCN(CO)CC4)cc3)nc2c1)c1ccc(N2CCOCC2)cc1]

Compound 416 was prepared according to the procedure similar to that described in Scheme III from 3,4-dinitro-N-(4-morpholinobenzoyl)aniline and 4-(2-hydroxymethyl)piperidinylbenzaldehyde. [M+H]$^+$ calcd for C$_{30}$H$_{33}$N$_5$O$_3$: 512.26. found: 512.09.

Example 317

N-(2-(2-(4-Hydroxypiperidinyl)thien-5-yl)-1H-benzimidazol-5-yl)-4-morpholinobenzamide (Compound 417)

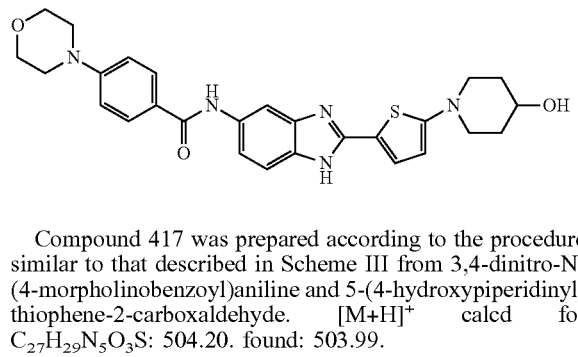

Compound 417 was prepared according to the procedure similar to that described in Scheme III from 3,4-dinitro-N-(4-morpholinobenzoyl)aniline and 5-(4-hydroxypiperidinyl)thiophene-2-carboxaldehyde. [M+H]$^+$ calcd for C$_{27}$H$_{29}$N$_5$O$_3$S: 504.20. found: 503.99.

Example 318

N-(2-(2-Morpholinothien-5-yl)-1H-benzimidazol-5-yl)-4-morpholinobenzamide (Compound 418)

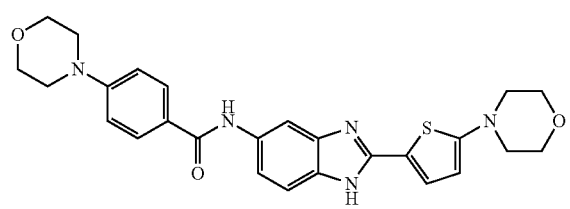 [SMILES: O=C(Nc1ccc2[nH]c(-c3ccc(N4CCOCC4)s3)nc2c1)c1ccc(N2CCOCC2)cc1]

Compound 418 was prepared according to the procedure similar to that described in Scheme III from 3,4-dinitro-N-(4-morpholinobenzoyl)aniline and 5-morpholinothiophene-2-carboxaldehyde. [M+H]$^+$ calcd for C$_{26}$H$_{27}$N$_5$O$_3$S: 490.18. found: 489.95.

Example 319

N-(2-(3-Morpholinomethylphenyl)-1H-benzimidazol-5-yl)-4-morpholinobenzamide (Compound 419)

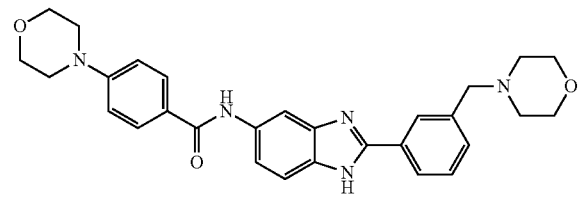 [SMILES: O=C(Nc1ccc2[nH]c(-c3cccc(CN4CCOCC4)c3)nc2c1)c1ccc(N2CCOCC2)cc1]

Compound 419 was prepared according to the procedure similar to that described in Scheme III from 3,4-dinitro-N-(4-morpholinobenzoyl)aniline and 3-morpholinomethylbenzaldehyde. [M+H]$^+$ calcd for C$_{29}$H$_{31}$N$_5$O$_3$: 498.2. found: 497.98.

Example 320

N-(2-(1-Methylpiperidin-4-yl)-1H-benzimidazol-5-yl)-4-morpholinobenzamide (Compound 420)

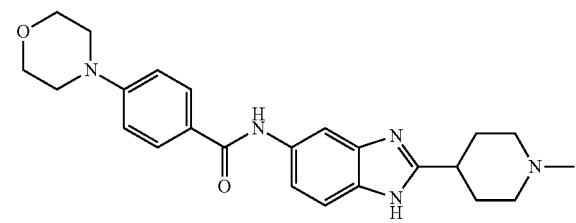 [SMILES: CN1CCC(c2nc3cc(NC(=O)c4ccc(N5CCOCC5)cc4)ccc3[nH]2)CC1]

Compound 420 was prepared according to the procedure similar to that described in Scheme III from 3,4-dinitro-N-

(4-morpholinobenzoyl)aniline and 4-(1-methylpiperidinyl) carboxaldehyde. [M+H]+ calcd for $C_{24}H_{29}N_5O_2$: 420.2. found: 420.04.

Example 321

N-(2-(4-(1,1-Dioxo-4-thiomorpholino)phenyl)-1H-benzimidazol-5-yl)-4-morpholinobenzamide (Compound 421)

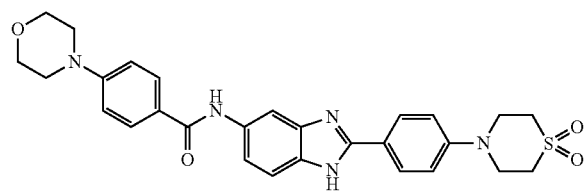 [SMILES: O=C(Nc1ccc2[nH]c(-c3ccc(N4CCS(=O)(=O)CC4)cc3)nc2c1)c1ccc(N2CCOCC2)cc1]

Compound 421 was prepared according to the procedure similar to that described in Scheme III from 3,4-dinitro-N-(4-morpholinobenzoyl)aniline and 4-(1,1-dioxo-4-thiomorpholino)benzaldehyde. [M+H]+ calcd for $C_{28}H_{29}N_5O_4S$: 532.1. found: 532.02.

Example 322

N-(2-(4-((4-methylpiperazin-1-yl)methyl)phenyl)-1H-benzo[d]imidazol-5-yl)-4-morpholinobenzamide (Compound 422)

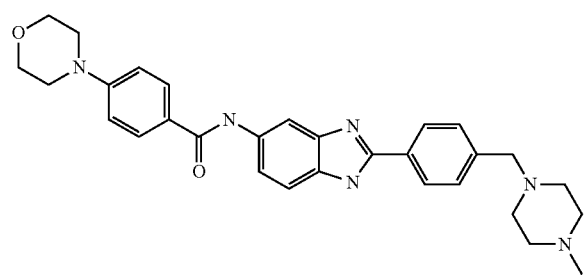 [SMILES: CN1CCN(Cc2ccc(-c3nc4cc(NC(=O)c5ccc(N6CCOCC6)cc5)ccc4[nH]3)cc2)CC1]

Compound 422 was prepared according to the procedure similar to that described in Scheme III from 3,4-dinitro-N-(4-morpholinobenzoyl)aniline and 4-piperazinomethylbenzaldehyde. [M+H]+ calcd for $C_{30}H_{34}N_6O_2$: 511.2. found: 511.07.

Example 323

N-(2-(4-(4-Methylpiperazino)phenyl)-1H-benzimidazol-5-yl)-4-morpholinobenzamide (Compound 423)

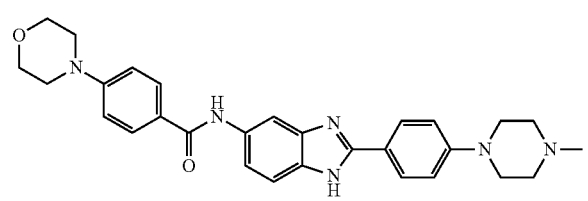 [SMILES: CN1CCN(c2ccc(-c3nc4cc(NC(=O)c5ccc(N6CCOCC6)cc5)ccc4[nH]3)cc2)CC1]

Compound 423 was prepared according to the procedure similar to that described in Scheme III from 3,4-dinitro-N-(4-morpholinobenzoyl)aniline and 4-(4-methylpiperazino)benzaldehyde. [M+H]+ calcd for $C_{29}H_{32}N_6O_2$: 497.2. found: 496.98.

Example 324

N-(2-(2-Methoxy-4-morpholinophenyl)-1H-benzimidazol-5-yl)-4-morpholinobenzamide (Compound 424)

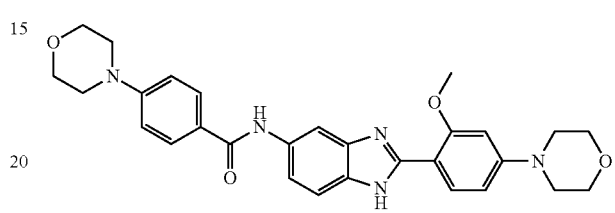

Compound 424 was prepared according to the procedure similar to that described in Scheme III from 3,4-dinitro-N-(4-morpholinobenzoyl)aniline and 2-methoxy-4-morpholinobenzaldehyde. [M+H]+ calcd for $C_{29}H_{31}N_5O_4$: 514.2. found: 514.05.

Example 325

N-(2-(4-Morpholinophenyl)-1H-benzimidazol-5-yl)-3,5-dihydroxybenzamide (Compound 425)

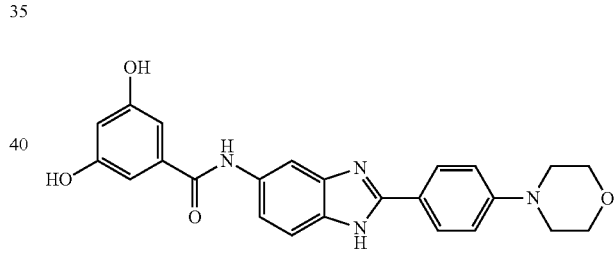

Compound 425 was prepared according to the procedure similar to that described in Scheme III from 3,4-dinitro-N-(3,5-dihydroxybenzoyl)aniline and 4-morpholinobenzaldehyde. [M+H]+ calcd for $C_{24}H_{22}N_4O_4$: 431.1. found: 431.18.

Example 326

N-(2-(4-Morpholinophenyl)-1H-benzimidazol-5-yl)-4-hydroxybenzamide (Compound 426)

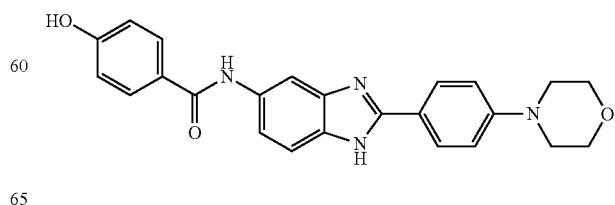

Compound 426 was prepared according to the procedure similar to that described in Scheme III from 3,4-dinitro-N-

(4-hydroxybenzoyl)aniline and 4-morpholinobenzaldehyde. [M+H]+ calcd for C24H22N4O3: 415.1. found: 415.17.

Example 327

N-(2-(4-Morpholinophenyl)-1H-benzimidazol-5-yl)-2-hydroxybenzamide (Compound 427)

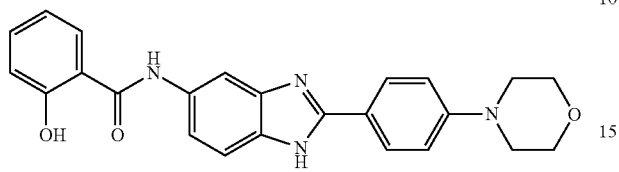

Compound 427 was prepared according to the procedure similar to that described in Scheme III from 3,4-dinitro-N-(2-hydroxybenzoyl)aniline and 4-morpholinobenzaldehyde. [M+H]+ calcd for C24H22N4O3: 415.1. found: 414.98.

Example 328

4-(4-(5-(5-(4-Morpholinophenyl)-1,3,4-oxadiazol-2-yl)-1H-benzimidazol-2-yl)phenyl) morpholine (Compound 428)

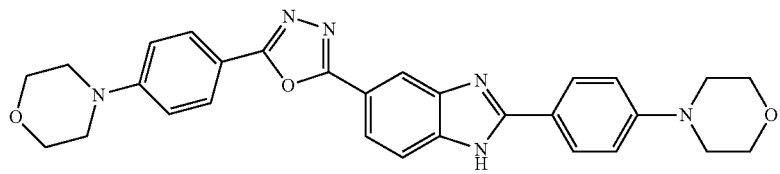 [SMILES: c1cc(N2CCOCC2)ccc1-c1nc2cc(-c3nnc(-c4ccc(N5CCOCC5)cc4)o3)ccc2[nH]1]

Compound 428 was prepared according to the procedure similar to that described in Scheme III from 3,4-dinitro-1-(5-(4-morpholinophenyl)-1,3,4-oxadiazol-2-yl)benzene and 4-morpholinobenzaldehyde. [M+H]+ calcd for C29H28N6O3: 590.23. found: 508.98.

Example 329

4-Dimethylamino-N-(2-(3-methoxyphenylamino)-1H-benzimidazol-5-yl)benzamide (Compound 429)

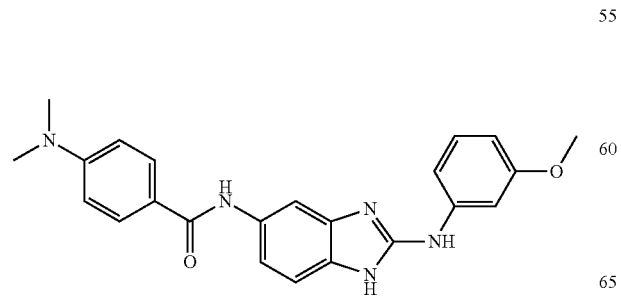

Compound 429 was prepared from 4-dimethylaminobenzoate and 5-amino-2-(3-methoxyphenylamino)benzimidazole by standard conditions. [M+H]+ calcd for C23H23N5O2: 402.1. found: 401.96.

Example 330

N-(2-Dimethylamino)-1H-benzimidazol-5-yl)-2-(4-dimethylaminophenyl)-1H-benzimidazole-5-carbamide (Compound 430)

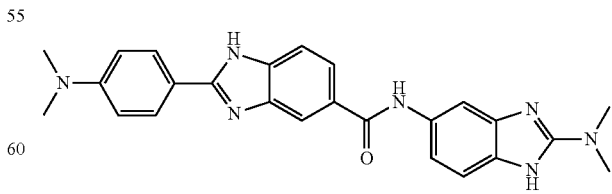

Compound 430 was prepared from 2-(4-dimethylaminophenyl)benzimidazole-5-carboxylate and 5-amino-2-(dimethylamino)benzimidazole by standard conditions. [M+H]+ calcd for C25H25N7O: 440.2. found: 440.01.

Example 331

2-(4-(2-Hydroxyethoxy)phenyl)-N-2-(4-(2-hydroxyethoxy)phenyl)-1H-benzimidazol-5-yl)-1H-benzimidazole-6-carboxamide (Compound 431)

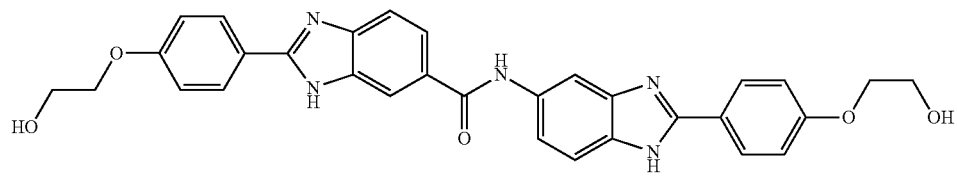 [SMILES: O=C(Nc1ccc2[nH]c(-c3ccc(OCCO)cc3)nc2c1)c1ccc2nc(-c3ccc(OCCO)cc3)[nH]c2c1]

Compound 431 was prepared according to the procedure similar to that described in Scheme V from 2-(4-(2-hydroxyethoxy)phenyl)-5-aminobenzimidazole and 2-(4-(2-hydroxyethoxy)phenyl)benzimidazole-5-carboxylate. $[M+H]^+$ calcd for $C_{31}H_{27}N_5O_5$: 550.2. found: 549.96.

Example 332

2-(4-Cyanophenyl)-N-2-(4-(2-hydroxyethoxy)phenyl)-1H-benzimidazol-5-yl)-1H-benzimidazole-6-carboxamide (Compound 432)

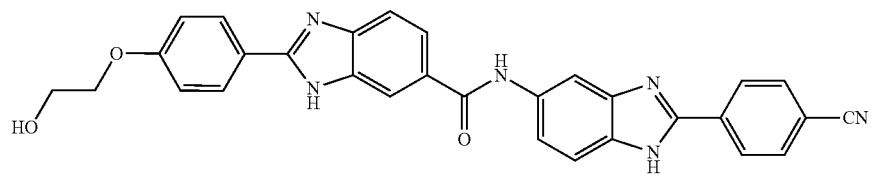 [SMILES: N#Cc1ccc(-c2nc3cc(NC(=O)c4ccc5nc(-c6ccc(OCCO)cc6)[nH]c5c4)ccc3[nH]2)cc1]

Compound 432 was prepared according to the procedure similar to that described in Scheme V from 2-(4-cyanophenyl)-5-aminobenzimidazole and 2-(4-(2-hydroxyethoxy)phenyl)benzimidazole-5-carboxylate. $[M+H]^+$ calcd for $C_{30}H_{22}N_6O_3$: 515.18. found: 514.92.

Example 333

2-(4-bis(2-Hydroxyethyl)aminophenyl)-N-2-(4-(2-hydroxyethoxy)phenyl)-1H-benzimidazol-5-yl)-1H-benzimidazole-6-carboxamide (Compound 433)

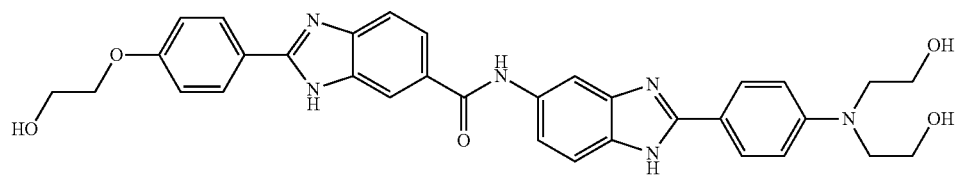 [SMILES: O=C(Nc1ccc2[nH]c(-c3ccc(N(CCO)CCO)cc3)nc2c1)c1ccc2nc(-c3ccc(OCCO)cc3)[nH]c2c1]

Compound 433 was prepared according to the procedure similar to that described in Scheme V from 2-(4-bis(2-hydroxyethyl)aminophenyl)-5-aminobenzimidazole and 2-(4-(2-hydroxyethoxy)phenyl)benzimidazole-5-carboxylate. $[M+H]^+$ calcd for $C_{33}H_{32}N_6O_5$: 593.2. found: 593.03.

Example 334

N,N'-bis-(2-(4-Morpholinophenyl)-1H-benzimidazol-5-yl)oxalamide (Compound 434)

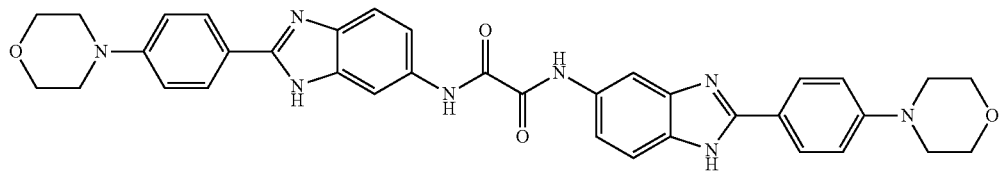 [SMILES: O=C(Nc1ccc2[nH]c(-c3ccc(N4CCOCC4)cc3)nc2c1)C(=O)Nc1ccc2nc(-c3ccc(N4CCOCC4)cc3)[nH]c2c1]

Compound 434 was prepared according to the procedure similar to that described in Scheme V from 2-(4-morpholinophenyl)-5-aminobenzimidazole and oxalic acid. [M+H]$^+$ calcd for $C_{36}H_{34}N_8O_4$: 643.2. found: 643.09.

Example 335

N,N'-bis(2-Dimethylamino-1H-benzimidazol-5-yl)terephthalamide (Compound 435)

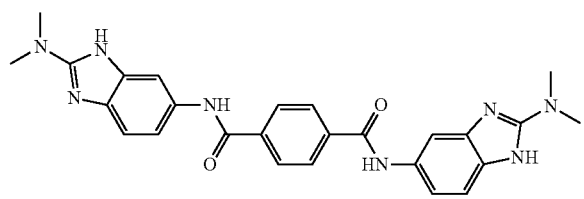

Compound 435 was prepared according to the procedure similar to that described in Scheme V from 2-dimethylamino-5-aminobenzimidazole and terephthalic acid. [M+H]$^+$ calcd for $C_{26}H_{26}N_8O_2$: 483.2. found: 483.02.

Example 336

N,N'-bis(2-Dimethylamino-1H-benzimidazol-5-yl)-3(E),3'(E)-(1,4-phenylene)bis(acrylamide) (Compound 436)

Compound 436 was prepared according to the procedure similar to that described in Scheme V from 2-dimethylamino-5-aminobenzimidazole and 3(E),3'(E)-(1,4-phenylene)bisacrylic acid. [M+H]$^+$ calcd for $C_{30}H_{30}N_8O_2$: 535.2. found: 535.09.

Example 337

N-(2-Dimethylamino)-1H-benzimidazol-5-yl)-4-(4-dimethylaminobenzamido)benzamide (Compound 437)

Compound 437 was prepared from 4-(4-dimethylaminobenzamido)benzoate and 5-amino-2-(dimethylamino)benzimidazole by standard conditions. [M+H]$^+$ calcd for $C_{25}H_{26}N_6O_2$: 443.2. found: 443.05.

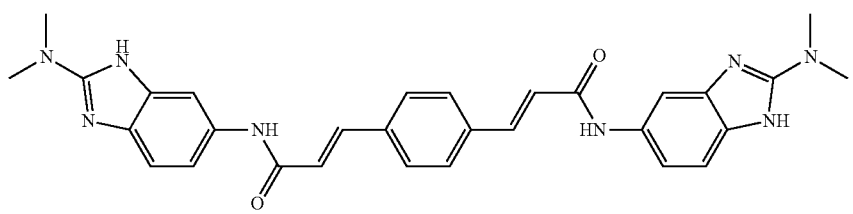

Example 338

N-(2-(3-Methoxyphenyl)amino)-1H-benzimidazol-5-yl)-4-(4-dimethylaminobenzamido)benzamide (Compound 438)

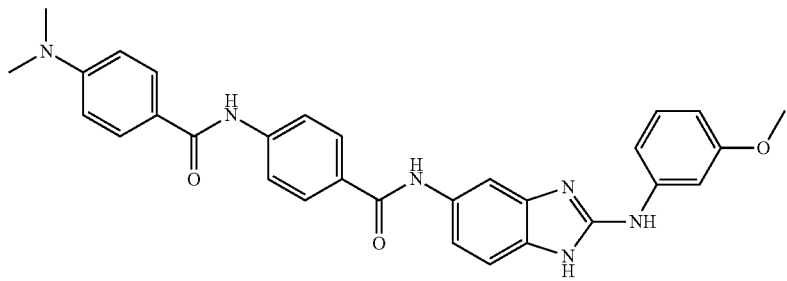

Compound 438 was prepared from 4-(4-dimethylaminobenzamido)benzoate and 5-amino-2-(3-methoxyphenyl)aminobenzimidazole by standard conditions. [M+H]$^+$ calcd for $C_{30}H_{28}N_6O_3$: 521.2. found: 521.06.

Example 339

N-(2-(3-Methoxyphenyl)amino-1H-benzimidazol-5-yl)-2-(4-dimethylaminophenyl)-1H-benzimidazole-5-carbamide (Compound 439)

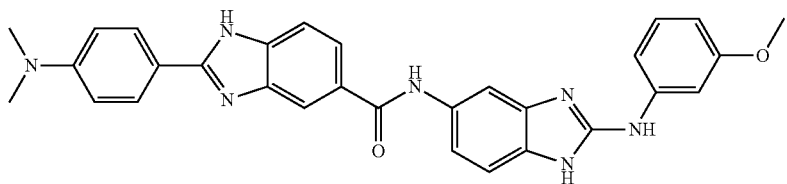

Compound 439 was prepared from 2-(4-dimethylaminophenyl)benzimidazole-5-carboxylate and 5-amino-2-(3-methoxyphenyl)aminobenzimidazole by standard conditions. [M+H]$^+$ calcd for $C_{30}H_{27}N_7O_2$: 518.2. found: 518.03.

Example 340

N-(2-(2,3-Dihydroxypropyl)amino-1H-benzimidazol-5-yl)-4-(4-dimethylaminobenzamido)benzamide (Compound 440)

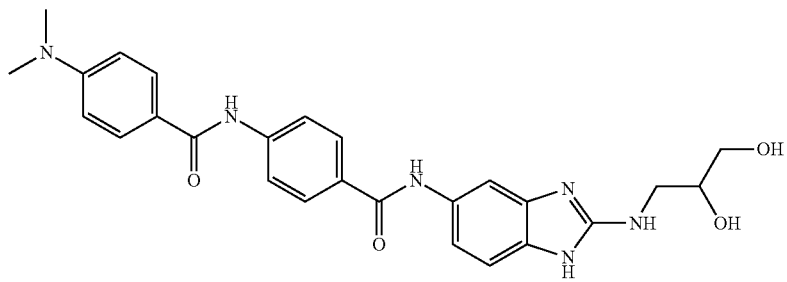 [SMILES: CN(C)c1ccc(C(=O)Nc2ccc(C(=O)Nc3ccc4[nH]c(NCC(O)CO)nc4c3)cc2)cc1]

Compound 440 was prepared from 4-(4-dimethylaminobenzamido)benzoate and 5-amino-2-(2,3-dihydroxypropylamino)benzimidazole by standard conditions. [M+H]+ calcd for $C_{26}H_{28}N_6O_4$: 489.2. found: 489.01.

Example 341

N,N'-(1,4-Cyclohexane)bis(2-(4-dimethylaminophenyl)-1H-benzimidazole-5-carboxamide) (Compound 441)

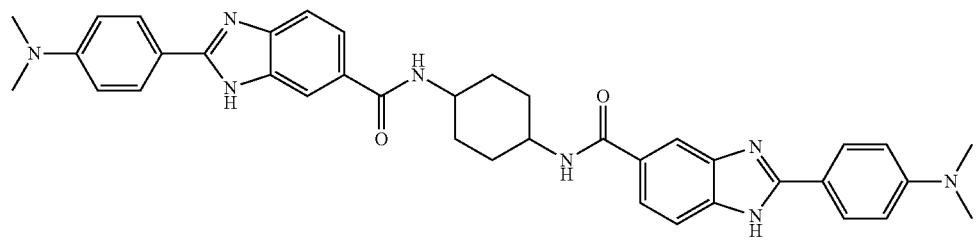

Compound 441 was prepared according to the procedure similar to that described in Scheme V from 1,4-cyclohexanediamine and 2-(4-dimethylaminophenyl)benzimidazole-5-carboxylate. [M+H]+ calcd for $C_{38}H_{40}N_8O_2$: 641.33. found: 641.24.

Example 342

N-(2-(4-Dimethylaminophenyl)-1H-benzimidazol-5-yl)-4-(4-dimethylaminobenzamido) benzamide (Compound 442)

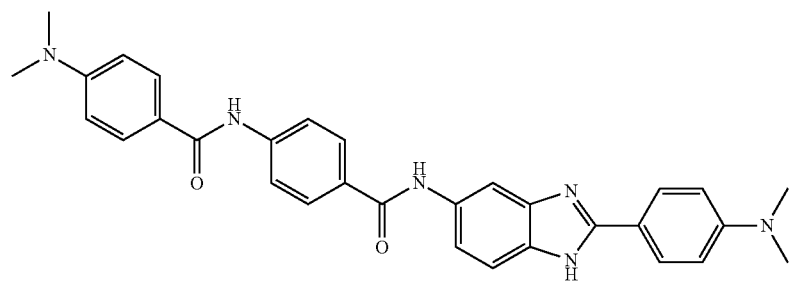

Compound 442 was prepared from 4-(4-dimethylaminobenzamido)benzoate and 5-amino-2-(4-dimethylaminophenyl)benzimidazole by standard conditions. [M+H]+ calcd for $C_{31}H_{30}N_6O_2$: 519.2. found: 518.99.

Example 343

N-(4-(4-Dimethylaminobenzamido)phenyl)-2-(4-dimethylaminophenyl)-1H-benzimidazole-5-carboxamide (Compound 443)

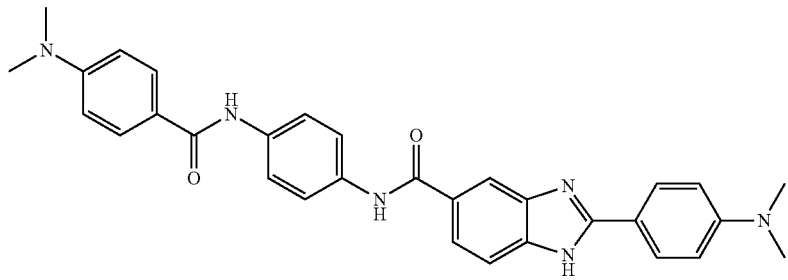

Compound 443 was prepared from 4-(4-dimethylaminobenzamido)aniline and 2-(4-dimethylaminophenyl)benzimidazole-5-carboxylate by standard conditions. [M+H]$^+$ calcd for $C_{31}H_{30}N_6O_2$: 519.2. found: 519.04.

Example 344

4-(dimethylamino)-N-(4-((2-(4-methoxyphenyl)-1H-benzo[d]imidazol-5-yl)carbamoyl)phenyl)benzamide (Compound 444)

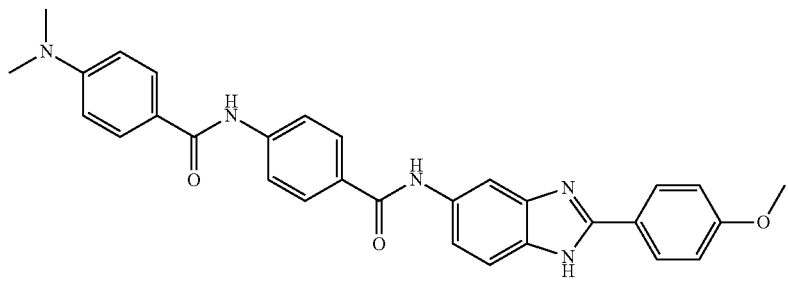

Compound 444 was prepared from 4-(4-dimethylaminobenzamido)aniline and 2-(4-methoxyphenyl)benzimidazole-5-carboxylate by standard conditions. [M+H]$^+$ calcd for $C_{30}H_{27}N_5O_3$: 506.2. found: 507.02.

Example 345

N-(4-(4-Dimethylaminobenzamido)phenyl)-1H-benzimidazole-5-carboxamide (Compound 445)

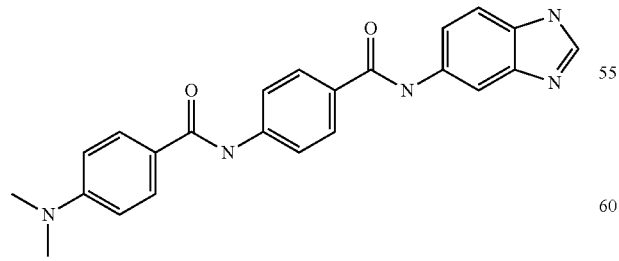

Compound 445 was prepared from 4-(4-dimethylaminobenzamido)aniline and benzimidazole-5-carboxylate by standard conditions. [M+H]$^+$ calcd for $C_{23}H_{21}N_5O_2$: 400.1. found: 400.01.

Example 346

N-(2-(4-(4-(2-Morpholinoethyl)piperidino)phenyl)-1H-benzimidazol-5-yl)-4-morpholinobenzamide (Compound 446)

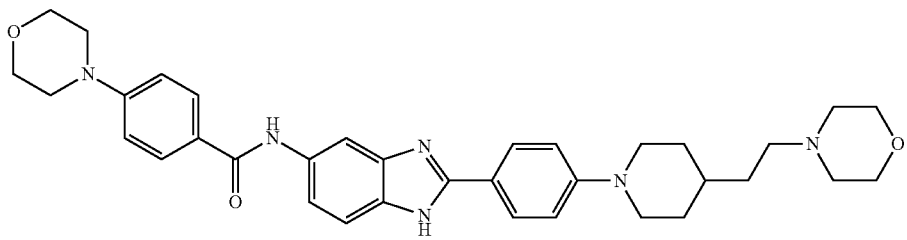 [SMILES: O=C(Nc1ccc2[nH]c(-c3ccc(N4CCC(CCN5CCOCC5)CC4)cc3)nc2c1)c1ccc(N2CCOCC2)cc1]

Compound 446 was prepared from 4-morpholinobenzoate and 5-amino-2-(4-(4-(2-morpholinoethyl)piperidino)phenyl)benzimidazole by standard conditions. [M+H]$^+$ calcd for: $C_{35}H_{42}N_6O_3$; 595.33 found: 595.12.

Example 347

N-(2-(4-(4-Morpholinocarbonyl)piperidino)phenyl)-1H-benzimidazol-5-yl)-4-morpholinobenzamide (Compound 447)

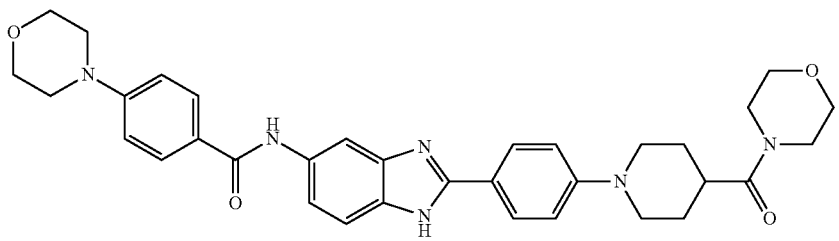 [SMILES: O=C(Nc1ccc2[nH]c(-c3ccc(N4CCC(C(=O)N5CCOCC5)CC4)cc3)nc2c1)c1ccc(N2CCOCC2)cc1]

Compound 447 was prepared from 4-morpholinobenzoate and 5-amino-2-(4-(4-morpholinocarbonyl)piperidino)phenylbenzimidazole by standard conditions. [M+H]$^+$ calcd for $C_{34}H_{38}N_6O_4$: 595.3. found: 595.13.

Example 348

N-(2-(4-(4-Morpholinocarbonylmethyl)piperazino)phenyl)-1H-benzimidazol-5-yl)-4-morpholinobenzamide (Compound 448)

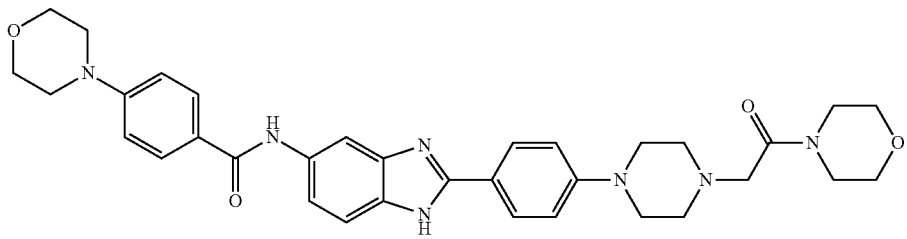 [SMILES: O=C(Nc1ccc2[nH]c(-c3ccc(N4CCN(CC(=O)N5CCOCC5)CC4)cc3)nc2c1)c1ccc(N2CCOCC2)cc1]

Compound 448 was prepared from 4-morpholinobenzoate and 5-amino-2-(4-(4-morpholinocarbonylmethyl)piperazino)phenylbenzimidazole by standard conditions. [M+H]$^+$ calcd for $C_{34}H_{39}N_7O_4$: 610.3. found: 610.11.

Example 349

4-(5-Methylsulfonylamido)-1H-benzimidazol-2-yl)-N-(4-morpholinophenyl)benzamide (Compound 449)

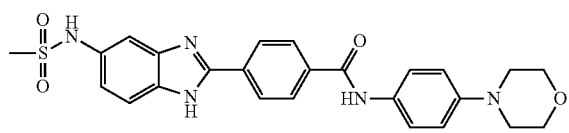 [SMILES: CS(=O)(=O)Nc1ccc2[nH]c(-c3ccc(C(=O)Nc4ccc(N5CCOCC5)cc4)cc3)nc2c1]

Compound 449 was prepared from 4-morpholinoaniline and 4-(5-methylsulfonylamino-1H-benzimidazol-2-yl)benzoate by standard conditions. $[M+H]^+$ calcd for $C_{25}H_{25}N_5O_4S$: 492.1. found: 491.97.

Example 350

4-(5-Cyano-1H-benzimidazol-2-yl)-N-(4-morpholinophenyl)benzamide (Compound 450)

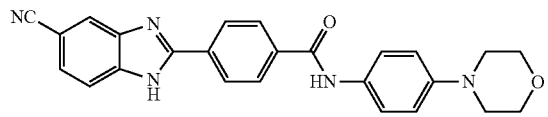 [SMILES: N#Cc1ccc2[nH]c(-c3ccc(C(=O)Nc4ccc(N5CCOCC5)cc4)cc3)nc2c1]

Compound 450 was prepared from 4-morpholinoaniline and 4-(5-cyano-1H-benzimidazol-2-yl)benzoate by standard conditions. $[M+H]^+$ calcd for $C_{25}H_{21}N_5O_2$: 424.1. found: 423.95.

Example 351

4-(5-(3-Methyl-5-oxo-2,5-dihydro-1H-pyrazol-1-yl)-1H-benzimidazol-2-yl)-N-(4-morpholinophenyl)benzamide (Compound 451)

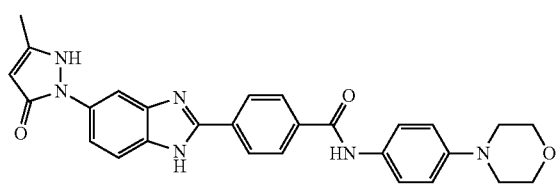 [SMILES: Cc1cc(=O)n(-c2ccc3[nH]c(-c4ccc(C(=O)Nc5ccc(N6CCOCC6)cc5)cc4)nc3c2)[nH]1]

Compound 451 was prepared from 4-morpholinoaniline and 4-(5-(3-methyl-5-oxo-2,5-dihydro-1H-pyrazol-1-yl)-1H-benzimidazol-2-yl)benzoate by standard conditions. $[M+H]^+$ calcd for $C_{28}H_{26}N_6O_3$: 495.2. found: 495.01.

Example 352

5-Amino-(2-(4-(4-morpholinocarbonylmethyl)piperazino)phenyl)-1H-benzimidazole (Compound 452)

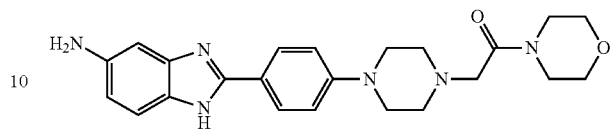

Compound 452 was prepared according to the procedure similar to that described in Scheme III from 3,4-dinitroaniline and 2-(4-(4-morpholinocarbonylmethyl)piperazino)benzaldehyde. $[M+H]^+$ calcd for $C_{23}H_{28}N_6O_2$: 421.2. found: 420.98.

Example 353

4-(5-Amino-1H-benzimidazol-2-yl)-N-(4-morpholinophenyl)benzamide (Compound 453)

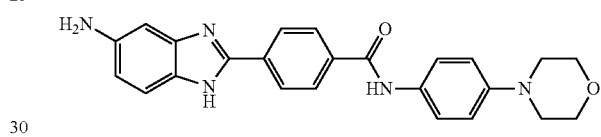

Compound 453 was prepared from 4-morpholinoaniline and 4-(5-amino-1H-benzimidazol-2-yl)benzoate by standard conditions. $[M+H]^+$ calcd for $C_{24}H_{23}N_5O_2$: 414.1. found: 413.97.

Example 354

4-(5-Acetamino-1H-benzimidazol-2-yl)-N-(4-morpholinophenyl)benzamide (Compound 454)

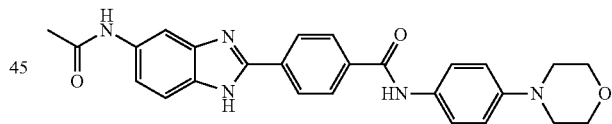

Compound 454 was prepared from 4-morpholinoaniline and 4-(5-acetamino-1H-benzimidazol-2-yl)benzoate by standard conditions. $[M+H]^+$ calcd for $C_{26}H_{25}N_5O_3$: 456.2. found: 455.95.

Example 355

4-(5-(2,2,2-Trifluoroethyl)amino-1H-benzimidazol-2-yl)-N-(4-morpholinophenyl)benzamide (Compound 455)

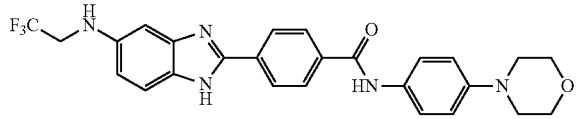

Compound 455 was prepared from 4-morpholinoaniline and 4-(5-bis(2,2,2-trifluoroethyl)amino-1H-benzimidazol-2-yl)benzoate by standard conditions. [M+H]+ calcd for C26H24F3N5O2: 496.1. found: 496.02.

Example 356

4-(5-bis(2,2,2-Trifluoroethyl)amino-1H-benzimidazol-2-yl)-N-(4-morpholinophenyl)benzamide (Compound 456)

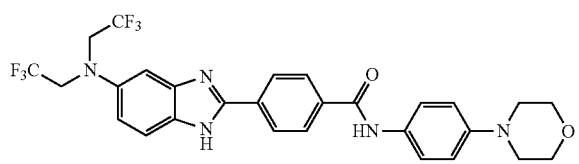 [SMILES: O=C(Nc1ccc(N2CCOCC2)cc1)c1ccc(-c2nc3cc(N(CC(F)(F)F)CC(F)(F)F)ccc3[nH]2)cc1]

Compound 456 was prepared from 4-morpholinoaniline and 4-(5-bis(2,2,2-trifluoroethyl)amino-1H-benzimidazol-2-yl)benzoate by standard conditions. [M+H]+ calcd for C28H25F6N5O2: 578.1. found: 578.04.

Example 357

4-(5-Morpholino-1H-benzimidazol-2-yl)-N-(4-morpholinophenyl)benzamide (Compound 457)

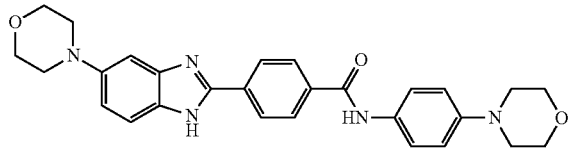 [SMILES: O=C(Nc1ccc(N2CCOCC2)cc1)c1ccc(-c2nc3cc(N4CCOCC4)ccc3[nH]2)cc1]

Compound 457 was prepared from 4-morpholinoaniline and 4-(5-morpholino-1H-benzimidazol-2-yl)benzoate by standard conditions. [M+H]+ calcd for C28H29N5O3: 484.2. found: 484.01.

Example 358

4-(1H-Benzimidazol-2-yl)-N-(4-morpholinophenyl)benzamide (Compound 458)

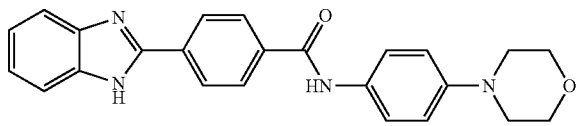 [SMILES: O=C(Nc1ccc(N2CCOCC2)cc1)c1ccc(-c2nc3ccccc3[nH]2)cc1]

Compound 458 was prepared from 4-morpholinoaniline and 4-(1H-benzimidazol-2-yl)benzoate by standard conditions. [M+H]+ calcd for C24H22N4O2: 399.17. found: 398.98.

Example 359

4-(5-Hydroxy-1H-benzimidazol-2-yl)-N-(4-morpholinophenyl)benzamide (Compound 459)

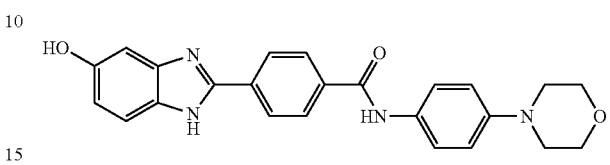

Compound 459 was prepared from 4-morpholinoaniline and 4-(5-hydroxy-1H-benzimidazol-2-yl)benzoate by standard conditions. [M+H]+ calcd for C24H22N4O3: 415.1. found: 415.05.

Example 360

4-(5-Methoxy-1H-benzimidazol-2-yl)-N-(4-morpholinophenyl)benzamide (Compound 460)

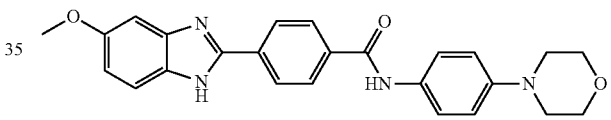

Compound 460 was prepared from 4-morpholinoaniline and 4-(5-methoxy-1H-benzimidazol-2-yl)benzoate by standard conditions. [M+H]+ calcd for C25H24N4O3: 429.1. found: 428.97.

Example 361

4-(1H-Benzimidazol-2-yl)-N-(4-(4-cyclopropanecarbonylpiperazino)phenyl)benzamide (Compound 461)

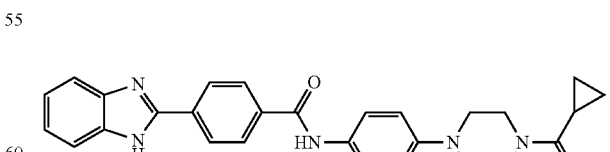

Compound 461 was prepared from 4-(4-cyclopropanecarbonyl)piperazinoaniline and 4-(1H-benzimidazol-2-yl)benzoate by standard conditions. [M+H]+ calcd for C28H27N5O2: 466.2. found: 465.99.

Example 362

4-(5-Amino-1H-benzimidazol-2-yl)-N-(4-(4-cyclopropanecarbonylpiperazino)phenyl)benzamide (Compound 462)

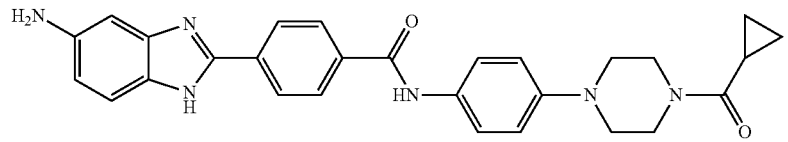 [SMILES: Nc1ccc2[nH]c(-c3ccc(C(=O)Nc4ccc(N5CCN(C(=O)C6CC6)CC5)cc4)cc3)nc2c1]

Compound 462 was prepared from 4-(4-cyclopropanecarbonyl)piperazinoaniline and 4-(5-amino-1H-benzimidazol-2-yl)benzoate by standard conditions. [M+H]$^+$ calcd for $C_{28}H_{28}N_6O_2$: 481.2. found: 481.05.

Example 363

4-(5-(2,2,2-Trifluoroethoxy)-1H-benzimidazol-2-yl)-N-(4-morpholinophenyl)benzamide (Compound 463)

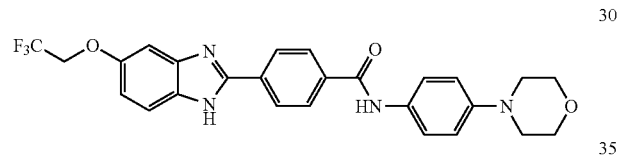

Compound 463 was prepared from 4-morpholinoaniline and 4-(5-(2,2,2-trifluoroethoxy)-1H-benzimidazol-2-yl)benzoate by standard conditions. [M+H]$^+$ calcd for $C_{26}H_{23}F_3N_4O_3$: 497.1. found: 496.97.

Example 364

N,N'-(4,4'-(1,3,4-Oxadiazole-2,5-diyl)bis(4,1-phenylene))bis(4-dimethylaminobenzamide) (Compound 464)

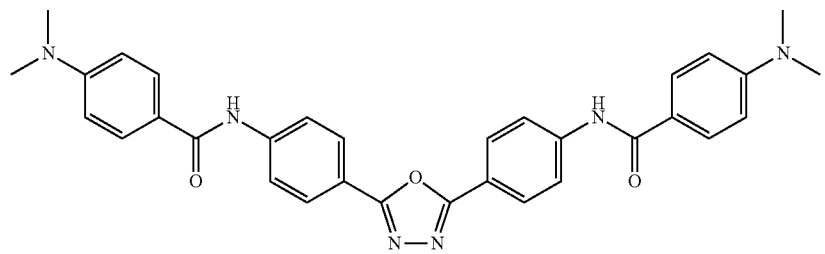

Compound 464 was prepared according to the procedure described in Scheme IV from 4,4'-(1,3,4-oxadiazole-2,5-diyl)bis(4,1-phenylene)diamine and 4-dimethylaminobenzoate. $^1$H NMR (500 MHz, DMSO-d$_6$) δ 10.20 (s, 2H), 8.06 (dq, J=2, 9 Hz, 8H), 7.90 (d, J=9 Hz, 4H), 6.77 (d, J=9 Hz, 4H), 3.01 (s, 12H).

Example 365

N,N'-bis(2-(4-Morpholinophenylamino)-2-oxoethyl)biphenyl-4,4'-dicarboxamide (Compound 465)

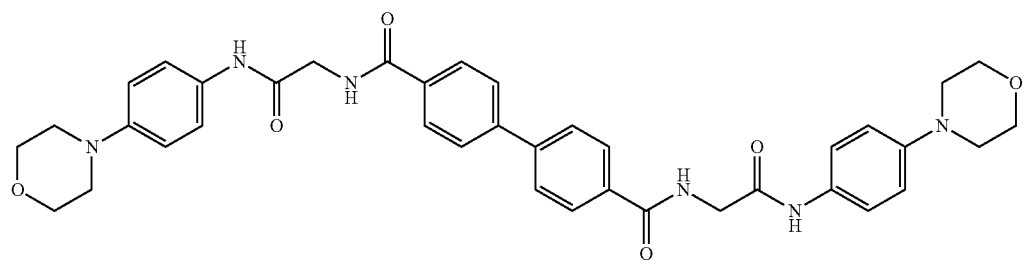 [SMILES: O=C(CNC(=O)c1ccc(-c2ccc(C(=O)NCC(=O)Nc3ccc(N4CCOCC4)cc3)cc2)cc1)Nc1ccc(N2CCOCC2)cc1]

Compound 465 was prepared according to the procedure described in Scheme IV from 4-morpholinoaniline, glycine, and 4,4'-biphenyldicarboxylate. [M+H]+ calcd for $C_{38}H_{40}N_6O_6$: 677.3. found: 677.23.

Example 366

4'-(2-(4-Morpholinophenylamino)-2-oxoethylcarbamoyl)biphenyl-4-carboxamide (Compound 466)

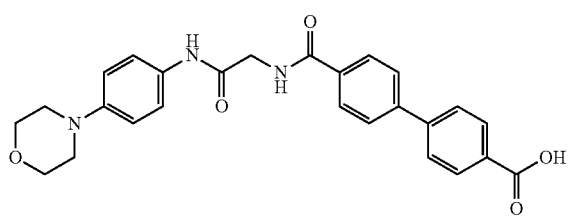 [SMILES: O=C(CNC(=O)c1ccc(-c2ccc(C(=O)O)cc2)cc1)Nc1ccc(N2CCOCC2)cc1]

Compound 466 was prepared according to the procedure described in Scheme IV from 4-morpholinoaniline, glycine, and 4,4'-biphenyldicarboxylic acid. [M+H]+ calcd for $C_{26}H_{25}N_3O_5$: 460.1. found: 459.92.

Example 367

N-(2-(4-Morpholinophenyl)amino-2-oxoethyl)-4-dimethylaminobenzamide (Compound 467)

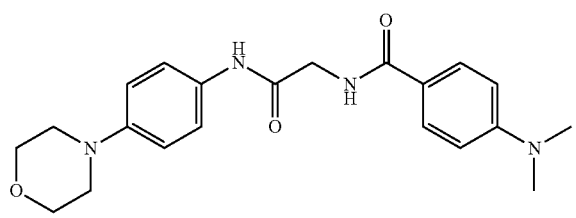 [SMILES: CN(C)c1ccc(C(=O)NCC(=O)Nc2ccc(N3CCOCC3)cc2)cc1]

Compound 467 was prepared according to the procedure described in Scheme IV from 4-morpholinoaniline, glycine, and 4-dimethylaminobenzoate. $^1$H NMR (500 MHz, CDCl$_3$) δ 8.46 (s, 1H), 7.74 (s, J=9 Hz, 2H), 6.82 (t, J=5.5 Hz, 1H), 6.68 (d, J=9 Hz, 2H), 4.25 (d, J=5.5 Hz, 2H), 3.85 (m, 4H), 3.11 (m, 4H), 3.04 (s, 6H).

Example 368

N,N'-bis(5-(Furan-2-yl)-1H-pyrazol-3-yl)biphenyl-4,4'-dicarboxamide (Compound 468)

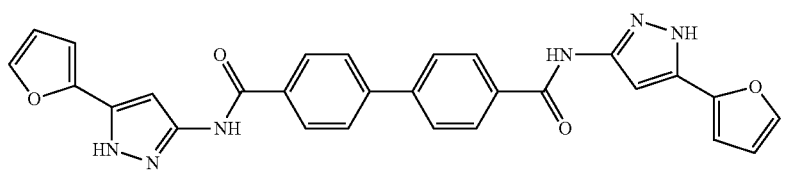 [SMILES: O=C(Nc1cc(-c2ccco2)[nH]n1)c1ccc(-c2ccc(C(=O)Nc3cc(-c4ccco4)[nH]n3)cc2)cc1]

Compound 468 was prepared from 3-amino-5-(2-furanyl)pyrazole and 4,4'-biphenyldicarboxylate. [M+H]+ calcd for $C_{28}H_{21}N_6O_4$: 505.1. found: 504.93.

Example 369

N,N'-bis(5-(Thiophen-2-yl)-1H-pyrazol-3-yl)biphenyl-4,4'-dicarboxamide (Compound 469)

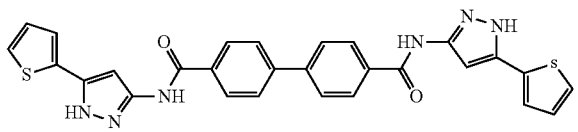

Compound 469 was prepared from 3-amino-5-(2-thienyl)pyrazole and 4,4'-biphenyldicarboxylate. [M+H]+ calcd for $C_{28}H_{21}N_6O_2S_2$: 537.1. found: 536.93.

Example 370

1,1'-bis(1,4-Phenylene)bis(3-(5-(4-methoxyphenyl)-1H-pyrazol-3-yl)thiourea) (Compound 470)

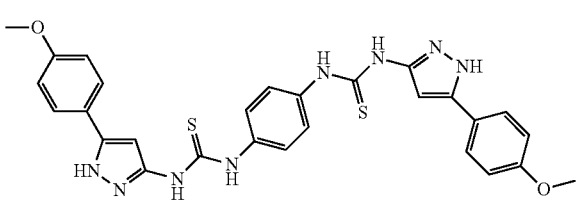

Compound 470 was prepared from 3-amino-5-(4-methoxyphenyl)pyrazole and 1,4-phenylenediamine [M+H]+ calcd for $C_{28}H_{27}N_8O_2S_2$: 571.1. found: 570.89.

Example 371

N-(5-(4-Methoxyphenyl)-1H-pyrazol-3-yl)-N'-(5-(4-methylphenyl)-1H-pyrazol-3-yl)terephthalamide (Compound 471)

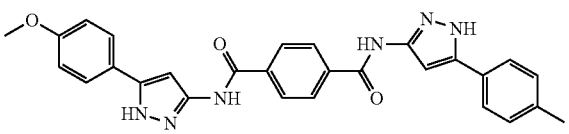

Compound 471 was prepared from 3-amino-5-(4-methoxyphenyl)pyrazole, 3-amino-5-(4-methylphenyl)pyrazole, and terephthalic acid. [M+H]+ calcd for $C_{28}H_{25}N_6O_3$: 493.2. found: 492.92.

Example 372

N,N'-bis(5-(4-Methylphenyl)-1H-pyrazol-3-yl)terephthalamide (Compound 472)

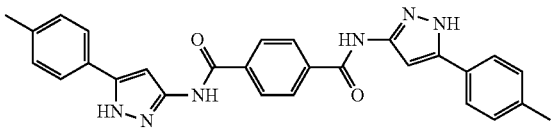

Compound 472 was prepared from 3-amino-5-(4-methylphenyl)pyrazole and terephthalic acid. [M+H]+ calcd for $C_{28}H_{25}N_6O_2$: 477.2. found: 476.92.

Example 373

N,N'-bis(5-(4-Methoxyphenyl)-1H-pyrazol-3-yl)terephthalamide (Compound 473)

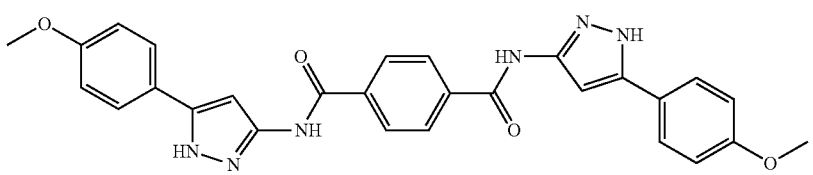

Compound 473 was prepared from 3-amino-5-(4-methoxyphenyl)pyrazole and terephthalic acid. [M+H]$^+$ calcd for $C_{28}H_{25}N_6O_4$: 509.1. found: 508.91.

Example 374

N,N'-bis(5-(4-Methoxyphenyl)-1H-pyrazol-3-yl)biphenyl-4,4'-dicarboxamide (Compound 474)

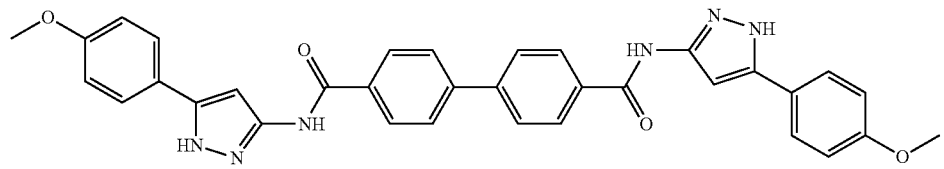

Compound 474 was prepared from 3-amino-5-(4-methoxyphenyl)pyrazole and biphenyl-4,4'-dicarboxylic acid. [M+H]$^+$ calcd for $C_{34}H_{29}N_6O_4$: 585.2. found: 585.01.

Example 375

N,N'-bis(5-Phenyl-1H-pyrazol-3-yl)biphenyl-4,4'-dicarboxamide (Compound 475)

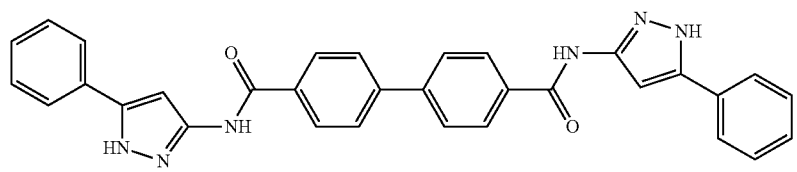 [SMILES: O=C(Nc1cc(-c2ccccc2)[nH]n1)c1ccc(-c2ccc(C(=O)Nc3cc(-c4ccccc4)[nH]n3)cc2)cc1]

Compound 475 was prepared from 3-amino-5-phenylpyrazole and biphenyl-4,4'-dicarboxylic acid. [M+H]$^+$ calcd for $C_{32}H_{25}N_6O_2$: 525.2. found: 524.98.

Example 376

N,N'-bis(5-(4-Methylphenyl)-1H-pyrazol-3-yl)biphenyl-4,4'-dicarboxamide (Compound 476)

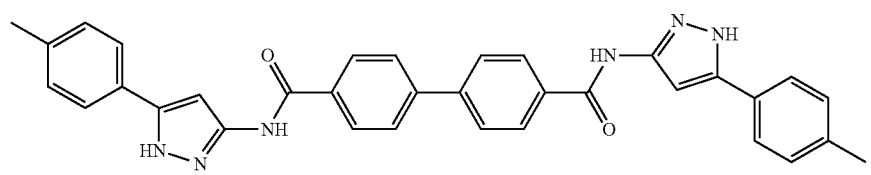

Compound 476 was prepared from 3-amino-5-(4-methylphenyl)pyrazole and biphenyl-4,4'-dicarboxylic acid. [M+H]$^+$ calcd for $C_{34}H_{29}N_6O_2$: 553.2. found: 553.06.

Example 377

N,N'-bis(5-(4-Methoxyphenyl)-1H-pyrazol-3-yl)-3 (E),3'(E)-(1,4-phenylene)bis(acrylamide) (Compound 477)

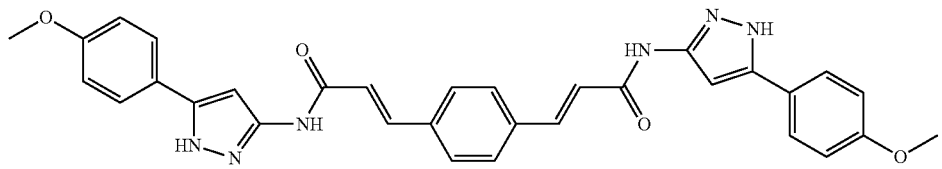

Compound 477 was prepared from 3-amino-5-(4-methoxyphenyl)pyrazole and 3 (E),3'(E)-(1,4-phenylene)bis (acrylic acid). [M+H]$^+$ calcd for $C_{32}H_{28}N_6O_4$: 561.23. found: 561.05.

Example 378

4,4'-(1,3-Phenylenebis(methylene)bis(azanediyl)bis (methylidene)bis(3-methyl-1-phenyl-1H-pyrazol-5 (4H)-one) (Compound 478)

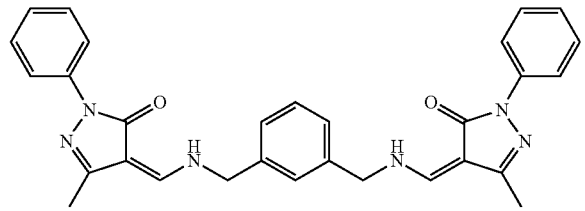 [SMILES: CC1=NN(c2ccccc2)C(=O)/C1=C\NCc1cccc(CN/C=C2\C(=O)N(c3ccccc3)N=C2C)c1]

Compound 478 was prepared from 3-methyl-1-phenyl-1H-pyrazol-5(4H)-one and 1,3-phenylenebis(methylamine). [M+H]$^+$ calcd for $C_{30}H_{28}N_6O_2$: 505.23. found: 505.07.

Example 379

N-(2-(4-(Pyridin-2-yl)phenyl)-1H-benzimidazol-5-yl)benzamide (Compound 479)

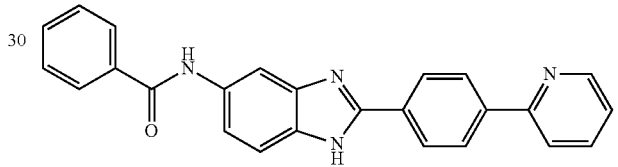

Compound 479 was prepared from 5-amino-2-(4-(pyridin-2-yl)phenyl)-1H-benzimidazole and benzoate by standard conditions. [M+H]$^+$ calcd for $C_{25}H_{18}N_4O$: 391.1. found: 390.91.

Example 380

4-(5-Cyclopropylpropiolamido-1H-benzimidazol-2-yl)-N-(4-morpholinophenyl)benzamide (Compound 480)

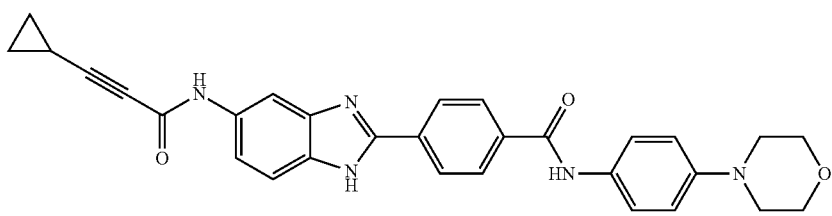 [SMILES: O=C(C#CC1CC1)Nc1ccc2[nH]c(-c3ccc(C(=O)Nc4ccc(N5CCOCC5)cc4)cc3)nc2c1]

Compound 480 was prepared from 4-morpholinoaniline and 4-(5-amino-1H-benzimidazol-2-yl)benzoate by standard conditions. [M+H]+ calcd for $C_{30}H_{27}N_5O_3$: 506.2. found: 506.01.

Example 381

4-(5-Trifluoromethoxy-1H-benzimidazol-2-yl)-N-(4-morpholinophenyl)benzamide (Compound 481)

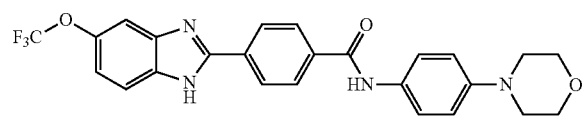

Compound 481 was prepared from 4-morpholinoaniline and 4-(5-trifluoromethoxy-1H-benzimidazol-2-yl)benzoate by standard conditions. [M+H]+ calcd for $C_{25}H_{21}F_3N_4O_3$: 483.1. found: 482.93.

Example 382

4-(5-Aminosulfonyl-1H-benzimidazol-2-yl)-N-(4-morpholinophenyl)benzamide (Compound 482)

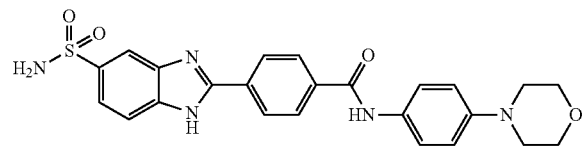 [SMILES: NS(=O)(=O)c1ccc2[nH]c(-c3ccc(C(=O)Nc4ccc(N5CCOCC5)cc4)cc3)nc2c1]

Compound 482 was prepared from 4-morpholinoaniline and 4-(5-aminosulfonyl-1H-benzimidazol-2-yl)benzoate by standard conditions. [M+H]+ calcd for $C_{24}H_{23}N_5O_4S$: 478.1. found: 477.93.

Example 383

N-(2-(4-(4-Dimethylaminophenylcarbamoyl)piperidino)-1H-benzimidazol-5-yl)4-dimethylaminobenzamide (Compound 483)

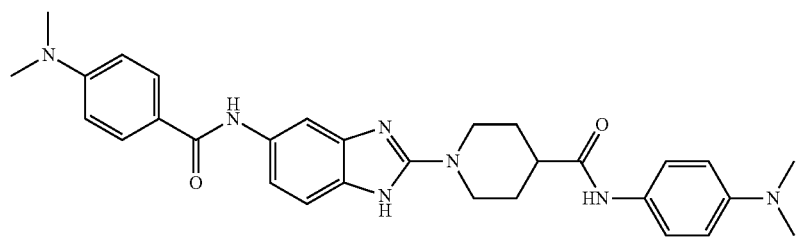

Compound 483 was prepared from 4-dimethylaminoaniline, 4-dimethylaminobenzoate, and 1-(5-amino-1H-benzimidazol-2-yl)piperidino-4-carboxylic acid by standard conditions.

[M+H]+ calcd for $C_{30}H_{35}N_7O_2$: 526.2. found: 526.13.

Example 384

N-(4-(4-Ethylaminobenzoyl)phenyl)-4-morpholinobenzamide (Compound 484)

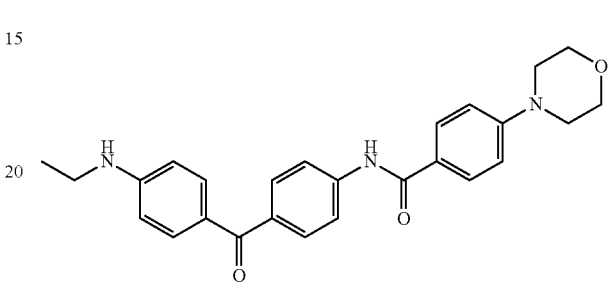

Compound 484 was prepared according to the procedure described in Scheme IV from 4,4'-diaminobenzophenone and 4-morpholinobenzoate. [M+H]+ calcd for $C_{26}H_{27}N_3O_3$: 430.0. found: 430.03.

Example 385

N-(4-(4-Aminobenzoyl)phenyl)-4-morpholinobenzamide (Compound 485)

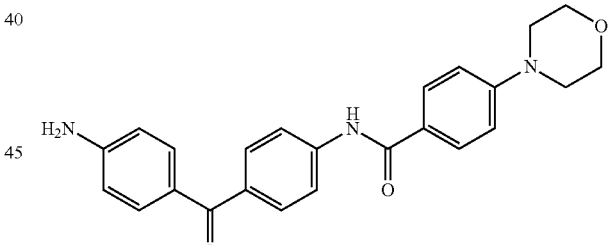

Compound 485 was prepared according to the procedure described in Scheme IV from 4,4'-diaminobenzophenone and 4-morpholinobenzoate. [M+H]+ calcd for $C_{24}H_{23}N_3O_3$: 402.0. found: 402.03.

Example 386

N-(4-(4-(2-Thienyl)carboxamido)benzoyl)phenyl)-4-fluorobenzamide (Compound 486)

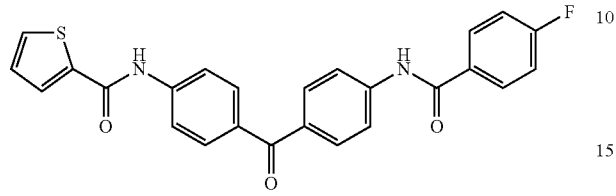

Compound 486 was prepared according to the procedure described in Scheme IV from 4,4'-diaminobenzophenone and 4-fluorobenzoate. [M+H]+ calcd for $C_{25}H_{17}FN_2O_3S$: 445.0. found: 444.94.

Example 387

N-(1-(4-Cyclopropanecarboxamidophenyl)-1H-indazol-5-yl)-4-(4-tert-butyloxycarbonylpiperazino)benzamide (Compound 487)

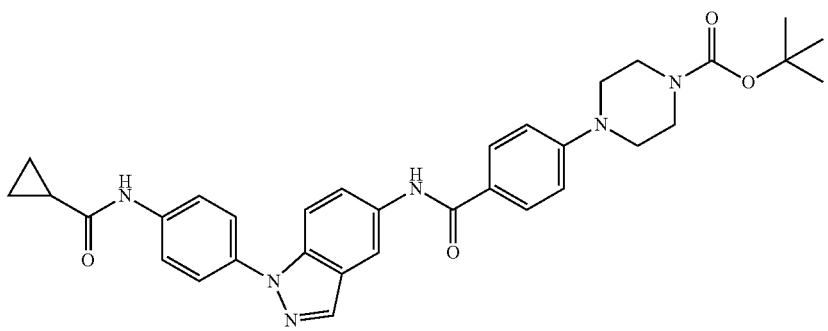 [SMILES: CC(C)(C)OC(=O)N1CCN(c2ccc(C(=O)Nc3ccc4c(cnn4-c4ccc(NC(=O)C5CC5)cc4)c3)cc2)CC1]

Compound 487 was prepared according to the procedure described in Scheme IV from 5-amino-1-(4-aminophenyl)indazole and 4-(4-tert-butyloxycarbonylpiperazino)benzoate. [M+H]+ calcd for $C_{33}H_{36}N_6O_4$: 581.28. found: 581.15.

Example 388

N-(1-(4-Cyclopropanecarboxamidophenyl)-1H-indazol-5-yl)-4-(4-cyclopropanecarbonylpiperazino)benzamide (Compound 488)

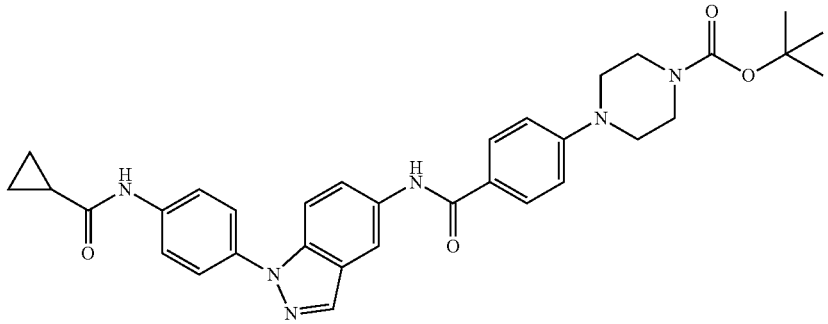 [SMILES: CC(C)(C)OC(=O)N1CCN(c2ccc(C(=O)Nc3ccc4c(cnn4-c4ccc(NC(=O)C5CC5)cc4)c3)cc2)CC1]

Compound 488 was prepared according to the procedure described in Scheme IV from 5-amino-1-(4-aminophenyl)indazole and 4-(4-cyclopropanecarbonylpiperazino)benzoate. [M+H]+ calcd for $C_{32}H_{32}N_6O_3$: 549.25. found: 549.16.

Example 389

N-(4-(4-(2-Thienylcarboxamido)benzoyl)phenyl)-4-morpholinobenzamide (Compound 489)

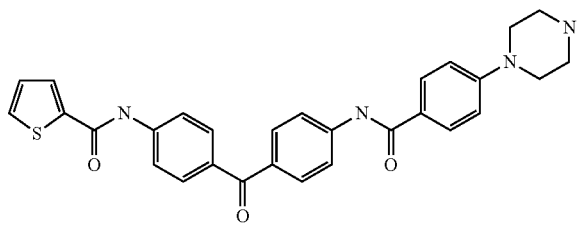 [SMILES: O=C(Nc1ccc(C(=O)c2ccc(NC(=O)c3cccs3)cc2)cc1)c1ccc(N2CCNCC2)cc1]

Compound 489 was prepared according to the procedure described in Scheme IV from 4,4'-diaminobenzophenone and 4-morpholinobenzoate. $^1$H NMR (500 MHz, CD$_3$OD) δ 7.98 (d, J=5 Hz, 1H), 7.90 (dd, J=2.5, 10.6 Hz, 6H), 7.82 (m, 4H), 7.76 (d, J=5 Hz, 1H), 7.20 (t, J=5 Hz, 1H), 7.03 (d, J=10.6 Hz, 2H), 3.33 (m, 4H), 2.98 (m, 4H).

Example 390

N-(4-(4-(3-Thienylcarboxamido)benzoyl)phenyl)-4-morpholinobenzamide (Compound 490)

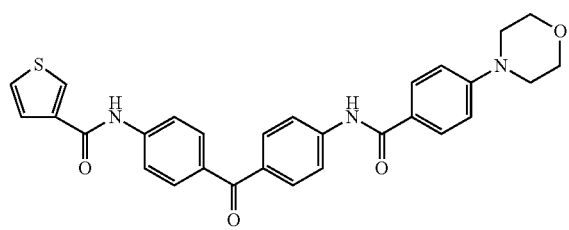 [SMILES: O=C(Nc1ccc(C(=O)c2ccc(NC(=O)c3ccsc3)cc2)cc1)c1ccc(N2CCOCC2)cc1]

Compound 490 was prepared according to the procedure described in Scheme IV from 4,4'-diaminobenzophenone and 4-morpholinobenzoate. [M+H]$^+$ calcd for C$_{29}$H$_{25}$N$_3$O$_4$S: 512.1. found: 512.09.

Example 391

N-(4-(4-(2-(5-Methylthienyl)carboxamido)benzoyl)phenyl)-4-morpholinobenzamide (Compound 491)

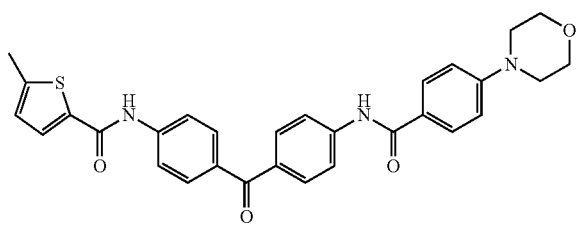 [SMILES: Cc1ccc(C(=O)Nc2ccc(C(=O)c3ccc(NC(=O)c4ccc(N5CCOCC5)cc4)cc3)cc2)s1]

Compound 491 was prepared according to the procedure described in Scheme IV from 4,4'-diaminobenzophenone and 4-morpholinobenzoate. [M+H]$^+$ calcd for C$_{30}$H$_{27}$N$_3$O$_4$S: 526.1. found: 526.13.

Example 392

N-(4-(4-(2-Thienyl)carboxamido)benzoyl)phenyl)-4-(2-hydroxyethoxy)benzamide (Compound 492)

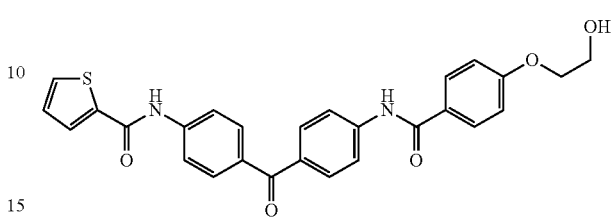

Compound 492 was prepared according to the procedure described in Scheme IV from 4,4'-diaminobenzophenone and 4-(2-hydroxyethoxy)benzoate. [M+H]$^+$ calcd for C$_{27}$H$_{22}$N$_2$O$_5$S: 487.0. found: 487.05.

Example 393

N-(4-(4-(2-Methoxyethylamino)benzoyl)phenyl)-4-morpholinobenzamide (Compound 493)

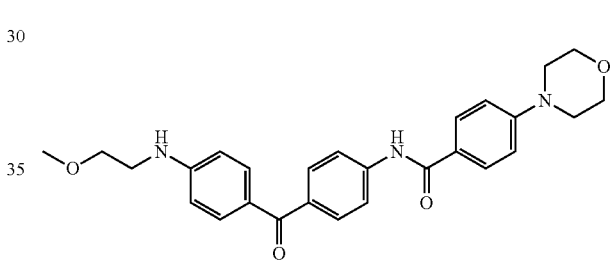

Compound 493 was prepared according to the procedure described in Scheme IV from 4,4'-diaminobenzophenone and 4-morpholinobenzoate. [M+H]$^+$ calcd for C$_{27}$H$_{29}$N$_3$O$_4$: 460.0. found: 460.12.

Example 394

N-(4-(4-(2-(3-Methylthienyl)carboxamido)benzoyl)phenyl)-4-morpholinobenzamide (Compound 494)

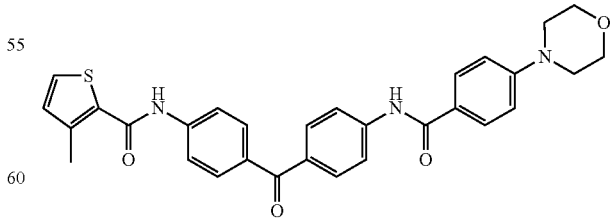

Compound 494 was prepared according to the procedure described in Scheme IV from 4,4'-diaminobenzophenone and 4-morpholinobenzoate. [M+H]$^+$ calcd for C$_{30}$H$_{27}$N$_3$O$_4$S: 526.1. found: 526.13.

Example 395

4-Morpholino-N-(4-(4-(thiophen-2-ylmethylamino)benzoyl)phenyl)benzamide (Compound 495)

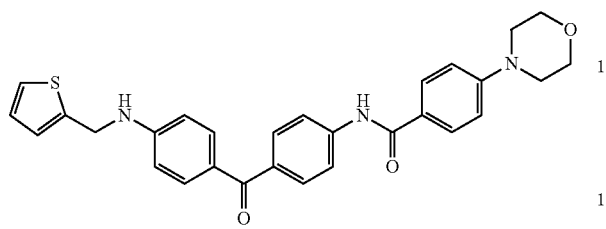

Compound 495 was prepared according to the procedure described in Scheme IV from 4,4'-diaminobenzophenone and 4-morpholinobenzoate. $[M+H]^+$ calcd for $C_{29}H_{27}N_3O_3S$: 498.1. found: 498.05.

Example 396

N-(4-(4-(2-(4-Methylthienyl)carboxamido)benzoyl)phenyl)-4-morpholinobenzamide (Compound 496)

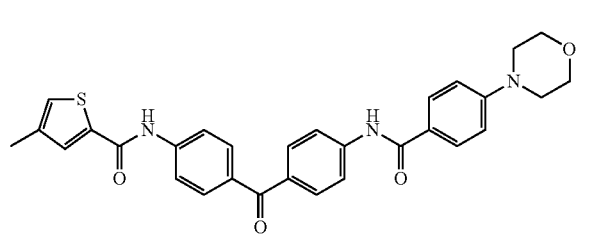 [SMILES: Cc1csc(C(=O)Nc2ccc(C(=O)c3ccc(NC(=O)c4ccc(N5CCOCC5)cc4)cc3)cc2)c1]

Compound 496 was prepared according to the procedure described in Scheme IV from 4,4'-diaminobenzophenone and 4-morpholinobenzoate. $[M+H]^+$ calcd for $C_{30}H_{27}N_3O_4S$: 526.1. found: 526.06.

Example 397

4-Morpholino-N-(4-(4-(cyclopropylmethylamino)benzoyl)phenyl)benzamide (Compound 497)

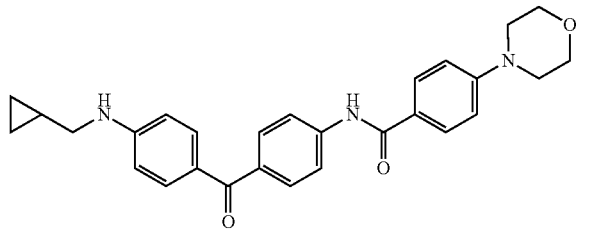 [SMILES: O=C(Nc1ccc(C(=O)c2ccc(NCC3CC3)cc2)cc1)c1ccc(N2CCOCC2)cc1]

Compound 497 was prepared according to the procedure described in Scheme IV from 4,4'-diaminobenzophenone and 4-morpholinobenzoate. $[M+H]^+$ calcd for $C_{28}H_{29}N_3O_3$: 456.0. found: 456.31.

Example 398

N-(4-(4-(4-Morpholinobenzamido)benzoyl)phenyl)pyrimidine-5-carboxamide (Compound 498)

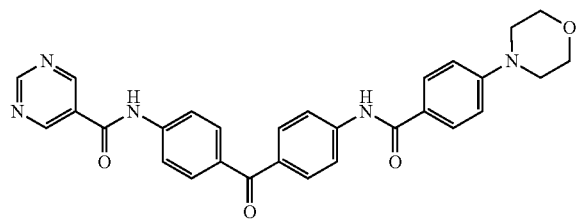 [SMILES: O=C(Nc1ccc(C(=O)c2ccc(NC(=O)c3cncnc3)cc2)cc1)c1ccc(N2CCOCC2)cc1]

Compound 498 was prepared according to the procedure described in Scheme IV from 4,4'-diaminobenzophenone and 4-morpholinobenzoate. $[M+H]^+$ calcd for $C_{29}H_{25}N_5O_4$: 508.0. found: 508.04.

Example 399

N-(4-(4-(4-Morpholinobenzamido)benzoyl)phenyl)-1H-pyrrole-2-carboxamide (Compound 499)

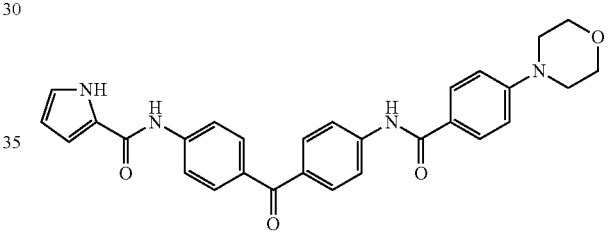

Compound 499 was prepared according to the procedure described in Scheme IV from 4,4'-diaminobenzophenone and 4-morpholinobenzoate. $[M+H]^+$ calcd for $C_{29}H_{26}N_4O_4$: 495.0. found: 495.28.

Example 400

3-Methyl-N-(4-(4-(4-morpholinobenzamido)benzoyl)phenyl)-1H-pyrazole-5-carboxamide (Compound 500)

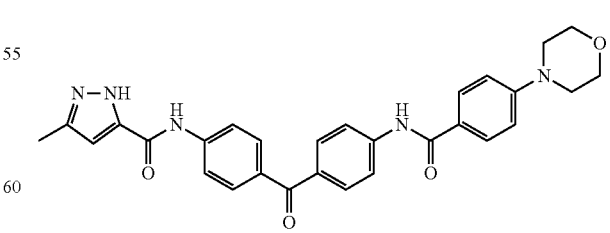

Compound 500 was prepared according to the procedure described in Scheme IV from 4,4'-diaminobenzophenone and 4-morpholinobenzoate. $[M+H]^+$ calcd for $C_{29}H_{27}N_5O_4$: 510.0. found: 510.06.

Example 401

N-(4-(4-(4-Morpholinobenzamido)benzoyl)phenyl)-1H-pyrazole-4-carboxamide (Compound 501)

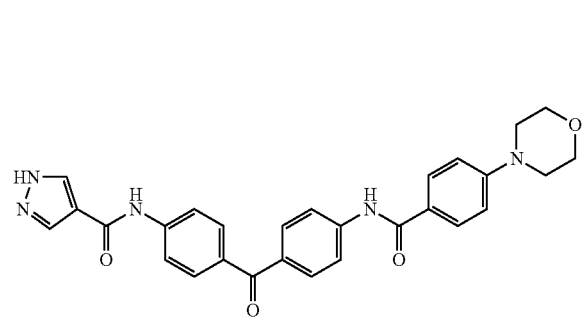 [SMILES: O=C(Nc1ccc(C(=O)c2ccc(NC(=O)c3cn[nH]c3)cc2)cc1)c1ccc(N2CCOCC2)cc1]

Compound 501 was prepared according to the procedure described in Scheme IV from 4,4'-diaminobenzophenone and 4-morpholinobenzoate. [M+H]$^+$ calcd for $C_{28}H_{25}N_5O_4$: 496.0. found: 496.09.

Example 402

N-(4-(4-(4-(4-Hydroxypiperidin-1-yl)benzamido)benzoyl)phenyl)thiophene-2-carboxamide (Compound 502)

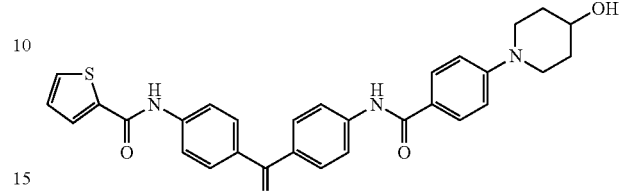

Compound 502 was prepared according to the procedure described in Scheme IV from 4,4'-diaminobenzophenone and 4-(4-hydroxypiperidinyl)benzoate. [M+H]$^+$ calcd for $C_{30}H_{27}N_3O_4S$: 526.1. found: 525.99.

Example 403

N-(4-(4-(4-Morpholinobenzamido)benzoyl)phenyl)biphenyl-4-carboxamide (Compound 503)

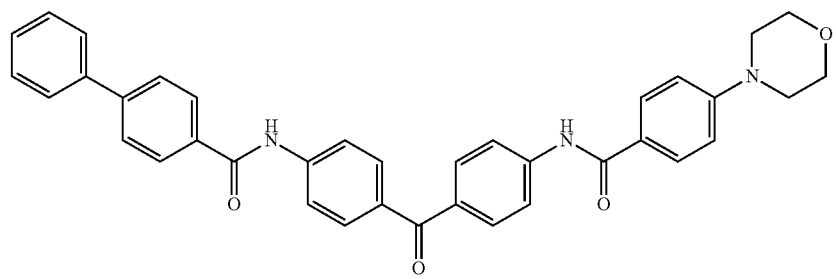 [SMILES: O=C(Nc1ccc(C(=O)c2ccc(NC(=O)c3ccc(N4CCOCC4)cc3)cc2)cc1)c1ccc(-c2ccccc2)cc1]

Compound 503 was prepared according to the procedure described in Scheme IV from 4,4'-diaminobenzophenone and 4-morpholinobenzoate. [M+H]$^+$ calcd for $C_{37}H_{31}N_3O_4$: 582.1. found: 582.16.

Example 404

N-(4-(4-(4-(4-Hydroxypiperidin-1-yl)benzamido)benzoyl)phenyl)pyridine-4-carboxamide (Compound 504)

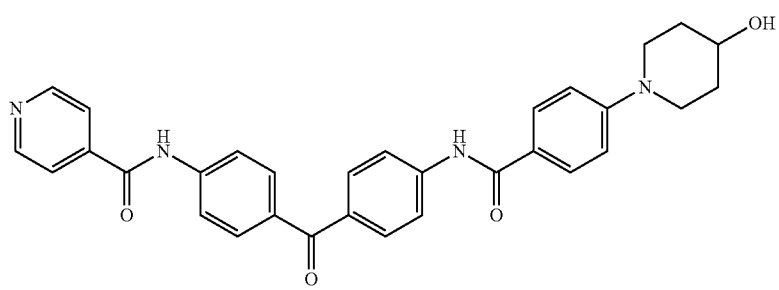 [SMILES: O=C(Nc1ccc(C(=O)c2ccc(NC(=O)c3ccc(N4CCC(O)CC4)cc3)cc2)cc1)c1ccncc1]

Compound 504 was prepared according to the procedure described in Scheme IV from 4,4'-diaminobenzophenone and 4-(4-hydroxypiperidinyl)benzoate. [M+H]$^+$ calcd for $C_{31}H_{28}N_4O_4$: 521.1. found: 521.06.

Example 405

N-(4-(4-(4-(4-Hydroxypiperidin-1-yl)benzamido)benzoyl)phenyl)pyridine-2-carboxamide (Compound 505)

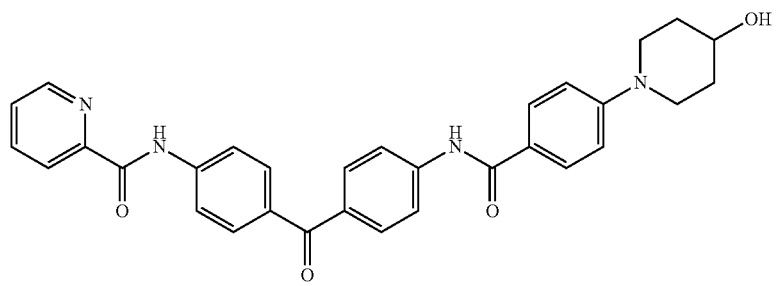 [SMILES: O=C(Nc1ccc(C(=O)c2ccc(NC(=O)c3ccccn3)cc2)cc1)c1ccc(N2CCC(O)CC2)cc1]

Compound 505 was prepared according to the procedure described in Scheme IV from 4,4'-diaminobenzophenone and 4-(4-hydroxypiperidinyl)benzoate. [M+H]$^+$ calcd for $C_{31}H_{28}N_4O_4$: 521.1. found: 521.06.

Example 406

N-(4-(5-(4-(4-Hydroxypiperidin-1-yl)benzamido)-1H-indazol-1-yl)phenyl)-1H-pyrrole-2-carboxamide (Compound 506)

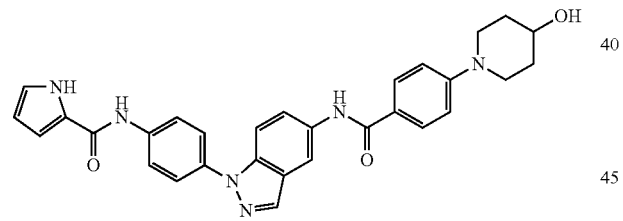

Compound 506 was prepared according to the procedure described in Scheme IV from 5-amino-1-(4-aminophenyl)indazole and 4-(4-hydroxypiperidin-1-yl)benzoate.

[M+H]$^+$ calcd for $C_{30}H_{28}N_6O_3$: 521.2. found: 521.06.

Example 407

(±)-N-(4-(5-(4-(3-Aminopyrrolidin-1-yl)benzamido)-1H-indazol-1-yl)phenyl)thiophene-2-carboxamide (Compound 507)

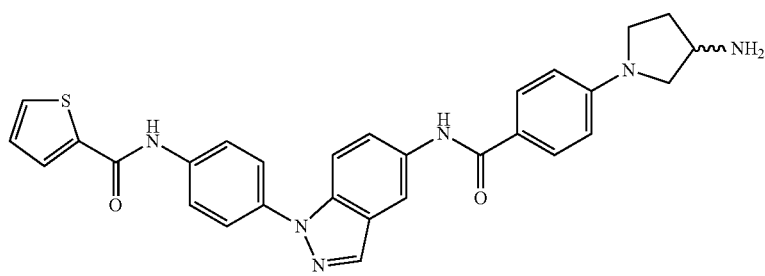 [SMILES: NC1CCN(c2ccc(C(=O)Nc3ccc4c(cnn4-c4ccc(NC(=O)c5cccs5)cc4)c3)cc2)C1]

Compound 507 was prepared according to the procedure described in Scheme IV from 5-amino-1-(4-aminophenyl)indazole and 4-(3-aminopyrrolidin-1-yl)benzoate.
[M+H]$^+$ calcd for $C_{29}H_{27}N_6O_2S$: 523.1. found: 523.02.

Example 408

N-(4-(5-(4-(4-Hydroxypiperidin-1-yl)benzamido)-1H-indazol-1-yl)phenyl)-1H-pyrazole-3-carboxamide (Compound 508)

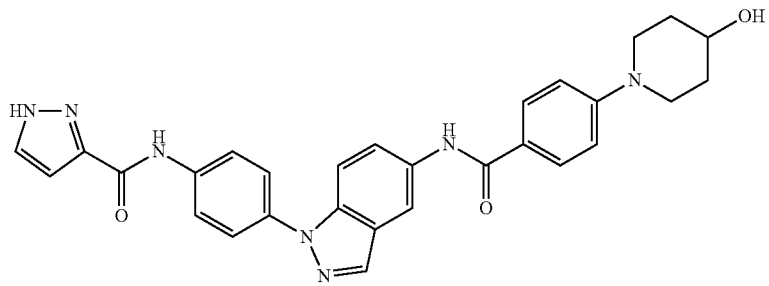 [SMILES: O=C(Nc1ccc2c(cnn2-c2ccc(NC(=O)c3cc[nH]n3)cc2)c1)c1ccc(N2CCC(O)CC2)cc1]

Compound 508 was prepared according to the procedure described in Scheme IV from 5-amino-1-(4-aminophenyl)indazole and 4-(4-hydroxypiperidin-1-yl)benzoate. [M+H]$^+$ calcd for $C_{29}H_{27}N_7O_3$: 522.2. found: 522.05.

Example 409

N-(4-(5-(4-(4-Hydroxymethylpiperidin-1-yl)benzamido)-1H-indazol-1-yl)phenyl)thiophene-2-carboxamide (Compound 509)

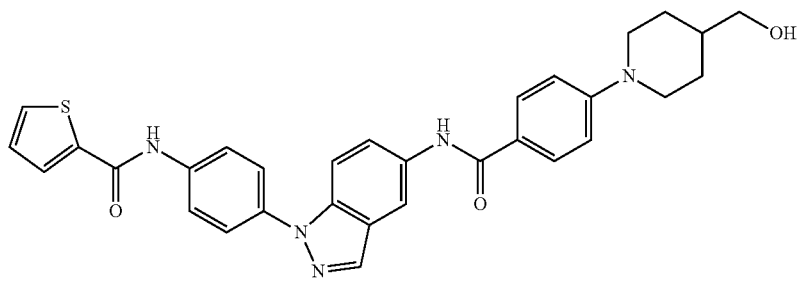 [SMILES: O=C(Nc1ccc2c(cnn2-c2ccc(NC(=O)c3cccs3)cc2)c1)c1ccc(N2CCC(CO)CC2)cc1]

Compound 509 was prepared according to the procedure described in Scheme IV from 5-amino-1-(4-aminophenyl)indazole and 4-(4-hydroxymethylpiperidin-1-yl)benzoate. [M+H]$^+$ calcd for $C_{31}H_{29}N_5O_3S$: 552.2. found: 552.05.

Example 410

N-(4-(5-(4-(4-Hydroxypiperidin-1-yl)benzamido)-1H-indazol-1-yl)phenyl)-1H-indole-6-carboxamide (Compound 510)

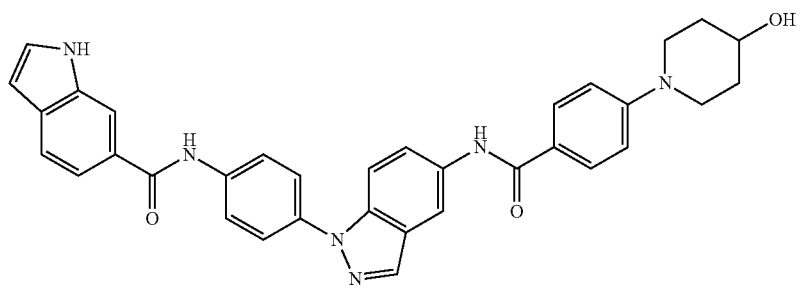 [SMILES: O=C(Nc1ccc2c(cnn2-c2ccc(NC(=O)c3ccc4cc[nH]c4c3)cc2)c1)c1ccc(N2CCC(O)CC2)cc1]

Compound 510 was prepared according to the procedure described in Scheme IV from 5-amino-1-(4-aminophenyl)indazole and 4-(4-hydroxypiperidin-1-yl)benzoate. [M+H]$^+$ calcd for $C_{34}H_{30}N_6O_3$: 571.2. found: 571.16.

Example 411

N-(4-(5-(4-(4-Hydroxypiperidin-1-yl)benzamido)-1H-indazol-1-yl)phenyl)-1H-indole-5-carboxamide (Compound 511)

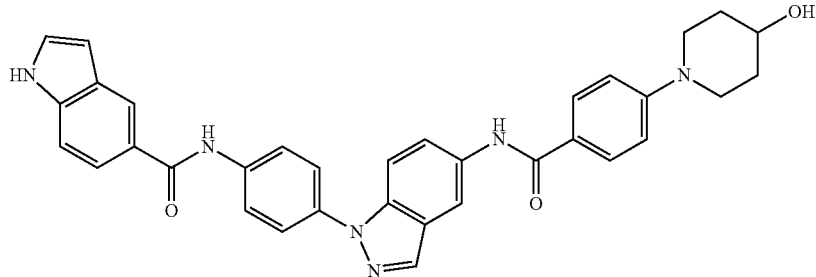 [SMILES: O=C(Nc1ccc2c(cnn2-c2ccc(NC(=O)c3ccc4[nH]ccc4c3)cc2)c1)c1ccc(N2CCC(O)CC2)cc1]

Compound 511 was prepared according to the procedure described in Scheme IV from 5-amino-1-(4-aminophenyl)indazole and 4-(4-hydroxypiperidin-1-yl)benzoate. [M+H]$^+$ calcd for $C_{34}H_{30}N_6O_3$: 571.2. found: 571.16.

Example 412

N-(4-(5-(4-(4-(2-Hydroxyethyl)piperidin-1-yl)benzamido)-1H-indazol-1-yl)phenyl)thiophene-2-carboxamide (Compound 512)

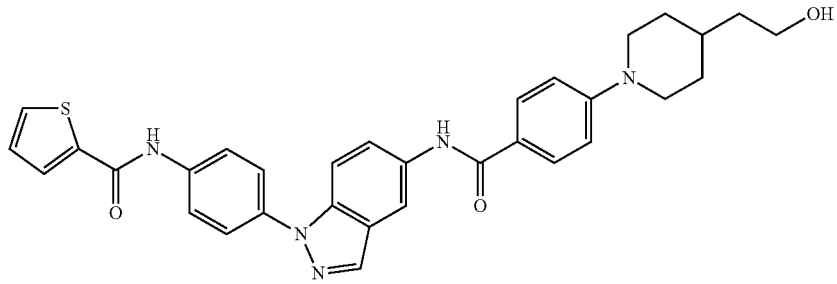 [SMILES: O=C(Nc1ccc2c(cnn2-c2ccc(NC(=O)c3cccs3)cc2)c1)c1ccc(N2CCC(CCO)CC2)cc1]

Compound 512 was prepared according to the procedure described in Scheme IV from 5-amino-1-(4-aminophenyl)indazole and 4-(4-(2-hydroxyethyl)piperidin-1-yl)benzoate. [M+H]$^+$ calcd for $C_{32}H_{31}N_5O_3S$: 566.2. found: 566.11.

Example 413

N-(4-(5-(4-(4-Cyclopropylcarbonylpiperiazin-1-yl)benzamido)-1H-indazol-1-yl)phenyl)thiophene-2-carboxamide (Compound 513)

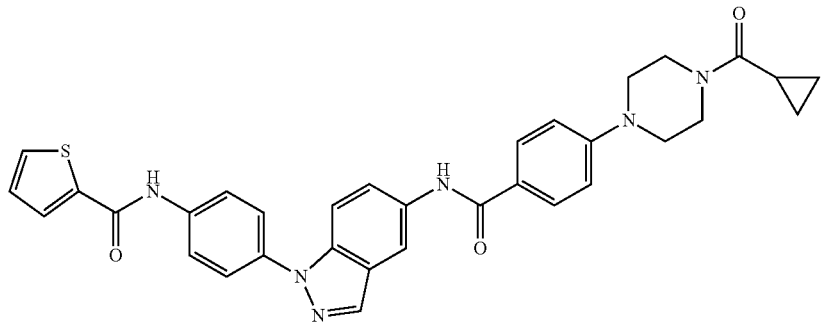 [SMILES: O=C(Nc1ccc2c(cnn2-c2ccc(NC(=O)c3cccs3)cc2)c1)c1ccc(N2CCN(C(=O)C3CC3)CC2)cc1]

Compound 513 was prepared according to the procedure described in Scheme IV from 5-amino-1-(4-aminophenyl)indazole and 4-(4-cyclopropylcarbonylpiperazin-1-yl)benzoate. [M+H]+ calcd for $C_{33}H_{30}N_6O_3S$: 591.21. found: 591.14.

Example 414

N-(4-(5-(4-(4-Morpholinopiperidin-1-yl)benzamido)-1H-indazol-1-yl)phenyl)thiophene-2-carboxamide (Compound 514)

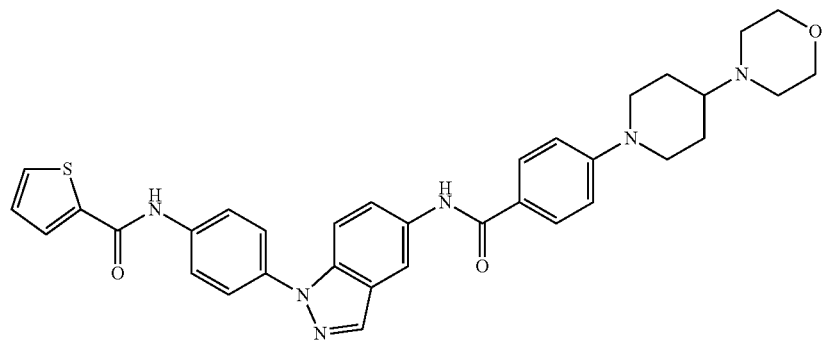 [SMILES: O=C(Nc1ccc2c(cnn2-c2ccc(NC(=O)c3cccs3)cc2)c1)c1ccc(N2CCC(N3CCOCC3)CC2)cc1]

Compound 514 was prepared according to the procedure described in Scheme IV from 5-amino-1-(4-aminophenyl)indazole and 4-(4-morpholinopiperidin-1-yl)benzoate. [M+H]+ calcd for $C_{34}H_{35}N_6O_3S$: 607.2. found: 607.19.

Example 415

N-(1-(4-Aminophenyl)-1H-indazol-5-yl)-4-(4-hydroxypiperidin-1-yl)benzamide (Compound 515)

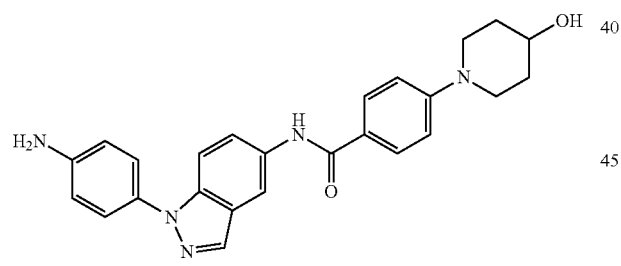

Compound 515 was prepared according to the procedure described in Scheme IV from 5-amino-1-(4-aminophenyl)indazole and 4-(4-hydroxypiperidin-1-yl)benzoate. [M+H]+ calcd for $C_{25}H_{25}N_5O_2$: 428.2. found: 427.93.

Example 416

N-(4-(5-(4-(4-((1H-Imidazol-1-yl)methyl)-4-hydroxypiperidin-1-yl)benzamido)-1H-indazol-1-yl)phenyl)thiophene-2-carboxamide (Compound 516)

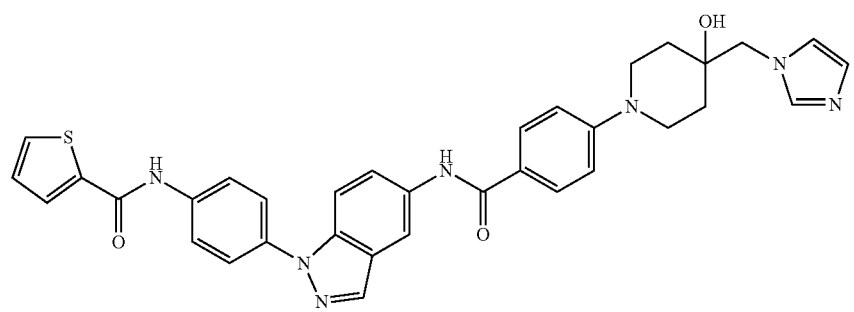 [SMILES: O=C(Nc1ccc2c(cnn2-c2ccc(NC(=O)c3cccs3)cc2)c1)c1ccc(N2CCC(O)(Cn3ccnc3)CC2)cc1]

Compound 516 was prepared according to the procedure described in Scheme IV from 5-amino-1-(4-aminophenyl)indazole and 4-(4-((1H-imidazol-1-yl)methyl)-4-hydroxypiperidin-1-yl)benzoate. [M+H]+ calcd for $C_{34}H_{31}N_7O_3S$: 618.2. found: 618.15.

Example 417

4-Cyano-N-(4-(5-(4-morpholinobenzamido)-1H-indazol-1-yl)phenyl)benzamide (Compound 517)

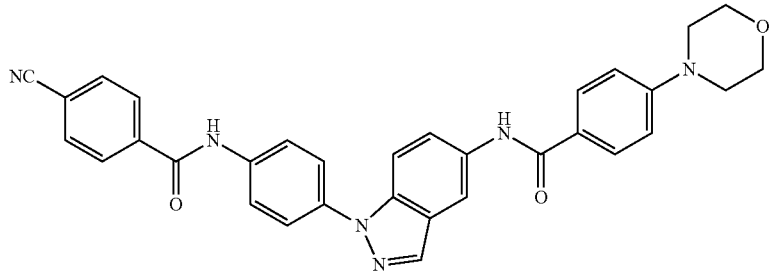 [SMILES: N#Cc1ccc(C(=O)Nc2ccc(-n3ncc4cc(NC(=O)c5ccc(N6CCOCC6)cc5)ccc43)cc2)cc1]

Compound 517 was prepared according to the procedure described in Scheme IV from 5-amino-1-(4-aminophenyl)indazole and 4-morpholinobenzoate. [M+H]+ calcd for $C_{32}H_{26}N_6O_3$: 543.2. found: 543.08.

Example 418

N-(4-(5-(4-(1,4-Dioxa-8-azaspiro[4,5]decan-8-yl)benzamido)-1H-indazol-1-yl)phenyl)thiophene-2-carboxamide (Compound 518)

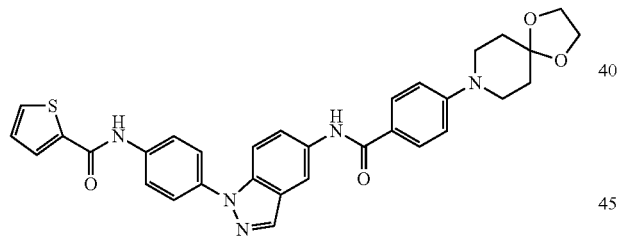

Compound 518 was prepared according to the procedure described in Scheme IV from 5-amino-1-(4-aminophenyl)indazole and 4-(1,4-dioxa-8-azaspiro[4,5]decan-8-yl)benzoate. [M+H]+ calcd for $C_{32}H_{29}N_5O_4S$: 580.1. found: 580.07.

Example 419

N-(4-(5-(4-Fluorobenzamido)-1H-indazol-1-yl)phenyl)-1H-indole-5-carboxamide (Compound 519)

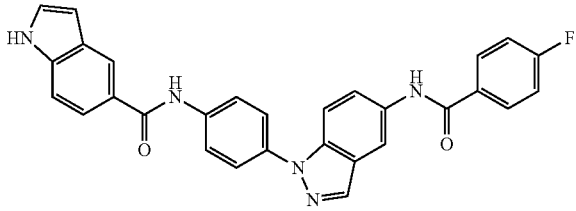 [SMILES: O=C(Nc1ccc2c(cnn2-c2ccc(NC(=O)c3ccc4[nH]ccc4c3)cc2)c1)c1ccc(F)cc1]

Compound 519 was prepared according to the procedure described in Scheme IV from 5-amino-1-(4-aminophenyl)indazole and 4-fluorobenzoate. [M+H]+ calcd for $C_{29}H_{20}FN_5O_2$: 490.1. found: 490.01.

Example 420

(±)-N-(4-(5-(4-(3-Hydroxymethyl)piperidin-1-yl)benzamido)-1H-indazol-1-yl)phenyl)thiophene-2-carboxamide (Compound 520)

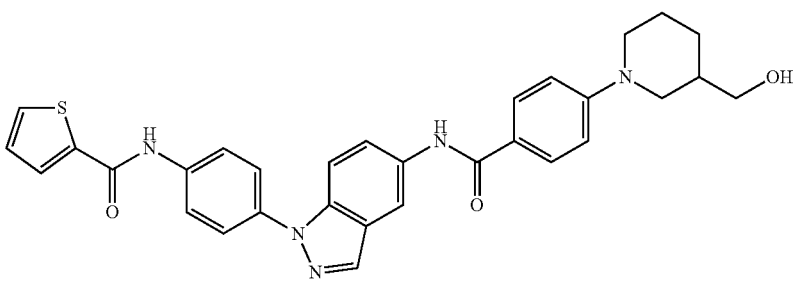 [SMILES: O=C(Nc1ccc2c(cnn2-c2ccc(NC(=O)c3cccs3)cc2)c1)c1ccc(N2CCCC(CO)C2)cc1]

Compound 520 was prepared according to the procedure described in Scheme IV from 5-amino-1-(4-aminophenyl)indazole and 4-(3-hydroxymethyl)piperidin-1-yl)benzoate. [M+H]+ calcd for $C_{31}H_{29}N_5O_3S$: 552.2. found: 552.07.

Example 421

(±)-N-(1-(4-(4-(Hexahydropyrrolo[1,2-a]pyrazin-2(1H)-yl)benzamido)phenyl)-1H-indazol-5-yl)thiophene-2-carboxamide (Compound 521)

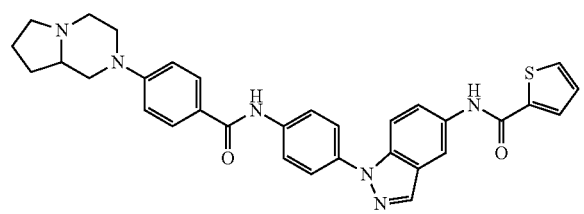 [SMILES: O=C(Nc1ccc(-n2ncc3cc(NC(=O)c4cccs4)ccc32)cc1)c1ccc(N2CCN3CCCC3C2)cc1]

Compound 521 was prepared according to the procedure described in Scheme IV from 5-amino-1-(4-aminophenyl)indazole and 4-(hexahydropyrrolo[1,2-a]pyrazin-2(1H)-yl)benzoate. [M+H]+ calcd for $C_{32}H_{30}N_6O_2S$: 563.2. found: 563.12.

Example 422

N-(1-(4-(4-(4-Dimethylaminopiperidin-1-yl)benzamido)phenyl)-1H-indazol-5-yl)thiophene-2-carboxamide (Compound 522)

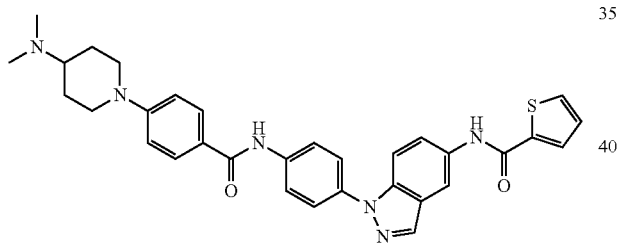

Compound 522 was prepared according to the procedure described in Scheme IV from 5-amino-1-(4-aminophenyl)indazole and 4-(4-dimethylaminopiperidin-1-yl))benzoate. [M+H]+ calcd for $C_{32}H_{32}N_6O_2S$: 565.2. found: 565.14.

Example 423

N-(4-(5-(1H-Indole-6-carboxamido)-1H-indazol-1-yl)phenyl)-1H-indole-6-carboxamide (Compound 523)

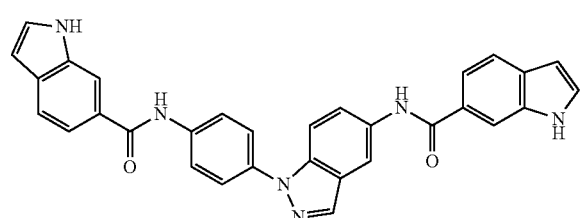

Compound 523 was prepared according to the procedure described in Scheme IV from 5-amino-1-(4-aminophenyl)indazole and 1H-indole-6-carboxylic acid. [M+H]+ calcd for $C_{31}H_{22}N_6O_2$: 511.1. found: 511.02.

Example 424

(±)-N-(1-(4-(4-(3-Dimethylaminopyrrolidin-1-yl)benzamido)phenyl)-1H-indazol-5-yl)thiophene-2-carboxamide (Compound 524)

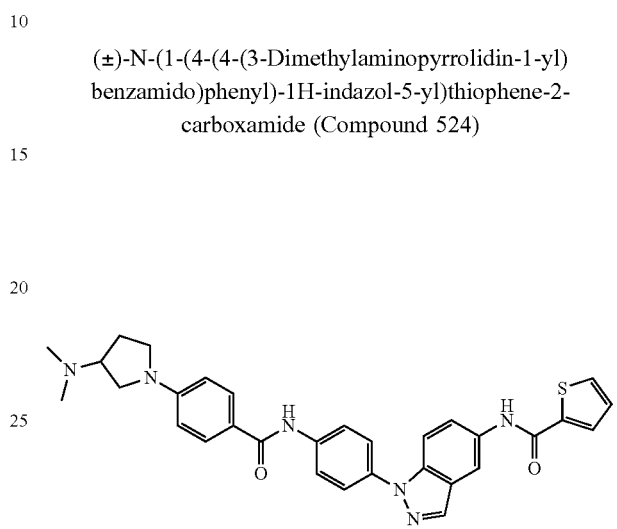

Compound 524 was prepared according to the procedure described in Scheme IV from 5-amino-1-(4-aminophenyl)indazole and 4-(3-dimethylaminopyrrolidin-1-yl)benzoate. [M+H]+ calcd for $C_{31}H_{30}N_6O_2S$: 551.2. found: 551.10.

Example 425

(±)-N-(1-(4-(4-((2-Hydroxyethyl)methylamino)benzamido)phenyl)-1H-indazol-5-yl)thiophene-2-carboxamide (Compound 525)

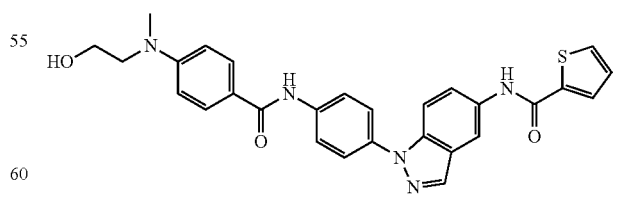

Compound 525 was prepared according to the procedure described in Scheme IV from 5-amino-1-(4-aminophenyl)indazole and 4-((2-hydroxyethyl)methylamino)benzoate. [M+H]+ calcd for $C_{28}H_{25}N_5O_3S$: 512.17. found: 512.02.

Example 426

N-(1-(4-(4-(4-Hydroxypiperidin-1-yl)benzamido)phenyl)-1H-indazol-5-yl)thiophene-2-carboxamide (Compound 526)

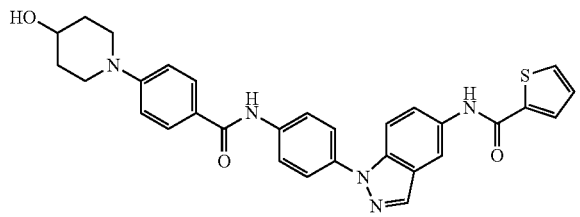 [SMILES: O=C(Nc1ccc(-n2ncc3cc(NC(=O)c4cccs4)ccc32)cc1)c1ccc(N2CCC(O)CC2)cc1]

Compound 526 was prepared according to the procedure described in Scheme IV from 5-amino-1-(4-aminophenyl)indazole and 4-(4-hydroxypiperidin-1-yl))benzoate.

[M+H]$^+$ calcd for $C_{30}H_{27}N_5O_3S$: 538.1. found: 538.06.

Example 427

N-(4-(5-(1H-Indole-5-carboxamido)-1H-indazol-1-yl)phenyl)-1H-indole-5-carboxamide (Compound 527)

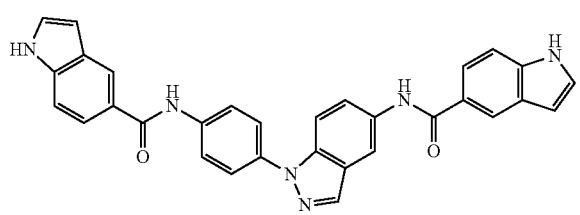 [SMILES: O=C(Nc1ccc(-n2ncc3cc(NC(=O)c4ccc5[nH]ccc5c4)ccc32)cc1)c1ccc2[nH]ccc2c1]

Compound 527 was prepared according to the procedure described in Scheme IV from 5-amino-1-(4-aminophenyl)indazole and 1H-indole-5-carboxylic acid. [M+H]$^+$ calcd for $C_{31}H_{22}N_6O_2$: 511.1. found: 511.03.

Example 428

N-(4-(5-(4-(4-Hydroxypiperidin-1-yl)benzamido)-1H-indazol-1-yl)phenyl)thiophene-2-carboxamide (Compound 528)

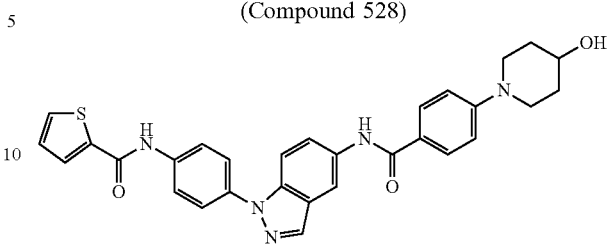

Compound 528 was prepared according to the procedure described in Scheme IV from 5-amino-1-(4-aminophenyl)indazole and 4-(4-hydroxypiperidin-1-yl)benzoate.

[M+H]$^+$ calcd for $C_{30}H_{27}N_5O_3S$: 538.1. found: 538.06.

Example 429

4-Morpholino-N-(4-(5-(4-morpholinobenzamido)-1H-indazol-1-yl)phenyl)piperidine-1-carboxamide (Compound 529)

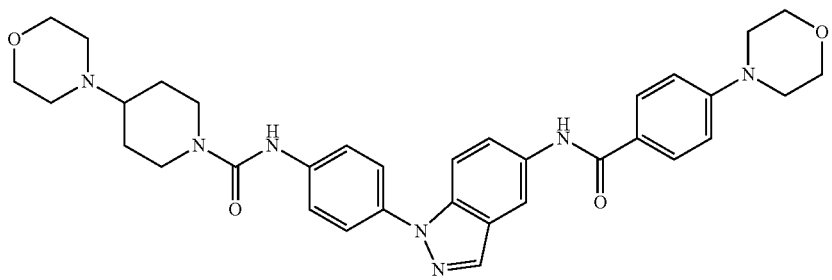 [SMILES: O=C(Nc1ccc2c(cnn2-c2ccc(NC(=O)N3CCC(N4CCOCC4)CC3)cc2)c1)c1ccc(N2CCOCC2)cc1]

Compound 529 was prepared according to the procedure described in Scheme IV from 5-amino-1-(4-aminophenyl)indazole and 4-morpholinobenzoate. [M+H]$^+$ calcd for $C_{34}H_{39}N_7O_4$: 610.3. found: 610.25.

Example 430

N-(1-(4-Cyclopropylmethylamino)phenyl)-1H-indazol-5-yl)-4-morpholinobenzamide (Compound 530)

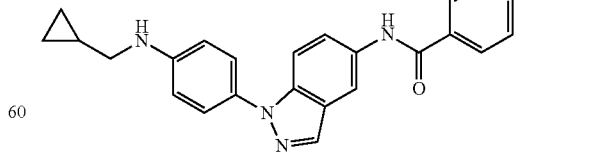

Compound 530 was prepared according to the procedure described in Scheme IV from 5-amino-1-(4-aminophenyl)indazole and 4-morpholinobenzoate. [M+H]$^+$ calcd for $C_{28}H_{29}N_5O_2$: 468.2. found: 468.08.

Example 431

N-(1-(4-Ethylamino)phenyl)-1H-indazol-5-yl)-4-morpholinobenzamide (Compound 531)

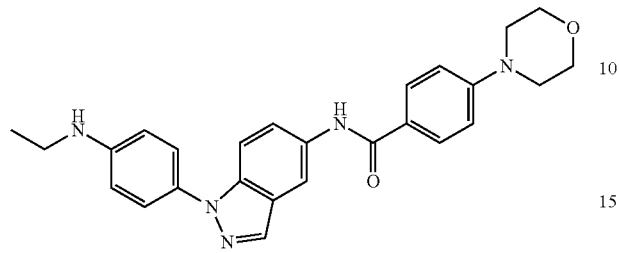

Compound 531 was prepared according to the procedure described in Scheme IV from 5-amino-1-(4-aminophenyl) indazole and 4-morpholinobenzoate. [M+H]$^+$ calcd for $C_{26}H_{27}N_5O_2$: 442.2. found: 442.05.

Example 432

Phenyl 4-(5-(4-morpholinobenzamido)-1H-indazol-5-yl)phenylcarbamate (Compound 532)

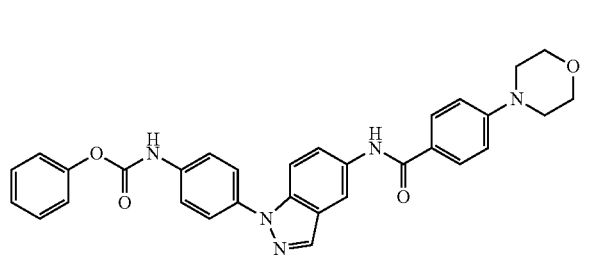 [SMILES: O=C(Nc1ccc(-n2ncc3cc(NC(=O)c4ccc(N5CCOCC5)cc4)ccc32)cc1)Oc1ccccc1]

Compound 532 was prepared according to the procedure described in Scheme IV from 5-amino-1-(4-aminophenyl) indazole and 4-morpholinobenzoate. $^1$H NMR (500 MHz, DMSO-d$_6$) δ 10.49 (s, 1H), 9.97 (s, 1H), 8.97 (s, 1H), 8.03 (d, J=7.5 Hz, 2H), 7.91 (d, J=8 Hz, 2H), 7.68 (m, 3H), 7.56 (d, J=9 Hz, 1H), 7.44 (t, J=7.5 Hz, 2H), 7.26 (m, 3H), 7.03 (d, J=7.5 Hz, 2H), 3.74 (m, 4H).

Example 433

N-(4-(5-(4-morpholinobenzamido)-1H-indazol-5-yl)phenyl)morpholine-4-carboxamide (Compound 533)

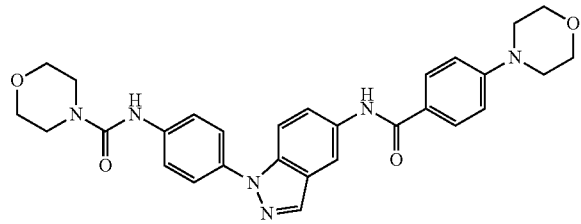 [SMILES: O=C(Nc1ccc2c(cnn2-c2ccc(NC(=O)N3CCOCC3)cc2)c1)c1ccc(N2CCOCC2)cc1]

Compound 533 was prepared according to the procedure described in Scheme IV from 5-amino-1-(4-aminophenyl) indazole and 4-morpholinobenzoate. [M+H]$^+$ calcd for $C_{29}H_{30}N_6O_4$: 527.2. found: 527.00.

Example 434

N-(1-(4-Cyclopropanecarboxamido)phenyl)-2-oxoindolin-5-yl)4-dimethylaminobenzamide (Compound 534)

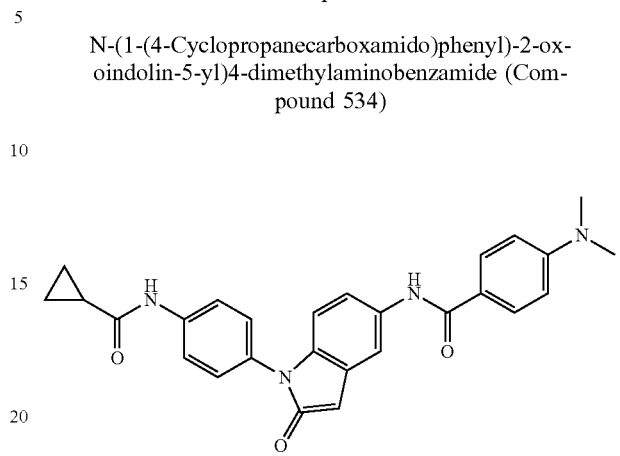

Compound 534 was prepared according to the procedure described in Scheme IV from 5-amino-1-(4-aminophenyl) oxindole and 4-dimethylaminobenzoate. [M+H]$^+$ calcd for $C_{27}H_{26}N_4O_3$: 455.2. found: 455.00.

Example 435

4-Morpholino-N-(1-(4-(thiazol-2-ylmethylamino)phenyl)-1H-indazol-5-yl)benzamide (Compound 535)

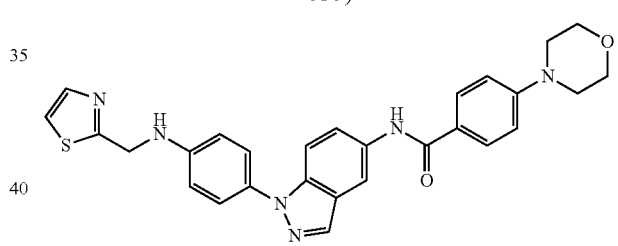

Compound 535 was prepared according to the procedure described in Scheme IV from 5-amino-1-(4-aminophenyl) indazole and 4-morpholinobenzoate. $^1$H NMR (500 MHz, CDCl$_3$) δ 8.17 (s, 1H), 8.12 (s, 1H), 7.85 (m, 3H), 7.78 (m, 1H), 7.59 (d, J=9 Hz, 1H), 7.49 (d, J=8 Hz, 1H), 7.30 (m, 1H), 6.95 (d, J=8 Hz, 2H), 6.82 (d, J=8.5 Hz, 2H), 4.76 (s, 2H), 3.89 (t, J=4 Hz, 4H), 3.29 (t, J=4.5 Hz, 4H).

Example 436

4-Morpholino-N-(1-(4-(thiazol-2-ylmethylideneamino)phenyl)-1H-indazol-5-yl)benzamide (Compound 536)

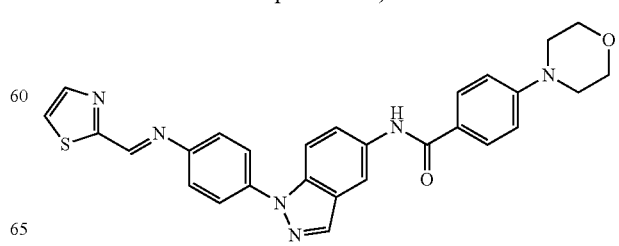

Compound 536 was prepared according to the procedure described in Scheme IV from 5-amino-1-(4-aminophenyl)indazole and 4-morpholinobenzoate. No data.

Example 437

4-Morpholino-N-(1-(4-morpholinophenyl)-1H-indazol-5-yl)benzamide (Compound 537)

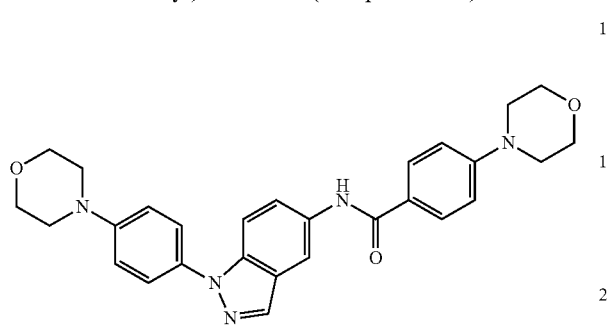

Compound 537 was prepared according to the procedure described in Scheme IV from 5-amino-1-(4-aminophenyl)indazole and 4-morpholinobenzoate. [M+H]$^+$ calcd for C$_{28}$H$_{29}$N$_5$O$_3$: 484.2. found: 484.11.

Example 438

4-Morpholino-N-(2-(4-morpholinophenyl)-2H-indazol-5-yl)benzamide (Compound 538)

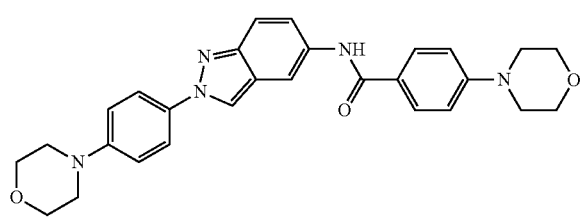 [SMILES: O=C(Nc1ccc2nn(-c3ccc(N4CCOCC4)cc3)cc2c1)c1ccc(N2CCOCC2)cc1]

Compound 538 was prepared according to the procedure described in Scheme IV from 5-amino-2-(4-aminophenyl)indazole and 4-morpholinobenzoate. [M+H]$^+$ calcd for C$_{28}$H$_{29}$N$_5$O$_3$: 484.2. found: 484.13.

Example 439

(±)-N-(4-(5-(4-(3-Hydroxypyrrolidin-1-yl)benzamido)-1H-indazol-1-yl)phenyl)thiophene-2-carboxamide (Compound 539)

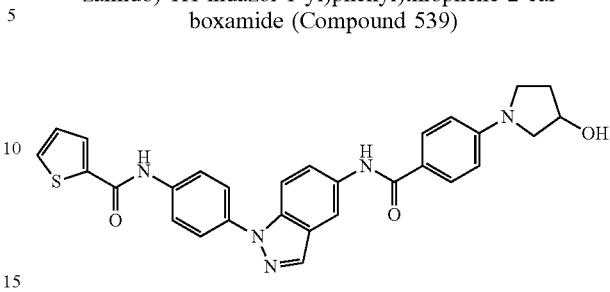

Compound 539 was prepared according to the procedure described in Scheme IV from 5-amino-1-(4-aminophenyl)indazole and 4-(3-hydroxypyrrolidinyl)benzoate. [M+H]$^+$ calcd for C$_{29}$H$_{25}$N$_5$O$_3$S: 524.1. found: 524.04.

Example 440

4-Morpholino-N-(2-(4-nitrophenyl)-2H-indazol-5-yl)benzamide (Compound 540)

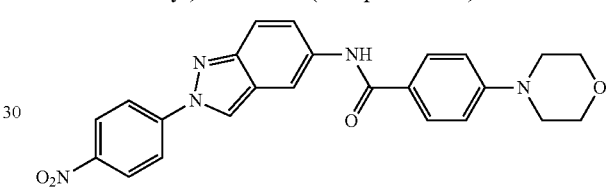

Compound 540 was prepared according to the procedure described in Scheme IV from 5-amino-2-(4-nitrophenyl)indazole and 4-morpholinobenzoate. [M+H]$^+$ calcd for C$_{24}$H$_{21}$N$_5$O$_4$: 444.1. found: 444.27.

Example 441

4-Morpholino-N-(1-(4-(3-(2-morpholinoethyl)ureido)phenyl)-1H-indazol-5-yl)phenyl)benzamide (Compound 541)

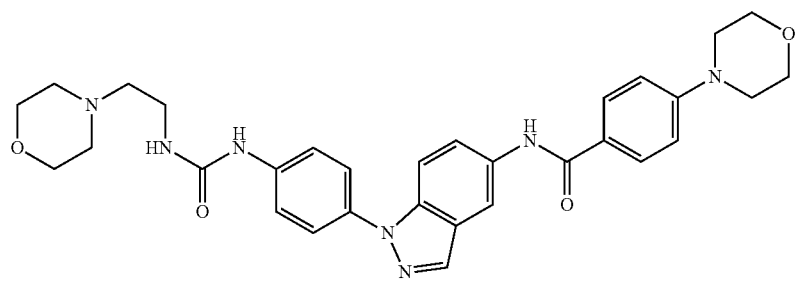 [SMILES: O=C(NCCN1CCOCC1)Nc1ccc(-n2ncc3cc(NC(=O)c4ccc(N5CCOCC5)cc4)ccc32)cc1]

Compound 541 was prepared according to the procedure described in Scheme IV from 5-amino-1-(4-aminophenyl)indazole and 4-morpholinobenzoate. [M+H]$^+$ calcd for C$_{31}$H$_{35}$N$_7$O$_4$: 570.2. found: 570.21.

Example 442

4-Morpholino-N-(2-(4-acetylphenyl)-2H-indazol-5-yl)benzamide (Compound 542)

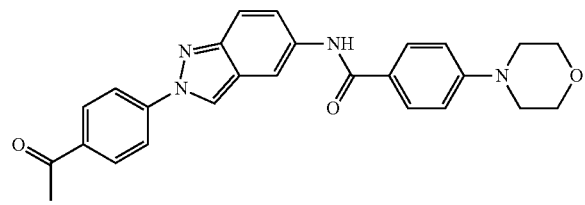 [SMILES: CC(=O)c1ccc(-n2cc3cc(NC(=O)c4ccc(N5CCOCC5)cc4)ccc3n2)cc1]

Compound 542 was prepared according to the procedure described in Scheme IV from 5-amino-2-(4-acetylphenyl) indazole and 4-morpholinobenzoate. [M+H]$^+$ calcd for $C_{26}H_{24}N_4O_3$: 441.1. found: 441.02.

Example 443

N-(2-(4-Cyanophenyl)-2H-indazol-5-yl)-4-(4-hydroxypiperidin-1-yl)benzamide (Compound 543)

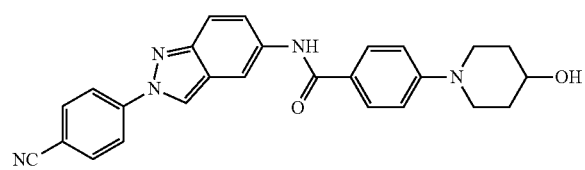 [SMILES: N#Cc1ccc(-n2cc3cc(NC(=O)c4ccc(N5CCC(O)CC5)cc4)ccc3n2)cc1]

Compound 543 was prepared according to the procedure described in Scheme IV from 5-amino-2-(4-acetylphenyl) indazole and 4-(4-hydroxypiperidin-1-yl)benzoate. [M+H]$^+$ calcd for $C_{26}H_{23}N_5O_2$: 438.1. found: 438.05.

Example 444

N-(4-(5-(Cyclopropanecarboxamido)-1H-indazol-1-yl)phenyl)-4-morpholinobenzamide (Compound 544)

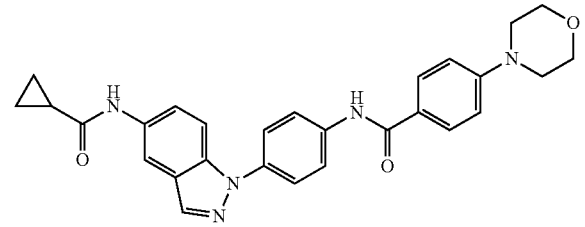 [SMILES: O=C(Nc1ccc(-n2ncc3cc(NC(=O)C4CC4)ccc32)cc1)c1ccc(N2CCOCC2)cc1]

Compound 544 was prepared according to the procedure described in Scheme IV from 5-amino-1-(4-aminophenyl) indazole and 4-morpholinobenzoate. [M+H]$^+$ calcd for $C_{28}H_{27}N_5O_3$: 482.2. found: 482.05.

Example 445

N-(4-(5-(4-Morpholinobenzamido)-1H-indazol-1-yl)phenyl)-4-oxopiperidine-1-carboxamide (Compound 545)

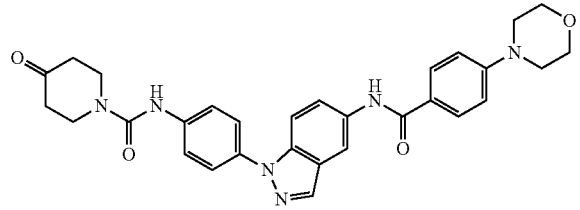 [SMILES: O=C1CCN(C(=O)Nc2ccc(-n3ncc4cc(NC(=O)c5ccc(N6CCOCC6)cc5)ccc43)cc2)CC1]

Compound 545 was prepared according to the procedure described in Scheme IV from 5-amino-1-(4-aminophenyl) indazole and 4-morpholinobenzoate. [M+H]$^+$ calcd for $C_{30}H_{30}N_6O_4$: 539.2. found: 539.12.

Example 446

4-Methyl-N-(4-(5-(4-morpholinobenzamido)-1H-indazol-1-yl)phenyl)thiazole-5-carboxamide (Compound 546)

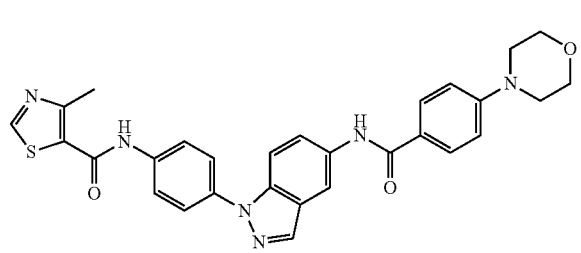 [SMILES: Cc1ncsc1C(=O)Nc1ccc(-n2ncc3cc(NC(=O)c4ccc(N5CCOCC5)cc4)ccc32)cc1]

Compound 546 was prepared according to the procedure described in Scheme IV from 5-amino-1-(4-aminophenyl) indazole and 4-morpholinobenzoate. [M+H]$^+$ calcd for $C_{29}H_{26}N_6O_3S$: 539.1. found: 539.09.

Example 447

N-(4-(5-(4-Morpholinobenzamido)-1H-indazol-1-yl)phenyl)thiazole-5-carboxamide (Compound 547)

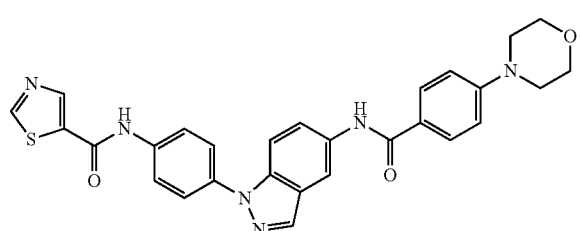

Compound 547 was prepared according to the procedure described in Scheme IV from 5-amino-1-(4-aminophenyl) indazole and 4-morpholinobenzoate. $^1$H NMR (500 MHz, DMSO-d$_6$) δ 10.66 (s, 1H), 10.12 (s, 1H), 9.34 (s, 1H), 8.75

(s, 1H), 8.40 (s, 1H), 8.36 (s, 1H), 7.94 (dd, J=3, 9 Hz, 4H), 7.87 (d, J=9 Hz, 1H), 7.81 (m, 3H), 7.05 (d, J=9 Hz, 2H), 3.76 (m, 4H).

Example 448

N-(4-(5-(4-Morpholinobenzamido)-1H-indazol-1-yl)phenyl)thiazole-2-carboxamide (Compound 548)

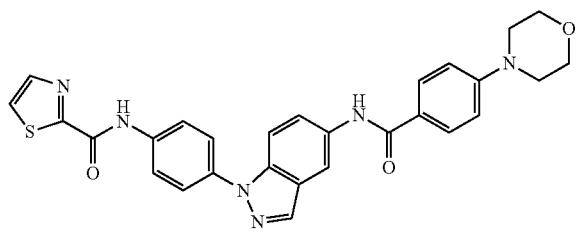 [SMILES: O=C(Nc1ccc2c(cnn2-c2ccc(NC(=O)c3nccs3)cc2)c1)c1ccc(N2CCOCC2)cc1]

Compound 548 was prepared according to the procedure described in Scheme IV from 5-amino-1-(4-aminophenyl)indazole and 4-morpholinobenzoate. [M+H]$^+$ calcd for $C_{28}H_{24}N_6O_3S$: 525.1. found: 525.04.

Example 449

N-(1-(4-(1-(Hydroxyimino)ethyl)phenyl)-1H-indazol-5-yl)morpholinobenzamide (Compound 549)

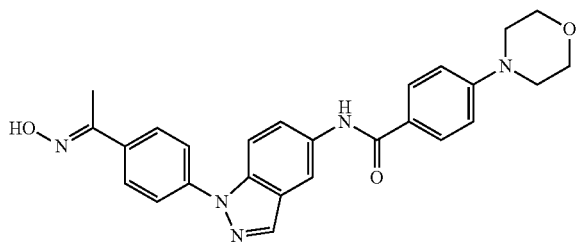 [SMILES: C/C(=N\O)c1ccc(-n2ncc3cc(NC(=O)c4ccc(N5CCOCC5)cc4)ccc32)cc1]

Compound 549 was prepared according to the procedure described in Scheme IV from 5-amino-1-(4-acetylphenyl)indazole and 4-morpholinobenzoate. [M+H]$^+$ calcd for $C_{26}H_{25}N_5O_3$: 456.2. found: 456.07.

Example 450

4-Methyl-N-(4-(5-(4-morpholinobenzamido)-1H-indazol-1-yl)phenyl)piperazine-1-carboxamide (Compound 550)

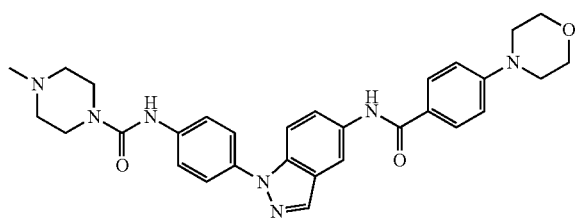 [SMILES: CN1CCN(C(=O)Nc2ccc(-n3ncc4cc(NC(=O)c5ccc(N6CCOCC6)cc5)ccc43)cc2)CC1]

Compound 550 was prepared according to the procedure described in Scheme IV from 5-amino-1-(4-aminophenyl)indazole and 4-morpholinobenzoate. [M+H]$^+$ calcd for $C_{30}H_{33}N_7O_3$: 540.2. found: 540.15.

Example 451

(±)-N-(4-(5-(4-(3-Hydroxypiperidin-1-yl)benzamido)-1H-indazol-1-yl)phenyl)thiophene-2-carboxamide (Compound 551)

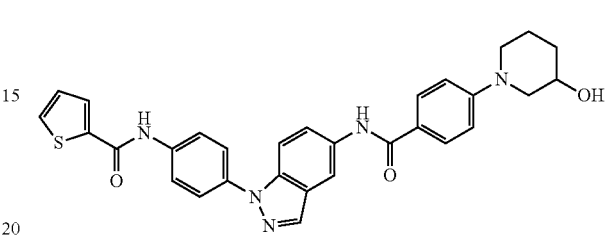

Compound 551 was prepared according to the procedure described in Scheme IV from 5-amino-1-(4-aminophenyl)indazole and 4-(3-hydroxypiperidinyl)benzoate. [M+H]$^+$ calcd for $C_{30}H_{27}N_5O_3S$: 538.1. found: 538.06.

Example 452

N-(1-(4-Cyclopropanecarboxamido)phenyl)-1H-indazol-5-yl)-2-morpholinopyrimidine-5-carboxamide (Compound 552)

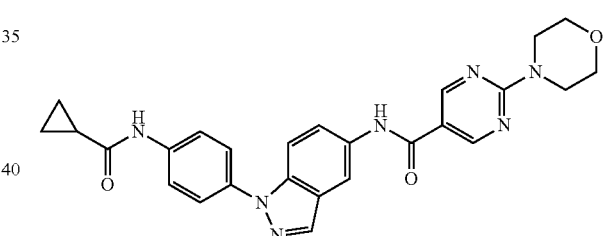

Compound 552 was prepared according to the procedure described in Scheme IV from 5-amino-1-(4-aminophenyl)indazole and 2-morpholino-5-pyrimidinecarboxylate.
[M+H]$^+$ calcd for $C_{26}H_{25}N_7O_3$: 484.2. found: 484.01.

Example 453

N-(1-(4-Aminophenyl)-1H-indazol-5-yl)-4-(1H-imidazol-1-yl)benzamide (Compound 553)

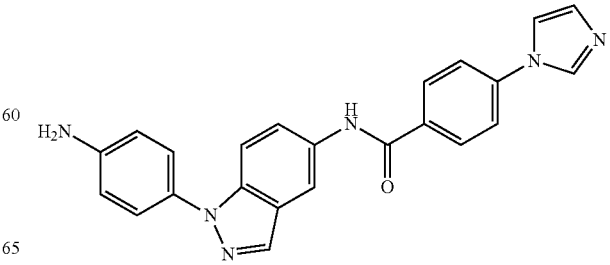

Compound 553 was prepared according to the procedure described in Scheme IV from 5-amino-1-(4-aminophenyl)indazole and 4-imidazolylbenzoate. $^1$H NMR (500 MHz, Acetone-d$_6$) δ 9.78 (s, 1H), 8.45 (s, 1H), 8.20 (m, 4H), 7.82-7.67 (m, 5H), 7.42 (d, J=8.5 Hz, 2H), 7.16 (s, 1H), 6.87 (d, J=8.5 Hz, 2H), 4.93 (s, 2H).

Example 454

N-(4-(5-(4-(1H-Imidazol-1-yl)benzamido)-1H-indazol-1-yl)phenyl)thiophene-2-carboxamide (Compound 554)

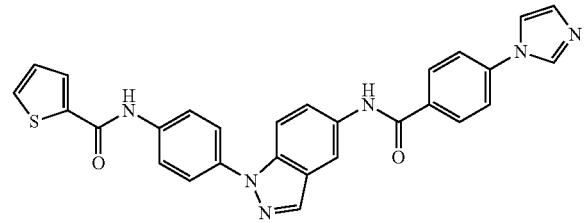 [SMILES: O=C(Nc1ccc2c(cnn2-c2ccc(NC(=O)c3cccs3)cc2)c1)c1ccc(-n2ccnc2)cc1]

Compound 554 was prepared according to the procedure described in Scheme IV from 5-amino-1-(4-aminophenyl)indazole and 4-imidazolylbenzoate. [M+H]$^+$ calcd for C$_{28}$H$_{20}$N$_6$O$_2$S: 505.1. found: 505.00.

Example 455

N-(4-(5-(4-(4-Hydroxypiperidin-1-yl)benzamido)-1H-indazol-1-yl)phenyl)pyrimidine-5-carboxamide (Compound 555)

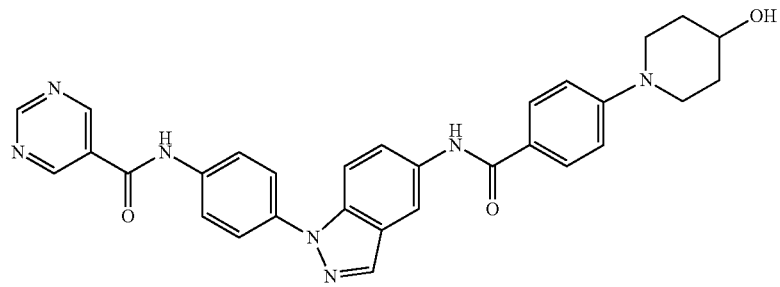 [SMILES: O=C(Nc1ccc2c(cnn2-c2ccc(NC(=O)c3cncnc3)cc2)c1)c1ccc(N2CCC(O)CC2)cc1]

Compound 555 was prepared according to the procedure described in Scheme IV from 5-amino-1-(4-aminophenyl)indazole and 4-(4-hydroxypiperidin-1-yl)benzoate. [M+H]$^+$ calcd for C$_{30}$H$_{27}$N$_7$O$_3$: 534.2. found: 534.09.

Example 456

N-(4-(5-(4-(Tetrahydropyran-4-yl)amino)benzamido)-1H-indazol-1-yl)phenyl)thiophene-2-carboxamide (Compound 556)

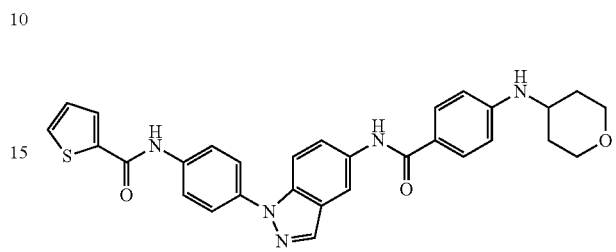

Compound 556 was prepared according to the procedure described in Scheme IV from 5-amino-1-(4-aminophenyl)indazole and 4-(tetrahydropyran-4-yl)aminobenzoate.

[M+H]$^+$ calcd for C$_{30}$H$_{28}$N$_5$O$_3$S: 538.1. found: 538.08.

Example 457

N-(1-(4-Aminophenyl)-1H-indazol-5-yl)-1H-indole-6-carboxamide (Compound 557)

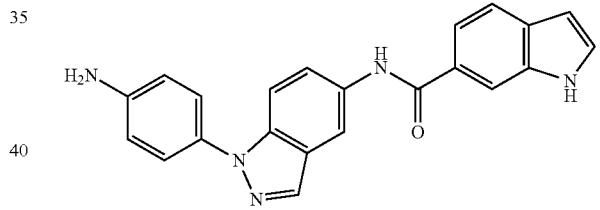

Compound 557 was prepared according to the procedure described in Scheme IV from 5-amino-1-(4-aminophenyl)indazole and indole-6-carboxylic acid. [M+H]$^+$ calcd for C$_{22}$H$_{17}$N$_5$O: 368.1. found: 367.90.

Example 458

N-(1-(4-(Cyclopropylcarboxamido)phenyl)-1H-indazol-5-yl)-1H-indole-6-carboxamide (Compound 558)

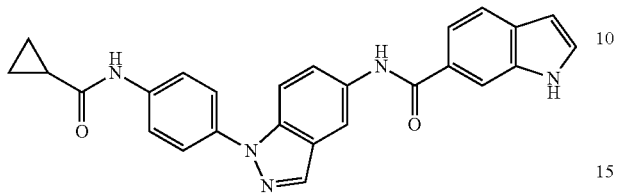

Compound 558 was prepared according to the procedure described in Scheme IV from 5-amino-1-(4-aminophenyl) indazole and indole-6-carboxylic acid. $^1$H NMR (500 MHz, Acetone-d6) δ 10.64 (s, 1H), 9.65 (m, 2H), 8.79 (s, 1H), 8.54 (m, 1H), 8.21 (m, 2H), 7.91-7.67 (m, 8H), 7.54 (m, 1H), 6.58 (m, 1H), 1.82 (m, 1H), 0.94 (m, 2H), 0.82 (m, 2H).

Example 459

N-(4-(5-(4-(4-Hydroxypiperidin-1-yl)benzamido)-1H-indazol-1-yl)phenyl)-1-methyl-1H-indole-5-carboxamide (Compound 559)

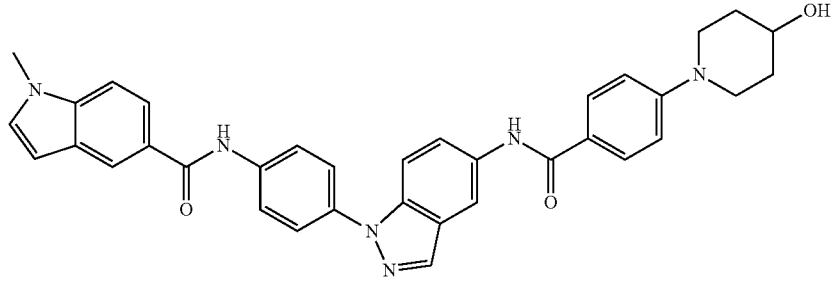 [SMILES: Cn1ccc2cc(C(=O)Nc3ccc(-n4ncc5cc(NC(=O)c6ccc(N7CCC(O)CC7)cc6)ccc54)cc3)ccc21]

Compound 559 was prepared according to the procedure described in Scheme IV from 5-amino-1-(4-aminophenyl) indazole and 4-(4-hydroxypiperidin-1-yl)benzoate. [M+H]$^+$ calcd for $C_{35}H_{32}N_6O_3$: 585.2. found: 585.19.

Example 460

N-(4-(5-(4-(4-Hydroxypiperidin-1-yl)benzamido)-1H-benzimidazol-1-yl)phenyl)cyclopropylcarboxamide (Compound 560)

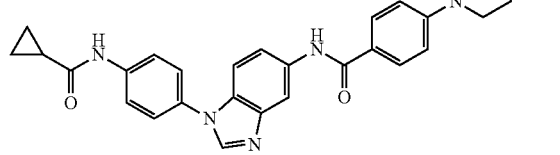

Compound 560 was prepared according to the procedure described in Scheme IV from 5-amino-1-(4-aminophenyl) benzimidazole and 4-(4-hydroxypiperidin-1-yl)benzoate. [M+H]$^+$ calcd for $C_{29}H_{29}N_5O_3$: 496.2. found: 496.08.

Example 461

N-(4-(5-(1H-Indole-6-carboxamido)-1H-benzimidazol-1-yl)phenyl)-1H-indole-6-carboxamide (Compound 561)

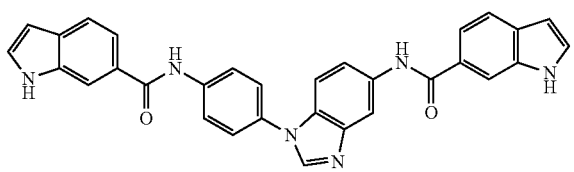 [SMILES: O=C(Nc1ccc(-n2cnc3cc(NC(=O)c4ccc5cc[nH]c5c4)ccc32)cc1)c1ccc2cc[nH]c2c1]

Compound 561 was prepared according to the procedure described in Scheme IV from 5-amino-1-(4-aminophenyl) benzimidazole and indole-6-carboxylic acid. [M+H]$^+$ calcd for $C_{31}H_{22}N_6O_2$: 511.1. found: 511.01.

Example 462

N-(1-(4-(4-Dimethylaminobenzamido)phenyl)-1H-benzimidazol-5-yl)thiophene-2-carboxamide (Compound 562)

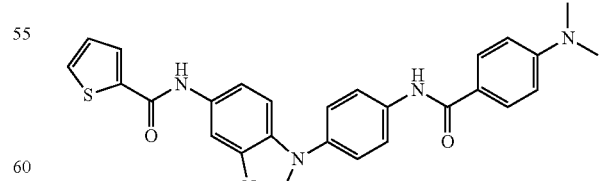

Compound 562 was prepared according to the procedure described in Scheme IV from 5-amino-1-(4-aminophenyl) benzimidazole and 4-dimethylaminobenzoate. [M+H]$^+$ calcd for $C_{27}H_{23}N_5O_2S$: 482.1. found: 481.98.

Example 463

N-(4-(5-(4-Morpholinobenzamido)-1H-benzimidazol-1-yl)phenyl)cyclopropylcarboxamide (Compound 563)

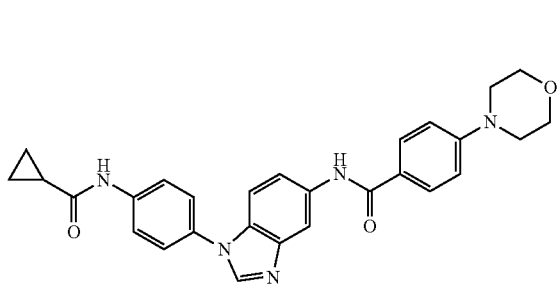 [SMILES: O=C(Nc1ccc2c(c1)ncn2-c1ccc(NC(=O)C2CC2)cc1)c1ccc(N2CCOCC2)cc1]

Compound 563 was prepared according to the procedure described in Scheme IV from 5-amino-1-(4-aminophenyl)benzimidazole and 4-morpholinobenzoate. [M+H]$^+$ calcd for $C_{28}H_{27}N_5O_3$: 482.2. found: 482.05.

Example 464

N-(4-(5-(1H-Indole-5-carboxamido)-1H-benzimidazol-1-yl)phenyl)-1H-indole-5-carboxamide (Compound 564)

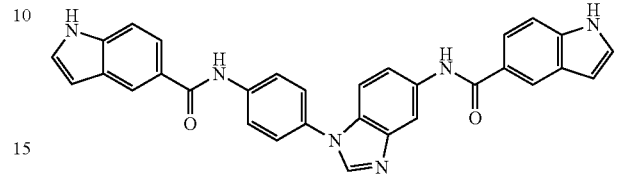

Compound 564 was prepared according to the procedure described in Scheme IV from 5-amino-1-(4-aminophenyl)benzimidazole and indole-5-carboxylic acid. [M+H]$^+$ calcd for $C_{31}H_{22}N_6O_2$: 511.1. found: 511.07.

Example 465

N,N'-(4,4'-Azanediylbis(4,1-phenylene))bis(4-(1H-imidazol-1-yl)benzamide) (Compound 565)

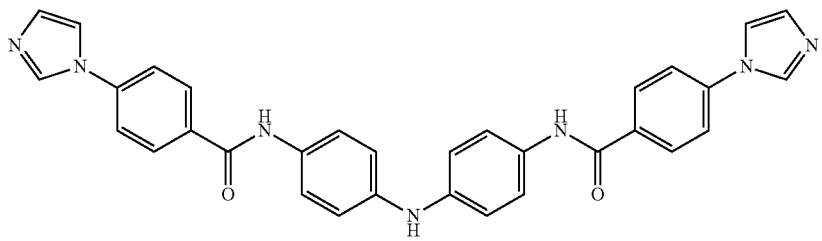 [SMILES: O=C(Nc1ccc(Nc2ccc(NC(=O)c3ccc(-n4ccnc4)cc3)cc2)cc1)c1ccc(-n2ccnc2)cc1]

Compound 565 was prepared according to the procedure described in Scheme IV from 4,4'-diaminodiphenylamine and 4-(imidazol-1-yl)benzoate. [M+H]$^+$ calcd for $C_{32}H_{25}N_7O_2$: 540.2. found 539.97.

Example 466

N,N'-(4,4'-Oxabis(4,1-phenylene))bis(4-(1H-imidazol-1-yl)benzamide) (Compound 566)

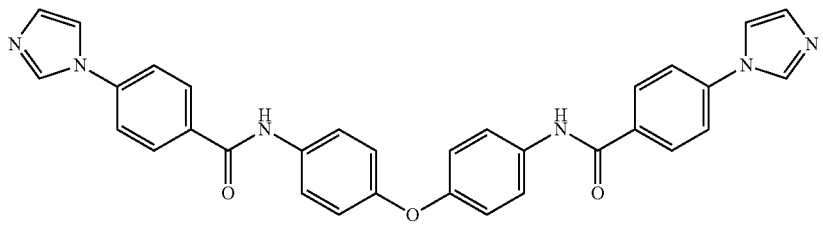 [SMILES: O=C(Nc1ccc(Oc2ccc(NC(=O)c3ccc(-n4ccnc4)cc3)cc2)cc1)c1ccc(-n2ccnc2)cc1]

Compound 566 was prepared according to the procedure described in Scheme IV from 4,4'-oxabisphenylamine and 4-(imidazol-1-yl)benzoate. [M+H]$^+$ calcd for $C_{32}H_{24}N_6O_3$: 541.2. found 541.05.

Example 467

N,N'-(4,4'-Azanediylbis(4,1-phenylene))bis(4-(1H-pyrazol-1-yl)benzamide) (Compound 567)

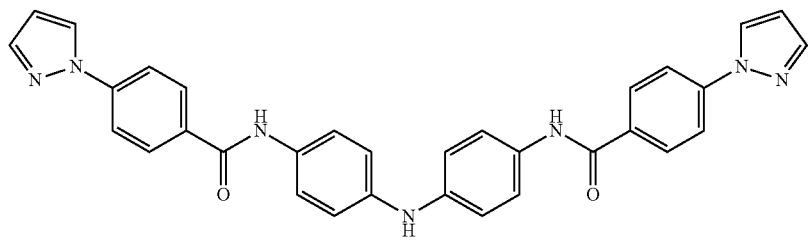 [SMILES: O=C(Nc1ccc(Nc2ccc(NC(=O)c3ccc(-n4cccn4)cc3)cc2)cc1)c1ccc(-n2cccn2)cc1]

Compound 567 was prepared according to the procedure described in Scheme IV from 4,4'-diaminodiphenylamine and 4-(pyrazol-1-yl)benzoate. [M+H]$^+$ calcd for $C_{32}H_{25}N_7O_2$: 540.2. found 539.97.

Example 468

N,N'-(4,4'-Azanediylbis(4,1-phenylene))bis(4-(1H-pyrrol-1-yl)benzamide) (Compound 568)

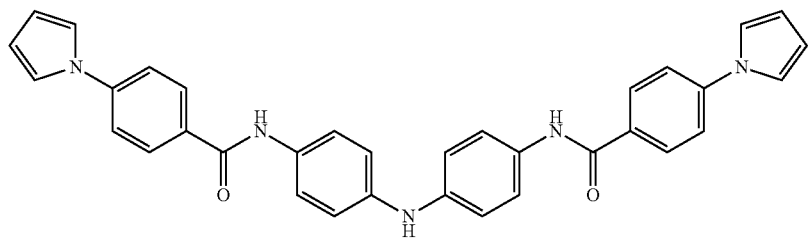 [SMILES: O=C(Nc1ccc(Nc2ccc(NC(=O)c3ccc(-n4cccc4)cc3)cc2)cc1)c1ccc(-n2cccc2)cc1]

Compound 568 was prepared according to the procedure described in Scheme IV from 4,4'-diaminodiphenylamine and 4-(pyrrol-1-yl)benzoate. [M+H]$^+$ calcd for $C_{34}H_{27}N_5O_2$: 538.2. found 538.09.

Example 469

N,N'-(4,4'-Azanediylbis(4,1-phenylene))bis(4-hydroxybenzamide) (Compound 569)

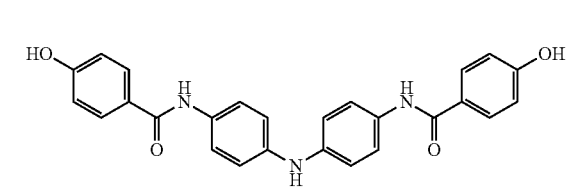 [SMILES: O=C(Nc1ccc(Nc2ccc(NC(=O)c3ccc(O)cc3)cc2)cc1)c1ccc(O)cc1]

Compound 569 was prepared according to the procedure described in Scheme IV from 4,4'-diaminodiphenylamine and 4-hydroxybenzoate. [M+H]$^+$ calcd for $C_{26}H_{21}N_3O_4$: 440.1. found 439.94.

Example 470

N,N'-(4,4'-Azanediylbis(4,1-phenylene))bis(3-hydroxybenzamide) (Compound 569)

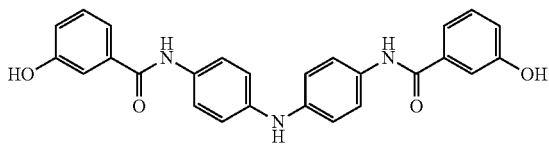 [SMILES: O=C(Nc1ccc(Nc2ccc(NC(=O)c3cccc(O)c3)cc2)cc1)c1cccc(O)c1]

Compound 570 was prepared according to the procedure described in Scheme IV from 4,4'-diaminodiphenylamine and 3-hydroxybenzoate. [M+H]$^+$ calcd for $C_{26}H_{21}N_3O_4$: 440.1. found 493.94.

Example 471

N,N'-(4,4'-Azanediylbis(4,1-phenylene))bis(4-methoxybenzamide) (Compound 571)

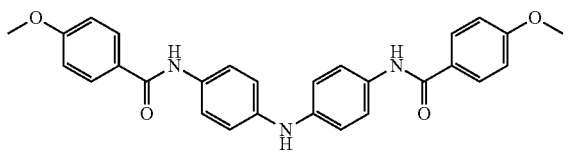

Compound 571 was prepared according to the procedure described in Scheme IV from 4,4'-diaminodiphenylamine and 4-methoxybenzoate. [M+H]$^+$ calcd for $C_{28}H_{25}N_3O_4$: 468.1. found 468.01.

Example 472

N,N'-(4,4'-Azanediylbis(4,1-phenylene))bis(1H-indole-2-carboxamide) (Compound 572)

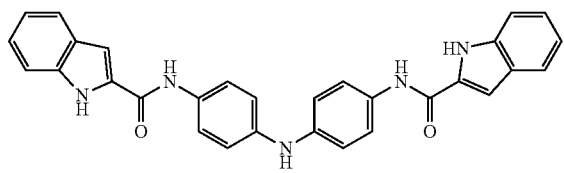 [SMILES: O=C(Nc1ccc(Nc2ccc(NC(=O)c3cc4ccccc4[nH]3)cc2)cc1)c1cc2ccccc2[nH]1]

Compound 572 was prepared according to the procedure described in Scheme IV from 4,4'-diaminodiphenylamine and indole-2-carboxylic acid. [M+H]$^+$ calcd for $C_{30}H_{23}N_5O_2$: 486.1. found 486.10.

Example 473

N,N'-(4,4'-Azanediylbis(4,1-phenylene))bis(4-(4-hydroxyphenyl)benzamide) (Compound 573)

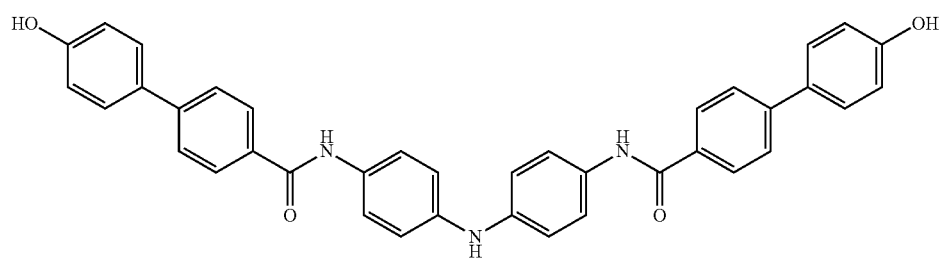 [SMILES: O=C(Nc1ccc(Nc2ccc(NC(=O)c3ccc(-c4ccc(O)cc4)cc3)cc2)cc1)c1ccc(-c2ccc(O)cc2)cc1]

Compound 573 was prepared according to the procedure described in Scheme IV from 4,4'-diaminodiphenylamine and 4-(4-hydroxyphenyl)benzoate. [M+H]$^+$ calcd for $C_{38}H_{29}N_3O_4$: 592.2. found 592.12.

Example 474

N,N'-(4,4'-Oxabis(4,1-phenylene))bis(4-aminobenzamide) (Compound 574)

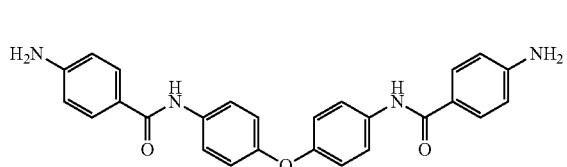

Compound 574 was prepared according to the procedure described in Scheme IV from 4,4'-oxabisphenylamine and 4-aminobenzoate. [M+H]$^+$ calcd for $C_{26}H_{22}N_4O_3$: 439.1. found 439.00.

Example 475

N,N'-(4,4'-Azanediylbis(4,1-phenylene))bis(1H-indole-6-carboxamide) (Compound 575)

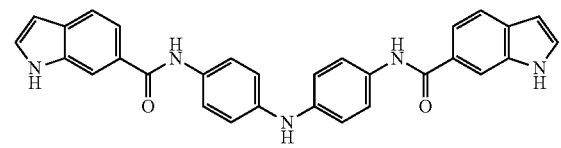 [SMILES: O=C(Nc1ccc(Nc2ccc(NC(=O)c3ccc4cc[nH]c4c3)cc2)cc1)c1ccc2cc[nH]c2c1]

Compound 575 was prepared according to the procedure described in Scheme IV from 4,4'-diaminodiphenylamine and indole-6-carboxylic acid. [M+H]$^+$ calcd for $C_{30}H_{23}N_5O_2$: 486.1. found 486.03.

Example 476

N,N'-(4,4'-Azanediylbis(4,1-phenylene))bis(1H-indole-5-carboxamide) (Compound 576)

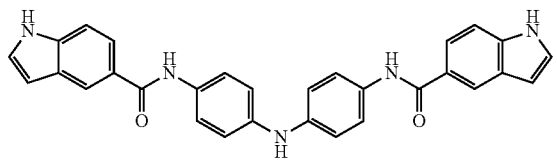 [SMILES: O=C(Nc1ccc(Nc2ccc(NC(=O)c3ccc4[nH]ccc4c3)cc2)cc1)c1ccc2[nH]ccc2c1]

Compound 576 was prepared according to the procedure described in Scheme IV from 4,4'-diaminodiphenylamine and indole-5-carboxylic acid. $[M+H]^+$ calcd for $C_{30}H_{23}N_5O_2$: 486.1. found 486.03.

Example 477

N,N'-(4,4'-Azanediylbis(4,1-phenylene))bis(4-(2-hydroxyethylamino)benzamide) (Compound 577)

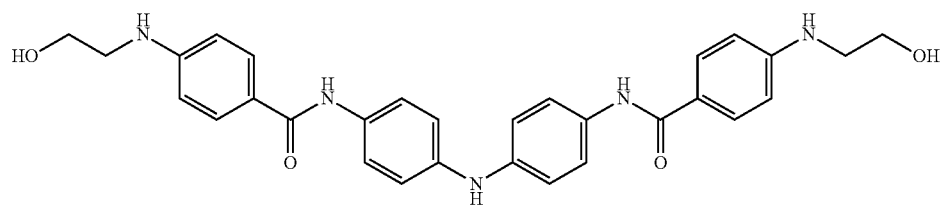 [SMILES: O=C(Nc1ccc(Nc2ccc(NC(=O)c3ccc(NCCO)cc3)cc2)cc1)c1ccc(NCCO)cc1]

Compound 577 was prepared according to the procedure described in Scheme IV from 4,4'-diaminodiphenylamine and 4-(2-hydroxyethylamino)benzoate. $[M+H]^+$ calcd for $C_{39}H_{32}N_5O_4$: 526.2. found: 526.08.

Example 478

N,N'-(4,4'-Azanediylbis(4,1-phenylene))bis(4-methanesulfonamidobenzamide) (Compound 578)

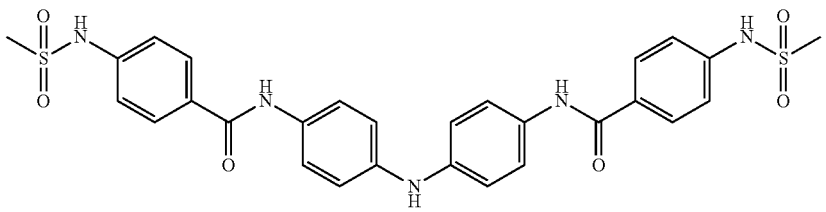

Compound 578 was prepared according to the procedure described in Scheme IV from 4,4'-diaminodiphenylamine and 4-methanesulfonamidobenzoate. $[M+H]^+$ calcd for $C_{28}H_{27}N_5O_6S_2$: 594.1. found 594.00.

Example 479

N,N'-(4,4'-Azanediylbis(4,1-phenylene))bis(4-tert-butyloxycarboxamidobenzamide) (Compound 579)

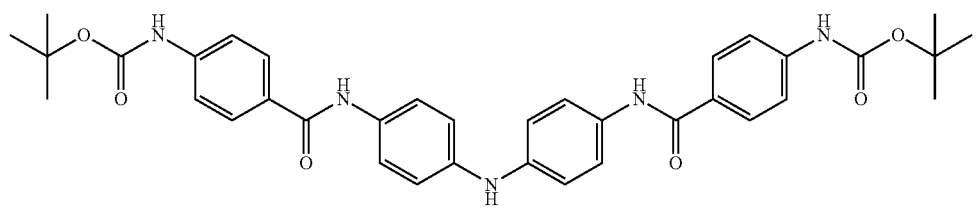 [SMILES: CC(C)(C)OC(=O)Nc1ccc(C(=O)Nc2ccc(Nc3ccc(NC(=O)c4ccc(NC(=O)OC(C)(C)C)cc4)cc3)cc2)cc1]

Compound 579 was prepared according to the procedure described in Scheme IV from 4,4'-diaminodiphenylamine and 4-tert-butyloxycarboxamidobenzoate. [M+H]$^+$ calcd for $C_{36}H_{39}N_5O_6$: 638.2. found 638.20.

Example 480

N,N'-(4,4'-Azanediylbis(4,1-phenylene))bis(4-aminobenzamide) (Compound 580)

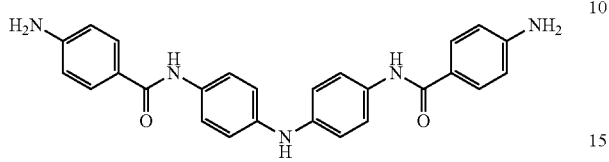

Compound 580 was prepared according to the procedure described in Scheme IV from 4,4'-diaminodiphenylamine and 4-aminobenzoate. [M+H]$^+$ calcd for $C_{26}H_{23}N_5O_2$: 438.1. found 438.05.

Example 481

N,N'-(4,4'-Azanediylbis(4,1-phenylene)bis(4-(2-aminoacetamidobenzamide) (Compound 581)

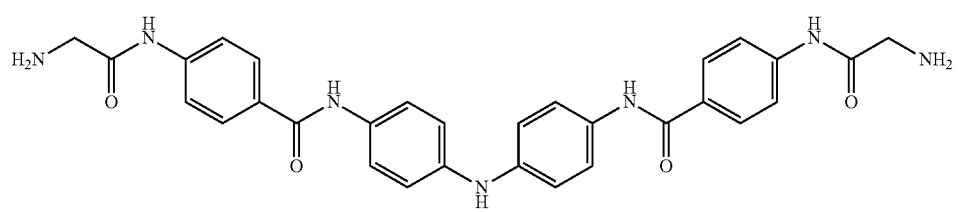 [SMILES: NCC(=O)Nc1ccc(C(=O)Nc2ccc(Nc3ccc(NC(=O)c4ccc(NC(=O)CN)cc4)cc3)cc2)cc1]

Compound 581 was prepared according to the procedure described in Scheme IV from 4,4'-diaminodiphenylamine and 4-(2-aminoacetamido)benzoate. [M+H]$^+$ calcd for $C_{30}H_{29}N_7O_4$: 552.2. found 552.12.

Example 482

N,N'-(4,4'-Azanediylbis(4,1-phenylene))bis(1-methyl-1H-indole-5-carboxamide) (Compound 582)

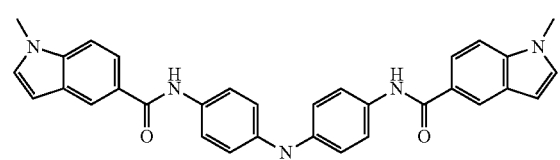

Compound 582 was prepared according to the procedure described in Scheme IV from 4,4'-diaminodiphenylamine and 1-methylindole-5-carboxylic acid. [M+H]$^+$ calcd for $C_{32}H_{27}N_5O_2$: 514.2. found 514.11.

Example 483

N,N'-(4,4'-Azanediylbis(4,1-phenylene))bis(thiophene-2-carboxamide) (Compound 583)

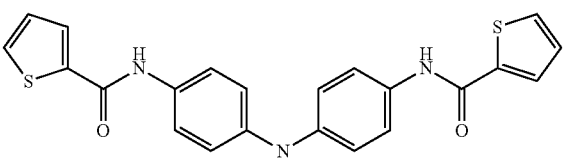

Compound 583 was prepared according to the procedure described in Scheme IV from 4,4'-diaminodiphenylamine and thiophene-2-carboxylic acid. [M+H]$^+$ calcd for $C_{22}H_{17}N_3O_2S_2$: 420.0. found 419.91.

Example 484

N,N'-(4,4'-Azanediylbis(4,1-phenylene))bis(4-pyrrolidinebenzamide) (Compound 584)

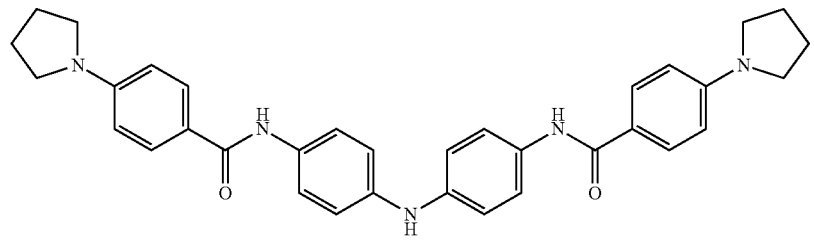 [SMILES: O=C(Nc1ccc(Nc2ccc(NC(=O)c3ccc(N4CCCC4)cc3)cc2)cc1)c1ccc(N2CCCC2)cc1]

Compound 584 was prepared according to the procedure described in Scheme IV from 4,4'-diaminodiphenylamine and 4-pyrrolidinebenzoate. [M+H]$^+$ calcd for $C_{34}H_{35}N_5O_2$: 546.2. found 546.07.

Example 485

N,N'-(4,4'-Oxabis(4,1-phenylene))bis(1H-indole-5-carboxamide) (Compound 585)

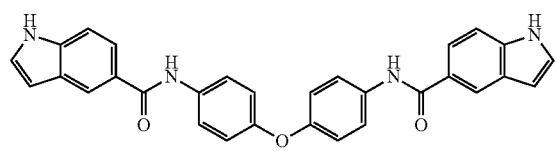 [SMILES: O=C(Nc1ccc(Oc2ccc(NC(=O)c3ccc4[nH]ccc4c3)cc2)cc1)c1ccc2[nH]ccc2c1]

Compound 585 was prepared according to the procedure described in Scheme IV from 4,4'-diaminodiphenylamine and indole-5-carboxylic acid. [M+H]$^+$ calcd for $C_{30}H_{22}N_4O_3$: 487.1. found 486.98.

Example 486

N,N'-(4,4'-Oxabis(4,1-phenylene))bis(4-N-methyl-N-(2-hydroxyethyl)aminobenzamide) (Compound 586)

Compound 586 was prepared according to the procedure described in Scheme IV from 4,4'-diaminodiphenylamine and 4-N-methyl-N-(2-hydroxyethyl)aminobenzoate. [M+H]$^+$ calcd for $C_{32}H_{34}N_4O_5$: 555.2. found 555.12.

Example 487

N,N'-(4,4'-Azanediylbis(4,1-phenylene))bis(1-methyl-1,4-benzoxazine-6-carboxamide) (Compound 587)

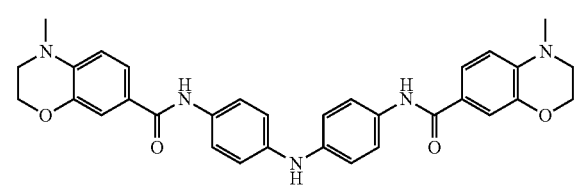

Compound 587 was prepared according to the procedure described in Scheme IV from 4,4'-diaminodiphenylamine and 1-methyl-1,4-benzoxazine-6-carboxylic acid. [M+H]$^+$ calcd for $C_{32}H_{31}N_5O_4$: 550.2. found 550.05.

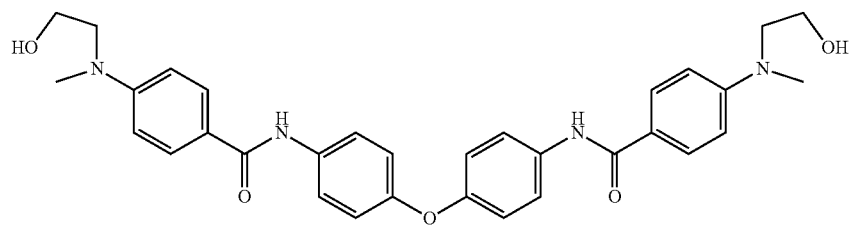 [SMILES: CN(CCO)c1ccc(C(=O)Nc2ccc(Oc3ccc(NC(=O)c4ccc(N(C)CCO)cc4)cc3)cc2)cc1]

Example 488

N,N'-(4,4'-Carbonylbis(4,1-phenylene))bis(4-aminobenzamide) (Compound 588)

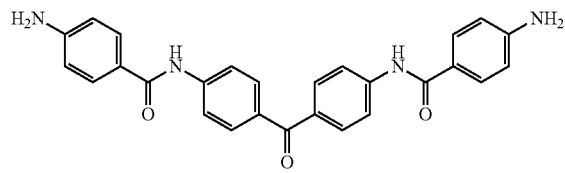 [SMILES: Nc1ccc(C(=O)Nc2ccc(C(=O)c3ccc(NC(=O)c4ccc(N)cc4)cc3)cc2)cc1]

Compound 588 was prepared according to the procedure described in Scheme IV from 4,4'-diaminobenzophenone and 4-aminobenzoate. [M+H]$^+$ calcd for $C_{27}H_{22}N_4O_3$: 451.1. found 450.94.

Example 489

N,N'-(4,4'-Carbonylbis(4,1-phenylene))bis(4-tert-butyloxycarbamidobenzamide) (Compound 589)

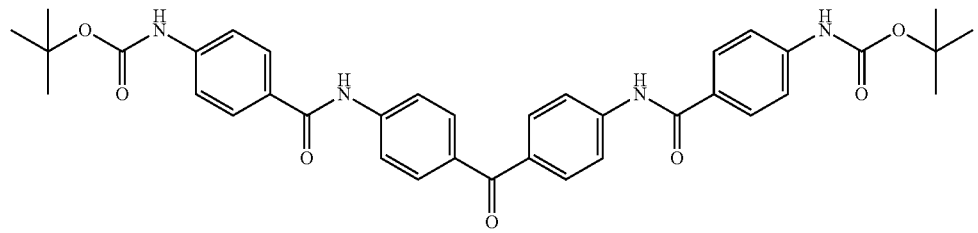 [SMILES: CC(C)(C)OC(=O)Nc1ccc(C(=O)Nc2ccc(C(=O)c3ccc(NC(=O)c4ccc(NC(=O)OC(C)(C)C)cc4)cc3)cc2)cc1]

Compound 589 was prepared according to the procedure described in Scheme IV from 4,4'-diaminobenzophenone and 4-tert-butyloxycarbamidobenzoate. [M+H]$^+$ calcd for $C_{37}H_{38}N_4O_7$: 651.2. found 651.10.

Example 490

N,N'-(4,4'-Azanediylbis(4,1-phenylene))bis(1H-benzimidazole-5-carboxamide) (Compound 590)

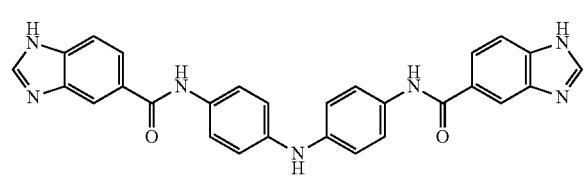 [SMILES: O=C(Nc1ccc(Nc2ccc(NC(=O)c3ccc4[nH]cnc4c3)cc2)cc1)c1ccc2[nH]cnc2c1]

Compound 590 was prepared according to the procedure described in Scheme IV from 4,4'-diaminodiphenylamine and benzimidazole-5-carboxylic acid. [M+H]$^+$ calcd for $C_{28}H_{21}N_7O_2$: 488.1. found 488.02.

Example 491

4-(4-Cyclopropylcarbonyl)piperazin-1-yl-N-(4-(4-ethylaminobenzoyl)phenyl)benzamide (Compound 591)

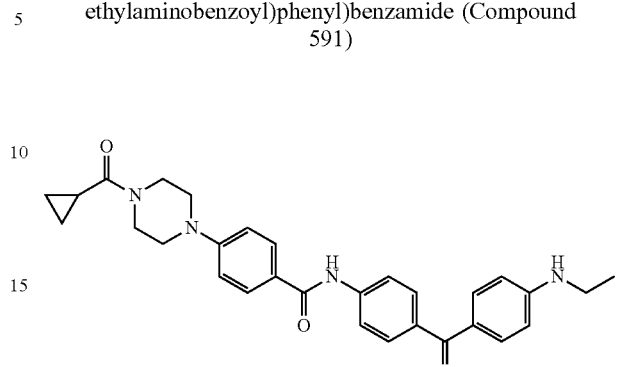

Compound 591 was prepared according to the procedure described in Scheme IV from 4,4'-diaminobenzophenone and (4-(4-cyclopropylcarbonyl)piperazin-1-yl)benzoate.

[M+H]$^+$ calcd for $C_{30}H_{32}N_4O_3$: 497.1. found: 497.33.

Example 492

4-Morpholino-N-(4-(4-diethylaminobenzoyl)phenyl)benzamide (Compound 592)

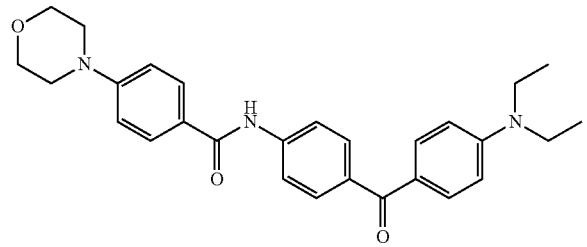 [SMILES: CCN(CC)c1ccc(C(=O)c2ccc(NC(=O)c3ccc(N4CCOCC4)cc3)cc2)cc1]

Compound 592 was prepared according to the procedure described in Scheme IV from 4,4'-diaminobenzophenone and 4-morpholinobenzoate. [M+H]$^+$ calcd for $C_{28}H_{31}N_3O_3$: 458.0. found: 458.31.

Example 493

4-Morpholino-N-(4-(4-propylaminobenzoyl)phenyl)benzamide (Compound 593)

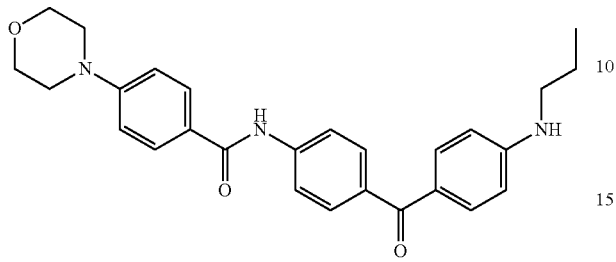

Compound 593 was prepared according to the procedure described in Scheme IV from 4,4'-diaminobenzophenone and 4-morpholinobenzoate. [M+H]$^+$ calcd for $C_{27}H_{29}N_3O_3$: 444.0. found: 444.31.

Example 494

4-Morpholino-N-(4-(4-allylaminobenzoyl)phenyl)benzamide (Compound 594)

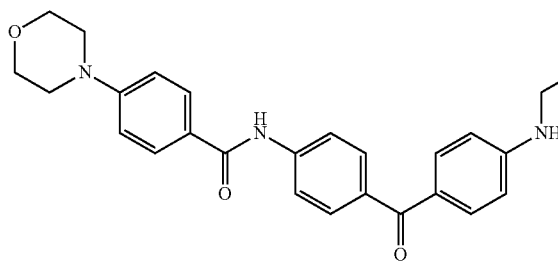

Compound 594 was prepared according to the procedure described in Scheme IV from 4,4'-diaminobenzophenone and 4-morpholinobenzoate. [M+H]$^+$ calcd for $C_{27}H_{27}N_3O_3$: 442.0. found: 442.30.

Example 495

4-Morpholino-N-(4-(4-(furan-2-carboxamido)benzoyl)phenyl)benzamide (Compound 595)

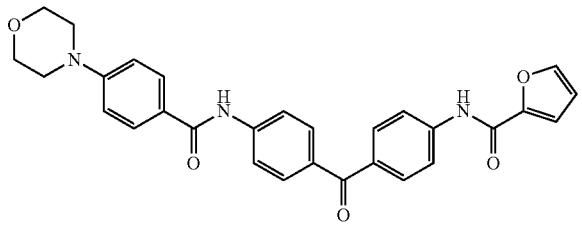 [SMILES: O=C(Nc1ccc(C(=O)c2ccc(NC(=O)c3ccco3)cc2)cc1)c1ccc(N2CCOCC2)cc1]

Compound 595 was prepared according to the procedure described in Scheme IV from 4,4'-diaminobenzophenone and 4-morpholinobenzoate. [M+H]$^+$ calcd for $C_{29}H_{25}N_3O_5$: 496.0. found: 496.09.

Example 496

N-(1-(4-Acetylpheyl)-1H-indazol-5-yl)morpholinobenzamide (Compound 596)

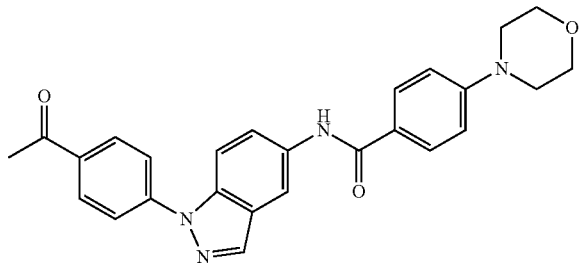 [SMILES: CC(=O)c1ccc(-n2ncc3cc(NC(=O)c4ccc(N5CCOCC5)cc4)ccc32)cc1]

Compound 596 was prepared according to the procedure described in Scheme IV from 5-amino-1-(4-acetylphenyl)indazole and 4-morpholinobenzoate. [M+H]$^+$ calcd for $C_{26}H_{24}N_4O_3$: 441.1. found: 441.02.

Example 497

4-Morpholino-N-(4-(4-(pyridine-4-carboxamido)benzoyl)phenyl)benzamide (Compound 597)

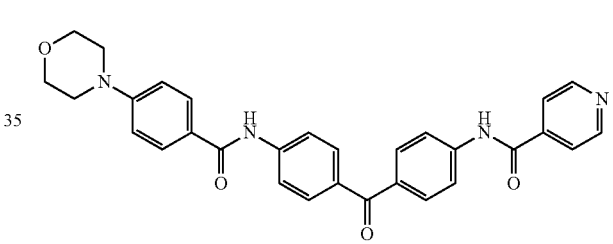

Compound 597 was prepared according to the procedure described in Scheme IV from 4,4'-diaminobenzophenone and 4-morpholinobenzoate. [M+H]$^+$ calcd for $C_{30}H_{27}N_4O_4$: 507.2. found: 507.02.

Example 498

4-Morpholino-N-(4-(4-(pyridine-3-carboxamido)benzoyl)phenyl)benzamide (Compound 598)

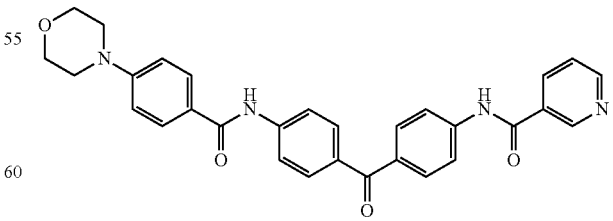

Compound 598 was prepared according to the procedure described in Scheme IV from 4,4'-diaminobenzophenone and 4-morpholinobenzoate. [M+H]$^+$ calcd for $C_{30}H_{26}N_4O_4$: 507.0. found: 507.09.

Example 499

4-Morpholino-N-(4-(4-(2-methoxycarbonylethyl)aminobenzoyl)phenyl)benzamide (Compound 599)

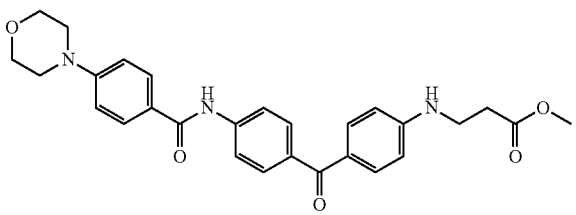 [SMILES: COC(=O)CCNc1ccc(C(=O)c2ccc(NC(=O)c3ccc(N4CCOCC4)cc3)cc2)cc1]

Compound 599 was prepared according to the procedure described in Scheme IV from 4,4'-diaminobenzophenone and 4-morpholinobenzoate. [M+H]$^+$ calcd for $C_{28}H_{29}N_3O_5$: 488.0. found: 488.08.

Example 500

4-Morpholino-N-(4-(4-(isoxazole-5-carboxamido)benzoyl)phenyl)benzamide (Compound 600)

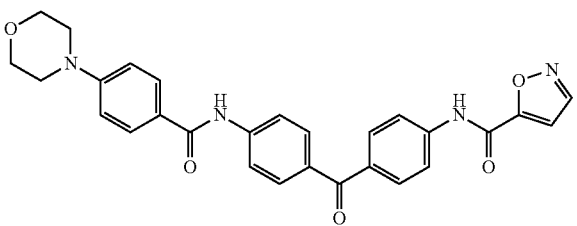 [SMILES: O=C(Nc1ccc(C(=O)c2ccc(NC(=O)c3ccno3)cc2)cc1)c1ccc(N2CCOCC2)cc1]

Compound 600 was prepared according to the procedure described in Scheme IV from 4,4'-diaminobenzophenone and 4-morpholinobenzoate. [M+H]$^+$ calcd for $C_{28}H_{24}N_4O_5$: 497.0. found: 497.03.

Example 501

4-(4-Cyclopropylcarbonyl)piperazin-1-yl-N-(4-(4-aminobenzoyl)phenyl)benzamide (Compound 601)

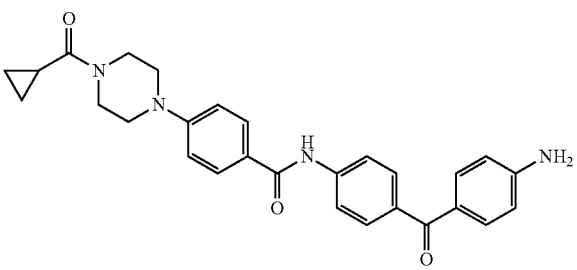 [SMILES: Nc1ccc(C(=O)c2ccc(NC(=O)c3ccc(N4CCN(C(=O)C5CC5)CC4)cc3)cc2)cc1]

Compound 601 was prepared according to the procedure described in Scheme IV from 4,4'-diaminobenzophenone and (4-(4-cyclopropylcarbonyl)piperazin-1-yl)benzoate.

[M+H]$^+$ calcd for $C_{28}H_{28}N_4O_3$: 469.0. found: 469.09.

Example 502

4-Morpholino-N-(4-(4-(1,2,4-triazole-3-carboxamido)benzoyl)phenyl)benzamide (Compound 602)

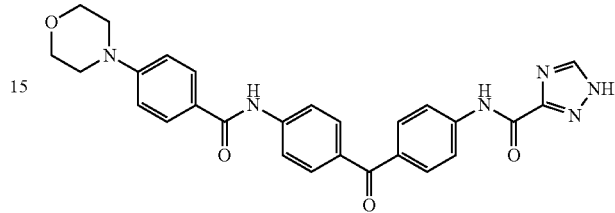

Compound 602 was prepared according to the procedure described in Scheme IV from 4,4'-diaminobenzophenone and 4-morpholinobenzoate. [M+H]$^+$ calcd for $C_{27}H_{24}N_6O_4$: 497.0. found: 497.03.

Example 503

4-Morpholino-N-(4-(4-(pyridazine-4-carboxamido)benzoyl)phenyl)benzamide (Compound 603)

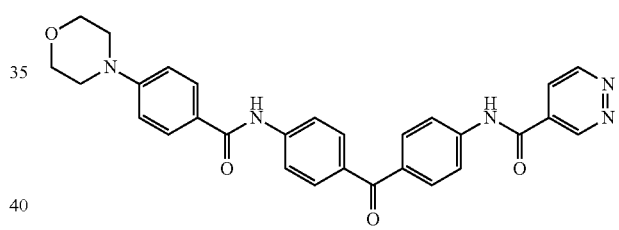

Compound 603 was prepared according to the procedure described in Scheme IV from 4,4'-diaminobenzophenone and 4-morpholinobenzoate. [M+H]$^+$ calcd for $C_{29}H_{25}N_5O_4$: 508.0. found: 508.04.

Example 504

4-Morpholino-N-(4-(4-(3-cyclopropylpyrazole-5-carboxamido)benzoyl)phenyl)benzamide (Compound 604)

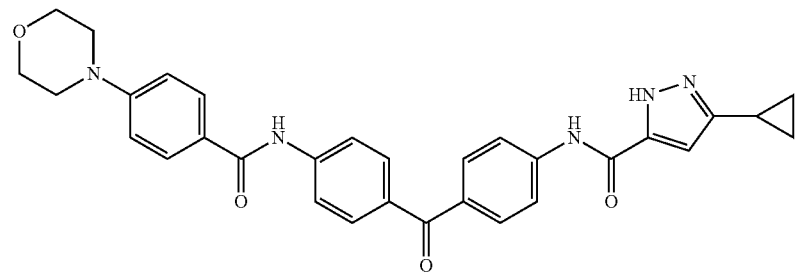 [SMILES: O=C(Nc1ccc(C(=O)c2ccc(NC(=O)c3cc(C4CC4)n[nH]3)cc2)cc1)c1ccc(N2CCOCC2)cc1]

Compound 604 was prepared according to the procedure described in Scheme IV from 4,4'-diaminobenzophenone and 4-morpholinobenzoate. [M+H]$^+$ calcd for $C_{31}H_{30}N_5O_4$: 536.2. found: 536.10.

Example 505

4-Morpholino-N-(4-(4-(1,2,3-thiodiazol-4-carboxamido)benzoyl)phenyl)benzamide (Compound 605)

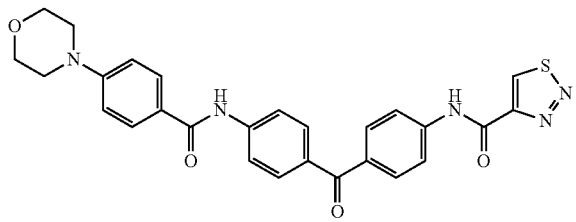 [SMILES: O=C(Nc1ccc(C(=O)c2ccc(NC(=O)c3csnn3)cc2)cc1)c1ccc(N2CCOCC2)cc1]

Compound 605 was prepared according to the procedure described in Scheme IV from 4,4'-diaminobenzophenone and 4-morpholinobenzoate. [M+H]$^+$ calcd for $C_{27}H_{23}N_5O_4S$: 514.0. found: 514.04.

Example 506

4-Morpholino-N-(4-(4-(thiazole-4-carboxamido)benzoyl)phenyl)benzamide (Compound 606)

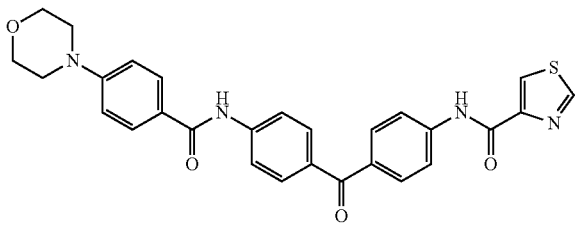 [SMILES: O=C(Nc1ccc(C(=O)c2ccc(NC(=O)c3cscn3)cc2)cc1)c1ccc(N2CCOCC2)cc1]

Compound 606 was prepared according to the procedure described in Scheme IV from 4,4'-diaminobenzophenone and 4-morpholinobenzoate. [M+H]$^+$ calcd for $C_{28}H_{24}N_4O_4S$: 513.1. found: 513.03.

Example 507

4-Morpholino-N-(4-(4-(imidazole-4-carboxamido)benzoyl)phenyl)benzamide (Compound 607)

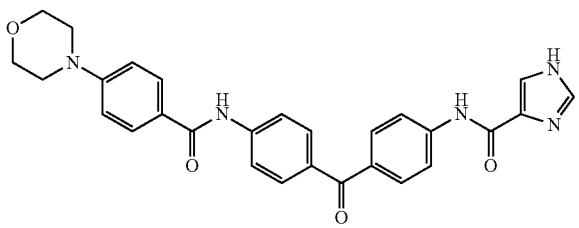 [SMILES: O=C(Nc1ccc(C(=O)c2ccc(NC(=O)c3c[nH]cn3)cc2)cc1)c1ccc(N2CCOCC2)cc1]

Compound 607 was prepared according to the procedure described in Scheme IV from 4,4'-diaminobenzophenone and 4-morpholinobenzoate. [M+H]$^+$ calcd for $C_{28}H_{26}N_5O_4$: 496.2. found: 496.02.

Example 508

4-Morpholino-N-(4-(4-(5-methylisoxazole-3-carboxamido)benzoyl)phenyl)benzamide (Compound 608)

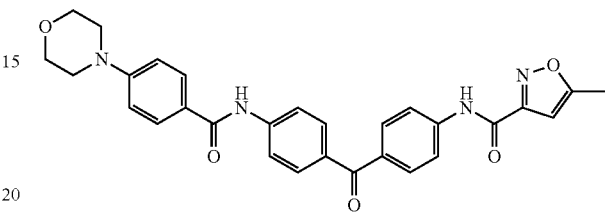

Compound 608 was prepared according to the procedure described in Scheme IV from 4,4'-diaminobenzophenone and 4-morpholinobenzoate. [M+H]$^+$ calcd for $C_{29}H_{26}N_4O_5$: 511.0. found: 511.07.

Example 509

4-Morpholino-N-(4-(4-(oxazole-4-carboxamido)benzoyl)phenyl)benzamide (Compound 609)

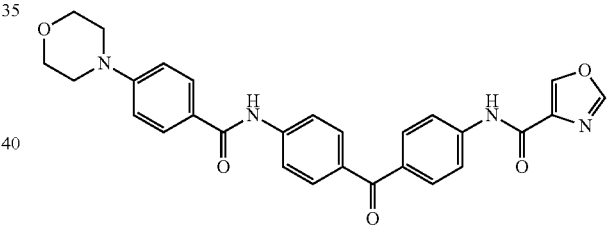

Compound 609 was prepared according to the procedure described in Scheme IV from 4,4'-diaminobenzophenone and 4-morpholinobenzoate. [M+H]$^+$ calcd for $C_{28}H_{24}N_4O_5$: 497.0. found: 497.03.

Example 510

4-Morpholino-N-(4-(4-(1,2,3-triazole-4-carboxamido)benzoyl)phenyl)benzamide (Compound 610)

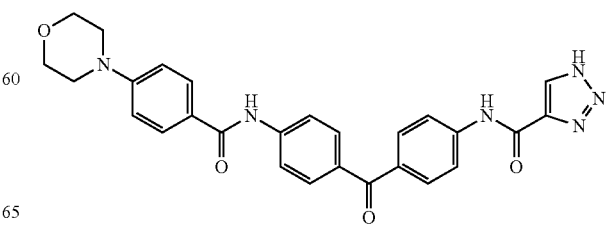

Compound 610 was prepared according to the procedure described in Scheme IV from 4,4'-diaminobenzophenone and 4-morpholinobenzoate. [M+H]$^+$ calcd for $C_{27}H_{24}N_6O_4$: 497.0. found: 497.03.

Example 511

4-Morpholino-N-(4-(4-(pyridine-2-carboxamido) benzoyl)phenyl)benzamide (Compound 611)

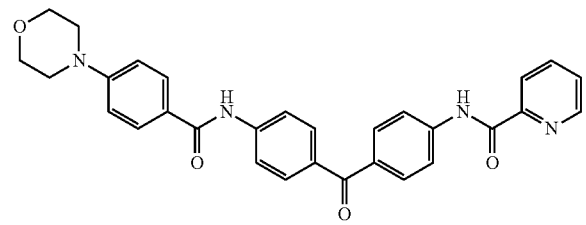 [SMILES: O=C(Nc1ccc(C(=O)c2ccc(NC(=O)c3ccccn3)cc2)cc1)c1ccc(N2CCOCC2)cc1]

Compound 611 was prepared according to the procedure described in Scheme IV from 4,4'-diaminobenzophenone and 4-morpholinobenzoate. [M+H]$^+$ calcd for $C_{30}H_{26}N_4O_4$: 507.0. found: 507.02.

Example 512

4-Morpholino-N-(4-(4-(pyridazine-3-carboxamido) benzoyl)phenyl)benzamide (Compound 612)

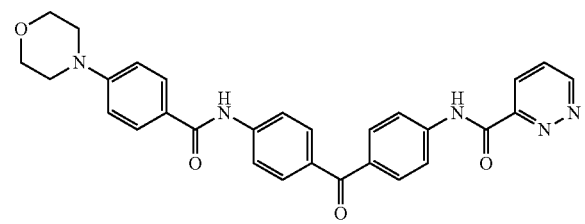 [SMILES: O=C(Nc1ccc(C(=O)c2ccc(NC(=O)c3cccnn3)cc2)cc1)c1ccc(N2CCOCC2)cc1]

Compound 612 was prepared according to the procedure described in Scheme IV from 4,4'-diaminobenzophenone and 4-morpholinobenzoate. [M+H]$^+$ calcd for $C_{29}H_{25}N_5O_4$: 508.0. found: 508.29.

Example 513

4-Morpholino-N-(4-(4-(1-methyl-1H-pyrazole-3-carboxamido)benzoyl)phenyl)benzamide (Compound 613)

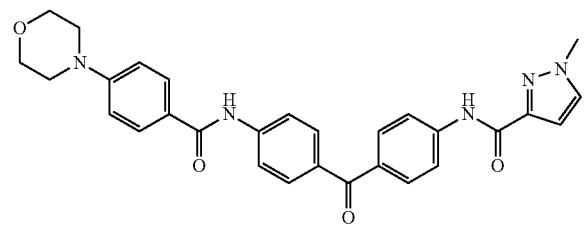 [SMILES: Cn1ccc(C(=O)Nc2ccc(C(=O)c3ccc(NC(=O)c4ccc(N5CCOCC5)cc4)cc3)cc2)n1]

Compound 613 was prepared according to the procedure described in Scheme IV from 4,4'-diaminobenzophenone and 4-morpholinobenzoate. [M+H]$^+$ calcd for $C_{29}H_{27}N_5O_4$: 510.0. found: 510.06.

Example 514

4-Morpholino-N-(4-(4-(pyrazine-2-carboxamido) benzoyl)phenyl)benzamide (Compound 614)

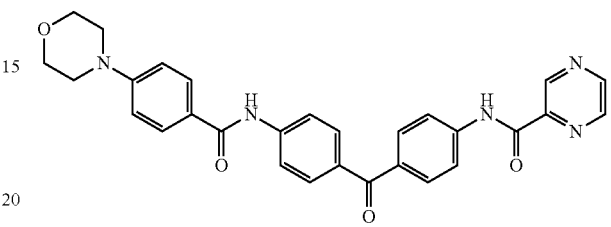

Compound 614 was prepared according to the procedure described in Scheme IV from 4,4'-diaminobenzophenone and 4-morpholinobenzoate. [M+H]$^+$ calcd for $C_{29}H_{25}N_5O_4$: 508.0. found: 508.04.

Example 515

4-Morpholino-N-(4-(4-(thiophene-2-carbanylcarboxamido)benzoyl)phenyl)benzamide (Compound 615)

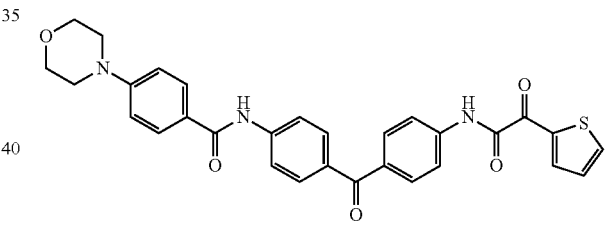

Compound 615 was prepared according to the procedure described in Scheme IV from 4,4'-diaminobenzophenone and 4-morpholinobenzoate. [M+H]$^+$ calcd for $C_{30}H_{25}N_3O_5S$: 540.1. found: 540.03.

Example 516

4-Morpholino-N-(4-(4-acetylcarboxamido)benzoyl) phenyl)benzamide (Compound 616)

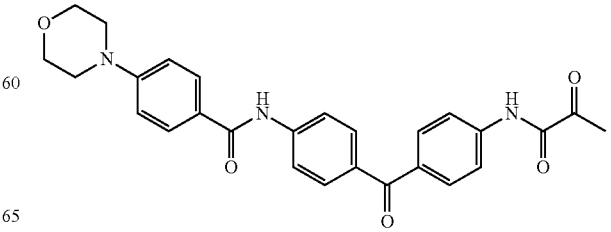

Compound 616 was prepared according to the procedure described in Scheme IV from 4,4'-diaminobenzophenone and 4-morpholinobenzoate. [M+H]+ calcd for $C_{27}H_{25}N_3O_5$: 472.0. found: 472.06.

Example 517

3-Chloro-4-morpholino-N-(4-(4-aminobenzoyl)phenyl)benzamide (Compound 617)

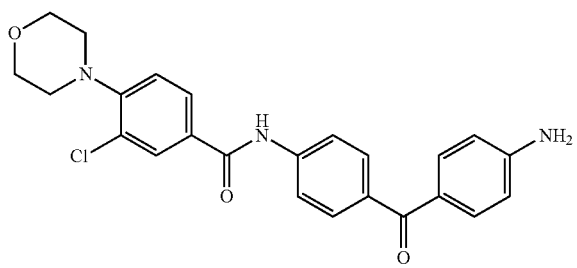 [SMILES: Nc1ccc(C(=O)c2ccc(NC(=O)c3ccc(N4CCOCC4)c(Cl)c3)cc2)cc1]

Compound 617 was prepared according to the procedure described in Scheme IV from 4,4'-diaminobenzophenone and 3-chloro-4-morpholinobenzoate. [M+H]+ calcd for $C_{24}H_{23}ClN_3O_3$: 436.1. found: 435.97.

Example 518

3-Chloro-4-morpholino-N-(4-(4-(thiophene-2-carboxamido)benzoyl)phenyl)benzamide (Compound 618)

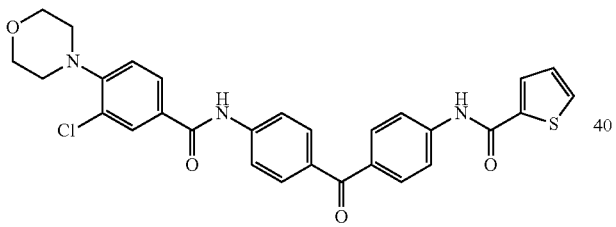

Compound 618 was prepared according to the procedure described in Scheme IV from 4,4'-diaminobenzophenone and 3-chloro-4-morpholinobenzoate. [M+H]+ calcd for $C_{29}H_{25}ClN_3O_4S$: 546.1. found: 546.08.

Example 519

4-Morpholino-N-(4-(4-(2,6-dichloropyridine-4-carboxamido)benzoyl)phenyl)benzamide (Compound 619)

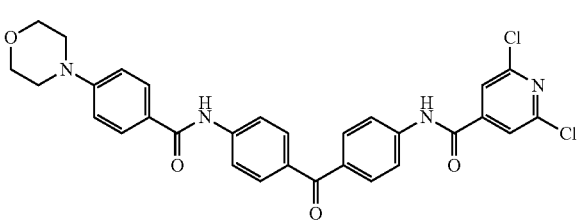

Compound 619 was prepared according to the procedure described in Scheme IV from 4,4'-diaminobenzophenone and 4-morpholinobenzoate. [M+H]+ calcd for $C_{30}H_{24}Cl_2N_4O_4$: 576.0. found: 576.15.

Example 520

4-Morpholino-N-(4-(4-(2-chloro-6-methylpyridine-4-carboxamido)benzoyl)phenyl)benzamide (Compound 620)

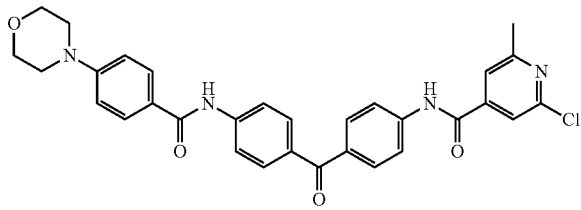 [SMILES: Cc1cc(C(=O)Nc2ccc(C(=O)c3ccc(NC(=O)c4ccc(N5CCOCC5)cc4)cc3)cc2)cc(Cl)n1]

Compound 620 was prepared according to the procedure described in Scheme IV from 4,4'-diaminobenzophenone and 4-morpholinobenzoate. [M+H]+ calcd for $C_{31}H_{27}ClN_4O_4$: 556.0. found: 556.17.

Example 521

4-Morpholino-N-(4-(4-(2-chloropyridine-4-carboxamido)benzoyl)phenyl)benzamide (Compound 621)

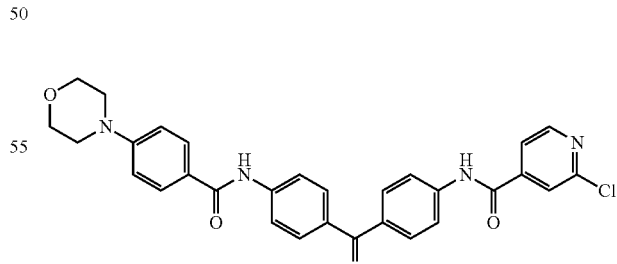

Compound 621 was prepared according to the procedure described in Scheme IV from 4,4'-diaminobenzophenone and 4-morpholinobenzoate. [M+H]+ calcd for $C_{30}H_{25}ClN_4O_4$: 542.0. found: 541.92.

Example 522

4-(6-(2-Methylthiazol-4-ylmethoxy)-1H-benzo[d]imidazol-2-yl)-N-(4-morpholinophenyl)benzamide (Compound 622)

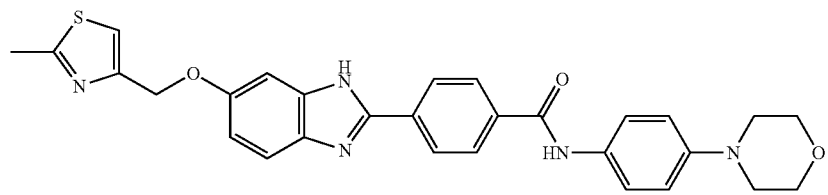

Compound 622 was prepared according to the procedure similar to that described in Scheme III from 1-(2-methylthiazol-4-yl)methoxy-3,4-dinitrobenzene and 4-(4-(4-morpholinophenyl)aminocarbonylbenzaldehyde. [M+H]$^+$ calcd for $C_{29}H_{27}N_5O_3S$: 526.18. found: 526.06.

Example 523

4-(Cyclopropanecarboxamido)-N-(4-(N-(4-(4-(cyclopropanecarboxamido)benzamido)phenyl)cyclopanecarboxamido)phenyl)benzamide (Compound 623)

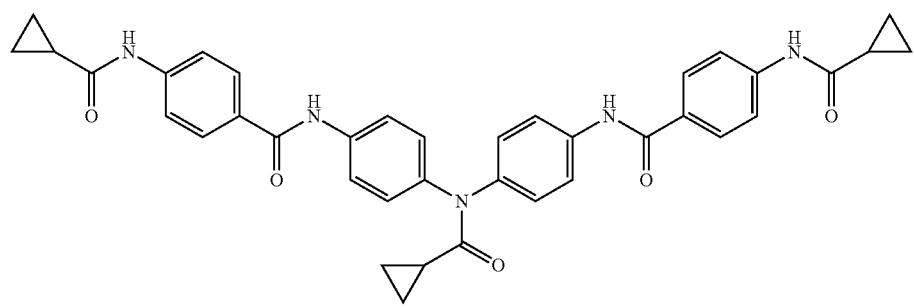 [SMILES: O=C(Nc1ccc(N(C(=O)C2CC2)c2ccc(NC(=O)c3ccc(NC(=O)C4CC4)cc3)cc2)cc1)c1ccc(NC(=O)C2CC2)cc1]

Compound 623 was prepared by a general amide formation reaction from cyclopropanecarboxylic acid and compound 580. [M+H]$^+$ calcd for $C_{38}H_{35}N_5O_5$: 642.26. found 642.19.

Example 524

4-(6-(Pyridin-2-ylmethoxy)-1H-benzo[d]imidazol-2-yl)-N-(4-morpholinophenyl)benzamide (Compound 624)

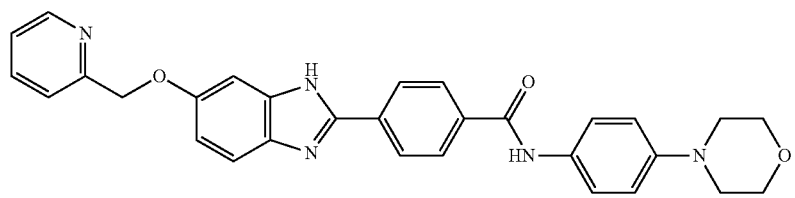 [SMILES: O=C(Nc1ccc(N2CCOCC2)cc1)c1ccc(-c2nc3ccc(OCc4ccccn4)cc3[nH]2)cc1]

Compound 624 was prepared according to the procedure similar to that described in Scheme III from 1-(pyridin-2-ylmethoxy)-3,4-dinitrobenzene and 4-(4-(4-morpholinophenyl)aminocarbonylbenzaldehyde. [M+H]+ calcd for $C_{30}H_{27}N_5O_3$: 506.21. found: 506.06.

Example 525

4-(Dimethylamino)-N-(4-(4-(6-methoxy-1H-benzo[d]imidazol-2-yl)benzamido)phenyl)benzamide (Compound 625)

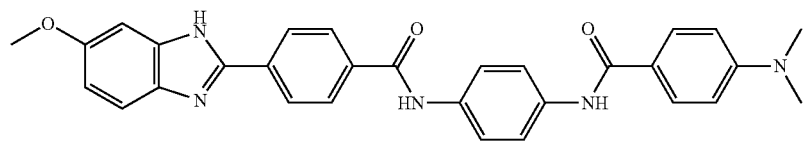

Compound 625 was prepared according to the procedure similar to that described in Scheme III from 4-(6-methoxy-1H-benzo[d]imidazol-2-yl)benzoic acid, 1,4-phenylenediamine, and 4dimethylaminobenzoic acid. [M+H]+ calcd for $C_{30}H_{27}N_5O_3$: 506.21. found: 506.05.

Example 526

4-(Dimethylamino)-N-(4-(6-(4-(dimethylamino)benzamido)-1H-indol-3-yl)phenyl)benzamide (Compound 626)

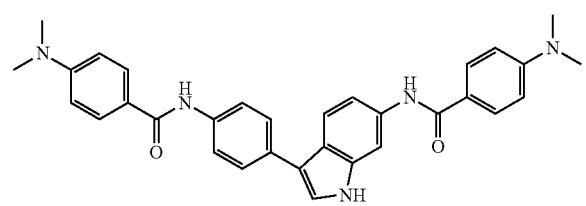

Compound 626 was prepared according to the procedure described in Scheme IV from 6-amino-3-(4-aminophenyl)-1H-indole and 4-dimethylaminobenzoate. [M+H]+ calcd for $C_{32}H_{31}N_5O_2$: 518.1. found: 518.09.

Example 527

N,N'-((Methylazanediyl)bis(4,1-phenylene))bis(4-dimethylaminobenzamide) (Compound 627)

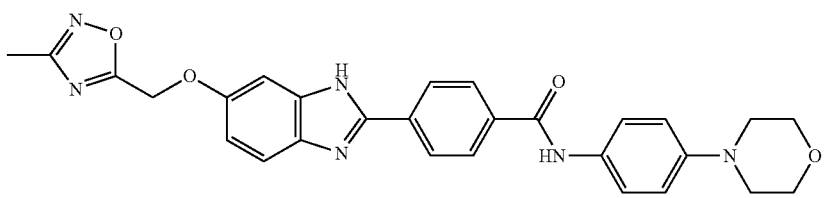 [SMILES: Cc1noc(COc2ccc3nc(-c4ccc(C(=O)Nc5ccc(N6CCOCC6)cc5)cc4)[nH]c3c2)n1]

Compound 627 was prepared by reductive methylation of compound 580.

Example 528

4-(6-((3-Methyl-1,2,4-oxadiazol-5-yl)methoxy)-1H-benzo[d]imidazol-2-yl)-N-(4-morpholinophenyl)benzamide (Compound 628)

Compound 628 was prepared according to the procedure similar to that described in Scheme III from 1-(3-methyl-1,2,4-oxadiazol-5-yl)methoxy-3,4-dinitrobenzene and 4-(4-(4-morpholinophenyl)aminocarbonylbenzaldehyde.
[M+H]$^+$ calcd for $C_{28}H_{26}N_6O_4$: 511.2. found: 511.04.

Example 529

4-(6-((5-Methylisoxazol-3-yl)methoxy)-1H-benzo[d]imidazol-2-yl)-N-(4-morpholinophenyl)benzamide (Compound 629)

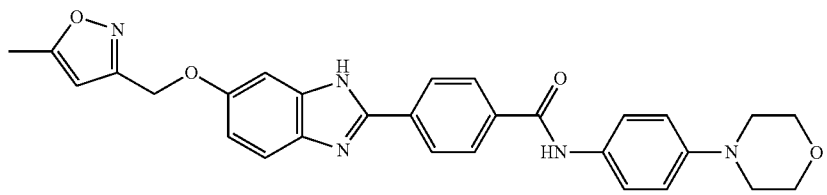

Compound 629 was prepared according to the procedure similar to that described in Scheme III from 1-(5-methylisoxazol-3-yl)methoxy-3,4-dinitrobenzene and 4-(4-(4-morpholinophenyl)aminocarbonylbenzaldehyde. [M+H]$^+$ calcd for $C_{29}H_{27}N_5O_4$: 510.2. found: 510.06.

Example 530

4-(6-((5-Cyclopropyl-1,3,4-oxadiazol-2-yl)methoxy)-1H-benzo[d]imidazol-2-yl)-N-(4-morpholinophenyl)benzamide (Compound 630)

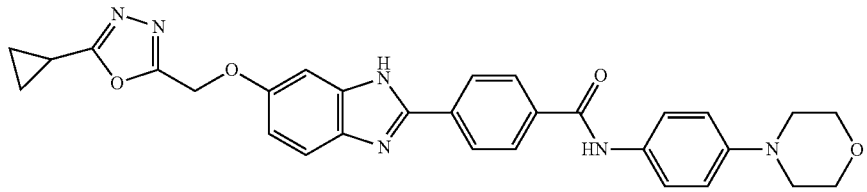 [SMILES: O=C(Nc1ccc(N2CCOCC2)cc1)c1ccc(-c2nc3ccc(OCc4nnc(C5CC5)o4)cc3[nH]2)cc1]

Compound 630 was prepared according to the procedure similar to that described in Scheme III from 1-(5-cyclopropyl-1,3,4-oxadiazol-2-yl)methoxy-3,4-dinitrobenzene and 4-(4-(4-morpholinophenyl)aminocarbonylbenzaldehyde. [M+H]$^+$ calcd for $C_{30}H_{28}N_6O_4$: 537.2. found: 537.06.

Example 531

4-(Dimethylamino)-N-(2-(4-dimethylaminophenyl)-1H-imidazo[4,5-b]pyridin-6-yl)benzamide (Compound 631)

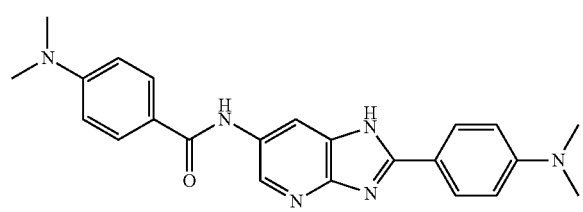

Compound 631 was prepared according to the procedure similar to that described in Scheme III from 4-dimethylaminobenzoic acid and 6-amino-2-(4-dimethylaminophenyl)-1H-imidazo[4,5-b]pyridine. [M+H]$^+$ calcd for $C_{23}H_{24}N_6O$: 401.20. found 401.07.

Example 532

4-(6-Allyloxy-1H-benzo[d]imidazol-2-yl)-N-(4-morpholinophenyl)benzamide (Compound 632)

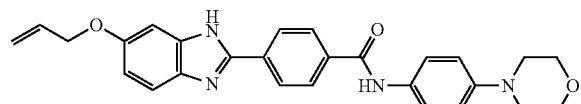

Compound 632 was prepared according to the procedure similar to that described in Scheme III from 1-allyloxy-3,4-dinitrobenzene and 4-(4-(4-morpholinophenyl)aminocarbonylbenzaldehyde. [M+H]$^+$ calcd for $C_{27}H_{26}N_4O_3$: 455.21. found: 455.00.

Example 533

2-(4-Methoxyphenyl)-5-methyl-N-(2-(4-morpholinophenyl)-1H-benzo[d]imidazol-6-yl)-1H-imidazole-4-carboxamide (Compound 633)

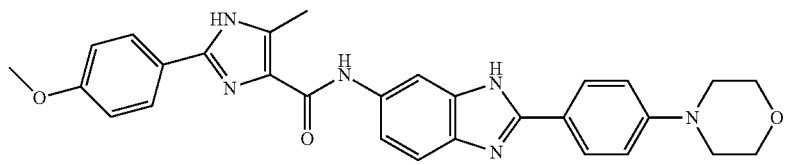 [SMILES: COc1ccc(-c2nc(C(=O)Nc3ccc4nc(-c5ccc(N6CCOCC6)cc5)[nH]c4c3)c(C)[nH]2)cc1]

Compound 633 was prepared according to the procedure similar to that described in Scheme III from 2-(4-methoxyphenyl)-1H-imidazole-4-carboxylic acid and 6-amino-2-(4-morpholinophenyl)benzimidazole. $[M+H]^+$ calcd for $C_{29}H_{28}N_6O_3$: 509.22. found 509.11.

Example 534

4-(5-Methoxy-1H-imidazo[4,5-b]pyridin-2-yl)-N-(4-morpholinophenyl)benzamide (Compound 632)

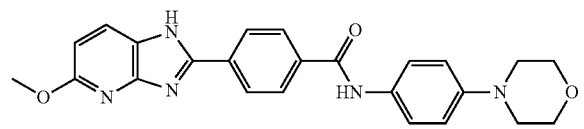

Compound 634 was prepared according to the procedure similar to that described in Scheme III from 4-(5-methoxy-1H-imidazo[4,5-b]pyridin-2-yl)benzoic acid and 4-morpholinoaniline. $[M+H]^+$ calcd for $C_{24}H_{23}N_5O_3$: 430.1. found 429.96.

Example 535

N-Cyclopropyl-4-(6-methoxy-1H-benzo[d]imidazol-2-yl)benzamide (Compound 635)

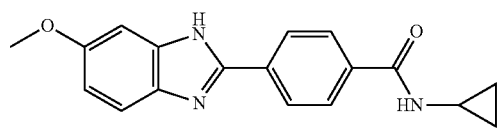 [SMILES: COc1ccc2nc(-c3ccc(C(=O)NC4CC4)cc3)[nH]c2c1]

Compound 635 was prepared according to the procedure similar to that described in Scheme III from 1-methoxy-3,4-dinitrobenzene and 4-cyclopropylaminocarbonylbenzaldehyde. $[M+H]^+$ calcd for $C_{18}H_{17}N_3O_2$: 308.14. found: 308.16.

Example 536

N-(1H-indazol-5-yl)-4-(6-methoxy-1H-benzo[d]imidazol-2-yl)benzamide (Compound 636)

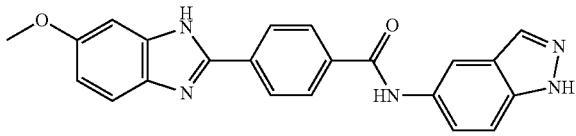

Compound 636 was prepared according to the procedure similar to that described in Scheme III from 1-methoxy-3,4-dinitrobenzene and 4-(1H-indazol-5-yl)aminocarbonyl)benzaldehyde. $[M+H]^+$ calcd for $C_{22}H_{17}N_5O_2$: 384.1. found: 384.20.

Example 537

4-(6-(2-Methoxyethyloxy)-1H-benzo[d]imidazol-2-yl)-N-(4-morpholinophenyl)benzamide (Compound 637)

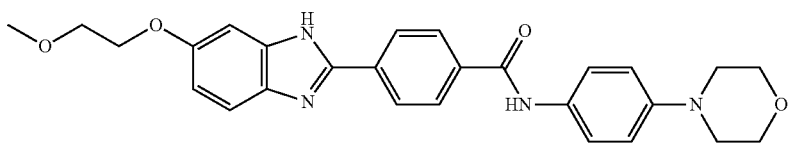 [SMILES: COCCOc1ccc2nc(-c3ccc(C(=O)Nc4ccc(N5CCOCC5)cc4)cc3)[nH]c2c1]

Compound 637 was prepared according to the procedure similar to that described in Scheme III from 1-(2-methoxyethyloxy)-3,4-dinitrobenzene and 4-(4-(4-morpholinophenyl)aminocarbonylbenzaldehyde. $[M+H]^+$ calcd for $C_{27}H_{28}N_4O_4$: 473.21. found: 473.08.

Example 538

4-(5-(Benzo[d]thiazol-2-yl)-1H-benzo[d]imidazol-2-yl)-N-(4-morpholinophenyl)benzamide (Compound 638)

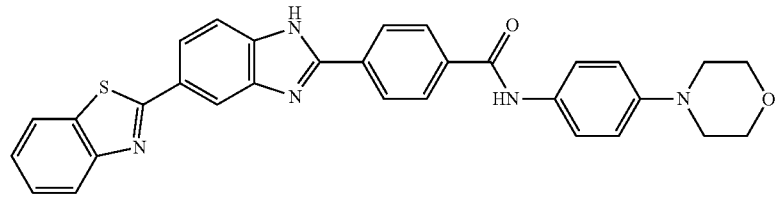 [SMILES: O=C(Nc1ccc(N2CCOCC2)cc1)c1ccc(-c2nc3cc(-c4nc5ccccc5s4)ccc3[nH]2)cc1]

Compound 638 was prepared according to the procedure similar to that described in Scheme III from 1-(benzothiazol-2-yl)-3,4-dinitrobenzene and 4-(4-(4-morpholinophenyl)aminocarbonylbenzaldehyde. $[M+H]^+$ calcd for $C_{31}H_{25}N_5O_2S$: 532.18. found: 532.07.

Example 539

4-(6-Benzyloxy-1H-benzo[d]imidazol-2-yl)-N-(4-morpholinophenyl)benzamide (Compound 639)

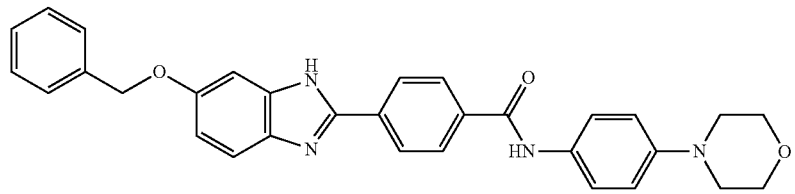 [SMILES: O=C(Nc1ccc(N2CCOCC2)cc1)c1ccc(-c2nc3ccc(OCc4ccccc4)cc3[nH]2)cc1]

Compound 639 was prepared according to the procedure similar to that described in Scheme III from 1-benzyloxy-3,4-dinitrobenzene and 4-(4-(4-morpholinophenyl)aminocarbonylbenzaldehyde. $[M+H]^+$ calcd for $C_{27}H_{28}N_4O_4$: 473.21. found: 473.08.

Example 540

4-(6-Cyclopropylmethoxy-1H-benzo[d]imidazol-2-yl)-N-(4-morpholinophenyl)benzamide (Compound 640)

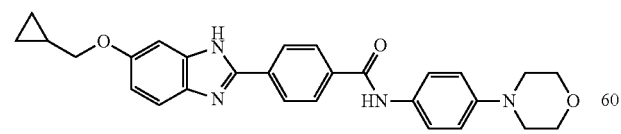

Compound 640 was prepared according to the procedure similar to that described in Scheme III from 1-cyclorpopylmethoxy-3,4-dinitrobenzene and 4-(4-(4-morpholinophenyl)aminocarbonylbenzaldehyde. $[M+H]^+$ calcd for $C_{28}H_{28}N_4O_3$: 469.22. found: 469.03.

Example 541

4-(6-(4-Cyanobenzyloxy)-1H-benzo[d]imidazol-2-yl)-N-(4-morpholinophenyl)benzamide (Compound 641)

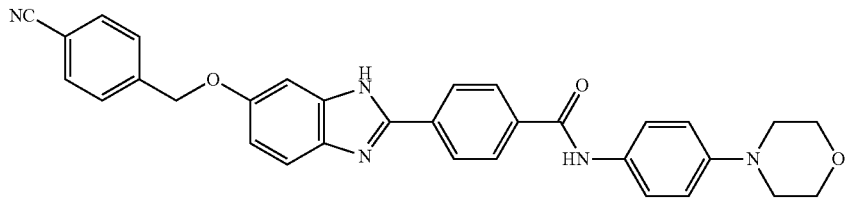 [SMILES: N#Cc1ccc(COc2ccc3nc(-c4ccc(C(=O)Nc5ccc(N6CCOCC6)cc5)cc4)[nH]c3c2)cc1]

Compound 641 was prepared according to the procedure similar to that described in Scheme III from 1-(4-cyanobenzyloxy)-3,4-dinitrobenzene and 4-(4-(4-morpholinophenyl)aminocarbonylbenzaldehyde. $[M+H]^+$ calcd for $C_{32}H_{27}N_5O_3$: 530.21. found: 530.10.

Example 542

4-(6-(2-(Morpholinoethyloxy)-1H-benzo[d]imidazol-2-yl)-N-(4-morpholinophenyl)benzamide (Compound 642)

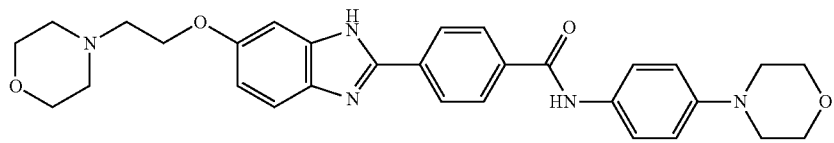 [SMILES: O=C(Nc1ccc(N2CCOCC2)cc1)c1ccc(-c2nc3ccc(OCCN4CCOCC4)cc3[nH]2)cc1]

Compound 642 was prepared according to the procedure similar to that described in Scheme III from 1-(2-morpholinoethyloxy)-3,4-dinitrobenzene and 4-(4-(4-morpholinophenyl)aminocarbonylbenzaldehyde. $[M+H]^+$ calcd for $C_{30}H_{33}N_5O_4$: 528.25. found: 528.15.

Example 543

4-(6-(2-(Diethylamino)ethyloxy)-1H-benzo[d]imidazol-2-yl)-N-(4-morpholinophenyl)benzamide (Compound 643)

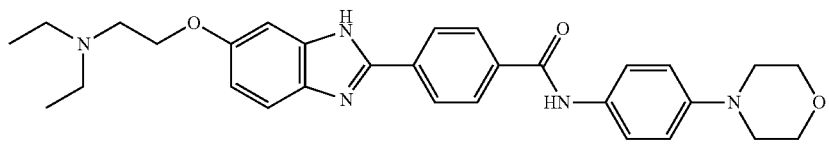 [SMILES: CCN(CC)CCOc1ccc2nc(-c3ccc(C(=O)Nc4ccc(N5CCOCC5)cc4)cc3)[nH]c2c1]

Compound 643 was prepared according to the procedure similar to that described in Scheme III from 1-(2-diethylaminoethyloxy)-3,4-dinitrobenzene and 4-(4-(4-morpholinophenyl)aminocarbonylbenzaldehyde. $[M+H]^+$ calcd for $C_{30}H_{35}N_5O_3$: 514.27. found: 514.13.

Example 544

(N-(4-(6-Phenyl-1H-benzo[d]imidazol-2-yl)phenyl)-1H-pyrrole-2-carboxamide (Compound 644)

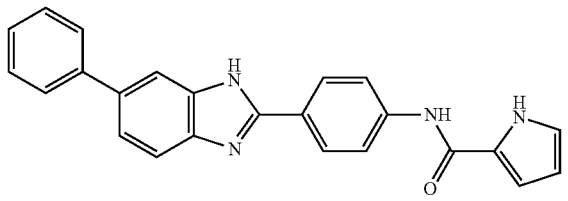 [SMILES: O=C(Nc1ccc(-c2nc3ccc(-c4ccccc4)cc3[nH]2)cc1)c1ccc[nH]1]

Compound 644 was prepared according to the procedure similar to that described in Scheme III from 1-phenyl-3,4-dinitrobenzene, 4-nitrobenzaldehyde, and 2-pyrrolecarboxylic acid. [M+H]$^+$ calcd for $C_{24}H_{18}N_4O$: 379.1. found: 378.96.

Example 545

1-Methyl-(N-(4-(6-phenyl-1H-benzo[d]imidazol-2-yl)phenyl)-1H-pyrrole-2-carboxamide (Compound 645)

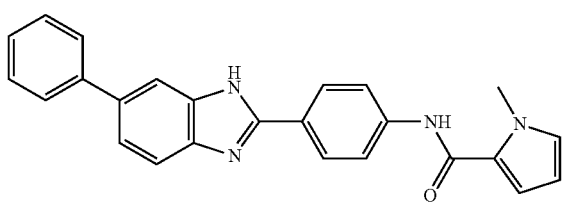 [SMILES: Cn1cccc1C(=O)Nc1ccc(-c2nc3ccc(-c4ccccc4)cc3[nH]2)cc1]

Compound 645 was prepared according to the procedure similar to that described in Scheme III from 1-phenyl-3,4-dinitrobenzene, 4-nitrobenzaldehyde, and 1-methylpyrrole-2-carboxylic acid. [M+H]$^+$ calcd for $C_{25}H_{20}N_4O$: 393.1. found: 392.99.

Example 546

(4-(6-(3-Hydroxyphenyl)-1H-benzo[d]imidazol-2-yl)-N-1H-indol-6-yl)benzamide (Compound 646)

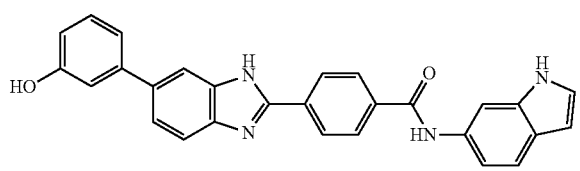 [SMILES: O=C(Nc1ccc2cc[nH]c2c1)c1ccc(-c2nc3ccc(-c4cccc(O)c4)cc3[nH]2)cc1]

Compound 646 was prepared according to the procedure similar to that described in Scheme III from 1-(3-hydroxyphenyl)-3,4-dinitrobenzene and 4-(6-indolylaminocarbonyl)benzaldehyde. [M+H]$^+$ calcd for $C_{28}H_{20}N_4O_2$: 445.1. found: 445.00.

Example 547

(4-(6-(4-Hydroxyphenyl)-1H-benzo[d]imidazol-2-yl)-N-1H-indol-6-yl)benzamide (Compound 647)

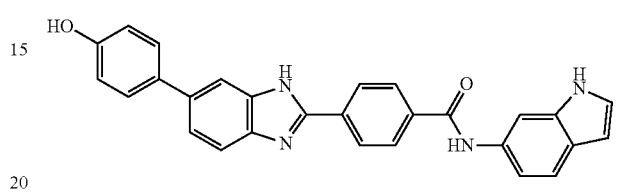

Compound 647 was prepared according to the procedure similar to that described in Scheme III from 1-(4-hydroxyphenyl)-3,4-dinitrobenzene and 4-(6-indolylaminocarbonyl)benzaldehyde. [M+H]$^+$ calcd for $C_{28}H_{20}N_4O_2$: 445.1. found: 445.00.

Example 548

(4-(6-(4-Methoxyphenyl)-1H-benzo[d]imidazol-2-yl)-N-1H-indol-6-yl)benzamide (Compound 648)

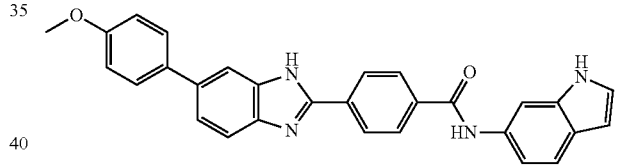

Compound 648 was prepared according to the procedure similar to that described in Scheme III from 1-(4-methoxyphenyl)-3,4-dinitrobenzene and 4-(6-indolylaminocarbonyl)benzaldehyde. [M+H]$^+$ calcd for $C_{29}H_{22}N_4O_2$: 459.1. found: 458.97.

Example 549

(4-(6-(4-Hydroxyphenyl)-1H-benzo[d]imidazol-2-yl)-N-(4-morpholinophenyl)benzamide (Compound 649)

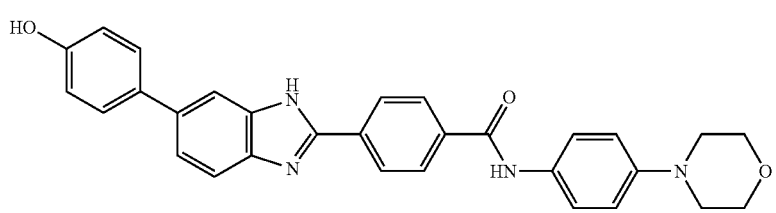 [SMILES: O=C(Nc1ccc(N2CCOCC2)cc1)c1ccc(-c2nc3ccc(-c4ccc(O)cc4)cc3[nH]2)cc1]

Compound 649 was prepared according to the procedure similar to that described in Scheme III from 1-(4-hydroxyphenyl)-3,4-dinitrobenzene and 4-(4-morpholinophenyl) aminocarbonyl)benzaldehyde. [M+H]+ calcd for $C_{30}H_{26}N_4O_3$: 491.20. found: 491.03.

Example 550

N-(1H-indol-6-yl)-4-(6-(pyridin-3-yl)-1H-benzo[d]imidazol-2-yl)-benzamide (Compound 650)

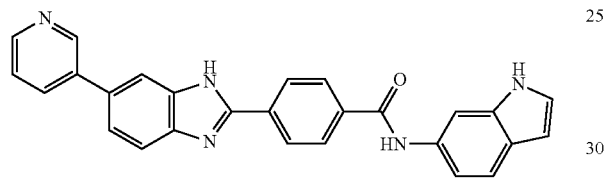

Compound 650 was prepared according to the procedure similar to that described in Scheme III from 1-(3-pyridinyl)-3,4-dinitrobenzene and 4-(6-indolylaminocarbonyl)benzaldehyde. [M+H]+ calcd for $C_{27}H_{19}N_5O$: 430.1. found: 429.96.

Example 551

4-(6-(3,5-Dimethylisoxazol-4-yl)-1H-benzo[d]imidazol-2-yl)-N-(1H-indol-6-yl)benzamide (Compound 651)

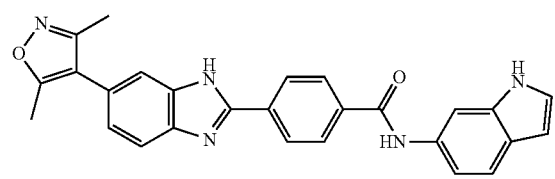 [SMILES: Cc1noc(C)c1-c1ccc2nc(-c3ccc(C(=O)Nc4ccc5cc[nH]c5c4)cc3)[nH]c2c1]

Compound 651 was prepared according to the procedure similar to that described in Scheme III from 1-(3,5-dimethylisoxazol-4-yl)-3,4-dinitrobenzene and 4-(6-indolylaminocarbonyl)benzaldehyde. [M+H]+ calcd for $C_{27}H_{21}N_5O_2$: 448.1. found: 447.97.

Example 552

(4-(6-(4-Methoxyphenyl)-1H-benzo[d]imidazol-2-yl)-N-(4-morpholinophenyl)benzamide (Compound 652)

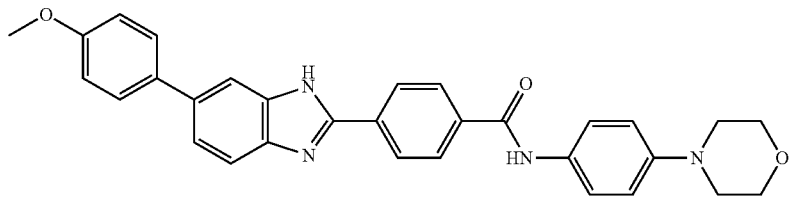 [SMILES: COc1ccc(-c2ccc3nc(-c4ccc(C(=O)Nc5ccc(N6CCOCC6)cc5)cc4)[nH]c3c2)cc1]

Compound 652 was prepared according to the procedure similar to that described in Scheme III from 1-(4-methoxyphenyl)-3,4-dinitrobenzene and 4-(4-morpholinophenyl) aminocarbonyl)benzaldehyde. [M+H]+ calcd for $C_{31}H_{28}N_4O_3$: 505.22. found: 505.07.

Example 553

4-(6-((5-Cyanothiophen-2-yl)methoxy)-1H-benzo[d]imidazol-2-yl)-N-(4-morpholinophenyl)benzamide (Compound 653)

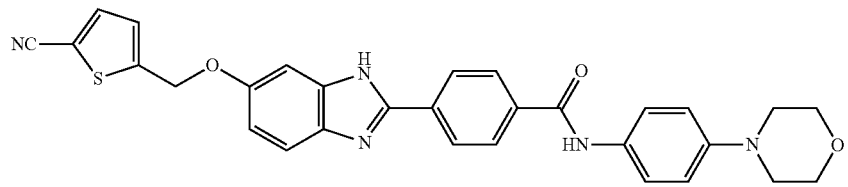 [SMILES: N#Cc1ccc(COc2ccc3nc(-c4ccc(C(=O)Nc5ccc(N6CCOCC6)cc5)cc4)[nH]c3c2)s1]

Compound 653 was prepared according to the procedure similar to that described in Scheme III from 1-(5-cyanothiophen-2-yl)methoxy)-3,4-dinitrobenzene and 4-(4-morpholinophenyl)aminocarbonyl)benzaldehyde. [M+H]+ calcd for $C_{30}H_{25}N_5O_3S$: 536.17. found: 536.05.

Example 554

N-(1H-Indol-5-yl)-4-(6-methoxy-1H-benzo[d]imidazol-2-yl)benzamide (Compound 654)

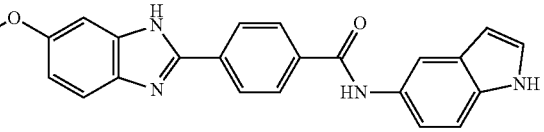

Compound 654 was prepared according to the procedure similar to that described in Scheme III from 3,4-dinitroanisole and 4-(5-indolylaminocarbonyl)benzaldehyde. [M+H]$^+$ calcd for $C_{23}H_{18}N_4O_2$: 383.1. found: 383.01.

Example 555

N-(1-Methylindol-5-yl)-4-(6-methoxy-1H-benzo[d]imidazol-2-yl)benzamide (Compound 655)

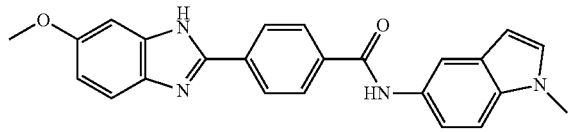

Compound 655 was prepared according to the procedure similar to that described in Scheme III from 3,4-dinitroanisole and 4-(5-(1-methylindolyl)aminocarbonyl)benzaldehyde. [M+H]$^+$ calcd for $C_{24}H_{20}N_4O_2$: 397.16. found: 396.97.

Example 556

4-(6-((3-Methyl-1,2,4-oxadiazol-5-yl)methoxy)-1H-benzo[d]imidazol-2-yl)-N-(1-methyl-1H-indol-5-yl)benzamide (Compound 656)

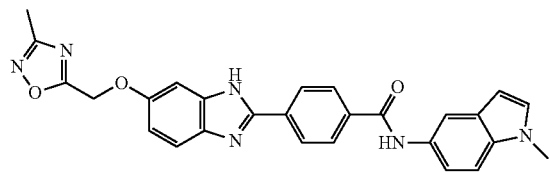 [SMILES: Cc1noc(COc2ccc3nc(-c4ccc(C(=O)Nc5ccc6c(ccn6C)c5)cc4)[nH]c3c2)n1]

Compound 656 was prepared according to the procedure similar to that described in Scheme III from 1-(3-methyl-1,2,4-oxadiazol-5-yl)methoxy-3,4-dinitrobenzene and 4-(5-(1-methylindolyl)aminocarbonyl)benzaldehyde. [M+H]$^+$ calcd for $C_{27}H_{22}N_6O_3$: 479.1. found: 479.01.

Example 557

N-(4-(1,4-Dioxa-8-azaspiro[4.5]decan-8-yl)phenyl)-4-(6-methoxy-1H-benzo[d]imidazol-2-yl)benzamide (Compound 657)

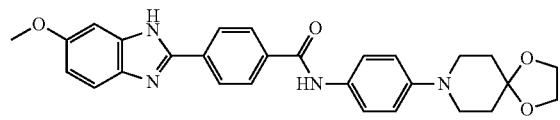 [SMILES: COc1ccc2nc(-c3ccc(C(=O)Nc4ccc(N5CCC6(CC5)OCCO6)cc4)cc3)[nH]c2c1]

Compound 657 was prepared according to the procedure similar to that described in Scheme III from 3,4-dinitroanisole and 4-(4-(1,4-dioxa-8-azaspiro[4.5]decan-8-yl)phenyl)aminocarbonyl)benzaldehyde. [M+H]$^+$ calcd for $C_{28}H_{28}N_4O_4$: 485.21. found: 485.09.

Example 558

4-(6-Methoxy-1H-benzo[d]imidazol-2-yl)-N-(1-methylindolin-5-yl)benzamide (Compound 658)

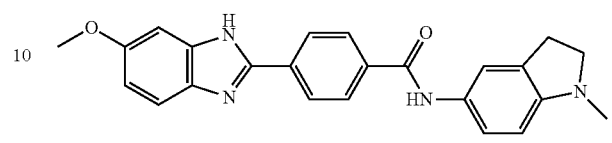

Compound 658 was prepared according to the procedure similar to that described in Scheme III from 3,4-dinitroanisole and 4-(5-(1-methylindolinyl)aminocarbonyl)benzaldehyde. [M+H]$^+$ calcd for $C_{24}H_{22}N_4O_2$: 399.17. found: 398.99.

Example 559

4-(6-((3-Methyl-1,2,4-oxadiazol-5-yl)methoxy)-1H-benzo[d]imidazol-2-yl)-N-(1H-indol-5-yl)benzamide (Compound 659)

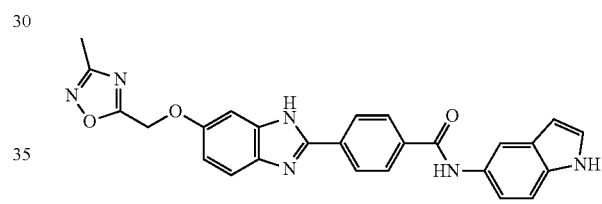

Compound 659 was prepared according to the procedure similar to that described in Scheme III from 1-(3-methyl-1,2,4-oxadiazol-5-yl)methoxy-3,4-dinitrobenzene and 4-(5-indolylaminocarbonyl)benzaldehyde. [M+H]$^+$ calcd for $C_{26}H_{20}N_6O_3$: 465.16. found: 464.98.

Example 560

4-(6-((3-Methyl-1,2,4-oxadiazol-5-yl)methoxy)-1H-benzo[d]imidazol-2-yl)-N-(1H-indol-6-yl)benzamide (Compound 660)

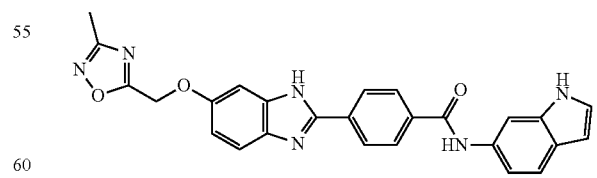

Compound 660 was prepared according to the procedure similar to that described in Scheme III from 1-(3-methyl-1,2,4-oxadiazol-5-yl)methoxy-3,4-dinitrobenzene and 4-(6-indolylaminocarbonyl)benzaldehyde. [M+H]$^+$ calcd for $C_{26}H_{20}N_6O_3$: 465.16. found: 465.04.

Example 561

4-(6-(2-Methoxyethoxy)-1H-benzo[d]imidazol-2-yl)-N-(1H-indol-5-yl)benzamide (Compound 661)

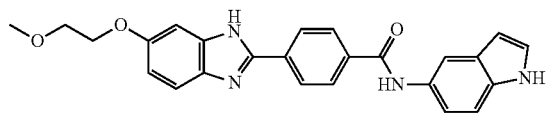 [SMILES: COCCOc1ccc2nc(-c3ccc(C(=O)Nc4ccc5[nH]ccc5c4)cc3)[nH]c2c1]

Compound 661 was prepared according to the procedure similar to that described in Scheme III from 1-(2-methoxyethoxy-3,4-dinitrobenzene and 4-(5-indolylaminocarbonyl) benzaldehyde. [M+H]$^+$ calcd for $C_{25}H_{22}N_4O_3$: 427.1. found: 426.99.

Example 562

4-(6-(2-Methoxyethoxy)-1H-benzo[d]imidazol-2-yl)-N-(2-methyl-1H-indol-5-yl)benzamide (Compound 662)

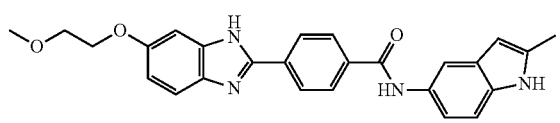

Compound 662 was prepared according to the procedure similar to that described in Scheme III from 1-(2-methoxyethoxy-3,4-dinitrobenzene and 4-(2-methyl-5-indolylaminocarbonyl)benzaldehyde. [M+H]$^+$ calcd for $C_{26}H_{24}N_4O_3$: 441.1. found: 441.02.

Example 563

4-(6-(2-Methoxyethoxy)-1H-benzo[d]imidazol-2-yl)-N-(1H-indol-2-yl)benzamide (Compound 663)

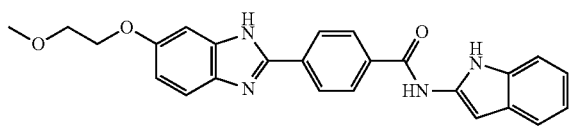 [SMILES: COCCOc1ccc2nc(-c3ccc(C(=O)Nc4cc5ccccc5[nH]4)cc3)[nH]c2c1]

Compound 663 was prepared according to the procedure similar to that described in Scheme III from 1-(2-methoxyethoxy-3,4-dinitrobenzene and 4-(2-indolylaminocarbonyl) benzaldehyde. [M+H]$^+$ calcd for $C_{25}H_{22}N_4O_3$: 427.1. found: 426.99.

Example 564

4-(6-(2-Methoxyethoxy)-1H-benzo[d]imidazol-2-yl)-N-(1H-indol-6-yl)benzamide (Compound 664)

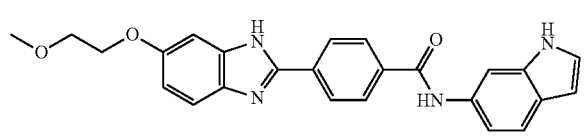 [SMILES: COCCOc1ccc2nc(-c3ccc(C(=O)Nc4ccc5cc[nH]c5c4)cc3)[nH]c2c1]

Compound 664 was prepared according to the procedure similar to that described in Scheme III from 1-(2-methoxyethoxy-3,4-dinitrobenzene and 4-(6-indolylaminocarbonyl) benzaldehyde. [M+H]$^+$ calcd for $C_{25}H_{22}N_4O_3$: 427.1. found: 426.99.

Example 565

4-(6-(2-Methoxyethoxy)-1H-benzo[d]imidazol-2-yl)-N-(1H-pyrrolo[2,3-b]pyridin-5-yl)benzamide (Compound 665)

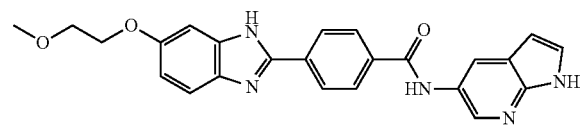 [SMILES: COCCOc1ccc2nc(-c3ccc(C(=O)Nc4cnc5[nH]ccc5c4)cc3)[nH]c2c1]

Compound 665 was prepared according to the procedure similar to that described in Scheme III from 1-(2-methoxyethoxy-3,4-dinitrobenzene and 4-(1H-pyrrolo[2,3-b]pyridin-5-yl)aminocarbonyl)benzaldehyde. $^1$H NMR (500 MHz, CD$_3$OD) δ 8.45 (s, 1H), 8.35 (s, 1H), 8.19 (d, J=8.5 Hz, 2H), 8.15 (d, J=8.5 Hz, 2H), 7.55 (d, J=9 Hz, 1H), 7.42 (d, J=3.5 Hz, 1H), 7.15 (s, 1H), 7.05 (d, J=9 Hz, 1H), 6.51 (d, J=3.5 Hz, 1H), 4.19 (t, J=4.5 Hz, 2H), 3.79 (t, J=4.5 Hz, 2H), 3.31 (s, 3H).

Example 566

4-(6-(2-Methoxyethoxy)-1H-benzo[d]imidazol-2-yl)-N-(2-oxoindolin-5-yl)benzamide (Compound 666)

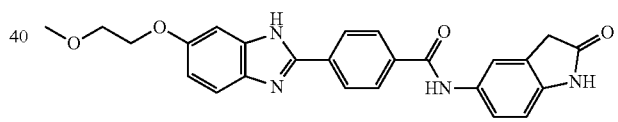

Compound 666 was prepared according to the procedure similar to that described in Scheme III from 1-(2-methoxyethoxy-3,4-dinitrobenzene and 4-((2-oxoindolin-5-yl)aminocarbonyl)benzaldehyde. [M+H]$^+$ calcd for $C_{25}H_{22}N_4O_4$: 443.1. found: 443.05.

Example 567

4-(6-(2-Methoxyethoxy)-1H-benzo[d]imidazol-2-yl)-N-(1H-pyrrolo[2,3-b]pyridin-6-yl)benzamide (Compound 667)

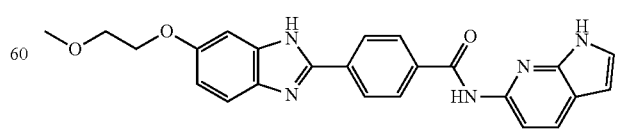

Compound 667 was prepared according to the procedure similar to that described in Scheme III from 1-(2-methoxyethoxy-3,4-dinitrobenzene and 4-(1H-pyrrolo[2,3-b]pyridin-6-yl)aminocarbonyl)benzaldehyde. [M+H]+ calcd for C24H21N5O3: 428.17. found: 428.00.

Example 568

4-(6-(2-Methoxyethoxy)-1H-benzo[d]imidazol-2-yl)-N-(1H-pyrrolo[3,2-c]pyridin-6-yl)benzamide (Compound 668)

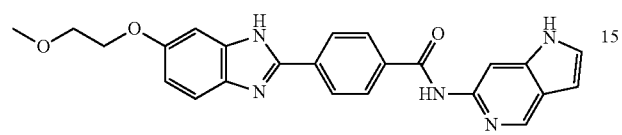

Compound 668 was prepared according to the procedure similar to that described in Scheme III from 1-(2-methoxyethoxy-3,4-dinitrobenzene and 4-(1H-pyrrolo[3,2-c]pyridin-6-yl)aminocarbonyl)benzaldehyde. [M+H]+ calcd for C24H21N5O3: 428.17. found: 428.07.

Example 569

4-(6-((4-Cyanobenzyl)oxy)-1H-benzo[d]imidazol-2-yl)-N-cyclopropylbenzamide (Compound 669)

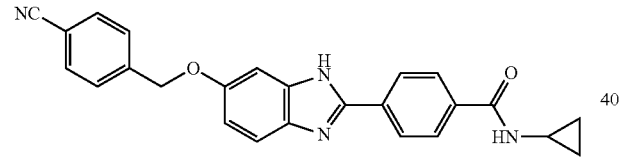

Compound 669 was prepared according to the procedure similar to that described in Scheme III from 1-(4-cyanobenzyl)oxy-3,4-dinitrobenzene and 4-(cyclopropylaminocarbonyl)benzaldehyde. [M+H]+ calcd for C25H20N4O2: 409.16. found: 409.04.

Example 570

N-(4-(4-Hydroxypiperidin-1-yl)phenyl)-4-(6-(2-methoxyethoxy)-1H-benzo[d]imidazol-2-yl)benzamide (Compound 670)

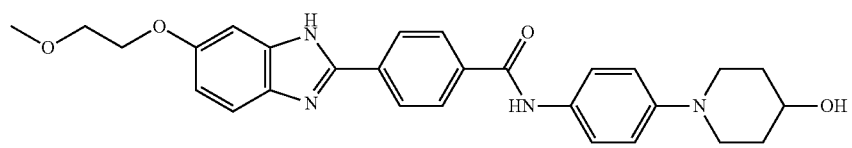 [SMILES: COCCOc1ccc2nc(-c3ccc(C(=O)Nc4ccc(N5CCC(O)CC5)cc4)cc3)[nH]c2c1]

Compound 670 was prepared according to the procedure similar to that described in Scheme III from 1-(2-methoxyethoxy-3,4-dinitrobenzene and 4-(4-(4-hydroxylpiperidin-1-yl)phenyl)aminocarbonyl)benzaldehyde. [M+H]+ calcd for C28H30N4O4: 487.2. found: 487.05.

Example 571

4-(6-((5-Cyanothiophen-2-yl)methoxy)-1H-benzo[d]imidazol-2-yl)-N-(1H-indol-6-yl)benzamide (Compound 671)

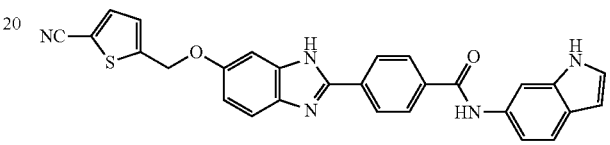

Compound 671 was prepared according to the procedure similar to that described in Scheme III from 1-(5-cyanothiophen-2-yl)methoxy)-3,4-dinitrobenzene and 4-(indol-6-yl)aminocarbonyl)benzaldehyde. [M+H]+ calcd for C28H19N5O2S: 490.13. found: 489.95.

Example 572

4-(6-(2-Hydroxyethoxy)-1H-benzo[d]imidazol-2-yl)-N-(1H-indol-6-yl)benzamide (Compound 672)

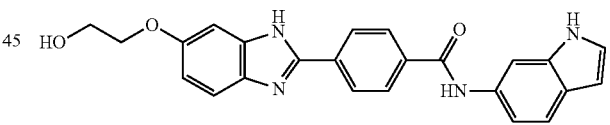

Compound 672 was prepared according to the procedure similar to that described in Scheme III from 1-(2-hydroxyethoxy)-3,4-dinitrobenzene and 4-(6-indolylaminocarbonyl)benzaldehyde. [M+H]+ calcd for C24H20N4O3: 413.1. found: 412.96.

Example 573

Methyl 2-((2-(4-(((1H-indol-6-yl)carbamoyl)phenyl)-1H-benzo[d]imidazol-6-yl)oxy)acetate (Compound 673)

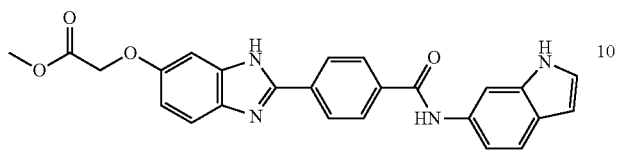

Compound 673 was prepared according to the procedure similar to that described in Scheme III from 1-(methoxycarbonylmethoxy)-3,4-dinitrobenzene and 4-(6-indolylaminocarbonyl)benzaldehyde. [M+H]$^+$ calcd for $C_{25}H_{20}N_4O_4$: 441.1. found: 440.96.

Example 574

4-(6-(2-Methoxyethoxy)-1H-benzo[d]imidazol-2-yl)-N-(1-(2-hydroxyethyl)indol-5-yl)benzamide (Compound 674)

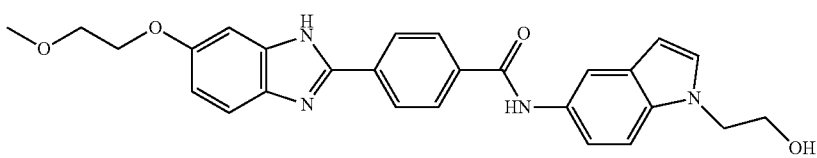 [SMILES: COCCOc1ccc2nc(-c3ccc(C(=O)Nc4ccc5c(ccn5CCO)c4)cc3)[nH]c2c1]

Compound 674 was prepared according to the procedure similar to that described in Scheme III from 1-(2-methoxyethoxy-3,4-dinitrobenzene and 4-(1-(2-hydroxyethyl)-5-indolylaminocarbonyl)benzaldehyde. [M+H]$^+$ calcd for $C_{27}H_{26}N_4O_4$: 471.2. found: 471.05.

Example 575

4-(6-(2-Methoxyethoxy)-1H-benzo[d]imidazol-2-yl)-N-(1-(2-methoxyethyl)-2-methylindol-5-yl)benzamide (Compound 675)

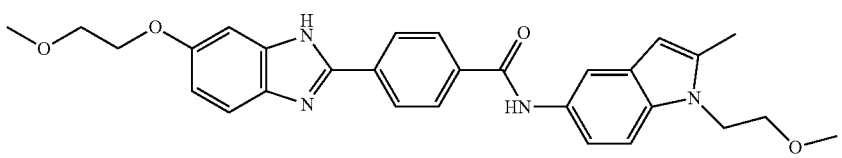

Compound 675 was prepared according to the procedure similar to that described in Scheme III from 1-(2-methoxyethoxy-3,4-dinitrobenzene and 4-(1-(2-methoxyethyl)2-methyl-5-indolylaminocarbonyl)benzaldehyde. [M+H]$^+$ calcd for $C_{29}H_{30}N_4O_4$: 499.2. found: 499.06.

Example 576

4-(6-(2-Methoxyethoxy)-1H-benzo[d]imidazol-2-yl)-N-(1-(2-morpholinoethyl)indol-5-yl)benzamide (Compound 676)

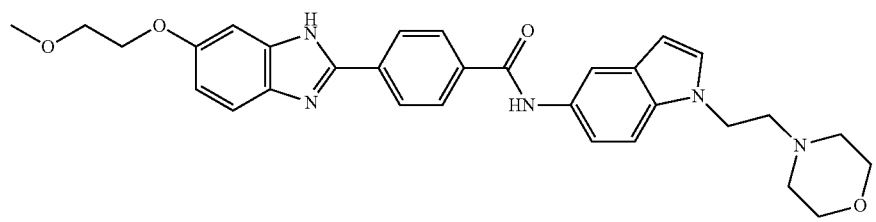 [SMILES: COCCOc1ccc2nc(-c3ccc(C(=O)Nc4ccc5c(ccn5CCN5CCOCC5)c4)cc3)[nH]c2c1]

Compound 676 was prepared according to the procedure similar to that described in Scheme III from 1-(2-methoxyethoxy-3,4-dinitrobenzene and 4-(1-(2-morpholinoethyl)-5-indolylaminocarbonyl)benzaldehyde. [M+H]$^+$ calcd for C$_{31}$H$_{33}$N$_5$O$_4$: 540.2. found: 540.10.

Example 577

(6-Phenyl-1H-benzo[d]imidazol-2-yl)-N-(4-morpholinophenyl)benzamide (Compound 677)

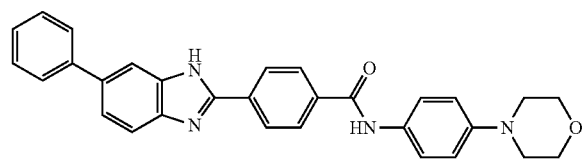 [SMILES: O=C(Nc1ccc(N2CCOCC2)cc1)c1ccc(-c2nc3ccc(-c4ccccc4)cc3[nH]2)cc1]

Compound 677 was prepared according to the procedure similar to that described in Scheme III from 1-phenyl-3,4-dinitrobenzene and 4-(4-morpholinophenyl)aminocarbonyl)benzaldehyde. [M+H]$^+$ calcd for C$_{30}$H$_{26}$N$_4$O$_2$: 475.22. found: 475.03.

Example 578

(6-Phenyl-1H-benzo[d]imidazol-2-yl)-N-1H-indol-6-yl)benzamide (Compound 678)

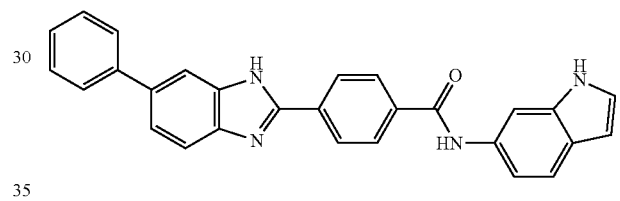

Compound 678 was prepared according to the procedure similar to that described in Scheme III from 1-phenyl-3,4-dinitrobenzene and 4-(6-indolylaminocarbonyl)benzaldehyde. [M+H]$^+$ calcd for C$_{28}$H$_{20}$N$_4$O: 429.1. found: 428.95.

Example 579

(4-(6-(3-Hydroxyphenyl)-1H-benzo[d]imidazol-2-yl)-N-(4-morpholinophenyl)benzamide (Compound 679)

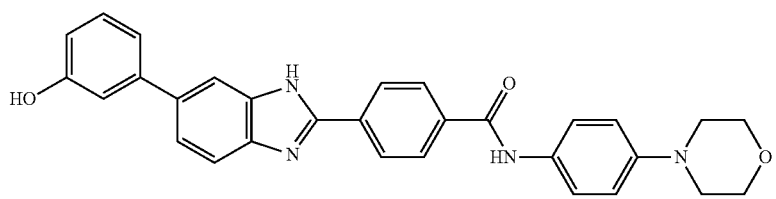 [SMILES: O=C(Nc1ccc(N2CCOCC2)cc1)c1ccc(-c2nc3ccc(-c4cccc(O)c4)cc3[nH]2)cc1]

Compound 679 was prepared according to the procedure similar to that described in Scheme III from 1-(3-hydroxyphenyl)-3,4-dinitrobenzene and 4-(4-morpholinophenyl)aminocarbonyl)benzaldehyde. [M+H]+ calcd for $C_{30}H_{26}N_4O_3$: 491.20. found: 491.03.

Example 580

Cyclopropyl(4-(4-(6-(4-hydroxyphenyl)-1H-benzo[d]imidazol-2-yl)phenyl)piperazin-1-yl)methanone (Compound 680)

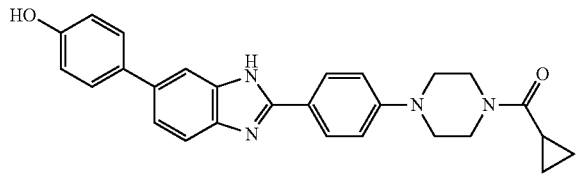 [SMILES: O=C(C1CC1)N1CCN(c2ccc(-c3nc4ccc(-c5ccc(O)cc5)cc4[nH]3)cc2)CC1]

Compound 680 was prepared according to the procedure similar to that described in Scheme III from 1-(4-hydroxyphenyl)-3,4-dinitrobenzene and 4-(4-(cyclopropylcarbonylpiperazin-1-yl)benzaldehyde. [M+H]+ calcd for $C_{27}H_{26}N_4O_2$: 439.21. found: 438.93.

Example 581

N-(2-(4-(Cyclopropanecarboxamido)phenyl)-2H-indazol-5-yl)-4-(4-hydroxypiperidin-1-yl)benzamide (Compound 681)

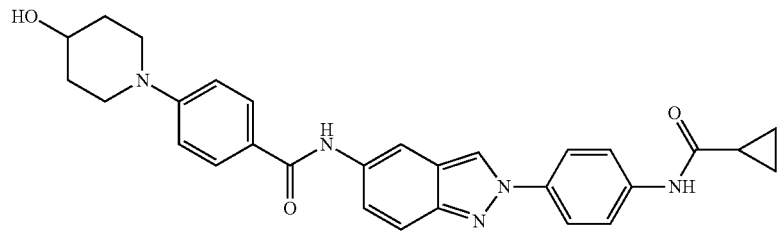 [SMILES: O=C(Nc1ccc2nn(-c3ccc(NC(=O)C4CC4)cc3)cc2c1)c1ccc(N2CCC(O)CC2)cc1]

Compound 681 was prepared according to the procedure similar to that described in Scheme IV from 4-(4-hydroxypiperidin-1-yl)benzoic acid, cyclopropanecarboxylic acid, and 2-(4-aminophenyl)-5-amino-2H-indazole. [M+H]+ calcd for $C_{29}H_{29}N_5O_3$: 496.2. found 496.05.

Example 582

4-(6-(2-Hydroxyethoxy)-1H-benzo[d]imidazol-2-yl)-N-(4-morpholinophenyl)benzamide (Compound 682)

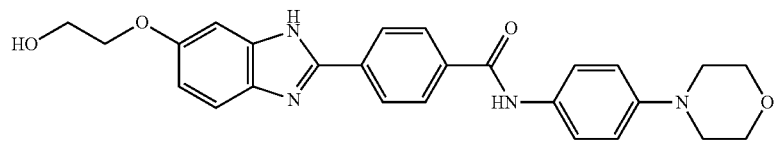 [SMILES: O=C(Nc1ccc(N2CCOCC2)cc1)c1ccc(-c2nc3ccc(OCCO)cc3[nH]2)cc1]

Compound 682 was prepared according to the procedure similar to that described in Scheme III from 1-(4-methoxyphenyl)-3,4-dinitrobenzene and 4-(4-morpholinophenyl)aminocarbonyl)benzaldehyde. [M+H]+ calcd for $C_{26}H_{26}N_4O_4$: 459.20. found: 458.97.

Example 583

N-(4-(4-(Cyclopropanecarboxamido)benzoyl)phenyl)-4-(4-hydroxypiperidin-1-yl)benzamide (Compound 683)

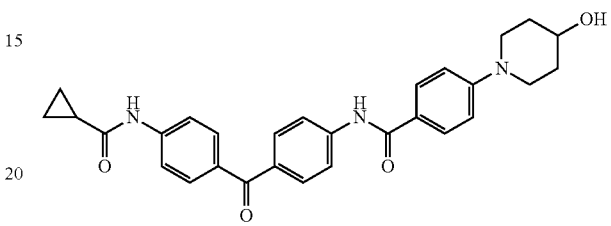

Compound 683 was prepared according to the procedure described in Scheme IV from 4,4'-diaminobenzophenone, cyclopropanecarboxylic and 4-(4-hydroxypiperidin-1-yl)benzoic acids. A solution of 4,4'-diaminobenzophenone (Aldrich, 150 mg, 0.71 mmol), 4-fluorobenzoic acid (Aldrich, 129 mg, 0.92 mmol), HATU (Aldrich, 349 mg, 0.92 mmol) and diisopropylethylamine (Aldrich, 160 µL, 0.92 mmol) in dimethylformamide (6 mL) was heated to 100° C. for 12 h. The reaction was cooled to room temperature and water (10 mL) was slowly added. The resulting solid was filtered and recrystallized from hot methanol to give N-(4-(4-aminobenzoyl)phenyl)-4-fluorobenzamide (147 mg, 0.44 mmol, 62%).

A solution of cyclopropanecarbonyl chloride (Aldrich, 448 mg, 4.31 mmol) in 5 mL of methylene chloride was slowly added over 5 minutes to N-(4-(4-aminobenzoyl)phenyl)-4-fluorobenzamide (1.2 g, 3.59 mmol) in 20 mL of methylene chloride containing 3 mL of pyridine. The reaction was stirred at room temperature for 12 h then quenched with 40 mL of water. The layers were separated and the aqueous layer was extracted with ethyl acetate (2×50 mL).

The combined organics were washed with 0.5 N HCl (100 mL), brine (100 mL), dried over sodium sulphate, and filtered. Concentration of the organics provided N-(4-(4-(cyclopropanecarboxamido)benzoyl)phenyl)-4-fluorobenzamide (1.3 g, 3.23 mmol) as a tan solid which was used without further purification.

To a solution of N-(4-(4-(cyclopropanecarboxamido)benzoyl)phenyl)-4-fluorobenzamide (1.3 g, 3.23 mmol) in dimethylsulfoxide (35 mL) was added 4-hydroxypiperidine (Aldrich, 5.2 g, 51.5 mmol) in a single portion. The reaction was heated to 110° C. for 24 h then cooled to room temperature. Water (100 mL) was slowly added to the reaction at room temperature over 3 h with stirring. Upon completion the reaction was allowed to stir an additional 12 h, then filtered under vacuum. The tan precipitate was washed with water (50 mL), methanol (50 mL) and dried under vacuum to yield compound 683 (1.2 g, 2.48 mmol) as a tan solid. [M+H]$^+$ calcd for $C_{29}H_{30}N_3O_4$: 484.2. found: 484.01.

Example 584

N-(4-(4-(4-morpholinobenzamido)benzoyl)phenyl)-1H-pyrazole-3-carboxamide (Compound 684)

Compound 684 was prepared according to the procedure described in Scheme IV from 4,4'-diaminobenzophenone, 3-pyrazolecarboxylic and 4-morpholinobenzoic acids.
[M+H]$^+$ calcd for $C_{28}H_{25}N_5O_4$: 496.0. found: 496.02.

Example 585

N-(4-(4-(4-(4-Hydroxypiperidin-1-yl)benzamido)benzoyl)phenyl)-1-methyl-1H-pyrrole-2-carboxamide (Compound 685)

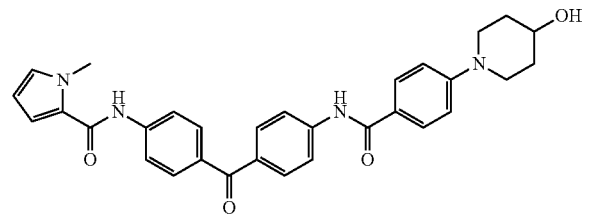 [SMILES: Cn1cccc1C(=O)Nc1ccc(C(=O)c2ccc(NC(=O)c3ccc(N4CCC(O)CC4)cc3)cc2)cc1]

Compound 685 was prepared according to the procedure described in Scheme IV from 4,4'-diaminobenzophenone, 1-methyl-2-pyrrolecarboxylic and 4-(4-hydroxypiperidin-1-yl)benzoic acids. [M+H]$^+$ calcd for $C_{31}H_{30}N_4O_4$: 523.1. found: 523.09.

Example 586

N-(4-(4-(4-(4-Hydroxypiperidin-1-yl)benzamido)benzoyl)phenyl)pyrimidine-5-carboxamide (Compound 686)

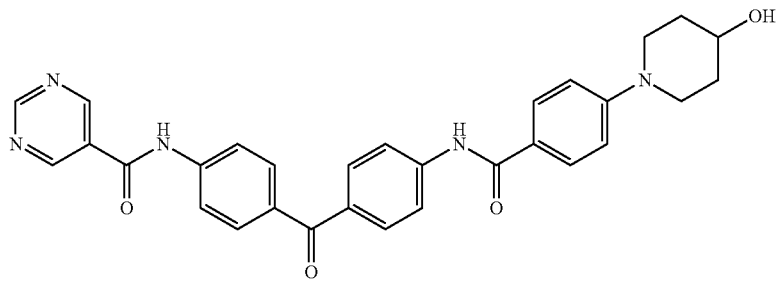 [SMILES: O=C(Nc1ccc(C(=O)c2ccc(NC(=O)c3cncnc3)cc2)cc1)c1ccc(N2CCC(O)CC2)cc1]

Compound 686 was prepared according to the procedure described in Scheme IV from 4,4'-diaminobenzophenone, pyrimidine-5-carboxylic and 4-(4-hydroxypiperidin-1-yl)benzoic acids. [M+H]$^+$ calcd for $C_{30}H_{27}N_5O_4$: 522.0. found: 522.08.

Example 587

N-Cyclopropyl-4-(4-(4-(4-hydroxypiperidin-1-yl)benzamido)benzoyl)benzamide (Compound 687)

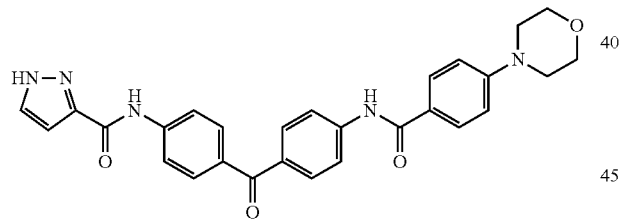

Compound 687 was prepared according to the procedure described in Scheme IV from N-cyclopropyl-4-(4-aminobenzoyl)benzamide and 4-(4-hydroxypiperidin-1-yl)benzoic acid. [M+H]$^+$ calcd for $C_{29}H_{30}N_3O_4$: 484.2. found: 484.08.

Example 588

N-(4-(4-(4-(4-Hydroxypiperidin-1-yl)benzamido)
benzoyl)phenyl)-1H-indolyl-3-carboxamide (Compound 688)

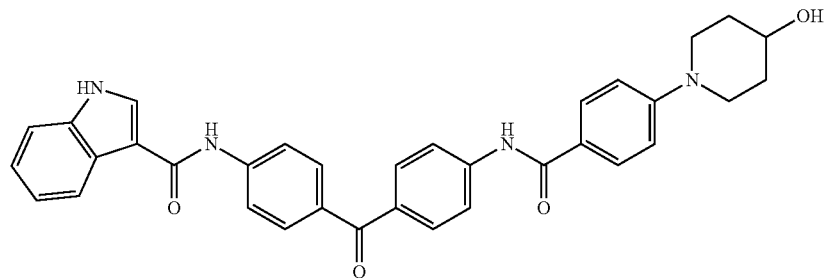 [SMILES: O=C(Nc1ccc(C(=O)c2ccc(NC(=O)c3c[nH]c4ccccc34)cc2)cc1)c1ccc(N2CCC(O)CC2)cc1]

Compound 688 was prepared according to the procedure described in Scheme IV from 4,4'-diaminobenzophenone, 3-indolecarboxylic and 4-(4-hydroxypiperidin-1-yl)benzoic acids. $[M+H]^+$ calcd for $C_{34}H_{30}N_4O_4$: 559.1. found: 559.14.

Example 589

N-(4-(4-(4-(4-Hydroxypiperidin-1-yl)benzamido)
benzoyl)phenyl)-1H-indolyl-4-carboxamide (Compound 689)

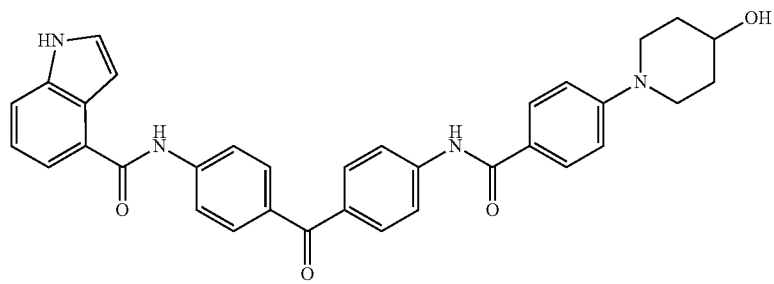 [SMILES: O=C(Nc1ccc(C(=O)c2ccc(NC(=O)c3cccc4[nH]ccc34)cc2)cc1)c1ccc(N2CCC(O)CC2)cc1]

Compound 689 was prepared according to the procedure described in Scheme IV from 4,4'-diaminobenzophenone, 4-indolecarboxylic and 4-(4-hydroxypiperidin-1-yl)benzoic acids. $[M+H]^+$ calcd for $C_{34}H_{30}N_4O_4$: 559.1. found: 559.14.

Example 590

N-(4-(4-(4-(4-Hydroxypiperidin-1-yl)benzamido)
benzoyl)phenyl)-1H-indolyl-7-carboxamide (Compound 690)

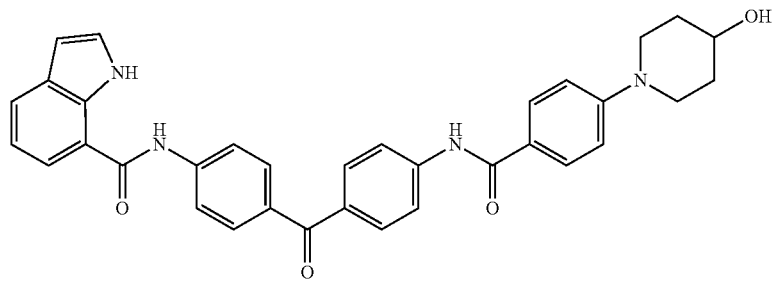 [SMILES: O=C(Nc1ccc(C(=O)c2ccc(NC(=O)c3cccc4cc[nH]c34)cc2)cc1)c1ccc(N2CCC(O)CC2)cc1]

Compound 690 was prepared according to the procedure described in Scheme IV from 4,4'-diaminobenzophenone, 7-indolecarboxylic and 4-(4-hydroxypiperidin-1-yl)benzoic acids. [M+H]+ calcd for $C_{34}H_{30}N_4O_4$: 559.1. found: 559.07.

Example 591

N-(4-(4-(4-(4-hydroxypiperidin-1-yl)benzamido)benzoyl)phenyl)-4-hydroxypiperidine-1-carboxamide (Compound 691)

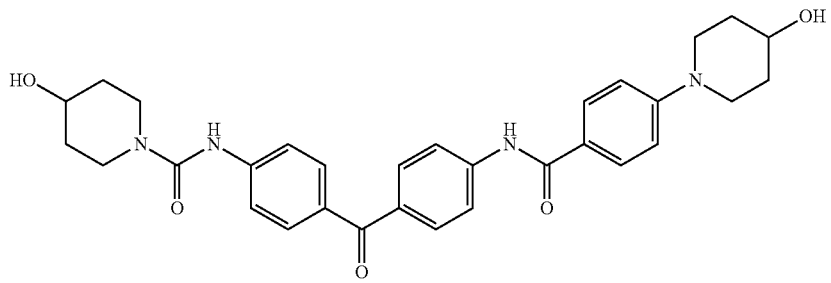 [SMILES: O=C(Nc1ccc(C(=O)c2ccc(NC(=O)N3CCC(O)CC3)cc2)cc1)c1ccc(N2CCC(O)CC2)cc1]

Compound 691 was prepared according to the procedure described in Scheme IV from 4,4'-diaminobenzophenone, 4-hydroxypiperidine, and 4-(4-hydroxypiperidin-1-yl)benzoic acid. [M+H]+ calcd for $C_{31}H_{35}N_4O_5$: 543.2. found: 543.07.

Example 592

N-(4-(4-(4-(4-hydroxypiperidin-1-yl)benzamido)benzoyl)phenyl)-1H-pyrrolo[2,3-b]pyridine-5-carboxamide (Compound 692)

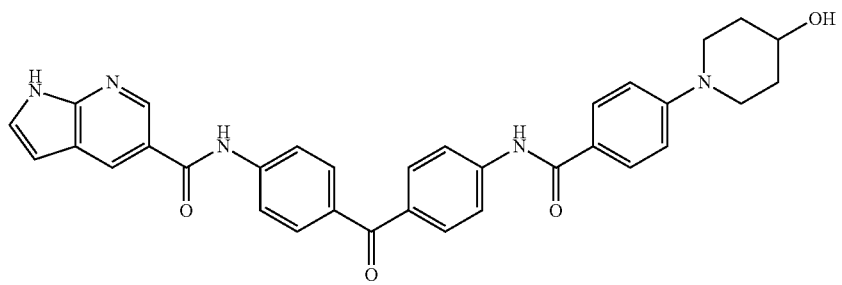 [SMILES: O=C(Nc1ccc(C(=O)c2ccc(NC(=O)c3cnc4[nH]ccc4c3)cc2)cc1)c1ccc(N2CCC(O)CC2)cc1]

Compound 692 was prepared according to the procedure described in Scheme IV from 4,4'-diaminobenzophenone, 1H-pyrrolo[2,3-b]pyridine-5-carboxylic and 4-(4-hydroxypiperidin-1-yl)benzoic acids. [M+H]+ calcd for $C_{33}H_{29}N_5O_4$: 560.14. found: 560.08.

Example 593

N-(4-(4-(4-(4-hydroxypiperidin-1-yl)benzamido)benzoyl)phenyl)benzo[b]thiophene-2-carboxamide (Compound 693)

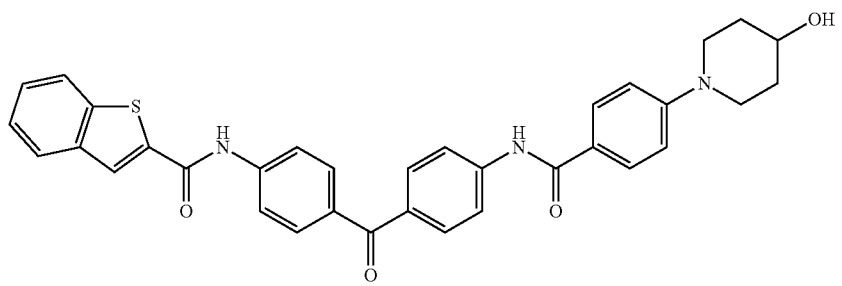 [SMILES: O=C(Nc1ccc(C(=O)c2ccc(NC(=O)c3cc4ccccc4s3)cc2)cc1)c1ccc(N2CCC(O)CC2)cc1]

Compound 693 was prepared according to the procedure described in Scheme IV from 4,4'-diaminobenzophenone, 2-benzothiophenecarboxylic and 4-(4-hydroxypiperidin-1-yl)benzoic acids. [M+H]$^+$ calcd for $C_{34}H_{29}N_3O_4S$: 576.20. found: 576.08.

Example 594

4-Azido-N-(4-(4-(4-morpholinobenzamido)benzoyl)phenyl)benzamide (Compound 694)

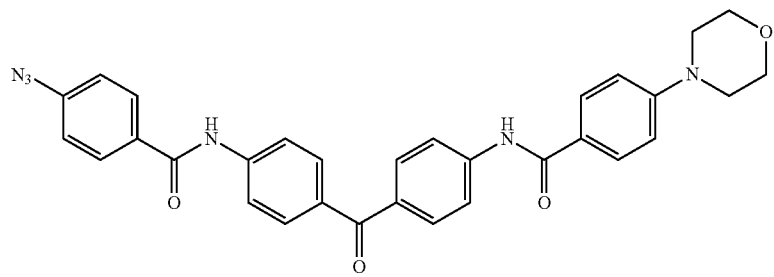 [SMILES: [N-]=[N+]=Nc1ccc(C(=O)Nc2ccc(C(=O)c3ccc(NC(=O)c4ccc(N5CCOCC5)cc4)cc3)cc2)cc1]

Compound 694 was prepared according to the procedure described in Scheme IV from 4,4'-diaminobenzophenone, 4-azidobenzoic and 4-morpholinobenzoic acids. $^1$H NMR (500 MHz, DMSO-d$_6$) δ 10.56 (s, 1H), 10.28 (s, 1H), 8.04 (d, J=8.8 Hz, 2H), 7.97 (d, J=9.0 Hz, 2H), 7.96 (d, J=8.8 Hz, 2H), 7.91 (d, J=9.0 Hz, 2H), 7.76 (d, J=8.5 Hz, 2H), 7.74 (d, J=8.8 Hz, 2H), 7.28 (d, J=8.5 Hz, 2H), 7.03 (d, J=9.0 Hz, 2H), 3.75-3.73 (m, 4H), 3.27-3.25 (m, 4H).

Example 595

N-(4-(4-(4-(4-Hydroxypiperidin-1-yl)benzamido)benzoyl)phenyl)-4-methyl-1H-pyrrole-2-carboxamide (Compound 695)

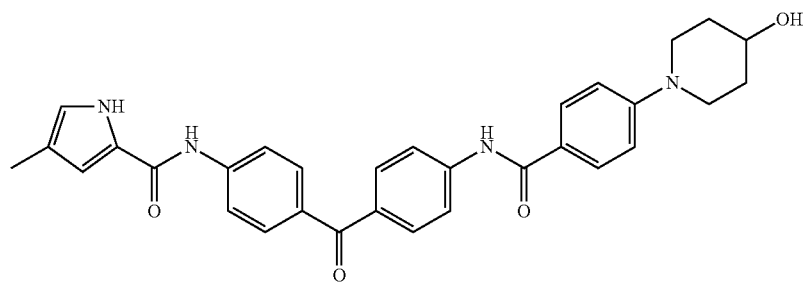 [SMILES: Cc1c[nH]c(C(=O)Nc2ccc(C(=O)c3ccc(NC(=O)c4ccc(N5CCC(O)CC5)cc4)cc3)cc2)c1]

Compound 695 was prepared according to the procedure described in Scheme IV from 4,4'-diaminobenzophenone, 4-methyl-2-pyrrolecarboxylic and 4-(4-hydroxypiperidin-1-yl)benzoic acids. [M+H]$^+$ calcd for $C_{31}H_{30}N_4O_4$: 523.1. found: 523.09.

Example 596

N-(4-(4-(4-(4-Hydroxypiperidin-1-yl)benzamido) benzoyl)phenyl)-1H-pyrrole-3-carboxamide (Compound 696)

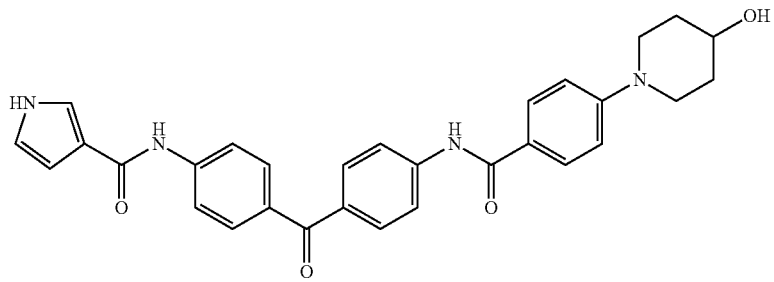 [SMILES: O=C(Nc1ccc(C(=O)c2ccc(NC(=O)c3cc[nH]c3)cc2)cc1)c1ccc(N2CCC(O)CC2)cc1]

Compound 696 was prepared according to the procedure described in Scheme IV from 4,4'-diaminobenzophenone, 3-pyrrolecarboxylic and 4-(4-hydroxypiperidin-1-yl)benzoic acids. [M+H]$^+$ calcd for $C_{30}H_{28}N_4O_4$: 509.0. found: 509.05.

Example 597

N-(4-(4-(4-(4-Hydroxypiperidin-1-yl)benzamido) benzoyl)phenyl)-1H-pyrrole-2-carboxamide (Compound 697)

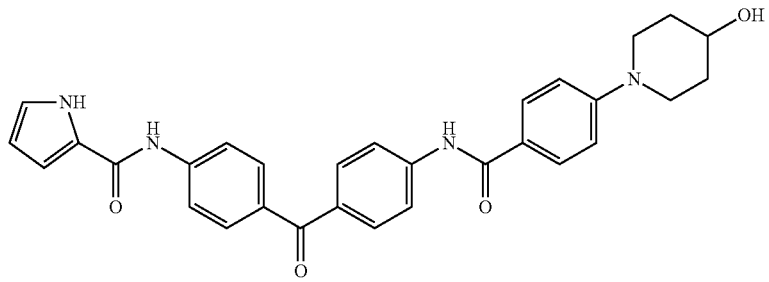 [SMILES: O=C(Nc1ccc(C(=O)c2ccc(NC(=O)c3ccc[nH]3)cc2)cc1)c1ccc(N2CCC(O)CC2)cc1]

Compound 697 was prepared according to the procedure described in Scheme IV from 4,4'-diaminobenzophenone, 2-pyrrolecarboxylic and 4-(4-hydroxypiperidin-1-yl)benzoic acids. [M+H]$^+$ calcd for $C_{30}H_{28}N_4O_4$: 509.0. found: 509.05.

Example 598

N-(4-(4-(4-(4-Hydroxypiperidin-1-yl)benzamido) benzoyl)phenyl)-4-(3-hydroxypropyl) piperazine-1-carboxamide (Compound 698)

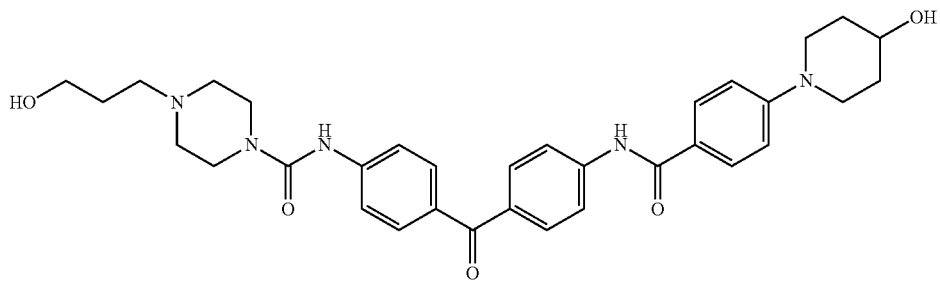 [SMILES: O=C(Nc1ccc(C(=O)c2ccc(NC(=O)N3CCN(CCCO)CC3)cc2)cc1)c1ccc(N2CCC(O)CC2)cc1]

Compound 698 was prepared according to the procedure described in Scheme IV from 4,4'-diaminobenzophenone, 4-(3-hydroxypropyl)piperazine, and 4-(4-hydroxypiperidin-1-yl)benzoic acid. [M+H]$^+$ calcd for $C_{33}H_{40}N_5O_5$: 586.3. found: 586.20.

Example 599

N-(4-(4-(4-(4-Hydroxypiperidin-1-yl)benzamido)benzoyl)phenyl)-4,5,6,7-tetrahydro-1H-indole-2-carboxamide (Compound 699)

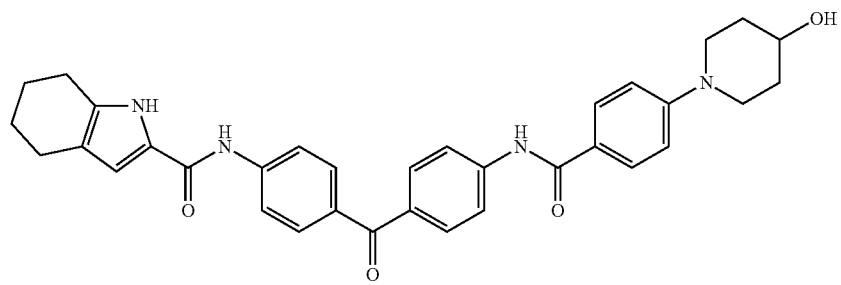 [SMILES: O=C(Nc1ccc(C(=O)c2ccc(NC(=O)c3cc4c([nH]3)CCCC4)cc2)cc1)c1ccc(N2CCC(O)CC2)cc1]

Compound 699 was prepared according to the procedure described in Scheme IV from 4,4'-diaminobenzophenone, 4,5,6,7-tetrahydroindole-2-carboxylic and 4-(4-hydroxypiperidin-1-yl)benzoic acids. [M+H]$^+$ calcd for $C_{34}H_{34}N_4O_4$: 563.1. found: 563.19.

Example 600

(±)-N-(4-(4-(4-(3-(Hydroxymethyl)piperidin-1-yl)benzamido)benzoyl)phenyl)-1H-pyrrole-2-carboxamide (Compound 700)

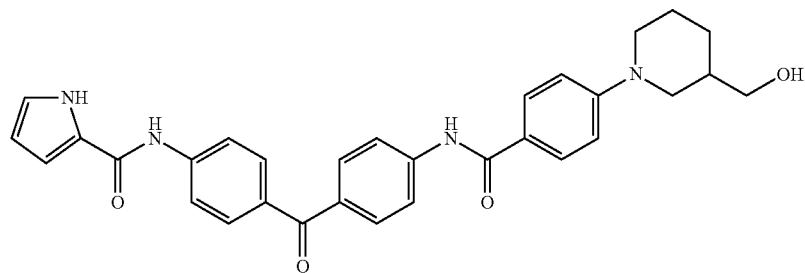 [SMILES: O=C(Nc1ccc(C(=O)c2ccc(NC(=O)c3ccc[nH]3)cc2)cc1)c1ccc(N2CCCC(CO)C2)cc1]

Compound 700 was prepared according to the procedure described in Scheme IV from 4,4'-diaminobenzophenone, 2-pyrrolecarboxylic and 4-(3-hydroxymethylpiperidin-1-yl) benzoic acids. $^1$H NMR (400 MHz, DMSO-d$_6$) δ 10.25 (s, 1H), 10.07 (s, 1H), 7.98 (dd, J=9.0, 10 Hz, 4H), 7.91 (d, J=9.0 Hz, 2H), 7.77 (dd, J=1.6, 8.7 Hz, 4H), 7.16 (bm, 1H), 7.02 (s, 1H), 7.01 (d, J=9.0 Hz, 2H), 6.22 (m, 1H), 4.59 (t, J=5.3 Hz, 1H), 1H), 3.88 (m, 2H), 2.86 (t, J=12 Hz, 1H), 1.75 (m, 4H), 1.54 (m, 2H), 1.21 (m, 2H).

Example 601

N,N'-(Ethene-1,1-diylbis(4,1-phenylene))bis(4-(dimethylamino)benzamide) (Compound 701)

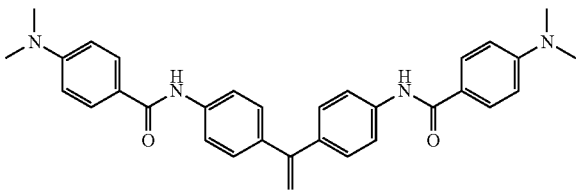

Compound 701 was prepared according to the procedure described in Scheme IV from 4,4'-(ethene-1,1-diyl)dianiline and 4-N,N-dimethylaminobenzoic acid. $^1$H NMR (500 MHz, DMSO-$d_6$) δ 9.94 (s, 2H), 7.86 (d, J=8.8 Hz, 4H), 7.77 (d, J=8.5 Hz, 4H), 7.26 (d, J=8.3 Hz, 4H), 6.75 (d, J=8.8 Hz, 4H), 5.38 (s, 2H), 2.99 (s, 12H).

Example 602

N,N'-(Ethene-1,1-diylbis(4,1-phenylene))bis(1-methyl-1H-indole-5-carboxamide) (Compound 702)

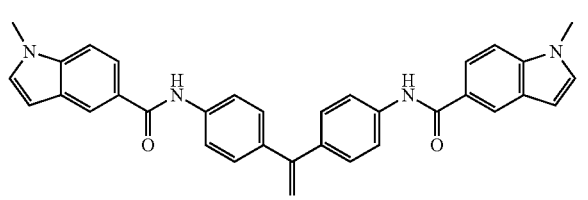 [SMILES: C=C(c1ccc(NC(=O)c2ccc3c(ccn3C)c2)cc1)c1ccc(NC(=O)c2ccc3c(ccn3C)c2)cc1]

Compound 702 was prepared according to the procedure described in Scheme IV from 4,4'-(ethene-1,1-diyl)dianiline and 1-methylindole-5-carboxylic acid. $^1$H NMR (500 MHz, CDCl$_3$) δ 8.20 (s, 2H), 7.93 (s, 2H), 7.79 (dd, J=1.7, 8.5 Hz, 2H), 7.66 (dd, J=1.7, 6.8 Hz, 4H), 7.42 (d, J=2.3 Hz, 2H), 7.39 (d, J=8.5 Hz, 4H), 7.15 (d, J=2.3 Hz, 2H), 6.61 (d, J=2.9 Hz, 2H), 5.44 (s, 2H), 3.86 (s, 6H).

Example 603

N,N'-(((Methoxyimino)methylene)bis(4,1-phenylene))bis(1H-indole-5-carboxamide) (Compound 703)

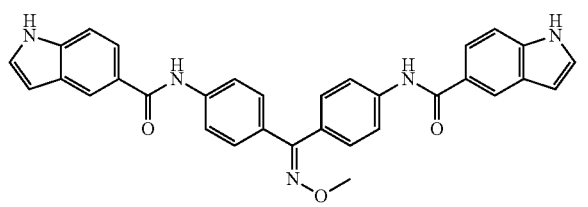 [SMILES: CON=C(c1ccc(NC(=O)c2ccc3[nH]ccc3c2)cc1)c1ccc(NC(=O)c2ccc3[nH]ccc3c2)cc1]

Compound 703 was prepared according to the procedure described in Scheme IV from 4,4'-diaminobenzophenone and 1-methylindole-5-carboxylic acid. [M+H]$^+$ calcd for C$_{32}$H$_{25}$N$_5$O$_3$: 528.1. found: 528.15.

Example 604

(Z/E)-N-(4-((4-(Cyclopropanecarboxamido)phenyl)(methoxyimino)methyl)phenyl)-1H-indole-5-carboxamide (Compound 704)

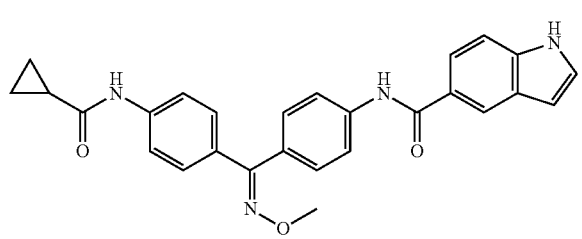 [SMILES: CO/N=C(\c1ccc(NC(=O)c2ccc3[nH]ccc3c2)cc1)c1ccc(NC(=O)C2CC2)cc1]

Compound 704 was prepared according to the procedure described in Scheme IV from 4,4'-diaminobenzophenone, cyclopropanecarboxylic, and indole-5-carboxylic acids.

[M+H]$^+$ calcd for C$_{27}$H$_{24}$N$_4$O$_3$: 453.0. found: 453.03.

Example 605

N-(4-(4-(1H-Pyrrole-2-carboxamido)benzoyl)phenyl)-1-(2-morpholinoethyl)-1H-indole-5-carboxamide (Compound 705)

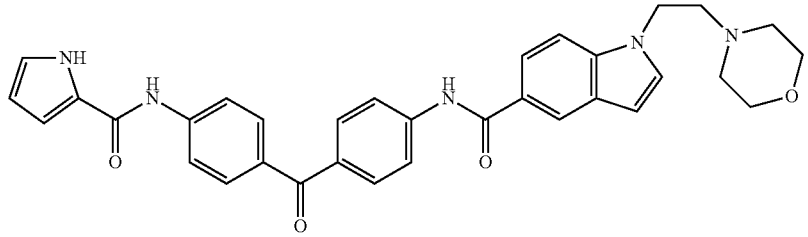 [SMILES: O=C(Nc1ccc(C(=O)c2ccc(NC(=O)c3ccc[nH]3)cc2)cc1)c1ccc2c(ccn2CCN2CCOCC2)c1]

Compound 705 was prepared according to the procedure described in Scheme IV from 4,4'-diaminobenzophenone, 2-pyrrolecarboxylic, and 1-(2-morpholinoethyl)indole-5-carboxylic acids. $[M+H]^+$ calcd for $C_{33}H_{31}N_5O_4$: 562.16. found: 562.11.

Example 606

(±)-N-(4-(4-(4-(2-(Hydroxymethyl)morpholino)benzamido)benzoyl)phenyl)-1H-pyrrole-2-carboxamide (Compound 706)

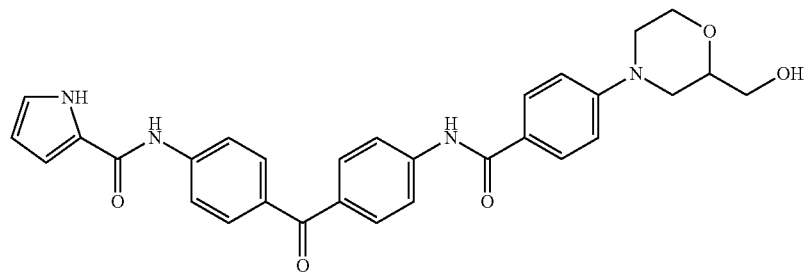 [SMILES: O=C(Nc1ccc(C(=O)c2ccc(NC(=O)c3ccc[nH]3)cc2)cc1)c1ccc(N2CCOC(CO)C2)cc1]

Compound 706 was prepared according to the procedure described in Scheme IV from 4,4'-diaminobenzophenone, 2-pyrrolecarboxylic, and 4-(2-hydroxymethyl)morpholino-4-)benzoic acids. $[M+H]^+$ calcd for $C_{30}H_{28}N_4O_5$: 525.21. found: 524.98.

Example 607

(±)-N-(4-(4-(4-(3-(Hydroxymethyl)piperidin-1-yl)benzamido)benzoyl)phenyl)-1methyl-1H-pyrrole-2-carboxamide (Compound 707)

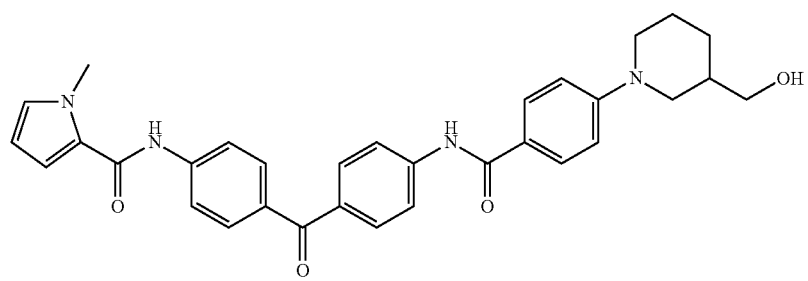 [SMILES: Cn1cccc1C(=O)Nc1ccc(C(=O)c2ccc(NC(=O)c3ccc(N4CCCC(CO)C4)cc3)cc2)cc1]

Compound 707 was prepared according to the procedure described in Scheme IV from 4,4'-diaminobenzophenone, 1-methyl-2-pyrrolecarboxylic, and 4-(3-hydroxymethylpiperidin-1-yl)benzoic acids. [M+H]+ calcd for $C_{32}H_{32}N_4O_4$: 537.24. found: 537.06.

Example 608

(±)-N-(4-(4-(4-(3-Hydroxypyrrolidin-1-yl)benzamido)benzoyl)phenyl)-1-methyl-1H-pyrrole-2-carboxamide (Compound 708)

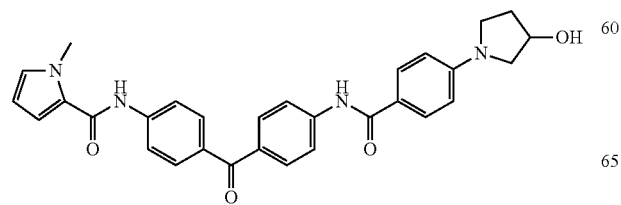

Compound 708 was prepared according to the procedure described in Scheme IV from 4,4'-diaminobenzophenone, 1-methyl-2-pyrrolecarboxylic, and 4-(3-hydroxypyrrolidin-1-yl)benzoic acids. [M+H]$^+$ calcd for $C_{30}H_{28}N_4O_4$: 509.2. found: 508.98.

Example 609

N-(4-(4-(4-(4-Hydroxypiperidin-1-yl)benzamido)benzoyl)phenyl)-4-morpholinecarboxamide (Compound 709)

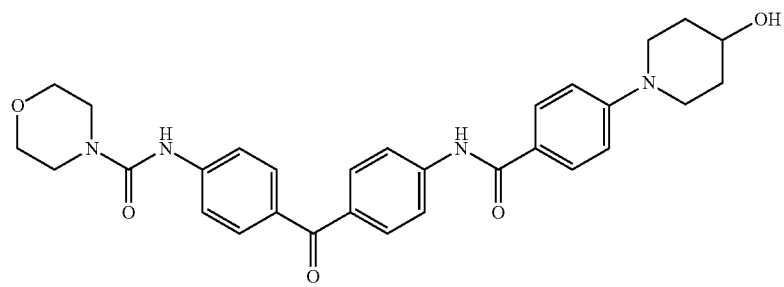 [SMILES: O=C(Nc1ccc(C(=O)c2ccc(NC(=O)N3CCOCC3)cc2)cc1)c1ccc(N2CCC(O)CC2)cc1]

Compound 709 was prepared according to the procedure described in Scheme IV from 4,4'-diaminobenzophenone, morpholine, and 4-(4-hydroxypiperidin-1-yl)benzoic acid. [M+H]$^+$ calcd for $C_{30}H_{32}N_4O_5$: 529.1. found: 529.03.

Example 610

(±)-N-(4-(4-(4-(2-(Hydroxymethyl)morpholino)benzamido)benzoyl)phenyl)-1-methyl-1H-pyrrole-2-carboxamide (Compound 710)

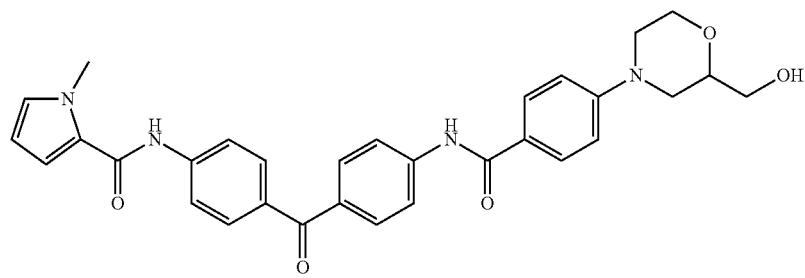 [SMILES: Cn1cccc1C(=O)Nc1ccc(C(=O)c2ccc(NC(=O)c3ccc(N4CCOC(CO)C4)cc3)cc2)cc1]

Compound 710 was prepared according to the procedure described in Scheme IV from 4,4'-diaminobenzophenone, 1-methyl-2-pyrrolecarboxylic, and 4-(2-hydroxymethyl)morpholino-4-)benzoic acids. [M+H]$^+$ calcd for $C_{31}H_{30}N_4O_5$: 539.22. found: 539.02.

Example 611

N-(4-(4-(4-(4-(Cyclopropanecarbonyl)piperazin-1-yl)benzamido)benzoyl)phenyl)-1-methyl-1H-pyrrole-2-carboxamide (Compound 711)

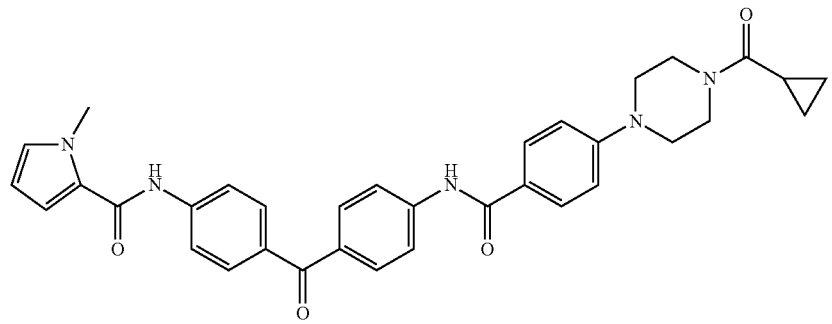 [SMILES: Cn1cccc1C(=O)Nc1ccc(C(=O)c2ccc(NC(=O)c3ccc(N4CCN(C(=O)C5CC5)CC4)cc3)cc2)cc1]

Compound 711 was prepared according to the procedure described in Scheme IV from 4,4'-diaminobenzophenone, 1-methyl-2-pyrrolecarboxylic, and 4-(4-cyclopropanecarbonyl)piperazinobenzoic acids. [M+H]$^+$ calcd for $C_{34}H_{33}N_5O_4$: 576.25. found: 576.08.

Example 612

(R)—N-(4-(4-(4-(3-Hydroxypyrrolidin-1-yl)benzamido)benzoyl)phenyl)-1-methyl-1H-pyrrole-2-carboxamide (Compound 712)

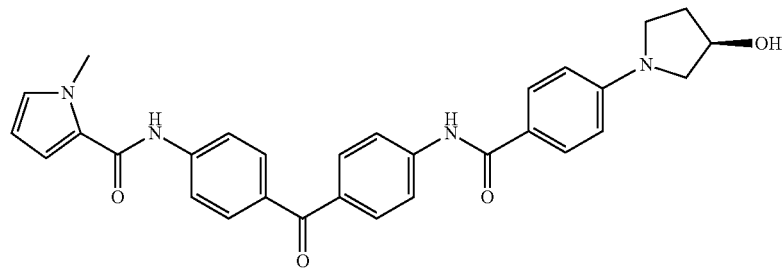 [SMILES: Cn1cccc1C(=O)Nc1ccc(C(=O)c2ccc(NC(=O)c3ccc(N4CC[C@@H](O)C4)cc3)cc2)cc1]

Compound 712 was prepared according to the procedure described in Scheme IV from 4,4'-diaminobenzophenone, 1-methyl-2-pyrrolecarboxylic, and (R)-4-(3-hydroxypyrrolidin-1-yl)benzoic acids. [M+H]$^+$ calcd for $C_{30}H_{28}N_4O_4$: 509.2. found: 508.98.

Example 613

(S)—N-(4-(4-(4-(3-Hydroxypyrrolidin-1-yl)benzamido)benzoyl)phenyl)-1-methyl-1H-pyrrole-2-carboxamide (Compound 713)

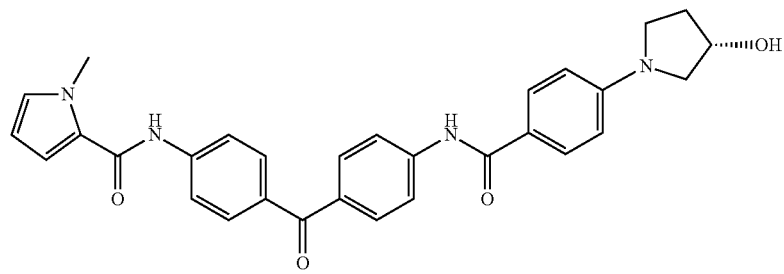 [SMILES: Cn1cccc1C(=O)Nc1ccc(C(=O)c2ccc(NC(=O)c3ccc(N4CC[C@H](O)C4)cc3)cc2)cc1]

Compound 713 was prepared according to the procedure described in Scheme IV from 4,4'-diaminobenzophenone, 1-methyl-2-pyrrolecarboxylic, and (S)-4-(3-hydroxypyrrolidin-1-yl)benzoic acids. $^1$H NMR (400 MHz, Acetone-d$_6$) δ 9.49 (s, 1H), 9.38 (s, 1H), 8.02 (d, J=8.8 Hz, 2H), 7.95 (t, J=9 Hz, 3H), 7.78 (d, J=7 Hz, 3H), 7.03 (dd, J=2, 4 Hz, 1H), 6.97 (t, J=2 Hz, 1H), 6.61 (d, J=9 Hz, 2H), 6.11 (dd, J=2.5, 4 Hz, 1H), 4.60 (m, 1H), 3.99 (s, 3H), 3.59-3.42 (m, 3H), 3.31 (m, 1H), 2.20-2.14 (m, 3H).

Example 614

4-Azido-N-(4-(4-(4-(dimethylamino)benzamido)benzoyl)phenyl)benzamide (Compound 714)

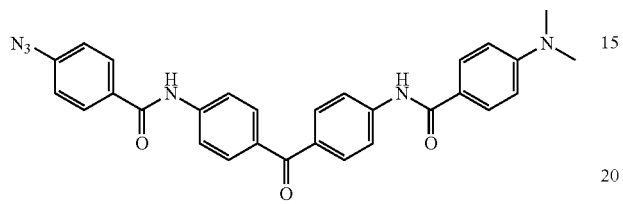

Compound 714 was prepared according to the procedure described in Scheme IV from 4,4'-diaminobenzophenone, 4-azidobenzoic, and 4-dimtheylaminobenzoic acids. [M+H]$^+$ calcd for $C_{29}H_{24}N_6O_3$: 505.1. found 504.93.

Example 615

N-(4-(4-(3-Fluoro-4-(4-hydroxypiperidin-1-yl)benzamido)benzoyl)phenyl)-1-methyl-1H-pyrrole-2-carboxamide (Compound 715)

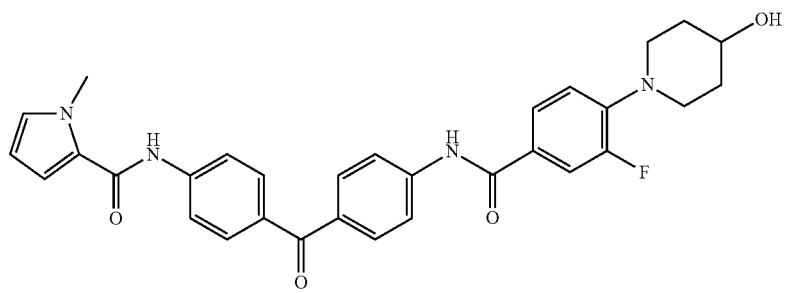 [SMILES: Cn1cccc1C(=O)Nc1ccc(C(=O)c2ccc(NC(=O)c3ccc(N4CCC(O)CC4)c(F)c3)cc2)cc1]

Compound 715 was prepared according to the procedure described in Scheme IV from 4,4'-diaminobenzophenone, 1-methyl-2-pyrrolecarboxylic, and 4-(4-hydroxypiperidin-1-yl)-3-fluorobenzoic acids. [M+H]$^+$ calcd for $C_{31}H_{29}FN_4O_4$: 541.22. found: 541.05.

Example 616

(E/Z)—N-(4-((4-(4-(4-Hydroxypiperidin-1-yl)benzamido)phenyl)(methoxyimino)methyl)phenyl)-1-methyl-1H-pyrrole-2-carboxamide (Compound 716)

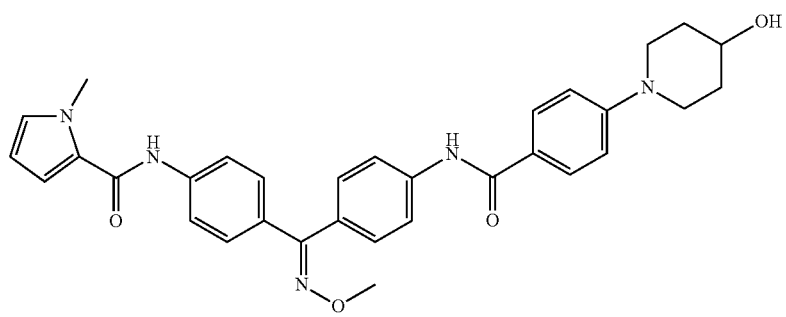 [SMILES: CO/N=C(\c1ccc(NC(=O)c2ccc(N3CCC(O)CC3)cc2)cc1)c1ccc(NC(=O)c2cccn2C)cc1]

Compound 716 was prepared according to the procedure described in Scheme IV from 4,4'-diaminobenzophenone, 1-methyl-2-pyrrolecarboxylic, and 4-(4-hydroxypiperidin-1-yl)benzoic acids. [M+H]$^+$ calcd for $C_{32}H_{33}N_5O_4$: 552.1. found: 552.05.

Example 617

N-(4-(4-(4-(4-Hydroxypiperidin-1-yl)benzamido)benzoyl)phenyl)-1H-pyrazole-5-carboxamide (Compound 717)

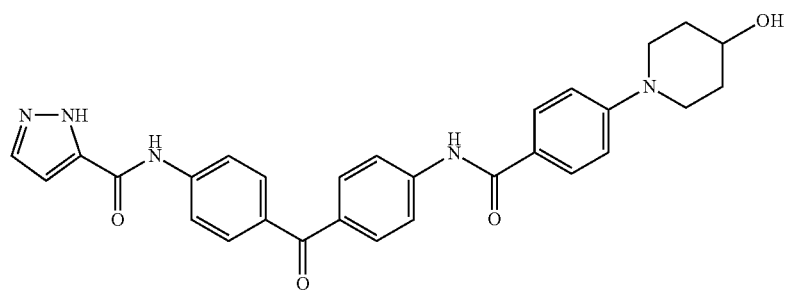 [SMILES: O=C(Nc1ccc(C(=O)c2ccc(NC(=O)c3ccn[nH]3)cc2)cc1)c1ccc(N2CCC(O)CC2)cc1]

Compound 717 was prepared according to the procedure described in Scheme IV from 4,4'-diaminobenzophenone, 5-pyrazolecarboxylic, and 4-(4-hydroxypiperidin-1-yl)benzoic acids. [M+H]$^+$ calcd for $C_{29}H_{27}N_5O_4$: 510.1. found: 509.99.

Example 618

N-(4-(4-(3-Trifluoromethyl-4-(4-hydroxypiperidin-1-yl)benzamido)benzoyl)phenyl)-1-methyl-1H-pyrrole-2-carboxamide (Compound 718)

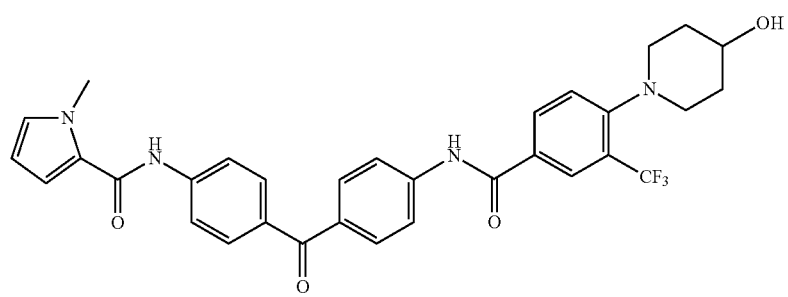 [SMILES: Cn1cccc1C(=O)Nc1ccc(C(=O)c2ccc(NC(=O)c3ccc(N4CCC(O)CC4)c(C(F)(F)F)c3)cc2)cc1]

Compound 718 was prepared according to the procedure described in Scheme IV from 4,4'-diaminobenzophenone, 1-methyl-2-pyrrolecarboxylic, and 4-(4-hydroxypiperidin-1-yl)-3-trifluoromethylbenzoic acids. [M+H]$^+$ calcd for $C_{32}H_{30}F_3N_4O_4$: 591.2. found: 591.07.

Example 619

N-(4-(4-(4-(4-Hydroxypiperidin-1-yl)benzamido)benzoyl)phenyl)-1H-pyrazole-4-carboxamide (Compound 719)

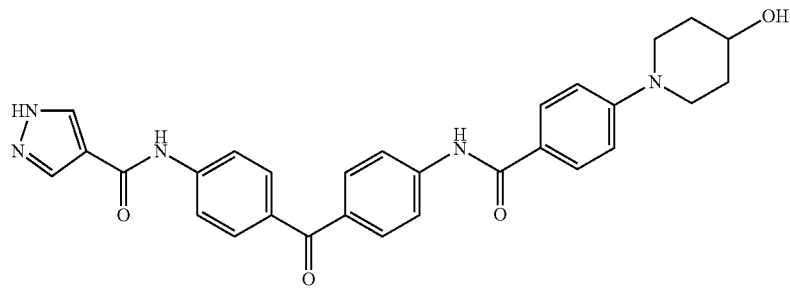 [SMILES: O=C(Nc1ccc(C(=O)c2ccc(NC(=O)c3cn[nH]c3)cc2)cc1)c1ccc(N2CCC(O)CC2)cc1]

Compound 719 was prepared according to the procedure described in Scheme IV from 4,4'-diaminobenzophenone, 4-pyrazolecarboxylic, and 4-(4-hydroxypiperidin-1-yl)benzoic acids. [M+H]$^+$ calcd for $C_{29}H_{27}N_5O_4$: 510.1. found: 509.99.

Example 620

N-(4-(4-(4-(4-Hydroxypiperidin-1-yl)benzamido)benzoyl)phenyl)-1-methyl-1H-pyrazole-5-carboxamide (Compound 720)

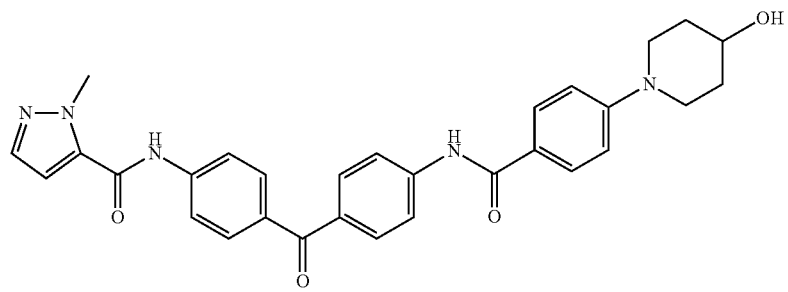 [SMILES: Cn1nccc1C(=O)Nc1ccc(C(=O)c2ccc(NC(=O)c3ccc(N4CCC(O)CC4)cc3)cc2)cc1]

Compound 720 was prepared according to the procedure described in Scheme IV from 4,4'-diaminobenzophenone, 1-methyl-5-pyrazolecarboxylic, and 4-(4-hydroxypiperidin-1-yl)benzoic acids. [M+H]$^+$ calcd for $C_{30}H_{29}N_5O_4$: 524.1. found: 524.03.

Example 621

N-(4-(4-(2-Methyl-4-(4-hydroxypiperidin-1-yl)benzamido)benzoyl)phenyl)-1-methyl-1H-pyrrole-2-carboxamide (Compound 721)

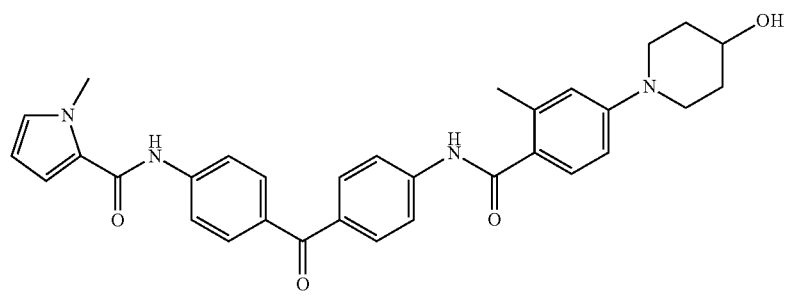 [SMILES: Cc1cc(N2CCC(O)CC2)ccc1C(=O)Nc1ccc(C(=O)c2ccc(NC(=O)c3cccn3C)cc2)cc1]

Compound 721 was prepared according to the procedure described in Scheme IV from 4,4'-diaminobenzophenone, 1-methyl-2-pyrrolecarboxylic, and 4-(4-hydroxypiperidin-1-yl)-2-methylbenzoic acids. [M+H]$^+$ calcd for $C_{32}H_{33}N_4O_4$: 537.25. found: 537.06.

Example 622

N-(4-(4-(3-Methoxy-4-(4-hydroxypiperidin-1-yl)benzamido)benzoyl)phenyl)-1-methyl-1H-pyrrole-2-carboxamide (Compound 722)

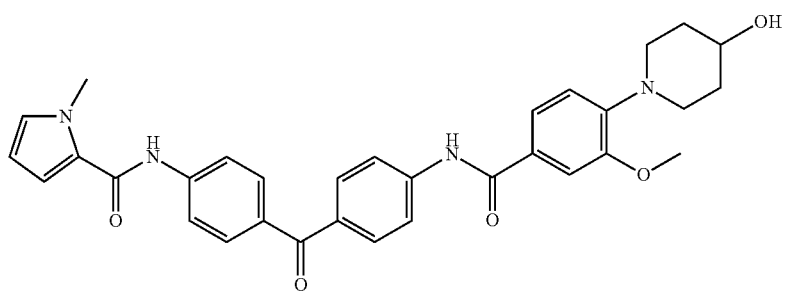 [SMILES: COc1cc(C(=O)Nc2ccc(C(=O)c3ccc(NC(=O)c4cccn4C)cc3)cc2)ccc1N1CCC(O)CC1]

Compound 722 was prepared according to the procedure described in Scheme IV from 4,4'-diaminobenzophenone, 1-methyl-2-pyrrolecarboxylic, and 4-(4-hydroxypiperidin-1-yl)-3-methoxybenzoic acids. [M+H]$^+$ calcd for $C_{32}H_{33}N_4O_5$: 553.25. found: 553.06.

Example 623

5-Chloro-N-(4-(4-(4-(4-hydroxypiperidin-1-yl)benzamido)benzoyl)phenyl)-1-isopropyl-1H-pyrrole-2-carboxamide (Compound 723)

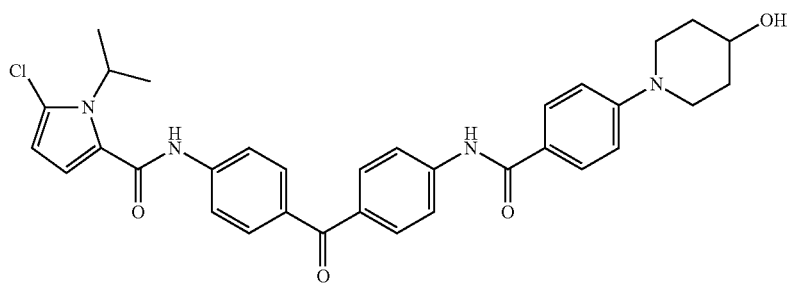 [SMILES: CC(C)n1c(Cl)ccc1C(=O)Nc1ccc(C(=O)c2ccc(NC(=O)c3ccc(N4CCC(O)CC4)cc3)cc2)cc1]

Compound 723 was prepared according to the procedure described in Scheme IV from 4,4'-diaminobenzophenone, 5-chloro-1-isopropyl-2-pyrrolecarboxylic, and 4-(4-hydroxypiperidin-1-yl)-3-trifluoromethylbenzoic acids. [M+H]$^+$ calcd for $C_{33}H_{33}ClN_4O_4$: 585.2. found: 585.06.

Example 624

N-(4-(4-(4-(4-Hydroxypiperidin-1-yl)benzamido)benzoyl)phenyl)-1-isopropyl-1H-pyrrole-2-carboxamide (Compound 724)

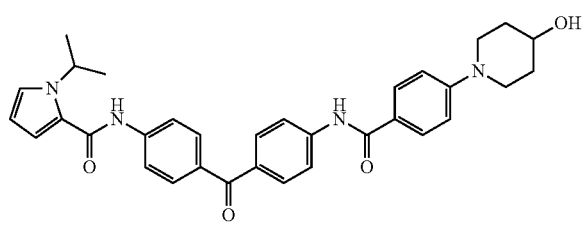

Compound 724 was prepared according to the procedure described in Scheme IV from 4,4'-diaminobenzophenone, 1-isopropyl-2-pyrrolecarboxylic, and 4-(4-hydroxypiperidin-1-yl)-3-trifluoromethylbenzoic acids. $^1$H NMR (400 MHz, CD$_3$OD) δ 7.93-7.81 (m, 10H), 7.22 (dd, J=1.7, 2.7 Hz, 1H), 7.05 (d, J=9 Hz, 2H), 7.00 (dd, J=1.7, 4 Hz, 1H), 6.22 (dd, J=2.7, 4 Hz, 1H), 5.51 (s, 1H), 3.84 (m, 3H), 3.10 (m, 2H), 1.9 (m, 2H), 1.64 (m, 2H), 1.50 (s, 3H), 1.48 (s, 3H).

Example 625

N-(4-(4-(4-(4-Hydroxypiperidin-1-yl)benzamido)benzoyl)phenyl)-1-methyl-1H-pyrazole-4-carboxamide (Compound 725)

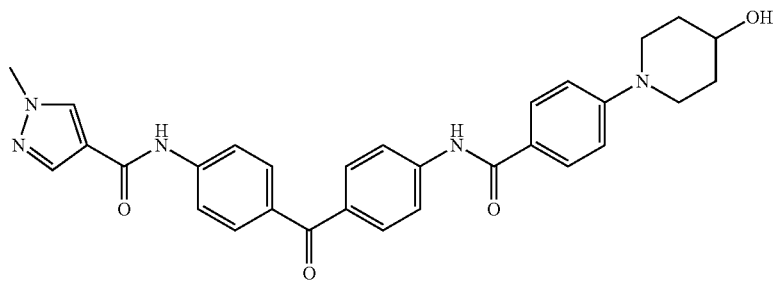 [SMILES: Cn1cc(C(=O)Nc2ccc(C(=O)c3ccc(NC(=O)c4ccc(N5CCC(O)CC5)cc4)cc3)cc2)cn1]

Compound 725 was prepared according to the procedure described in Scheme IV from 4,4'-diaminobenzophenone, 1-methyl-4-pyrazolecarboxylic, and 4-(4-hydroxypiperidin-1-yl)benzoic acids. [M+H]$^+$ calcd for C$_{30}$H$_{29}$N$_5$O$_4$: 524.1. found: 524.03.

Example 626

Methyl 5-((4-(4-(4-(4-hydroxypiperidin-1-yl)benzamido)benzoyl)phenyl)carbamoyl)-1H-pyrrole-2-carboxylate (Compound 726)

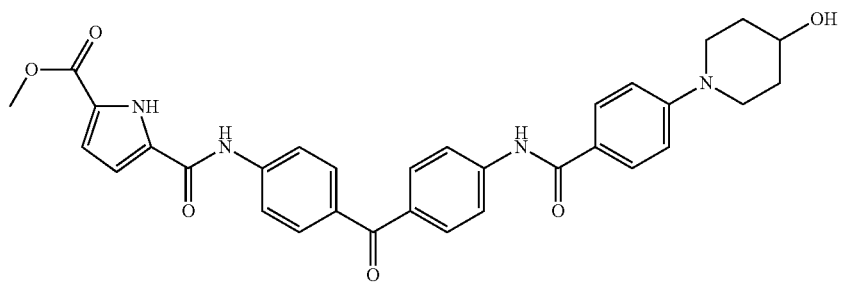 [SMILES: COC(=O)c1ccc(C(=O)Nc2ccc(C(=O)c3ccc(NC(=O)c4ccc(N5CCC(O)CC5)cc4)cc3)cc2)[nH]1]

Compound 726 was prepared according to the procedure described in Scheme IV from 4,4'-diaminobenzophenone, 1-isopropyl-2-pyrrolecarboxylic, and 4-(4-hydroxypiperidin-1-yl)-3-trifluoromethylbenzoic acids. [M+H]$^+$ calcd for $C_{32}H_{30}N_4O_6$: 567.1. found: 567.04.

Example 627

N-(4-(4-(4-(4-Hydroxypiperidin-1-yl)benzamido)benzoyl)phenyl)-1-methyl-1H-pyrazole-3-carboxamide (Compound 727)

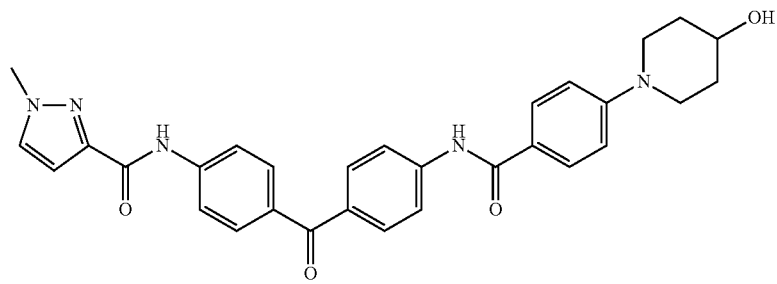 [SMILES: Cn1ccc(C(=O)Nc2ccc(C(=O)c3ccc(NC(=O)c4ccc(N5CCC(O)CC5)cc4)cc3)cc2)n1]

Compound 727 was prepared according to the procedure described in Scheme IV from 4,4'-diaminobenzophenone, 1-methyl-3-pyrazolecarboxylic, and 4-(4-hydroxypiperidin-1-yl)benzoic acids. [M+H]$^+$ calcd for $C_{30}H_{29}N_5O_4$: 524.1. found: 524.03.

Example 628

N-(4-(4-(3-Methyl-4-(4-hydroxypiperidin-1-yl)benzamido)benzoyl)phenyl)-1-methyl-1H-pyrrole-2-carboxamide (Compound 728)

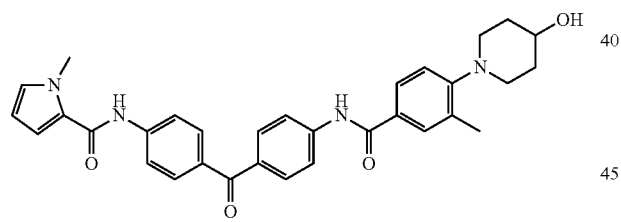

Compound 728 was prepared according to the procedure described in Scheme IV from 4,4'-diaminobenzophenone, 1-methyl-2-pyrrolecarboxylic, and 4-(4-hydroxypiperidin-1-yl)-3-methylbenzoic acids. [M+H]$^+$ calcd for $C_{32}H_{33}N_4O_4$: 537.25. found: 537.11.

Example 629

N-(4-(4-(4-(4-Hydroxypiperidin-1-yl)benzamido)benzoyl)phenyl)-1-vinyl-4,5,6,7-tetrahydro-1H-indole-2-carboxamide (Compound 729)

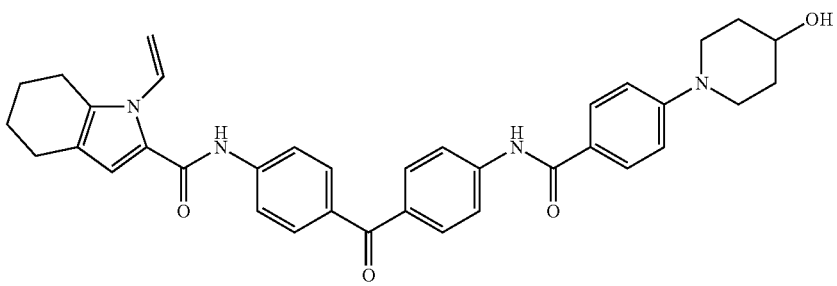 [SMILES: C=Cn1c(C(=O)Nc2ccc(C(=O)c3ccc(NC(=O)c4ccc(N5CCC(O)CC5)cc4)cc3)cc2)cc2c1CCCC2]

Compound 729 was prepared according to the procedure described in Scheme IV from 4,4'-diaminobenzophenone, 1-vinyl-4,5,6,7-tetrahydroindole-2-carboxylic, and 4-(4-hydroxypiperidin-1-yl)benzoic acids. [M+H]+ calcd for $C_{36}H_{36}N_4O_4$: 589.27. found: 589.12.

Example 630

N-(4-(4-(2-Chloro-4-(4-hydroxypiperidin-1-yl)benzamido)benzoyl)phenyl)-1-methyl-1H-pyrrole-2-carboxamide (Compound 730)

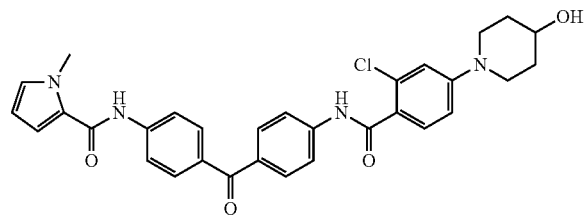 [SMILES: Cn1cccc1C(=O)Nc1ccc(C(=O)c2ccc(NC(=O)c3ccc(N4CCC(O)CC4)cc3Cl)cc2)cc1]

Compound 730 was prepared according to the procedure described in Scheme IV from 4,4'-diaminobenzophenone, 1-methyl-2-pyrrolecarboxylic, and 4-(4-hydroxypiperidin-1-yl)-2-chlorobenzoic acids. [M+H]+ calcd for $C_{31}H_{30}ClN_4O_4$: 557.20. found: 556.98.

Example 631

N-(4-(4-(4-(4-Hydroxypiperidin-1-yl)benzamido)benzoyl)phenyl)-1-methyl-1H-pyrrole-3-carboxamide (Compound 731)

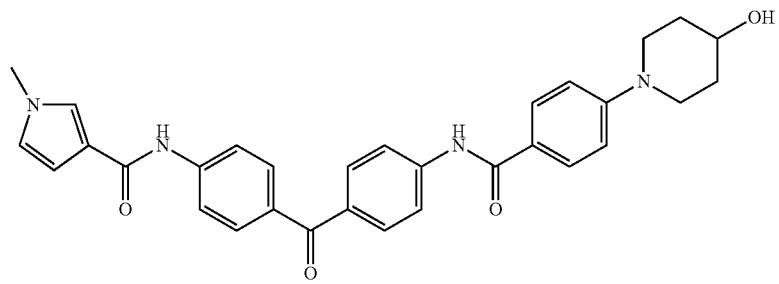

Compound 731 was prepared according to the procedure described in Scheme IV from 4,4'-diaminobenzophenone, 1-methyl-3-pyrrolecarboxylic, and 4-(4-hydroxypiperidin-1-yl)benzoic acids. [M+H]+ calcd for $C_{31}H_{30}N_4O_4$: 523.1. found: 522.95.

Example 632

N-(4-(4-(2-Chloro-4-(4-hydroxypiperidin-1-yl)benzamido)benzoyl)phenyl)-1-ethyl-1H-pyrrole-2-carboxamide (Compound 732)

Compound 732 was prepared according to the procedure described in Scheme IV from 4,4'-diaminobenzophenone, 1-ethyl-2-pyrrolecarboxylic, and 4-(4-hydroxypiperidin-1-yl)benzoic acids. $^1$H NMR (400 MHz, CD$_3$OD) δ 7.89-7.79 (m, 10H), 7.02 (m, 4H), 6.15 (m, 1H), 4.41 (q, J=7.5 Hz, 2H), 3.82 (m, 3H), 3.07 (dt, J=3, 13 Hz, 2H), 1.96 (m, 2H), 1.60 (m, 2H), 1.39 (t, J=7.1 Hz, 3H).

Example 633

N-(4-(4-(4-(4-Hydroxypiperidin-1-yl)benzamido)benzoyl)phenyl)-4-oxo-4,5,6,7-tetrahydro-1H-indole-3-carboxamide (Compound 733)

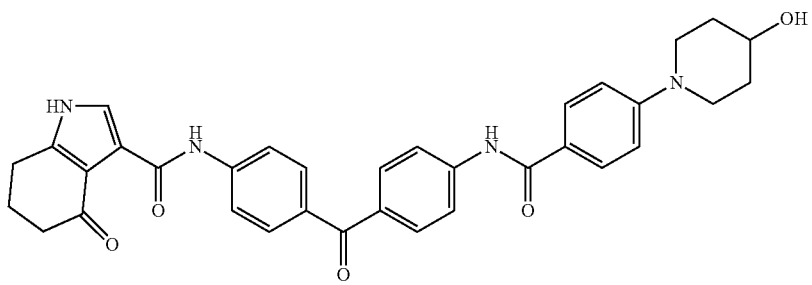 [SMILES: O=C(Nc1ccc(C(=O)c2ccc(NC(=O)c3c[nH]c4c3C(=O)CCC4)cc2)cc1)c1ccc(N2CCC(O)CC2)cc1]

Compound 733 was prepared according to the procedure described in Scheme IV from 4,4'-diaminobenzophenone, 4-oxo-4,5,6,7-tetrahydroindole-3-carboxylic, and 4-(4-hydroxypiperidin-1-yl)benzoic acids. $^1$H NMR (500 MHz, DMSO-$d_6$) δ 12.91 (s, 1H), 12.20 (s, 1H), 10.24 (s, 1H), 7.98 (d, J=14 Hz, 2H), 7.90 (q, J=2, 14 Hz, 4H), 7.79 (m, 4H), 7.62 (s, 1H), 7.03 (d, J=10 Hz, 2H), 4.72 (d, J=8 Hz, 1H), 3.73 (m, 3H), 3.06 (m, 2H), 2.89 (t, J=8, 10 Hz, 2H), 2.61 (m, 2H), 2.11 (m, 2H), 1.82 (m, 2H), 1.47 (m, 2H).

Example 634

N-(4-(4-(4-(4-Hydroxypiperidin-1-yl)benzamido)benzoyl)phenyl)-2,5-dimethyl-1H-pyrrole-3-carboxamide (Compound 734)

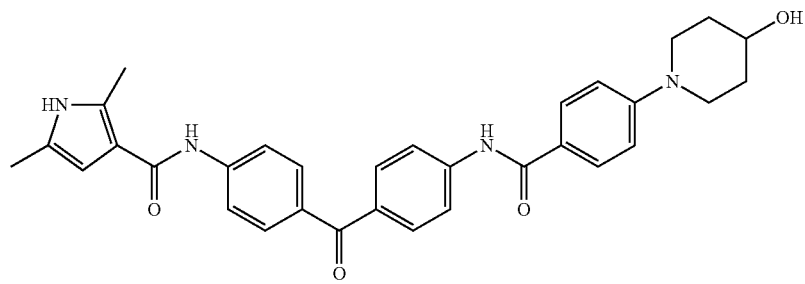 [SMILES: Cc1cc(C(=O)Nc2ccc(C(=O)c3ccc(NC(=O)c4ccc(N5CCC(O)CC5)cc4)cc3)cc2)c(C)[nH]1]

Compound 734 was prepared according to the procedure described in Scheme IV from 4,4'-diaminobenzophenone, 2,5-dimethyl-3-pyrrolecarboxylic, and 4-(4-hydroxypiperidin-1-yl)benzoic acids. $^1$H NMR (500 MHz, DMSO-$d_6$) δ 10.99 (s, 1H), 10.23 (s, 1H), 9.52 (s, 1H), 7.98 (dd, J=12, 12 Hz, 4H), 7.89 (d, J=8 Hz, 2H), 7.72 (dd, J=8, 12 Hz, 4H), 7.02 (d, J=10 Hz, 2H), 6.40 (s, 1H), 4.71 (d, J=3 Hz, 1H), 3.72 (m, 3H), 3.05 (m, 2H), 1.83 (m, 2H), 1.45 (m, 2H).

Example 635

N-(4-(4-(4-(4-Hydroxypiperidin-1-yl)benzamido)benzoyl)phenyl)-1,2,5-trimethyl-1H-pyrrole-3-carboxamide (Compound 735)

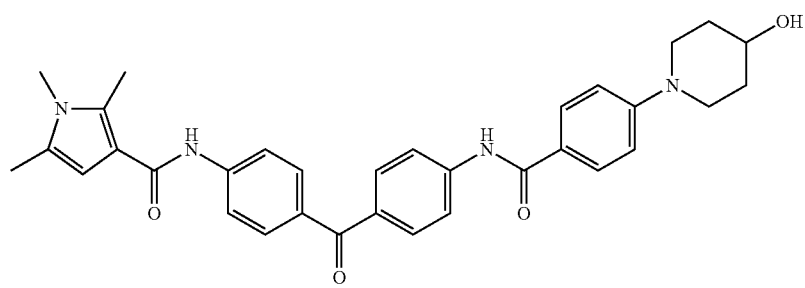 [SMILES: Cc1cc(C(=O)Nc2ccc(C(=O)c3ccc(NC(=O)c4ccc(N5CCC(O)CC5)cc4)cc3)cc2)c(C)n1C]

Compound 735 was prepared according to the procedure described in Scheme IV from 4,4'-diaminobenzophenone, 1,2,5-trimethyl-3-pyrrolecarboxylic, and 4-(4-hydroxypiperidin-1-yl)benzoic acids. $^1$H NMR (500 MHz, DMSO-$d_6$) δ 10.24 (s, 1H), 9.57 (s, 1H), 7.98 (dd, J=10, 16 Hz, 4H), 7.89 (d, J=8 Hz, 2H), 7.72 (dd, J=10, 12 Hz, 4H), 7.02 (d, J=8 Hz, 2H), 6.49 (s, 1H), 4.71 (d, J=4 Hz, 1H), 3.72 (m, 3H), 3.41 (s, 3H), 3.06 (m, 2H), 1.86 (m, 2H), 1.48 (m, 2H).

Example 636

N-(4-(4-(2-Chloro-4-(4-hydroxypiperidin-1-yl)benzamido)benzoyl)phenyl)-1-cyanomethyl-1H-pyrrole-2-carboxamide (Compound 736)

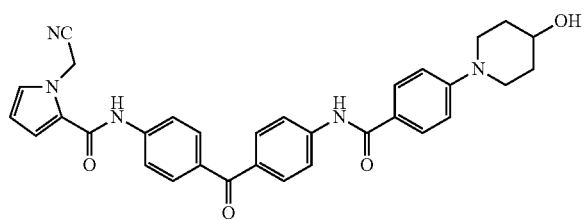 [SMILES: N#CCn1cccc1C(=O)Nc1ccc(C(=O)c2ccc(NC(=O)c3ccc(N4CCC(O)CC4)cc3)cc2)cc1]

Compound 736 was prepared according to the procedure described in Scheme IV from 4,4'-diaminobenzophenone, 1-cyanomethyl-2-pyrrolecarboxylic, and 4-(4-hydroxypiperidin-1-yl)benzoic acids. [M+H]$^+$ calcd for $C_{32}H_{29}N_5O_4$: 548.2. found: 548.07.

Example 637

N-(4-(4-(4-(4-(3-Hydroxypropyl)piperazin-1-yl)benzamido)benzoyl)phenyl)-1-methyl-1H-pyrrole-2-carboxamide (Compound 737)

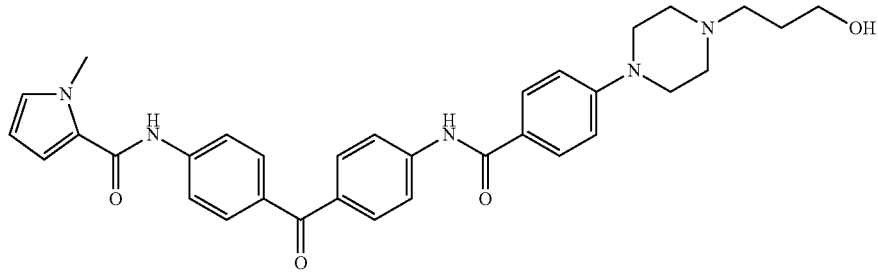 [SMILES: Cn1cccc1C(=O)Nc1ccc(C(=O)c2ccc(NC(=O)c3ccc(N4CCN(CCCO)CC4)cc3)cc2)cc1]

Compound 737 was prepared according to the procedure described in Scheme IV from 4,4'-diaminobenzophenone, 1-ethyl-2-pyrrolecarboxylic, and 4-(4-(3-hydroxypropyl)piperazin-1-yl)benzoic acids. [M+H]$^+$ calcd for $C_{33}H_{36}N_5O_4$: 566.28. found: 566.12.

Example 638

N-(4-(4-(2-Chloro-4-(4-hydroxypiperidin-1-yl)benzamido)benzoyl)phenyl)-1-vinyl-1H-pyrrole-2-carboxamide (Compound 738)

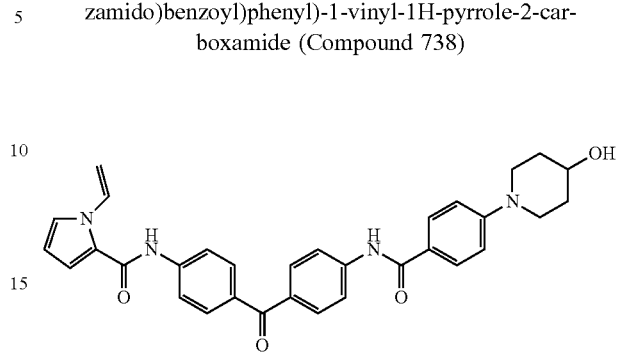

Compound 738 was prepared according to the procedure described in Scheme IV from 4,4'-diaminobenzophenone, 1-vinyl-2-pyrrolecarboxylic, and 4-(4-hydroxypiperidin-1-yl)benzoic acids. $^1$H NMR (500 MHz, DMSO-d$_6$) δ 10.38 (s, 1H), 10.35 (s, 1H), 7.99 (d, J=8 Hz, 2H), 7.90 (m, 4H), 7.77 (d, J=10 Hz, 4H), 7.63 (s, 1H), 7.20 (s, 1H), 7.02 (d, J=10 Hz, 2H), 6.34 (s, 1H), 5.42 (d, J=12 Hz, 1H), 4.88 (d, J=8 Hz, 1H), 4.71 (d, J=4 Hz, 1H), 3.81 (m, 3H), 3.05 (m, 2H), 1.83 (m, 2H), 1.47 (m, 2H).

Example 639

N-(4-((4-(4-(4-Hydroxypiperidin-1-yl)benzamido)phenyl)amino)phenyl)pyrimidine-5-carboxamide (Compound 739)

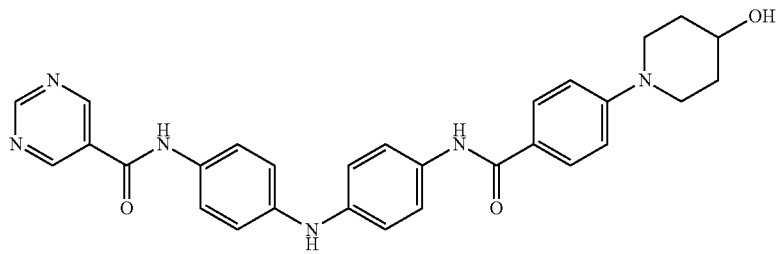 [SMILES: O=C(Nc1ccc(Nc2ccc(NC(=O)c3cncnc3)cc2)cc1)c1ccc(N2CCC(O)CC2)cc1]

Compound 739 was prepared according to the general procedure described in Scheme IV. Preparation of N-(4-nitrophenyl)benzene-1,4-diamine: Benzene-1,4-diamine (5.4 g, 50 mmol) and 1-fluoro-4-nitrobenzene (5.3 mL, 50 mmol) were dissolved in 75 mL dimethylsulfoxide and potassium carbonate (13.8 g, 100 mmol) was added. The reaction mixture was heated in an oil bath at 90° C. and stirred overnight under nitrogen atmosphere. The reaction mixture was cooled to room temperature and added to 250 mL water in a slow stream and stirred till a solid was precipitated out. The reaction mixture was filtered out and the resulting dark brown solid was washed with plenty of water. Flash column chromatography on silica gel eluted with 20% to 40% Ethyl acetate in hexanes provided the title compound (6.1 g, 53% yield).

Preparation of 4-(4-hydroxypiperidin-1-yl)-N-(4-((4-nitrophenyl)amino)phenyl)-benzamide: N-4(-4-nitrophenyl)benzene-1,4-diamine (1.15 g, 5.0 mmol) and 4-(4-hydroxypiperidine-1-yl)benzoic acid (1.2 g, 5.5 mmol) were dissolved in 20 mL pyridine and EDCI (1.2 g, 6.0 mmole) added and stirred at room temperature under nitrogen atmosphere overnight. Water (80 mL) was added and the mixture was stirred for an extra 15 minutes till a solid was precipitated out. The reaction mixture was filtered and the resulting red-color solid was washed with water, ethyl acetate, and hexanes, then dried to give the title compound (1.6 g, 80% yield.) This compound was used for next step without any further purification.

Preparation of Compound 739: 4-(4-Hydroxypiperidin-1-yl)-N-(4-((4-nitrophenyl)amino)phenyl)benzamide (1.8 g, 4.2 mmol) was hydrogenated using palladium hydroxide (1.6 g) in absolute ethanol (75 mL). The reaction mixture was stirred under hydrogen gas balloon overnight. It was filtered through celite and evaporated to dryness to give 4-(4-hydroxypiperidin-1-yl)-N-(4-((4-nitrophenyl)amino)phenyl)benzamide over 98% pure (1.6 g, 95% yield). Part of the product (22 mg, 0.05 mmol) and pyrimidine-4-carboxylic acid (8 mg, 0.06 mmole) were dissolved in 1 mL pyridine and was added EDCI (19 mg, 0.1 mmol). The reaction mixture was stirred at room temperature under nitrogen atmosphere overnight. Water (5 mL) was added and the mixture was stirred for an extra 15 minutes till a solid was precipitated out. The reaction mixture was filtered and the resulting red color solid was washed with water, ethyl acetate, hexanes, and then dried to give crude compound 739 (20 mg 78% yield). Further purification was carried on using prep HPLC for the final sample. $[M+H]^+$ calcd for $C_{29}H_{28}N_6O_3$: 509.2. found 508.98.

Example 640

N-(4-((4-(4-(4-Hydroxypiperidin-1-yl)benzamido)phenyl)amino)phenyl)nicotinamide (Compound 740)

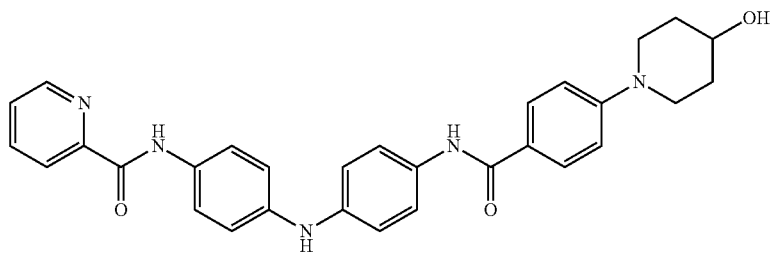 [SMILES: O=C(Nc1ccc(Nc2ccc(NC(=O)c3ccccn3)cc2)cc1)c1ccc(N2CCC(O)CC2)cc1]

Compound 740 was prepared according to the procedure described in Scheme IV from 4,4'-diaminodiphenylamine, nicotinic and 4-(4-hydroxypiperidin-1-yl)benzoic acids. $[M+H]^+$ calcd for $C_{30}H_{29}N_5O_3$: 508.2. found 507.97.

Example 641

N-(4-((4-(4-(4-Hydroxypiperidin-1-yl)benzamido)phenyl)amino)phenyl)-4,5,6,7-tetrahydro-1H-indole-2-carboxamide (Compound 741)

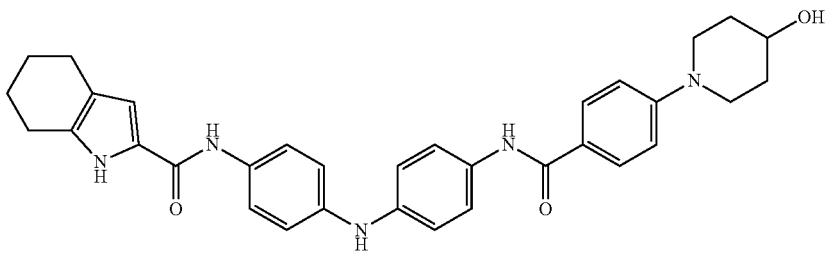 [SMILES: O=C(Nc1ccc(Nc2ccc(NC(=O)c3cc4c([nH]3)CCCC4)cc2)cc1)c1ccc(N2CCC(O)CC2)cc1]

Compound 741 was prepared according to the procedure described in Scheme IV from 4,4'-diaminodiphenylamine, 4,5,6,7-tetrahydro-1H-indole-2-carboxylic, and 4-(4-hydroxypiperidin-1-yl)benzoic acids. [M+H]+ calcd for $C_{33}H_{35}N_5O_3$: 550.27. found 550.09.

Example 642

N-(4-((4-(4-(4-Hydroxypiperidin-1-yl)benzamido)phenyl)amino)phenyl)-1H-pyrrolo[2,3-b]pyridine-5-carboxamide (Compound 742)

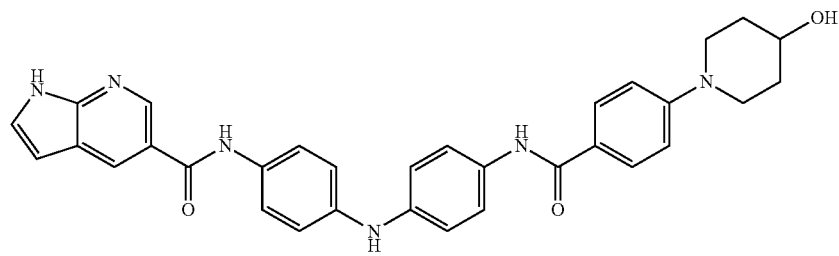 [SMILES: O=C(Nc1ccc(Nc2ccc(NC(=O)c3cnc4[nH]ccc4c3)cc2)cc1)c1ccc(N2CCC(O)CC2)cc1]

Compound 742 was prepared according to the procedure described in Scheme IV from 4,4'-diaminodiphenylamine, 1H-pyrrolo[2,3-b]pyridine-5-carboxylic, and 4-(4-hydroxypiperidin-1-yl)benzoic acids. [M+H]+ calcd for $C_{32}H_{30}N_6O_3$: 547.24. found 547.12.

Example 643

N-(4-((4-(4-(4-Hydroxypiperidin-1-yl)benzamido)phenyl)amino)phenyl)-1H-pyrrole-2-carboxamide (Compound 743)

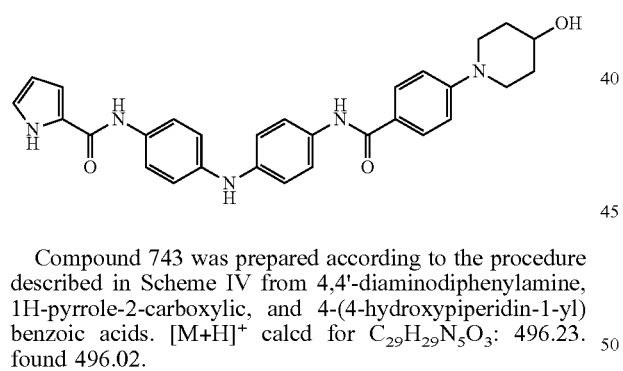

Compound 743 was prepared according to the procedure described in Scheme IV from 4,4'-diaminodiphenylamine, 1H-pyrrole-2-carboxylic, and 4-(4-hydroxypiperidin-1-yl)benzoic acids. [M+H]+ calcd for $C_{29}H_{29}N_5O_3$: 496.23. found 496.02.

Example 644

N-(4-((4-(4-(4-Hydroxypiperidin-1-yl)benzamido)phenyl)amino)phenyl)-1-methyl-1H-pyrrole-2-carboxamide (Compound 744)

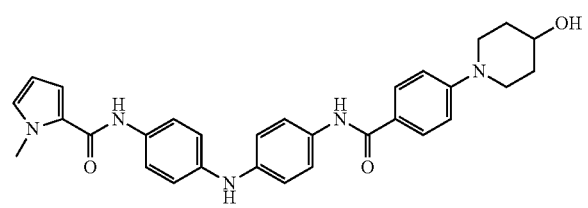 [SMILES: Cn1cccc1C(=O)Nc1ccc(Nc2ccc(NC(=O)c3ccc(N4CCC(O)CC4)cc3)cc2)cc1]

Compound 744 was prepared according to the procedure described in Scheme IV from 4,4'-diaminodiphenylamine, 1-methylpyrrole-2-carboxylic, and 4-(4-hydroxypiperidin-1-yl)benzoic acids. [M+H]+ calcd for $C_{30}H_{31}N_5O_3$: 510.24. found 519.99.

Example 645

N-(4-((4-(4-(4-Hydroxypiperidin-1-yl)benzamido)phenyl)-1-methyl-N-(4-(1-methyl-1H-pyrrole-2-carboxamido)phenyl)-1H-pyrrole-2-carboxamide (Compound 745)

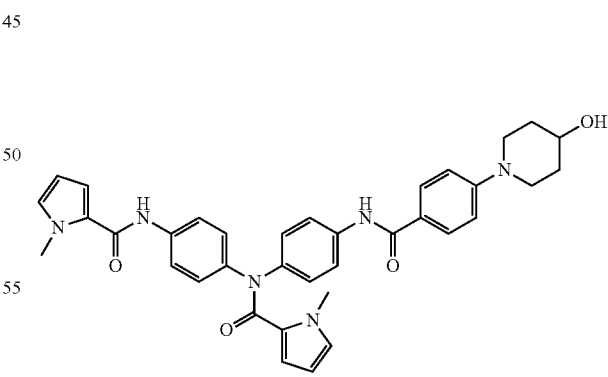

Compound 745 was prepared according to the procedure described in Scheme IV from 4,4'-diaminodiphenylamine, 1-methylpyrrole-2-carboxylic, and 4-(4-hydroxypiperidin-1-yl)benzoic acids. [M+H]+ calcd for $C_{36}H_{36}N_6O_4$: 617.28. found 617.27.

Example 646

N-(4-((4-(4-(4-(4-Hydroxypiperidin-1-yl)benzamido)phenyl)amino)phenyl)-1H-pyrrole-3-carboxamide (Compound 746)

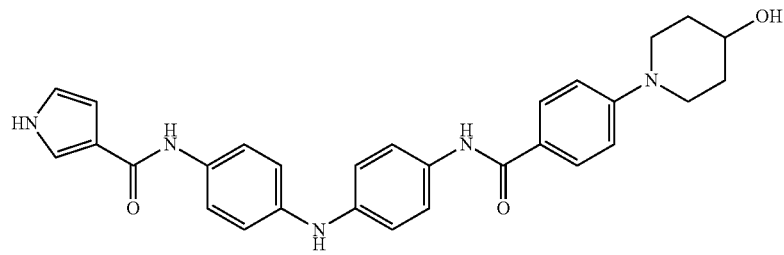 [SMILES: O=C(Nc1ccc(Nc2ccc(NC(=O)c3cc[nH]c3)cc2)cc1)c1ccc(N2CCC(O)CC2)cc1]

Compound 746 was prepared according to the procedure described in Scheme IV from 4,4'-diaminodiphenylamine, 1H-pyrrole-3-carboxylic, and 4-(4-hydroxypiperidin-1-yl)benzoic acids. [M+H]+ calcd for $C_{29}H_{29}N_5O_3$: 496.23. found 496.02.

Example 647

N,N'-(Azanediylbis(4,1-phenylene))bis(4-(4H-1,2,4-triazol-4-yl)benzamide) (Compound 747)

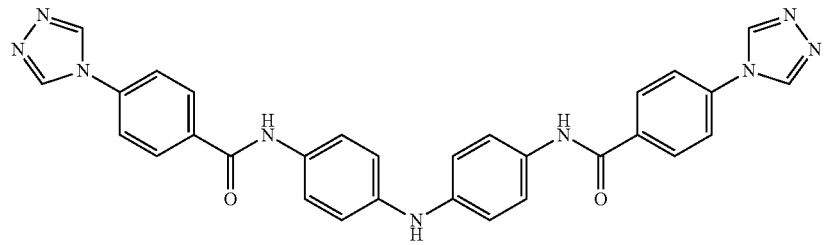 [SMILES: O=C(Nc1ccc(Nc2ccc(NC(=O)c3ccc(-n4cnnc4)cc3)cc2)cc1)c1ccc(-n2cnnc2)cc1]

Compound 747 was prepared according to the procedure described in Scheme IV from 4,4'-diaminodiphenylamine and 4-(4H-1,2,4-triazol-4-yl)benzoic acid. [M+H]$^+$ calcd for $C_{30}H_{23}NO_2$: 542.20. found 541.99.

Example 648

N,N'-(Azanediylbis(4,1-phenylene))bis(4-acetylbenzamide) (Compound 748)

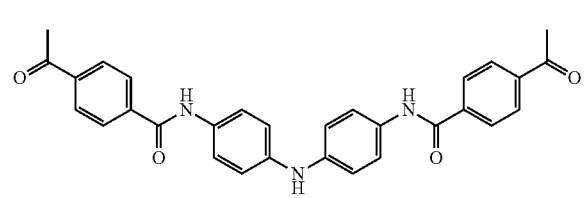 [SMILES: CC(=O)c1ccc(C(=O)Nc2ccc(Nc3ccc(NC(=O)c4ccc(C(C)=O)cc4)cc3)cc2)cc1]

Compound 748 was prepared according to the procedure described in Scheme IV from 4,4'-diaminodiphenylamine and 4-acetylbenzoic acid. [M+H]$^+$ calcd for $C_{30}H_{25}N_3O_4$: 492.18. found 492.00.

Example 649

N-(4-((4-Aminophenyl)amino)phenyl)-4-(4-hydroxypiperidin-1-yl)benzamide (Compound 749)

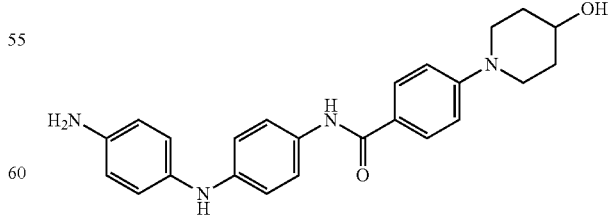

Compound 749 was prepared according to the procedure described in Scheme IV from 4,4'-diaminodiphenylamine and 4-(4-hydroxypiperidin-1-yl)benzoic acid. [M+H]$^+$ calcd for $C_{25}H_{26}N_4O_3$: 403.21. found 403.04.

Example 650

N-(4-((4-(4-(4-Hydroxypiperidin-1-yl)benzamido)
phenyl)amino)phenyl)-1H-indole-5-carboxamide
(Compound 750)

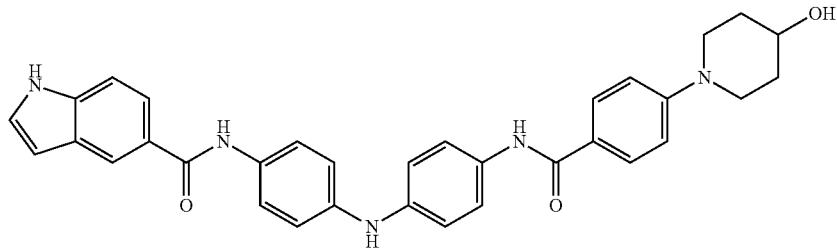

Compound 750 was prepared according to the procedure described in Scheme IV from 4,4'-diaminodiphenylamine, 1H-indole-5-carboxylic, and 4-(4-hydroxypiperidin-1-yl) benzoic acids. [M+H]$^+$ calcd for $C_{33}H_{31}N_5O_3$: 546.24. found 546.04.

Example 651

N-(4-((4-(4-(4-Hydroxypiperidin-1-yl)benzamido)
phenyl)amino)phenyl)-1H-indole-6-carboxamide
(Compound 751)

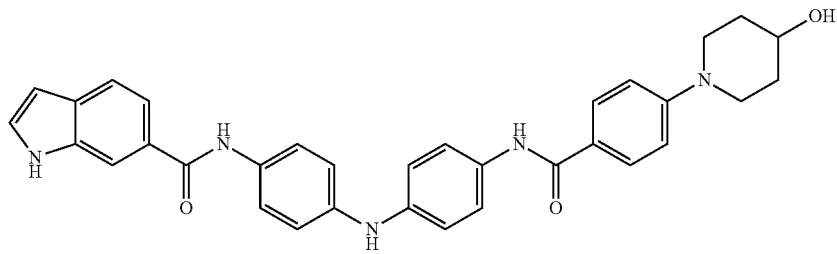 [SMILES: O=C(Nc1ccc(Nc2ccc(NC(=O)c3ccc4cc[nH]c4c3)cc2)cc1)c1ccc(N2CCC(O)CC2)cc1]

Compound 751 was prepared according to the procedure described in Scheme IV from 4,4'-diaminodiphenylamine, 1H-indole-6-carboxylic, and 4-(4-hydroxypiperidin-1-yl) benzoic acids. [M+H]$^+$ calcd for $C_{33}H_{31}N_5O_3$: 546.24. found 546.11.

Example 652

N-(4-((4-(4-(4-Hydroxypiperidin-1-yl)benzamido)
phenyl)amino)phenyl)-1H-indole-3-carboxamide
(Compound 752)

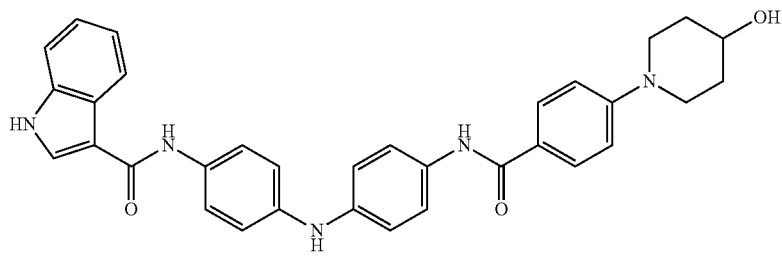 [SMILES: O=C(Nc1ccc(Nc2ccc(NC(=O)c3c[nH]c4ccccc34)cc2)cc1)c1ccc(N2CCC(O)CC2)cc1]

Compound 752 was prepared according to the procedure described in Scheme IV from 4,4'-diaminodiphenylamine, 1H-indole-3-carboxylic, and 4-(4-hydroxypiperidin-1-yl)benzoic acids. [M+H]+ calcd for $C_{33}H_{31}N_5O_3$: 546.24. found 545.97.

Example 653

N-(4-((4-(4-(4-Hydroxypiperidin-1-yl)benzamido)phenyl)amino)phenyl)cyclopropanecarboxamide (Compound 753)

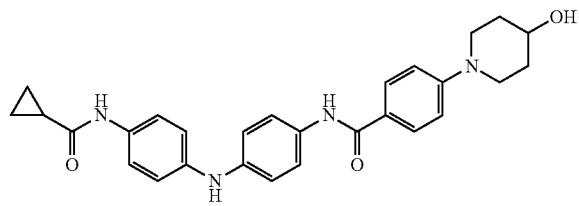 [SMILES: O=C(Nc1ccc(Nc2ccc(NC(=O)C3CC3)cc2)cc1)c1ccc(N2CCC(O)CC2)cc1]

Compound 753 was prepared according to the procedure described in Scheme IV from 4,4'-diaminodiphenylamine, cyclopropanecarboxylic, and 4-(4-hydroxypiperidin-1-yl)benzoic acids. [M+H]+ calcd for $C_{28}H_{30}N_4O_3$: 471.23. found 471.05.

Example 654

$N^1,N^{1'}$-(Azanediylbis(4,1-phenylene))diterephthalamide (Compound 754)

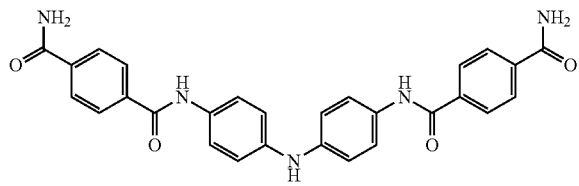 [SMILES: NC(=O)c1ccc(C(=O)Nc2ccc(Nc3ccc(NC(=O)c4ccc(C(N)=O)cc4)cc3)cc2)cc1]

Compound 754 was prepared according to the procedure described in Scheme IV from 4,4'-diaminodiphenylamine and 4-carbamoylbenzoic acid. [M+H]+ calcd for $C_{28}H_{23}N_5O_4$: 494.18. found 494.00.

Example 655

N-(4-((2-Fluoro-4-(4-(4-hydroxypiperidin-1-yl)benzamido)phenyl)amino)phenyl)-1H-pyrrole-2-carboxamide (Compound 755)

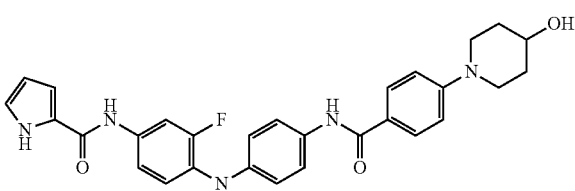

Compound 755 was prepared according to the procedure described in Scheme IV from $N^1$-(4-aminophenyl)-2-fluorobenzene-1,4-diamine, 1H-pyrrole-2-carboxylic, and 4-(4-hydroxypiperidin-1-yl)benzoic acids. [M+H]+ calcd for $C_{29}H_{28}FN_5O_3$: 514.22. found: 513.98.

Example 656

N-(3-Fluoro-4-((4-(4-(4-hydroxypiperidin-1-yl)benzamido)phenyl)amino)phenyl)-1H-pyrrole-2-carboxamide (Compound 756)

Compound 756 was prepared according to the procedure described in Scheme IV from $N^1$-(4-aminophenyl)-2-fluorobenzene-1,4-diamine, 1H-pyrrole-2-carboxylic, and 4-(4-hydroxypiperidin-1-yl)benzoic acids. [M+H]+ calcd for $C_{29}H_{28}FN_5O_3$: 514.22. found: 513.98.

Example 657

N-(4-((2-Fluoro-4-(4-(4-hydroxypiperidin-1-yl)benzamido)phenyl)amino)phenyl)-1,5-dimethyl-1H-pyrrole-2-carboxamide (Compound 757)

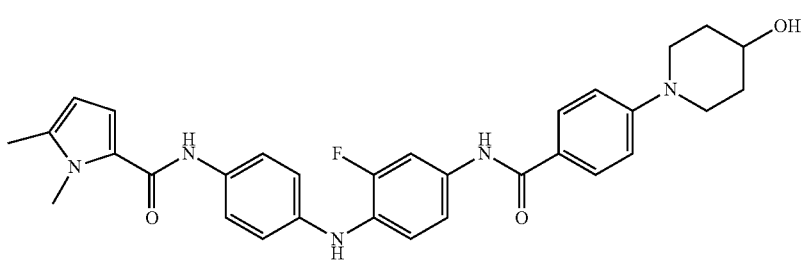 [SMILES: Cc1ccc(C(=O)Nc2ccc(Nc3ccc(NC(=O)c4ccc(N5CCC(O)CC5)cc4)cc3F)cc2)n1C]

Compound 757 was prepared according to the procedure described in Scheme IV from $N^1$-(4-aminophenyl)-2-fluorobenzene-1,4-diamine, 1,5-dimethyl-1H-pyrrole-2-carboxylic, and 4-(4-hydroxypiperidin-1-yl)benzoic acids. $[M+H]^+$ calcd for $C_{31}H_{32}FN_5O_3$: 542.2. found: 542.06.

Example 658

N-(4-((4-(4-(4-Hydroxypiperidin-1-yl)benzamido) phenyl)amino)phenyl)-1,5-dimethyl-1H-pyrrole-2-carboxamide (Compound 758)

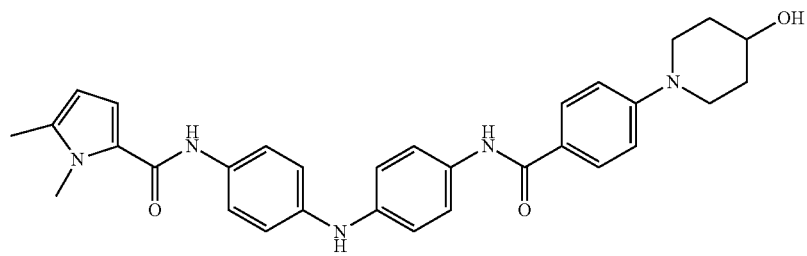 [SMILES: Cc1ccc(C(=O)Nc2ccc(Nc3ccc(NC(=O)c4ccc(N5CCC(O)CC5)cc4)cc3)cc2)n1C]

Compound 758 was prepared according to the procedure described in Scheme IV from 4,4'-diaminodiphenylamine, 1,5-dimethyl-1H-pyrrole-2-carboxylic, and 4-(4-hydroxypiperidin-1-yl)benzoic acids. $[M+H]^+$ calcd for $C_{31}H_{33}N_5O_3$: 524.26. found: 524.03.

Example 659

N-(4-((2-Fluoro-4-(4-(4-hydroxypiperidin-1-yl)benzamido)phenyl)amino)phenyl)-1-ethyl-1H-pyrrole-2-carboxamide (Compound 759)

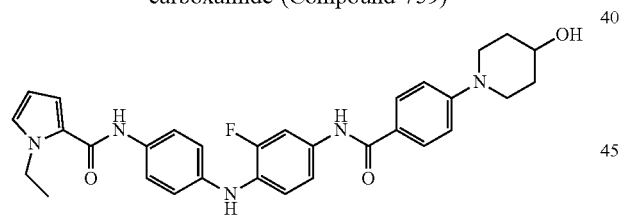

Compound 759 was prepared according to the procedure described in Scheme IV from $N^1$-(4-aminophenyl)-2-fluorobenzene-1,4-diamine, 1-ethyl-1H-pyrrole-2-carboxylic, and 4-(4-hydroxypiperidin-1-yl)benzoic acids. $[M+H]^+$ calcd for $C_{31}H_{32}FN_5O_3$: 524.2. found: 542.06.

Example 660

N-(3-Fluoro-4-((4-(4-(4-hydroxypiperidin-1-yl)benzamido)phenyl)amino)phenyl)-1,5-dimethyl-1H-pyrrole-2-carboxamide (Compound 760)

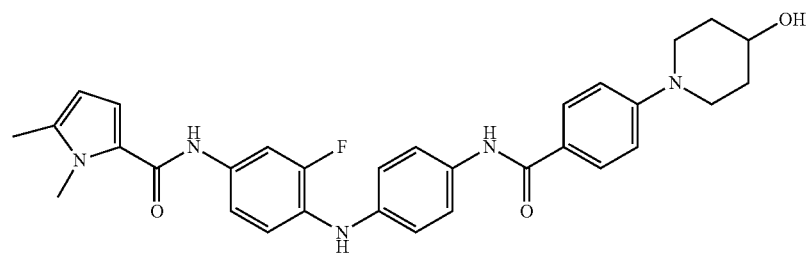 [SMILES: Cc1ccc(C(=O)Nc2ccc(Nc3ccc(NC(=O)c4ccc(N5CCC(O)CC5)cc4)cc3)c(F)c2)n1C]

Compound 760 was prepared according to the procedure described in Scheme IV from $N^1$-(4-aminophenyl)-2-fluorobenzene-1,4-diamine, 1,5-dimethyl-1H-pyrrole-2-carboxylic, and 4-(4-hydroxypiperidin-1-yl)benzoic acids. [M+H]+ calcd for $C_{31}H_{32}FN_5O_3$: 542.2. found: 542.06.

Example 661

N-(4-((4-(4-(4-Hydroxypiperidin-1-yl)benzamido)phenyl)amino)phenyl)-5-methyl-1H-pyrrole-2-carboxamide (Compound 761)

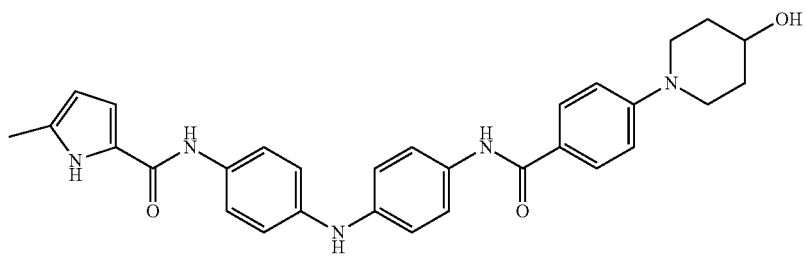 [SMILES: Cc1ccc(C(=O)Nc2ccc(Nc3ccc(NC(=O)c4ccc(N5CCC(O)CC5)cc4)cc3)cc2)[nH]1]

Compound 761 was prepared according to the procedure described in Scheme IV from 4,4'-diaminodiphenylamine, 5-methyl-1H-pyrrole-2-carboxylic, and 4-(4-hydroxypiperidin-1-yl)benzoic acids. $^1$H NMR (400 MHz, Acetone-$d_6$) δ 10.54 (s, 1H), 9.14 (s, 1H), 8.93 (s, 1H), 7.90 (d, J=9 Hz, 2H), 7.70 (d, J=8.9 Hz, 2H), 7.64 (d, J=9.0 Hz, 2H), 7.18 (s, 1H), 7.07 (dd, J=3.0, 9.0 Hz, 4H), 7.00 (d, J=9.0 Hz, 2H), 6.84 (t, J=3.4 Hz, 1H), 5.89 (t, J=3.4 Hz, 1H), 3.85 (m, 2H), 3.75 (m, 2H), 3.08 (ddd, J=3.0, 3.2, 11 Hz, 2H), 2.32 (s, 3H), 1.94 (m, 2H), 1.60 (m, 2H).

Example 662

N-(3-Fluoro-4-((4-(4-(4-hydroxypiperidin-1-yl)benzamido)phenyl)amino)phenyl)-5-methyl-1H-pyrrole-2-carboxamide (Compound 762)

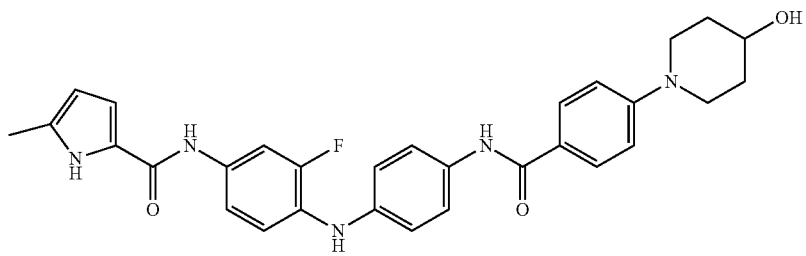 [SMILES: Cc1ccc(C(=O)Nc2ccc(Nc3ccc(NC(=O)c4ccc(N5CCC(O)CC5)cc4)cc3)c(F)c2)[nH]1]

Compound 762 was prepared according to the procedure described in Scheme IV from $N^1$-(4-aminophenyl)-2-fluorobenzene-1,4-diamine, 5-methyl-1H-pyrrole-2-carboxylic, and 4-(4-hydroxypiperidin-1-yl)benzoic acids. [M+H]$^+$ calcd for $C_{30}H_{30}FN_5O_3$: 528.2. found: 528.02.

Example 663

5-Formyl-N-(4-((4-(4-(4-hydroxypiperidin-1-yl)benzamido)phenyl)amino)phenyl)-1H-pyrrole-2-carboxamide (Compound 763)

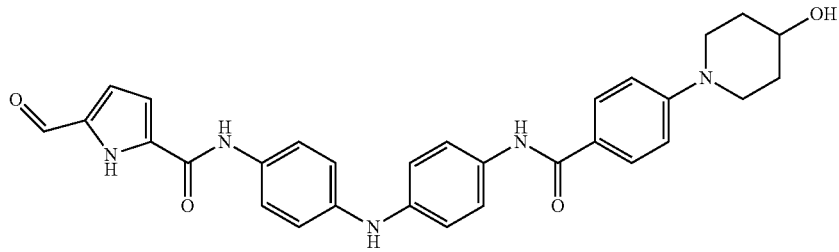 [SMILES: O=Cc1ccc(C(=O)Nc2ccc(Nc3ccc(NC(=O)c4ccc(N5CCC(O)CC5)cc4)cc3)cc2)[nH]1]

Compound 763 was prepared according to the procedure described in Scheme IV from 4,4'-diaminodiphenylamine, 5-formyl-1H-pyrrole-2-carboxylic, and 4-(4-hydroxypiperidin-1-yl)benzoic acids. [M+H]$^+$ calcd for $C_{30}H_{29}N_5O_4$: 524.1. found: 524.03.

Example 664

N-(3-Fluoro-4-((4-(4-(4-hydroxypiperidin-1-yl)benzamido)phenyl)amino)phenyl)-1H-pyrrole-3-carboxamide (Compound 764)

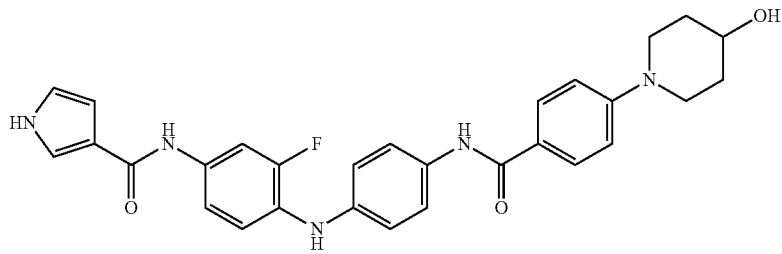

Compound 764 was prepared according to the procedure described in Scheme IV from N$^1$-(4-aminophenyl)-2-fluorobenzene-1,4-diamine, 1H-pyrrole-3-carboxylic, and 4-(4-hydroxypiperidin-1-yl)benzoic acids. [M+H]$^+$ calcd for $C_{29}H_{28}FN_5O_3$: 514.22. found 513.98.

Example 665

N-(3-Fluoro-4-((4-(4-(4-hydroxypiperidin-1-yl)benzamido)phenyl)amino)phenyl)-1-ethyl-1H-pyrrole-3-carboxamide (Compound 765)

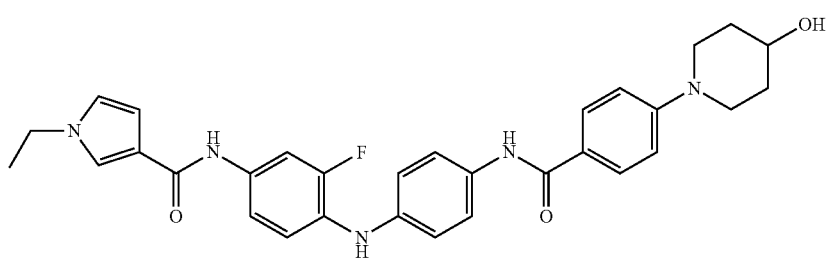 [SMILES: CCn1ccc(C(=O)Nc2ccc(Nc3ccc(NC(=O)c4ccc(N5CCC(O)CC5)cc4)cc3)c(F)c2)c1]

Compound 765 was prepared according to the procedure described in Scheme IV from $N^1$-(4-aminophenyl)-2-fluorobenzene-1,4-diamine, 1-ethyl-1H-pyrrole-3-carboxylic, and 4-(4-hydroxypiperidin-1-yl)benzoic acids. $[M+H]^+$ calcd for $C_{31}H_{32}FN_5O_3$: 542.2. found: 542.06.

Example 666

N-(3-Fluoro-4-((4-(4-(4-hydroxypiperidin-1-yl)benzamido)phenyl)amino)phenyl)-1-methyl-1H-pyrrole-3-carboxamide (Compound 766)

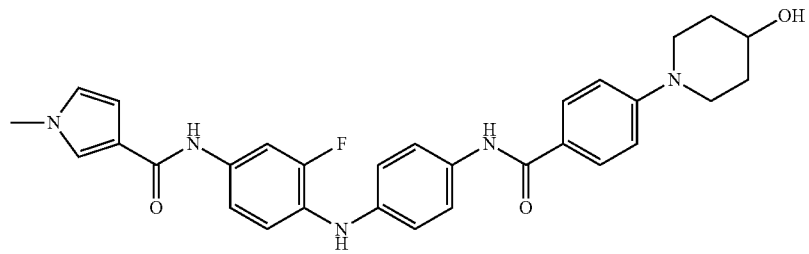 [SMILES: Cn1ccc(C(=O)Nc2ccc(Nc3ccc(NC(=O)c4ccc(N5CCC(O)CC5)cc4)cc3)c(F)c2)c1]

Compound 766 was prepared according to the procedure described in Scheme IV from $N^1$-(4-aminophenyl)-2-fluorobenzene-1,4-diamine, 1-methyl-1H-pyrrole-3-carboxylic, and 4-(4-hydroxypiperidin-1-yl)benzoic acids. $[M+H]^+$ calcd for $C_{30}H_{30}FN_5O_3$: 528.23. found 528.02.

Example 667

N-(4-((4-(4-(4-Hydroxypiperidin-1-yl)benzamido)phenyl)amino)phenyl)-1-ethyl-1H-pyrrole-3-carboxamide (Compound 767)

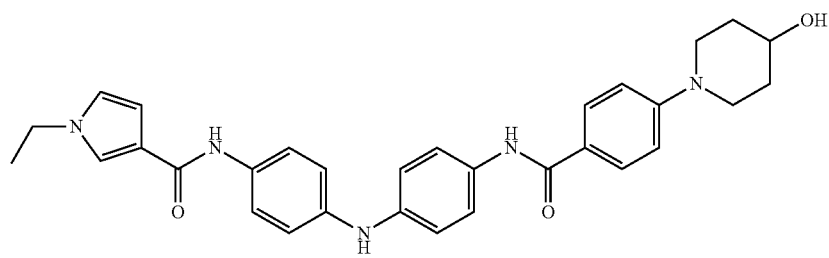 [SMILES: CCn1ccc(C(=O)Nc2ccc(Nc3ccc(NC(=O)c4ccc(N5CCC(O)CC5)cc4)cc3)cc2)c1]

Compound 767 was prepared according to the procedure described in Scheme IV from 4,4'-diaminodiphenylamine, 1-ethyl-1H-pyrrole-3-carboxylic, and 4-(4-hydroxypiperidin-1-yl)benzoic acids. $[M+H]^+$ calcd for $C_{31}H_{33}N_5O_3$: 524.2. found: 524.03.

Example 668

N-(4-((4-(4-(4-Hydroxypiperidin-1-yl)benzamido)phenyl)amino)phenyl)-1-methyl-1H-pyrrole-3-carboxamide (Compound 768)

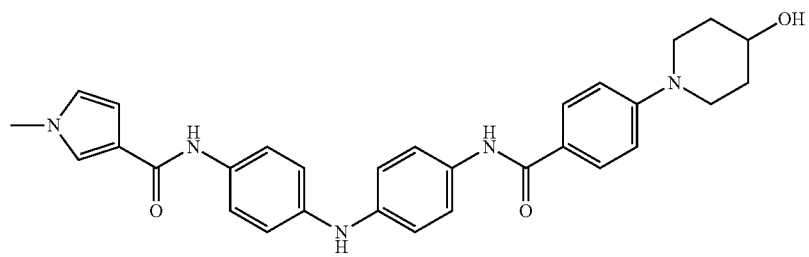 [SMILES: Cn1ccc(C(=O)Nc2ccc(Nc3ccc(NC(=O)c4ccc(N5CCC(O)CC5)cc4)cc3)cc2)c1]

Compound 768 was prepared according to the procedure described in Scheme IV from 4,4'-diaminodiphenylamine, 1-methyl-1H-pyrrole-3-carboxylic, and 4-(4-hydroxypiperidin-1-yl)benzoic acids. [M+H]$^+$ calcd for $C_{30}H_{31}N_5O_3$: 510.24. found 509.99.

Example 669

N-Cyclopropyl-4-((4-(4-(4-hydroxypiperidin-1-yl)benzamido)phenyl)amino)benzamide (Compound 769)

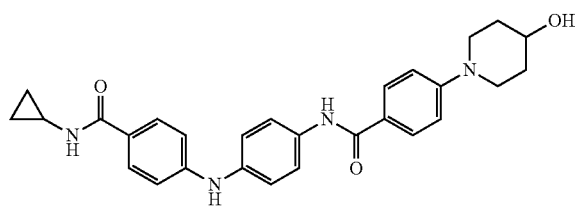 [SMILES: O=C(Nc1ccc(Nc2ccc(C(=O)NC3CC3)cc2)cc1)c1ccc(N2CCC(O)CC2)cc1]

Compound 769 was prepared according to the procedure described in Scheme IV from cyclopropylamine, 4-(4-aminophenylamino)benzoic, and 4-(4-hydroxypiperidin-1-yl)benzoic acids. [M+H]$^+$ calcd for $C_{28}H_{30}N_4O_3$: 471.23. found 471.05.

Example 670

N-(4-((4-(4-(4-Hydroxypiperidin-1-yl)benzamido)phenyl)amino)phenyl)-6-methylpicolinamide (Compound 770)

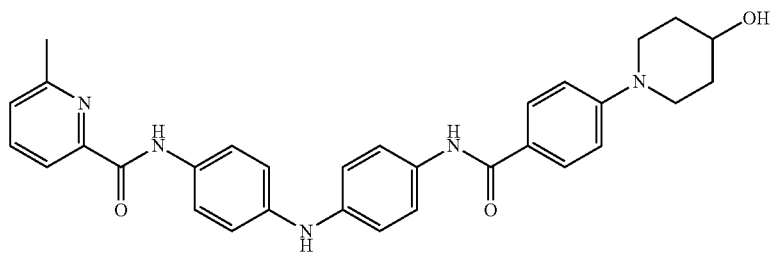 [SMILES: Cc1cccc(C(=O)Nc2ccc(Nc3ccc(NC(=O)c4ccc(N5CCC(O)CC5)cc4)cc3)cc2)n1]

Compound 770 was prepared according to the procedure described in Scheme IV from 4,4'-diaminodiphenylamine, 6-methylpicolinic, and 4-(4-hydroxypiperidin-1-yl)benzoic acids. [M+H]$^+$ calcd for $C_{31}H_{31}N_5O_3$: 522.24. found 522.08.

Example 671

N-(4-((4-(((1H-Indol-6-yl)carbamoyl)phenyl)amino)phenyl)-4-(4-hydroxypiperidin-1-yl)benzamide (Compound 771)

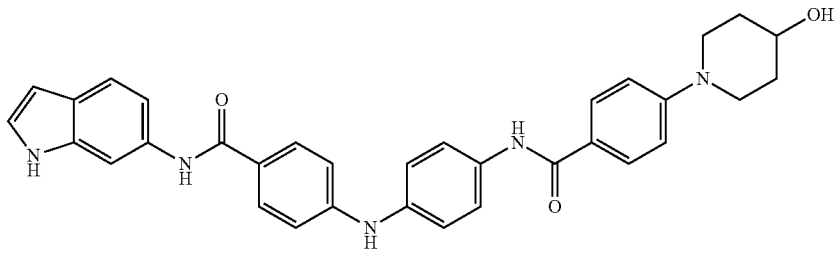 [SMILES: O=C(Nc1ccc(Nc2ccc(C(=O)Nc3ccc4cc[nH]c4c3)cc2)cc1)c1ccc(N2CCC(O)CC2)cc1]

Compound 771 was prepared according to the procedure described in Scheme IV from 6-aminoindole, 4-(4-aminophenylamino)benzoic, and 4-(4-hydroxypiperidin-1-yl)benzoic acids. [M+H]$^+$ calcd for $C_{33}H_{31}N_5O_3$: 546.24. found 546.04.

Example 672

N-(4-((4-(4-(4-Hydroxypiperidin-1-yl)benzamido)phenyl)amino)phenyl)-1-(2-hydroxyethyl)-1H-indole-6-carboxamide (Compound 772)

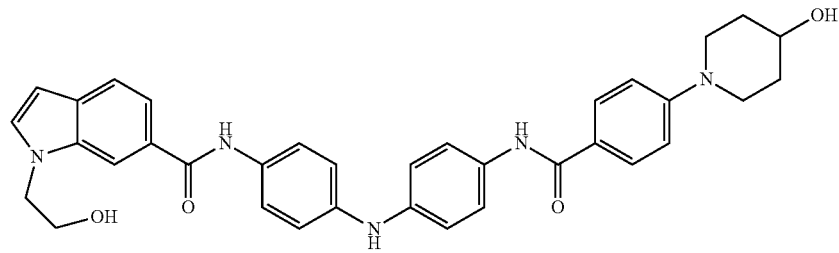 [SMILES: O=C(Nc1ccc(Nc2ccc(NC(=O)c3ccc4ccn(CCO)c4c3)cc2)cc1)c1ccc(N2CCC(O)CC2)cc1]

Compound 772 was prepared according to the procedure described in Scheme IV from 4,4'-diaminodiphenylamine, 1-(2-hydroxyethyl)-1H-indole-6-carboxylic, and 4-(4-hydroxypiperidin-1-yl)benzoic acids. [M+H]$^+$ calcd for $C_{35}H_{35}N_5O_4$: 590.27. found 590.20.

Example 673

N-(4-((4-(4-(4-Hydroxypiperidin-1-yl)benzamido)phenyl)amino)phenyl)-1-methyl-1H-indole-2-carboxamide (Compound 773)

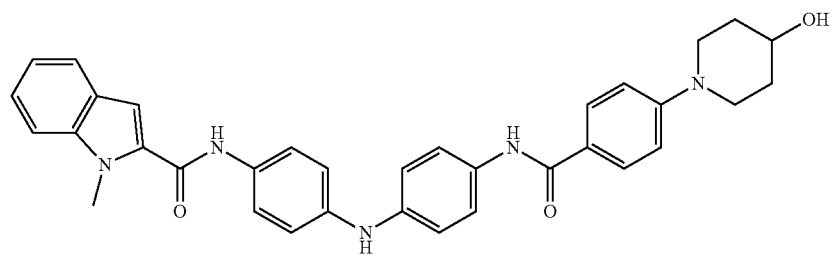 [SMILES: Cn1c(C(=O)Nc2ccc(Nc3ccc(NC(=O)c4ccc(N5CCC(O)CC5)cc4)cc3)cc2)cc2ccccc21]

Compound 773 was prepared according to the procedure described in Scheme IV from 4,4'-diaminodiphenylamine, 1-methyl-1H-indole-2-carboxylic, and 4-(4-hydroxypiperidin-1-yl)benzoic acids. [M+H]$^+$ calcd for $C_{34}H_{33}N_5O_3$: 560.26. found 560.02.

Example 674

N-(4-((4-(4-(4-Hydroxypiperidin-1-yl)benzamido)phenyl)amino)phenyl)-1-methyl-1H-indole-3-carboxamide (Compound 774)

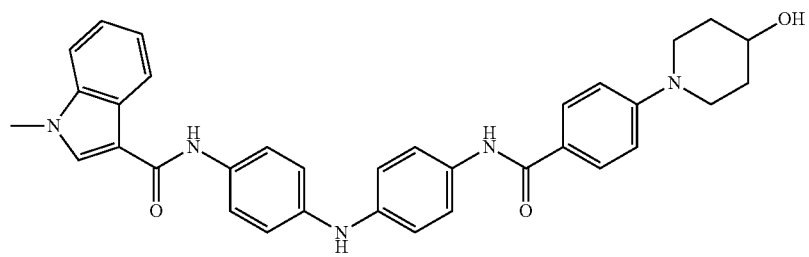 [SMILES: Cn1cc(C(=O)Nc2ccc(Nc3ccc(NC(=O)c4ccc(N5CCC(O)CC5)cc4)cc3)cc2)c2ccccc21]

Compound 774 was prepared according to the procedure described in Scheme IV from 4,4'-diaminodiphenylamine, 1-methyl-1H-indole-3-carboxylic, and 4-(4-hydroxypiperidin-1-yl)benzoic acids. [M+H]+ calcd for $C_{34}H_{33}N_5O_3$: 560.26. found 560.02.

Example 675

N-(4-((4-(4-(4-Hydroxypiperidin-1-yl)benzamido)phenyl)amino)phenyl)-1-(2-hydroxyethyl)-1H-indole-5-carboxamide (Compound 775)

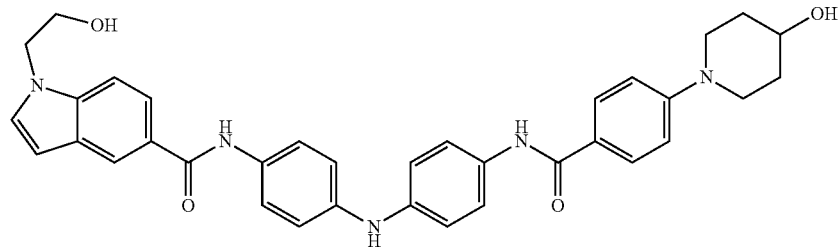 [SMILES: O=C(Nc1ccc(Nc2ccc(NC(=O)c3ccc4c(ccn4CCO)c3)cc2)cc1)c1ccc(N2CCC(O)CC2)cc1]

Compound 775 was prepared according to the procedure described in Scheme IV from 4,4'-diaminodiphenylamine, 1-(2-hydroxyethyl)-1H-indole-5-carboxylic, and 4-(4-hydroxypiperidin-1-yl)benzoic acids. [M+H]+ calcd for $C_{35}H_{35}N_5O_4$: 590.27. found 590.06.

Example 676

N-(4-((4-(1H-Pyrrole-2-carboxamido)phenyl)amino)phenyl)-1-(2-hydroxyethyl)-1H-indole-6-carboxamide (Compound 776)

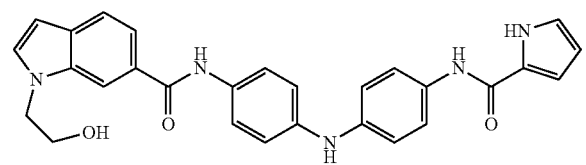 [SMILES: O=C(Nc1ccc(Nc2ccc(NC(=O)c3ccc[nH]3)cc2)cc1)c1ccc2ccn(CCO)c2c1]

Compound 776 was prepared according to the procedure described in Scheme IV from 4,4'-diaminodiphenylamine, 1-(2-hydroxyethyl)-1H-indole-6-carboxylic, and 2-pyrrolecarboxylic acids. [M+H]+ calcd for $C_{28}H_{25}N_5O_3$: 480.20. found 480.03.

Example 677

N-(4-((4-(1H-Pyrrole-2-carboxamido)phenyl)amino)phenyl)-1-(2-hydroxyethyl)-1-methyl-1H-indole-6-carboxamide (Compound 777)

Compound 777 was prepared according to the procedure described in Scheme IV from 4,4'-diaminodiphenylamine, 1-(2-hydroxyethyl)-1H-indole-6-carboxylic, and 1-methyl-2-pyrrolecarboxylic acids. [M+H]+ calcd for $C_{29}H_{27}N_5O_3$: 494.21. found 494.06.

Example 678

(±)-N-(4-((4-(4-(3-(Hydroxymethyl)piperidin-1-yl)benzamido)phenyl)amino)phenyl)-1H-indole-6-carboxamide (Compound 778)

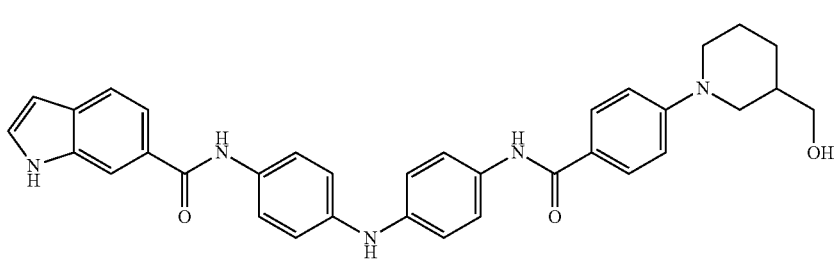 [SMILES: O=C(Nc1ccc(Nc2ccc(NC(=O)c3ccc4cc[nH]c4c3)cc2)cc1)c1ccc(N2CCCC(CO)C2)cc1]

Compound 778 was prepared according to the procedure described in Scheme IV from 4,4'-diaminodiphenylamine, 1H-indole-6-carboxylic, and 4-(3-hydroxymethylpiperidin-1-yl)benzoic acids. [M+H]+ calcd for $C_{34}H_{33}N_5O_3$: 560.26. found: 560.08.

Example 679

(±)-N-(4-((4-(4-(3-(Hydroxymethyl)piperidin-1-yl)benzamido)phenyl)amino)phenyl)-1H-pyrrole-2-carboxamide (Compound 779)

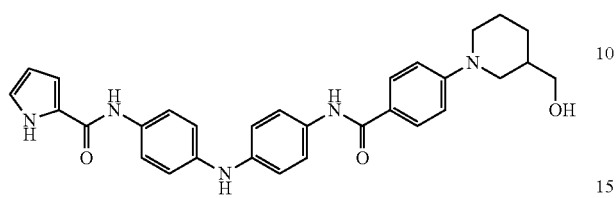

Compound 779 was prepared according to the procedure described in Scheme IV from 4,4'-diaminodiphenylamine, 1H-pyrrole-2-carboxylic, and 4-(3-hydroxymethylpiperidin-1-yl)benzoic acids. [M+H]$^+$ calcd for $C_{30}H_{31}N_5O_3$: 510.24. found: 509.99.

Example 680

N-(4-((4-(4-(4-Hydroxypiperidin-1-yl)benzamido)phenyl)amino)phenyl)-1-(2-morpholinoethyl)-1H-indole-5-carboxamide (Compound 780)

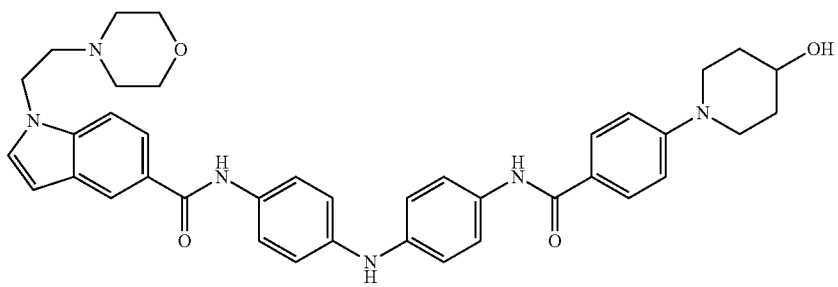 [SMILES: O=C(Nc1ccc(Nc2ccc(NC(=O)c3ccc4c(ccn4CCN4CCOCC4)c3)cc2)cc1)c1ccc(N2CCC(O)CC2)cc1]

Compound 780 was prepared according to the procedure described in Scheme IV from 4,4'-diaminodiphenylamine, 1-(2-morpholinoethyl)-1H-indole-5-carboxylic, and 4-(4-hydroxypiperidin-1-yl)benzoic acids. [M+H]$^+$ calcd for $C_{39}H_{42}N_6O_4$: 659.33. found 659.20.

Example 681

N-(4-((4-(4-(4-Hydroxypiperidin-1-yl)benzamido)phenyl)amino)phenyl)morpholine-4-carboxamide (Compound 781)

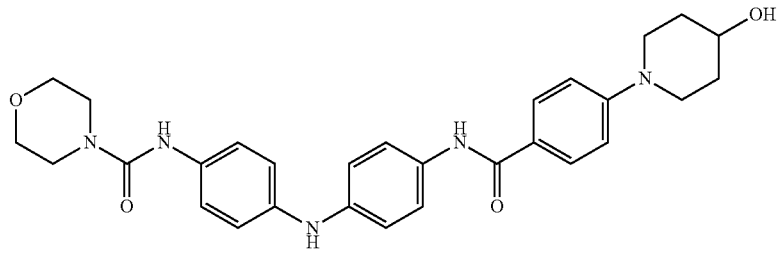 [SMILES: O=C(Nc1ccc(Nc2ccc(NC(=O)N3CCOCC3)cc2)cc1)c1ccc(N2CCC(O)CC2)cc1]

Compound 781 was prepared according to the procedure described in Scheme IV from 4,4'-diaminodiphenylamine, 4-morpholinecarbonyl chloride, and 4-(4-hydroxypiperidin-1-yl)benzoic acid. [M+H]$^+$ calcd for $C_{29}H_{33}N_5O_4$: 516.25. found 516.07.

Example 682

N-(4-((4-(4-(4-Hydroxypiperidin-1-yl)benzamido)phenyl)amino)phenyl)-1H-pyrazole-3-carboxamide (Compound 782)

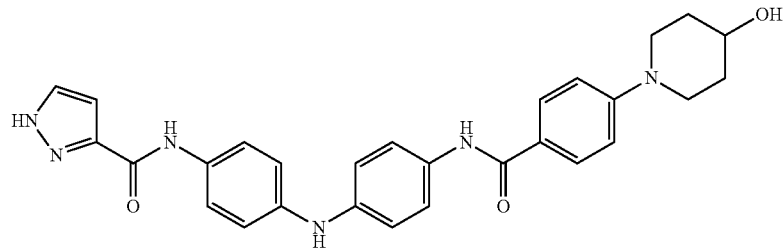 [SMILES: O=C(Nc1ccc(Nc2ccc(NC(=O)c3cc[nH]n3)cc2)cc1)c1ccc(N2CCC(O)CC2)cc1]

Compound 782 was prepared according to the procedure described in Scheme IV from 4,4'-diaminodiphenylamine, 1H-pyrazole-3-carboxylic, and 4-(4-hydroxypiperidin-1-yl) benzoic acids. [M+H]$^+$ calcd for $C_{28}H_{28}N_6O_3$: 497.22. found 496.97.

Example 683

N-(4-((4-(4-(4-Hydroxypiperidin-1-yl)benzamido)phenyl)amino)phenyl)-1H-pyrazole-4-carboxamide (Compound 783)

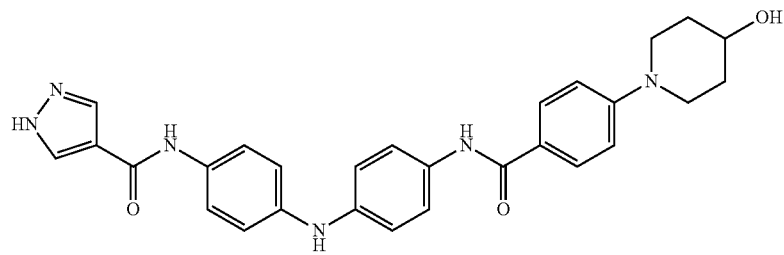 [SMILES: O=C(Nc1ccc(Nc2ccc(NC(=O)c3cn[nH]c3)cc2)cc1)c1ccc(N2CCC(O)CC2)cc1]

Compound 783 was prepared according to the procedure described in Scheme IV from 4,4'-diaminodiphenylamine, 1H-pyrazole-4-carboxylic, and 4-(4-hydroxypiperidin-1-yl) benzoic acids. [M+H]$^+$ calcd for $C_{28}H_{28}N_6O_3$: 497.22. found 496.97.

Example 684

N-(4-((4-(4-(4-Hydroxypiperidin-1-yl)benzamido)phenyl)amino)phenyl)-1-methyl-1H-pyrazole-3-carboxamide (Compound 784)

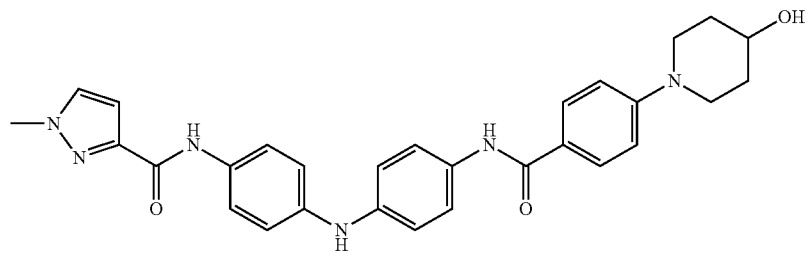 [SMILES: Cn1ccc(C(=O)Nc2ccc(Nc3ccc(NC(=O)c4ccc(N5CCC(O)CC5)cc4)cc3)cc2)n1]

Compound 784 was prepared according to the procedure described in Scheme IV from 4,4'-diaminodiphenylamine, 1-methyl-1H-pyrazole-3-carboxylic, and 4-(4-hydroxypiperidin-1-yl)benzoic acids. [M+H]$^+$ calcd for $C_{29}H_{30}N_6O_3$: 511.24. found 511.01.

Example 685

N-(4-((4-(4-(4-Hydroxypiperidin-1-yl)benzamido)phenyl)amino)phenyl)-1-methyl-1H-pyrazole-4-carboxamide (Compound 785)

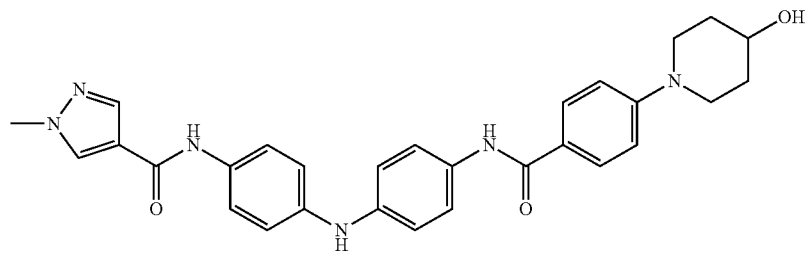

Compound 785 was prepared according to the procedure described in Scheme IV from 4,4'-diaminodiphenylamine, 1-methyl-1H-pyrazole-4-carboxylic, and 4-(4-hydroxypiperidin-1-yl)benzoic acids. [M+H]$^+$ calcd for $C_{29}H_{30}N_6O_3$: 511.24. found 511.01.

Example 686

N-(4-((4-(4-(4-Hydroxypiperidin-1-yl)benzamido)phenyl)amino)phenyl)-1-methyl-1H-pyrazole-5-carboxamide (Compound 786)

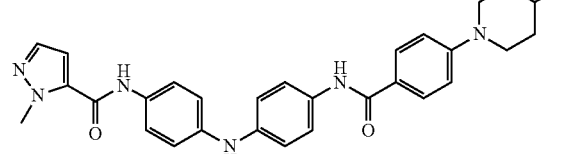

Compound 786 was prepared according to the procedure described in Scheme IV from 4,4'-diaminodiphenylamine, 1-methyl-1H-pyrazole-5-carboxylic, and 4-(4-hydroxypiperidin-1-yl)benzoic acids. [M+H]$^+$ calcd for $C_{29}H_{30}N_6O_3$: 511.24. found 511.01.

Example 687

N-(4-((4-(4-(4-Hydroxypiperidin-1-yl)benzamido)phenyl)amino)phenyl)butamide (Compound 787)

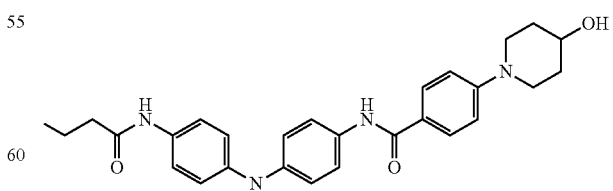

Compound 787 was prepared according to the procedure described in Scheme IV from 4,4'-diaminodiphenylamine, butanoic, and 4-(4-hydroxypiperidin-1-yl)benzoic acids. [M+H]$^+$ calcd for $C_{28}H_{32}N_4O_3$: 473.2. found: 473.01.

Example 688

N-(4-((4-(4-(4-Hydroxypiperidin-1-yl)benzamido)
phenyl)amino)phenyl)-4-methyl-1H-pyrrole-3-carboxamide (Compound 788)

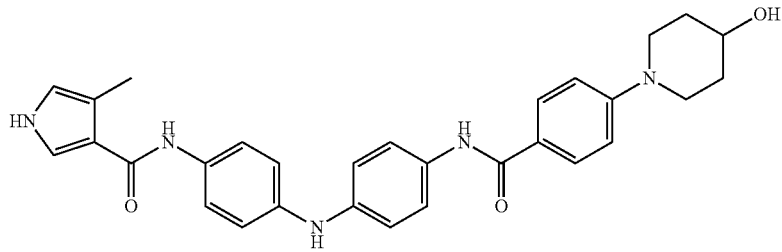 [SMILES: Cc1c[nH]cc1C(=O)Nc1ccc(Nc2ccc(NC(=O)c3ccc(N4CCC(O)CC4)cc3)cc2)cc1]

Compound 788 was prepared according to the procedure described in Scheme IV from 4,4'-diaminodiphenylamine, 4-methyl-1H-pyrrole-3-carboxylic, and 4-(4-hydroxypiperidin-1-yl)benzoic acids. $[M+H]^+$ calcd for $C_{30}H_{31}N_5O_3$: 510.2. found: 509.99.

Example 689

N-(4-((4-(4-(4-Hydroxypiperidin-1-yl)benzamido)
phenyl)amino)phenyl)-1,2,5-trimethyl-1H-pyrrole-3-carboxamide (Compound 789)

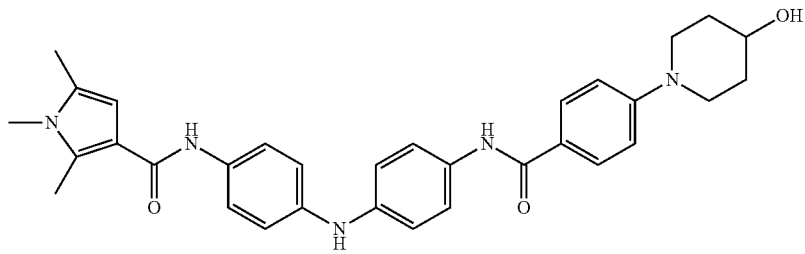 [SMILES: Cc1cc(C(=O)Nc2ccc(Nc3ccc(NC(=O)c4ccc(N5CCC(O)CC5)cc4)cc3)cc2)c(C)n1C]

Compound 789 was prepared according to the procedure described in Scheme IV from 4,4'-diaminodiphenylamine, 1,2,5-trimethyl-1H-pyrrole-3-carboxylic, and 4-(4-hydroxypiperidin-1-yl)benzoic acids. $[M+H]^+$ calcd for $C_{32}H_{35}N_5O_3$: 538.27. found 538.08.

Example 690

N-(4-((4-(4-(4-Hydroxypiperidin-1-yl)benzamido)
phenyl)amino)phenyl)-2,5-dimethyl-1H-pyrrole-3-carboxamide (Compound 790)

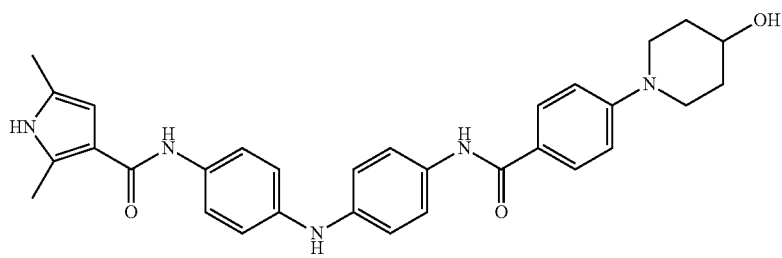 [SMILES: Cc1cc(C(=O)Nc2ccc(Nc3ccc(NC(=O)c4ccc(N5CCC(O)CC5)cc4)cc3)cc2)c(C)[nH]1]

Compound 790 was prepared according to the procedure described in Scheme IV from 4,4'-diaminodiphenylamine, 2,5-dimethyl-1H-pyrrole-3-carboxylic, and 4-(4-hydroxypiperidin-1-yl)benzoic acids. [M+H]$^+$ calcd for $C_{31}H_{33}N_5O_3$: 524.26. found 525.10.

Example 691

N-(4-((4-(3,3-Dimethylureido)phenyl)amino)phenyl)-4-(4-hydroxypiperidin-1-yl)benzamide (Compound 791)

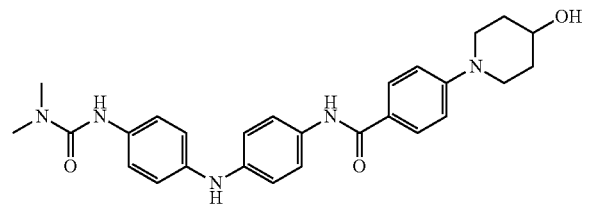 [SMILES: CN(C)C(=O)Nc1ccc(Nc2ccc(NC(=O)c3ccc(N4CCC(O)CC4)cc3)cc2)cc1]

Compound 791 was prepared according to the procedure described in Scheme IV from 4,4'-diaminodiphenylamine, N,N-dimethylchloroformate, and 4-(4-hydroxypiperidin-1-yl)benzoic acid. [M+H]$^+$ calcd for $C_{27}H_{31}N_5O_3$: 474.24. found 473.95.

Example 692

4-Hydroxy-N-(4-((4-(4-(4-hydroxypiperidin-1-yl)benzamido)phenyl)amino)phenyl)piperidine-1-carboxamide (Compound 792)

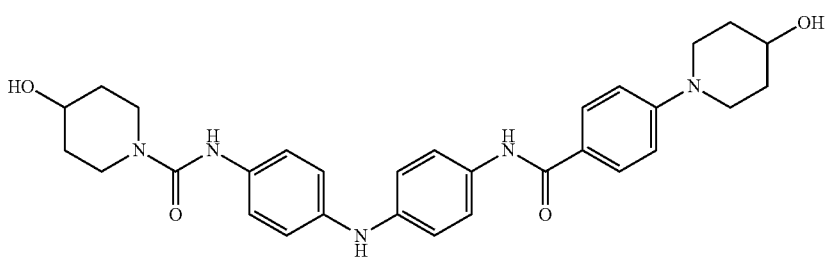 [SMILES: O=C(Nc1ccc(Nc2ccc(NC(=O)N3CCC(O)CC3)cc2)cc1)c1ccc(N2CCC(O)CC2)cc1]

Compound 792 was prepared according to the procedure described in Scheme IV from 4,4'-diaminodiphenylamine, (4-hydroxypiperidin-1-yl)carbonyl chloride, and 4-(4-hydroxypiperidin-1-yl)benzoic acid. [M+H]$^+$ calcd for $C_{30}H_{35}N_5O_4$: 530.28. found: 530.04.

Example 693

N-(4-((4-(4-(4-Hydroxypiperidin-1-yl)benzamido)phenyl)amino)phenyl)-2,3-dimethyl-1H-indole-5-carboxamide (Compound 793)

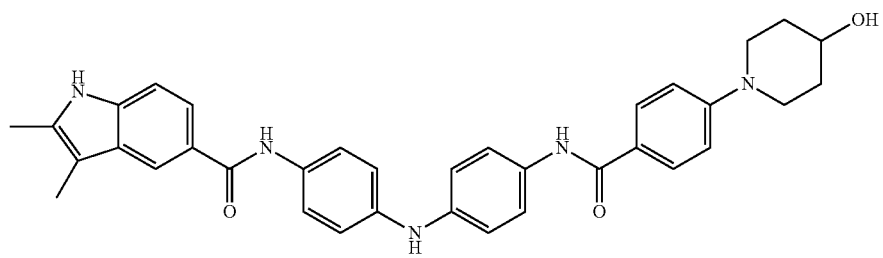 [SMILES: Cc1[nH]c2ccc(C(=O)Nc3ccc(Nc4ccc(NC(=O)c5ccc(N6CCC(O)CC6)cc5)cc4)cc3)cc2c1C]

Compound 793 was prepared according to the procedure described in Scheme IV from 4,4'-diaminodiphenylamine, 2,3-dimethyl-1H-indole-5-carboxylic, and 4-(4-hydroxypiperidin-1-yl)benzoic acids. [M+H]+ calcd for $C_{35}H_{35}N_5O_3$: 574.27. found 574.06.

Example 694

N-(4-((4-(4-(4-Hydroxypiperidin-1-yl)benzamido)phenyl)amino)phenyl)-1-methyl-1H-indole-5-carboxamide (Compound 794)

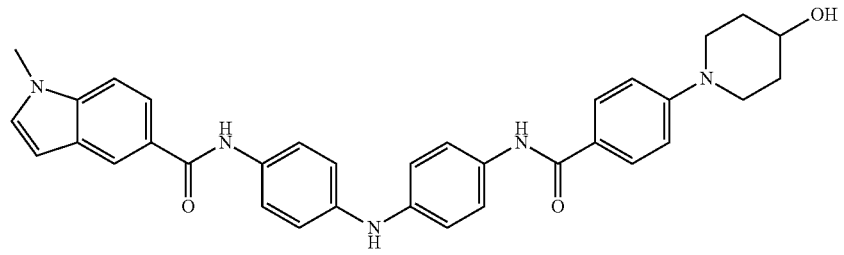 [SMILES: Cn1ccc2cc(C(=O)Nc3ccc(Nc4ccc(NC(=O)c5ccc(N6CCC(O)CC6)cc5)cc4)cc3)ccc21]

Compound 794 was prepared according to the procedure described in Scheme IV from 4,4'-diaminodiphenylamine, 1-methyl-1H-indole-5-carboxylic, and 4-(4-hydroxypiperidin-1-yl)benzoic acids. [M+H]+ calcd for $C_{34}H_{33}N_5O_3$: 560.26. found 560.02.

Example 695

N-(4-((4-(4-(4-Hydroxypiperidin-1-yl)benzamido)phenyl)amino)phenyl)-1-methyl-1H-indole-6-carboxamide (Compound 795)

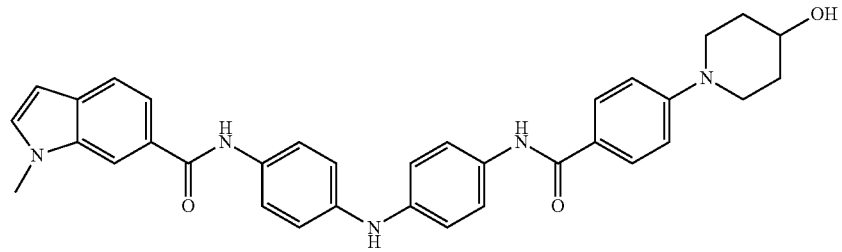 [SMILES: Cn1ccc2ccc(C(=O)Nc3ccc(Nc4ccc(NC(=O)c5ccc(N6CCC(O)CC6)cc5)cc4)cc3)cc21]

Compound 795 was prepared according to the procedure described in Scheme IV from 4,4'-diaminodiphenylamine, 1-methyl-1H-indole-6-carboxylic, and 4-(4-hydroxypiperidin-1-yl)benzoic acids. [M+H]+ calcd for $C_{34}H_{33}N_5O_3$: 560.26. found 560.07.

Example 696

N-(3-Chloro-4-((4-(4-(4-hydroxypiperidin-1-yl)benzamido)phenyl)amino)phenyl)-1-methyl-1H-pyrrole-2-carboxamide (Compound 796)

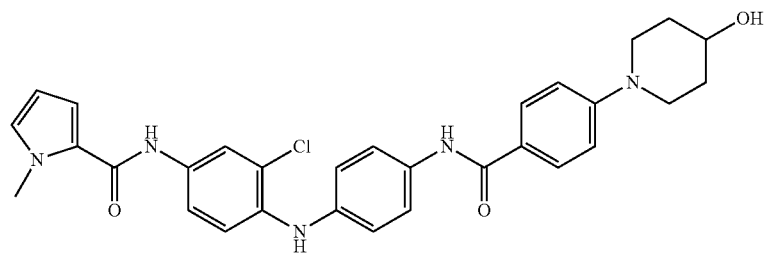 [SMILES: Cn1cccc1C(=O)Nc1ccc(Nc2ccc(NC(=O)c3ccc(N4CCC(O)CC4)cc3)cc2)c(Cl)c1]

Compound 796 was prepared according to the procedure described in Scheme IV from N¹-(4-aminophenyl)-2-chlorobenzene-1,4-diamine, 1-methyl-1H-pyrrole-2-carboxylic, and 4-(4-hydroxypiperidin-1-yl)benzoic acids. [M+H]⁺ calcd for $C_{30}H_{30}ClN_5O_3$: 544.2. found 544.02.

Example 697

N-(4-((4-(4-((2-Hydroxyethyl)(methyl)amino)benzamido)phenyl)amino)phenyl)-1-methyl-1H-pyrrole-2-carboxamide (Compound 797)

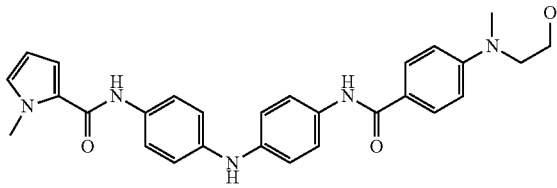

Compound 797 was prepared according to the procedure described in Scheme IV from 4,4'-diaminodiphenylamine, 1-methyl-1H-pyrrole-2-carboxylic, and (4-(2-hydroxyethyl)methylamino)benzoic acids. [M+H]⁺ calcd for $C_{28}H_{29}N_5O_3$: 484.24. found: 484.01.

Example 698

1-Methyl-N-(4-((4-(4-(4-methylpiperazin-1-yl)benzamido)phenyl)amino)phenyl)-1H-pyrrole-2-carboxamide (Compound 798)

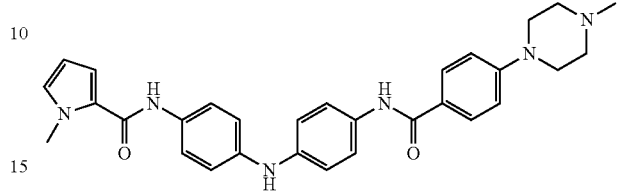

Compound 798 was prepared according to the procedure described in Scheme IV from 4,4'-diaminodiphenylamine, 1-methyl-1H-pyrrole-2-carboxylic, and 4-(4-methylpiperazin-1-yl)benzoic acids. [M+H]⁺ calcd for $C_{30}H_{32}N_6O_2$: 509.2. found: 509.05.

Example 699

N-(4-((4-(4-(4-Hydroxypiperidin-1-yl)benzamido)phenyl)amino)phenyl)-4-acetyl-3,5-dimethyl-1H-pyrrole-2-carboxamide (Compound 799)

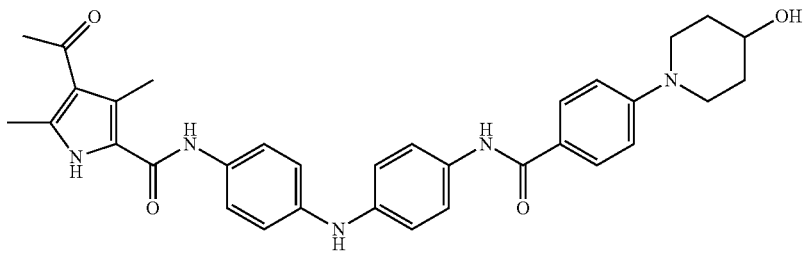 [SMILES: CC(=O)c1c(C)[nH]c(C(=O)Nc2ccc(Nc3ccc(NC(=O)c4ccc(N5CCC(O)CC5)cc4)cc3)cc2)c1C]

Compound 799 was prepared according to the procedure described in Scheme IV from 4,4'-diaminodiphenylamine, 4-acetyl-3,5-dimethyl-1H-pyrrole-2-carboxylic, and 4-(4-hydroxypiperidin-1-yl)benzoic acids. [M+H]⁺ calcd for $C_{33}H_{35}N_5O_4$: 566.2. found 566.09.

Example 700

N-(4-((4-(4-(4-Hydroxymethylpiperidin-1-yl)benzamido)phenyl)amino)phenyl)-1-methyl-1H-pyrrole-2-carboxamide (Compound 800)

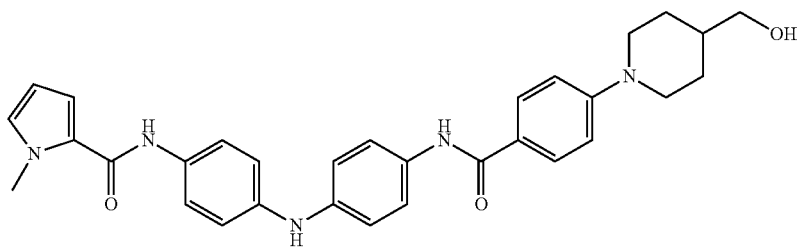 [SMILES: Cn1cccc1C(=O)Nc1ccc(Nc2ccc(NC(=O)c3ccc(N4CCC(CO)CC4)cc3)cc2)cc1]

Compound 800 was prepared according to the procedure described in Scheme IV from 4,4'-diaminodiphenylamine, 1-methyl-1H-pyrrole-2-carboxylic, and 4-(4-hydroxymethylpiperidin-1-yl)benzoic acids. [M+H]$^+$ calcd for $C_{31}H_{33}N_5O_3$: 524.26. found: 523.64.

Example 701

N-(4-((4-(4-(4-Hydroxypiperidin-1-yl)benzamido) phenyl)amino)phenyl)-1H-imidazole-2-carboxamide (Compound 801)

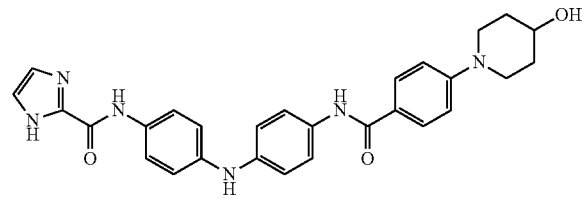 [SMILES: O=C(Nc1ccc(Nc2ccc(NC(=O)c3ncc[nH]3)cc2)cc1)c1ccc(N2CCC(O)CC2)cc1]

Compound 801 was prepared according to the procedure described in Scheme IV from 4,4'-diaminodiphenylamine, 1H-imidazole-2-carboxylic, and 4-(4-hydroxypiperidin-1-yl)benzoic acids. [M+H]$^+$ calcd for $C_{28}H_{28}N_6O_3$: 497.2. found 496.97.

Example 702

N-(4-((4-(4-(4-Hydroxypiperidin-1-yl)benzamido) phenyl)amino)phenyl)-1-methyl-1H-imidazole-4-carboxamide (Compound 802)

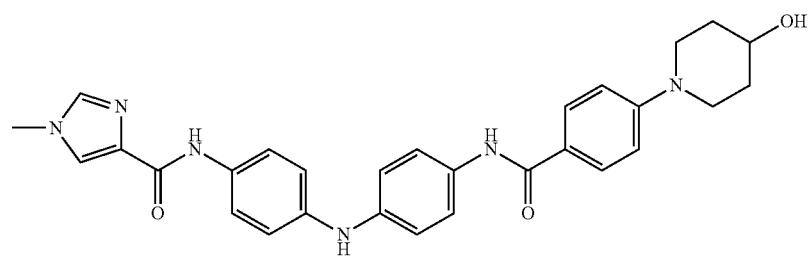

Compound 802 was prepared according to the procedure described in Scheme IV from 4,4'-diaminodiphenylamine, 1-methyl-1H-imidazole-4-carboxylic, and 4-(4-hydroxypiperidin-1-yl)benzoic acids. [M+H]$^+$ calcd for $C_{29}H_{30}N_6O_3$: 511.2. found 511.01.

Example 703

N-(4-((4-(4-(4-Hydroxypiperidin-1-yl)benzamido) phenyl)amino)phenyl)-1-methyl-1H-imidazole-5-carboxamide (Compound 803)

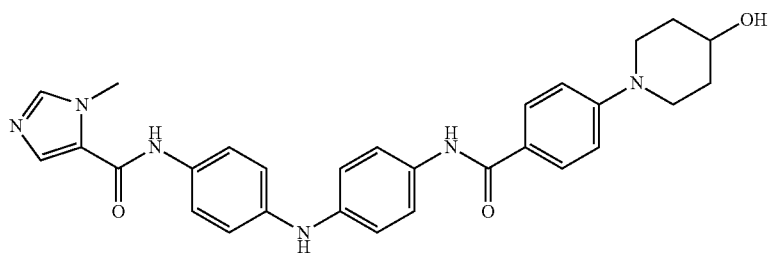 [SMILES: Cn1cncc1C(=O)Nc1ccc(Nc2ccc(NC(=O)c3ccc(N4CCC(O)CC4)cc3)cc2)cc1]

Compound 803 was prepared according to the procedure described in Scheme IV from 4,4'-diaminodiphenylamine, 1-methyl-1H-imidazole-5-carboxylic, and 4-(4-hydroxypiperidin-1-yl)benzoic acids. [M+H]+ calcd for $C_{29}H_{30}N_6O_3$: 511.2. found 511.01.

Example 704 tert-Butyl 4-(4-((4-((4-(4-(4-hydroxypiperidin-1-yl)benzamido)phenyl)amino)phenyl) carbamoyl)phenyl)piperazine-1-carboxylate (Compound 804)

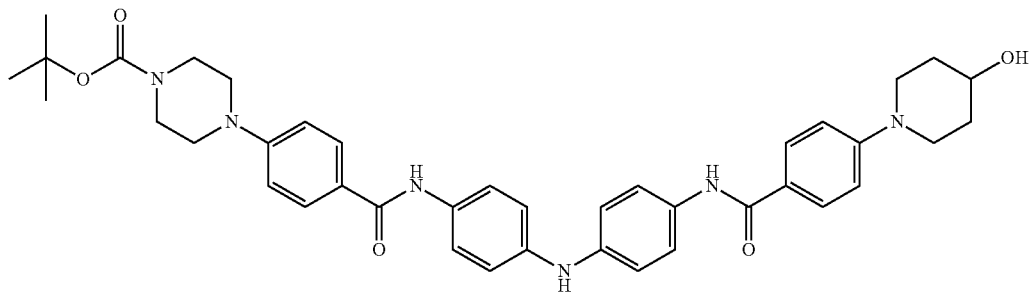 [SMILES: CC(C)(C)OC(=O)N1CCN(c2ccc(C(=O)Nc3ccc(Nc4ccc(NC(=O)c5ccc(N6CCC(O)CC6)cc5)cc4)cc3)cc2)CC1]

Compound 804 was prepared according to the procedure described in Scheme IV from 4,4'-diaminodiphenylamine, 4-(4-t-BOC-piperazin-1-yl)benzoic, and 4-(4-hydroxypiperidin-1-yl)benzoic acids. [M+H]+ calcd for $C_{40}H_{46}N_6O_5$: 691.3. found 691.23.

Example 705

(±)-Benzyl 2-((4-((4-(4-(4-hydroxypiperidin-1-yl)benzamido)phenyl)amino)phenyl) carbamoyl)pyrrolidine-1-carboxylate (Compound 805)

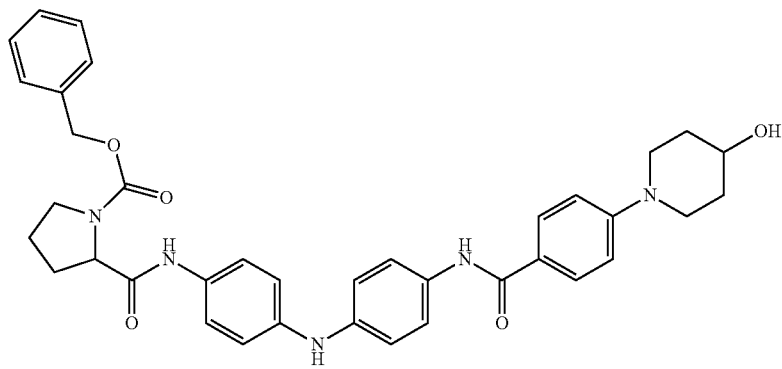 [SMILES: O=C(Nc1ccc(Nc2ccc(NC(=O)C3CCCN3C(=O)OCc3ccccc3)cc2)cc1)c1ccc(N2CCC(O)CC2)cc1]

Compound 805 was prepared according to the procedure described in Scheme IV from 4,4'-diaminodiphenylamine, 1-benzyloxycarbanylpyrrolidine-2-carboxylic, and 4-(4-hydroxypiperidin-1-yl)benzoic acids. [M+H]+ calcd for $C_{37}H_{39}N_5O_5$: 634.30. found 634.15.

Example 706

N-(4-((4-(1H-Pyrrole-2-carboxamido)phenyl)amino)phenyl)-4-morpholino-1H-pyrrole-2-carboxamide (Compound 806)

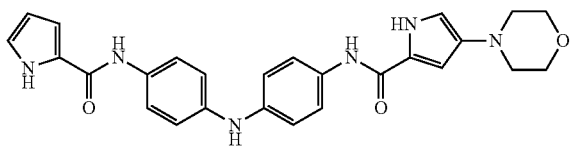 [SMILES: O=C(Nc1ccc(Nc2ccc(NC(=O)c3cc(N4CCOCC4)c[nH]3)cc2)cc1)c1ccc[nH]1]

Compound 806 was prepared according to the procedure described in Scheme IV from 4,4'-diaminodiphenylamine, 1H-pyrrole-2-carboxylic, and 4-morpholino-1H-pyrrole-2-carboxylic acids. $^1$H NMR (400 MHz, Acetone-$d_6$) δ 10.75 (s, 1H), 10.31 (s, 1H), 9.01 (s, 1H), 8.91 (s, 1H), 7.62 (d, J=8.6 Hz, 4H), 7.04 (m, 5H), 6.67 (s, 1H), 6.58 (s, 1H), 6.18 (s, 1H), 4.04 (dq, J=1.8, 7 Hz, 2H), 3.72 (m, 4H), 1.19 (dq, J=1.8, 7 Hz, 4H).

Example 707

N-(4-((4-Amino-2-fluorophenyl)amino)phenyl)-4-(4-hydroxypiperidin-1-yl)benzamide (Compound 807)

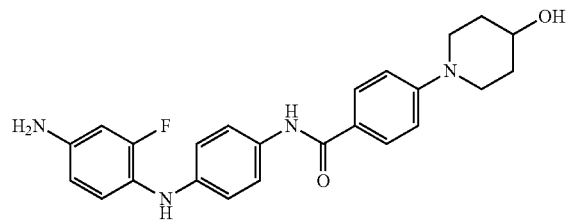 [SMILES: Nc1ccc(Nc2ccc(NC(=O)c3ccc(N4CCC(O)CC4)cc3)cc2)c(F)c1]

Compound 807 was prepared according to the procedure described in Scheme IV from $N^1$-(4-aminophenyl)-2-fluorobenzene-1,4-diamine and 4-(4-hydroxypiperidin-1-yl)benzoic acid. [M+H]$^+$ calcd for $C_{24}H_{25}FN_4O_2$: 421.2. found 420.98.

Example 708

N-(3-Fluoro-4-((4-(4-(4-hydroxypiperidin-1-yl)benzamido)phenyl)amino)phenyl)-1-methyl-1H-pyrrole-2-carboxamide (Compound 808)

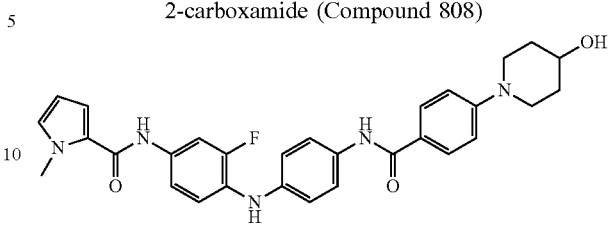

Compound 808 was prepared according to the procedure described in Scheme IV from $N^1$-(4-aminophenyl)-2-fluorobenzene-1,4-diamine, 1-methyl-1H-pyrrole-2-carboxylic, and 4-(4-hydroxypiperidin-1-yl)benzoic acids. [M+H]$^+$ calcd for $C_{30}H_{30}FN_5O_3$: 528.2. found 528.02.

Example 709

N-(3-Fluoro-4-((4-(4-(4-hydroxypiperidin-1-yl)benzamido)phenyl)amino)phenyl)-1-methyl-1H-indole-6-carboxamide (Compound 809)

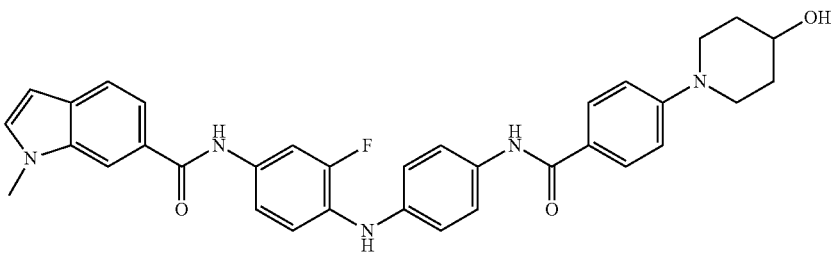 [SMILES: Cn1ccc2ccc(C(=O)Nc3ccc(Nc4ccc(NC(=O)c5ccc(N6CCC(O)CC6)cc5)cc4)c(F)c3)cc21]

Compound 809 was prepared according to the procedure described in Scheme IV from $N^1$-(4-aminophenyl)-2-fluorobenzene-1,4-diamine, 1-methyl-1H-indole-6-carboxylic, and 4-(4-hydroxypiperidin-1-yl)benzoic acids. [M+H]$^+$ calcd for $C_{34}H_{32}FN_5O_3$: 578.2. found 578.04.

Example 710

(±)-N-(4-((4-(4-(3-Hydroxypyrrolidin-1-yl)benzamido)phenyl)amino)phenyl)-1-methyl-1H-pyrrole-2-carboxamide (Compound 810)

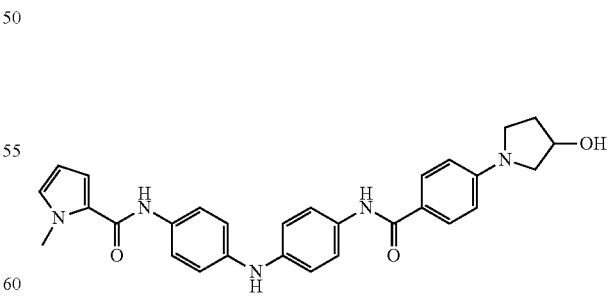

Compound 810 was prepared according to the procedure described in Scheme IV from 4,4'-diaminodiphenylamine, 1-methyl-1H-pyrrole-2-carboxylic, and 4-(3-hydroxypyrrolidin-1-yl)benzoic acids. [M+H]$^+$ calcd for $C_{29}H_{29}N_5O_3$: 496.2. found: 495.95.

Example 711

(S)—N-(4-((4-(4-(2-(Hydroxymethyl)pyrrolidin-1-yl)benzamido)phenyl)amino)phenyl)-1-methyl-1H-pyrrole-2-carboxamide (Compound 811)

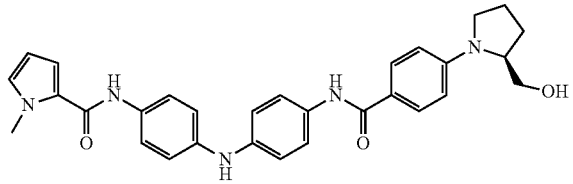 [SMILES: Cn1cccc1C(=O)Nc1ccc(Nc2ccc(NC(=O)c3ccc(N4CCC[C@H]4CO)cc3)cc2)cc1]

Compound 811 was prepared according to the procedure described in Scheme IV from 4,4'-diaminodiphenylamine, 1-methyl-1H-pyrrole-2-carboxylic, and (S)-4-(2-hydroxymethylpyrrolidin-1-yl)benzoic acids. [M+H]$^+$ calcd for C$_{30}$H$_{31}$N$_5$O$_3$: 510.24. found: 510.06.

Example 712

N-(4-((4-(4-(2-Hydroxyethyl)benzamido)phenyl)amino)phenyl)-1-methyl-1H-pyrrole-2-carboxamide (Compound 812)

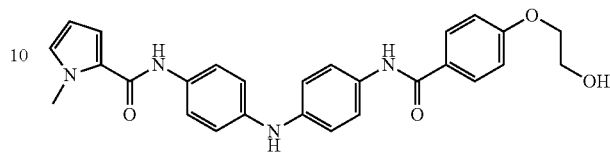

Compound 812 was prepared according to the procedure described in Scheme IV from 4,4'-diaminodiphenylamine, 1-methyl-1H-pyrrole-2-carboxylic, and 4-(2-hydroxyethyl)benzoic acids. [M+H]$^+$ calcd for C$_{27}$H$_{26}$N$_4$O$_4$: 471.2. found: 470.92.

Example 713

4-Azido-N-(4-((4-(4-(4-hydroxypiperidin-1-yl)benzamido)phenyl)amino)phenyl)benzamide (Compound 813)

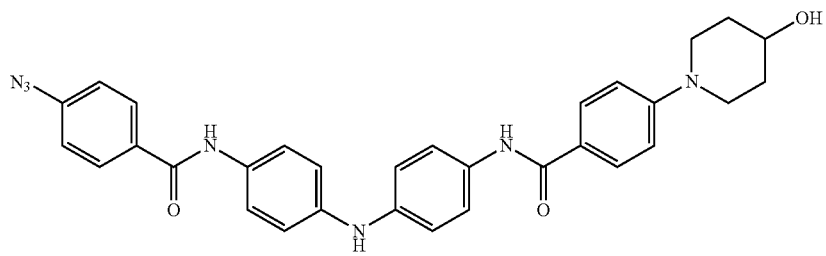 [SMILES: [N-]=[N+]=Nc1ccc(C(=O)Nc2ccc(Nc3ccc(NC(=O)c4ccc(N5CCC(O)CC5)cc4)cc3)cc2)cc1]

Compound 813 was prepared according to the procedure described in Scheme IV from 4,4'-diaminodiphenylamine, 4-azidobenzoic, and 4-(4-hydroxypiperidin-1-yl)benzoic acids. [M+H]$^+$ calcd for C$_{31}$H$_{29}$N$_7$O$_3$: 548.2. found 548.07.

Example 714

N-(4-((4-(4-(4-Hydroxypiperidin-1-yl)benzamido)phenyl)amino)phenyl)-1-ethyl-1H-pyrrole-2-carboxamide (Compound 814)

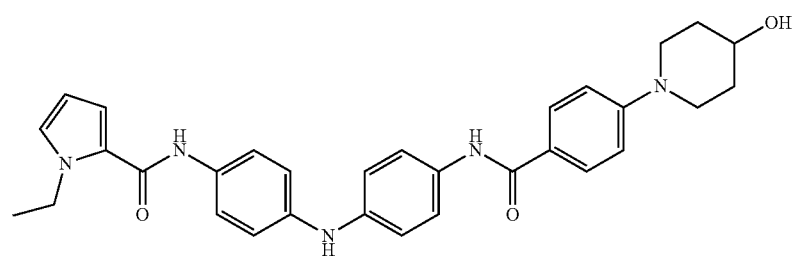 [SMILES: CCn1cccc1C(=O)Nc1ccc(Nc2ccc(NC(=O)c3ccc(N4CCC(O)CC4)cc3)cc2)cc1]

Compound 814 was prepared according to the procedure described in Scheme IV from 4,4'-diaminodiphenylamine, 1-ethyl-1H-pyrrole-2-carboxylic, and 4-(4-hydroxypiperidin-1-yl)benzoic acids. [M+H]+ calcd for $C_{31}H_{33}N_5O_3$: 524.2. found: 524.03.

Example 715

N-(4-((4-(3-Fluoro-4-(4-hydroxypiperidin-1-yl)benzamido)phenyl)amino)phenyl)-1-methyl-1H-pyrrole-2-carboxamide (Compound 815)

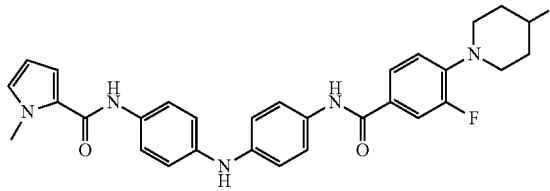

Compound 815 was prepared according to the procedure described in Scheme IV from 4,4'-diaminodiphenylamine, 1-methyl-1H-pyrrole-2-carboxylic, and 3-fluoro-4-(4-hydroxypiperidin-1-yl)benzoic acids. $^1$H NMR (400 MHz, Acetone-$d_6$) δ 9.25 (s, 1H), 8.94 (s, 1H), 7.75 (dd, J=1.9, 8.4 Hz, 1H), 7.69 (m, 3H), 7.63 (d, J=8.8 Hz, 2H), 7.22 (s, 1H), 7.08 (m, 5H), 6.89 (m, 2H), 6.05 (m, 1H), 3.95 (s, 3H), 3.47 (m, 2H), 2.95 (ddd, J=3, 9.8, 12.4 Hz, 2H), 1.67 (m, 2H), 1.27 (m, 2H).

Example 716

N-(4-((4-(4-(4-Hydroxypiperidin-1-yl)benzamido)-2-(trifluoromethyl)phenyl)amino)phenyl)-1-methyl-1H-pyrrole-2-carboxamide (Compound 816)

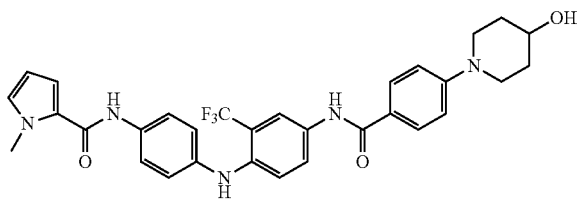 [SMILES: Cn1cccc1C(=O)Nc1ccc(Nc2ccc(NC(=O)c3ccc(N4CCC(O)CC4)cc3)cc2C(F)(F)F)cc1]

Compound 816 was prepared according to the procedure described in Scheme IV from N$^1$-(4-aminophenyl)-2-trifluoromethylbenzene-1,4-diamine, 1-methyl-1H-pyrrole-2-carboxylic, and 4-(4-hydroxypiperidin-1-yl)benzoic acids. [M+H]+ calcd for $C_{31}H_{30}F_3N_5O_3$: 578.2. found: 578.04.

Example 717

N-(4-((4-(4-(4-Hydroxypiperidin-1-yl)benzamido)-2-(cyano)phenyl)amino)phenyl)-1-methyl-1H-pyrrole-2-carboxamide (Compound 817)

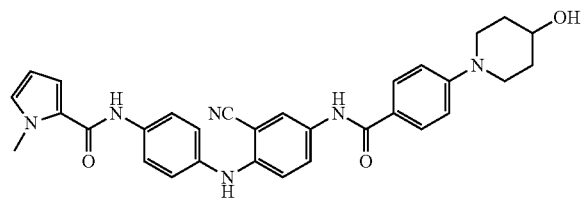 [SMILES: Cn1cccc1C(=O)Nc1ccc(Nc2ccc(NC(=O)c3ccc(N4CCC(O)CC4)cc3)cc2C#N)cc1]

Compound 817 was prepared according to the procedure described in Scheme IV from N$^1$-(4-aminophenyl)-2-cyanobenzene-1,4-diamine, 1-methyl-1H-pyrrole-2-carboxylic, and 4-(4-hydroxypiperidin-1-yl)benzoic acids. [M+H]+ calcd for $C_{31}H_{30}N_6O_3$: 535.2. found: 535.04.

Example 718

N-(4-((4-(2-Chloro-4-(4-hydroxypiperidin-1-yl)benzamido)phenyl)amino)phenyl)-1-methyl-1H-pyrrole-2-carboxamide (Compound 818)

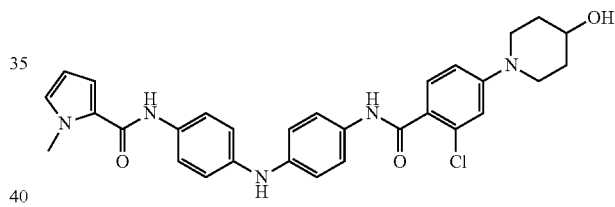

Compound 818 was prepared according to the procedure described in Scheme IV from 4,4'-diaminodiphenylamine, 1-methyl-1H-pyrrole-2-carboxylic, and 2-chloro-4-(4-hydroxypiperidin-1-yl)benzoic acids. [M+H]+ calcd for $C_{30}H_{30}ClN_5O_3$: 544.20. found: 544.02.

Example 719

N-(4-((4-(4-(4-Hydroxypiperidin-1-yl)benzamido)phenyl)amino)phenyl)-1-isopropyl-1H-pyrrole-2-carboxamide (Compound 819)

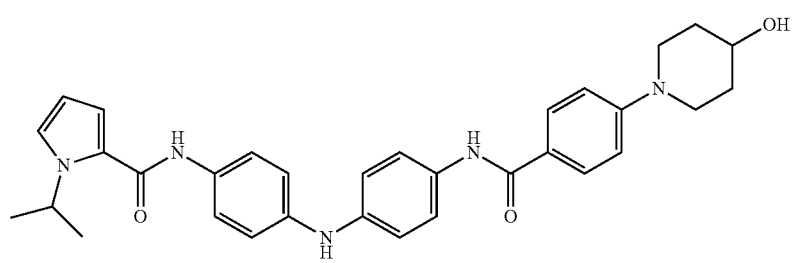 [SMILES: CC(C)n1cccc1C(=O)Nc1ccc(Nc2ccc(NC(=O)c3ccc(N4CCC(O)CC4)cc3)cc2)cc1]

Compound 819 was prepared according to the procedure described in Scheme IV from 4,4'-diaminodiphenylamine, 1-isopropyl-1H-pyrrole-2-carboxylic, and 4-(4-hydroxypiperidin-1-yl)benzoic acids. [M+H]+ calcd for $C_{32}H_{35}N_5O_3$: 538.2. found: 538.08.

Example 720

N-(4-((4-(4-(4-Hydroxy-4-trifluoromethylpiperidin-1-yl)benzamido)phenyl)amino)phenyl)-1-methyl-1H-pyrrole-2-carboxamide (Compound 820)

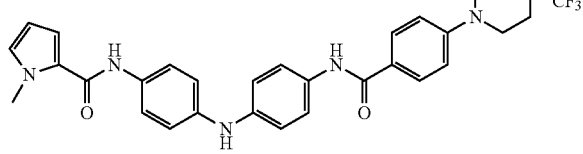

Compound 820 was prepared according to the procedure described in Scheme IV from 4,4'-diaminodiphenylamine, 1-methyl-1H-pyrrole-2-carboxylic, and 4-(4-hydroxy-4-trifluoromethylpiperidin-1-yl)benzoic acids. [M+H]+ calcd for $C_{31}H_{30}F_3N_5O_3$: 578.2. found 578.04.

Example 721

(±)-N-(4-((4-(4-(2-Hydroxymethylmorpholi-4-no)benzamido)phenyl)amino)phenyl)-1-methyl-1H-pyrrole-2-carboxamide (Compound 821)

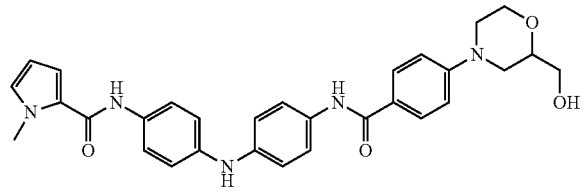 [SMILES: Cn1cccc1C(=O)Nc1ccc(Nc2ccc(NC(=O)c3ccc(N4CCOC(CO)C4)cc3)cc2)cc1]

Compound 821 was prepared according to the procedure described in Scheme IV from 4,4'-diaminodiphenylamine, 1-methyl-1H-pyrrole-2-carboxylic, and 4-(2-hydroxymethylmorpholi-4-no)benzoic acids. [M+H]+ calcd for $C_{30}H_{31}N_5O_4$: 526.24. found: 525.99.

Example 722

(±)-N-(4-((4-(4-(4-Hydroxypiperidin-1-yl)benzamido)phenyl)amino)phenyl)pyrrolidine-2-carboxamide (Compound 822)

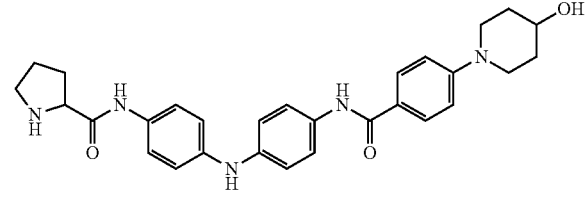 [SMILES: O=C(Nc1ccc(Nc2ccc(NC(=O)C3CCCN3)cc2)cc1)c1ccc(N2CCC(O)CC2)cc1]

Compound 822 was prepared according to the procedure described in Scheme IV from 4,4'-diaminodiphenylamine, pyrrolidine-2-carboxylic, and 4-(4-hydroxypiperidin-1-yl)benzoic acids. [M+H]+ calcd for $C_{29}H_{33}N_5O_3$: 500.2. found 499.94.

Example 723

N-(4-((4-(4-(1,4-Dioxa-8-azaspiro[4.5]decan-8-yl)benzamido)phenyl)amino)phenyl)-1-methyl-1H-pyrrole-2-carboxamide (Compound 823)

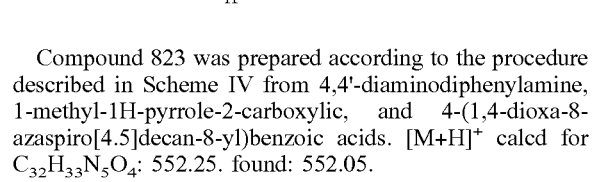

Compound 823 was prepared according to the procedure described in Scheme IV from 4,4'-diaminodiphenylamine, 1-methyl-1H-pyrrole-2-carboxylic, and 4-(1,4-dioxa-8-azaspiro[4.5]decan-8-yl)benzoic acids. [M+H]+ calcd for $C_{32}H_{33}N_5O_4$: 552.25. found: 552.05.

Example 724

N-(4-((4-(4-(4-Hydroxypiperidin-1-yl)benzamido)phenyl)amino)phenyl)-1-vinyl-1H-pyrrole-2-carboxamide (Compound 824)

Compound 824 was prepared according to the procedure described in Scheme IV from 4,4'-diaminodiphenylamine, 1-vinyl-1H-pyrrole-2-carboxylic, and 4-(4-hydroxypiperidin-1-yl)benzoic acids. [M+H]$^+$ calcd for $C_{31}H_{31}N_5O_3$: 522.2. found 522.01.

Example 725

3-Fluoro-4-(4-hydroxypiperidin-1-yl)-N-(4-((4-(4-(4-hydroxypiperidin-1-yl)benzamido)phenyl)amino)phenyl)benzamide (Compound 825)

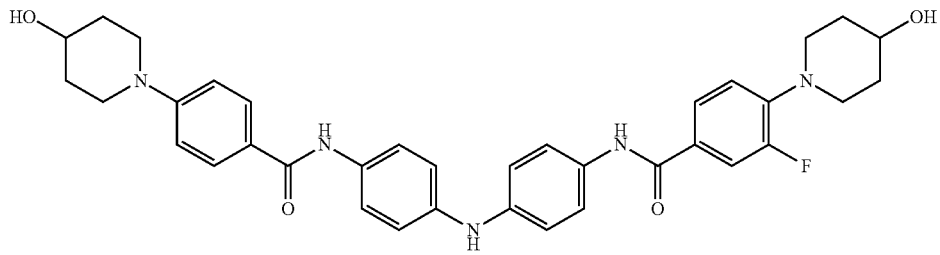 [SMILES: O=C(Nc1ccc(Nc2ccc(NC(=O)c3ccc(N4CCC(O)CC4)c(F)c3)cc2)cc1)c1ccc(N2CCC(O)CC2)cc1]

Compound 825 was prepared according to the procedure described in Scheme IV from 4,4'-diaminodiphenylamine, 3-fluoro-4-(4-hydroxypiperidin-1-yl)benzoic, and 4-(4-hydroxypiperidin-1-yl)benzoic acids. [M+H]$^+$ calcd for $C_{36}H_{38}FN_5O_4$: 624.29. found 624.13.

Example 726

N-(3-Chloro-4-((4-(4-(4-hydroxypiperidin-1-yl)benzamido)phenyl)amino)phenyl)-4-(4-hydroxypiperidin-1-yl)benzamide (Compound 826)

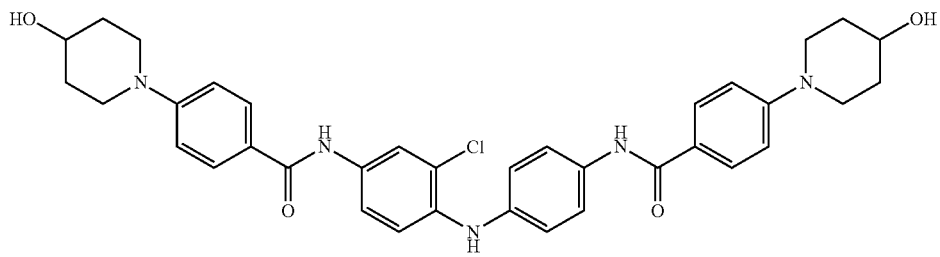 [SMILES: O=C(Nc1ccc(Nc2ccc(NC(=O)c3ccc(N4CCC(O)CC4)cc3)cc2Cl)cc1)c1ccc(N2CCC(O)CC2)cc1]

Compound 826 was prepared according to the procedure described in Scheme IV from $N^1$-(4-aminophenyl)-2-chlorobenzene-1,4-diamine and 4-(4-hydroxypiperidin-1-yl)benzoic acid. [M+H]$^+$ calcd for $C_{36}H_{38}ClN_5O_4$: 640.2. found 640.12.

Example 727

N-(4-((4-(4-(4-Hydroxypiperidin-1-yl)benzamido)-2-(methoxycarbonyl)phenyl)amino)phenyl)-1-methyl-1H-pyrrole-2-carboxamide (Compound 827)

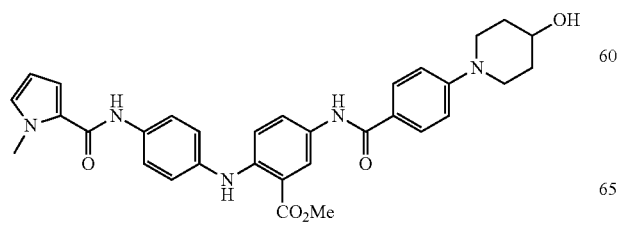

Compound 827 was prepared according to the procedure described in Scheme IV from $N^1$-(4-aminophenyl)-2-methoxycarbonylbenzene-1,4-diamine, 1-methyl-1H-pyrrole-2-carboxylic, and 4-(4-hydroxypiperidin-1-yl)benzoic acids. $[M+H]^+$ calcd for $C_{32}H_{33}N_5O_5$: 568.2. found: 568.05.

Example 728

5-(4-(4-Hydroxypiperidin-1-yl)benzamido)-2-((4-(1-methyl-1H-pyrrole-2-carboxamido)phenyl)amino)benzoic acid (Compound 828)

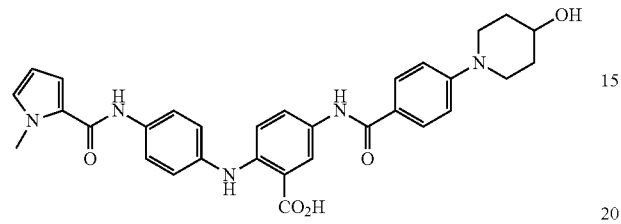

Compound 828 was prepared by hydrolysis of Compound 827. $[M+H]^+$ calcd for $C_{31}H_{31}N_5O_5$: 554.2. found: 554.01.

Example 729

N-(4-((4-(4-(4-Hydroxypiperidin-1-yl)benzamido)phenyl)amino)phenyl)-1-cyanomethyl-1H-pyrrole-2-carboxamide (Compound 829)

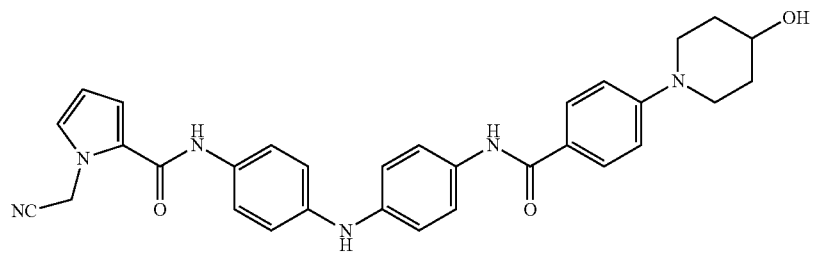 [SMILES: N#CCn1cccc1C(=O)Nc1ccc(Nc2ccc(NC(=O)c3ccc(N4CCC(O)CC4)cc3)cc2)cc1]

Compound 829 was prepared according to the procedure described in Scheme IV from 4,4'-diaminodiphenylamine, 1-cyanomethyl-1H-pyrrole-2-carboxylic, and 4-(4-hydroxypiperidin-1-yl)benzoic acids. $[M+H]^+$ calcd for $C_{31}H_{30}N_6O_3$: 535.24. found: 535.04.

Example 730

Ethyl 2-(2-chloro-5-((4-((4-(4-(4-hydroxypiperidin-1-yl)benzamido)phenyl)amino)phenyl)carbamoyl)-1H-pyrrol-1-yl)acetate (Compound 830)

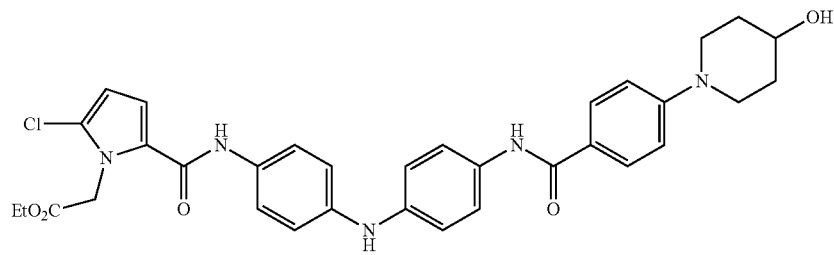 [SMILES: CCOC(=O)Cn1c(Cl)ccc1C(=O)Nc1ccc(Nc2ccc(NC(=O)c3ccc(N4CCC(O)CC4)cc3)cc2)cc1]

Compound 830 was prepared according to the procedure described in Scheme IV from 4,4'-diaminodiphenylamine, 5-chloro-1-ethoxycarbonylmethyl-1H-pyrrole-2-carboxylic, and 4-(4-hydroxypiperidin-1-yl)benzoic acids. [M+H]$^+$ calcd for $C_{33}H_{34}ClN_5O_5$: 616.2. found: 616.06.

Example 731

N-(4-((4-(4-(4-Hydroxypiperidin-1-yl)benzamido)-2-fluorophenyl)amino)phenyl)-1-methyl-1H-pyrrole-2-carboxamide (Compound 831)

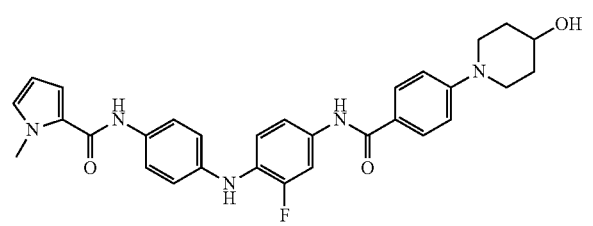 [SMILES: Cn1cccc1C(=O)Nc1ccc(Nc2ccc(NC(=O)c3ccc(N4CCC(O)CC4)cc3)cc2F)cc1]

Compound 831 was prepared according to the procedure described in Scheme IV from N$^1$-(4-aminophenyl)-2-fluorobenzene-1,4-diamine, 1-methyl-1H-pyrrole-2-carboxylic, and 4-(4-hydroxypiperidin-1-yl)benzoic acids. [M+H]$^+$ calcd for $C_{30}H_{30}FN_5O_3$: 528.2. found 528.02.

Example 732

N-(4-((4-(4-(4-Hydroxypiperidin-1-yl)benzamido)-2-chlorophenyl)amino)phenyl)-1-methyl-1H-pyrrole-2-carboxamide (Compound 832)

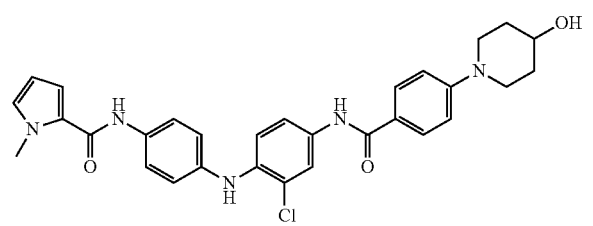 [SMILES: Cn1cccc1C(=O)Nc1ccc(Nc2ccc(NC(=O)c3ccc(N4CCC(O)CC4)cc3)cc2Cl)cc1]

Compound 832 was prepared according to the procedure described in Scheme IV from N$^1$-(4-aminophenyl)-2-chlorobenzene-1,4-diamine, 1-methyl-1H-pyrrole-2-carboxylic, and 4-(4-hydroxypiperidin-1-yl)benzoic acids. [M+H]$^+$ calcd for $C_{30}H_{30}ClN_5O_3$: 544.2. found 544.02.

Example 733

N-(5-((4-(4-(4-Hydroxypiperidin-1-yl)benzamido)phenyl)amino)pyridin-2-yl)-1-methyl-1H-pyrrole-2-carboxamide (Compound 833)

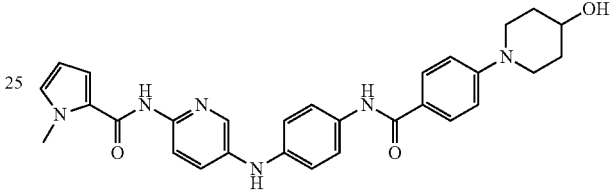

Compound 833 was prepared according to the procedure described in Scheme IV from N$^5$-(4-aminophenyl)pyridine-2,5-diamine, 1-methyl-1H-pyrrole-2-carboxylic, and 4-(4-hydroxypiperidin-1-yl)benzoic acids. [M+H]$^+$ calcd for $C_{29}H_{30}N_6O_3$: 511.2. found 511.01.

Example 734

N-(3-Cyano-4-((4-(4-(4-hydroxypiperidin-1-yl)benzamido)phenyl)amino)phenyl)-4-(4-hydroxypiperidin-1-yl)benzamide (Compound 834)

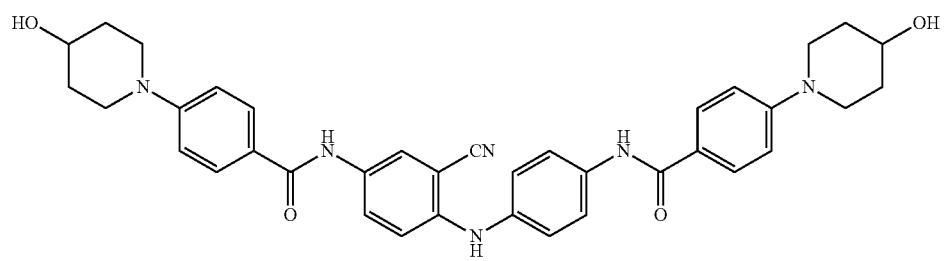 [SMILES: N#Cc1cc(NC(=O)c2ccc(N3CCC(O)CC3)cc2)ccc1Nc1ccc(NC(=O)c2ccc(N3CCC(O)CC3)cc2)cc1]

Compound 834 was prepared according to the procedure described in Scheme IV from $N^1$-(4-aminophenyl)-2-cyanobenzene-1,4-diamine and 4-(4-hydroxypiperidin-1-yl)benzoic acid. [M+H]$^+$ calcd for $C_{37}H_{38}N_6O_4$: 631.3. found: 631.11.

Example 735

N-(4-((4-(4-(4-(2-Hydroxyethoxy)piperidin-1-yl)benzamido)phenyl)amino)phenyl)-1-methyl-1H-pyrrole-2-carboxamide (Compound 835)

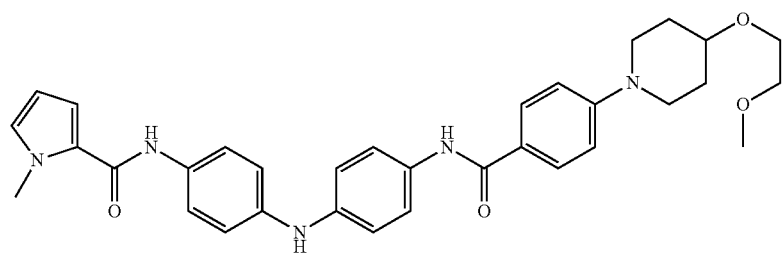 [SMILES: COCCOC1CCN(c2ccc(C(=O)Nc3ccc(Nc4ccc(NC(=O)c5cccn5C)cc4)cc3)cc2)CC1]

Compound 835 was prepared according to the procedure described in Scheme IV from 4,4'-diaminodiphenylamine, 1-methyl-1H-pyrrole-2-carboxylic, and 4-(4-(2-hydroxyethoxy)piperidin-1-yl)benzoic acids. [M+H]$^+$ calcd for $C_{33}H_{37}N_5O_4$: 568.28. found: 568.12.

Example 736

2-(2-((4-((4-(4-(4-Hydroxypiperidin-1-yl)benzamido)phenyl)amino)phenyl)carbamoyl)-1H-pyrrol-1-yl)acetic acid (Compound 836)

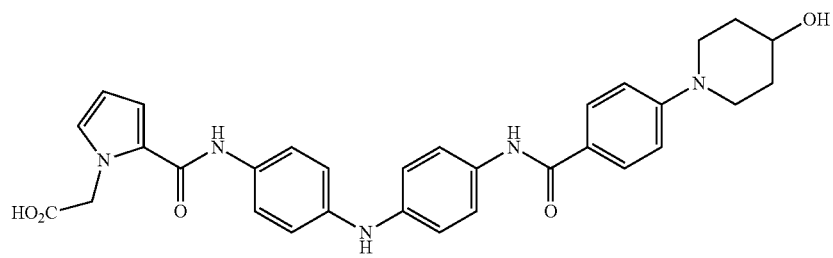 [SMILES: O=C(O)Cn1cccc1C(=O)Nc1ccc(Nc2ccc(NC(=O)c3ccc(N4CCC(O)CC4)cc3)cc2)cc1]

Compound 836 was prepared according to the procedure described in Scheme IV from 4,4'-diaminodiphenylamine, 1-methoxycarbonylmethyl-1H-pyrrole-2-carboxylic, and 4-(4-hydroxypiperidin-1-yl)benzoic acids. [M+H]$^+$ calcd for $C_{31}H_{31}N_5O_5$: 554.2. found: 554.01.

Example 737

N-(4-((4-(3-Methyl-4-(4-hydroxypiperidin-1-yl)benzamido)phenyl)amino)phenyl)-1-methyl-1H-pyrrole-2-carboxamide (Compound 837)

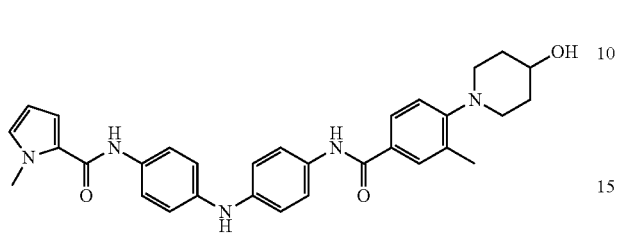

Compound 837 was prepared according to the procedure described in Scheme IV from 4,4'-diaminodiphenylamine, 1-methyl-1H-pyrrole-2-carboxylic, and 3-methyl-4-(4-hydroxypiperidin-1-yl)benzoic acids. [M+H]$^+$ calcd for C$_{31}$H$_{33}$N$_5$O$_3$: 524.26. found: 524.03.

Example 738

(±)-N-(4-((4-(4-(4-(2,6-Dimethyl)morpholi-4-no)benzamido)phenyl)amino)phenyl)-1-methyl-1H-pyrrole-2-carboxamide (Compound 838)

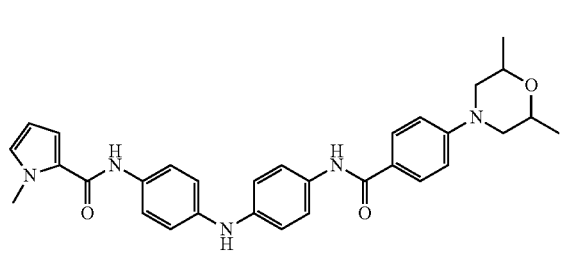 [SMILES: CC1CN(c2ccc(C(=O)Nc3ccc(Nc4ccc(NC(=O)c5cccn5C)cc4)cc3)cc2)CC(C)O1]

Compound 838 was prepared according to the procedure described in Scheme IV from 4,4'-diaminodiphenylamine, 1-methyl-1H-pyrrole-2-carboxylic, and 4-(2,6-dimethylmorpholi-4-no)benzoic acids. [M+H]$^+$ calcd for C$_{31}$H$_{33}$N$_5$O$_3$: 524.26. found: 524.03.

Example 739

N-(4-((4-(3-Methoxy-4-(4-hydroxypiperidin-1-yl)benzamido)phenyl)amino)phenyl)-1-methyl-1H-pyrrole-2-carboxamide (Compound 839)

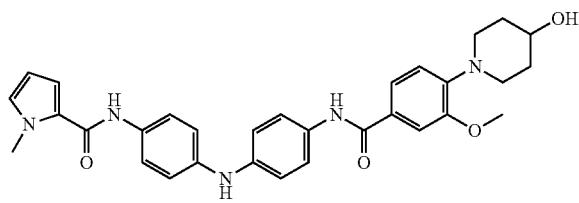 [SMILES: COc1cc(C(=O)Nc2ccc(Nc3ccc(NC(=O)c4cccn4C)cc3)cc2)ccc1N1CCC(O)CC1]

Compound 839 was prepared according to the procedure described in Scheme IV from 4,4'-diaminodiphenylamine, 1-methyl-1H-pyrrole-2-carboxylic, and 3-methoxy-4-(4-hydroxypiperidin-1-yl)benzoic acids. [M+H]$^+$ calcd for C$_{31}$H$_{33}$N$_5$O$_4$: 540.25. found: 540.03.

Example 740

N-(4-((4-(3-Trifluoromethyl-4-(4-hydroxypiperidin-1-yl)benzamido)phenyl)amino)phenyl)-1-methyl-1H-pyrrole-2-carboxamide (Compound 840)

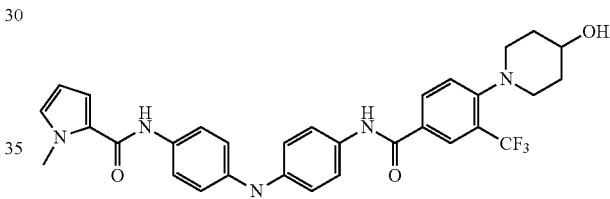

Compound 840 was prepared according to the procedure described in Scheme IV from 4,4'-diaminodiphenylamine, 1-methyl-1H-pyrrole-2-carboxylic, and 3-trifluoromethyl-4-(4-hydroxypiperidin-1-yl)benzoic acids. [M+H]$^+$ calcd for C$_{31}$H$_{30}$F$_3$N$_5$O$_3$: 578.2. found: 578.04.

Example 741

N-(4-((4-(4-(4-Hydroxypiperidin-1-yl)benzamido)phenyl)amino)phenyl)-2,4-dimethyl-1H-pyrrole-3-carboxamide (Compound 841)

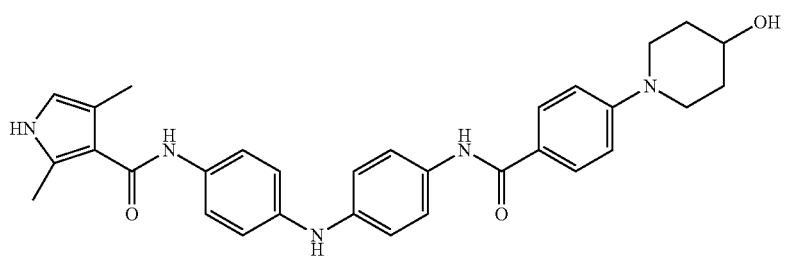 [SMILES: Cc1c[nH]c(C)c1C(=O)Nc1ccc(Nc2ccc(NC(=O)c3ccc(N4CCC(O)CC4)cc3)cc2)cc1]

Compound 841 was prepared according to the procedure described in Scheme IV from 4,4'-diaminodiphenylamine, 2,4-dimethyl-1H-pyrrole-3-carboxylic, and 4-(4-hydroxypiperidin-1-yl)benzoic acids. [M+H]$^+$ calcd for $C_{31}H_{33}N_5O_3$: 524.26. found 524.03.

Example 742

N-(4-((4-(4-(4-Hydroxypiperidin-1-yl)benzamido)phenyl)amino)phenyl)-1-(2-hydroxyethyl)-1H-pyrrole-2-carboxamide (Compound 842)

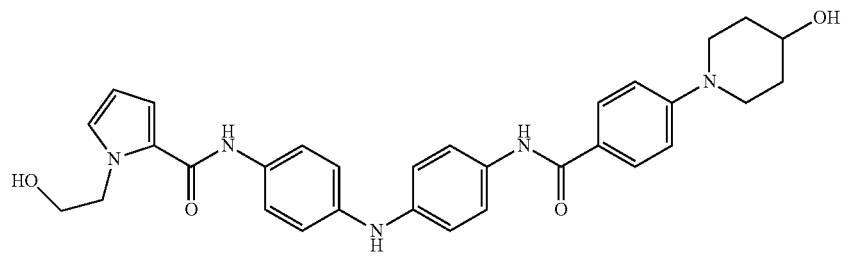 [SMILES: O=C(Nc1ccc(Nc2ccc(NC(=O)c3cccn3CCO)cc2)cc1)c1ccc(N2CCC(O)CC2)cc1]

Compound 842 was prepared according to the procedure described in Scheme IV from 4,4'-diaminodiphenylamine, 1-(2-hydroxyethyl)-1H-pyrrole-2-carboxylic, and 4-(4-hydroxypiperidin-1-yl)benzoic acids. [M+H]$^+$ calcd for $C_{31}H_{33}N_5O_4$: 540.25. found: 540.03.

Example 743

1-Ethyl-N-(3-fluoro-4-((4-(4-(4-hydroxypiperidin-1-yl)benzamido)phenyl)amino)phenyl)-1H-pyrrole-2-carboxamide (Compound 843)

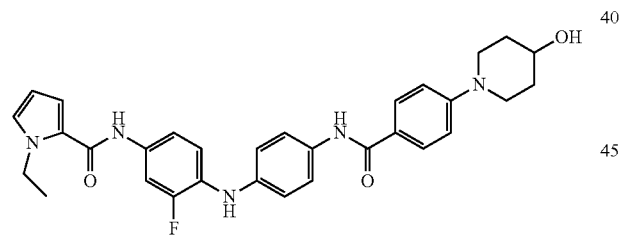

Compound 843 was prepared according to the procedure described in Scheme IV from N$^1$-(4-aminophenyl)-2-fluorobenzene-1,4-diamine, 1-ethyl-1H-pyrrole-2-carboxylic, and 4-(4-hydroxypiperidin-1-yl)benzoic acids. [M+H]+ calcd for $C_{31}H_{32}FN_5O_3$: 542.2. found: 542.06.

Example 744

N-(3-Fluoro-4-((4-(4-(4-hydroxypiperidin-1-yl)benzamido)phenyl)amino)phenyl)-1-methyl-1H-indole-2-carboxamide (Compound 844)

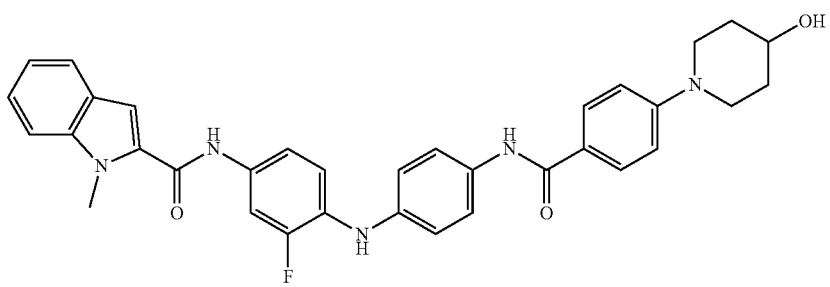

Compound 844 was prepared according to the procedure described in Scheme IV from $N^1$-(4-aminophenyl)-2-fluorobenzene-1,4-diamine, 1-methyl-1H-indole-2-carboxylic, and 4-(4-hydroxypiperidin-1-yl)benzoic acids. $[M+H]^+$ calcd for $C_{34}H_{32}FN_5O_3$: 578.2. found 578.11.

Example 745

N-(3-Fluoro-4-((4-(4-(4-hydroxypiperidin-1-yl)benzamido)phenyl)amino)phenyl)-5-methyl-1H-indole-2-carboxamide (Compound 845)

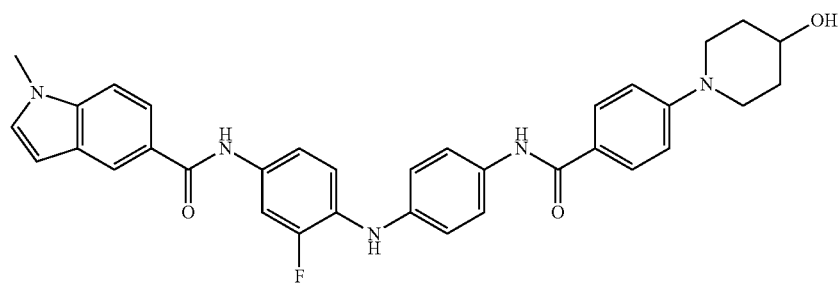

Compound 845 was prepared according to the procedure described in Scheme IV from $N^1$-(4-aminophenyl)-2-fluorobenzene-1,4-diamine, 1-methyl-1H-indole-5-carboxylic, and 4-(4-hydroxypiperidin-1-yl)benzoic acids. $[M+H]^+$ calcd for $C_{34}H_{32}FN_5O_3$: 578.2. found 578.11.

Example 746

N-(3-Chloro-4-((4-(4-(4-hydroxypiperidin-1-yl)benzamido)phenyl)amino)phenyl)-1-methyl-1H-indole-2-carboxamide (Compound 846)

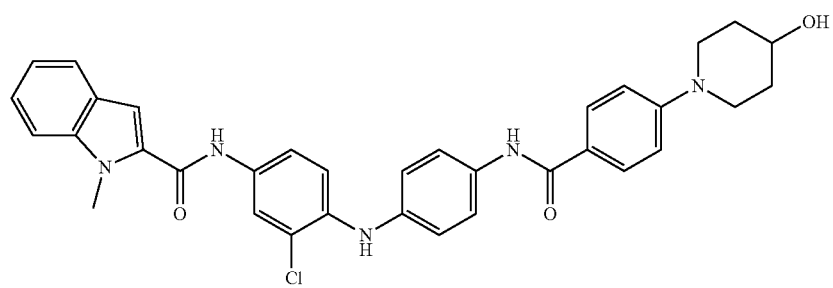 [SMILES: Cn1c(C(=O)Nc2ccc(Nc3ccc(NC(=O)c4ccc(N5CCC(O)CC5)cc4)cc3)c(F)c2)cc2ccccc21]

Compound 846 was prepared according to the procedure described in Scheme IV from $N^1$-(4-aminophenyl)-2-chlorobenzene-1,4-diamine, 1-methyl-1H-indole-2-carboxylic, and 4-(4-hydroxypiperidin-1-yl)benzoic acids. $[M+H]^+$ calcd for $C_{34}H_{32}ClN_5O_3$: 594.2. found 594.11.

Example 747

N-(3-Chloro-4-((4-(4-(4-hydroxypiperidin-1-yl)benzamido)phenyl)amino)phenyl)-5-methyl-1H-indole-2-carboxamide (Compound 847)

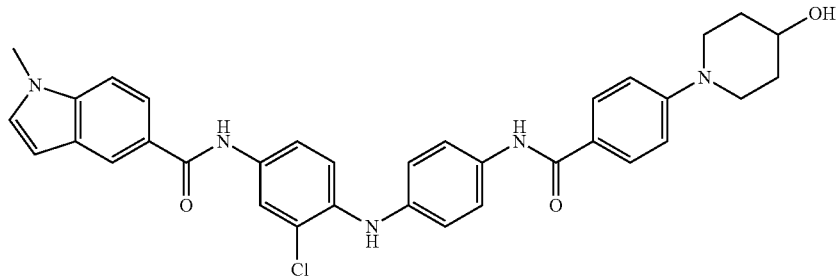 [SMILES: Cn1ccc2cc(C(=O)Nc3ccc(Nc4ccc(NC(=O)c5ccc(N6CCC(O)CC6)cc5)cc4)c(F)c3)ccc21]

Compound 847 was prepared according to the procedure described in Scheme IV from $N^1$-(4-aminophenyl)-2-chlorobenzene-1,4-diamine, 1-methyl-1H-indole-5-carboxylic, and 4-(4-hydroxypiperidin-1-yl)benzoic acids. $[M+H]^+$ calcd for $C_{34}H_{32}ClN_5O_3$: 594.2. found 594.11.

Example 748

N-(4-((2-Cyano-4-(4-(4-hydroxypiperidin-1-yl)benzamido)phenyl)amino)phenyl)-1-ethyl-1H-pyrrole-2-carboxamide (Compound 848)

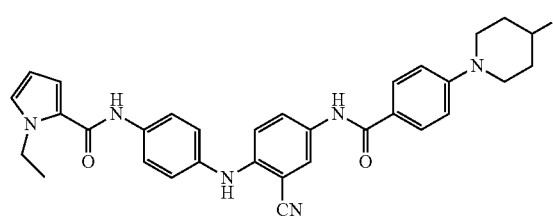

Compound 848 was prepared according to the procedure described in Scheme IV from $N^1$-(4-aminophenyl)-2-cyanobenzene-1,4-diamine, 1-ethyl-1H-pyrrole-2-carboxylic, and 4-(4-hydroxypiperidin-1-yl)benzoic acids. $[M+H]^+$ calcd for $C_{32}H_{32}N_6O_3$: 549.2. found: 549.08.

Example 749

N-(3-Methyl-4-((4-(4-(4-hydroxypiperidin-1-yl)benzamido)phenyl)amino)phenyl)-1-methyl-1H-pyrrole-2-carboxamide (Compound 849)

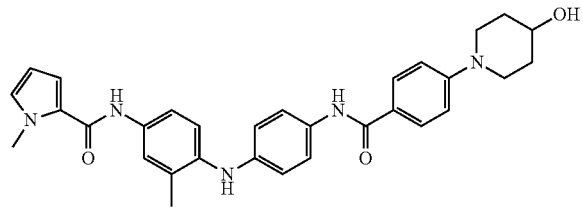 [SMILES: Cc1cc(NC(=O)c2cccn2C)ccc1Nc1ccc(NC(=O)c2ccc(N3CCC(O)CC3)cc2)cc1]

Compound 849 was prepared according to the procedure described in Scheme IV from $N^1$-(4-aminophenyl)-2-methylbenzene-1,4-diamine, 1-methyl-1H-pyrrole-2-carboxylic, and 4-(4-hydroxypiperidin-1-yl)benzoic acids. $[M+H]^+$ calcd for $C_{31}H_{33}N_5O_3$: 524.2. found 524.03.

Example 750

N-(4-((4-(4-(4-Hydroxypiperidin-1-yl)benzamido)phenyl)amino)-2-methylphenyl)-1-methyl-1H-pyrrole-2-carboxamide (Compound 850)

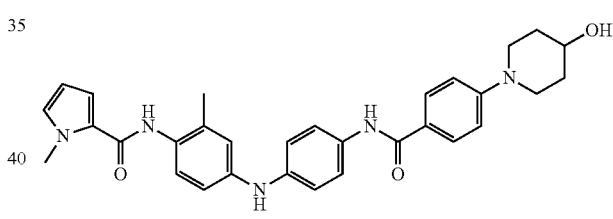

Compound 850 was prepared according to the procedure described in Scheme IV from $N^1$-(4-aminophenyl)-3-methylbenzene-1,4-diamine, 1-methyl-1H-pyrrole-2-carboxylic, and 4-(4-hydroxypiperidin-1-yl)benzoic acids. $[M+H]^+$ calcd for $C_{31}H_{33}N_5O_3$: 524.2. found 524.03.

Example 751

N-(4-((2-Methyl-4-(4-(4-hydroxypiperidin-1-yl)benzamido)phenyl)amino)phenyl)-1-ethyl-1H-pyrrole-2-carboxamide (Compound 851)

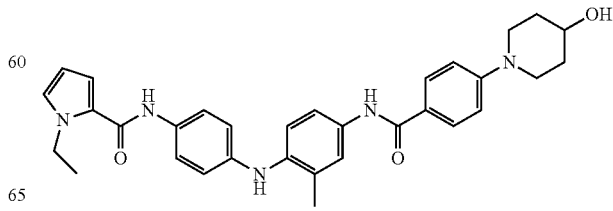

Compound 851 was prepared according to the procedure described in Scheme IV from N¹-(4-aminophenyl)-2-methylbenzene-1,4-diamine, 1-ethyl-1H-pyrrole-2-carboxylic, and 4-(4-hydroxypiperidin-1-yl)benzoic acids. ¹H NMR (400 MHz, Acetone-$d_6$) δ 9.09 (s, 1H), 8.95 (s, 1H), 7.89 (d, J=9.0 Hz, 2H), 7.66 (m, 3H), 7.54 (dd. J=2.4, 8.6 Hz, 1H), 7.16 (d, J=8.6 Hz, 1H), 6.99 (m, 3H), 6.94 (dd, J=2.6, 4.0 Hz, 1H), 6.89 (d, J=9.0 Hz, 2H), 6.57 (s, 1H), 6.09 (dd, J=2.6, 4.0 Hz, 1H), 4.46 (q, J=7.1 Hz, 2H), 3.85 (m, 1H), 3.75 (dt, J=4.4, 13 Hz, 2H), 3.08 (ddd, J=3.2, 9.8, 13.0 Hz, 2H), 2.26 (s, 3H), 1.93 (m, 2H), 1.60 (m, 2H), 1.39 (t, J=7.1 Hz, 3H).

Example 752

N-(3-Cyano-4-((4-(4-(4-hydroxypiperidin-1-yl)benzamido)phenyl)amino)phenyl)-1-methyl-1H-pyrrole-3-carboxamide (Compound 852)

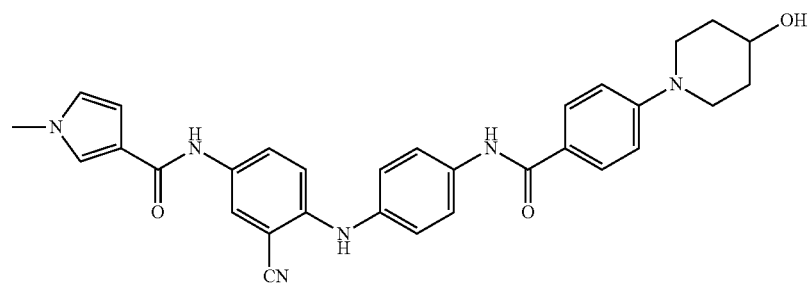 [SMILES: Cn1ccc(C(=O)Nc2ccc(Nc3ccc(NC(=O)c4ccc(N5CCC(O)CC5)cc4)cc3)c(C#N)c2)c1]

Compound 852 was prepared according to the procedure described in Scheme IV from N¹-(4-aminophenyl)-2-cyanobenzene-1,4-diamine, 1-methyl-1H-pyrrole-3-carboxylic, and 4-(4-hydroxypiperidin-1-yl)benzoic acids. [M+H]⁺ calcd for $C_{31}H_{30}N_6O_3$: 535.2. found: 535.04.

Example 753

N-(4-((2-Cyano-4-(4-(4-hydroxypiperidin-1-yl)benzamido)phenyl)amino)phenyl)-1-methyl-1H-pyrrole-3-carboxamide (Compound 853)

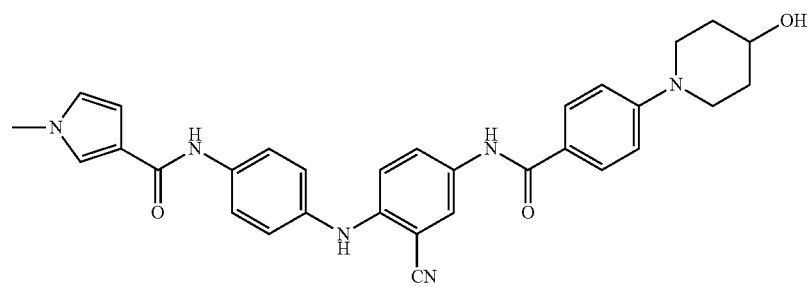 [SMILES: Cn1ccc(C(=O)Nc2ccc(Nc3ccc(NC(=O)c4ccc(N5CCC(O)CC5)cc4)cc3C#N)cc2)c1]

Compound 853 was prepared according to the procedure described in Scheme IV from N¹-(4-aminophenyl)-2-cyanobenzene-1,4-diamine, 1-methyl-1H-pyrrole-3-carboxylic, and 4-(4-hydroxypiperidin-1-yl)benzoic acids. [M+H]⁺ calcd for $C_{31}H_{30}N_6O_3$: 535.2. found: 535.04.

Example 754

(R)—N-(4-((4-(4-(3-Hydroxypyrrolidin-1-yl)benzamido)phenyl)amino)phenyl)-1-methyl-1H-pyrrole-3-carboxamide (Compound 854)

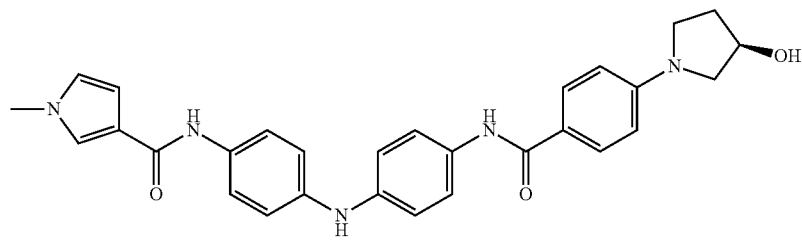 [SMILES: Cn1ccc(C(=O)Nc2ccc(Nc3ccc(NC(=O)c4ccc(N5CC[C@@H](O)C5)cc4)cc3)cc2)c1]

Compound 854 was prepared according to the procedure described in Scheme IV from 4,4'-diaminodiphenylamine, 1-methyl-1H-pyrrole-3-carboxylic, and (R)-4-(3-hydroxypyrrolidin-1-yl)benzoic acids. [M+H]$^+$ calcd for $C_{29}H_{29}N_5O_3$: 496.23. found: 495.95.

Example 755

N-(4-((4-(4-(4-Hydroxypiperidin-1-yl)benzamido)phenyl)amino)phenyl)-4,5-dimethyl-1H-pyrrole-3-carboxamide (Compound 855)

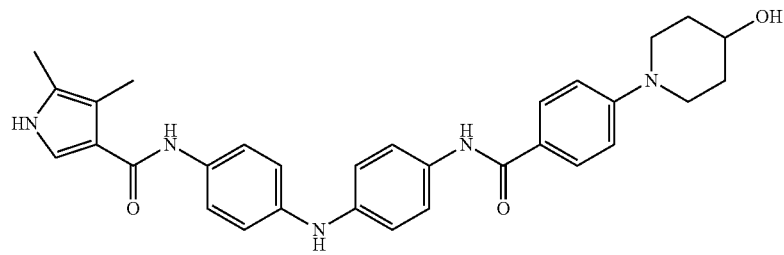

Compound 855 was prepared according to the procedure described in Scheme IV from 4,4'-diaminodiphenylamine, 4,5-dimethyl-1H-pyrrole-3-carboxylic, and 4-(4-hydroxypiperidin-1-yl)benzoic acids. [M+H]$^+$ calcd for $C_{31}H_{33}N_5O_3$: 524.26. found: 524.03.

Example 756

Methyl 5-((4-((4-(4-(4-hydroxypiperidin-1-yl)benzamido)phenyl)amino)phenyl)carbamoyl)-1H-pyrrole-2-carboxylate (Compound 856)

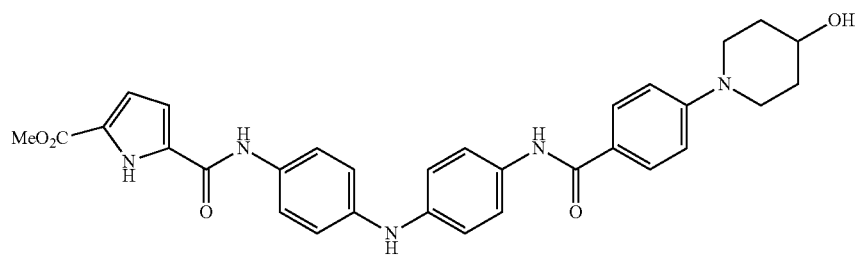 [SMILES: COC(=O)c1ccc(C(=O)Nc2ccc(Nc3ccc(NC(=O)c4ccc(N5CCC(O)CC5)cc4)cc3)cc2)[nH]1]

Compound 856 was prepared according to the procedure described in Scheme IV from 4,4'-diaminodiphenylamine, 5-methoxycarbonyl-1H-pyrrole-2-carboxylic, and 4-(4-hydroxypiperidin-1-yl)benzoic acids. [M+H]$^+$ calcd for $C_{31}H_{31}N_5O_5$: 554.13. found: 554.07.

Example 757

(R)—N-(4-((2-Fluoro-4-(4-(3-hydroxypyrrolidin-1-yl)benzamido)phenyl)amino)phenyl)-1-methyl-1H-pyrrole-3-carboxamide (Compound 857)

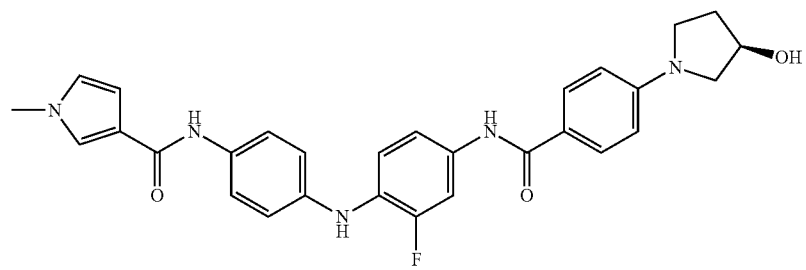 [SMILES: Cn1ccc(C(=O)Nc2ccc(Nc3ccc(NC(=O)c4ccc(N5CC[C@@H](O)C5)cc4)cc3F)cc2)c1]

Compound 857 was prepared according to the procedure described in Scheme IV from N$^1$-(4-aminophenyl)-2-fluorobenzene-1,4-diamine, 1-methyl-1H-pyrrole-3-carboxylic, and (R)-4-(3-hydroxypyrrolidin-1-yl)benzoic acids. [M+H]$^+$ calcd for $C_{29}H_{28}FN_5O_3$: 514.2. found: 513.98.

Example 758

N-(4-((4-(4-(4-Hydroxypiperidin-1-yl)benzamido)phenyl)amino)phenyl)-4-(methoxymethyl)-1-methyl-1H-pyrrole-2-carboxamide (Compound 858)

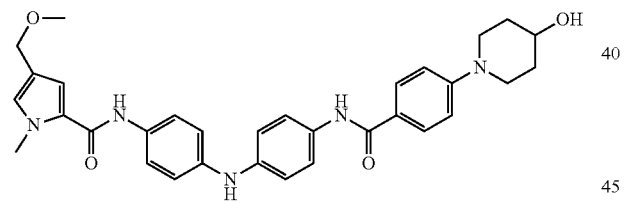

Compound 858 was prepared according to the procedure described in Scheme IV from 4,4'-diaminodiphenylamine, 4-methoxymethyl-1-methyl-1H-pyrrole-2-carboxylic, and 4-(4-hydroxypiperidin-1-yl)benzoic acids. [M+H]$^+$ calcd for $C_{32}H_{36}N_5O_4$: 554.2. found: 554.07.

Example 759

N-(4-((2-Fluoro-4-(4-(4-hydroxypiperidin-1-yl)benzamido)phenyl)amino)phenyl)-1-methyl-1H-pyrrole-3-carboxamide (Compound 859)

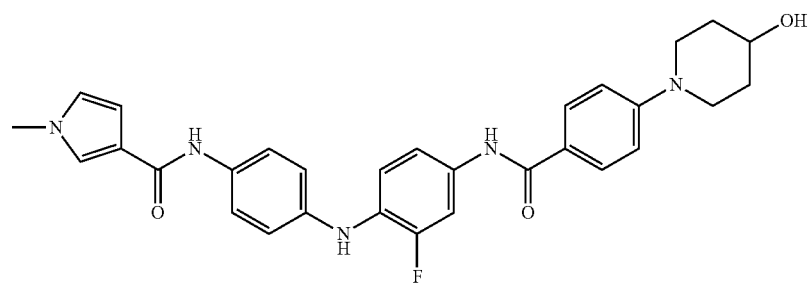

Compound 859 was prepared according to the procedure described in Scheme IV from N$^1$-(4-aminophenyl)-2-fluorobenzene-1,4-diamine, 1-methyl-1H-pyrrole-3-carboxylic, and 4-(4-hydroxypiperidin-1-yl)benzoic acids. [M+H]$^+$ calcd for C$_{30}$H$_{30}$FN$_5$O$_3$: 528.2. found 528.02.

Example 760

N-(4-((2-Fluoro-4-(4-(4-hydroxypiperidin-1-yl)benzamido)phenyl)amino)phenyl)-1H-pyrrole-3-carboxamide (Compound 860)

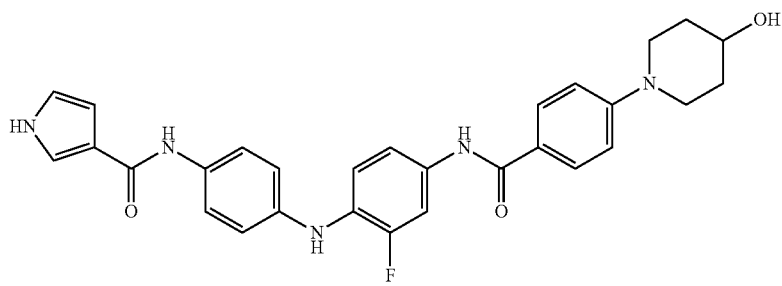 [SMILES: O=C(Nc1ccc(Nc2ccc(NC(=O)c3cc[nH]c3)cc2)c(F)c1)c1ccc(N2CCC(O)CC2)cc1]

Compound 860 was prepared according to the procedure described in Scheme IV from N$^1$-(4-aminophenyl)-2-fluorobenzene-1,4-diamine, 1H-pyrrole-3-carboxylic, and 4-(4-hydroxypiperidin-1-yl)benzoic acids. [M+H]$^+$ calcd for C$_{29}$H$_{28}$FN$_5$O$_3$: 514.22. found 513.98.

Example 761

N-(4-((4-(1H-Pyrrole-3-carboxamido)phenyl)amino)-3-fluorophenyl)-1-methyl-1H-pyrrole-2-carboxamide (Compound 861)

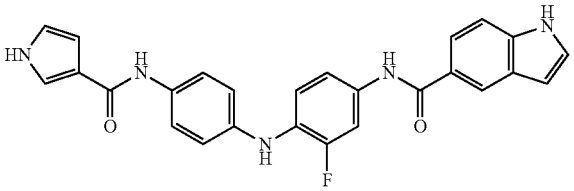 [SMILES: O=C(Nc1ccc(Nc2ccc(NC(=O)c3ccc4[nH]ccc4c3)cc2F)cc1)c1cc[nH]c1]

Compound 861 was prepared according to the procedure described in Scheme IV from N$^1$-(4-aminophenyl)-2-fluorobenzene-1,4-diamine and 1H-pyrrole-3-carboxylic acid. [M+H]$^+$ calcd for C$_{23}$H$_{20}$FN$_5$O$_2$: 418.1. found 417.88.

Example 762

N-(4-((4-(1H-pyrrole-3-carboxamido)phenyl)amino)-3-fluorophenyl)-1H-indole-5-carboxamide (Compound 862)

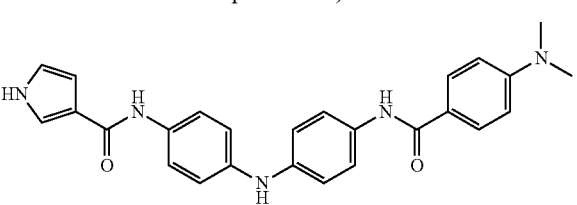

Compound 862 was prepared according to the procedure described in Scheme IV from N$^1$-(4-aminophenyl)-2-fluorobenzene-1,4-diamine, 1H-indole-5-carboxylic, and 1H-pyrrole-3-carboxylic acids. [M+H]$^+$ calcd for C$_{26}$H$_{20}$FN$_5$O$_2$: 454.1. found 453.91.

Example 763

N-(4-((4-(4-(Dimethylamino)benzamido)phenyl)amino)phenyl)-1H-pyrrole-3-carboxamide (Compound 863)

Compound 863 was prepared according to the procedure described in Scheme IV from 4,4'-diaminodiphenylamine, 4-dimethylaminobenzoic, and 1H-pyrrole-3-carboxylic acids. [M+H]$^+$ calcd for C$_{26}$H$_{25}$N$_5$O$_2$: 440.2. found 439.94.

Example 764

4-Azido-N-(4-((4-(4-(dimethylamino)benzamido)phenyl)amino)phenyl)benzamide (Compound 864)

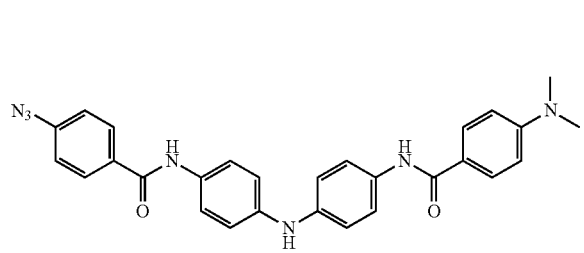 [SMILES: CN(C)c1ccc(C(=O)Nc2ccc(Nc3ccc(NC(=O)c4ccc(N=[N+]=[N-])cc4)cc3)cc2)cc1]

Compound 864 was prepared according to the procedure described in Scheme IV from 4,4'-diaminodiphenylamine, 4-dimethylaminobenzoic, and 4-azidobenzoic acids.

[M+H]$^+$ calcd for $C_{28}H_{25}N_7O_2$: 492.2. found 491.97.

Example 765

N-(4-((4-(4-(1H-Pyrrole-3-carboxamido)benzamido)phenyl)amino)phenyl)-1H-pyrrole-3-carboxamide (Compound 865)

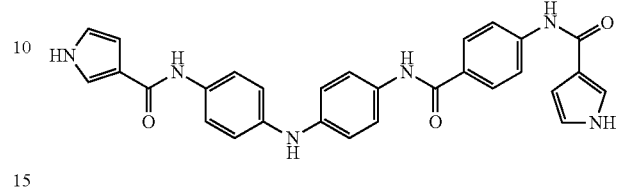

Compound 865 was prepared according to the procedure described in Scheme IV from 4,4'-diaminodiphenylamine, 4-aminobenzoic, and 1H-pyrrole-3-carboxylic acids.

[M+H]$^+$ calcd for $C_{29}H_{24}N_6O_3$: 505.1. found 504.93.

Example 766

(R)—N-(4-((4-(4-(3-Hydroxypyrrolidin-1-yl)benzamido)phenyl)amino)phenyl)-2,4-dimethyl-1H-pyrrole-3-carboxamide (Compound 866)

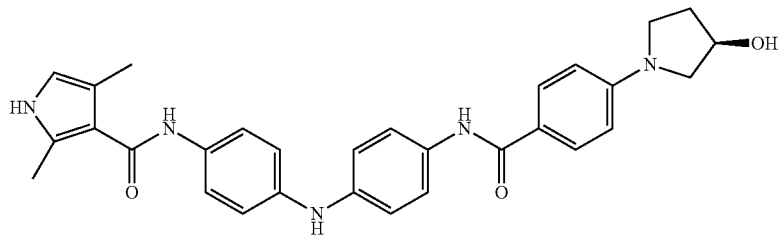 [SMILES: Cc1c[nH]c(C)c1C(=O)Nc1ccc(Nc2ccc(NC(=O)c3ccc(N4CC[C@@H](O)C4)cc3)cc2)cc1]

Compound 866 was prepared according to the procedure described in Scheme IV from 4,4'-diaminodiphenylamine, 2,4-dimethyl-1H-pyrrole-3-carboxylic, and (R)-4-(3-hydroxypyrrolidin-1-yl)benzoic acids. [M+H]$^+$ calcd for $C_{30}H_{31}N_5O_3$: 510.24. found: 509.99.

Example 767

N-(4-((4-(4-(4-Hydroxypiperidin-1-yl)benzamido)phenyl)amino)phenyl)-5-methyl-1H-pyrrole-3-carboxamide (Compound 867)

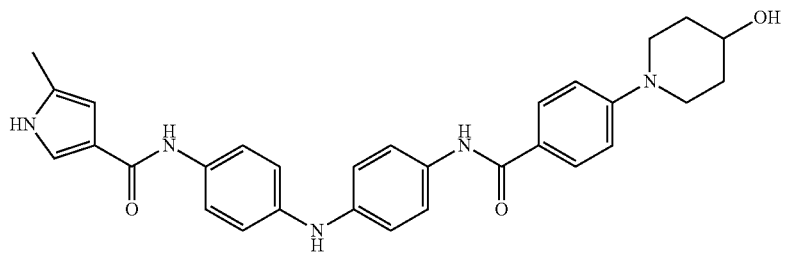 [SMILES: Cc1cc(C(=O)Nc2ccc(Nc3ccc(NC(=O)c4ccc(N5CCC(O)CC5)cc4)cc3)cc2)c[nH]1]

Compound 867 was prepared according to the procedure described in Scheme IV from 4,4'-diaminodiphenylamine, 5-methyl-1H-pyrrole-3-carboxylic, and 4-(4-hydroxypiperidin-1-yl)benzoic acids. [M+H]$^+$ calcd for $C_{30}, H_{31}N_5O_3$: 510.2. found: 509.99.

Example 768

N-(3-Cyano-4-((4-(4-(4-hydroxypiperidin-1-yl)benzamido)phenyl)amino)phenyl)-1-ethyl-1H-pyrrole-2-carboxamide (Compound 868)

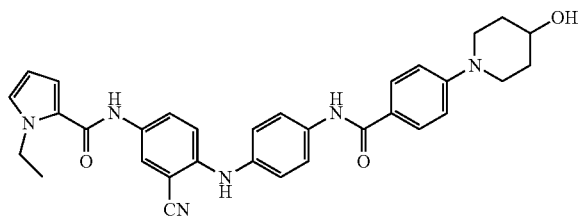 [SMILES: CCn1cccc1C(=O)Nc1ccc(Nc2ccc(NC(=O)c3ccc(N4CCC(O)CC4)cc3)cc2)c(C#N)c1]

Compound 868 was prepared according to the procedure described in Scheme IV from $N^1$-(4-aminophenyl)-2-cyanobenzene-1,4-diamine, 1-ethyl-1H-pyrrole-2-carboxylic, and 4-(4-hydroxypiperidin-1-yl)benzoic acids. $[M+H]^+$ calcd for $C_{32}H_{32}N_6O_3$: 549.2. found: 549.08.

Example 769

N-(3-Cyano-4-((4-(4-(4-hydroxypiperidin-1-yl)benzamido)phenyl)amino)phenyl)-1H-pyrrole-3-carboxamide (Compound 869)

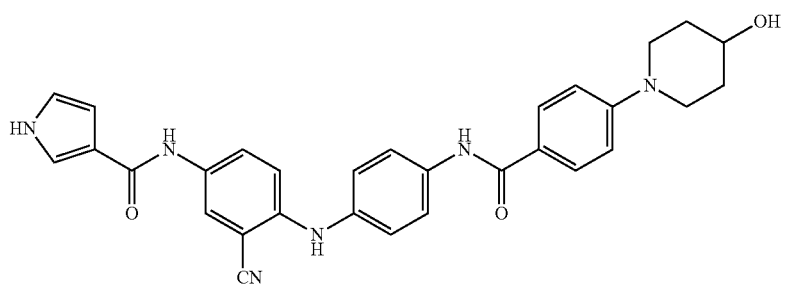

Compound 869 was prepared according to the procedure described in Scheme IV from $N^1$-(4-aminophenyl)-2-cyanobenzene-1,4-diamine, 1H-pyrrole-3-carboxylic, and 4-(4-hydroxypiperidin-1-yl)benzoic acids. $[M+H]^+$ calcd for $C_{30}H_{28}N_6O_3$: 521.22. found: 521.00.

Example 770

N-(3-Fluoro-4-((4-(4-(4-hydroxypiperidin-1-yl)benzamido)phenyl)amino)phenyl)-2,4-dimethyl-1H-pyrrole-3-carboxamide (Compound 870)

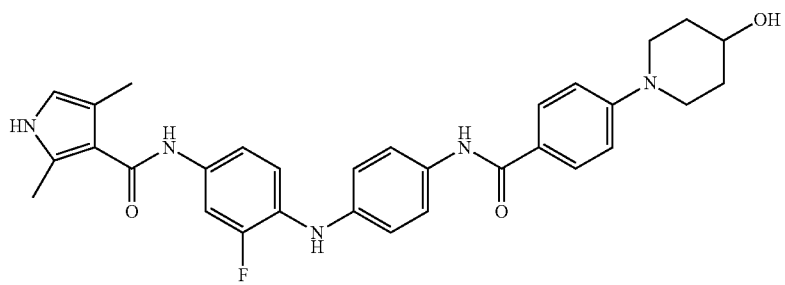 [SMILES: Cc1c[nH]c(C)c1C(=O)Nc1ccc(Nc2ccc(NC(=O)c3ccc(N4CCC(O)CC4)cc3)cc2)c(F)c1]

Compound 870 was prepared according to the procedure described in Scheme IV from $N^1$-(4-aminophenyl)-2-fluorobenzene-1,4-diamine, 2,4-dimethyl-1H-pyrrole-3-carboxylic, and 4-(4-hydroxypiperidin-1-yl)benzoic acids. $[M+H]^+$ calcd for $C_{31}H_{32}FN_5O_3$: 542.2. found 542.06.

Example 771

N-(3-Chloro-4-((4-(4-(4-hydroxypiperidin-1-yl)benzamido)phenyl)amino)phenyl)-1H-pyrrole-3-carboxamide (Compound 871)

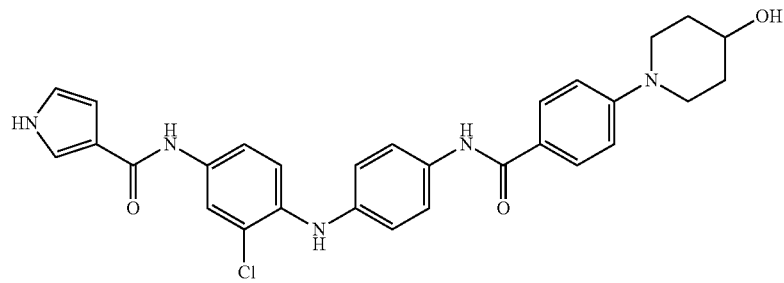 [SMILES: O=C(Nc1ccc(Nc2ccc(NC(=O)c3cc[nH]c3)cc2Cl)cc1)c1ccc(N2CCC(O)CC2)cc1]

Compound 871 was prepared according to the procedure described in Scheme IV from $N^1$-(4-aminophenyl)-2-chlorobenzene-1,4-diamine, 1H-pyrrole-3-carboxylic, and 4-(4-hydroxypiperidin-1-yl)benzoic acids. $[M+H]^+$ calcd for $C_{29}H_{28}ClN_5O_3$: 530.1. found 529.97.

Example 772

N-(3-Chloro-4-((4-(4-(4-hydroxypiperidin-1-yl)benzamido)phenyl)amino)phenyl)-1-methyl-1H-pyrrole-3-carboxamide (Compound 872)

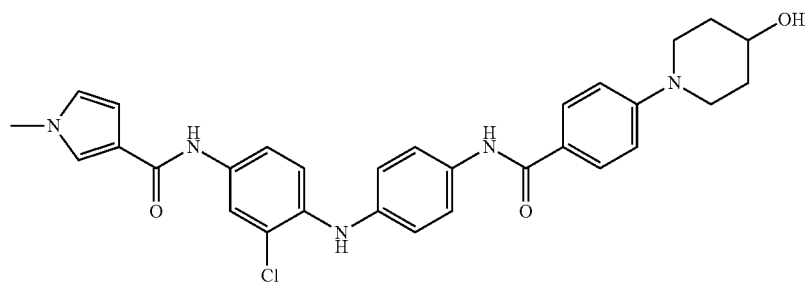 [SMILES: Cn1ccc(C(=O)Nc2ccc(Nc3ccc(NC(=O)c4ccc(N5CCC(O)CC5)cc4)cc3)c(Cl)c2)c1]

Compound 872 was prepared according to the procedure described in Scheme IV from $N^1$-(4-aminophenyl)-2-chlorobenzene-1,4-diamine, 1-methyl-1H-pyrrole-3-carboxylic, and 4-(4-hydroxypiperidin-1-yl)benzoic acids. $[M+H]^+$ calcd for $C_{30}H_{30}ClN_5O_3$: 544.2. found 544.02.

Example 773

N-(3-Chloro-4-((4-(4-(4-hydroxypiperidin-1-yl)benzamido)phenyl)amino)phenyl)-1-methyl-1H-pyrazole-4-carboxamide (Compound 873)

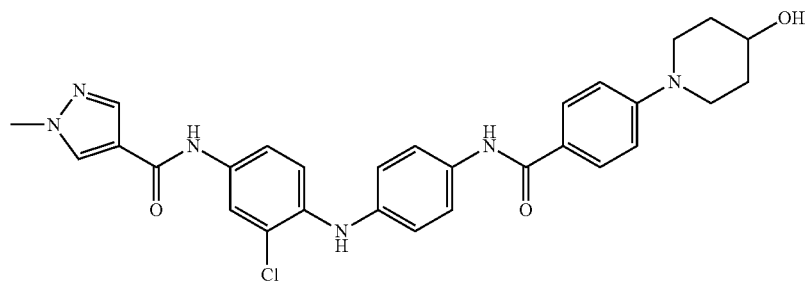 [SMILES: Cn1cc(C(=O)Nc2ccc(Nc3ccc(NC(=O)c4ccc(N5CCC(O)CC5)cc4)cc3)c(Cl)c2)cn1]

Compound 873 was prepared according to the procedure described in Scheme IV from $N^1$-(4-aminophenyl)-2-chlorobenzene-1,4-diamine, 1-methyl-1H-pyrazole-4-carboxylic, and 4-(4-hydroxypiperidin-1-yl)benzoic acids. $[M+H]^+$ calcd for $C_{29}H_{29}ClN_6O_3$: 545.2. found 544.96.

Example 774

N-(3-Fluoro-4-((4-(4-(4-hydroxypiperidin-1-yl)benzamido)phenyl)amino)phenyl)-1-methyl-1H-pyrazole-5-carboxamide (Compound 874)

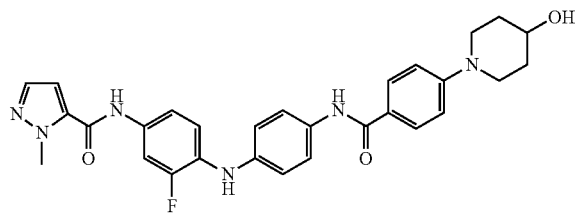 [SMILES: Cn1nccc1C(=O)Nc1ccc(Nc2ccc(NC(=O)c3ccc(N4CCC(O)CC4)cc3)cc2)c(F)c1]

Compound 874 was prepared according to the procedure described in Scheme IV from $N^1$-(4-aminophenyl)-2-fluorobenzene-1,4-diamine, 1-methyl-1H-pyrazole-5-carboxylic, and 4-(4-hydroxypiperidin-1-yl)benzoic acids. $[M+H]^+$ calcd for $C_{29}H_{29}FN_6O_3$: 529.2. found 529.03.

Example 775

N-(3-Chloro-4-((4-(4-(4-hydroxypiperidin-1-yl)benzamido)phenyl)amino)phenyl)-1-methyl-1H-pyrazole-5-carboxamide (Compound 875)

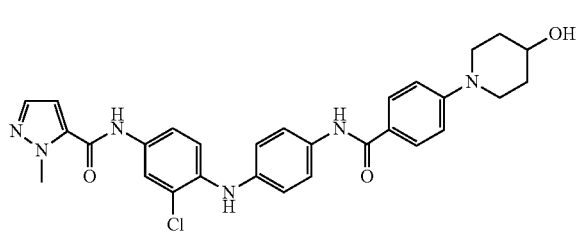 [SMILES: Cn1nccc1C(=O)Nc1ccc(Nc2ccc(NC(=O)c3ccc(N4CCC(O)CC4)cc3)cc2)c(Cl)c1]

Compound 875 was prepared according to the procedure described in Scheme IV from $N^1$-(4-aminophenyl)-2-chlorobenzene-1,4-diamine, 1-methyl-1H-pyrazole-5-carboxylic, and 4-(4-hydroxypiperidin-1-yl)benzoic acids. $[M+H]^+$ calcd for $C_{29}H_{29}ClN_6O_3$: 545.2. found 544.96.

Example 776

N-(3-Fluoro-4-((4-(4-(4-hydroxypiperidin-1-yl)benzamido)phenyl)amino)phenyl)-1-methyl-1H-pyrazole-4-carboxamide (Compound 876)

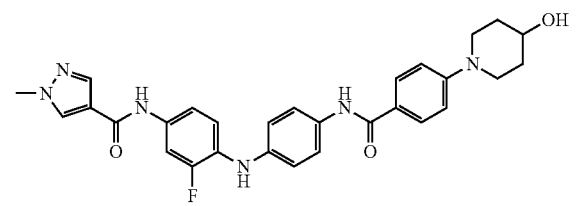 [SMILES: Cn1cc(C(=O)Nc2ccc(Nc3ccc(NC(=O)c4ccc(N5CCC(O)CC5)cc4)cc3)c(F)c2)cn1]

Compound 876 was prepared according to the procedure described in Scheme IV from $N^1$-(4-aminophenyl)-2-fluorobenzene-1,4-diamine, 1-methyl-1H-pyrazole-4-carboxylic, and 4-(4-hydroxypiperidin-1-yl)benzoic acids. $[M+H]^+$ calcd for $C_{29}H_{29}FN_6O_3$: 529.2. found 529.03.

Example 777

N-(4-((4-(4-(4-Hydroxypiperidin-1-yl)benzamido)-2-methylphenyl)amino)phenyl)-1-methyl-1H-pyrrole-2-carboxamide (Compound 877)

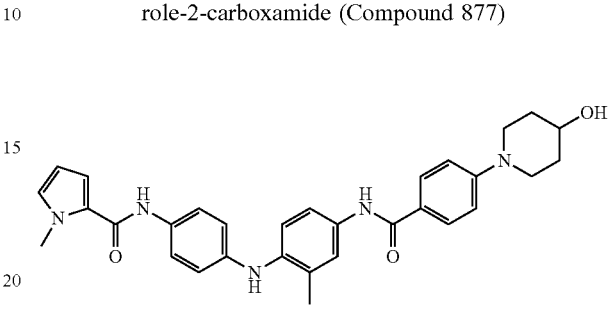

Compound 877 was prepared according to the procedure described in Scheme IV from $N^1$-(4-aminophenyl)-2-methylbenzene-1,4-diamine, 1-methyl-1H-pyrrole-2-carboxylic, and 4-(4-hydroxypiperidin-1-yl)benzoic acids. $[M+H]^+$ calcd for $C_{31}H_{33}N_5O_3$: 524.2. found 524.03.

Example 778

N-(4-((2-Cyano-4-(4-(4-hydroxypiperidin-1-yl)benzamido)phenyl)amino)phenyl)-1H-pyrrole-3-carboxamide (Compound 878)

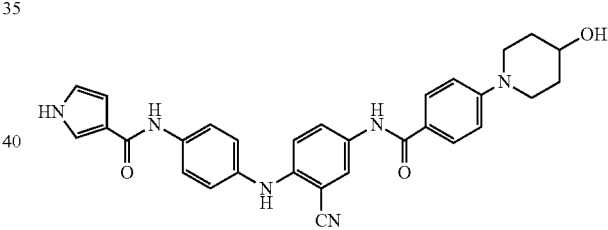

Compound 878 was prepared according to the procedure described in Scheme IV from $N^1$-(4-aminophenyl)-2-cyanobenzene-1,4-diamine, 1H-pyrrole-3-carboxylic, and 4-(4-hydroxypiperidin-1-yl)benzoic acids. $[M+H]^+$ calcd for $C_{30}H_{28}N_6O_3$: 521.22. found: 521.00.

Example 779

N-(3-Chloro-4-((4-(4-(4-hydroxypiperidin-1-yl)benzamido)phenyl)amino)phenyl)-1-ethyl-1H-pyrrole-2-carboxamide (Compound 879)

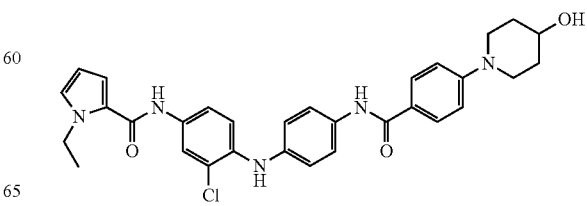

Compound 879 was prepared according to the procedure described in Scheme IV from $N^1$-(4-aminophenyl)-2-chlorobenzene-1,4-diamine, 1-ethyl-1H-pyrrole-2-carboxylic, and 4-(4-hydroxypiperidin-1-yl)benzoic acids. [M+H]+ calcd for $C_{31}H_{32}ClN_5O_3$: 558.2. found 558.06.

Example 780

N-(3-Chloro-4-((4-(4-(4-hydroxypiperidin-1-yl)benzamido)phenyl)amino)phenyl)-1H-indole-5-carboxamide (Compound 880)

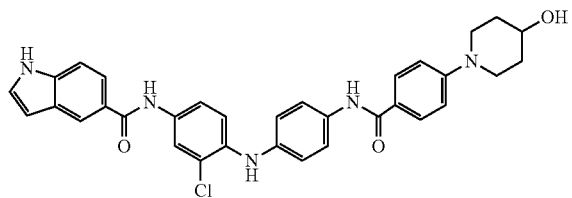 [SMILES: O=C(Nc1ccc(Nc2ccc(NC(=O)c3ccc4[nH]ccc4c3)cc2Cl)cc1)c1ccc(N2CCC(O)CC2)cc1]

Compound 880 was prepared according to the procedure described in Scheme IV from $N^1$-(4-aminophenyl)-2-chlorobenzene-1,4-diamine, 1H-indole-5-carboxylic, and 4-(4-hydroxypiperidin-1-yl)benzoic acids. [M+H]+ calcd for $C_{33}H_{30}ClN_5O_3$: 580.20. found 580.00.

Example 781

N-(3-Fluoro-4-((4-(4-(4-ethoxypiperidin-1-yl)benzamido)phenyl)amino)phenyl)-1H-pyrrole-3-carboxamide (Compound 881)

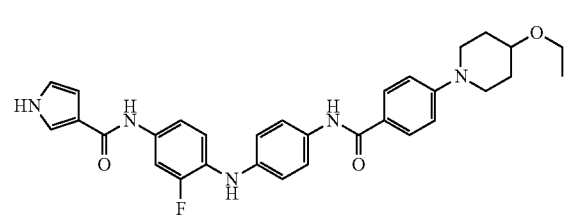 [SMILES: CCOC1CCN(c2ccc(C(=O)Nc3ccc(Nc4ccc(NC(=O)c5cc[nH]c5)cc4F)cc3)cc2)CC1]

Compound 881 was prepared according to the procedure described in Scheme IV from $N^1$-(4-aminophenyl)-2-fluorobenzene-1,4-diamine, 1H-pyrrole-3-carboxylic, and 4-(4-ethoxypiperidin-1-yl)benzoic acids. [M+H]+ calcd for $C_{31}H_{32}FN_5O_3$: 542.25. found: 542.06.

Example 782

N-(3-Fluoro-4-((4-(4-(4-ethoxypiperidin-1-yl)benzamido)phenyl)amino)phenyl)-1-methyl-1H-pyrazole-5-carboxamide (Compound 882)

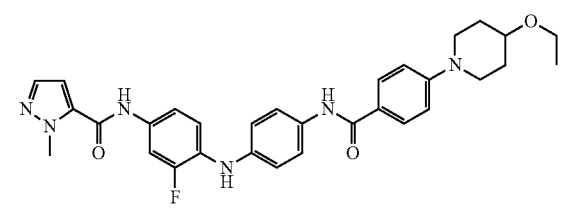 [SMILES: CCOC1CCN(c2ccc(C(=O)Nc3ccc(Nc4ccc(NC(=O)c5ccnn5C)cc4F)cc3)cc2)CC1]

Compound 882 was prepared according to the procedure described in Scheme IV from $N^1$-(4-aminophenyl)-2-fluorobenzene-1,4-diamine, 1-methyl-1H-pyrazole-5-carboxylic, and 4-(4-ethoxypiperidin-1-yl)benzoic acids. [M+H]+ calcd for $C_{31}H_{33}FN_6O_3$: 557.2. found: 557.11.

Example 783

N-(4-((5-(4-(4-Hydroxypiperidin-1-yl)benzamido)pyridin-2-yl)amino)phenyl)-1-methyl-1H-pyrrole-3-carboxamide (Compound 883)

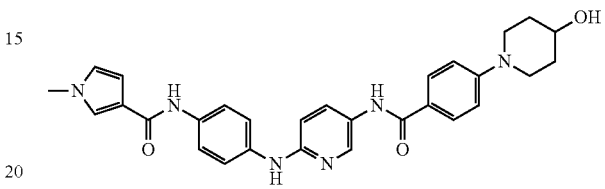

Compound 883 was prepared according to the procedure described in Scheme IV from $N^2$-(4-aminophenyl)pyridine-2,5-diamine, 1-methyl-1H-pyrrole-3-carboxylic, and 4-(4-hydroxypiperidin-1-yl)benzoic acids. [M+H]+ calcd for $C_{29}H_{30}N_6O_3$: 511.2. found 511.01.

Example 784

N-(6-((4-(4-(4-Hydroxypiperidin-1-yl)benzamido)phenyl)amino)pyridin-3-yl)-1-methyl-1H-pyrrole-3-carboxamide (Compound 884)

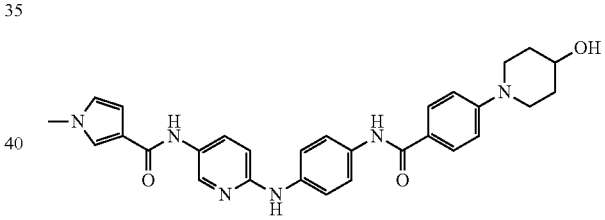

Compound 884 was prepared according to the procedure described in Scheme IV from $N^2$-(4-aminophenyl)pyridine-2,5-diamine, 1-methyl-1H-pyrrole-3-carboxylic, and 4-(4-hydroxypiperidin-1-yl)benzoic acids. [M+H]+ calcd for $C_{29}H_{30}N_6O_3$: 511.2. found 511.01.

Example 785

N-(4-((2-Cyano-4-(4-(4-trifluoromethylpiperidin-1-yl)benzamido)phenyl)amino)phenyl)-1H-pyrrole-3-carboxamide (Compound 885)

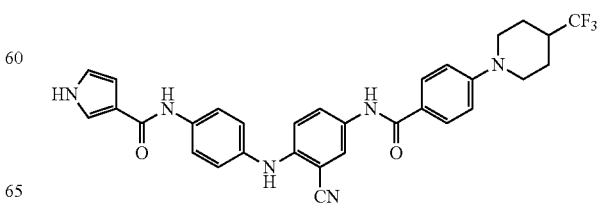

Compound 885 was prepared according to the procedure described in Scheme IV from $N^1$-(4-aminophenyl)-2-cyanobenzene-1,4-diamine, 1H-pyrrole-3-carboxylic, and 4-(4-trifluoromethylpiperidin-1-yl)benzoic acids. $[M+H]^+$ calcd for $C_{31}H_{27}F_3N_6O_2$: 573.2. found: 573.05.

Example 786

N-(3-Fluoro-4-((4-(4-(4-hydroxypiperidin-1-yl)benzamido)phenyl)amino)phenyl)-4-methyl-1H-pyrrole-3-carboxamide (Compound 886)

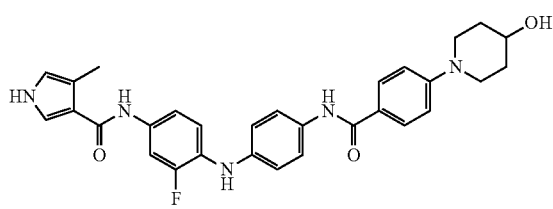 [SMILES: Cc1c[nH]cc1C(=O)Nc1ccc(Nc2ccc(NC(=O)c3ccc(N4CCC(O)CC4)cc3)cc2)c(F)c1]

Compound 886 was prepared according to the procedure described in Scheme IV from $N^1$-(4-aminophenyl)-2-fluorobenzene-1,4-diamine, 4-methyl-1H-pyrrole-3-carboxylic, and 4-(4-hydroxypiperidin-1-yl)benzoic acids. $[M+H]^+$ calcd for $C_{30}H_{30}FN_5O_3$: 528.2. found: 528.02.

Example 787

N-(3-Fluoro-4-((4-(4-(4-hydroxypiperidin-1-yl)benzamido)phenyl)amino)phenyl)-5-methyl-1H-pyrrole-3-carboxamide (Compound 887)

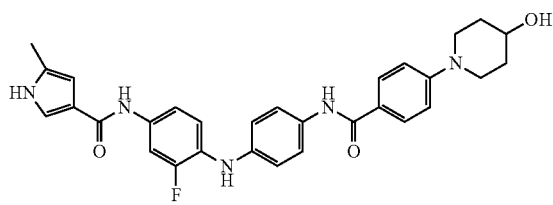 [SMILES: Cc1cc(C(=O)Nc2ccc(Nc3ccc(NC(=O)c4ccc(N5CCC(O)CC5)cc4)cc3)c(F)c2)c[nH]1]

Compound 887 was prepared according to the procedure described in Scheme IV from $N^1$-(4-aminophenyl)-2-fluorobenzene-1,4-diamine, 5-methyl-1H-pyrrole-3-carboxylic, and 4-(4-hydroxypiperidin-1-yl)benzoic acids. $[M+H]^+$ calcd for $C_{30}H_{30}FN_5O_3$: 528.2. found: 528.08.

Example 788

N-(3-Fluoro-4-((4-(4-(4-hydroxypiperidin-1-yl)benzamido)phenyl)amino)phenyl)-1H-indole-5-carboxamide (Compound 888)

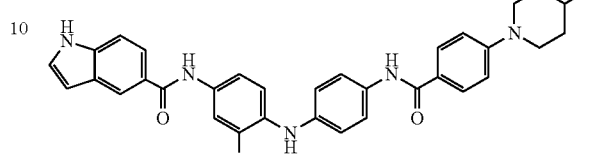

Compound 888 was prepared according to the procedure described in Scheme IV from $N^1$-(4-aminophenyl)-2-fluorobenzene-1,4-diamine, 1H-indole-5-carboxylic, and 4-(4-hydroxypiperidin-1-yl)benzoic acids. $[M+H]^+$ calcd for $C_{33}H_{30}FN_5O_3$: 564.23. found 564.07.

Example 789

N-(4-((2-Cyano-4-(4-(4-hydroxypiperidin-1-yl)benzamido)phenyl)amino)phenyl)-1H-indole-5-carboxamide (Compound 889)

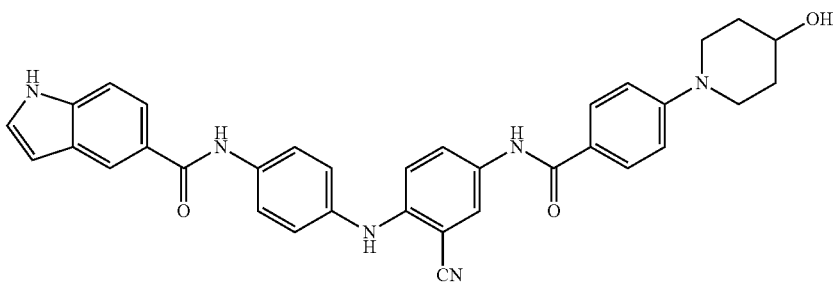 [SMILES: N#Cc1cc(NC(=O)c2ccc(N3CCC(O)CC3)cc2)ccc1Nc1ccc(NC(=O)c2ccc3[nH]ccc3c2)cc1]

Compound 889 was prepared according to the procedure described in Scheme IV from $N^1$-(4-aminophenyl)-2-cyanobenzene-1,4-diamine, 1H-indole-5-carboxylic, and 4-(4-hydroxypiperidin-1-yl)benzoic acids. $[M+H]^+$ calcd for $C_{34}H_{30}N_6O_3$: 571.25. found: 571.02.

Example 790

N-(4-((2-Cyano-4-(4-(4-hydroxypiperidin-1-yl)benzamido)phenyl)amino)phenyl)-1-methyl-1H-pyrazole-5-carboxamide (Compound 890)

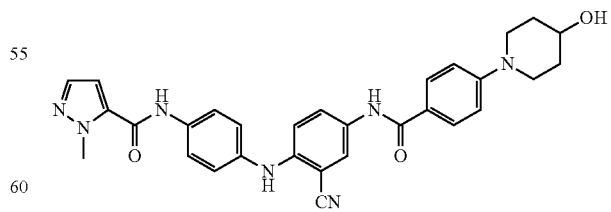

Compound 890 was prepared according to the procedure described in Scheme IV from $N^1$-(4-aminophenyl)-2-cyanobenzene-1,4-diamine, 1-methyl-1H-pyrazole-5-carboxylic, and 4-(4-hydroxypiperidin-1-yl)benzoic acids. $[M+H]^+$ calcd for $C_{30}H_{29}N_7O_3$: 536.2. found: 536.05.

Example 791

N-(4-((4-(4-(4-Hydroxypiperidin-1-yl)benzamido)phenyl)amino)phenyl)-1,3-dimethyl-1H-pyrazole-4-carboxamide (Compound 891)

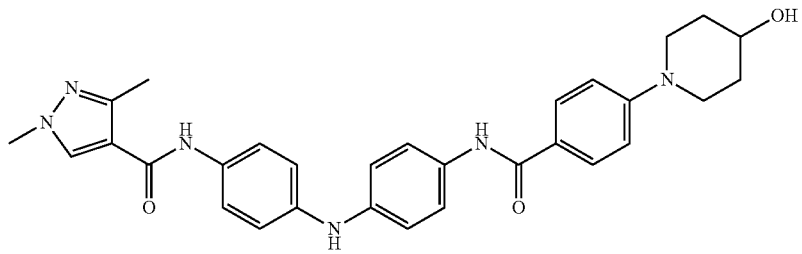 [SMILES: Cc1nn(C)cc1C(=O)Nc1ccc(Nc2ccc(NC(=O)c3ccc(N4CCC(O)CC4)cc3)cc2)cc1]

Compound 891 was prepared according to the procedure described in Scheme IV from 4,4'-diaminodiphenylamine, 1,3-dimethyl-1H-pyrazole-4-carboxylic, and 4-(4-hydroxypiperidin-1-yl)benzoic acids. [M+H]+ calcd for $C_{30}H_{32}N_6O_3$: 525.25. found 525.05.

Example 792

N-(3-Fluoro-4-((4-(4-(4-hydroxypiperidin-1-yl)benzamido)phenyl)amino)phenyl)-1,3-dimethyl-1H-pyrazole-4-carboxamide (Compound 892)

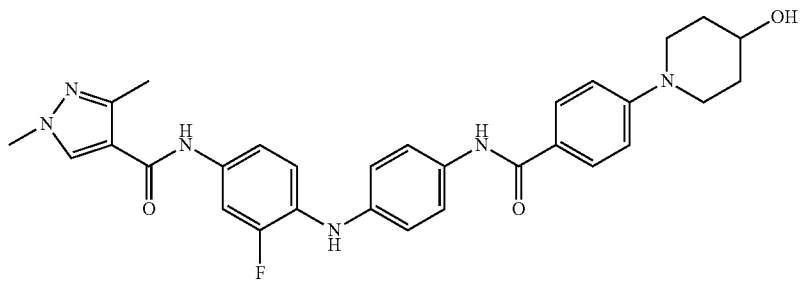 [SMILES: Cc1nn(C)cc1C(=O)Nc1ccc(Nc2ccc(NC(=O)c3ccc(N4CCC(O)CC4)cc3)cc2)c(F)c1]

Compound 892 was prepared according to the procedure described in Scheme IV from $N^1$-(4-aminophenyl)-2-fluorobenzene-1,4-diamine, 1,3-dimethyl-1H-pyrazole-4-carboxylic, and 4-(4-hydroxypiperidin-1-yl)benzoic acids. [M+H]+ calcd for $C_{30}H_{31}FN_6O_3$: 543.2. found 543.07.

Example 793

N-(4-((4-(4-(4-Hydroxypiperidin-1-yl)benzamido)phenyl)amino)phenyl)-1,5-dimethyl-1H-pyrazole-4-carboxamide (Compound 893)

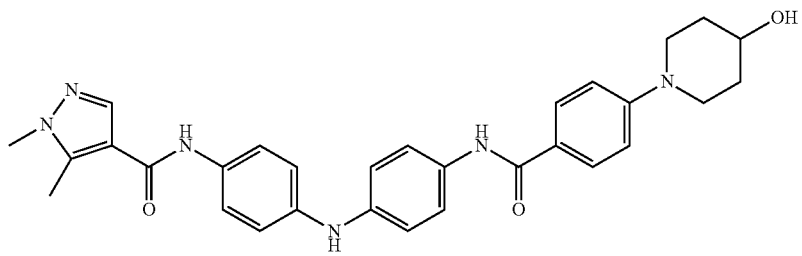 [SMILES: Cc1c(C(=O)Nc2ccc(Nc3ccc(NC(=O)c4ccc(N5CCC(O)CC5)cc4)cc3)cc2)cnn1C]

Compound 893 was prepared according to the procedure described in Scheme IV from 4,4'-diaminodiphenylamine, 1,5-dimethyl-1H-pyrazole-4-carboxylic, and 4-(4-hydroxypiperidin-1-yl)benzoic acids. [M+H]$^+$ calcd for $C_{30}H_{32}N_6O_3$: 525.25. found 525.05.

Example 794

N-(3-Fluoro-4-((4-(4-(4-hydroxypiperidin-1-yl)benzamido)phenyl)amino)phenyl)-1,5-dimethyl-1H-pyrazole-4-carboxamide (Compound 894)

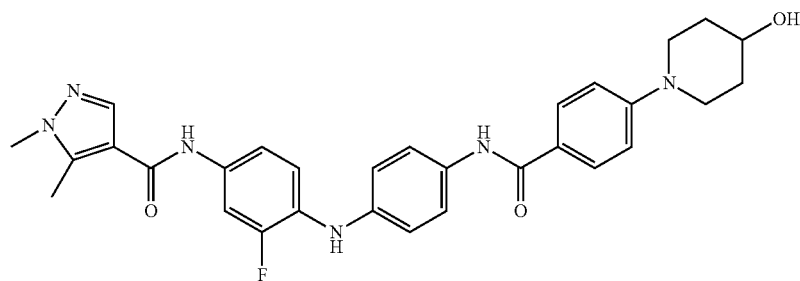

Compound 894 was prepared according to the procedure described in Scheme IV from N$^1$-(4-aminophenyl)-2-fluorobenzene-1,4-diamine, 1,5-dimethyl-1H-pyrazole-4-carboxylic, and 4-(4-hydroxypiperidin-1-yl)benzoic acids. [M+H]$^+$ calcd for $C_{30}H_{31}FN_6O_3$: 543.2. found 543.07.

Example 795

N-(3-Chloro-4-((4-(4-(4-hydroxypiperidin-1-yl)benzamido)phenyl)amino)phenyl)-1,5-dimethyl-1H-pyrazole-4-carboxamide (Compound 895)

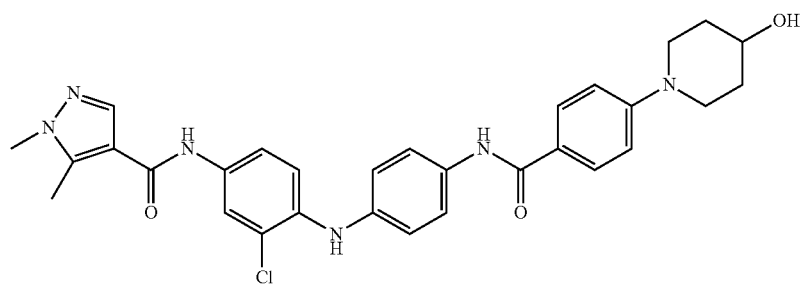 [SMILES: Cc1c(C(=O)Nc2ccc(Nc3ccc(NC(=O)c4ccc(N5CCC(O)CC5)cc4)cc3)c(F)c2)cnn1C]

Compound 895 was prepared according to the procedure described in Scheme IV from N$^1$-(4-aminophenyl)-2-chlorobenzene-1,4-diamine, 1,5-dimethyl-1H-pyrazole-4-carboxylic, and 4-(4-hydroxypiperidin-1-yl)benzoic acids. [M+H]$^+$ calcd for $C_{30}H_{31}ClN_6O_3$: 559.2. found 559.00.

Example 796

N-(3-Chloro-4-((4-(4-(4-hydroxypiperidin-1-yl)benzamido)phenyl)amino)phenyl)-1,3-dimethyl-1H-pyrazole-4-carboxamide (Compound 896)

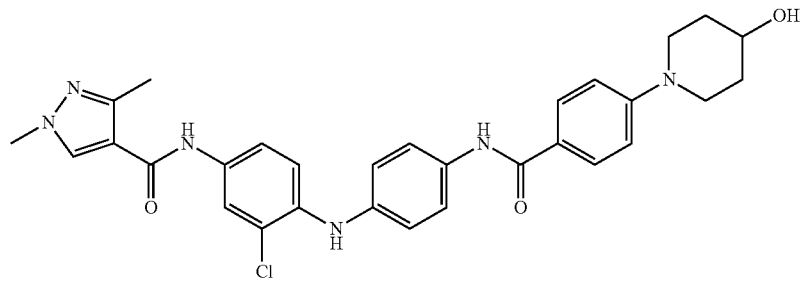 [SMILES: Cc1nn(C)cc1C(=O)Nc1ccc(Nc2ccc(NC(=O)c3ccc(N4CCC(O)CC4)cc3)cc2)c(Cl)c1]

Compound 896 was prepared according to the procedure described in Scheme IV from $N^1$-(4-aminophenyl)-2-chlorobenzene-1,4-diamine, 1,3-dimethyl-1H-pyrazole-4-carboxylic, and 4-(4-hydroxypiperidin-1-yl)benzoic acids. $[M+H]^+$ calcd for $C_{30}H_{31}ClN_6O_3$: 559.2. found 559.00.

Example 797

N-(4-((4-(4-(4-Hydroxypiperidin-1-yl)benzamido)phenyl)amino)phenyl)-3,5-dimethyl-1H-pyrazole-4-carboxamide (Compound 897)

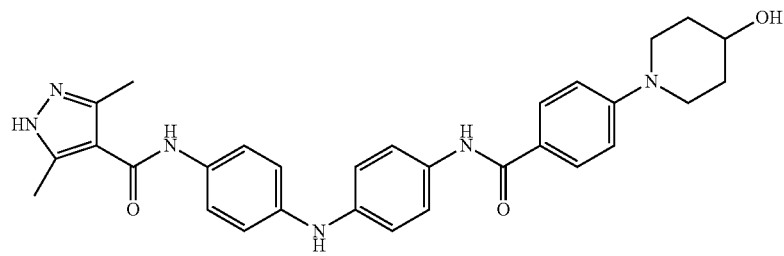

Compound 897 was prepared according to the procedure described in Scheme IV from 4,4'-diaminodiphenylamine, 3,5-dimethyl-1H-pyrazole-4-carboxylic, and 4-(4-hydroxypiperidin-1-yl)benzoic acids. $[M+H]^+$ calcd for $C_{30}H_{32}N_6O_3$: 525.25. found 525.05.

Example 798

N-(4-((2-Fluoro-4-(4-(4-hydroxypiperidin-1-yl)benzamido)phenyl)amino)phenyl)-1-methyl-1H-pyrazole-5-carboxamide (Compound 898)

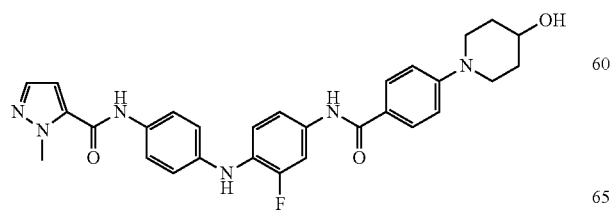

Compound 898 was prepared according to the procedure described in Scheme IV from $N^1$-(4-aminophenyl)-2-fluorobenzene-1,4-diamine, 1-methyl-1H-pyrazole-5-carboxylic, and 4-(4-hydroxypiperidin-1-yl)benzoic acids. [M+H]$^+$ calcd for $C_{29}H_{29}FN_6O_3$: 529.2. found: 529.03.

Example 799

N-(4-((4-(4-(4-Hydroxypiperidin-1-yl)benzamido)phenyl)amino)phenyl)-1,4,5,6-tetrahydrocyclopenta[c]pyrazole-3-carboxamide (Compound 899)

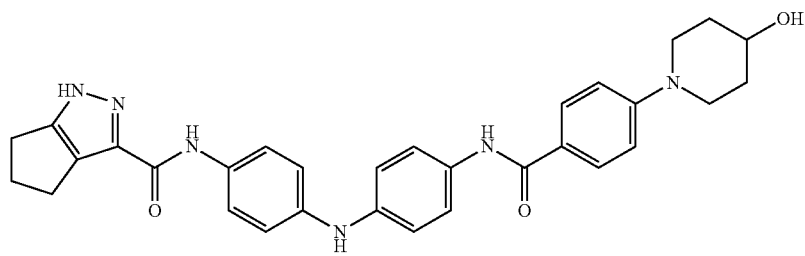 [SMILES: O=C(Nc1ccc(Nc2ccc(NC(=O)c3n[nH]c4c3CCC4)cc2)cc1)c1ccc(N2CCC(O)CC2)cc1]

Compound 899 was prepared according to the procedure described in Scheme IV from 4,4'-diaminodiphenylamine, 1,4,5,6-tetrahydrocyclopenta[c]pyrazole-3-carboxylic, and 4-(4-hydroxypiperidin-1-yl)benzoic acids. [M+H]$^+$ calcd for $C_{31}H_{32}N_6O_3$: 537.2. found 537.06.

Example 800

N-(4-((4-(4-(4-Hydroxypiperidin-1-yl)benzamido)phenyl)amino)phenyl)-1-ethyl-5-methyl-1H-pyrrole-2-carboxamide (Compound 900)

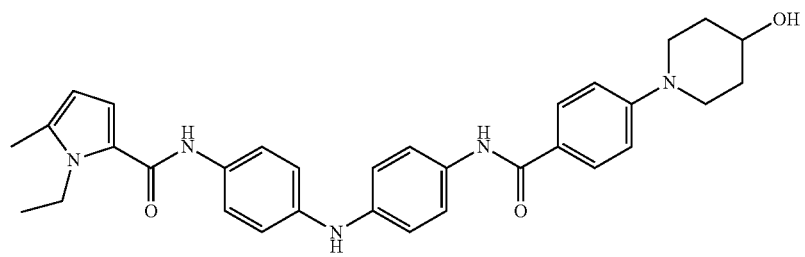 [SMILES: CCn1c(C)ccc1C(=O)Nc1ccc(Nc2ccc(NC(=O)c3ccc(N4CCC(O)CC4)cc3)cc2)cc1]

Compound 900 was prepared according to the procedure described in Scheme IV from 4,4'-diaminodiphenylamine, 1-ethyl-5-methyl-1H-pyrrole-2-carboxylic, and 4-(4-hydroxypiperidin-1-yl)benzoic acids. [M+H]$^+$ calcd for $C_{32}H_{35}N_5O_3$: 538.27. found: 538.08.

Example 801

N-(4-((4-(4-(4-Hydroxypiperidin-1-yl)benzamido)phenyl)amino)phenyl)-5-hydroxymethyl-1H-pyrrole-2-carboxamide (Compound 901)

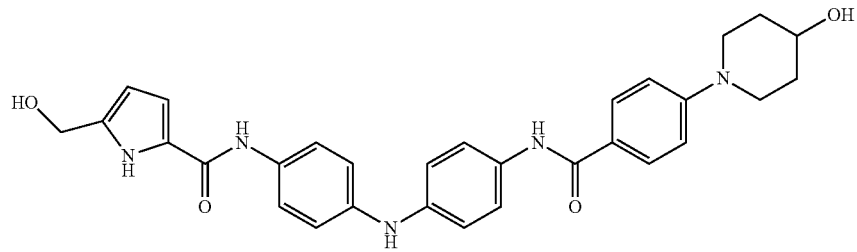 [SMILES: O=C(Nc1ccc(Nc2ccc(NC(=O)c3ccc(CO)[nH]3)cc2)cc1)c1ccc(N2CCC(O)CC2)cc1]

Compound 901 was prepared according to the procedure described in Scheme IV from 4,4'-diaminodiphenylamine, 5-hydroxymethyl-1H-pyrrole-2-carboxylic, and 4-(4-hydroxypiperidin-1-yl)benzoic acids. [M+H]$^+$ calcd for $C_{32}H_{33}N_5O_5$: 568.16. found: 568.05.

Example 802

Methyl 4-((4-((4-(4-(4-hydroxypiperidin-1-yl)benzamido)phenyl)amino)phenyl)carbamoyl)-1H-pyrrole-2-carboxylate (Compound 902)

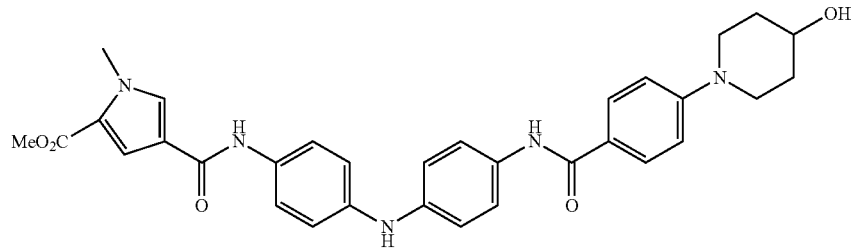 [SMILES: COC(=O)c1cc(C(=O)Nc2ccc(Nc3ccc(NC(=O)c4ccc(N5CCC(O)CC5)cc4)cc3)cc2)cn1C]

Compound 902 was prepared according to the procedure described in Scheme IV from 4,4'-diaminodiphenylamine, 5-methoxycarbonyl-1H-pyrrole-3-carboxylic, and 4-(4-hydroxypiperidin-1-yl)benzoic acids. [M+H]$^+$ calcd for $C_{30}H_{31}N_5O_4$: 526.12. found: 526.06.

Example 803

N-(3-Fluoro-4-((2-fluoro-4-(4-(4-hydroxypiperidin-1-yl)benzamido)phenyl)amino)phenyl)-1H-pyrrole-2-carboxamide (Compound 903)

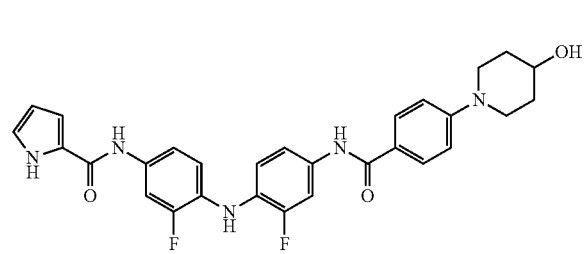 [SMILES: O=C(Nc1ccc(Nc2ccc(NC(=O)c3ccc[nH]3)cc2F)c(F)c1)c1ccc(N2CCC(O)CC2)cc1]

Compound 903 was prepared according to the procedure described in Scheme IV from 4,4'-diamino-2,2'-difluorodiphenylamine, 1H-pyrrole-2-carboxylic, and 4-(4-hydroxypiperidin-1-yl)benzoic acids. [M+H]$^+$ calcd for $C_{29}H_{27}F_2N_5O_3$: 532.21. found: 532.00.

Example 804

N-(3-Fluoro-4-((2-fluoro-4-(4-(4-hydroxypiperidin-1-yl)benzamido)phenyl)amino)phenyl)-1-methyl-1H-pyrazole-5-carboxamide (Compound 904)

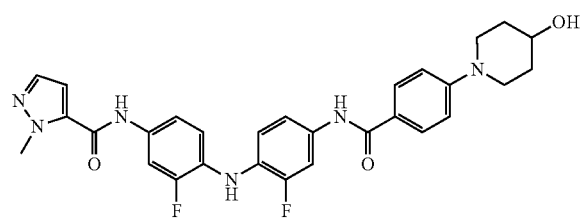 [SMILES: Cn1nccc1C(=O)Nc1ccc(Nc2ccc(NC(=O)c3ccc(N4CCC(O)CC4)cc3)cc2F)c(F)c1]

Compound 904 was prepared according to the procedure described in Scheme IV from 4,4'-diamino-2,2'-difluorodiphenylamine, 1-methyl-1H-pyrazole-5-carboxylic, and 4-(4-hydroxypiperidin-1-yl)benzoic acids. [M+H]$^+$ calcd for $C_{29}H_{28}F_2N_6O_3$: 547.2. found: 547.05.

Example 805

N-(3-Fluoro-4-((2-fluoro-4-(4-(4-hydroxypiperidin-1-yl)benzamido)phenyl)amino)phenyl)-1H-pyrrole-3-carboxamide (Compound 905)

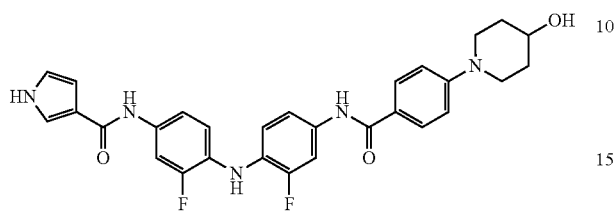

Compound 905 was prepared according to the procedure described in Scheme IV from 4,4'-diamino-2,2'-difluorodiphenylamine, 1H-pyrrole-3-carboxylic, and 4-(4-hydroxypiperidin-1-yl)benzoic acids. [M+H]$^+$ calcd for $C_{29}H_{27}F_2N_5O_3$: 532.21. found 532.00.

Example 806

N-(4-((2-Fluoro-4-(4-(4-hydroxypiperidin-1-yl)benzamido)phenyl)amino)phenyl)-5-methyl-1H-pyrrole-3-carboxamide (Compound 906)

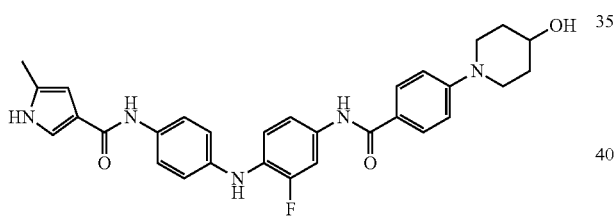

Compound 906 was prepared according to the procedure described in Scheme IV from N$^1$-(4-aminophenyl)-2-fluorobenzene-1,4-diamine, 5-methyl-1H-pyrrole-3-carboxylic, and 4-(4-hydroxypiperidin-1-yl)benzoic acids. [M+H]$^+$ calcd for $C_{30}H_{30}FN_5O_3$: 528.2. found: 528.02.

Example 807

N-(4-((2-Fluoro-4-(4-(4-hydroxypiperidin-1-yl)benzamido)phenyl)amino)phenyl)-4-methyl-1H-pyrrole-3-carboxamide (Compound 907)

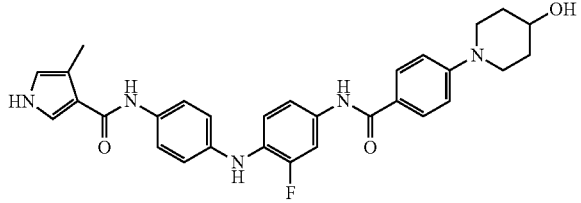 [SMILES: Cc1c[nH]cc1C(=O)Nc1ccc(Nc2ccc(NC(=O)c3ccc(N4CCC(O)CC4)cc3)cc2F)cc1]

Compound 907 was prepared according to the procedure described in Scheme IV from N$^1$-(4-aminophenyl)-2-fluorobenzene-1,4-diamine, 4-methyl-1H-pyrrole-3-carboxylic, and 4-(4-hydroxypiperidin-1-yl)benzoic acids. [M+H]$^+$ calcd for $C_{30}H_{30}FN_5O_3$: 528.2. found: 528.02.

Example 808

N-(4-((2-Chloro-4-(4-(4-hydroxypiperidin-1-yl)benzamido)phenyl)amino)phenyl)-1H-pyrrole-3-carboxamide (Compound 908)

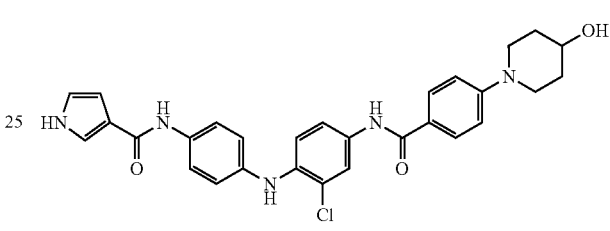

Compound 908 was prepared according to the procedure described in Scheme IV from N$^1$-(4-aminophenyl)-2-chlorobenzene-1,4-diamine, 1H-pyrrole-3-carboxylic, and 4-(4-hydroxypiperidin-1-yl)benzoic acids. [M+H]$^+$ calcd for $C_{29}H_{28}ClN_5O_3$: 530.1. found 529.97.

Example 809

N-(4-((2-Chloro-4-(4-(4-hydroxypiperidin-1-yl)benzamido)phenyl)amino)phenyl)-1-methyl-1H-pyrrole-3-carboxamide (Compound 909)

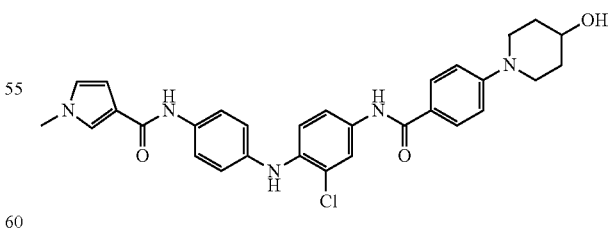

Compound 909 was prepared according to the procedure described in Scheme IV from N$^1$-(4-aminophenyl)-2-chlorobenzene-1,4-diamine, 1-methyl-1H-pyrrole-3-carboxylic, and 4-(4-hydroxypiperidin-1-yl)benzoic acids. [M+H]$^+$ calcd for $C_{30}H_{30}ClN_5O_3$: 544.2. found 544.02.

Example 810

N—,N'-(Azanediylbis(3-fluoro-4,1-phenylene))bis(4-(4-hydroxypiperidin-1-yl)benzamide) (Compound 910)

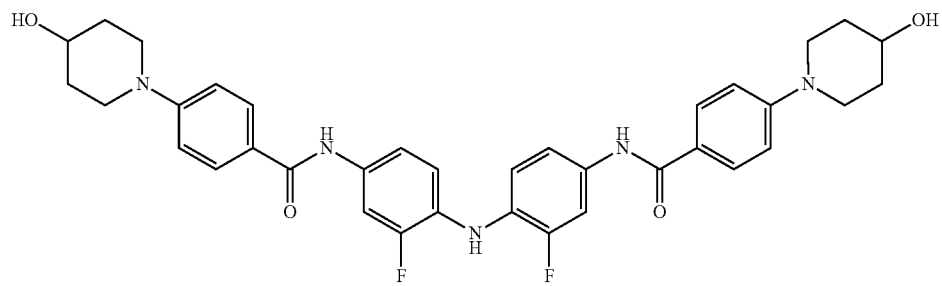 [SMILES: O=C(Nc1ccc(Nc2ccc(NC(=O)c3ccc(N4CCC(O)CC4)cc3)cc2F)c(F)c1)c1ccc(N2CCC(O)CC2)cc1]

Compound 910 was prepared according to the procedure described in Scheme IV from 4,4'-diamino-2,2'-difluorodiphenylamine and 4-(4-hydroxypiperidin-1-yl)benzoic acid. [M+H]$^+$ calcd for $C_{36}H_{37}F_2N_5O_4$: 642.2. found 642.12

Example 811

N-(4-((2-Fluoro-4-(4-(4,4-difluoropiperidin-1-yl)benzamido)phenyl)amino)phenyl)-1H-pyrrole-3-carboxamide (Compound 911)

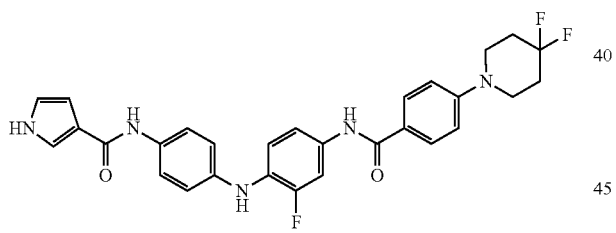

Compound 911 was prepared according to the procedure described in Scheme IV from N$^1$-(4-aminophenyl)-2-fluorobenzene-1,4-diamine, 1H-pyrrole-3-carboxylic, and 4-(4,4-difluoropiperidin-1-yl)benzoic acids. $^1$H NMR (400 MHz, Acetone-d$_6$) δ 10.54 (s, 1H), 9.39 (s, 1H), 8.88 (s, 1H), 7.92 (m, 3H), 7.69 (d, J=8.8 Hz, 2H), 7.54 (m, 1H), 7.43 (d, J=8.8 Hz, 1H), 7.25 (t, J=9.2 Hz, 1H), 7.07 (t, J=8.8 Hz, 4H), 6.91 (s, 1H), 6.85 (q, J=2.3 Hz, 1H), 6.71 (q, J=1.6 Hz, 1H), 3.55 (t, J=5.8 Hz, 4H), 2.11 (m, 4H).

Example 812

N-(4-((2-Fluoro-4-(4-(4-hydroxypiperidin-1-yl)benzamido)phenyl)amino)phenyl)-1H-indole-5-carboxamide (Compound 912)

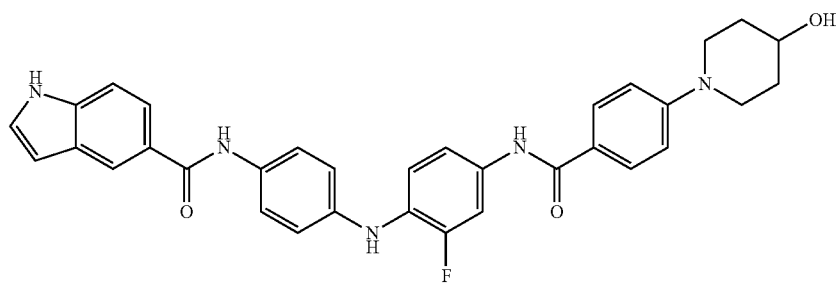 [SMILES: O=C(Nc1ccc(Nc2ccc(NC(=O)c3ccc4[nH]ccc4c3)cc2)c(F)c1)c1ccc(N2CCC(O)CC2)cc1]

Compound 912 was prepared according to the procedure described in Scheme IV from N¹-(4-aminophenyl)-2-fluorobenzene-1,4-diamine, 1H-indole-5-carboxylic, and 4-(4-hydroxypiperidin-1-yl)benzoic acids. [M+H]⁺ calcd for $C_{33}H_{30}FN_5O_3$: 564.23. found 564.07.

Example 813

N-(3-Fluoro-4-((4-(4-(4-hydroxypiperidin-1-yl)benzamido)phenyl)amino)phenyl)-1,4,5-trimethyl-1H-pyrrole-3-carboxamide (Compound 913)

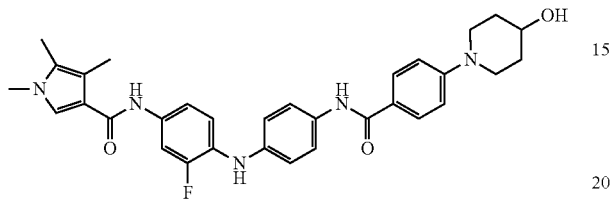

Compound 913 was prepared according to the procedure described in Scheme IV from N¹-(4-aminophenyl)-2-fluorobenzene-1,4-diamine, 1,4,5-trimethyl-1H-pyrrole-3-carboxylic, and 4-(4-hydroxypiperidin-1-yl)benzoic acids. [M+H]⁺ calcd for $C_{32}H_{34}FN_5O_3$: 556.2. found: 556.03.

Example 814

N—,N'-(Oxybis(4,1-phenylene))bis(4-(4-hydroxypiperidin-1-yl)benzamide) (Compound 914)

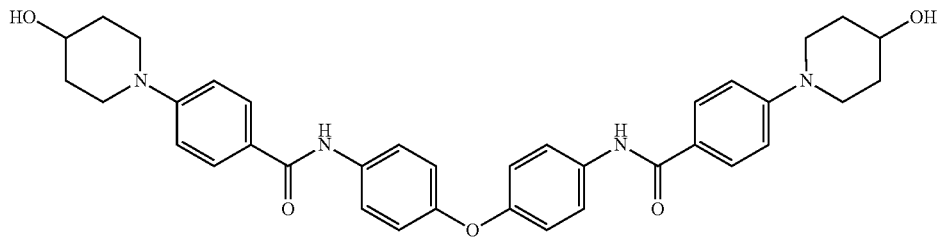 [SMILES: O=C(Nc1ccc(Oc2ccc(NC(=O)c3ccc(N4CCC(O)CC4)cc3)cc2)cc1)c1ccc(N2CCC(O)CC2)cc1]

Compound 914 was prepared according to the procedure described in Scheme IV from 4,4'-oxydianiline and 4-(4-hydroxypiperidin-1-yl)benzoic acid. [M+H]⁺ calcd for $C_{36}H_{38}N_4O_5$: 607.2. found 607.21.

Example 815

N-(4-(4-(4-(4-Hydroxypiperidin-1-yl)benzamido)phenoxy)phenyl)-1-methyl-1H-pyrrole-2-carboxamide (Compound 915)

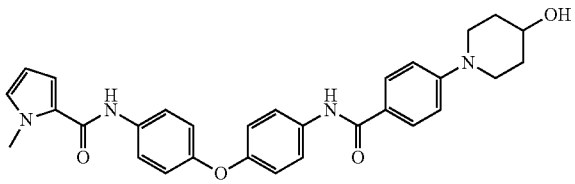 [SMILES: Cn1cccc1C(=O)Nc1ccc(Oc2ccc(NC(=O)c3ccc(N4CCC(O)CC4)cc3)cc2)cc1]

Compound 915 was prepared according to the procedure described in Scheme IV from 4,4'-oxydianiline, 1-methyl-1H-pyrrole-2-carboxylic, and 4-(4-hydroxypiperidin-1-yl)benzoic acids. [M+H]⁺ calcd for $C_{30}H_{30}N_4O_4$: 511.2. found 511.01.

Example 816

N-(4-(4-(4-(4-Hydroxypiperidin-1-yl)benzamido)phenoxy)phenyl)-1H-pyrrole-2-carboxamide (Compound 916)

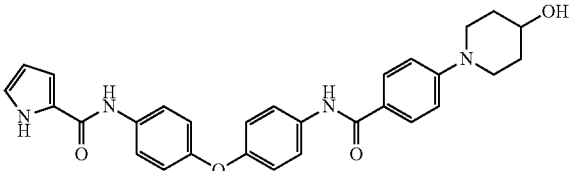

Compound 916 was prepared according to the procedure described in Scheme IV from 4,4'-oxydianiline, 1H-pyrrole-2-carboxylic, and 4-(4-hydroxypiperidin-1-yl)benzoic acids. [M+H]⁺ calcd for $C_{29}H_{28}N_4O_4$: 497.2. found 496.97.

Example 817

N-(4-(4-(4-(4-Hydroxypiperidin-1-yl)benzamido)phenoxy)phenyl)-1H-indole-6-carboxamide (Compound 917)

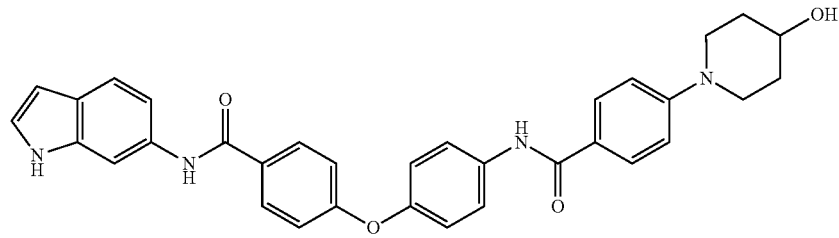 [SMILES: O=C(Nc1ccc(Oc2ccc(C(=O)Nc3ccc4cc[nH]c4c3)cc2)cc1)c1ccc(N2CCC(O)CC2)cc1]

Compound 917 was prepared according to the procedure described in Scheme IV from 4,4'-oxydianiline, 1H-indole-6-carboxylic, and 4-(4-hydroxypiperidin-1-yl)benzoic acids. [M+H]$^+$ calcd for $C_{33}H_{30}N_4O_4$: 547.2. found 547.05.

Example 818

N-(4-(4-(4-(4-Hydroxypiperidin-1-yl)benzamido)phenoxy)phenyl)-1-methyl-1H-indole-3-carboxamide (Compound 918)

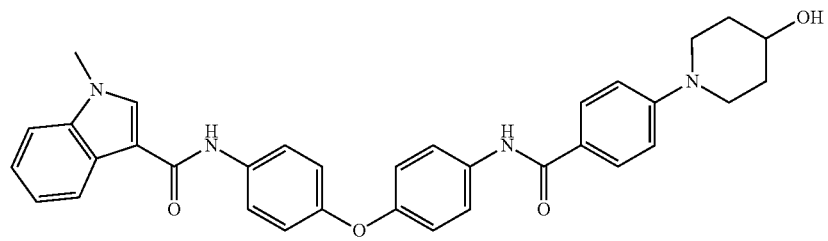 [SMILES: Cn1cc(C(=O)Nc2ccc(Oc3ccc(NC(=O)c4ccc(N5CCC(O)CC5)cc4)cc3)cc2)c2ccccc21]

Compound 918 was prepared according to the procedure described in Scheme IV from 4,4'-oxydianiline, 1-methyl-1H-indole-3-carboxylic, and 4-(4-hydroxypiperidin-1-yl)benzoic acids. [M+H]$^+$ calcd for $C_{34}H_{32}N_4O_4$: 561.2. found 561.10.

Example 819

N-(4-(4-Aminophenoxy)phenyl)-4-(4-hydroxypiperidin-1-yl)benzamide (Compound 919)

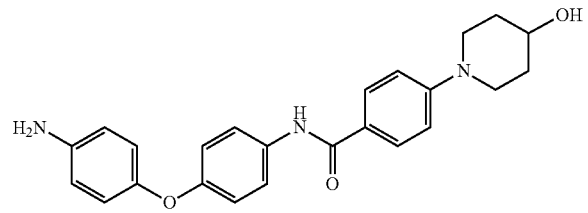 [SMILES: Nc1ccc(Oc2ccc(NC(=O)c3ccc(N4CCC(O)CC4)cc3)cc2)cc1]

Compound 919 was prepared according to the procedure described in Scheme IV from 4,4'-oxydianiline and 4-(4-hydroxypiperidin-1-yl)benzoic acid. [M+H]$^+$ calcd for $C_{24}H_{25}N_3O_3$: 404.1. found 404.05.

Example 820

N-(3-((1H-Indol-6-yl)amino)-3-oxopropyl)-4-(4-(4-hydroxypiperidin-1-yl)benzamido)benzamide (Compound 920)

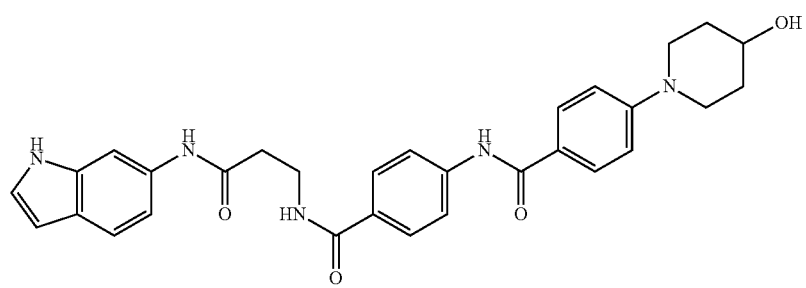 [SMILES: O=C(CCNC(=O)c1ccc(NC(=O)c2ccc(N3CCC(O)CC3)cc2)cc1)Nc1ccc2cc[nH]c2c1]

Compound 920 was prepared according to the procedure described in Scheme IV from 6-aminoindole, 3-aminopropanoic, 4-aminobenzoic, and 4-(4-hydroxypiperidin-1-yl)benzoic acid. [M+H]+ calcd for $C_{30}H_{31}N_5O_4$: 526.2. found 525.99.

Example 821

N-(4-(5-(4-(4-Methoxypiperidin-1-yl)benzamido)-1H-indazol-1-yl)phenyl)thiophene-2-carboxamide (Compound 921)

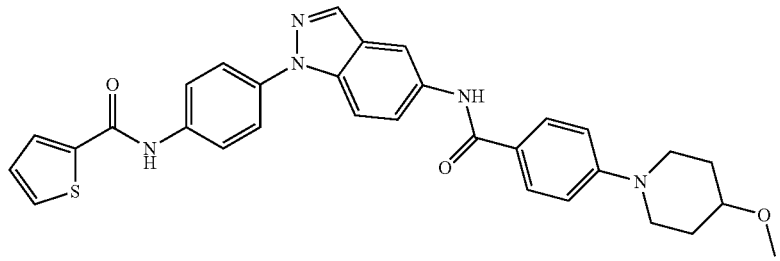 [SMILES: COC1CCN(c2ccc(C(=O)Nc3ccc4c(cnn4-c4ccc(NC(=O)c5cccs5)cc4)c3)cc2)CC1]

Compound 921 was prepared according to the general procedure described in Scheme IV. Preparation of 4-fluoro-N-(1H-indazol-5-yl)benzamide: 1H-Indazol-5-amine (5.5 g, 41 mmol), hydroxybenzotriazole (558 mg, 4.13 mmol), triethylamine (6.3 mL, 45 mmol), and 4-fluorobenzoic acid (6.36 g, 45 mmol) were taken up in DMF (207 mL) and stirred. EDC (8.7 g, 45 mmol) was added to the solution last. After the addition, the solution was stirred at room temperature for 4 h. Water was then added to the solution and stirred for 10 min. The formed precipitate was filtered and washed well with water, followed by hexanes. The solid was dried under vacuum to give 10.3 g (98%) of the product as a light purple solid.

Preparation of N-(1-(4-aminophenyl)-1H-indazol-5-yl)-4-fluorobenzamide: 4-Fluoro-N-(1H-indazol-5-yl)benzamide (10.3 g, 40 mmol), 4-fluoronitrobenze (4.3 mL, 40 mmol) and cesium carbonate (13 g, 40 mmol) were taken up in DMSO (400 mL). The solution was heated to 100° C. and stirred for 24 h. After the solution was cooled it was diluted with water until a precipitate formed and stirred well for 5 min Filtration gave a yellow solid, which was then washed well with water, followed by hexanes. After the solid was dried under vacuum it was taken up in ethanol and stirred at RT under nitrogen. The solution was treated with Pd(OH)$_2$ (100 mg) and placed under a balloon of H$_2$ gas. After stirring at RT for 24 h, the catalyst was removed via filtration through celite. The filtrate was concentrated under reduced pressure to give 9.36 g (67%) of a crude product as a yellow solid Preparation of N-(4-(5-(4-fluorobenzamido)-1H-indazol-1-yl)phenyl)thiophene-2-carboxamide: N-(1-(4-Aminophenyl)-1H-indazol-5-yl)-4-fluorobenzamide (400 mg, 1.15 mmol) was taken up in anhydrous pyridine (5.8 mL) and stirred at RT. Thiophene-2-carbonyl chloride (0.15 mL, 1.44 mmol) was then added dropwise and the solution was stirred at RT for 4 h. Added water, EtOAc and hexanes to the solution and stirred vigorously for 1 h. to form a precipitate. Filtered off the solid and dried under vacuum to obtain 539 mg (94%) of the product as an off-white solid.

Preparation of Compound 921: N-(4-(5-(4-Fluorobenzamido)-1H-indazol-1-yl)phenyl)thiophene-2-carboxamide (25 mg, 0.05 mmol), 4-methoxypiperidine (165 mg, 1.09 mmol), cesium carbonate (357 mg, 1.09 mmol) and DMSO (1 mL) were added to a microwave vial. The mixture was heated in a microwave at 130° C. for 5 h. Water was added to the cooled solution and shaken vigorously, which formed a precipitate. The solid was filtered and washed with water, followed by hexanes. Took up the solid with a CH$_2$Cl$_2$/MeOH mixture and concentrated under reduced pressure onto silica. Purification via flash chromatography (0-10% MeOH/CH$_2$Cl$_2$) produced 18.6 mg (61%) of compound 921. $^1$H NMR (500 MHz, DMSO-d$_6$) 10.41 (s, 1H), 10.06 (s, 1H), 8.37 (s, 1H), 8.32 (s, 1H), 8.05 (d, J=5 Hz, 1H), 7.94 (d, J=9 Hz, 2H), 7.88 (d, J=9 Hz, 2H), 7.86 (d, J=1 Hz, 1H), 7.83 (d, J=9 Hz, 2H), 7.77 (d, J=9.5 Hz, 1H), 7.77 (d, J=9 Hz, 2H), 7.24 (dd, J=4, 5 Hz, 1H), 7.00 (d, J=9 Hz, 2H), 5.75 (s, 3H), 3.66-3.63 (m, 2H), 3.07-3.02 (m, 2H), 1.94-1.88 (m, 2H), 1.52-1.45 (m, 2H).

Example 822

N-(4-(5-(4-(4-Hydroxypiperidin-1-yl)benzamido)-1H-indazol-1-yl)phenyl)benzo[d]thiazole-5-carboxamide (Compound 922)

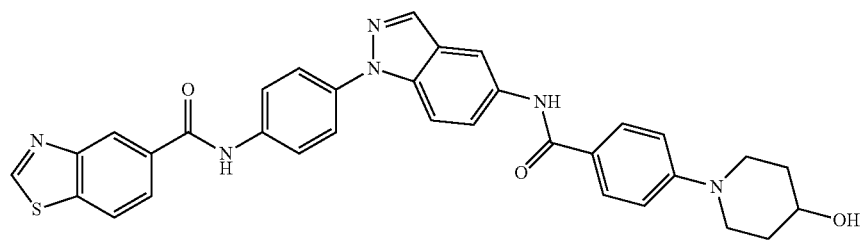 [SMILES: O=C(Nc1ccc2c(cnn2-c2ccc(NC(=O)c3ccc4scnc4c3)cc2)c1)c1ccc(N2CCC(O)CC2)cc1]

Compound 922 was prepared according to the procedure described in Scheme IV from 5-amino-1-(4-aminophenyl)indazole, benzo[d]thiazole-5-carboxylic, and 4-(4-hydroxypiperidin-1-yl)benzoic acids. [M+H]+ calcd for $C_{33}H_{28}N_6O_3S$: 589.19. found: 589.12.

Example 823

N-(4-(5-(4-(4-Hydroxypiperidin-1-yl)benzamido)-1H-indazol-1-yl)phenyl)isonicotinamide (Compound 923)

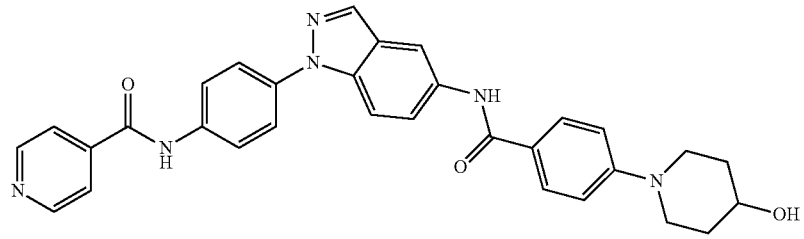

Compound 923 was prepared according to the procedure described in Scheme IV from 5-amino-1-(4-aminophenyl)indazole, isonicotinic, and 4-(4-hydroxypiperidin-1-yl)benzoic acids. [M+H]+ calcd for $C_{31}H_{28}N_6O_3$: 533.2. found: 533.14.

Example 824

N-(1-(4-(Cyclopropanecarboxamido)phenyl)-1H-indazol-5-yl)-4-(4-(2-hydroxyethyl)piperidin-1-yl)benzamide (Compound 924)

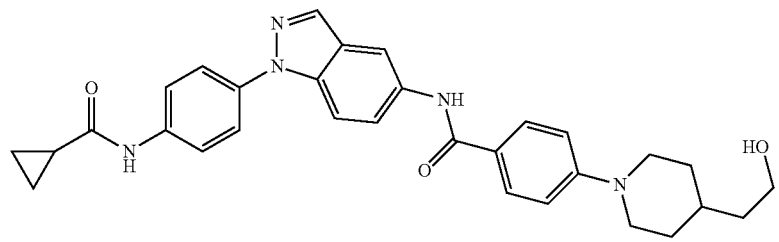 [SMILES: O=C(Nc1ccc2c(cnn2-c2ccc(NC(=O)C3CC3)cc2)c1)c1ccc(N2CCC(CCO)CC2)cc1]

Compound 924 was prepared according to the procedure described in Scheme IV from 5-amino-1-(4-aminophenyl)indazole, cyclopropanecarboxylic, and 4-(4-(2-hydroxyethyl)piperidin-1-yl)benzoic acids. [M+H]+ calcd for $C_{31}H_{33}N_5O_3$: 524.26. found: 524.10.

Example 825

(±)-N-(1-(4-(Cyclopropanecarboxamido)phenyl)-1H-indazol-5-yl)-4-(3-hydroxypiperidin-1-yl)benzamide (Compound 925)

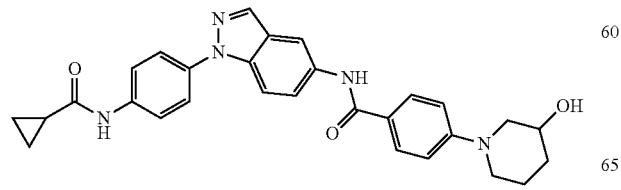

Compound 925 was prepared according to the procedure described in Scheme IV from 5-amino-1-(4-aminophenyl)indazole, cyclopropanecarboxylic, and 4-(3-hydroxypiperidin-1-yl)benzoic acids. [M+H]$^+$ calcd for $C_{29}H_{29}N_5O_3$: 496.2. found: 496.14.

Example 826

N-(1-(4-(2,2-Difluorocyclopropanecarboxamido)phenyl)-1H-indazol-5-yl)-4-(4-hydroxypiperidin-1-yl)benzamide (Compound 926)

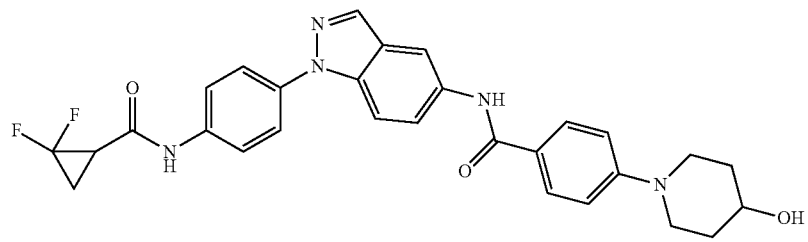 [SMILES: O=C(Nc1ccc2c(cnn2-c2ccc(NC(=O)C3CC3(F)F)cc2)c1)c1ccc(N2CCC(O)CC2)cc1]

Compound 926 was prepared according to the procedure described in Scheme IV from 5-amino-1-(4-aminophenyl)indazole, 2,2-difluorocyclopropanecarboxylic, and 4-(4-hydroxypiperidin-1-yl)benzoic acids. $^1$H NMR (500 MHz, DMSO-d$_6$) δ 7.38 (s, 1H), 7.37 (m, 1H), 7.04 (d, J=5 Hz, 1H), 7.94 (d, J=8.5 Hz, 2H), 6.98 (d, J=9 Hz, 2H), 6.87 (d, J=11 Hz, 2H), 6.85 (d, J=9 Hz, 2H), 6.19 (d, J=9 Hz, 2H), 3.01-2.93 (m, 3H), 2.22 (ddd, J=3, 10.5, 13 Hz, 2H), 1.94-1.88 (m, 1H), 1.32-1.27 (m, 1H), 1.16-1.12 (m, 2H), 1.07-1.00 (m, 1H), 0.82-0.74 (m, 2H).

Example 827

N-(4-(5-(4-(4-Hydroxypiperidin-1-yl)benzamido)-1H-indazol-1-yl)phenyl)-1-methyl-1H-indole-6-carboxamide (Compound 927)

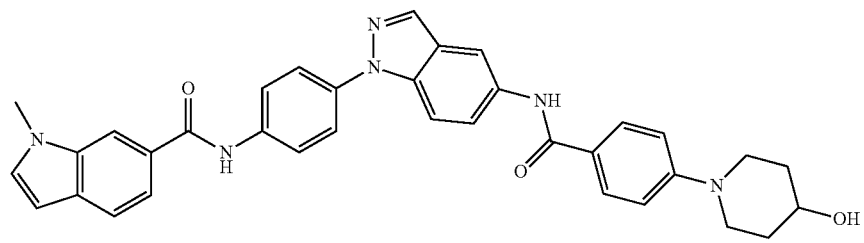 [SMILES: Cn1ccc2ccc(C(=O)Nc3ccc(-n4ncc5cc(NC(=O)c6ccc(N7CCC(O)CC7)cc6)ccc54)cc3)cc21]

Compound 927 was prepared according to the procedure described in Scheme IV from 5-amino-1-(4-aminophenyl)indazole, 1-methyl-1H-indole-6-carboxylic, and 4-(4-hydroxypiperidin-1-yl)benzoic acids. [M+H]$^+$ calcd for $C_{35}H_{32}N_6O_3$: 585.25. found: 585.15.

Example 828

(±)-N-(1-(4-(Cyclopropanecarboxamido)phenyl)-1H-indazol-5-yl)-4-(3-hydroxymethylpiperidin-1-yl)benzamide (Compound 928)

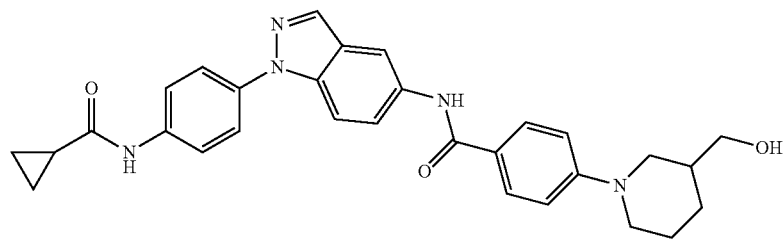 [SMILES: O=C(Nc1ccc2c(cnn2-c2ccc(NC(=O)C3CC3)cc2)c1)c1ccc(N2CCCC(CO)C2)cc1]

Compound 928 was prepared according to the procedure described in Scheme IV from 5-amino-1-(4-aminophenyl)indazole, cyclopropanecarboxylic, and 4-(3-hydroxymethylpiperidin-1-yl)benzoic acids. [M+H]$^+$ calcd for C$_{30}$H$_{31}$N$_5$O$_3$: 510.24. found: 510.12.

Example 829

N-(1-(4-(Cyclopropanecarboxamido)phenyl)-1H-indazol-5-yl)-4-(4-oxopiperidin-1-yl)benzamide (Compound 929)

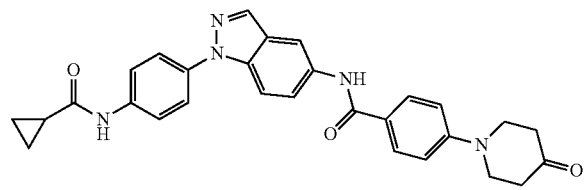 [SMILES: O=C1CCN(c2ccc(C(=O)Nc3ccc4c(cnn4-c4ccc(NC(=O)C5CC5)cc4)c3)cc2)CC1]

Compound 929 was prepared according to the procedure described in Scheme IV from 5-amino-1-(4-aminophenyl)indazole, cyclopropanecarboxylic, and 4-(4-oxopiperidin-1-yl)benzoic acids. [M+H]$^+$ calcd for C$_{29}$H$_{27}$N$_5$O$_3$: 494.2. found: 494.06.

Example 830

N-(1-(4-(Cyclopropanecarboxamido)phenyl)-1H-indazol-5-yl)-1-methyl-1H-indole-5-carboxamide (Compound 930)

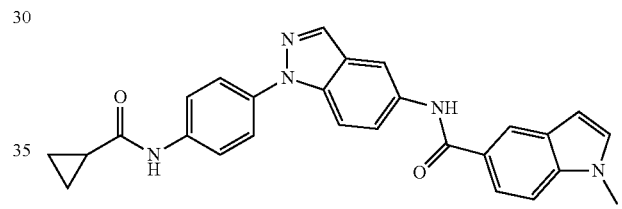

Compound 930 was prepared according to the procedure described in Scheme IV from 5-amino-1-(4-aminophenyl)indazole, cyclopropanecarboxylic, and 1-methyl-1H-indole-5-carboxylic acids. [M+H]$^+$ calcd for C$_{27}$H$_{23}$N$_5$O$_2$: 450.1. found: 450.06.

Example 831

N-(1-(4-(Cyclopropanecarboxamido)phenyl)-1H-indazol-5-yl)-4-(4-(hydroxyimino)piperidin-1-yl)benzamide (Compound 931)

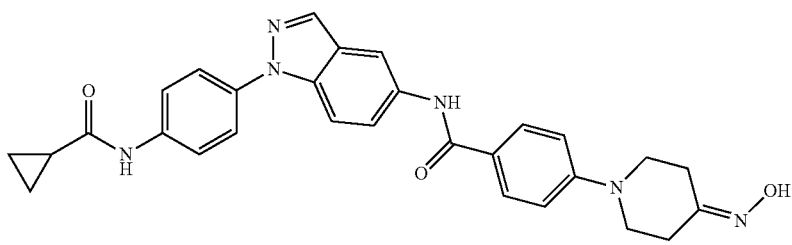 [SMILES: O=C(Nc1ccc2c(cnn2-c2ccc(NC(=O)C3CC3)cc2)c1)c1ccc(N2CCC(=NO)CC2)cc1]

Compound 931 was prepared according to the procedure described in Scheme IV from 5-amino-1-(4-aminophenyl)indazole, cyclopropanecarboxylic, and 4-(4-(hydroxyimino)piperidin-1-yl)benzoic acids. [M+H]$^+$ calcd for $C_{29}H_{28}N_6O_3$: 509.22. found: 509.10.

Example 832

(±)-N-(1-(4-(2-Methylcyclopropanecarboxamido)phenyl)-1H-indazol-5-yl)-4-(4-hydroxypiperidin-1-yl)benzamide (Compound 932)

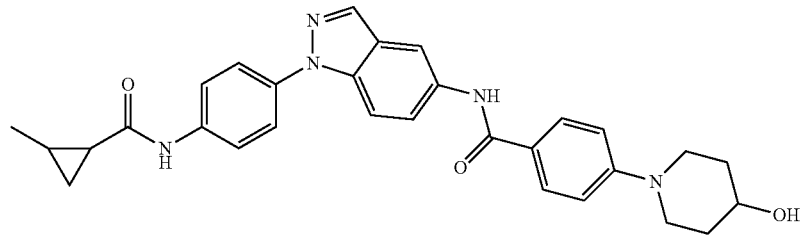 [SMILES: CC1CC1C(=O)Nc1ccc(-n2ncc3cc(NC(=O)c4ccc(N5CCC(O)CC5)cc4)ccc32)cc1]

Compound 932 was prepared according to the procedure described in Scheme IV from 5-amino-1-(4-aminophenyl)indazole, 2-methylcyclopropanecarboxylic, and 4-(4-hydroxypiperidin-1-yl)benzoic acids. [M+H]$^+$ calcd for $C_{30}H_{31}N_5O_3$: 510.24. found: 510.13.

Example 833

N-(1-(4-(Cyclopropanecarboxamido)phenyl)-1H-indazol-5-yl)-4-(4-hydroxy-4-(pyrrolidin-1-ylmethyl)piperidin-1-yl)benzamide (Compound 933)

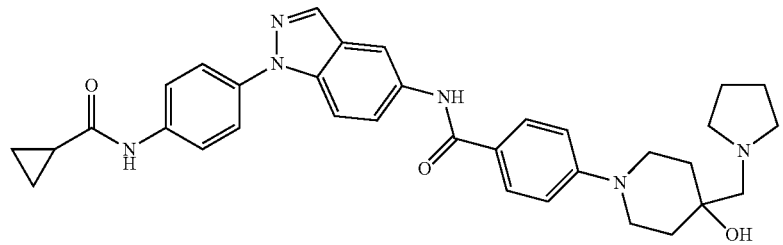 [SMILES: O=C(Nc1ccc2c(cnn2-c2ccc(NC(=O)C3CC3)cc2)c1)c1ccc(N2CCC(O)(CN3CCCC3)CC2)cc1]

Compound 933 was prepared according to the procedure described in Scheme IV from 5-amino-1-(4-aminophenyl)indazole, cyclopropanecarboxylic, and 4-(4-hydroxy-4-(pyrrolidin-1-ylmethyl)piperidin-1-yl)benzoic acids.

Example 834

N-(1-(4-(Cyclopropanecarboxamido)phenyl)-1H-indazol-5-yl)-4-(2-hydroxyethylamino)benzamide (Compound 934)

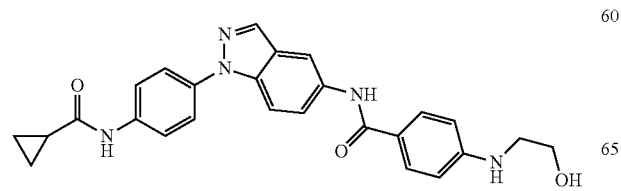

Compound 934 was prepared according to the procedure described in Scheme IV from 5-amino-1-(4-aminophenyl)indazole, cyclopropanecarboxylic, and 4-(2-hydroxyethylamino)benzoic acids. [M+H]+ calcd for $C_{26}H_{25}N_5O_3$: 456.2. found 456.03.

Example 835

(±)-N-(1-(4-(Cyclopropanecarboxamido)phenyl)-1H-indazol-5-yl)-4-((2,3-dihydroxypropyl)amino)benzamide (Compound 935)

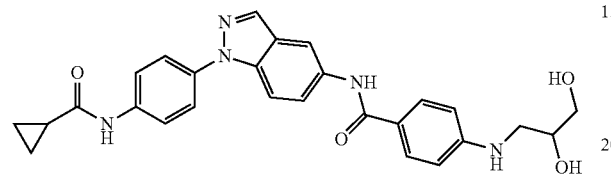

Compound 935 was prepared according to the procedure described in Scheme IV from 5-amino-1-(4-aminophenyl)indazole, cyclopropanecarboxylic, and 4-(2,3-dihydroxypropylamino)benzoic acids. [M+H]+ calcd for $C_{27}H_{27}N_5O_4$: 486.2. found 486.03.

Example 836

N-(1-(4-(Cyclopropanecarboxamido)phenyl)-1H-indazol-5-yl)-4-(4-methoxypiperidin-1-yl)benzamide (Compound 936)

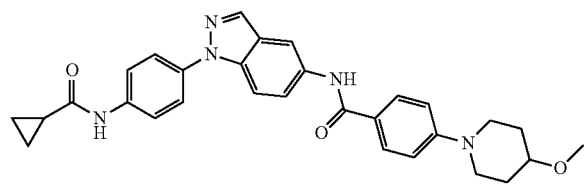 [SMILES: COC1CCN(c2ccc(C(=O)Nc3ccc4c(cnn4-c4ccc(NC(=O)C5CC5)cc4)c3)cc2)CC1]

Compound 936 was prepared according to the procedure described in Scheme IV from 5-amino-1-(4-aminophenyl)indazole, cyclopropanecarboxylic, and 4-(4-methoxypiperidin-1-yl)benzoic acids. [M+H]+ calcd for $C_{30}H_{31}N_5O_3$: 510.2. found: 510.12.

Example 837

N-(1-(4-(Cyclopropanecarboxamido)phenyl)-1H-indazol-5-yl)-4-(4-(3-hydroxypropyl)piperazin-1-yl)benzamide (Compound 937)

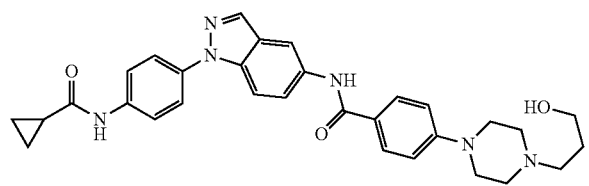 [SMILES: O=C(Nc1ccc2c(cnn2-c2ccc(NC(=O)C3CC3)cc2)c1)c1ccc(N2CCN(CCCO)CC2)cc1]

Compound 937 was prepared according to the procedure described in Scheme IV from 5-amino-1-(4-aminophenyl)indazole, cyclopropanecarboxylic, and 4-(4-(3-hydroxypropyl)piperazin-1-yl)benzoic acids. [M+H]+ calcd for $C_{31}H_{34}N_6O_3$: 539.17. found: 539.16.

Example 838

(±)-N-(1-(4-(Cyclopropanecarboxamido)phenyl)-1H-indazol-5-yl)-4-(3-hydroxypyrrolidin-1-yl)benzamide (Compound 938)

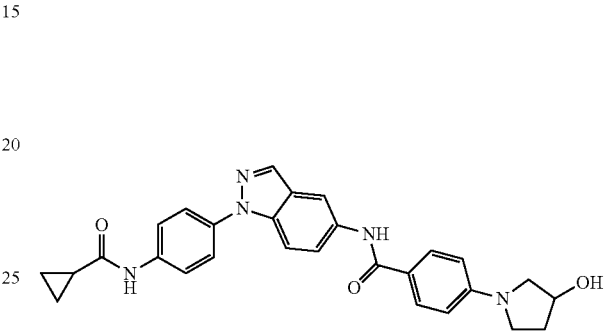

Compound 938 was prepared according to the procedure described in Scheme IV from 5-amino-1-(4-aminophenyl)indazole, cyclopropanecarboxylic, and 4-(3-hydroxypyrrolidin-1-yl)benzoic acids. $^1$H NMR (500 MHz, CD$_3$OD) δ 8.19 (s, 1H), 8.17 (s, 1H), 7.86 (d, J=8.5 Hz, 2H), 7.77 (d, J=8.5 Hz, 2H), 7.70-7.63 (m, 4H), 6.62 (d, J=8.5 Hz, 2H), 4.55 (s, 1H), 3.56-3.50 (m, 2H), 3.43 (dd, J=3, 9 Hz, 1H), 2.20-2.13 (m, 1H), 2.08-2.04 (m, 1H), 1.83-1.78 (m, 1H), 1.28 (s, 1H), 1.00-0.97 (m, 2H), 0.90-0.86 (m, 2H).

Example 839

N-(1-(4-(Cyclopropanecarboxamido)phenyl)-1H-indazol-5-yl)-1-(2-hydroxyethyl)-1H-indole-5-carboxamide (Compound 939)

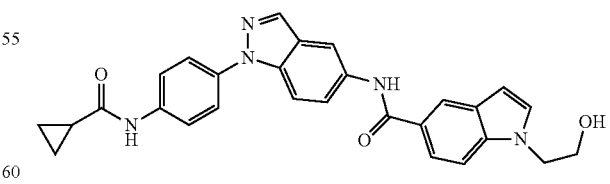

Compound 939 was prepared according to the procedure described in Scheme IV from 5-amino-1-(4-aminophenyl)indazole, cyclopropanecarboxylic, and 1-(2-hydroxyethyl)-1H-indole-5-carboxylic acids. [M+H]+ calcd for $C_{28}H_{25}N_5O_3$: 480.20. found 480.03.

Example 840

N-(1-(4-(Cyclopropanecarboxamido)phenyl)-1H-indazol-5-yl)-4-(4-hydroxymethylpiperidin-1-yl)benzamide (Compound 940)

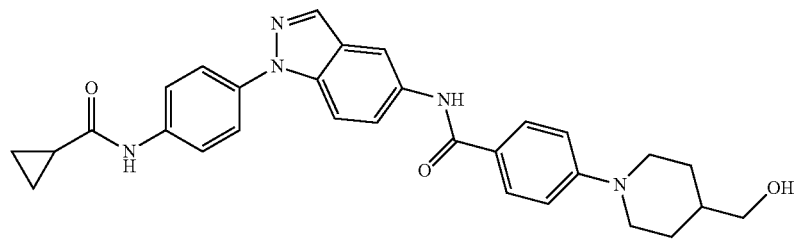 [SMILES: O=C(Nc1ccc2c(cnn2-c2ccc(NC(=O)C3CC3)cc2)c1)c1ccc(N2CCC(CO)CC2)cc1]

Compound 940 was prepared according to the procedure described in Scheme IV from 5-amino-1-(4-aminophenyl)indazole, cyclopropanecarboxylic, and 4-(4-hydroxymethylpiperidin-1-yl)benzoic acids. $^1$H NMR (500 MHz, DMSO-d$_6$) δ 10.38 (s, 1H), 10.04 (s, 1H), 8.36 (s, 1H), 8.31 (s, 1H), 7.88 (d, J=9 Hz, 2H), 7.81-7.75 (m, 6H), 7.69 (d, J=8.5 Hz, 2H), 7.01 (d, J=9.5 Hz, 2H), 4.72 (d, J=4 Hz, 2H), 1.85-1.79 (m, 2H), 1.46-1.42 (m, 2H), 0.86-0.81 (m, 4H).

Example 841

N-(1-(4-(Cyclopropanecarboxamido)phenyl)-1H-indazol-5-yl)-1-(3-hydroxypropyl)-1H-indole-6-carboxamide (Compound 941)

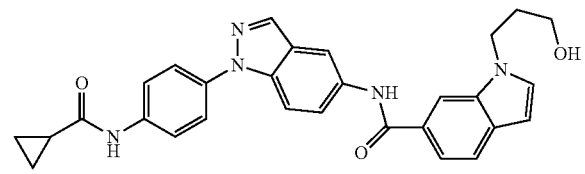 [SMILES: O=C(Nc1ccc2c(cnn2-c2ccc(NC(=O)C3CC3)cc2)c1)c1ccc2ccn(CCCO)c2c1]

Compound 941 was prepared according to the procedure described in Scheme IV from 5-amino-1-(4-aminophenyl)indazole, cyclopropanecarboxylic, and 1-(3-hydroxypropyl)-1H-indole-6-carboxylic acids. [M+H]$^+$ calcd for C$_{29}$H$_{27}$N$_5$O$_3$: 494.21. found: 494.00.

Example 842

N-(1-(4-(Cyclopropanecarboxamido)phenyl)-1H-indazol-5-yl)-1H-indole-5-carboxamide (Compound 942)

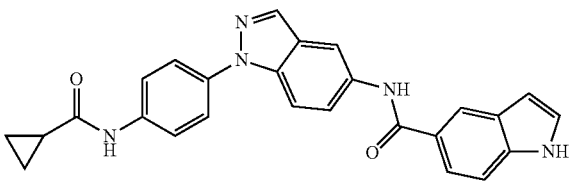 [SMILES: O=C(Nc1ccc2c(cnn2-c2ccc(NC(=O)C3CC3)cc2)c1)c1ccc2[nH]ccc2c1]

Compound 942 was prepared according to the procedure described in Scheme IV from 5-amino-1-(4-aminophenyl)indazole, cyclopropanecarboxylic, and 1H-indole-5-carboxylic acids. [M+H]$^+$ calcd for C$_{26}$H$_{21}$N$_5$O$_2$: 436.1. found: 436.02.

Example 843

(±)-4-(4-Hydroxypiperidin-1-yl)-N-(1-(4-((trans)-2-phenylcyclopropanecarboxamido)phenyl)-1H-indazol-5-yl)benzamide (Compound 943)

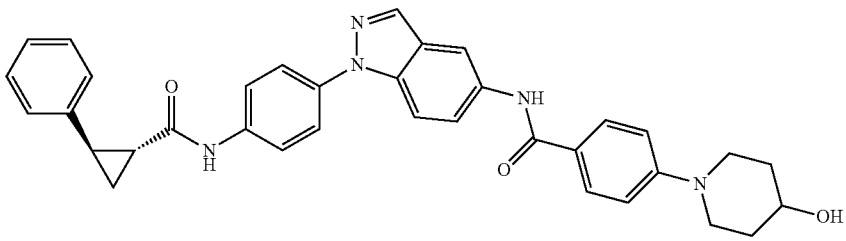 [SMILES: O=C(Nc1ccc2c(cnn2-c2ccc(NC(=O)[C@@H]3C[C@H]3c3ccccc3)cc2)c1)c1ccc(N2CCC(O)CC2)cc1]

Compound 943 was prepared according to the procedure described in Scheme IV from 5-amino-1-(4-aminophenyl)indazole, 2-trans-phenylcyclopropanecarboxylic, and 4-(4-hydroxypiperidin-1-yl)benzoic acids. [M+H]$^+$ calcd for C$_{35}$H$_{33}$N$_5$O$_3$: 572.2. found 572.17.

Example 844

N-(3-(4-(Cyclopropanecarboxamido)phenyl)-1H-indol-6-yl)-1-methyl-1H-indole-5-carboxamide (Compound 944)

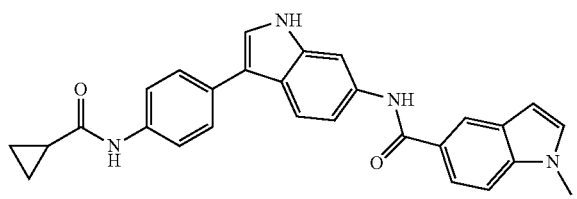 [SMILES: Cn1ccc2cc(C(=O)Nc3ccc4c(-c5ccc(NC(=O)C6CC6)cc5)c[nH]c4c3)ccc21]

Compound 944 was prepared according to the general procedure described in Scheme IV. Preparation of 3-bromo-6-nitro-1H-indole: To a solution of 6-nitro-1H-indole (3.00 g, 18.5 mmol) in methylene chloride (100 mL) was added N-bromosuccinimide (3.29 g, 18.5 mmol) as four equal portions over 2 h. The reaction was stirred overnight, and the formed precipitate was filtered off and rinsed with water. The collected, biphasic filtrate was separated by removing the organic phase and extracting the aqueous phase with methylene chloride (3×200 mL). The combined organic phases were concentrated to give a crude solid. The solids collected from the filtration and the extractions were recrystallized using methanol/water and gave 3-bromo-6-nitro-1H-indole (3.95 g, 16.4 mmol, 89%) as a yellow solid after filtration.

Preparation of 3-bromo-6-nitro-1-(phenylsulfonyl)-1H-indole: Sodium hydride (461 mg, 11.5 mmol) was slowly added to a solution of 3-bromo-6-nitro-1H-indole (2.32 g, 9.61 mmol) in tetrahydrofuran (10.0 mL). After stirring for 5 min, benzenesulfonyl chloride (1.47 mL, 11.5 mmol) was added dropwise over 10 min. The reaction was stirred an additional 1.5 h before quenching with 5.0 mL of methanol, followed by 10.0 mL water and 20.0 mL methylene chloride. The precipitate was filtered off and washed with an excess of methylene chloride and methanol to give a crème-colored powder for 3-bromo-6-nitro-1-(phenylsulfonyl)-1H-indole (2.80 g, 7.35 mmol, 76%).

Preparation of 3-bromo-1-(phenylsulfonyl)-1H-indol-6-amine: To a slurry of 3-bromo-6-nitro-1-(phenylsulfonyl)-1H-indole (2.80 g, 7.35 mmol) in ethanol (73.5 mL) was added a solution of tin (II) chloride monohydrate (6.63 g, 29.4 mmol) in water (11.0 mL) at 30° C. Once the addition was complete, the reaction was heated to reflux for 3.5 h, then quenched with 2.0 N sodium hydroxide to a pH of 8. The remaining slurry was diluted with ethyl acetate (100 mL), and the aqueous layer was removed and filtered. The organic phase was washed with 2.0 N sodium hydroxide (2×100 mL), and the combined aqueous layers were extracted with ethyl acetate (3×200 mL). The combined organic phases were concentrated to give a tacky, orange solid for 3-bromo-1-(phenylsulfonyl)-1H-indol-6-amine (2.35 g, 6.69 mmol, 91%).

Preparation of 3-(4-nitrophenyl)-1H-indol-6-amine: A 1.0 M aqueous potassium carbonate solution (9.96 mL, 9.96 mmol) was added to a mixture of 3-bromo-1-(phenylsulfonyl)-1H-indol-6-amine (1.00 g, 2.84 mmol), (4-nitrophenyl) boronic acid (1.19 g, 7.12 mmol) and palladium tetrakis (triphenylphosphine) (164 mg, 0.14 mmol) in tetrahydrofuran (13.7 mL). The biphasic mixture was heated in a microwave at 130° C. for 10 min and was then diluted with a saturated solution of sodium bicarbonate (10.0 mL) and ethyl acetate (10.0 mL). The organic layer was washed with a saturated solution of sodium bicarbonate (2×10.0 mL), and the combined aqueous layers were extracted with ethyl acetate (3×30.0 mL). The combined organic phases were dried over magnesium sulfate, filtered and concentrated. The crude residue was purified by flash chromatography (10-25-50-71% ethyl acetate/hexane) to give an orange solid for 3-(4-nitrophenyl)-1-(phenylsulfonyl)-1H-indol-6-amine (726 mg, 1.85 mmol, 65%). 3-(4-nitrophenyl)-1H-indol-6-amine. To a solution of the protected indol-6-amine (300 mg, 0.76 mmol) in methanol (9.00 mL) was added potassium hydroxide (941 mg, 16.8 mmol). The reaction was warmed to 70° C. for 4 h. After that time, the reaction was diluted with water (10.0 mL) and methylene chloride (15.0 mL) and the organic phase was removed. The aqueous layer was extracted with methylene chloride (3×15.0 mL), and the combined organic phases were concentrated. The crude residue that remained was purified by flash chromatography (10-25-50% ethyl acetate/hexane) to give a burgundy red solid for 3-(4-nitrophenyl)-1H-indol-6-amine (66.3 mg, 0.26 mmol, 34%).

Preparation of 1-methyl-N-(3-(4-nitrophenyl)-1H-indol-6-yl)-1H-indole-5-carboxamide: A mixture of 3-(4-nitrophenyl)-1H-indol-6-amine (66.3 mg, 0.26 mmol), 1-methyl-1H-indole-5-carboxylic acid (50.4 mg, 0.29 mmol), hydroxybenzotriazole (3.5 mg, 0.03 mmol) and triethylamine (40.1 µL, 0.29 mmol) in DMF (1.00 mL) was stirred for 5 min before 1-ethyl-3-(3-dimethylaminopropyl) carbodiimide hydrochloride (55.2 mg, 0.29 mmol) was added. The reaction was stirred overnight at room temperature and was then diluted with water (5.0 mL). The precipitate that formed was filtered off and sequentially washed with excess methylene chloride and methanol. The solid was recrystallized using hot methanol and gave a bright yellow solid for 1-methyl-N-(3-(4-nitrophenyl)-1H-indol-6-yl)-1H-indole-5-carboxamide (59.8 mg, 0.15 mmol, 56%) after filtration.

Preparation of N-(3-(4-aminophenyl)-1H-indol-6-yl)-1-methyl-1H-indole-5-carboxamide: To a slurry of 1-methyl-N-(3-(4-nitrophenyl)-1H-indol-6-yl)-1H-indole-5-carboxamide (59.0 mg, 0.14 mmol) in ethanol (1.50 mL) under an atmosphere of nitrogen was added 20 wt % palladium hydroxide on carbon (5.9 mg, 10 wt %), followed by a balloon of hydrogen. The reaction was stirred overnight at room temperature and was then filtered through a pad of Celite, rinsing with excess methanol and methylene chloride. The filtrate was concentrated to give a grey-pink solid for N-(3-(4-aminophenyl)-1H-indol-6-yl)-1-methyl-1H-indole-5-carboxamide (56.9 mg, 0.14 mmol, 100%).

Preparation of Compound 944: A mixture of N-(3-(4-aminophenyl)-1H-indol-6-yl)-1-methyl-1H-indole-5-carboxamide (55.8 mg, 0.15 mmol), cyclopropanecarboxylic acid (12.8 µL, 0.16 mmol), hydroxybenzotriazole (1.9 mg, 0.02 mmol) and triethylamine (22.5 µL, 0.16 mmol) in N,N-dimethylformamide (1.00 mL) was stirred for 5 min before 1-ethyl-3-(3-dimethylaminopropyl) carbodiimide hydrochloride (30.9 mg, 0.16 mmol) was added. The reaction was stirred overnight at room temperature and was then diluted with water (5.0 mL).

The precipitate that formed was filtered off and sequentially washed with excess methylene chloride and methanol. The solid was recrystallized using hot methanol and gave a yellow solid for N-(3-(4-(cyclopropanecarboxamido)phenyl)-1H-indol-6-yl)-1-methyl-1H-indole-5-carboxamide (46.8 mg, 0.10 mmol, 70%) after filtration. MS [M+H]+ calcd for $C_{28}H_{24}N_4O_2$: 449.0. found: 449.05.

Example 845

1-(4-(Cyclopropanecarboxamido)phenyl)-N-(4-(4-hydroxypiperidin-1-yl)phenyl)-1H-indazole-5-carboxamide (Compound 945)

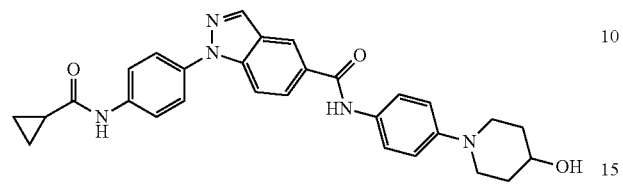

Compound 945 was prepared according to the general procedure described in Scheme IV. Preparation of N-(4-(4-hydroxypiperidin-1-yl)phenyl)-1H-indazole-5-carboxamide: 1H-indazole-5-carboxylic acid hydrochloride (100 mg, 0.50 mmol), hydroxybenzotriazole (7 mg, 0.05 mmol), triethylamine (0.2 mL, 1.3 mmol), and 1-(4-aminophenyl) piperidin-4-ol (193 mg, 1.00 mmol) were taken up in DMF (2.51 mL) and stirred. EDC (106 mg, 0.05 mmol) was added to the solution last. After the addition, the solution was stirred at room temperature for 24 h. The solution was partitioned between water and EtOAc. The aqueous layer was extracted with EtOAc. The combined organic layers were washed with brine and dried over $Na_2SO_4$. Filtration and concentration gave the crude amide. Purification via flash chromatography 0-10% MeOH/$CH_2Cl_2$ gave 55 mg (32%) of the product as a white solid.

Preparation of 1-(4-aminophenyl)-N-(4-(4-hydroxypiperidin-1-yl)phenyl)-1H-indazole-5-carboxamide: N-(4-(4-Hydroxypiperidin-1-yl)phenyl)-1H-indazole-5-carboxamide (10 mg, 0.03 mmol), 4-fluoronitrobenze (3.1 uL, 0.03 mmol) and potassium carbonate (4 mg, 0.03 mmol) were taken up in DMSO (0.3 mL). The solution was heated to 120° C. and stirred for 24 h. After the solution was cooled it was diluted with water until a precipitate formed and stirred well for 5 min Filtration gave a yellow solid, which was then washed well with water, followed by hexanes. After the solid was dried under vacuum it was taken up in methanol and stirred at RT under nitrogen. The solution was treated with Pd(OH)$_2$ (3 mg) and placed under a balloon of H$_2$ gas. After stirring at RT for 24 h, the catalyst was removed via filtration through celite. The filtrate was concentrated under reduced pressure to give 10.23 mg (80%) of a crude product.

Preparation of Compound 945: 1-(4-Aminophenyl)-N-(4-(4-hydroxypiperidin-1-yl)phenyl)-1H-indazole-5-carboxamide (10 mg, 0.02 mmol), EDC (6.7 mg, 0.03 mmol) and cyclopropanecarboxylic acid (2.1 mg, 0.02 mmol) were taken up in pyridine (0.23 mL). The solution was heated to 60° C. and stirred for 1 h. The solution was partitioned between $CH_2Cl_2$ and water. The aqueous layer was extracted with $CH_2Cl_2$. The combined organic layers were washed with brine and dried over $Na_2SO_4$. Filtration and concentration gave the crude cyclopropyl amide. Purification via flash chromatography 0-10% MeOH/$CH_2Cl_2$ gave 8.8 mg (76%) of Compound 945. [M+H]+ calcd for $C_{29}H_{29}N_5O_3$: 496.2. found: 496.02.

Example 846

4-(5-(cyclopropanecarboxamido)-1H-indol-1-yl)-N-(4-(4-hydroxypiperidin-1-yl)phenyl)benzamide (Compound 946)

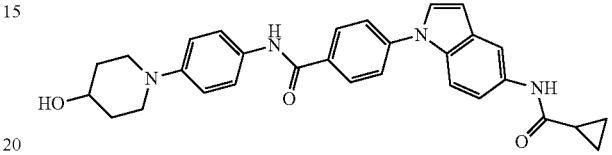

Compound 946 was prepared according to the procedure described in Scheme IV from 1-(4-aminophenyl)-1H-indole-5-carboxylic acid, cyclopropanecarboxylic acid, and 4-(4-hydroxypiperidin-1-yl)aniline. [M+H]+ calcd for $C_{30}H_{30}N_4O_3$: 495.23. found: 495.08.

Example 847

N-(1-(4-(Cyclopropylcarbamoyl)phenyl)-1H-indol-5-yl)-1-(2-hydroxyethyl)-1H-indole-5-carboxamide (Compound 947)

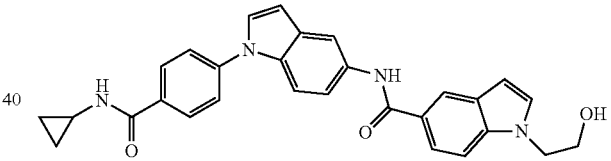

Compound 947 was prepared according to the procedure described in Scheme IV from 4-(5-amino-1H-indol-1-yl) benzoic acid, cyclopropaneamine, and 1-(2-hydroxy ethyl)-1H-indole-5-carboxylic acid. [M+H]+ calcd for $C_{29}H_{26}N_4O_3$: 479.20. found: 479.01.

Example 848

(±)-4-(4-Hydroxypiperidin-1-yl)-N-(1-(4-(2-hydroxymethylcyclopropanecarboxamido)phenyl)-1H-indazol-5-yl)benzamide (Compound 948)

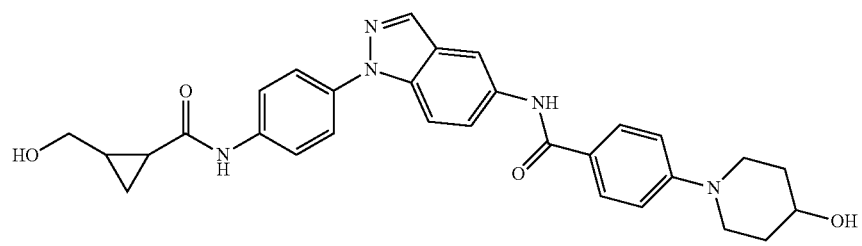 [SMILES: O=C(Nc1ccc2c(cnn2-c2ccc(NC(=O)C3CC3CO)cc2)c1)c1ccc(N2CCC(O)CC2)cc1]

Compound 948 was prepared according to the procedure described in Scheme IV from 5-amino-1-(4-aminophenyl)indazole, 2-hydroxymethylcyclopropanecarboxylic, and 4-(4-hydroxypiperidin-1-yl)benzoic acids. $^1$H NMR (500 MHz, CD$_3$OD) δ 8.21 (m, 2H), 7.88 (d, J=9.1 Hz, 2H), 7.79 (d, J=8.8 Hz, 2H), 7.74-7.65 (m, 4), 7.04 (d, J=8.8 Hz, 2H), 3.84-3.77 (m, 3H), 3.09-3.04 (m, 2H), 1.98-1.96 (m, 1H), 1.65-1.58 (m, 4H), 1.22-1.19 (m, 1H), 0.94-0.88 (m, 2H).

Example 849

N-Cyclopropyl-1-(4-(4-(4-hydroxypiperidin-1-yl)benzamido)phenyl)-1H-indole-5-carboxamide (Compound 949)

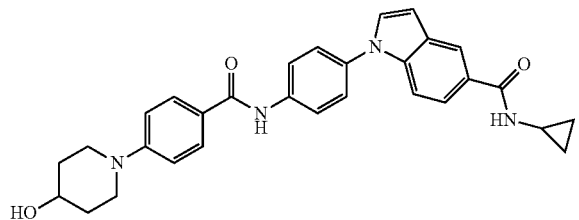 [SMILES: O=C(Nc1ccc(-n2ccc3cc(C(=O)NC4CC4)ccc32)cc1)c1ccc(N2CCC(O)CC2)cc1]

Compound 949 was prepared according to the procedure described in Scheme IV from cylopropylamine, 1-(4-aminophenyl)-1H-indole-5-carboxylic, and 4-(4-hydroxypiperidin-1-yl)benzoic acids. [M+H]$^+$ calcd for C$_{30}$H$_{31}$N$_4$O$_3$: 495.2. found: 495.08.

Example 850

N-Cyclopropyl-1-(4-((4-(4-hydroxypiperidin-1-yl)phenyl)carbamoyl)phenyl)-1H-indazole-5-carboxamide (Compound 950)

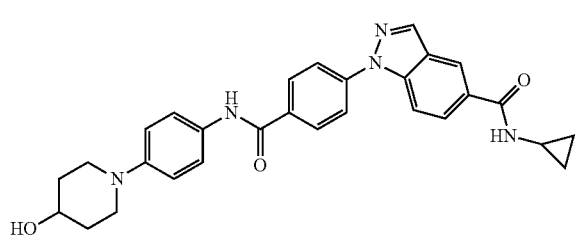 [SMILES: O=C(Nc1ccc(N2CCC(O)CC2)cc1)c1ccc(-n2ncc3cc(C(=O)NC4CC4)ccc32)cc1]

Compound 950 was prepared according to the procedure described in Scheme IV from cylopropylamine, 1-(4-carboxyphenyl)-1H-indazole-5-carboxylic acid, and 4-(4-hydroxypiperidin-1-yl)aniline. [M+H]$^+$ calcd for C$_{29}$H$_{29}$N$_5$O$_3$: 496.2. found: 496.02.

Example 851

4-(4-(Allyloxy)piperidin-1-yl)-N-(1-(4-(cyclopropylcarbamoyl)phenyl)-1H-indol-5-yl)benzamide (Compound 951)

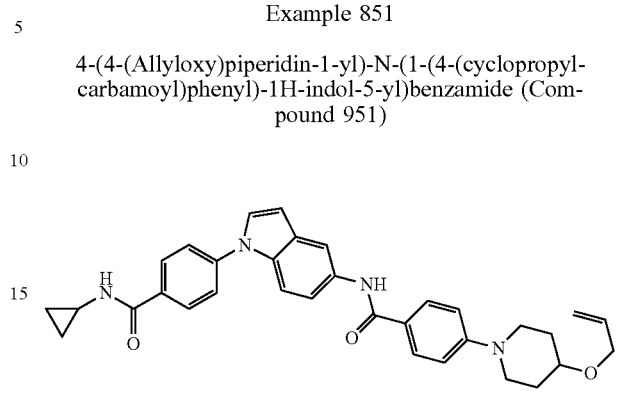

Compound 951 was prepared according to the procedure described in Scheme IV from 4-(5-amino-1H-indol-1-yl)benzoic acid, cyclopropaneamine, and 4-(4-allyloxypiperidin-1-yl)benzoic acid. [M+H]$^+$ calcd for C$_{33}$H$_{34}$N$_4$O$_3$: 535.2. found 535.10.

Example 852

N-Cyclopropyl-4-(5-(4-((2-hydroxyethyl)(methyl)amino)benzamido)-1H-indol-1-yl)benzamide (Compound 952)

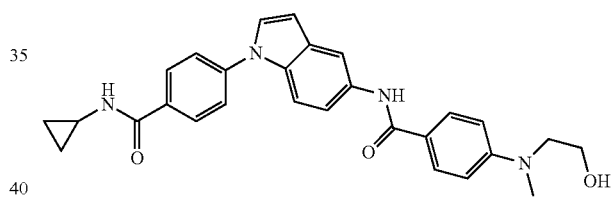

Compound 952 was prepared according to the procedure described in Scheme IV from 4-(5-amino-1H-indol-1-yl)benzoic acid, cyclopropaneamine, and 4-(N-2-hydroxyethyl-N-methylamino)benzoic acid. [M+H]$^+$ calcd for C$_{28}$H$_{28}$N$_4$O$_3$: 469.22. found 468.96.

Example 853

4-(4-Hydroxypiperidin-1-yl)-N-(1-(4-(thiazol-2-ylcarbamoyl)phenyl)-1H-indol-5-yl)benzamide (Compound 953)

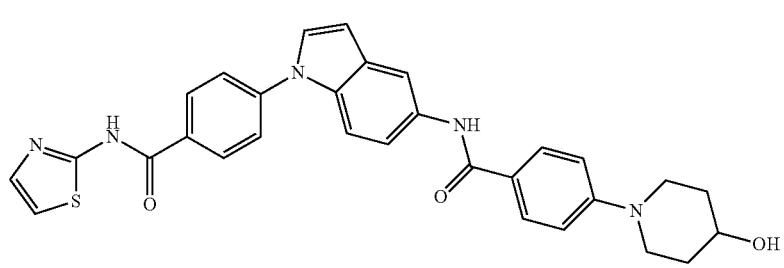 [SMILES: O=C(Nc1ccc2c(ccn2-c2ccc(C(=O)Nc3nccs3)cc2)c1)c1ccc(N2CCC(O)CC2)cc1]

Compound 953 was prepared according to the procedure described in Scheme IV from 4-(5-amino-1H-indol-1-yl)benzoic acid, 2-aminothiazole, and 4-(4-hydroxypiperidin-1-yl)benzoic acid. [M+H]$^+$ calcd for $C_{30}H_{27}N_5O_3S$: 538.1. found: 539.02.

Example 854

4-(4-Hydroxypiperidin-1-yl)-N-(1-(4-(4-methylthiazol-2-ylcarbamoyl)phenyl)-1H-indol-5-yl)benzamide (Compound 954)

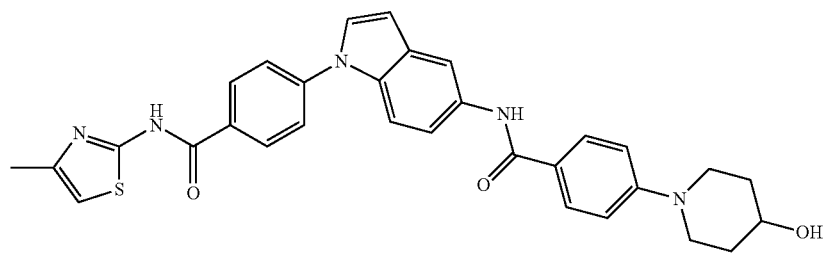 [SMILES: Cc1csc(NC(=O)c2ccc(-n3ccc4cc(NC(=O)c5ccc(N6CCC(O)CC6)cc5)ccc43)cc2)n1]

Compound 954 was prepared according to the procedure described in Scheme IV from 4-(5-amino-1H-indol-1-yl)benzoic acid, 2-amino-4-methylthiazole, and 4-(4-hydroxypiperidin-1-yl)benzoic acid. [M+H]$^+$ calcd for $C_{31}H_{29}N_5O_3S$: 552.10. found: 552.05.

Example 855

4-(4-Hydroxypiperidin-1-yl)-N-(1-(4-(2-methyl-1H-indole-5-ylcarbamoyl)phenyl)-1H-indol-5-yl)benzamide (Compound 955)

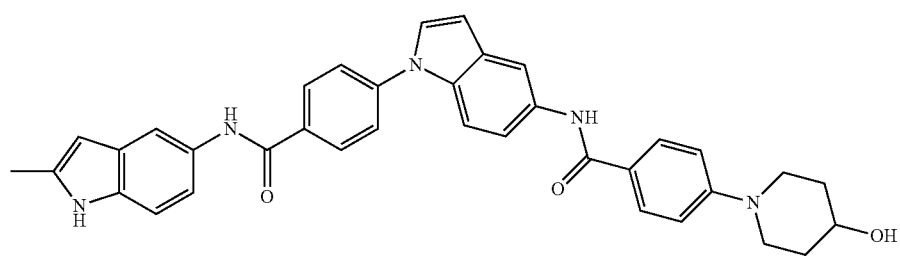 [SMILES: Cc1cc2cc(NC(=O)c3ccc(-n4ccc5cc(NC(=O)c6ccc(N7CCC(O)CC7)cc6)ccc54)cc3)ccc2[nH]1]

Compound 955 was prepared according to the procedure described in Scheme IV from 5-amino-2methylindole, 4-(5-amino-1H-indol-1-yl)benzoic, and 4-(4-hydroxypiperidin-1-yl)benzoic acids. $^1$H NMR (500 MHz, DMSO-d$_6$) δ 10.85 (s, 1H), 10.11 (s, 1H), 9.90 (s, 1H), 8.17 (d, J=8.5 Hz, 2H), 8.14 (d, J=2 Hz, 1H), 7.88 (d, J=9 Hz, 2H), 7.86 (d, J=2 Hz, 1H), 7.77 (d, J=8.5 Hz, 2H), 7.75 (d, J=3 Hz, 1H), 7.65 (d, J=9 Hz, 1H), 7.56 (dd, J=2, 9 Hz, 1H), 7.33 (dd, J=1.5, 8.5 Hz, 1H), 7.23 (d, J=8.5 Hz, 1H), 7.00 (d, J=9 Hz, 2H), 6.74 (d, J=3.5 Hz, 1H), 6.11 (t, J=1 Hz, 1H), 4.71 (d, J=4 Hz, 1H), 3.72-3.66 (m, 3H), 3.00 (dd, J=3, 10 Hz, 2H), 2.37 (s, 3H), 1.83-1.80 (m, 2H), 1.47-1.40 (m, 2H).

Example 856

4-(4-Hydroxypiperidin-1-yl)-N-(1-(4-((1-(2-morpholinoethyl)-1H-indol-5-yl)carbamoyl)phenyl)-1H-indol-5-yl)benzamide (Compound 956)

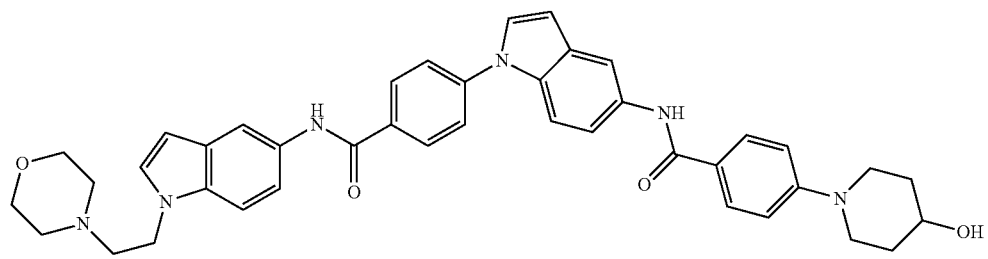 [SMILES: O=C(Nc1ccc2c(ccn2CCN2CCOCC2)c1)c1ccc(-n2ccc3cc(NC(=O)c4ccc(N5CCC(O)CC5)cc4)ccc32)cc1]

Compound 956 was prepared according to the procedure described in Scheme IV from 1-(2-morpholinoethyl)-5-amino-1H-indole, 4-(5-amino-1H-indol-1-yl)benzoic, and 4-(4-hydroxypiperidin-1-yl)benzoic acids. [M+H]$^+$ calcd for $C_{41}H_{42}N_6O_4$: 683.3. found: 683.31.

Example 857

N-(5-Fluoropyridin-2-yl)-4-(5-(4-(4-hydroxypiperidin-1-yl)benzamido)-1H-indol-1-yl)benzamide (Compound 957)

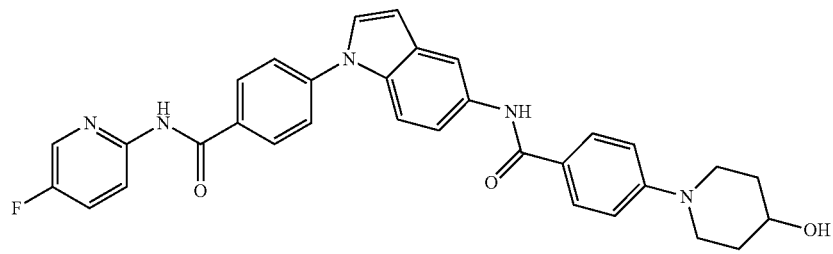 [SMILES: O=C(Nc1ccc2c(ccn2-c2ccc(C(=O)Nc3ccc(F)cn3)cc2)c1)c1ccc(N2CCC(O)CC2)cc1]

Compound 957 was prepared according to the procedure described in Scheme IV from 2-amino-5-fluoropyridine, 4-(5-amino-1H-indol-1-yl)benzoic, and 4-(4-hydroxypiperidin-1-yl)benzoic acids. $^1$H NMR (500 MHz, DMSO-d$_6$) δ 11.01 (s, 1H), 9.90 (s, 1H), 8.42 (d, J=3.5 Hz, 1H), 8.27 (d, J=4 Hz, 1H), 8.24 (dd, J=1.5, 6.5 Hz, 2H), 8.14 (d, J=2 Hz, 1H), 7.88 (d, J=9 Hz, 2H), 7.84-7.80 (m, 1H), 7.78-7.77 (m, 1H), 7.76 (t, J=3.5 Hz, 2H), 7.66 (d, J=9 Hz, 1H), 7.56 (dd, J=2, 9 Hz, 1H), 7.00 (d, J=9 Hz, 2H), 6.75 (d, J=3.5 Hz, 1H), 4.70 (d, J=4 Hz, 1H), 3.71-3.66 (m, 3H), 3.03-2.98 (m, 1H), 1.83-1.79 (m, 2H), 1.47-1.40 (m, 2H).

Example 858

4-(4-Hydroxypiperidin-1-yl)-N-(1-(4-((1H-indol-6-yl)carbamoyl)phenyl)-1H-indol-5-yl)benzamide (Compound 958)

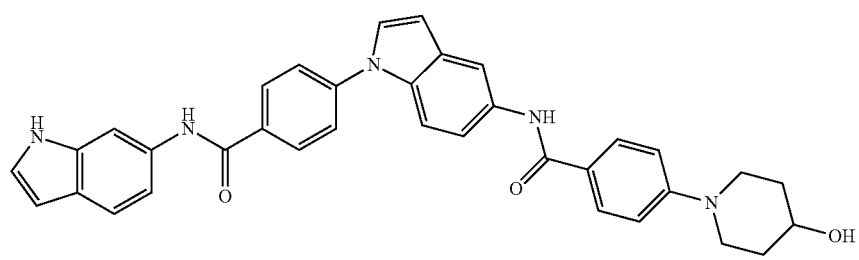 [SMILES: O=C(Nc1ccc2c(ccn2-c2ccc(C(=O)Nc3ccc4cc[nH]c4c3)cc2)c1)c1ccc(N2CCC(O)CC2)cc1]

Compound 958 was prepared according to the procedure described in Scheme IV from 6-aminoindole, 4-(5-amino-1H-indol-1-yl)benzoic, and 4-(4-hydroxypiperidin-1-yl)benzoic acids. $^1$H NMR (500 MHz, DMSO-$d_6$) δ 11.05 (s, 1H), 10.23 (s, 1H), 9.90 (s, 1H), 8.18 (d, J=8.5 Hz, 2H), 8.13 (d, J=2 Hz, 1H), 8.10 (s, 1H), 7.87 (d, J=10 Hz, 2H), 7.77 (d, J=9 Hz, 2H), 7.74 (d, J=3.5 Hz, 1H), 7.65 (d, J=9 Hz, 1H), 7.56 (dd, J=2, 9.5 Hz, 1H), 7.48 (d, J=8.5 Hz, 1H), 7.29 (m, 2H), 6.99 (d, J=9 Hz, 2H), 6.74 (d, J=3 Hz, 1H), 6.38 (m, 1H), 4.70 (d, J=4.5 Hz, 1H), 3.69 (m, 3H), 1.80 (m, 2H), 1.44 (m, 2H).

Example 859

4-(4-Hydroxypiperidin-1-yl)-N-(1-(4-(cyclopropyl-carbamoyl)phenyl)-2-methyl-1H-indol-5-yl)benz-amide (Compound 959)

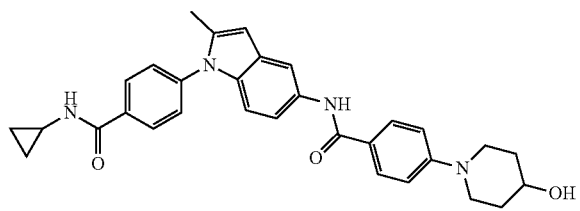 [SMILES: Cc1cc2cc(NC(=O)c3ccc(N4CCC(O)CC4)cc3)ccc2n1-c1ccc(C(=O)NC2CC2)cc1]

Compound 959 was prepared according to the procedure described in Scheme IV from 4-(5-amino-2-methyl-1H-indol-1-yl)benzoic acid, cyclopropaneamine, and 4-(4-hydroxypiperidin-1-yl)benzoic acid. [M+H]$^+$ calcd for $C_{31}H_{32}N_4O_3$: 509.25. found: 509.12.

Example 860

N-(1-(4-(Cyclopropylcarbamoyl)phenyl)-1H-indol-5-yl)-1-(2-morpholinoethyl)-1H-indole-5-carboxam-ide (Compound 960)

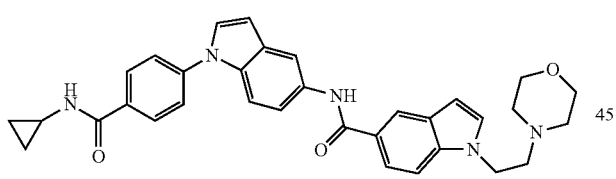

Compound 960 was prepared according to the procedure described in Scheme IV from 4-(5-amino-1H-indol-1-yl)benzoic acid, cyclopropaneamine, and 1-(2-morpholino-ethyl)-1H-indole-5-carboxylic acid. [M+H]$^+$ calcd for $C_{33}H_{33}N_5O_3$: 548.26. found 548.13.

Example 861

N-Cyclopropyl-4-(5-(4-(4-methylpiperazin-1-yl)benzamido)-1H-indol-1-yl)benzamide (Compound 961)

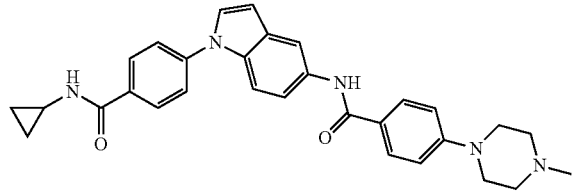 [SMILES: CN1CCN(c2ccc(C(=O)Nc3ccc4c(ccn4-c4ccc(C(=O)NC5CC5)cc4)c3)cc2)CC1]

Compound 961 was prepared according to the procedure described in Scheme IV from 4-(5-amino-1H-indol-1-yl)benzoic acid, cyclopropaneamine, and 4-(4-methylpiper-azin-1-yl)benzoic acid. [M+H]$^+$ calcd for $C_{30}H_{31}N_5O_2$: 494.2. found 494.06.

Example 862

Ethyl 2-(5-(4-(5-(4-(4-hydroxypiperidin-1-yl)ben-zamido)-1H-indol-1-yl)benzamido)-1H-indol-1-yl)acetate (Compound 962)

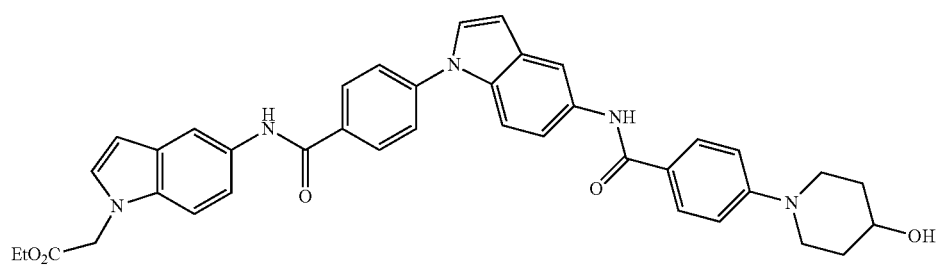 [SMILES: CCOC(=O)Cn1ccc2cc(NC(=O)c3ccc(-n4ccc5cc(NC(=O)c6ccc(N7CCC(O)CC7)cc6)ccc54)cc3)ccc21]

Compound 962 was prepared according to the procedure described in Scheme IV from ethyl 5-amino-1H-indole-1-acetate, 4-(5-amino-1H-indol-1-yl)benzoic, and 4-(4-hydroxypiperidin-1-yl)benzoic acids. [M+H]$^+$ calcd for $C_{39}H_{37}N_5O_5$: 656.28. found 656.23.

Example 863

N-(1-(4-(((1H-Indol-2-yl)methyl)carbamoyl)phenyl)-1H-indol-5-yl)-1-(2-hydroxyethyl)-1H-indole-5-carboxamide (Compound 963)

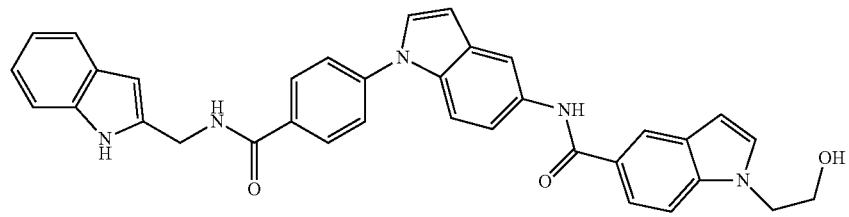 [SMILES: O=C(NCc1cc2ccccc2[nH]1)c1ccc(-n2ccc3cc(NC(=O)c4ccc5c(ccn5CCO)c4)ccc32)cc1]

Compound 963 was prepared according to the procedure described in Scheme IV from 4-(5-amino-1H-indol-1-yl) benzoic acid, 2-aminomethylindole, and 1-(2-hydroxyethyl)-1H-indole-5-carboxylic acid. $^1$H NMR (500 MHz, DMSO-d$_6$) δ 10.14 (s, 1H), 9.42 (s, 1H), 8.31 (dd, J=1.0, 5.5 Hz, 2H), 8.14 (d, J=8.5 Hz, 2H), 8.06 (t, J=5.5 Hz, 1H), 7.87 (dd, J=1.5, 9 Hz, 1H), 7.74 (d, J=8 Hz, 1H), 7.66 (d, J=9 Hz, 2H), 7.62 (d, J=2 Hz, 1H), 7.61 (s, 1H), 7.57 (d, J=3 Hz, 1H), 7.55 (d, J=9 Hz, 1H), 7.37 (d, J=2.5 Hz, 1H), 7.11 (ddd, J=1, 7, 9 Hz, 1H) 7.03 (ddd, J=1, 7, 8.5 Hz, 1H), 6.70 (d, J=3.5 Hz, 1H), 6.56 (d, J=3.5 Hz, 1H), 4.82 (d, J=5.5 Hz, 2H), 4.35 (t, J=5.5 Hz, 2H), 3.92 (q, J=5 Hz, 2H), 3.31 (d, J=5 Hz, 1H).

Example 864

2-(5-(4-(5-(4-(4-Hydroxypiperidin-1-yl)benzamido)-1H-indol-1-yl)benzamido)-1H-indol-1-yl)acetic acid (Compound 964)

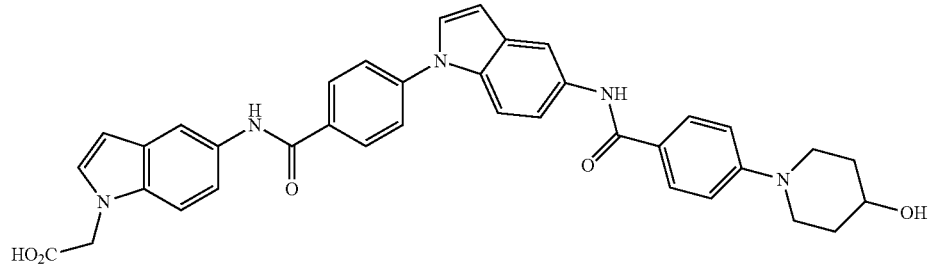 [SMILES: O=C(O)Cn1ccc2cc(NC(=O)c3ccc(-n4ccc5cc(NC(=O)c6ccc(N7CCC(O)CC7)cc6)ccc54)cc3)ccc21]

Compound 964 was prepared by hydrolysis of Compound 962. [M+H]$^+$ calcd for $C_{37}H_{33}N_5O_5$: 628.2. found 628.14.

Example 865

(±)-N-Cyclopropyl-4-(5-(4-(3-(hydroxymethyl)piperidin-1-yl)benzamido)-1H-indol-1-yl)benzamide (Compound 965)

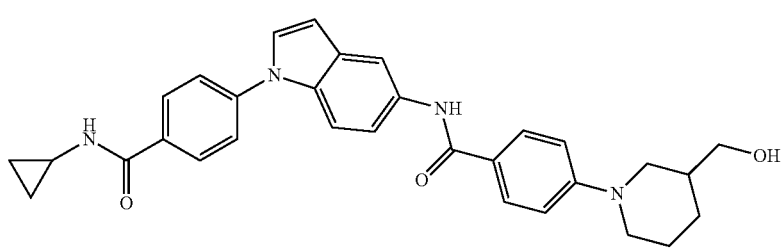 [SMILES: O=C(Nc1ccc2c(ccn2-c2ccc(C(=O)NC3CC3)cc2)c1)c1ccc(N2CCCC(CO)C2)cc1]

Compound 965 was prepared according to the procedure described in Scheme IV from 4-(5-amino-1H-indol-1-yl)benzoic acid, cyclopropaneamine, and 4-(3-(hydroxymethyl)piperazin-1-yl)benzoic acid. [M+H]$^+$ calcd for $C_{31}H_{32}N_4O_3$: 509.25. found: 509.05.

Example 866

4-(4-Hydroxypiperidin-1-yl)-N-(1-(4-((1-(2-methoxyethyl)-2-methyl-1H-indol-5-yl)carbamoyl)phenyl)-1H-indol-5-yl)benzamide (Compound 966)

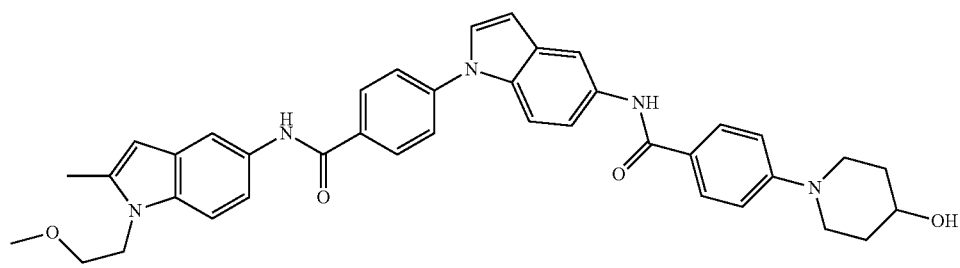 [SMILES: COCCn1c(C)cc2cc(NC(=O)c3ccc(-n4ccc5cc(NC(=O)c6ccc(N7CCC(O)CC7)cc6)ccc54)cc3)ccc21]

Compound 966 was prepared according to the procedure described in Scheme IV from ethyl 5-amino-2-methyl-1-(2-methoxyethyl)-1H-indole, 4-(5-amino-1H-indol-1-yl)benzoic, and 4-(4-hydroxypiperidin-1-yl)benzoic acids. [M+H]$^+$ calcd for $C_{39}H_{39}N_5O_4$: 642.3. found: 642.26.

Example 867

N-Cyclopropyl-4-(5-(4-(1,1-dioxidothiomorpholino)benzamido)-1H-indol-1-yl)benzamide (Compound 967)

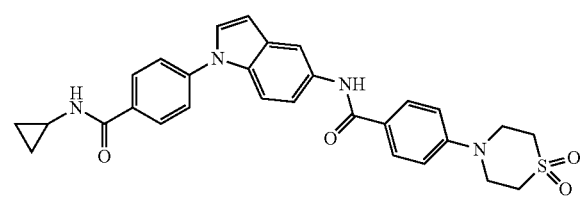 [SMILES: O=C(Nc1ccc2c(ccn2-c2ccc(C(=O)NC3CC3)cc2)c1)c1ccc(N2CCS(=O)(=O)CC2)cc1]

Compound 967 was prepared according to the procedure described in Scheme IV from 4-(5-amino-1H-indol-1-yl)benzoic acid, cyclopropaneamine, and 4-(1,1-dioxidothiomorpholino)piperazin-1-yl)benzoic acid. $^1$H NMR (500 MHz, DMSO-d$_6$) δ 9.98 (s, 1H), 8.53 (d, J=4 Hz, 1H), 8.13 (d, J=1.5 Hz, 1H), 8.02 (d, J=8.5 Hz, 2H), 7.94 (d, J=9 Hz, 2H), 7.72 (m, 3H), 7.62 (d, J=9 Hz, 1H), 7.55 (dd, J=2, 9 Hz, 1H), 7.14 (d, J=9 Hz, 2H), 6.73 (d, J=3 Hz, 1H), 3.93 (bs, 4H), 3.14 (bs, 4H), 2.89 (m, 1H), 0.72 (m, 2H), 0.61 (m, 2H).

Example 868

N-(1-(4-((1H-Indol-6-yl)carbamoyl)phenyl)-1H-indol-5-yl)-4-(morpholinomethyl)benzamide (Compound 968)

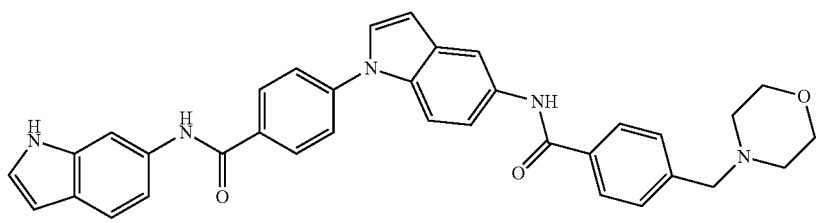 [SMILES: O=C(Nc1ccc2c(ccn2-c2ccc(C(=O)Nc3ccc4cc[nH]c4c3)cc2)c1)c1ccc(CN2CCOCC2)cc1]

Compound 968 was prepared according to the procedure described in Scheme IV from 6-aminoindole, 4-(5-amino-1H-indol-1-yl)benzoic, and 4-(morpholinomethyl)benzoic acids. [M+H]$^+$ calcd for $C_{35}H_{31}N_5O_3$: 570.2. found: 570.14.

Example 869

N-(1-(2-(Cyclopropylamino)-2-oxoethyl)-1H-indol-5-yl)-4-(5-(4-(4-hydroxypiperidin-1-yl)benzamido)-1H-indol-1-yl)benzamide (Compound 969)

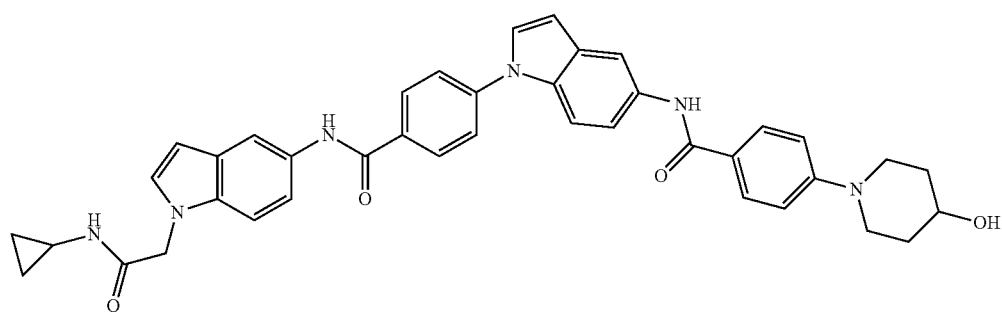 [SMILES: O=C(Cn1ccc2cc(NC(=O)c3ccc(-n4ccc5cc(NC(=O)c6ccc(N7CCC(O)CC7)cc6)ccc54)cc3)ccc21)NC1CC1]

Compound 969 was prepared by treatment of Compound 962 with cyclopropylamine. [M+H]$^+$ calcd for $C_{40}H_{38}N_6O_4$: 667.3. found 667.31.

Example 870

N-(1-(2-((Cyanomethyl)amino)-2-oxoethyl)-1H-indol-5-yl)-4-(5-(4-(4-hydroxypiperidin-1-yl)benzamido)-1H-indol-1-yl)benzamide (Compound 970)

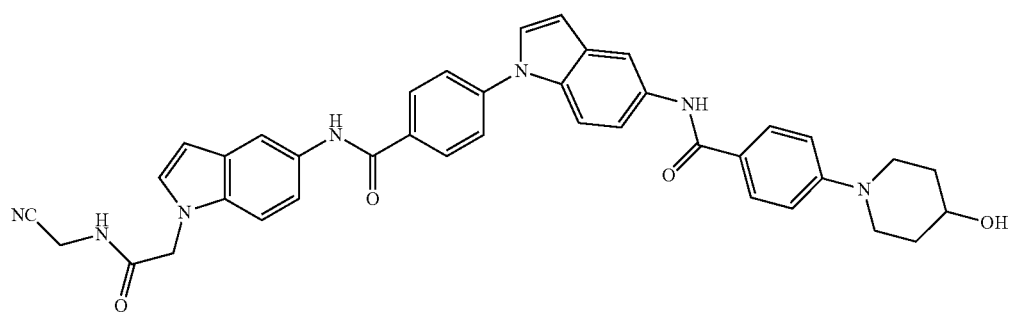 [SMILES: N#CCNC(=O)Cn1ccc2cc(NC(=O)c3ccc(-n4ccc5cc(NC(=O)c6ccc(N7CCC(O)CC7)cc6)ccc54)cc3)ccc21]

Compound 970 was prepared by treatment of Compound 962 with cyanoethylamine. [M+H]$^+$ calcd for $C_{39}H_{35}N_7O_4$: 666.2. found 666.23.

Example 871

Methyl 2-(2-(5-(4-(5-(4-(4-hydroxypiperidin-1-yl)
benzamido)-1H-indol-1-yl)benzamido)-1H-indol-1-
yl)acetamido)acetate (Compound 971)

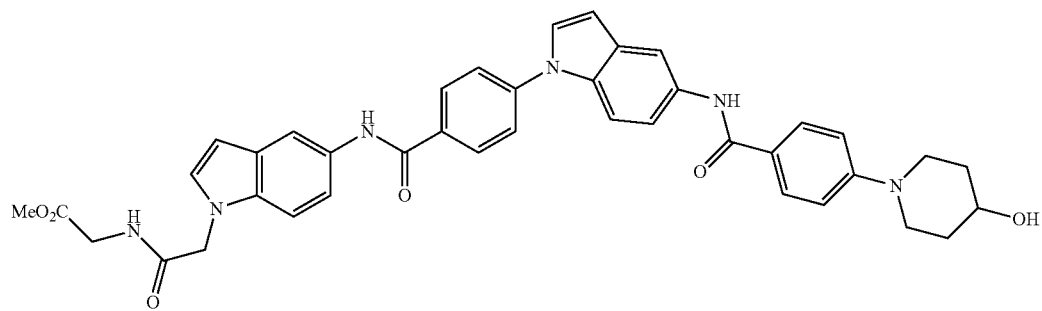 [SMILES: COC(=O)CNC(=O)Cn1ccc2cc(NC(=O)c3ccc(-n4ccc5cc(NC(=O)c6ccc(N7CCC(O)CC7)cc6)ccc54)cc3)ccc21]

Compound 971 was prepared by treatment of Compound 962 with methyl aminoacetate. [M+H]$^+$ calcd for $C_{40}H_{38}N_6O_6$: 699.2. found 699.25.

Example 872

N-(1-(4-((1H-Indol-6-yl)carbamoyl)phenyl)-1H-
indol-5-yl)-1-(2-morpholinoethyl)-1H-indole-5-car-
boxamide (Compound 972)

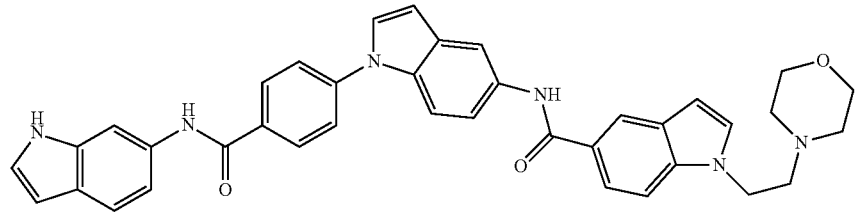 [SMILES: O=C(Nc1ccc2cc[nH]c2c1)c1ccc(-n2ccc3cc(NC(=O)c4ccc5c(ccn5CCN5CCOCC5)c4)ccc32)cc1]

Compound 972 was prepared according to the procedure described in Scheme IV from 4-(5-amino-1H-indol-1-yl) benzoic acid, 6-aminoindole, and 1-(2-morpholinoethyl)-1H-indole-5-carboxylic acid. [M+H]$^+$ calcd for $C_{38}H_{34}N_6O_3$: 623.27. found 623.15.

Example 873

Ethyl 4-(5-(4-(5-(4-(4-hydroxypiperidin-1-yl)ben-
zamido)-1H-indol-1-yl)benzamido)-1H-indol-1-yl)
butanoate (Compound 973)

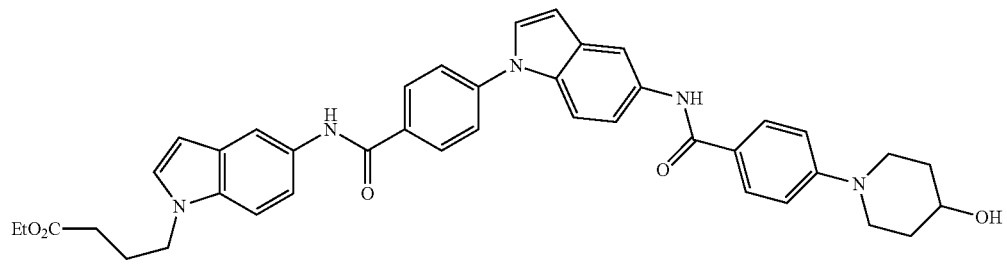 [SMILES: O=C(O)CCCn1ccc2cc(NC(=O)c3ccc(-n4ccc5cc(NC(=O)c6ccc(N7CCC(O)CC7)cc6)ccc54)cc3)ccc21]

Compound 973 was prepared according to the procedure described in Scheme IV from ethyl 4-(5-amino-1H-indol-1-yl)butanoate, 4-(5-amino-1H-indol-1-yl)benzoic, and 4-(4-hydroxypiperidin-1-yl)benzoic acids. [M+H]$^+$ calcd for $C_{41}H_{41}N_5O_5$: 684.3. found 684.19.

Example 874

4-(5-(4-(5-(4-(4-Hydroxypiperidin-1-yl)benzamido)-1H-indol-1-yl)benzamido)-1H-indol-1-yl)butanoic acid (Compound 974)

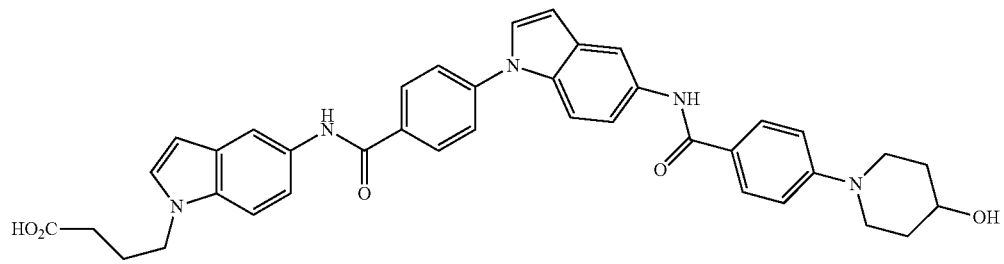

Compound 974 was prepared hydrolysis of Compound 973. [M+H]$^+$ calcd for $C_{39}H_{37}N_5O_5$: 656.2. found 656.17.

Example 875

Methyl 2-(2-(5-(4-(5-(4-(4-hydroxypiperidin-1-yl)benzamido)-1H-indol-1-yl)benzamido)-1H-indol-1-yl)acetamido)acetate (Compound 975)

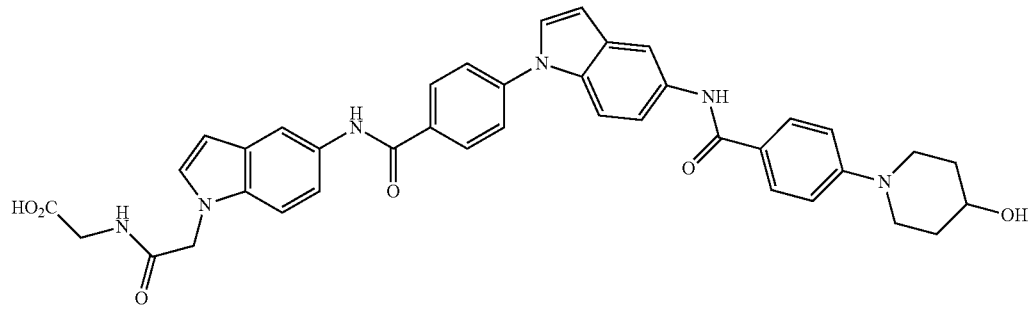 [SMILES: O=C(O)CNC(=O)Cn1ccc2cc(NC(=O)c3ccc(-n4ccc5cc(NC(=O)c6ccc(N7CCC(O)CC7)cc6)ccc54)cc3)ccc21]

Compound 975 was prepared by hydrolysis of Compound 971. [M+H]$^+$ calcd for $C_{39}H_{36}N_6O_6$: 685.2. found 685.14.

Example 876

N-(3-(4-Aminophenyl)-1H-indazol-6-yl)-4-(4-hydroxypiperidin-1-yl)benzamide (Compound 976)

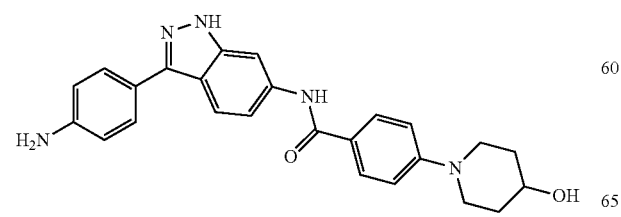

Compound 976 was prepared according to the procedure described in Scheme IV from 6-amino-3-(4-aminophenyl)-1H-indazole, and 4-(4-hydroxypiperidin-1-yl)benzoic acid. [M+H]⁺ calcd for $C_{25}H_{25}N_5O_2$: 428.2. found 428.07.

Example 877

N-(3-(4-(Cyclopropanecarboxamido)phenyl)-1H-indazol-6-yl)-4-(4-hydroxypiperidin-1-yl)benzamide (Compound 977)

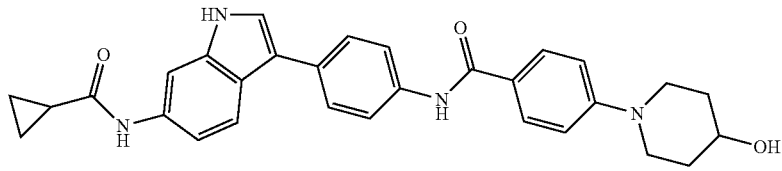 [SMILES: O=C(Nc1ccc(-c2c[nH]c3cc(NC(=O)C4CC4)ccc23)cc1)c1ccc(N2CCC(O)CC2)cc1]

Compound 977 was prepared according to the procedure described in Scheme IV from 6-amino-3-(4-aminophenyl)-1H-indazole, cyclopropanecarboxylic, and 4-(4-hydroxypiperidin-1-yl)benzoic acids. [M+H]⁺ calcd for $C_{30}H_{30}N_4O_3$: 495.11. found: 495.08.

Example 878

N-(4-(6-(4-(4-Hydroxypiperidin-1-yl)benzamido)-1H-indazol-3-yl)phenyl)-1H-pyrrole-2-carboxamide (Compound 978)

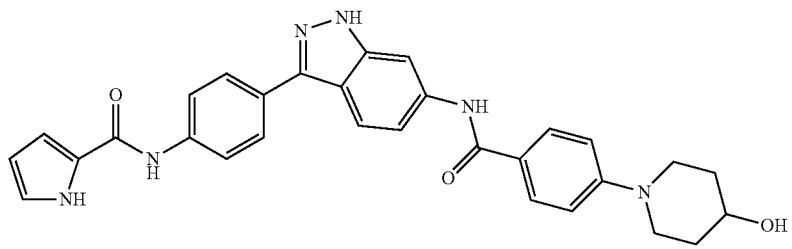 [SMILES: O=C(Nc1ccc2c(-c3ccc(NC(=O)c4ccc[nH]4)cc3)n[nH]c2c1)c1ccc(N2CCC(O)CC2)cc1]

Compound 978 was prepared according to the procedure described in Scheme IV from 6-amino-3-(4-aminophenyl)-1H-indazole, pyrrole-2-carboxylic, and 4-(4-hydroxypiperidin-1-yl)benzoic acids. [M+H]⁺ calcd for $C_{30}H_{28}N_6O_3$: 521.2. found 521.07.

Example 879

N-(3-(4-((1H-Indol-6-yl)carbamoyl)phenyl)-1H-indol-6-yl)-1-methyl-1H-pyrrole-2-carboxamide (Compound 979)

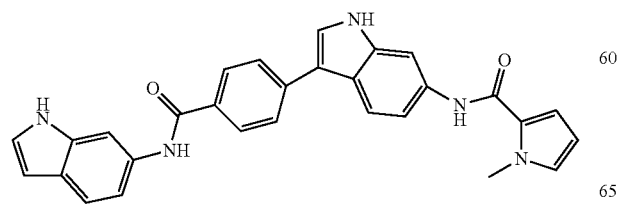

Compound 979 was prepared according to the procedure described in Scheme IV from 4-(6-amino-1H-indol-3-yl)benzoic acid, 1-methylpyrrole-2-carboxylic acid, and 6-aminoindole. [M+H]+ calcd for $C_{29}H_{23}N_5O_2$: 474.0. found: 474.02.

Example 880

N-(3-(4-(4-(4-Hydroxypiperidin-1-yl)benzamido)phenyl)-1H-indol-6-yl)-1-methyl-1H-pyrrole-2-carboxamide (Compound 980)

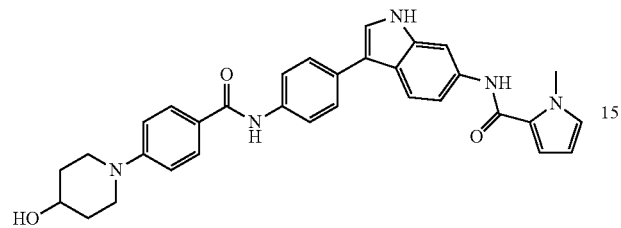

Compound 980 was prepared according to the procedure described in Scheme IV from 6-amino-3-(4-aminophenyl)indole, 1-methylpyrrole-2-carboxylic, and 4-(4-hydroxypiperidin-1-yl)benzoic acids. [M+H]+ calcd for $C_{32}H_{31}N_5O_3$: 534.1. found: 534.09.

Example 881

N-(3-(4-((4-(4-Hydroxypiperidin-1-yl)phenyl)carbamoyl)phenyl)-1H-indol-6-yl)-1-methyl-1H-pyrrole-2-carboxamide (Compound 981)

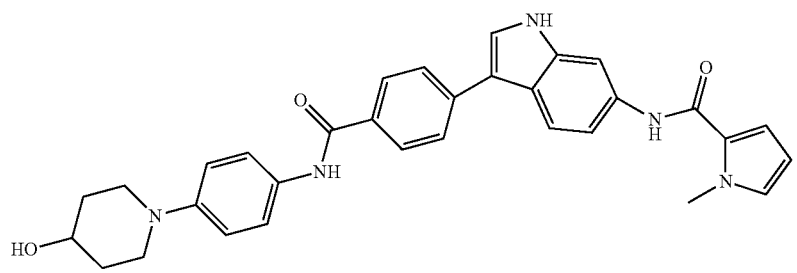 [SMILES: Cn1cccc1C(=O)Nc1ccc2c(-c3ccc(C(=O)Nc4ccc(N5CCC(O)CC5)cc4)cc3)c[nH]c2c1]

Compound 981 was prepared according to the procedure described in Scheme IV from 4-(6-amino-1H-indol-3-yl)benzoic acid, 1-methylpyrrole-2-carboxylic acid, and 4-(4-hydroxypiperidin-1-yl) aniline. [M+H]+ calcd for $C_{32}H_{31}N_5O_3$: 534.15. found: 534.09.

Example 882

N-(4-(5-(4-(4-Hydroxypiperidin-1-yl)benzamido)-1H-pyrazolo[3,4-c]pyridin-1-yl)phenyl)-1-methyl-1H-pyrrole-2-carboxamide (Compound 982)

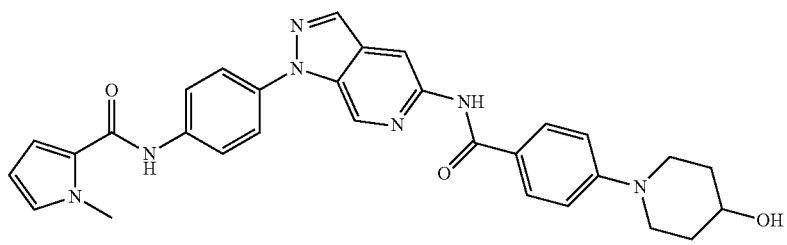 [SMILES: Cn1cccc1C(=O)Nc1ccc(-n2ncc3cc(NC(=O)c4ccc(N5CCC(O)CC5)cc4)ncc32)cc1]

Compound 982 was prepared according to the procedure described in Scheme IV from 1-(4-aminophenyl)-1H-pyrazolo[3,4-c]pyridin-5-amine, 1-methylpyrrole-2-carboxylic, and 4-(4-hydroxypiperidin-1-yl)benzoic acids. [M+H]+ calcd for $C_{30}H_{29}N_7O_3$: 536.2. found 536.05.

Example 883

2-(4-(4-((1-(4-(Cyclopropanecarboxamido)phenyl)-1H-indol-5-yl)carbamoyl)phenyl)piperazin-1-yl) acetic acid (Compound 983)

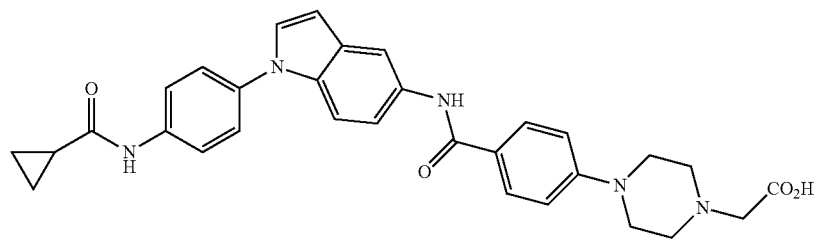 [SMILES: O=C(O)CN1CCN(c2ccc(C(=O)Nc3ccc4c(ccn4-c4ccc(NC(=O)C5CC5)cc4)c3)cc2)CC1]

Compound 983 was prepared according to the procedure described in Scheme IV from 5-amino-1-(4-aminophenyl)indole, cyclopropanecarboxylic acid, and 4-(4-(hydroxycarbonylmethyl)piperazin-1-yl)benzoic ester. $^1$H NMR (500 MHz, Acetone-$d_6$) δ 9.27 (s, 1H), 8.25 (s, 1H), 8.07 (dd, J=2, 6.5 Hz, 2H), 7.95 (d, J=9 Hz, 2H), 7.82 (s, 1H), 7.60 (dd, J=2, 6.5 Hz, 2H), 7.59-7.58 (m, 3H), 7.04 (d, J=9 Hz, 2H), 6.70 (d, J=3 Hz, 1H), 3.39 (m, 3H), 2.17 (m, 1H), 1.29 (m, 8H), 0.77-0.74 (m, 2H), 0.65-0.64 (m, 2H).

Example 884

4-(4-Hydroxypiperidin-1-yl)-N-(1-(4-(cyclopropylcarbamoyl)phenyl)-3-acetyl-1H-indol-5-yl)benzamide (Compound 984)

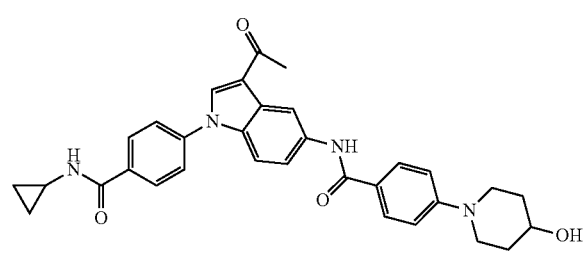 [SMILES: CC(=O)c1cn(-c2ccc(C(=O)NC3CC3)cc2)c2ccc(NC(=O)c3ccc(N4CCC(O)CC4)cc3)cc12]

Compound 984 was prepared according to the procedure described in Scheme IV from 4-(5-amino-3-acetyl-1H-indol-1-yl)benzoic acid, cyclopropaneamine, and 4-(4-hydroxypiperidin-1-yl)benzoic acid. [M+H]+ calcd for $C_{32}H_{32}N_4O_4$: 537.24. found: 537.06.

Example 885

4-(4-Hydroxypiperidin-1-yl)-N-(1-(4-(cyclopropylcarbamoyl)phenyl)-1H-indazol-5-yl)benzamide (Compound 985)

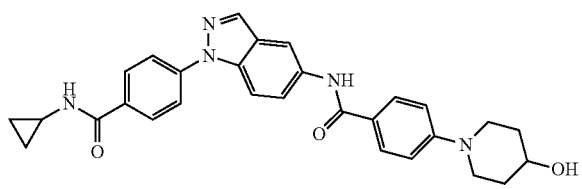 [SMILES: O=C(Nc1ccc2c(cnn2-c2ccc(C(=O)NC3CC3)cc2)c1)c1ccc(N2CCC(O)CC2)cc1]

Compound 985 was prepared according to the procedure described in Scheme IV from 4-(5-amino-1H-indazol-1-yl)benzoic acid, cyclopropaneamine, and 4-(4-hydroxypiperidin-1-yl)benzoic acid. [M+H]+ calcd for $C_{29}H_{29}N_5O_3$: 496.2. found 496.09.

Example 886

1-(4-Aminophenyl)-N-(4-(4-hydroxypiperidin-1-yl)phenyl)-1H-indazole-5-carboxamide (Compound 986)

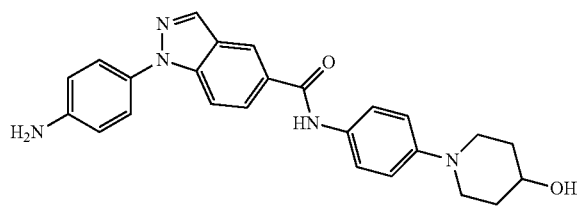 [SMILES: Nc1ccc(-n2ncc3cc(C(=O)Nc4ccc(N5CCC(O)CC5)cc4)ccc32)cc1]

Compound 986 was prepared according to the procedure described in Scheme IV from 1-(4-aminophenyl-1H-indazol-5-yl)carboxylic acid, and 4-(4-hydroxypiperidin-1-yl)aniline. [M+H]+ calcd for $C_{25}H_{25}N_5O_2$: 428.2. found: 428.00.

Example 887 tert-Butyl 2-((4-(5-(4-morpholinobenzamido)-1H-indazol-1-yl)phenyl)amino)acetate (Compound 987)

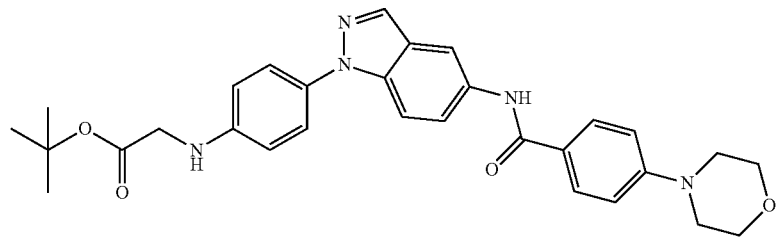 [SMILES: CC(C)(C)OC(=O)CNc1ccc(-n2ncc3cc(NC(=O)c4ccc(N5CCOCC5)cc4)ccc32)cc1]

Compound 987 was prepared according to the procedure described in Scheme IV from 5-amino-1-(4-aminophenyl) indazole, t-butyl bromoacetate, and 4-morpholinobenzoic acid. $^1$H NMR (500 MHz, CDCl$_3$) δ 8.15 (s, 1H), 8.09 (s, 1H), 7.98 (s, 1H), 7.84 (d, J=7.5 Hz, 2H), 7.55 (d, J=9 Hz, 1H), 7.48 (d, J=10 Hz, 1H), 7.46 (d, J=7 Hz, 2H), 7.26 (s, 1H), 6.90 (d, J=7.5 Hz, 2H), 6.71 (d, J=7 Hz, 2H), 4.45 (s, 1H), 3.87-3.83 (m, 6H), 3.27-3.25 (m, 4H), 1.51 (m, 9H).

Example 888

N-(4-(5-(Benzyloxy)-1H-indazol-1-yl)phenyl)-4-(4-hydroxypiperidin-1-yl)benzamide (Compound 988)

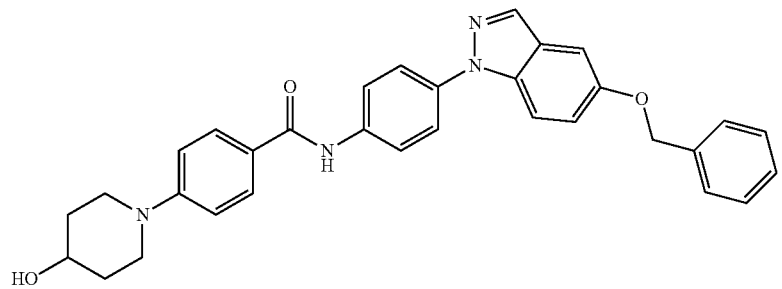 [SMILES: O=C(Nc1ccc(-n2ncc3cc(OCc4ccccc4)ccc32)cc1)c1ccc(N2CCC(O)CC2)cc1]

Compound 988 was prepared according to the procedure described in Scheme IV from 5-benzyloxy-1-(4-aminophenyl)indazole and 4-(4-hydroxypiperidin-1-yl)benzoic acid. [M+H]$^+$ calcd for C$_{32}$H$_{30}$N$_4$O$_3$: 519.2. found: 519.11.

Example 889

N-(4-(5-(4-Fluorobenzamido)-1H-indazol-1-yl)phenyl)isonicotinamide (Compound 989)

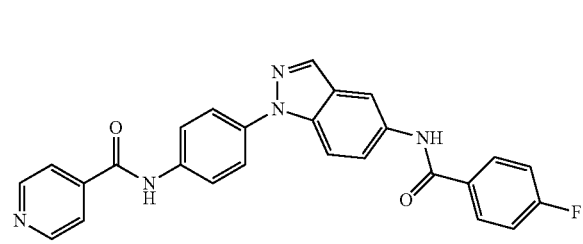 [SMILES: O=C(Nc1ccc(-n2ncc3cc(NC(=O)c4ccc(F)cc4)ccc32)cc1)c1ccncc1]

Compound 989 was prepared according to the procedure described in Scheme IV from 5-amino-1-(4-aminophenyl) indazole, isonicotinic, and 4-fluorobenzoic acids.
[M+H]$^+$ calcd for C$_{26}$H$_{18}$FN$_5$O$_2$: 452.1. found: 451.95.

Example 890

N-(4-(5-(Hydroxy)-1H-indazol-1-yl)phenyl)-4-(4-hydroxypiperidin-1-yl)benzamide (Compound 990)

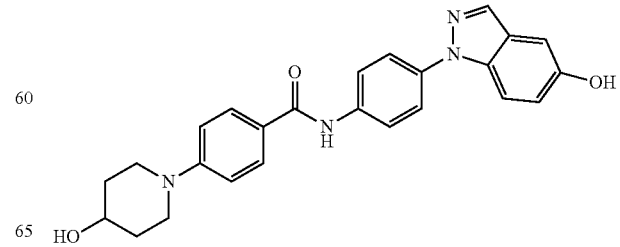

Compound 990 was prepared according to the procedure described in Scheme IV from 5-hydroxy-1-(4-aminophenyl)indazole and 4-(4-hydroxypiperidin-1-yl)benzoic acid. [M+H]⁺ calcd for $C_{25}H_{24}N_4O_3$: 429.1. found: 429.07.

Example 891

4-(Dimethylamino)-N-(4-(6-(4-(dimethylamino)benzamido)-1-(phenylsulfonyl)-1H-indol-3-yl)phenyl)benzamide (Compound 991)

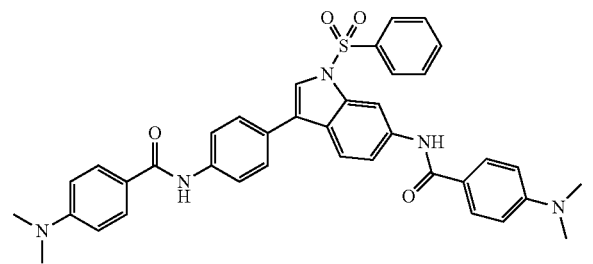

Compound 991 was prepared according to the procedure described in Scheme IV from 6-amino-3-(4-aminophenyl)-1-(phenylsulfonyl)indole and 4-dimethylaminobenzoic acid. [M+H]⁺ calcd for $C_{38}H_{35}N_5O_4S$: 658.3. found: 658.19.

Example 892

N-(4-(5-(4-(4-Hydroxypiperidin-1-yl)benzamido)-1H-benzo[d]imidazol-1-yl)phenyl)-1H-indole-6-carboxamide (Compound 992)

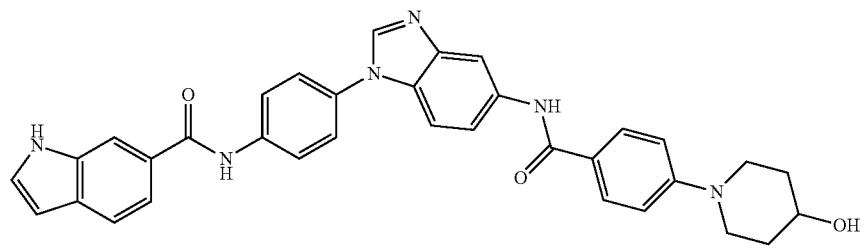 [SMILES: O=C(Nc1ccc2c(c1)ncn2-c1ccc(NC(=O)c2ccc3cc[nH]c3c2)cc1)c1ccc(N2CCC(O)CC2)cc1]

Compound 992 was prepared according to the procedure described in Scheme IV from 5-amino-1-(4-aminophenyl)benzimidazole, 6-indolecarboxylic, and 4-(4-hydroxypiperidin-1-yl)benzoic acids. [M+H]⁺ calcd for $C_{34}H_{30}N_6O_3$: 571.2. found: 571.15.

Example 893

N-(4-(5-(Cyclopropanecarboxamido)-1H-indazol-1-yl)phenyl)-4-(4-hydroxypiperidin-1-yl)benzamide (Compound 993)

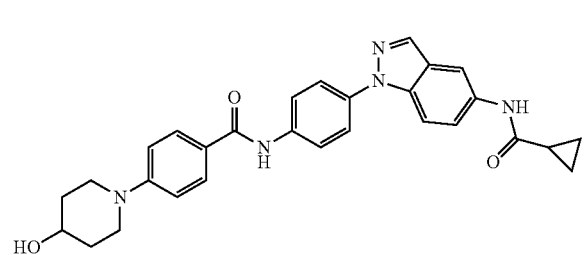 [SMILES: O=C(Nc1ccc(-n2ncc3cc(NC(=O)C4CC4)ccc32)cc1)c1ccc(N2CCC(O)CC2)cc1]

Compound 993 was prepared according to the procedure described in Scheme IV from 5-amino-1-(4-aminophenyl)indazole, cyclopropanecarboxylic, and 4-(4-hydroxypiperidin-1-yl)benzoic acids. ¹H NMR (500 MHz, Acetone-d₆) δ 9.55 (s, 1H), 9.48 (s, 1H), 8.34 (m, 1H), 8.19 (m, 1H), 8.07 (d, J=8.5 Hz, 1H), 7.94 (d, J=9 Hz, 1H), 7.86 (d, J=9 Hz, 1H), 7.80-7.69 (m, 4H), 7.61 (m, 1H), 7.04 (d, J=9 Hz, 2H), 3.80 (m, 3H), 3.11 (m, 1H), 2.09 (m, 2H), 1.94 (m, 1H), 1.80 (m, 1H), 1.60 (m, 1H), 0.93 (m, 2H), 0.80 (m, 2H).

Example 894

(±)-N-(4-(5-(Cyclopropanecarboxamido)-1H-indazol-1-yl)phenyl)-4-(3,4-cis-dihydroxypiperidin-1-yl)benzamide (Compound 994)

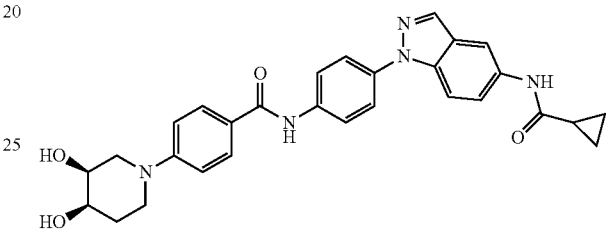

Compound 994 was prepared according to the procedure described in Scheme IV from 5-amino-1-(4-aminophenyl)indazole, cyclopropanecarboxylic, and 4-(3,4-cis-dihydroxypiperidin-1-yl)benzoic acids. [M+H]⁺ calcd for $C_{29}H_{29}N_5O_4$: 512.22. found 512.09.

Example 895

4-(2-Hydroxyethoxy)-N-(4-(5-(4-(2-hydroxyethoxy)benzamido)-1H-indazol-1-yl)phenyl)benzamide (Compound 995)

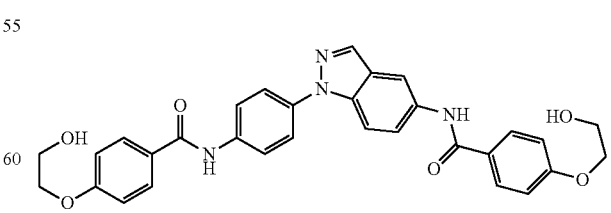

Compound 995 was prepared according to the procedure described in Scheme IV from 5-amino-1-(4-aminophenyl)indazole and 4-(2-hydroxyethoxy)benzoic acid. [M+H]⁺ calcd for $C_{31}H_{29}N_4O_6$: 553.2. found: 553.10.

Example 896

N-(4-(5-(4-(4-Hydroxypiperidin-1-yl)benzamido)-
1H-indazol-1-yl)phenyl)thiazole-2-carboxamide
(Compound 996)

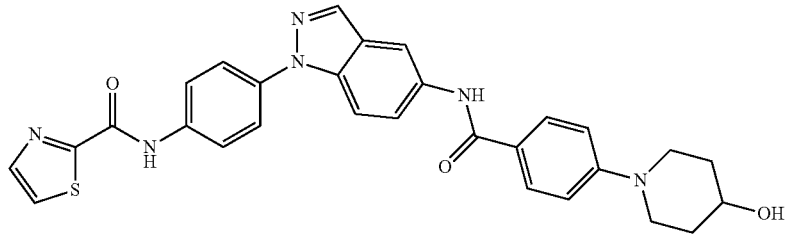 [SMILES: O=C(Nc1ccc2c(cnn2-c2ccc(NC(=O)c3nccs3)cc2)c1)c1ccc(N2CCC(O)CC2)cc1]

Compound 996 was prepared according to the procedure described in Scheme IV from 5-amino-1-(4-aminophenyl)indazole, thiozole-2-carboxylic and 4-(4-hydroxypiperidin-1-yl)benzoic acids. [M+H]+ calcd for $C_{29}H_{26}N_6O_3S$: 539.19. found: 539.02.

Example 897

N-(4-(5-(4-(4-Hydroxypiperidin-1-yl)benzamido)-
1H-indazol-1-yl)phenyl)-2-(methylamino)isonicotinamide (Compound 997)

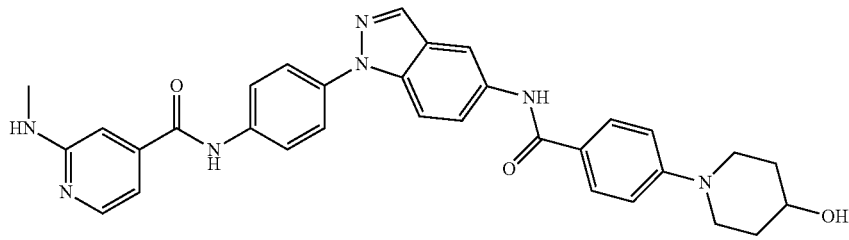 [SMILES: CNc1cc(C(=O)Nc2ccc(-n3ncc4cc(NC(=O)c5ccc(N6CCC(O)CC6)cc5)ccc43)cc2)ccn1]

Compound 997 was prepared according to the procedure described in Scheme IV from 5-amino-1-(4-aminophenyl)indazole, 2-(methylamino)isonicotinic and 4-(4-hydroxypiperidin-1-yl)benzoic acids. [M+H]$^+$ calcd for $C_{32}H_{31}N_7O_3$: 562.2. found: 562.13.

Example 898

N-(4-(5-(4-(4-Hydroxypiperidin-1-yl)benzamido)-
1H-indazol-1-yl)phenyl)-2-(methyl)isonicotinamide
(Compound 998)

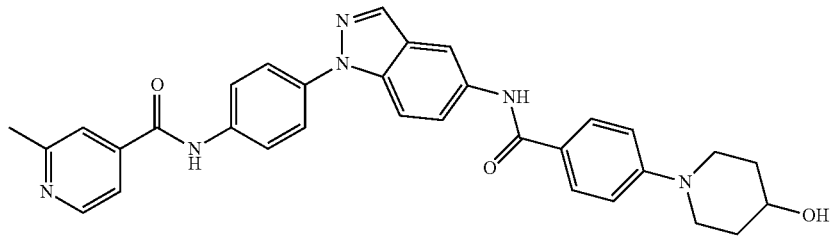 [SMILES: Cc1cc(C(=O)Nc2ccc(-n3ncc4cc(NC(=O)c5ccc(N6CCC(O)CC6)cc5)ccc43)cc2)ccn1]

Compound 998 was prepared according to the procedure described in Scheme IV from 5-amino-1-(4-aminophenyl)indazole, 2-methylisonicotinic, and 4-(4-hydroxypiperidin-1-yl)benzoic acids. [M+H]$^+$ calcd for $C_{32}H_{30}N_6O_3$: 547.1. found: 547.12.

Example 899

4-((4-(5-(4-(4-Hydroxypiperidin-1-yl)benzamido)-
1H-indazol-1-yl)phenyl)carbamoyl)pyridine 1-oxide
(Compound 999)

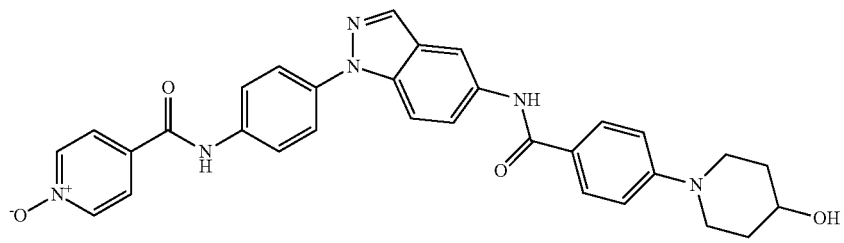

Compound 999 was prepared according to the procedure described in Scheme IV from 5-amino-1-(4-aminophenyl)indazole, 4-carboxypyridine 1-oxide, and 4-(4-hydroxypiperidin-1-yl)benzoic acid. [M+H]$^+$ calcd for $C_{31}H_{28}N_6O_4$: 549.1. found: 549.08.

Example 900

4-(2-Hydroxyethoxy)-N-(4-(5-(4-(4-hydroxypiperidin-1-yl)benzamido)-1H-indazol-1-yl)phenyl)benzamide (Compound 1000)

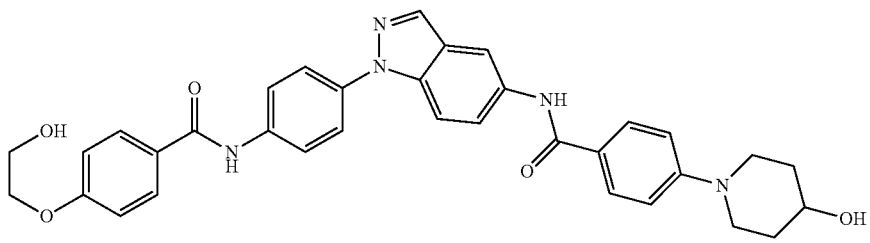 [SMILES: O=C(Nc1ccc(-n2ncc3cc(NC(=O)c4ccc(N5CCC(O)CC5)cc4)ccc32)cc1)c1ccc(OCCO)cc1]

Compound 1000 was prepared according to the procedure described in Scheme IV from 5-amino-1-(4-aminophenyl)indazole, 4-(2-hydroxyethoxy)benzoic, and 4-(4-hydroxypiperidin-1-yl)benzoic acids. [M+H]$^+$ calcd for $C_{34}H_{33}N_5O_5$: 592.18. found: 592.15.

Example 901

4-(2-Hydroxyethoxy)-N-(1-(4-isobutyramidophenyl)-1H-indazol-5-yl)benzamide (Compound 1001)

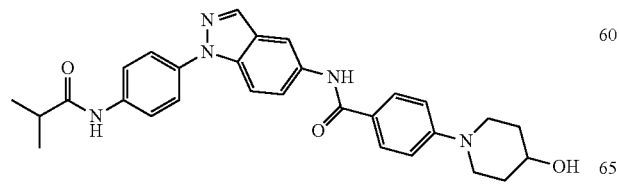

Compound 1001 was prepared according to the procedure described in Scheme IV from 5-amino-1-(4-aminophenyl) indazole, isobutyric, and 4-(4-hydroxypiperidin-1-yl)benzoic acids. [M+H]$^+$ calcd for $C_{29}H_{31}N_5O_3$: 498.2. found 498.11.

Example 902

N-(1-(4-(Cyclopent-1-enecarboxamido)phenyl)-1H-indazol-5-yl)-4-(4-hydroxypiperidin-1-yl)benzamide (Compound 1002)

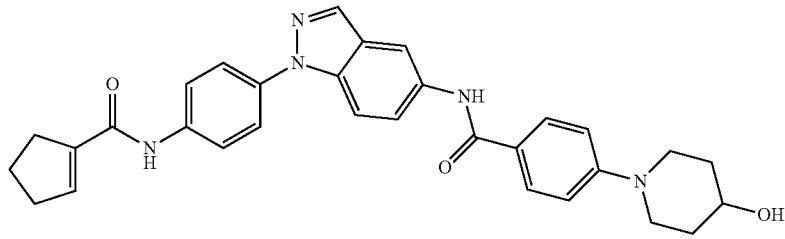 [SMILES: O=C(Nc1ccc(-n2ncc3cc(NC(=O)c4ccc(N5CCC(O)CC5)cc4)ccc32)cc1)C1=CCCC1]

Compound 1002 was prepared according to the procedure described in Scheme IV from 5-amino-1-(4-aminophenyl) indazole, cyclopentenecarboxylic, and 4-(4-hydroxypiperidin-1-yl)benzoic acids. [M+H]$^+$ calcd for $C_{31}H_{31}N_5O_3$: 522.2. found 522.14.

Example 903

1-(2-Hydroxyethyl)-N-(4-(5-(4-(4-hydroxypiperidin-1-yl)benzamido)-1H-indazol-1-yl)phenyl)-1H-indole-5-carboxamide (Compound 1003)

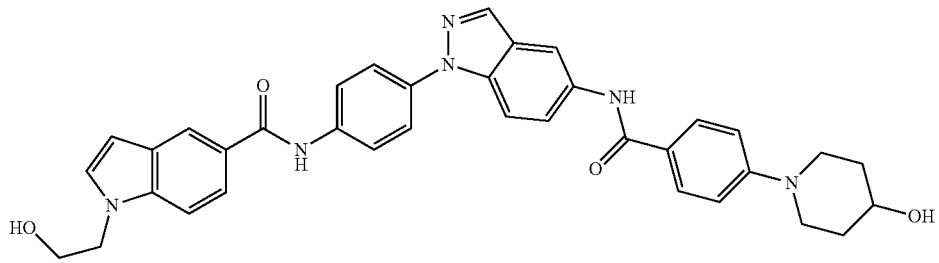 [SMILES: O=C(Nc1ccc2c(cnn2-c2ccc(NC(=O)c3ccc4c(ccn4CCO)c3)cc2)c1)c1ccc(N2CCC(O)CC2)cc1]

Compound 1003 was prepared according to the procedure described in Scheme IV from 5-amino-1-(4-aminophenyl) indazole, 1-(hydroxyethyl)indole-5-carboxylic, and 4-(4-hydroxypiperidin-1-yl)benzoic acids. [M+H]$^+$ calcd for $C_{36}H_{34}N_6O_4$: 615.26. found 615.20.

Example 904

1-Methyl-N-(4-(5-(1-methyl-1H-indole-5-carboxamido)-1H-indazol-1-yl)phenyl)-1H-indole-5-carboxamide (Compound 1004)

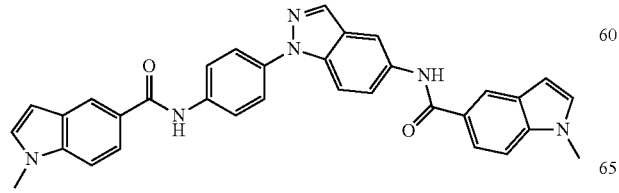

Compound 1004 was prepared according to the procedure described in Scheme IV from 5-amino-1-(4-aminophenyl)indazole and 1-methylindole-5-carboxylic acid. [M+H]$^+$ calcd for $C_{33}H_{26}N_6O_2$: 539.2. found: 539.11.

Example 905

N-(4-(5-(4-(4-Hydroxypiperidin-1-yl)benzamido)-1H-indazol-1-yl)phenyl)-1H-pyrrolo[3,2-b]pyridine-6-carboxamide (Compound 1005)

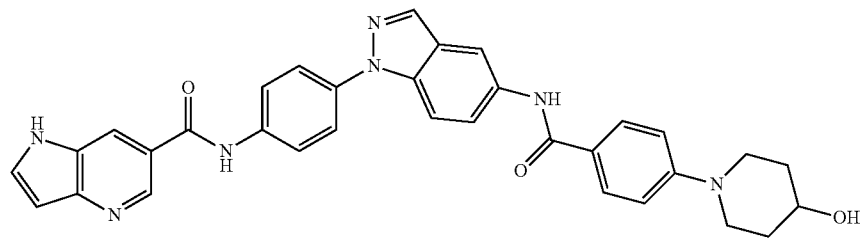 [SMILES: O=C(Nc1ccc2c(cnn2-c2ccc(NC(=O)c3cnc4cc[nH]c4c3)cc2)c1)c1ccc(N2CCC(O)CC2)cc1]

Compound 1005 was prepared according to the procedure described in Scheme IV from 5-amino-1-(4-aminophenyl)indazole, 1H-pyrrolo[3,2-b]pyridine-6-carboxylic, and 4-(4-hydroxypiperidin-1-yl)benzoic acids. [M+H]$^+$ calcd for $C_{33}H_{29}N_7O_3$: 572.2. found: 572.16.

Example 906

4-(4-Hydroxypiperidin-1-yl)-N-(1-(4-(3-methylbut-2-enamido)phenyl)-1H-indazol-5-yl)benzamide (Compound 1006)

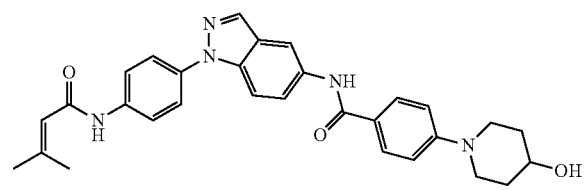 [SMILES: CC(C)=CC(=O)Nc1ccc(-n2ncc3cc(NC(=O)c4ccc(N5CCC(O)CC5)cc4)ccc32)cc1]

Compound 1006 was prepared according to the procedure described in Scheme IV from 5-amino-1-(4-aminophenyl)indazole, 3-methyl-2-butenoic, and 4-(4-hydroxypiperidin-1-yl)benzoic acids. [M+H]$^+$ calcd for $C_{30}H_{31}N_5O_3$: 510.2. found 510.13.

Example 907

N-(1-(4-(1H-Pyrrole-2-carboxamido)phenyl)-1H-indazol-5-yl)-1-methyl-1H-indole-5-carboxamide (Compound 1007)

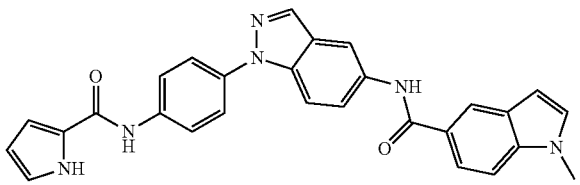 [SMILES: Cn1ccc2cc(C(=O)Nc3ccc4c(cnn4-c4ccc(NC(=O)c5ccc[nH]5)cc4)c3)ccc21]

Compound 1007 was prepared according to the procedure described in Scheme IV from 5-amino-1-(4-aminophenyl)indazole, 2-pyrrolecarboxylic, and 1-methylindole-5-carboxylic acids. [M+H]$^+$ calcd for $C_{28}H_{22}N_6O_2$: 475.1. found: 474.97.

Example 908

1-(2-Hydroxyethyl)-N-(1-(4-(1-methyl-1H-indole-5-carboxamido)phenyl)-1H-indazol-5-yl)-1H-indole-5-carboxamide (Compound 1008)

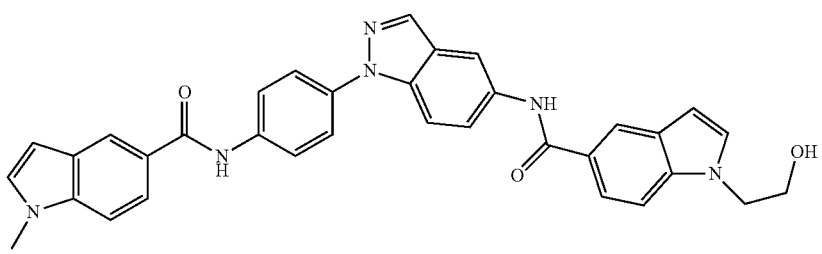 [SMILES: Cn1ccc2cc(C(=O)Nc3ccc(-n4ncc5cc(NC(=O)c6ccc7c(ccn7CCO)c6)ccc54)cc3)ccc21]

Compound 1008 was prepared according to the procedure described in Scheme IV from 5-amino-1-(4-aminophenyl)indazole, 1-(2-hydroxyethyl)indole-5-carboxylic, and 1-methylindole-5-carboxylic acids. $^1$H NMR (500 MHz, Acetone-$d_6$) δ 9.67 (s, 1H), 9.59 (s, 1H), 8.55 (s, 1H), 8.35 (m, 2H), 8.26 (s, 1H), 8.14 (d, J=8 Hz, 2H), 7.90 (m, 4H), 7.81 (d, J=8.5 Hz, 2H), 7.59 (d, J=8.5 Hz, 1H), 7.53 (d, J=9 Hz, 1H), 7.44 (d, J=2.5 Hz, 1H), 7.36 (d, J=3 Hz, 1H), 6.60 (m, 2H), 4.37 (t, J=5.5 Hz, 2H), 3.94 (t, J=3.5 Hz, 2H), 3.91 (s, 3H).

Example 909

N-(1-(4-(1H-Pyrrole-2-carboxamido)phenyl)-1H-indazol-5-yl)-1-(2-hydroxyethyl)-1H-indole-5-carboxamide (Compound 1009)

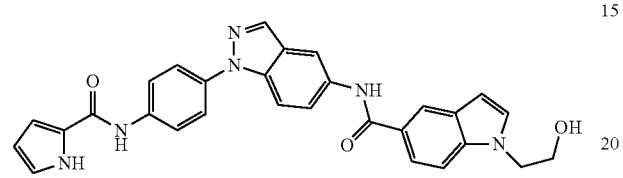

Compound 1009 was prepared according to the procedure described in Scheme IV from 5-amino-1-(4-aminophenyl)indazole, 2-pyrrolecarboxylic, and 1-(2-hydroxyethyl)indole-5-carboxylic acids. [M+H]$^+$ calcd for $C_{29}H_{24}N_6O_3$: 505.19. found 505.10.

Example 910 tert-Butyl (4-((4-(5-(4-fluorobenzamido)-1H-indazol-1-yl)phenyl)carbamoyl)phenyl)carbamate (Compound 1010)

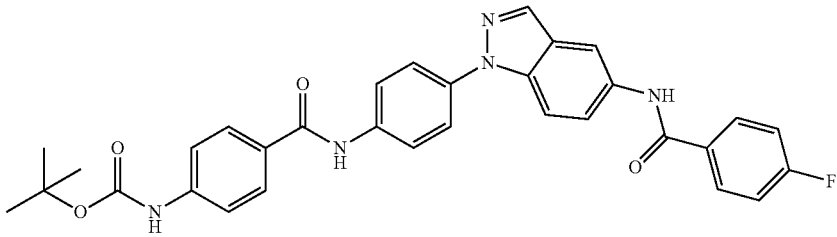 [SMILES: CC(C)(C)OC(=O)Nc1ccc(C(=O)Nc2ccc(-n3ncc4cc(NC(=O)c5ccc(F)cc5)ccc43)cc2)cc1]

Compound 1010 was prepared according to the procedure described in Scheme IV from 5-amino-1-(4-aminophenyl)indazole, 4-(tert-butoxycarbamoyl)benzoic, and 4-fluorobenzoic acids. [M+H]$^+$ calcd for $C_{32}H_{28}FN_5O_4$: 566.2. found 566.02.

Example 911

N-(4-(5-(4-(4-Hydroxypiperidin-1-yl)benzamido)-1H-indazol-1-yl)phenyl)pyridazine-4-carboxamide (Compound 1011)

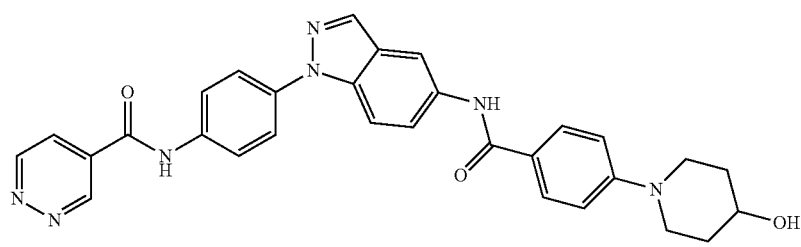 [SMILES: O=C(Nc1ccc2c(cnn2-c2ccc(NC(=O)c3ccnnc3)cc2)c1)c1ccc(N2CCC(O)CC2)cc1]

Compound 1011 was prepared according to the procedure described in Scheme IV from 5-amino-1-(4-aminophenyl)indazole, pyridazine-4-carboxylic, and 4-(4-hydroxypiperidin-1-yl)benzoic acids. [M+H]$^+$ calcd for $C_{30}H_{27}N_7O_3$: 534.2. found: 534.09.

Example 912

N-(4-(5-(4-(4-Hydroxypiperidin-1-yl)benzamido)-1H-indazol-1-yl)phenyl)-5-methylisoxazole-3-carboxamide (Compound 1012)

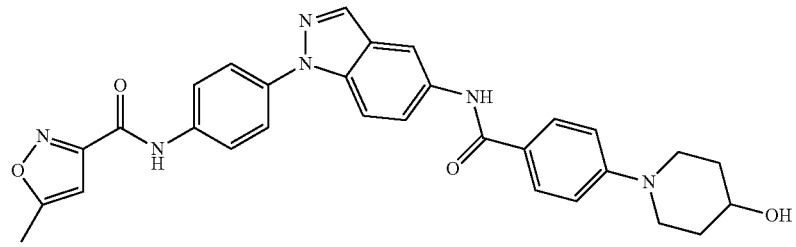 [SMILES: Cc1cc(C(=O)Nc2ccc(-n3ncc4cc(NC(=O)c5ccc(N6CCC(O)CC6)cc5)ccc43)cc2)no1]

Compound 1012 was prepared according to the procedure described in Scheme IV from 5-amino-1-(4-aminophenyl)indazole, 5-methylisoxazole-3-carboxylic, and 4-(4-hydroxypiperidin-1-yl)benzoic acids. [M+H]$^+$ calcd for $C_{30}H_{26}N_6O_4$: 537.33. found: 537.12.

Example 913

N-(4-(5-(4-(4-Hydroxypiperidin-1-yl)benzamido)-1H-indazol-1-yl)phenyl)-6-methylpicolinamide (Compound 1013)

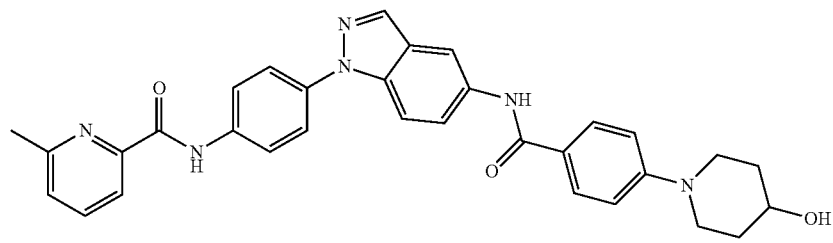 [SMILES: Cc1cccc(C(=O)Nc2ccc(-n3ncc4cc(NC(=O)c5ccc(N6CCC(O)CC6)cc5)ccc43)cc2)n1]

Compound 1013 was prepared according to the procedure described in Scheme IV from 5-amino-1-(4-aminophenyl)indazole, 6-methylpicolinic, and 4-(4-hydroxypiperidin-1-yl)benzoic acids. [M+H]$^+$ calcd for $C_{32}H_{30}N_6O_3$: 547.1. found: 547.12.

Example 914

N-(4-(5-(4-(4-Hydroxypiperidin-1-yl)benzamido)-1H-indazol-1-yl)phenyl)pyrimidine-4-carboxamide (Compound 1014)

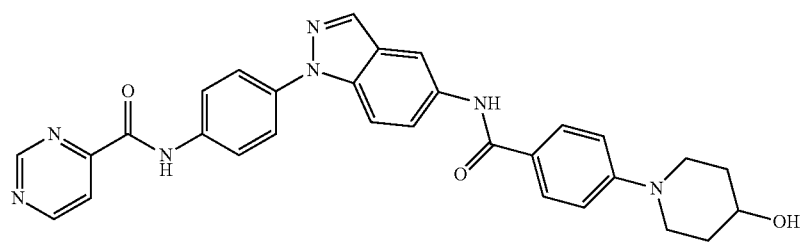 [SMILES: O=C(Nc1ccc2c(cnn2-c2ccc(NC(=O)c3ccncn3)cc2)c1)c1ccc(N2CCC(O)CC2)cc1]

Compound 1014 was prepared according to the procedure described in Scheme IV from 5-amino-1-(4-aminophenyl)indazole, pyrimidine-4-carboxylic, and 4-(4-hydroxypiperidin-1-yl)benzoic acids. [M+H]$^+$ calcd for $C_{30}H_{27}N_7O_3$: 534.1. found: 534.16.

Example 915

N-(4-(5-(4-(4-Hydroxypiperidin-1-yl)benzamido)-1H-indazol-1-yl)phenyl)-1-methyl-1H-indole-5-carboxamide (Compound 1015)

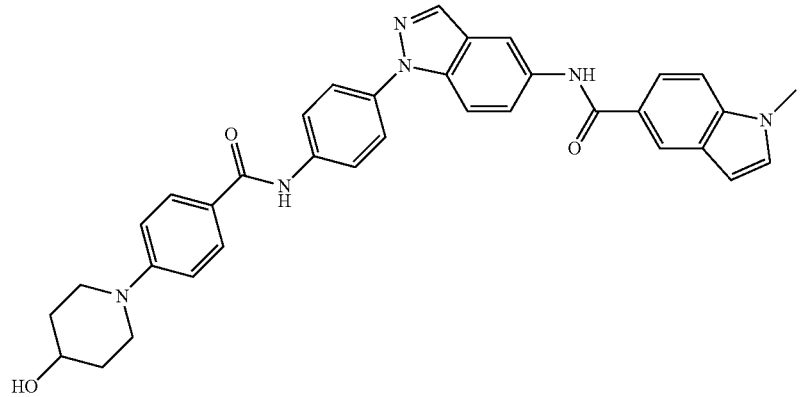 [SMILES: Cn1ccc2cc(C(=O)Nc3ccc4c(cnn4-c4ccc(NC(=O)c5ccc(N6CCC(O)CC6)cc5)cc4)c3)ccc21]

Compound 1015 was prepared according to the procedure described in Scheme IV from 5-amino-1-(4-aminophenyl)indazole, 1-methylindole-5-carboxylic, and 4-(4-hydroxypiperidin-1-yl)benzoic acids. [M+H]$^+$ calcd for $C_{35}H_{32}N_6O_3$: 585.25. found: 585.20.

Example 916

N-(4-(5-(4-(4-Hydroxypiperidin-1-yl)benzamido)-1H-indazol-1-yl)phenyl)-1-(3-hydroxypropyl)-1H-indole-6-carboxamide (Compound 1016)

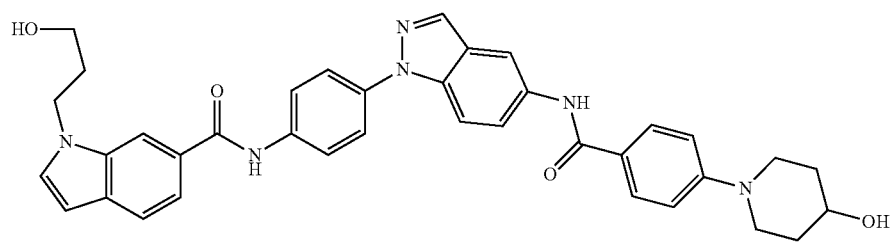 [SMILES: O=C(Nc1ccc2c(cnn2-c2ccc(NC(=O)c3ccc4ccn(CCCO)c4c3)cc2)c1)c1ccc(N2CCC(O)CC2)cc1]

Compound 1016 was prepared according to the procedure described in Scheme IV from 5-amino-1-(4-aminophenyl)indazole, 1-(3-hydroxypropyl)-1H-indole-6-carboxylic, and 4-(4-hydroxypiperidin-1-yl)benzoic acids. $^1$H NMR (500 MHz, CD$_3$OD) δ 8.23 (s, 1H), 8.21 (s, 1H), 8.16 (s, 1H), 7.98 (d, J=8.5 Hz, 2H), 7.88 (d, J=8.5 Hz, 2H), 7.77-7.65 (m, 7H), 7.44 (d, J=3 Hz, 1H), 7.03 (d, J=9 Hz, 2H), 6.55 (d, J=3 Hz, 1H), 4.40 (t, J=6.5 Hz, 2H), 3.83-3.76 (m, 3H), 3.56 (t, J=6.5 Hz, 2H), 3.05 (t, J=10 Hz, 2H), 2.12-2.07 (m, 2H), 1.98-1.94 (m, 2H), 1.64-1.57 (m, 2H).

Example 917

N-(1-(4-Benzamidophenyl)-1H-indazol-5-yl)-4-(4-hydroxypiperidin-1-yl)benzamide (Compound 1017)

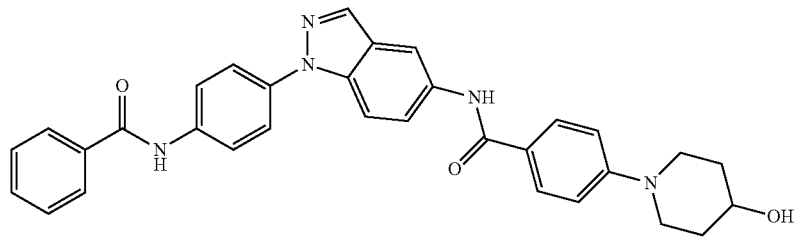 [SMILES: O=C(Nc1ccc(-n2ncc3cc(NC(=O)c4ccc(N5CCC(O)CC5)cc4)ccc32)cc1)c1ccccc1]

Compound 1017 was prepared according to the procedure described in Scheme IV from 5-amino-1-(4-aminophenyl) indazole, benzoic, and 4-(4-hydroxypiperidin-1-yl)benzoic acids. [M+H]$^+$ calcd for $C_{32}H_{30}N_5O_3$: 532.2. found: 532.13.

Example 918

N-(4-(5-(4-(4-Hydroxypiperidin-1-yl)benzamido)-1H-indazol-1-yl)phenyl)-1H-indole-2-carboxamide (Compound 1018)

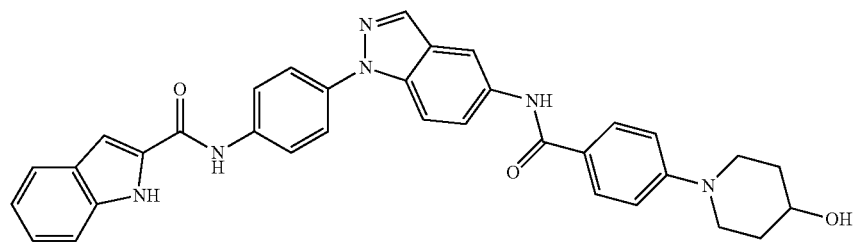 [SMILES: O=C(Nc1ccc2c(cnn2-c2ccc(NC(=O)c3cc4ccccc4[nH]3)cc2)c1)c1ccc(N2CCC(O)CC2)cc1]

Compound 1018 was prepared according to the procedure described in Scheme IV from 5-amino-1-(4-aminophenyl) indazole, indole-2-carboxylic, and 4-(4-hydroxypiperidin-1-yl)benzoic acids. [M+H]$^+$ calcd for $C_{34}H_{30}N_6O_3$: 571.2. found: 571.16.

Example 919

N-(1-(4-(2-Hydroxy-2-methylpropanamido)phenyl)-1H-indazol-5-yl)-4-(4-hydroxypiperidin-1-yl)benzamide (Compound 1019)

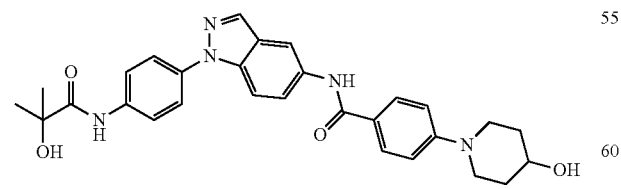

Compound 1019 was prepared according to the procedure described in Scheme IV from 5-amino-1-(4-aminophenyl) indazole, 2-hydroxy-2-methylpropanoic, and 4-(4-hydroxypiperidin-1-yl)benzoic acids. [M+H]$^+$ calcd for $C_{29}H_{31}N_5O_4$: 514.24. found 514.11.

Example 920

4-Hydroxy-N-(4-((4-(5-(4-(4-hydroxypiperidin-1-yl)benzamido)-1H-indazol-1-yl)phenyl)carbamoyl)phenyl)piperidine-1-carboxamide (Compound 1020)

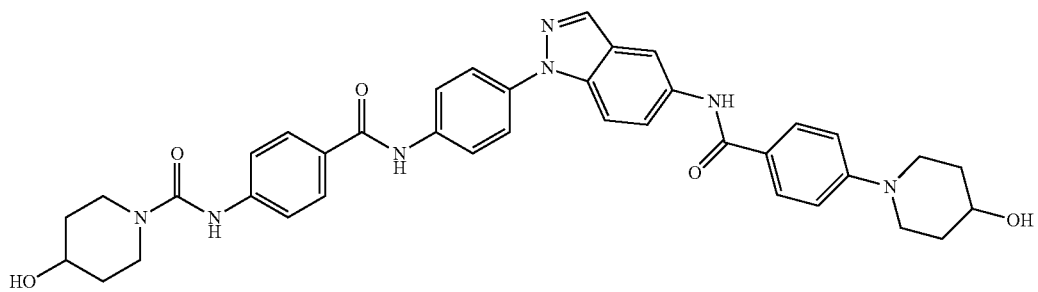 [SMILES: O=C(Nc1ccc(-n2ncc3cc(NC(=O)c4ccc(N5CCC(O)CC5)cc4)ccc32)cc1)c1ccc(NC(=O)N2CCC(O)CC2)cc1]

Compound 1020 was prepared according to the procedure described in Scheme IV from 5-amino-1-(4-aminophenyl)indazole, 4-(4-hydroxypiperidin-1-yl)carbamoylbenzoic, and 4-(4-hydroxypiperidin-1-yl)benzoic acids. [M+H]$^+$ calcd for $C_{38}H_{39}N_7O_5$: 674.3. found 674.33.

Example 921

N-(1-(4-(1-Methyl-1H-pyrrole-2-carboxamido)phenyl)-1H-indazol-5-yl)-1H-indole-5-carboxamide (Compound 1021)

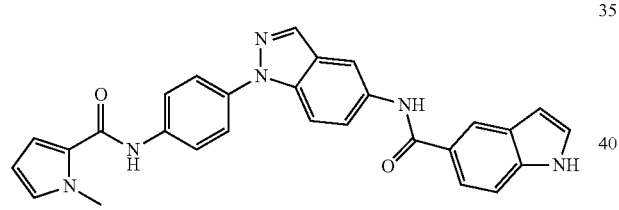

Compound 1021 was prepared according to the procedure described in Scheme IV from 5-amino-1-(4-aminophenyl)indazole, 1-methyl-2-pyrrolecarboxylic, and indole-5-carboxylic acids. [M+H]$^+$ calcd for $C_{28}H_{22}N_6O_2$: 475.0. found: 475.03.

Example 922

N-(1-(4-(1-Methyl-1H-pyrazole-5-carboxamido)phenyl)-1H-indazol-5-yl)-1H-indole-5-carboxamide (Compound 1022)

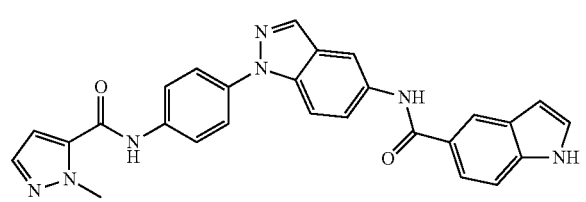 [SMILES: Cn1nccc1C(=O)Nc1ccc(-n2ncc3cc(NC(=O)c4ccc5[nH]ccc5c4)ccc32)cc1]

Compound 1022 was prepared according to the procedure described in Scheme IV from 5-amino-1-(4-aminophenyl)indazole, 1-methyl-5-pyrazolecarboxylic, and indole-5-carboxylic acids. [M+H]$^+$ calcd for $C_{27}H_{21}N_7O_2$: 476.0. found: 476.11.

Example 923

N-(1-(4-(5-Aminopicolinamido)phenyl)-1H-indazol-5-yl)-1H-indole-5-carboxamide (Compound 1023)

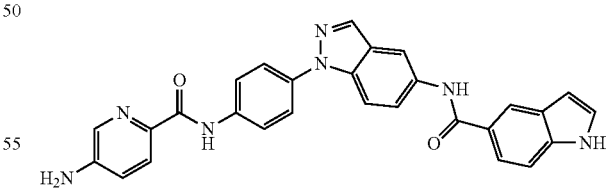

Compound 1023 was prepared according to the procedure described in Scheme IV from 5-amino-1-(4-aminophenyl)indazole, 5-aminopicolic, and indole-5-carboxylic acids. [M+H]$^+$ calcd for $C_{28}H_{21}N_7O_2$: 488.0. found: 488.06.

Example 924

1-(2-Hydroxyethyl)-N-(4-(5-(1-(2-hydroxyethyl)-1H-indole-5-carboxamido)-1H-indazol-1-yl)phenyl)-1H-indole-5-carboxamide (Compound 1024)

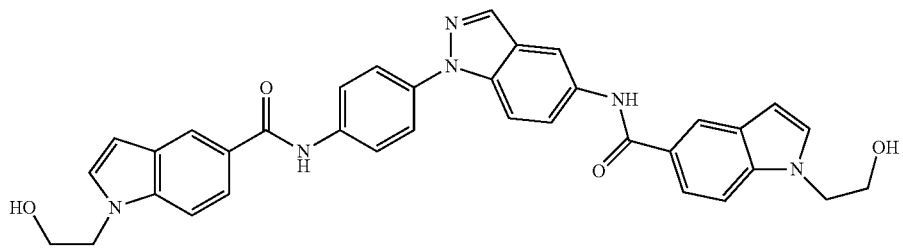 [SMILES: O=C(Nc1ccc(-n2ncc3cc(NC(=O)c4ccc5c(ccn5CCO)c4)ccc32)cc1)c1ccc2c(ccn2CCO)c1]

Compound 1024 was prepared according to the procedure described in Scheme IV from 5-amino-1-(4-aminophenyl)indazole and 1-(2-hydroxyethyl)indole-5-carboxylic.
[M+H]$^+$ calcd for $C_{35}H_{31}N_6O_4$: 599.2. found: 599.08.

Example 925

5-Cyano-N-(4-(5-(4-(4-hydroxypiperidin-1-yl)benzamido)-1H-indazol-1-yl)phenyl)picolinamide (Compound 1025)

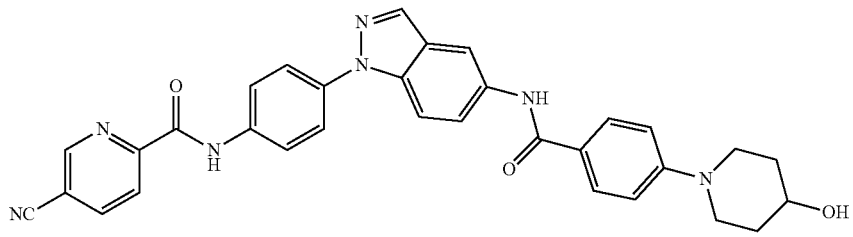 [SMILES: N#Cc1ccc(C(=O)Nc2ccc(-n3ncc4cc(NC(=O)c5ccc(N6CCC(O)CC6)cc5)ccc43)cc2)nc1]

Compound 1025 was prepared according to the procedure described in Scheme IV from 5-amino-1-(4-aminophenyl)indazole, 5-cyanopicolic, and 4-(4-hydroxypiperidin-1-yl)benzoic acids. [M+H]$^+$ calcd for $C_{32}H_{27}N_7O_3$: 558.1. found: 558.13.

Example 926

N-(4-(5-(4-(4-Hydroxypiperidin-1-yl)benzamido)-1H-indazol-1-yl)phenyl)-1H-pyrrolo[3,2-b]pyridine-5-carboxamide (Compound 1026)

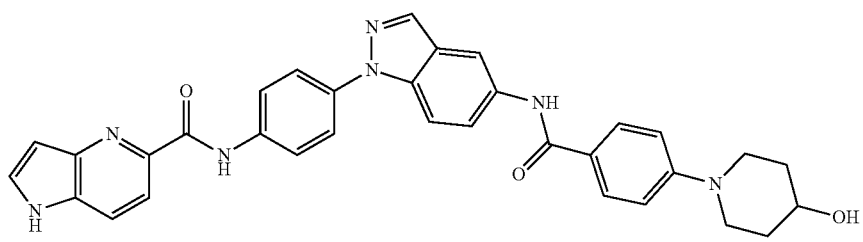 [SMILES: O=C(Nc1ccc2c(cnn2-c2ccc(NC(=O)c3ccc4[nH]ccc4n3)cc2)c1)c1ccc(N2CCC(O)CC2)cc1]

Compound 1026 was prepared according to the procedure described in Scheme IV from 5-amino-1-(4-aminophenyl)indazole, 1H-pyrrolo[3,2-b]pyridine-5-carboxylic, and 4-(4-hydroxypiperidin-1-yl)benzoic acids. [M+H]$^+$ calcd for $C_{33}H_{29}N_7O_3$: 572.2. found: 572.16.

Example 927

N-(4-(5-(4-(4-Hydroxypiperidin-1-yl)benzamido)-1H-indazol-1-yl)phenyl)-1H-pyrrolo[2,3-b]pyridine-5-carboxamide (Compound 1027)

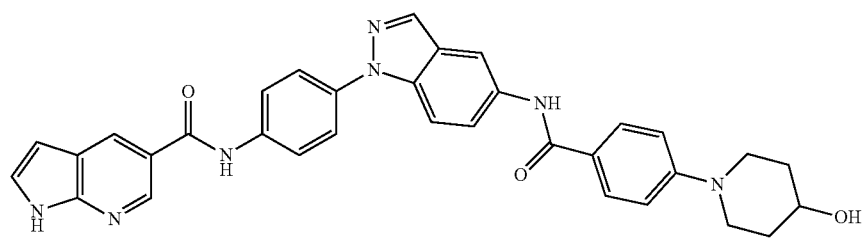 [SMILES: O=C(Nc1ccc2c(cnn2-c2ccc(NC(=O)c3cnc4[nH]ccc4c3)cc2)c1)c1ccc(N2CCC(O)CC2)cc1]

Compound 1027 was prepared according to the procedure described in Scheme IV from 5-amino-1-(4-aminophenyl)indazole, 1H-pyrrolo[2,3-b]pyridine-5-carboxylic, and 4-(4-hydroxypiperidin-1-yl)benzoic acids. [M+H]$^+$ calcd for $C_{33}H_{29}N_7O_3$: 572.2. found: 572.17.

Example 928

N-(4-(5-(4-(4-Hydroxypiperidin-1-yl)benzamido)-1H-indazol-1-yl)phenyl)-4-methyl-1H-pyrrole-2-carboxamide (Compound 1028)

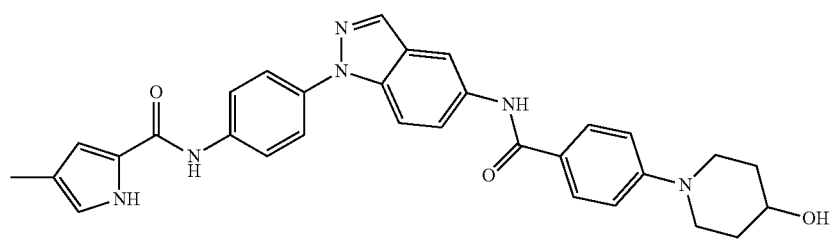 [SMILES: Cc1c[nH]c(C(=O)Nc2ccc(-n3ncc4cc(NC(=O)c5ccc(N6CCC(O)CC6)cc5)ccc43)cc2)c1]

Compound 1028 was prepared according to the procedure described in Scheme IV from 5-amino-1-(4-aminophenyl)indazole, 4-methylpyrrole-2-carboxylic, and 4-(4-hydroxypiperidin-1-yl)benzoic acids. [M+H]$^+$ calcd for $C_{31}H_{39}N_6O_3$: 535.13. found: 535.10.

Example 929

N-(4-(5-(4-(4-Hydroxypiperidin-1-yl)benzamido)-1H-indazol-1-yl)phenyl)-1H-pyrrole-3-carboxamide
(Compound 1029)

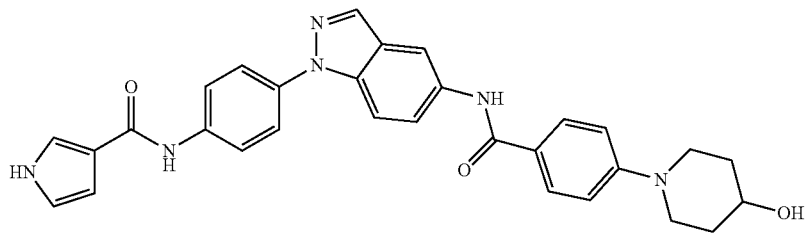 [SMILES: O=C(Nc1ccc2c(cnn2-c2ccc(NC(=O)c3cc[nH]c3)cc2)c1)c1ccc(N2CCC(O)CC2)cc1]

Compound 1029 was prepared according to the procedure described in Scheme IV from 5-amino-1-(4-aminophenyl)indazole, pyrrole-3-carboxylic, and 4-(4-hydroxypiperidin-1-yl)benzoic acids. [M+H]$^+$ calcd for $C_{30}H_{28}N_6O_3$: 521.1. found: 521.13.

Example 930

Ethyl 4-(5-(4-(4-hydroxypiperidin-1-yl)benzamido)-1H-indazol-1-yl)benzoate (Compound 1030)

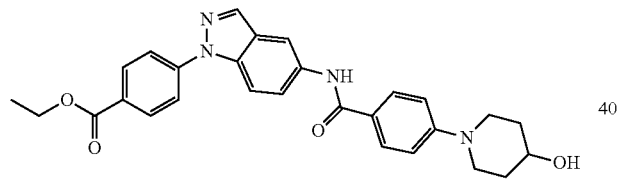

Compound 1030 was prepared according to the procedure described in Scheme IV from ethyl 4-(5-amino-1H-indazol-1-yl)benzoate and 4-(4-hydroxypiperidin-1-yl)benzoic acid. [M+H]$^+$ calcd for $C_{28}H_{28}N_4O_4$: 485.2. found: 485.09.

Example 931

N-(1-(4-(((1H-Indol-6-yl)carbamoyl)phenyl)-1H-indazol-5-yl)-4-(4-hydroxypiperidin-1-yl)benzamide
(Compound 1031)

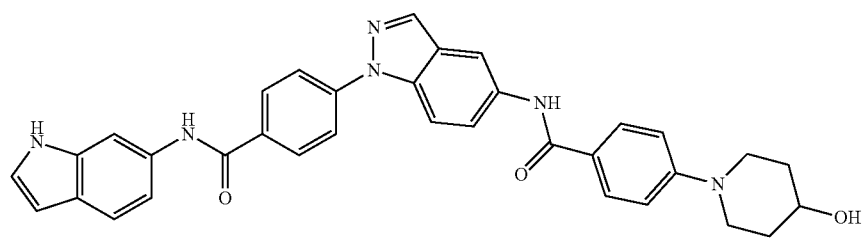 [SMILES: O=C(Nc1ccc2c(cnn2-c2ccc(C(=O)Nc3ccc4cc[nH]c4c3)cc2)c1)c1ccc(N2CCC(O)CC2)cc1]

Compound 1031 was prepared according to the procedure described in Scheme IV from 6-aminoindole, 4-(5-amino-1H-indazol-1-yl)benzoic, and 4-(4-hydroxypiperidin-1-yl)benzoic acids. [M+H]$^+$ calcd for $C_{34}H_{30}N_6O_3$: 571.2. found 571.16.

Example 932

N-(1-(4-((1H-Indol-5-yl)carbamoyl)phenyl)-1H-indazol-5-yl)-4-(4-hydroxypiperidin-1-yl)benzamide (Compound 1032)

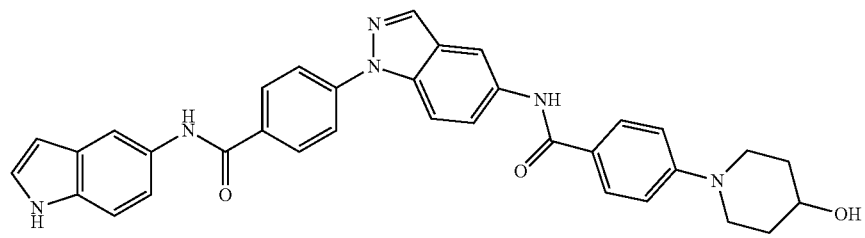 [SMILES: O=C(Nc1ccc2[nH]ccc2c1)c1ccc(-n2ncc3cc(NC(=O)c4ccc(N5CCC(O)CC5)cc4)ccc32)cc1]

Compound 1032 was prepared according to the procedure described in Scheme IV from 5-aminoindole, 4-(5-amino-1H-indazol-1-yl)benzoic, and 4-(4-hydroxypiperidin-1-yl)benzoic acids. [M+H]$^+$ calcd for $C_{34}H_{30}N_6O_3$: 571.2. found 571.17.

Example 933

4-(4-Hydroxypiperidin-1-yl)-N-(1-(4-((2-methyl-1H-indol-5-yl)carbamoyl)phenyl)-1H-indazol-5-yl)benzamide (Compound 1033)

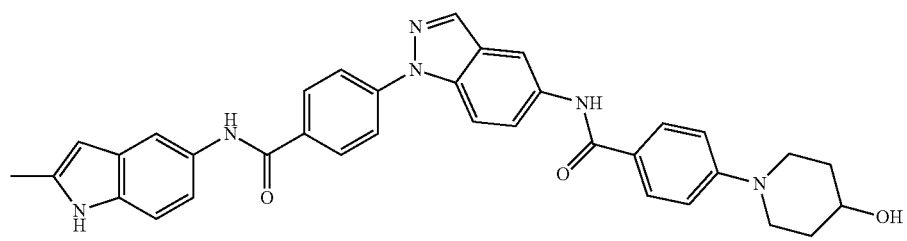 [SMILES: Cc1cc2cc(NC(=O)c3ccc(-n4ncc5cc(NC(=O)c6ccc(N7CCC(O)CC7)cc6)ccc54)cc3)ccc2[nH]1]

Compound 1033 was prepared according to the procedure described in Scheme IV from 2-methyl-5-aminoindole, 4-(5-amino-1H-indazol-1-yl)benzoic, and 4-(4-hydroxypiperidin-1-yl)benzoic acids. [M+H]$^+$ calcd for $C_{35}H_{32}N_6O_3$: 585.2. found 585.20.

Example 934

4-(4-Hydroxypiperidin-1-yl)-N-(1-(4-((1-methyl-1H-indol-5-yl)carbamoyl)phenyl)-1H-indazol-5-yl)benzamide (Compound 1034)

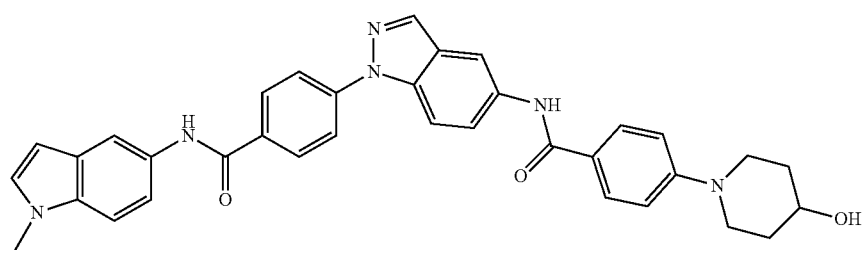 [SMILES: Cn1ccc2cc(NC(=O)c3ccc(-n4ncc5cc(NC(=O)c6ccc(N7CCC(O)CC7)cc6)ccc54)cc3)ccc21]

Compound 1034 was prepared according to the procedure described in Scheme IV from 1-methyl-5-aminoindole, 4-(5-amino-1H-indazol-1-yl)benzoic, and 4-(4-hydroxypiperidin-1-yl)benzoic acids. [M+H]+ calcd for $C_{35}H_{32}N_6O_3$: 585.2. found 585.20.

Example 935

4-(4-Hydroxypiperidin-1-yl)-N-(1-(4-(isopropylcarbamoyl)phenyl)-1H-indazol-5-yl)benzamide (Compound 1035)

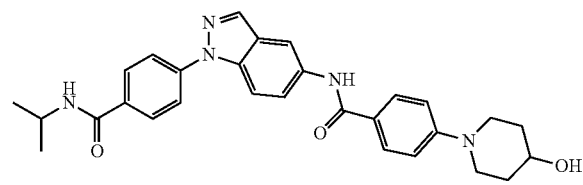 [SMILES: CC(C)NC(=O)c1ccc(-n2ncc3cc(NC(=O)c4ccc(N5CCC(O)CC5)cc4)ccc32)cc1]

Compound 1035 was prepared according to the procedure described in Scheme IV from isopropylamine, 4-(5-amino-1H-indazol-1-yl)benzoic, and 4-(4-hydroxypiperidin-1-yl)benzoic acids. [M+H]+ calcd for $C_{29}H_{31}N_5O_3$: 498.2. found 498.11.

Example 936

4-Amino-N-(4-(5-(4-fluorobenzamido)-1H-indazol-1-yl)phenyl)benzamide (Compound 1036)

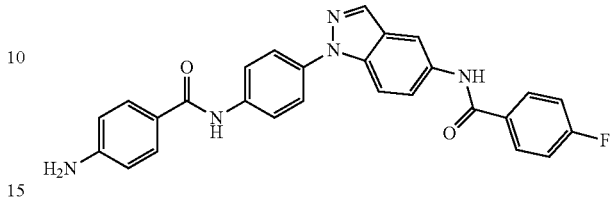

Compound 1036 was prepared according to the procedure described in Scheme IV from 5-amino-1-(4-aminophenyl)indazole, 4-aminobenzoic, and 4-fluorobenzoic acids. [M+H]+ calcd for $C_{27}H_{20}FN_5O_2$: 466.1. found 465.99.

Example 937

N-(4-(5-(4-(4-Hydroxypiperidin-1-yl)benzamido)-1H-indazol-1-yl)phenyl)-1-methyl-1H-pyrrole-2-carboxamide (Compound 1037)

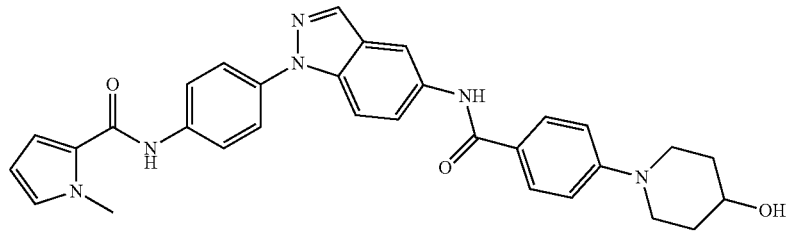 [SMILES: Cn1cccc1C(=O)Nc1ccc(-n2ncc3cc(NC(=O)c4ccc(N5CCC(O)CC5)cc4)ccc32)cc1]

Compound 1037 was prepared according to the procedure described in Scheme IV from 5-amino-1-(4-aminophenyl)indazole, 1-methylpyrrole-2-carboxylic, and 4-(4-hydroxypiperidin-1-yl)benzoic acids. [M+H]+ calcd for $C_{31}H_{30}N_6O_3$: 535.13. found: 535.10.

Example 938

N-(4-(5-(4-(4-Hydroxypiperidin-1-yl)benzamido)-1H-indol-1-yl)phenyl)-1-methyl-1H-indole-5-carboxamide (Compound 1038)

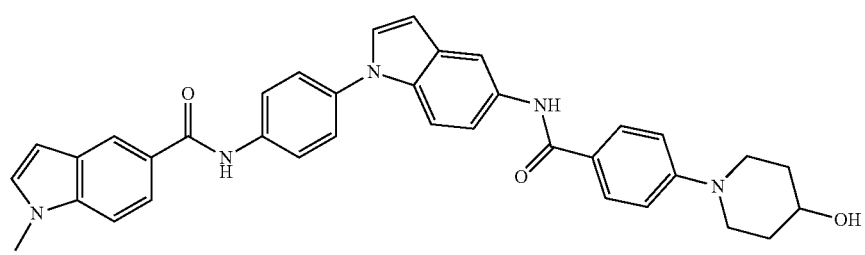 [SMILES: Cn1ccc2cc(C(=O)Nc3ccc(-n4ccc5cc(NC(=O)c6ccc(N7CCC(O)CC7)cc6)ccc54)cc3)ccc21]

Compound 1038 was prepared according to the procedure described in Scheme IV from 5-amino-1-(4-aminophenyl) indole, 1-methyl-1H-indole-5-carboxylic, and 4-(4-hydroxypiperidin-1-yl)benzoic acids. [M+H]+ calcd for C36H33N5O3: 584.26. found: 584.12.

Example 939

Ethyl 4-(5-(1-(2-hydroxyethyl)-1H-indole-5-carboxamido)-1H-indazol-1-yl)benzoate (Compound 1039)

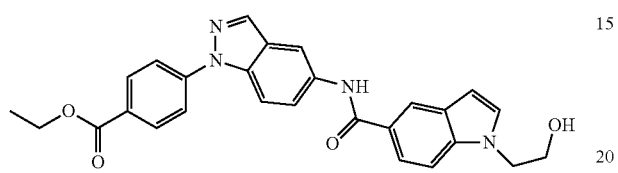

Compound 1039 was prepared according to the procedure described in Scheme IV from ethyl 4-(5-amino-1H-indazol-1-yl)benzoate and 1-(2-hydroxyethyl)indole-5-carboxylic acid. [M+H]+ calcd for C27H24N4O4: 469.1. found 469.03.

Example 940

N-(1-(4-(Cyclopropylcarbamoyl)phenyl)-1H-indazol-5-yl)-1-(2-hydroxyethyl)-1H-indole-5-carboxamide (Compound 1040)

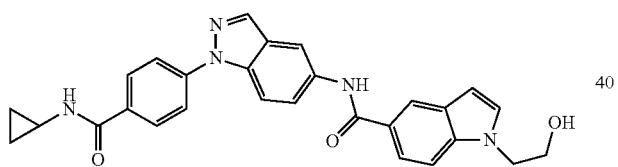

Compound 1040 was prepared according to the procedure described in Scheme IV from cyclopropylamine, 4-(5-amino-1H-indazol-1-yl)benzoic, and 1-(2-hydroxyethyl)indole-5-carboxylic acids. [M+H]+ calcd for C28H25N5O3: 480.20. found 480.03.

Example 941

N-(Cyclopropylmethyl)-4-(5-(4-(4-hydroxypiperidin-1-yl)benzamido)-1H-indazol-1-yl)benzamide (Compound 1041)

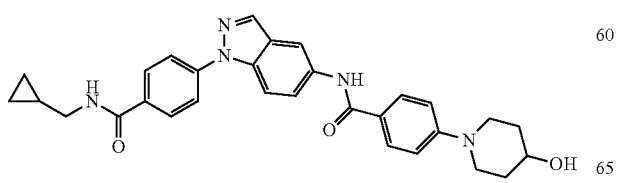

Compound 1041 was prepared according to the procedure described in Scheme IV from cyclopropylmethylamine, 4-(5-amino-1H-indazol-1-yl)benzoic, and 4-(4-hydroxypiperidin-1-yl)benzoic acids. [M+H]+ calcd for C30H31N5O3: 510.2. found 510.06.

Example 942

4-(4-Hydroxypiperidin-1-yl)-N-(1-(4-((5-methylthiazol-2-yl)carbamoyl)phenyl)-1H-indazol-5-yl)benzamide (Compound 1042)

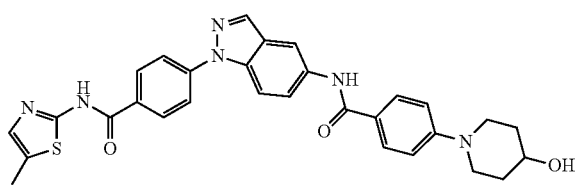 [SMILES: Cc1cnc(NC(=O)c2ccc(-n3ncc4cc(NC(=O)c5ccc(N6CCC(O)CC6)cc5)ccc43)cc2)s1]

Compound 1042 was prepared according to the procedure described in Scheme IV from 5-methylthiazol-2-ylamine, 4-(5-amino-1H-indazol-1-yl)benzoic, and 4-(4-hydroxypiperidin-1-yl)benzoic acids. [M+H]+ calcd for C30H28N6O3S: 553.1. found 553.06.

Example 943

N-(1-(1H-Indol-5-yl)-1H-indazol-5-yl)-4-(4-hydroxypiperidin-1-yl)benzamide (Compound 1043)

Compound 1043 was prepared according to the procedure described in Scheme IV from 5-amino-1-(indol-5-yl)indazole and 4-(4-hydroxypiperidin-1-yl)benzoic acid.

[M+H]+ calcd for C27H26N5O2: 452.2. found: 452.02.

Example 944

4-(4-Hydroxypiperidin-1-yl)-N-(1-(4-((2-morpholinoethyl)carbamoyl)phenyl)-1H-indazol-5-yl)benzamide (Compound 1044)

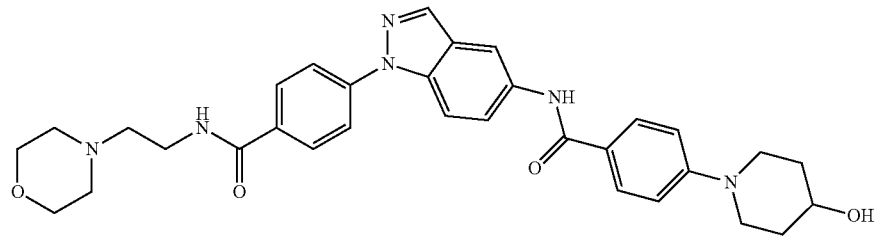 [SMILES: O=C(NCCN1CCOCC1)c1ccc(-n2ncc3cc(NC(=O)c4ccc(N5CCC(O)CC5)cc4)ccc32)cc1]

Compound 1044 was prepared according to the procedure described in Scheme IV from 2-morpholinoethylamine, 4-(5-amino-1H-indazol-1-yl)benzoic, and 4-(4-hydroxypiperidin-1-yl)benzoic acids. [M+H]$^+$ calcd for $C_{32}H_{36}N_6O_4$: 569.2. found: 569.33.

Example 945

N-(Cyanomethyl)-4-(5-(4-(4-hydroxypiperidin-1-yl)benzamido)-1H-indazol-1-yl)benzamide (Compound 1045)

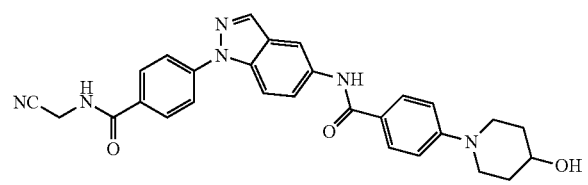 [SMILES: N#CCNC(=O)c1ccc(-n2ncc3cc(NC(=O)c4ccc(N5CCC(O)CC5)cc4)ccc32)cc1]

Compound 1045 was prepared according to the procedure described in Scheme IV from cyanomethylamine, 4-(5-amino-1H-indazol-1-yl)benzoic, and 4-(4-hydroxypiperidin-1-yl)benzoic acids. [M+H]$^+$ calcd for $C_{28}H_{26}N_6O_3$: 495.2. found 495.01.

Example 946

4-(4-Hydroxypiperidin-1-yl)-N-(1-(4-((4-methylthiazol-2-yl)carbamoyl)phenyl)-1H-indazol-5-yl)benzamide (Compound 1046)

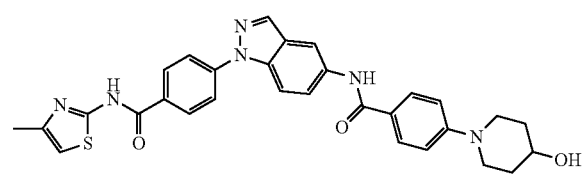 [SMILES: Cc1csc(NC(=O)c2ccc(-n3ncc4cc(NC(=O)c5ccc(N6CCC(O)CC6)cc5)ccc43)cc2)n1]

Compound 1046 was prepared according to the procedure described in Scheme IV from 4-methylthiazol-2-ylamine, 4-(5-amino-1H-indazol-1-yl)benzoic, and 4-(4-hydroxypiperidin-1-yl)benzoic acids. [M+H]$^+$ calcd for $C_{30}H_{28}N_6O_3S$: 553.2. found 553.06.

Example 947

4-(4-Hydroxypiperidin-1-yl)-N-(1-(4-(thiazol-2-ylcarbamoyl)phenyl)-1H-indazol-5-yl)benzamide (Compound 1047)

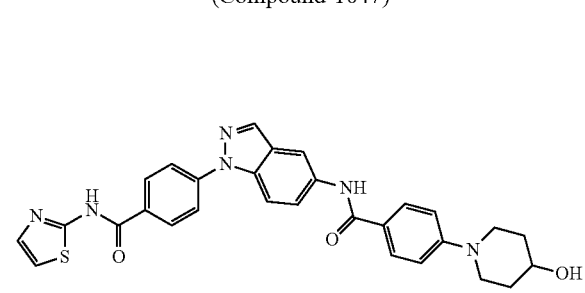

Compound 1047 was prepared according to the procedure described in Scheme IV from thiazol-2-ylamine, 4-(5-amino-1H-indazol-1-yl)benzoic, and 4-(4-hydroxypiperidin-1-yl)benzoic acids. [M+H]$^+$ calcd for $C_{29}H_{26}N_6O_3S$: 539.1. found 539.02.

Example 948 tert-Butyl (1-(4-(5-(4-(4-hydroxypiperidin-1-yl)benzamido)-1H-indazol-1-yl)benzoyl)piperidin-4-yl)carbamate (Compound 1048)

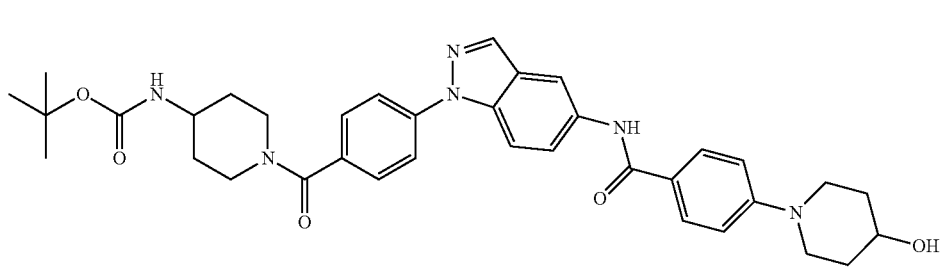 [SMILES: CC(C)(C)OC(=O)NC1CCN(C(=O)c2ccc(-n3ncc4cc(NC(=O)c5ccc(N6CCC(O)CC6)cc5)ccc43)cc2)CC1]

Compound 1048 was prepared according to the procedure described in Scheme IV from tert-butyl piperidin-4-ylcarbamate, 4-(5-amino-1H-indazol-1-yl)benzoic, and 4-(4-hydroxypiperidin-1-yl)benzoic acids. $^1$H NMR (500 MHz, DMSO-$d_6$) δ 10.07 (s, 1H), 8.39 (d, J=0.5 Hz, 2H), 7.92 (d, J=9 Hz, 1H), 7.87 (m, 4H), 7.80 (dd, J=2, 9 Hz, 1H), 7.57 (d, J=6.5 Hz, 2H), 7.00 (d, J=9 Hz, 2H), 6.90 (d, J=7.5 Hz, 1H), 4.70 (d, J=4 Hz, 1H), 4.30 (bs, 1H), 3.70 (m, 4H), 3.52 (m, 2H), 3.00 (m, 4H), 1.80 (m, 4H), 1.44 (m, 2H), 1.37 (s, 9H).

Example 949

4-(4-Hydroxypiperidin-1-yl)-N-(1-(4-(4-hydroxypiperidine-1-carbonyl)phenyl)-1H-indazol-5-yl)benzamide (Compound 1049)

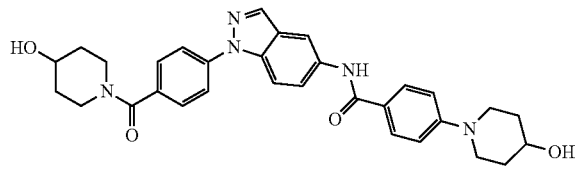 [SMILES: O=C(Nc1ccc2c(cnn2-c2ccc(C(=O)N3CCC(O)CC3)cc2)c1)c1ccc(N2CCC(O)CC2)cc1]

Compound 1049 was prepared according to the procedure described in Scheme IV from 4-hydroxypiperidine, 4-(5-amino-1H-indazol-1-yl)benzoic, and 4-(4-hydroxypiperidin-1-yl)benzoic acids. [M+H]$^+$ calcd for $C_{31}H_{33}N_5O_4$: 540.2. found: 540.10.

Example 950 tert-Butyl 4-(4-(5-(4-(4-hydroxypiperidin-1-yl)benzamido)-1H-indazol-1-yl)benzamido) piperidine-1-carboxylate (Compound 1050)

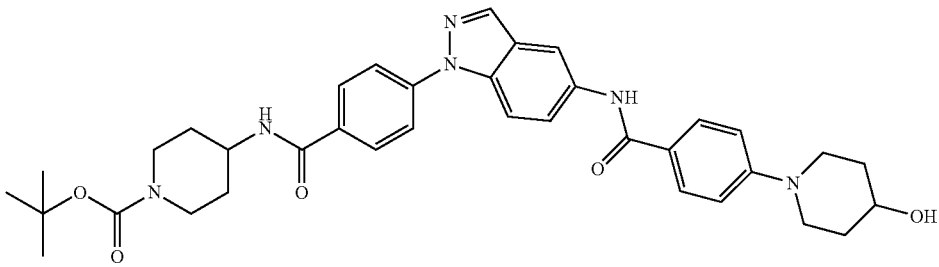 [SMILES: CC(C)(C)OC(=O)N1CCC(NC(=O)c2ccc(-n3ncc4cc(NC(=O)c5ccc(N6CCC(O)CC6)cc5)ccc43)cc2)CC1]

Compound 1050 was prepared according to the procedure described in Scheme IV from 4-amino-1-tert-butoxycarbonylpiperidine, 4-(5-amino-1H-indazol-1-yl)benzoic, and 4-(4-hydroxypiperidin-1-yl)benzoic acids. [M+H]$^+$ calcd for $C_{36}H_{42}N_6O_5$: 639.3. found 583.24 (-t-butyl group).

Example 951

4-(4-Hydroxypiperidin-1-yl)-N-(1-(4-(morpholine-4-carbonyl)phenyl)-1H-indazol-5-yl)benzamide (Compound 1051)

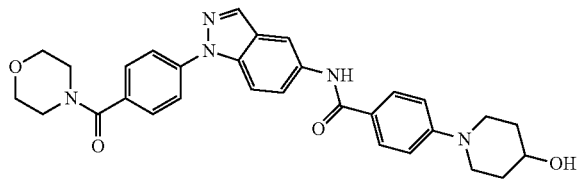 [SMILES: O=C(Nc1ccc2c(cnn2-c2ccc(C(=O)N3CCOCC3)cc2)c1)c1ccc(N2CCC(O)CC2)cc1]

Compound 1051 was prepared according to the procedure described in Scheme IV from morpholine, 4-(5-amino-1H-indazol-1-yl)benzoic, and 4-(4-hydroxypiperidin-1-yl)benzoic acids. [M+H]$^+$ calcd for $C_{30}H_{31}N_5O_4$: 526.2. found 526.13.

Example 952

4-(4-Hydroxypiperidin-1-yl)-N-(1-(4-(piperidin-4-ylcarbamoyl)phenyl)-1H-indazol-5-yl)benzamide (Compound 1052)

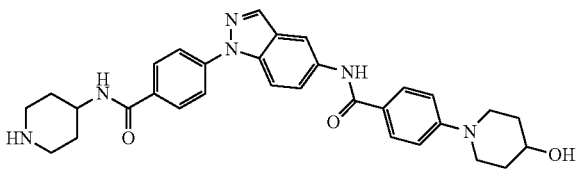 [SMILES: O=C(Nc1ccc2c(cnn2-c2ccc(C(=O)NC3CCNCC3)cc2)c1)c1ccc(N2CCC(O)CC2)cc1]

Compound 1052 was prepared by hydrolysis of Compound 1050. [M+H]$^+$ calcd for $C_{31}H_{34}N_6O_3$: 539.2. found 539.16.

Example 953

N-(1-(4-(4-Aminopiperidine-1-carbonyl)phenyl)-1H-indazol-5-yl)-4-(4-hydroxypiperidin-1-yl)benzamide (Compound 1053)

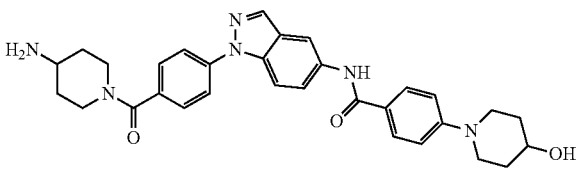 [SMILES: NC1CCN(C(=O)c2ccc(-n3ncc4cc(NC(=O)c5ccc(N6CCC(O)CC6)cc5)ccc43)cc2)CC1]

Compound 1053 was prepared by hydrolysis of Compound 1048.
[M+H]$^+$ calcd for $C_{31}H_{34}N_6O_3$: 539.2. found 539.16.

Example 954

N-Benzyl-4-(5-(4-(4-hydroxypiperidin-1-yl)benzamido)-1H-indazol-1-yl)benzamide (Compound 1054)

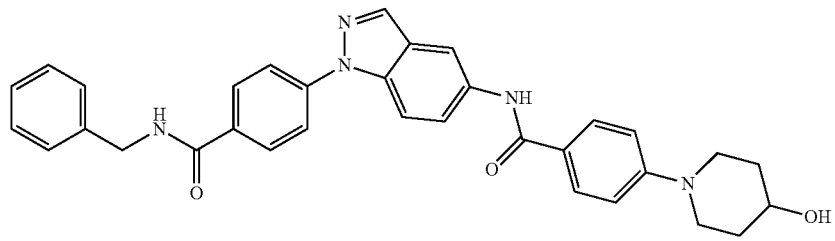 [SMILES: O=C(NCc1ccccc1)c1ccc(-n2ncc3cc(NC(=O)c4ccc(N5CCC(O)CC5)cc4)ccc32)cc1]

Compound 1054 was prepared according to the procedure described in Scheme IV from benzylamine, 4-(5-amino-1H-indazol-1-yl)benzoic, and 4-(4-hydroxypiperidin-1-yl)benzoic acids. [M+H]$^+$ calcd for $C_{33}H_{31}N_5O_3$: 546.2. found 546.11.

Example 955

N-(1-(4-(Cyclopropylcarbamoyl)phenyl)-1H-indazol-5-yl)-1-(2-hydroxyethyl)-1H-indole-6-carboxamide (Compound 1055)

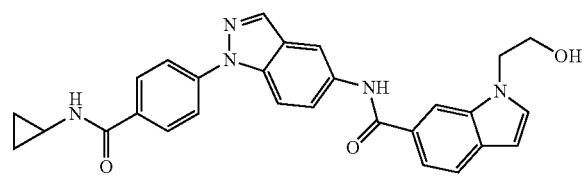 [SMILES: O=C(Nc1ccc2c(cnn2-c2ccc(C(=O)NC3CC3)cc2)c1)c1ccc2ccn(CCO)c2c1]

Compound 1055 was prepared according to the procedure described in Scheme IV from cyclopropylamine, 4-(5-amino-1H-indazol-1-yl)benzoic, and 1-(2-hydroxyethyl)indole-6-carboxylic acids. [M+H]$^+$ calcd for $C_{28}H_{25}N_5O_3$: 480.20. found: 480.03.

Example 956

1-(2-Hydroxyethyl)-N-(1-(4-((1-methyl-1H-indol-5-yl)carbamoyl)phenyl)-1H-indazol-5-yl)-1H-indole-5-carboxamide (Compound 1056)

Compound 1056 was prepared according to the procedure described in Scheme IV from 5-amino-1-methylindole, 4-(5-amino-1H-indazol-1-yl)benzoic, and 1-(2-hydroxyethyl)indole-5-carboxylic acids. [M+H]$^+$ calcd for $C_{34}H_{28}N_6O_3$: 569.22. found 569.13.

Example 957

N-Cyclopropyl-4-(5-(4-(4-hydroxypiperidin-1-yl)benzamido)-1H-benzo[d]imidazol-1-yl)benzamide (Compound 1057)

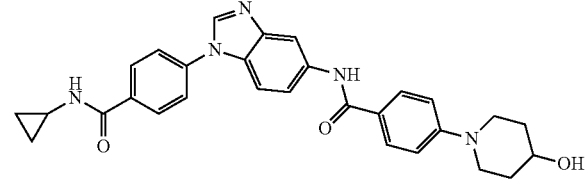

Compound 1057 was prepared according to the procedure described in Scheme IV from cyclopropylamine, 4-(5-amino-1H-benzo[d]imidazol-1-yl)benzoic, and 4-(4-hydroxypiperidin-1-yl)benzoic acids. [M+H]$^+$ calcd for $C_{29}H_{29}N_5O_3$: 496.24. found: 496.09.

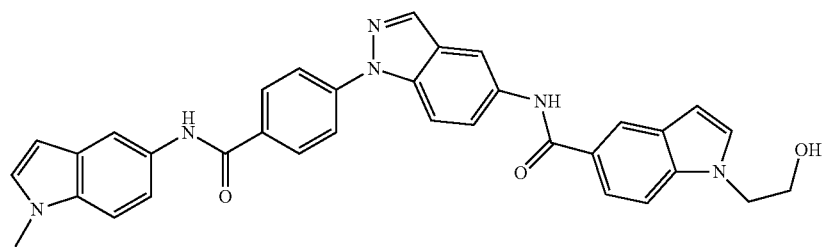 [SMILES: Cn1ccc2cc(NC(=O)c3ccc(-n4ncc5cc(NC(=O)c6ccc7c(ccn7CCO)c6)ccc54)cc3)ccc21]

Example 958

N-Cyclopropyl-4-(5-(4-(4-hydroxypiperidin-1-yl)benzamido)-1H-indol-1-yl)benzamide (Compound 1058)

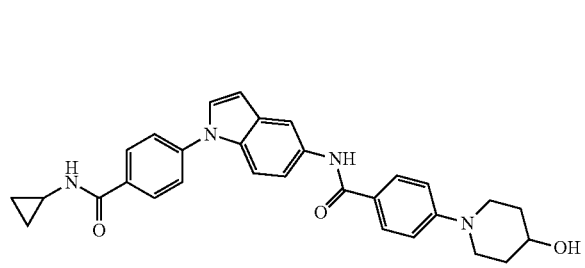

Compound 1058 was prepared according to the procedure described in Scheme IV from cyclopropylamine, 4-(5-amino-1H-indol-1-yl)benzoic, and 4-(4-hydroxypiperidin-1-yl)benzoic acids. [M+H]$^+$ calcd for $C_{30}H_{30}N_4O_3$: 495.2. found: 495.14.

Example 959

N-(1-(4-(Cyclopropylcarbamoyl)phenyl)-1H-benzo[d]imidazol-5-yl)-1H-indole-6-carboxamide (Compound 1059)

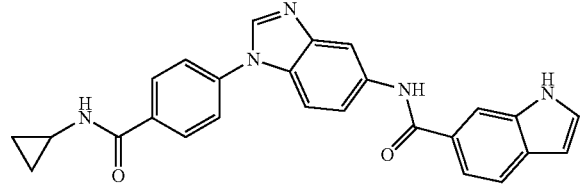 [SMILES: O=C(Nc1ccc2c(c1)ncn2-c1ccc(C(=O)NC2CC2)cc1)c1ccc2cc[nH]c2c1]

Compound 1059 was prepared according to the procedure described in Scheme IV from cyclopropylamine, 4-(5-amino-1H-benzo[d]imidazol-1-yl)benzoic, and 6-indolecarboxylic acids. [M+H]$^+$ calcd for $C_{26}H_{21}N_5O_2$: 436.1. found: 436.03.

Example 960

N-(1-(4-(Cyclopropylcarbamoyl)phenyl)-1H-benzo[d]imidazol-5-yl)-1H-indole-2-carboxamide (Compound 1060)

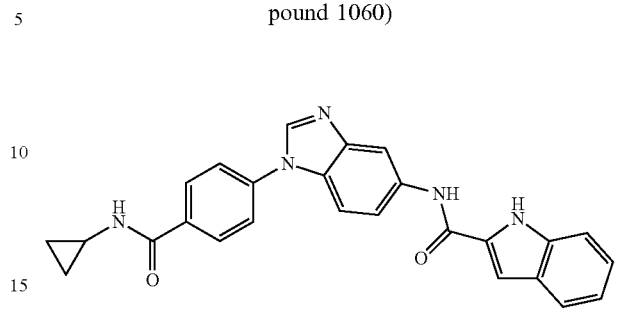

Compound 1060 was prepared according to the procedure described in Scheme IV from cyclopropylamine, 4-(5-amino-1H-benzo[d]imidazol-1-yl)benzoic, and 2-indolecarboxylic acids. [M+H]$^+$ calcd for $C_{26}H_{21}N_5O_2$: 436.1. found: 436.03.

Example 961

N-(3-(4-(1H-Pyrrole-2-carboxamido)phenyl)-1H-indol-6-yl)-1-methyl-1H-indole-5-carboxamide (Compound 1061)

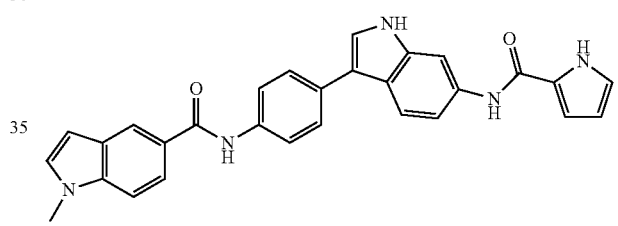

Compound 1061 was prepared according to the procedure described in Scheme IV from 6-amino-3-(4-aminophenyl)indole, 2-pyrrolecarboxylic, and 1-methylindole-5-carboxylic acids. [M+H]$^+$ calcd for $C_{29}H_{23}N_5O_2$: 474.0. found: 474.09.

Example 962

N-(1-(2-Hydroxyethyl)-1H-indol-5-yl)-4-(5-(4-(4-hydroxypiperidin-1-yl)benzamido)-1H-indazol-1-yl)benzamide (Compound 1062)

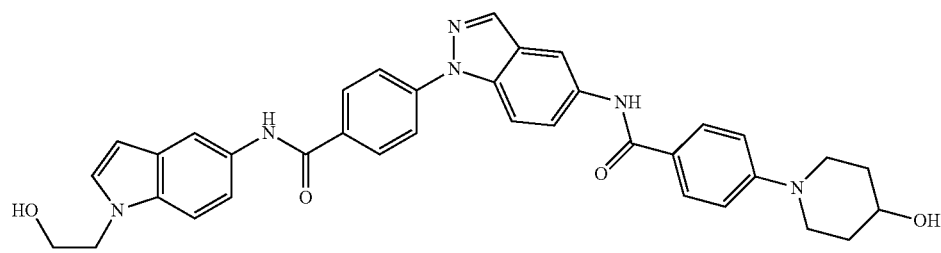 [SMILES: O=C(Nc1ccc2c(ccn2CCO)c1)c1ccc(-n2ncc3cc(NC(=O)c4ccc(N5CCC(O)CC5)cc4)ccc32)cc1]

Compound 1062 was prepared according to the procedure described in Scheme IV from 5-amino-1-(2-hydroxyethyl)indole, 4-(5-amino-1H-indazol-1-yl)benzoic, and 4-(4-hydroxypiperidin-1-yl)benzoic acids. $[M+H]^+$ calcd for $C_{36}H_{34}N_6O_4$: 615.26. found 615.18.

Example 963

4-(4-Hydroxypiperidin-1-yl)-N-(1-(4-((1-methyl-1H-indol-5-yl)carbamoyl)phenyl)-1H-indol-5-yl)benzamide (Compound 1063)

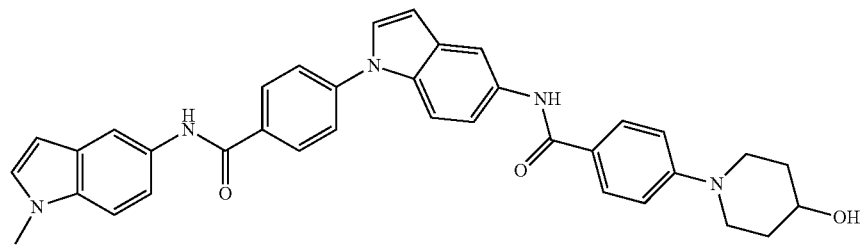 [SMILES: Cn1ccc2cc(NC(=O)c3ccc(-n4ccc5cc(NC(=O)c6ccc(N7CCC(O)CC7)cc6)ccc54)cc3)ccc21]

Compound 1063 was prepared according to the procedure described in Scheme IV from 5-amino-1-methylindole, 4-(5-amino-1H-indol-1-yl)benzoic, and 4-(4-hydroxypiperidin-1-yl)benzoic acids. $[M+H]^+$ calcd for $C_{36}H_{33}N_5O_3$: 584.2. found: 584.19.

Example 964

N-(4-(6-(4-(4-Hydroxypiperidin-1-yl)benzamido)-1H-indol-3-yl)phenyl)-1-methyl-1H-indole-5-carboxamide (Compound 1064)

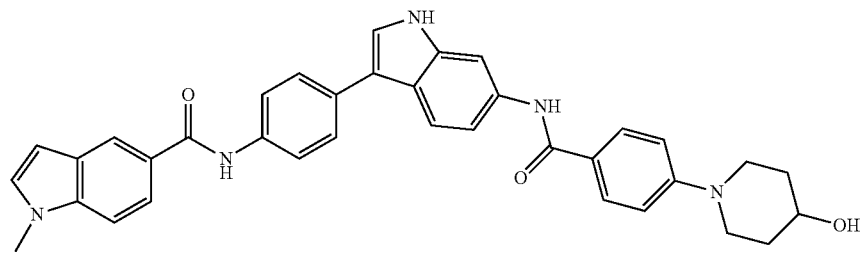 [SMILES: Cn1ccc2cc(C(=O)Nc3ccc(-c4c[nH]c5cc(NC(=O)c6ccc(N7CCC(O)CC7)cc6)ccc45)cc3)ccc21]

Compound 1064 was prepared according to the procedure described in Scheme IV from 6-amino-3-(4-aminophenyl)indole, 1-methylindole-5-carboxylic, and 4-(4-hydroxypiperidin-1-yl)benzoic acids. $[M+H]^+$ calcd for $C_{36}H_{33}N_5O_3$: 584.2. found: 584.19.

Example 965

4-(4-Hydroxypiperidin-1-yl)-N-(1-(4-((1-(2-morpholinoethyl)-1H-indol-5-yl)carbamoyl)phenyl)-1H-indazol-5-yl)benzamide (Compound 1065)

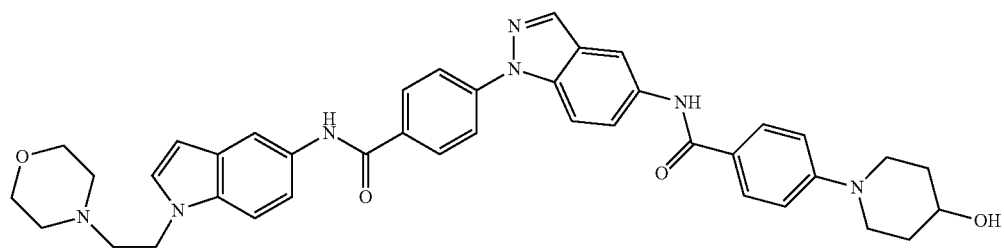 [SMILES: O=C(Nc1ccc2c(ccn2CCN2CCOCC2)c1)c1ccc(-n2ncc3cc(NC(=O)c4ccc(N5CCC(O)CC5)cc4)ccc32)cc1]

Compound 1065 was prepared according to the procedure described in Scheme IV from 5-amino-1-(2-morpholinoethyl)indole, 4-(5-amino-1H-indazol-1-yl)benzoic, and 4-(4-hydroxypiperidin-1-yl)benzoic acids. [M+H]$^+$ calcd for $C_{40}H_{41}N_7O_4$: 684.32. found 684.32.

Example 966 tert-Butyl 2-(5-(4-(5-(4-(4-hydroxypiperidin-1-yl)benzamido)-1H-indazol-1-yl)benzamido)-1H-indol-1-yl)acetate (Compound 1066)

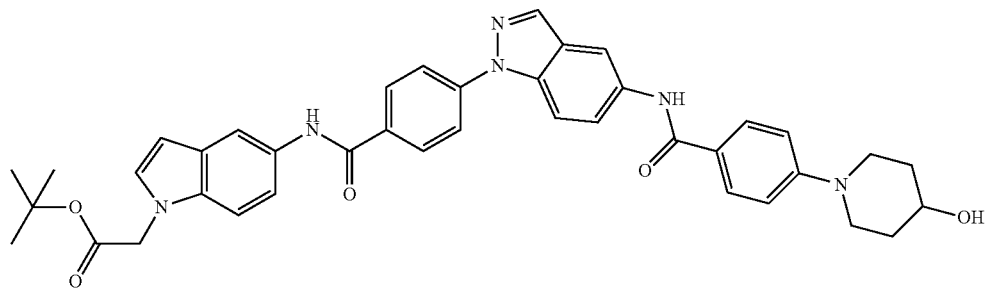 [SMILES: CC(C)(C)OC(=O)Cn1ccc2cc(NC(=O)c3ccc(-n4ncc5cc(NC(=O)c6ccc(N7CCC(O)CC7)cc6)ccc54)cc3)ccc21]

Compound 1066 was prepared according to the procedure described in Scheme IV from tert-butyl 5-aminoindol-1-ylacetate, 4-(5-amino-1H-indazol-1-yl)benzoic, and 4-(4-hydroxypiperidin-1-yl)benzoic acids. [M+H]$^+$ calcd for $C_{40}H_{40}N_6O_5$: 685.31. found 685.27.

Example 967

4-(4-Hydroxypiperidin-1-yl)-N-(1-(4-((1-methyl-1H-imidazo[4,5-b]pyridin-6-yl)carbamoyl)phenyl)-1H-indol-5-yl)benzamide (Compound 1067)

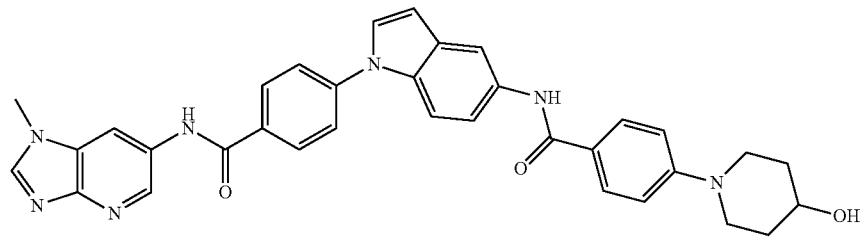 [SMILES: Cn1cnc2ncc(NC(=O)c3ccc(-n4ccc5cc(NC(=O)c6ccc(N7CCC(O)CC7)cc6)ccc54)cc3)cc21]

Compound 1067 was prepared according to the procedure described in Scheme IV from 1-methyl-1H-imidazo[4,5-b]pyridin-6-ylamine, 4-(5-amino-1H-indol-1-yl)benzoic, and 4-(4-hydroxypiperidin-1-yl)benzoic acids. [M+H]$^+$ calcd for $C_{34}H_{31}N_7O_3$: 586.2. found: 586.14.

Example 968

N-(1-(4-((1H-Pyrrolo[2,3-b]pyridin-5-yl)carbamoyl)phenyl)-1H-indol-5-yl)-4-(4-hydroxypiperidin-1-yl)benzamide (Compound 1068)

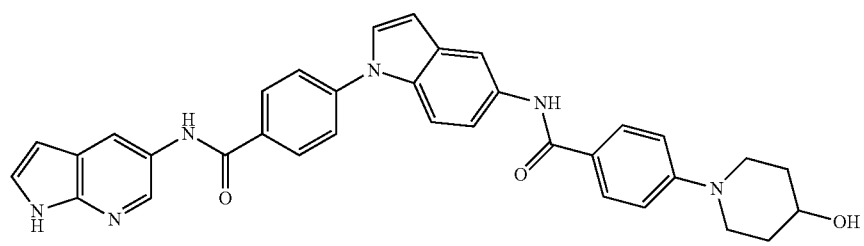 [SMILES: O=C(Nc1cnc2[nH]ccc2c1)c1ccc(-n2ccc3cc(NC(=O)c4ccc(N5CCC(O)CC5)cc4)ccc32)cc1]

Compound 1068 was prepared according to the procedure described in Scheme IV from 5-amino-1H-Pyrrolo[2,3-b]pyridine, 4-(5-amino-1H-indol-1-yl)benzoic, and 4-(4-hydroxypiperidin-1-yl)benzoic acids. [M+H]+ calcd for $C_{34}H_{30}N_6O_3$: 571.25. found: 571.16.

Example 969

4-(4-Hydroxypiperidin-1-yl)-N-(1-(4-((5-methylthiazol-2-yl)carbamoyl)phenyl)-1H-indol-5-yl)benzamide (Compound 1069)

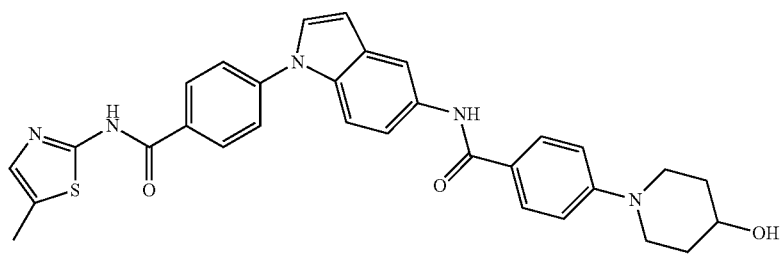 [SMILES: Cc1cnc(NC(=O)c2ccc(-n3ccc4cc(NC(=O)c5ccc(N6CCC(O)CC6)cc5)ccc43)cc2)s1]

Compound 1069 was prepared according to the procedure described in Scheme IV from 2-amino-5-methylthiazole, 4-(5-amino-1H-indol-1-yl)benzoic, and 4-(4-hydroxypiperidin-1-yl)benzoic acids. [M+H]+ calcd for $C_{31}H_{29}N_5O_3$: 552.0. found: 552.12.

Example 970

N-(4-(3-cyclopropyl-5-(4-(4-hydroxypiperidin-1-yl)benzamido)-1H-indol-1-yl)phenyl)-1-methyl-1H-pyrrole-3-carboxamide (Compound 1070)

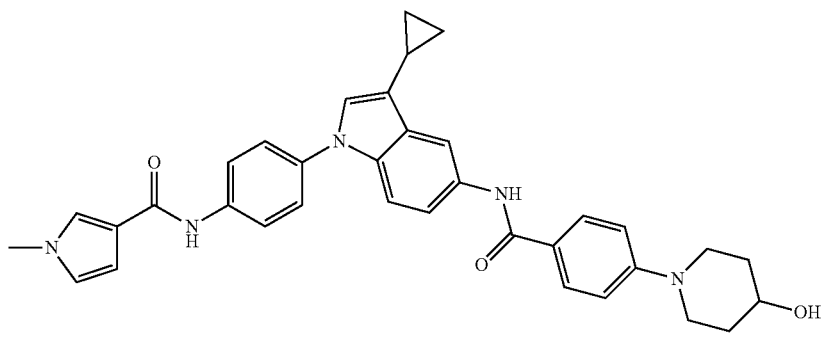 [SMILES: Cn1ccc(C(=O)Nc2ccc(-n3cc(C4CC4)c4cc(NC(=O)c5ccc(N6CCC(O)CC6)cc5)ccc43)cc2)c1]

Compound 1070 was prepared according to the procedure described in Scheme IV from 3-amino-1-methylpyrrole, 4-(5-amino-3-cyclopropyl-1H-indol-1-yl)benzoic, and 4-(4-hydroxypiperidin-1-yl)benzoic acids. $^1$H NMR (400 MHz, Acetone-$d_6$) δ 9.13 (s, 1H), 9.12 (s, 1H), 8.08 (d, J=1.8 Hz, 1H), 8.04 (d, J=8.8 Hz, 2H), 7.93 (d, J=9 Hz, 2H), 7.45 (m, 3H), 7.40 (dd, J=1.8, 8.8 Hz, 1H), 7.02 (d, J=9 Hz, 1H), 7.02 (d, J=9 Hz, 2H), 6.75 (t, J=2.6 Hz, 1H), 6.68 (dd, J=1.8, 2.8 Hz, 1H), 6.20 (s, 1H), 3.84 (m, 2H), 3.77 (s, 3H), 3.74 (m, 2H), 3.08 (ddd, J=3.2, 9.8, 13 Hz, 2H), 1.95 (m, 2H), 1.75 (m, 1H), 1.61 (m, 2H), 0.90 (m, 2H), 0.80 (m, 2H).

Example 971

The following additional compounds are known and prepared according to standard literature procedures and Table 1 summarises the structure and names of the compounds.

TABLE 1

| Cpd # | Structure | Name |
|---|---|---|
| 1700 | 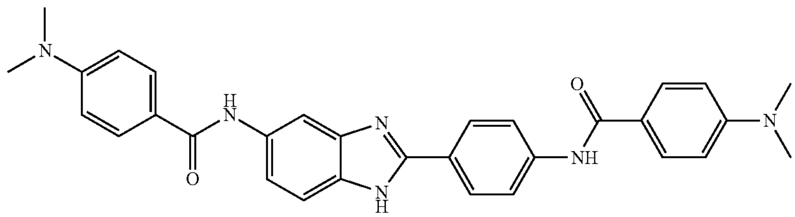 | 4-Dimethylamino-N-(4-(5-(4-dimethylaminobenzamido)-1H-benzimidazol-2-yl)phenyl)benzamide |
| 1701 | 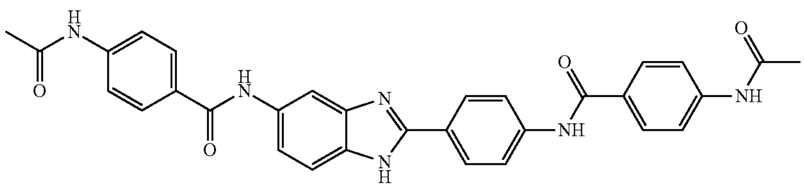 [SMILES: CC(=O)Nc1ccc(C(=O)Nc2ccc(-c3nc4cc(NC(=O)c5ccc(NC(C)=O)cc5)ccc4[nH]3)cc2)cc1] | 4-(Acetamido)-N-(4-(5-(4-acetamidobenzamido)-1H-benzimidazol-2-yl)phenyl)benzamide |
| 1702 | 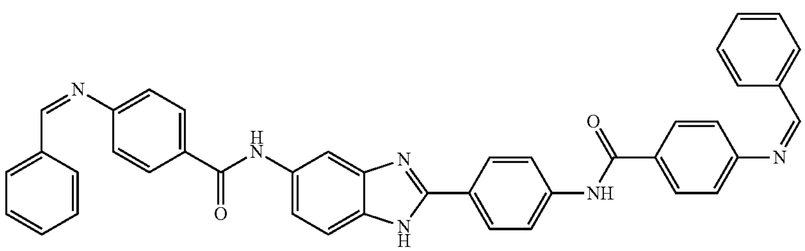 [SMILES: O=C(Nc1ccc(-c2nc3cc(NC(=O)c4ccc(/N=C\c5ccccc5)cc4)ccc3[nH]2)cc1)c1ccc(/N=C\c2ccccc2)cc1] | 4-(Benzylideneamino)-N-(4-(5-(4-benzylideneamino-benzamido)-1H-benzimidazol-2-yl)phenyl)benzamide |
| 1703 | 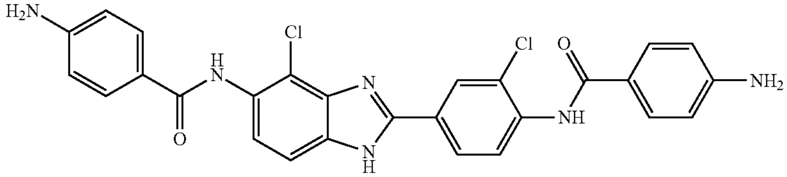 [SMILES: Nc1ccc(C(=O)Nc2ccc(-c3nc4c(Cl)c(NC(=O)c5ccc(N)cc5)ccc4[nH]3)cc2Cl)cc1] | 4-Amino-N-(4-(5-(4-aminobenzamido)-4-chloro-1H-benzimidazol-2-yl)-2-chlorophenyl)benzamide |
| 1704 | 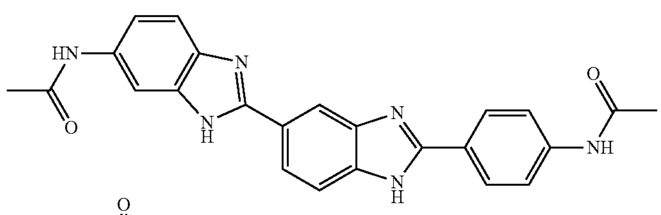 | N-(4-(6-Acetamido-1H,1'H-2,5'-bibenzamidazol-2-yl)phenyl)acetamide |
| 1705 | 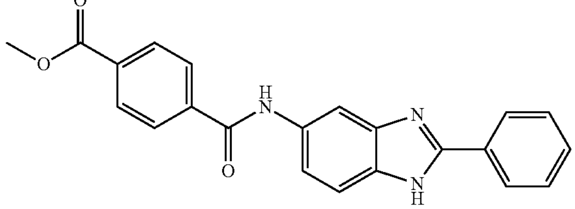 | Methyl 4-(2-phenyl-1H-benzimidazol-5-ylcarbamoyl)-benzoate |
| 1706 | 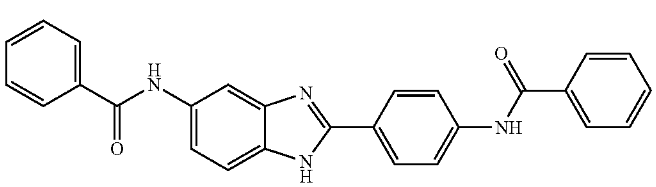 [SMILES: O=C(Nc1ccc(-c2nc3cc(NC(=O)c4ccccc4)ccc3[nH]2)cc1)c1ccccc1] | N-(4-(5-Benzamido-1H-benzimidazol-2-yl)phenyl)benzamide |

| Cpd # | Structure | Name |
|---|---|---|
| 1707 | 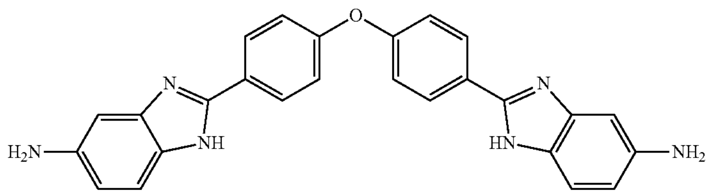 [SMILES: Nc1ccc2[nH]c(-c3ccc(Oc4ccc(-c5nc6cc(N)ccc6[nH]5)cc4)cc3)nc2c1] | 2,2'-(4,4'-Oxybis(4,1-phenylene))bis(1H-benzimidazole-5-amine) |
| 1708 | 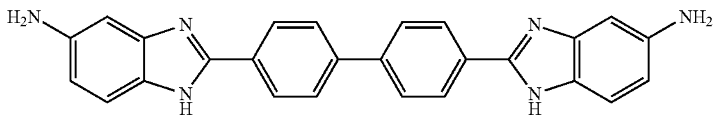 [SMILES: Nc1ccc2[nH]c(-c3ccc(-c4ccc(-c5nc6cc(N)ccc6[nH]5)cc4)cc3)nc2c1] | 2,2'-(Biphenyl-4,4'-diyl)bis(1H-benzimidazol-5-amine) |
| 1709 | 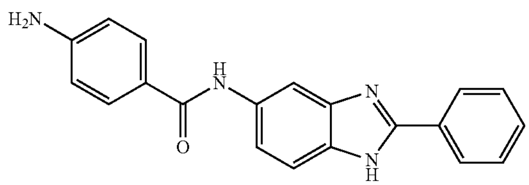 [SMILES: Nc1ccc(C(=O)Nc2ccc3[nH]c(-c4ccccc4)nc3c2)cc1] | 4-Amino-N-(2-phenyl-1H-benzimidazol-5-yl)benzamide |
| 1710 | 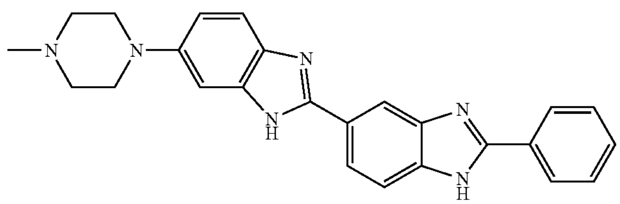 [SMILES: CN1CCN(c2ccc3nc(-c4ccc5[nH]c(-c6ccccc6)nc5c4)[nH]c3c2)CC1] | 5-(6-(4-Methylpiperazino)-1H-benzimidazol-2-yl)-2-phenyl-1H-benzimidazole |
| 1711 | 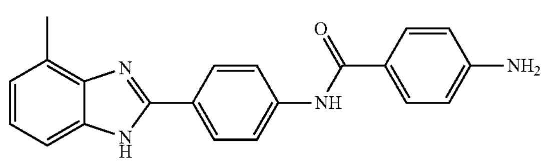 [SMILES: Cc1cccc2[nH]c(-c3ccc(NC(=O)c4ccc(N)cc4)cc3)nc12] | 4-Amino-N-(4-(4-methyl-1H-benzimidazol-2-yl)phenyl)benzamide |
| 1712 | 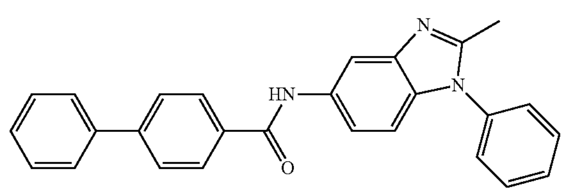 [SMILES: Cc1nc2cc(NC(=O)c3ccc(-c4ccccc4)cc3)ccc2n1-c1ccccc1] | N-(2-Methyl-1-phenyl-1H-benzimidazol-5-yl)biphenyl-4-carboxamide |
| 1713 | 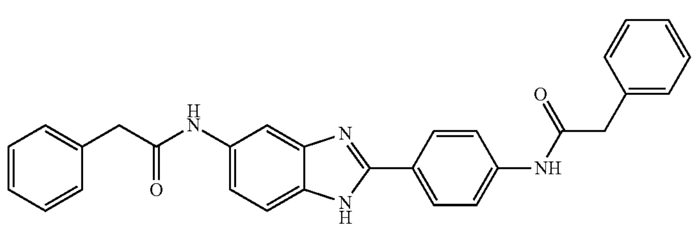 [SMILES: O=C(Cc1ccccc1)Nc1ccc(-c2nc3cc(NC(=O)Cc4ccccc4)ccc3[nH]2)cc1] | 2-Phenyl-N-(4-(5-(2-phenylacetamido)-1H-benzimidazol-2-yl)phenyl)acetamide |
| 1714 | 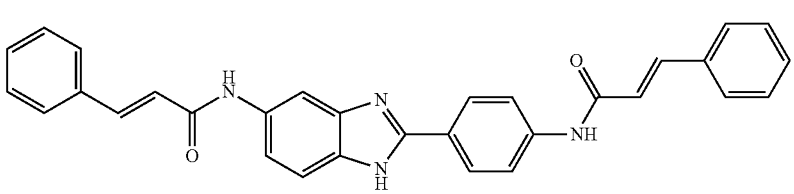 [SMILES: O=C(/C=C/c1ccccc1)Nc1ccc(-c2nc3cc(NC(=O)/C=C/c4ccccc4)ccc3[nH]2)cc1] | N-(2-(4-(3(E)-Phenylacrylamido)phenyl)-1H-benzimidazol-5-yl)-3(E)-phenylacrylamide |

TABLE 1-continued

| Cpd # | Structure | Name |
|---|---|---|
| 1715 | 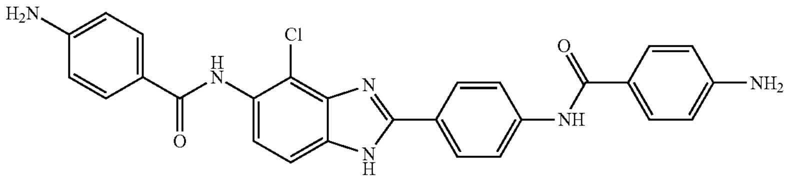 | 4-Amino-N-(4-(5-(4-aminobenzamido)-4-chloro-1H-benzimidazol-2-yl)phenyl)benzamide |
| 1716 | 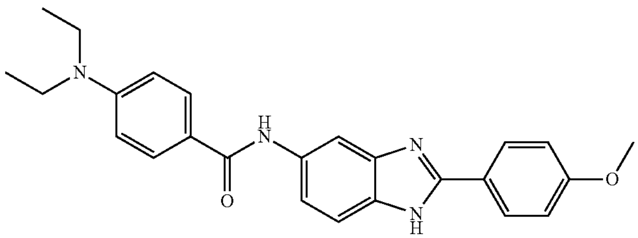 [SMILES: CCN(CC)c1ccc(C(=O)Nc2ccc3[nH]c(-c4ccc(OC)cc4)nc3c2)cc1] | 4-Diethylamino-N-(2-(4-methoxyphenyl)-1H-benzimidazol-5-yl)benzamide |
| 1717 | 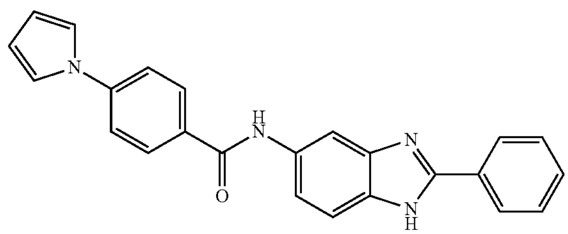 [SMILES: O=C(Nc1ccc2[nH]c(-c3ccccc3)nc2c1)c1ccc(-n2cccc2)cc1] | N-(2-Phenyl-1H-benzimidazol-5-yl)-4-pyrrolylbenzamide |
| 1718 | 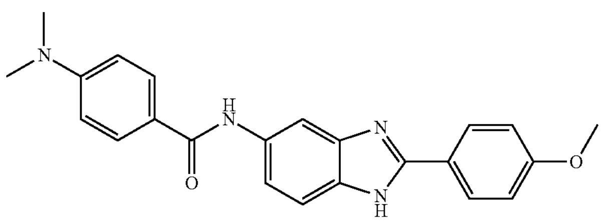 | 4-Dimethylamino-N-(2-(4-methoxyphenyl)-1H-benzimidazol-5-yl)benzamide |
| 1719 | 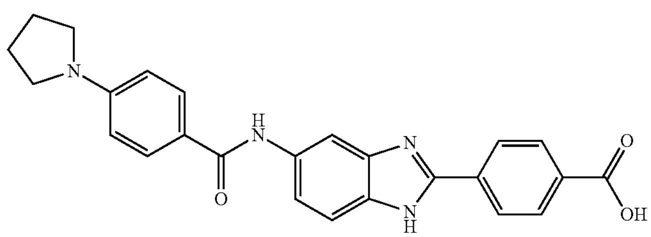 [SMILES: O=C(O)c1ccc(-c2nc3cc(NC(=O)c4ccc(N5CCCC5)cc4)ccc3[nH]2)cc1] | (4-(5-(4-Pyrrolidinobenzamido)-1H-benzimidazol-2-yl)benzoic acid |
| 1720 | 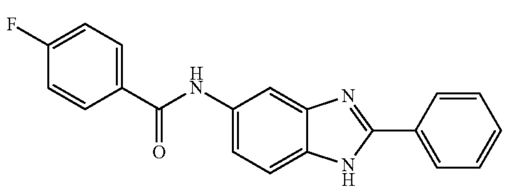 [SMILES: O=C(Nc1ccc2[nH]c(-c3ccccc3)nc2c1)c1ccc(F)cc1] | 4-Fluoro-N-(2-phenyl-1H-benzimidazol-5-yl)benzamide |
| 1721 | 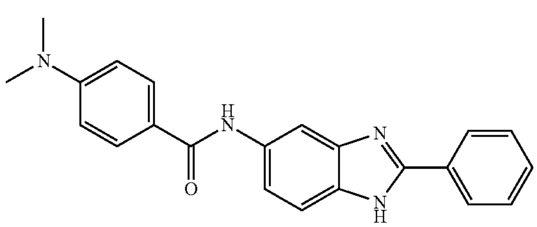 [SMILES: CN(C)c1ccc(C(=O)Nc2ccc3[nH]c(-c4ccccc4)nc3c2)cc1] | 4-Dimethylamino-N-(2-phenyl-1H-benzimidazol-5-yl)benzamide |

TABLE 1-continued

| Cpd # | Structure | Name |
|---|---|---|
| 1722 | 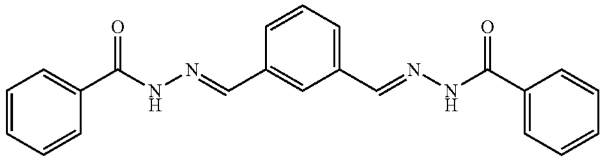 [SMILES: O=C(N/N=C/c1cccc(/C=N/NC(=O)c2ccccc2)c1)c1ccccc1] | 2,2'-(1,3-Phenylenebis(methylidene) dibenzohydrazide |
| 1723 | 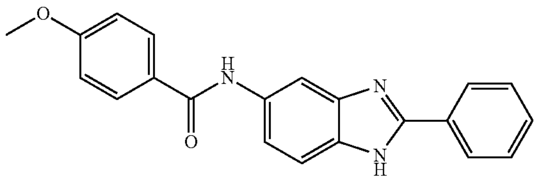 [SMILES: COc1ccc(C(=O)Nc2ccc3[nH]c(-c4ccccc4)nc3c2)cc1] | 4-Methoxy-N-(2-phenyl-1H-benzimidazol-5-yl)benzamide |
| 1724 | 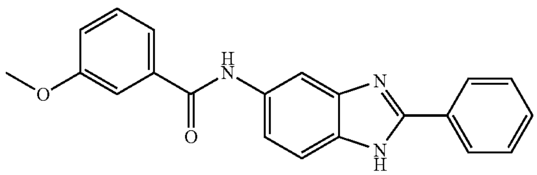 [SMILES: COc1cccc(C(=O)Nc2ccc3[nH]c(-c4ccccc4)nc3c2)c1] | 3-Methoxy-N-(2-phenyl-1H-benzimidazol-5-yl)benzamide |
| 1725 | 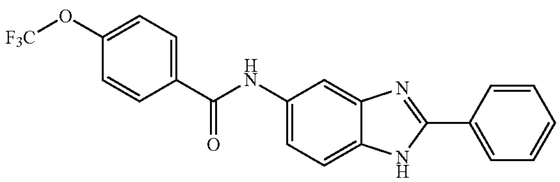 [SMILES: O=C(Nc1ccc2[nH]c(-c3ccccc3)nc2c1)c1ccc(OC(F)(F)F)cc1] | 4-Trifluoromethoxy-N-(2-phenyl-1H-benzimidazol-5-yl)benzamide |
| 1726 | 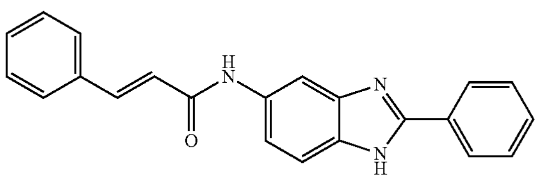 [SMILES: O=C(/C=C/c1ccccc1)Nc1ccc2[nH]c(-c3ccccc3)nc2c1] | N-(2-Phenyl-1H-benzimidazol-5-yl)-3(E)-phenylacrylamide |
| 1727 | 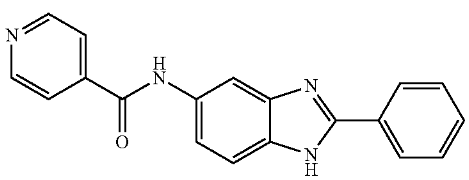 [SMILES: O=C(Nc1ccc2[nH]c(-c3ccccc3)nc2c1)c1ccncc1] | N-(2-Phenyl-1H-benzimidazol-5-yl)isonicotinamide |
| 1728 | 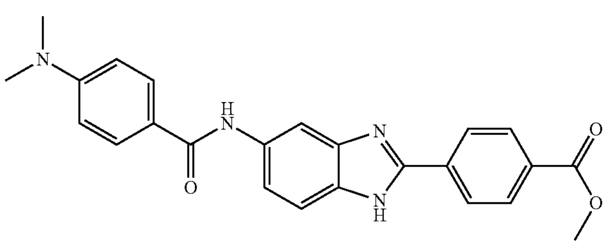 [SMILES: COC(=O)c1ccc(-c2nc3cc(NC(=O)c4ccc(N(C)C)cc4)ccc3[nH]2)cc1] | Methyl (4-(5-(4-dimethylaminobenzamido)-1H-benzimidazol-2-yl)benzoate |
| 1729 | 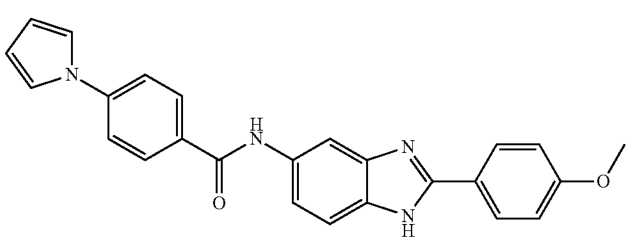 [SMILES: COc1ccc(-c2nc3cc(NC(=O)c4ccc(-n5cccc5)cc4)ccc3[nH]2)cc1] | N-(2-(4-Methoxyphenyl)-1H-benzimidazol-5-yl)-4-pyrrolylbenzamide |

TABLE 1-continued

| Cpd # | Structure | Name |
|---|---|---|
| 1730 | 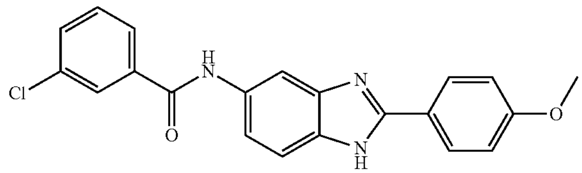 [SMILES: COc1ccc(-c2nc3cc(NC(=O)c4cccc(Cl)c4)ccc3[nH]2)cc1] | N-(2-(4-Methoxyphenyl)-1H-benzimidazol-5-yl)-3-chlorobenzamide |
| 1731 | 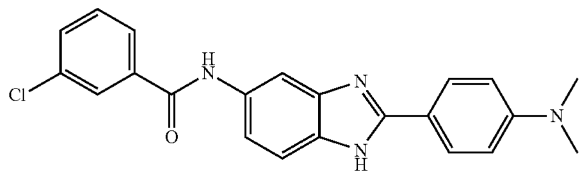 [SMILES: CN(C)c1ccc(-c2nc3cc(NC(=O)c4cccc(Cl)c4)ccc3[nH]2)cc1] | N-(2-(4-Dimethylaminophenyl)-1H-benzimidazol-5-yl)-3-chlorobenzamide |
| 1732 | 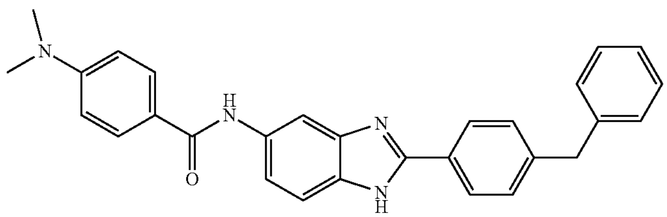 [SMILES: CN(C)c1ccc(C(=O)Nc2ccc3[nH]c(-c4ccc(Cc5ccccc5)cc4)nc3c2)cc1] | N-(2-(4-Benzylphenyl)-1H-benzimidazol-5-yl)-4-dimethylaminobenzamide |
| 1733 | 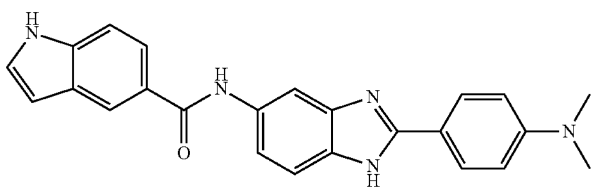 [SMILES: CN(C)c1ccc(-c2nc3cc(NC(=O)c4ccc5[nH]ccc5c4)ccc3[nH]2)cc1] | N-(2-(4-Dimethylaminophenyl)-1H-benzimidazol-5-yl)-1H-indole-5-carboxamide |
| 1734 | 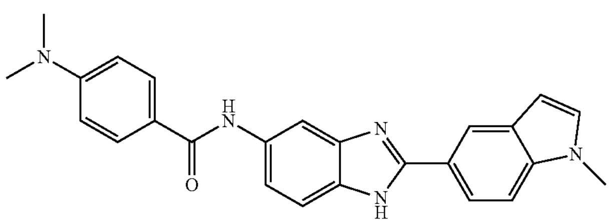 | N-(2-(1-Methyl-1H-indol-5-yl)benzimidazol-5-yl)-4-dimethylaminobenzamide |
| 1735 | 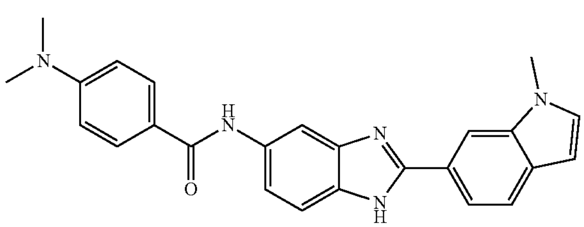 [SMILES: CN(C)c1ccc(C(=O)Nc2ccc3[nH]c(-c4ccc5ccn(C)c5c4)nc3c2)cc1] | N-(2-(1-Methyl-1H-indol-6-yl)benzimidazol-5-yl)-4-dimethylaminobenzamide |
| 1736 | 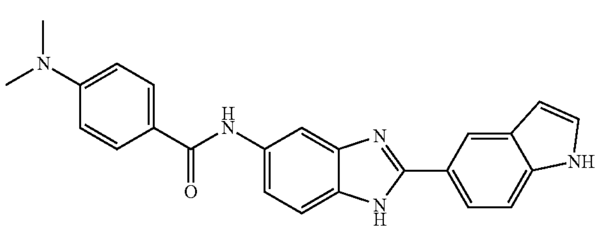 [SMILES: CN(C)c1ccc(C(=O)Nc2ccc3[nH]c(-c4ccc5[nH]ccc5c4)nc3c2)cc1] | N-(2-(1H-Indol-5-yl)benzimidazol-5-yl)-4-dimethylaminobenzamide |

TABLE 1-continued

| Cpd # | Structure | Name |
|---|---|---|
| 1737 | 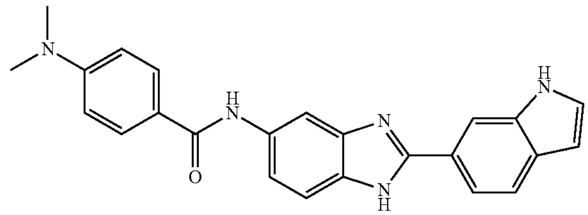 | N-(2-(1H-Indol-6-yl)benzimidazol-5-yl)-4-dimethylaminobenzamide |
| 1738 | 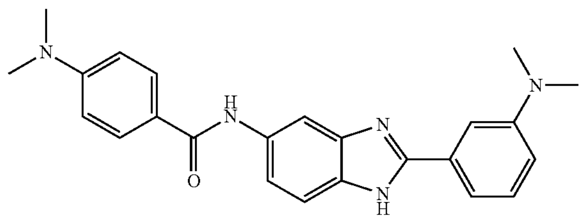 | 4-Dimethylamino-N-(2-(3-dimethylaminophenyl)-1H-benzimidazol-5-yl)benzamide |
| 1739 | 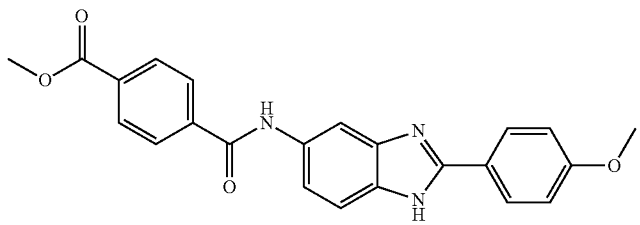 | Methyl 4-(2-(4-methoxyphenyl)-1H-benzimidazol-5-ylcarbamoyl)-benzoate |
| 1740 | 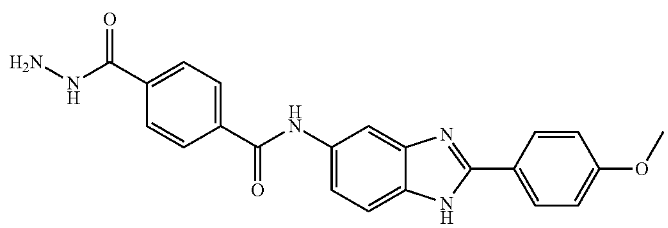 [SMILES: COc1ccc(-c2nc3cc(NC(=O)c4ccc(C(=O)NN)cc4)ccc3[nH]2)cc1] | 4-(2-(4-Methoxyphenyl)-1H-benzimidazol-5-ylcarbamoyl)-benzohydrazide |
| 1741 | 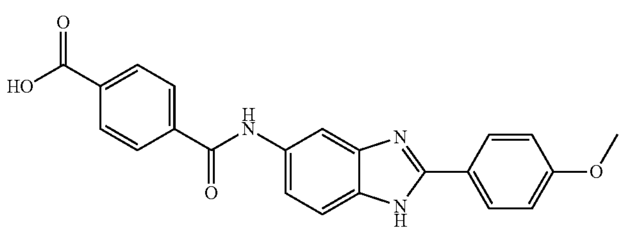 [SMILES: COc1ccc(-c2nc3cc(NC(=O)c4ccc(C(=O)O)cc4)ccc3[nH]2)cc1] | 4-(2-(4-Methoxyphenyl)-1H-benzimidazol-5-ylcarbamoyl)-benzoic acid |
| 1742 | 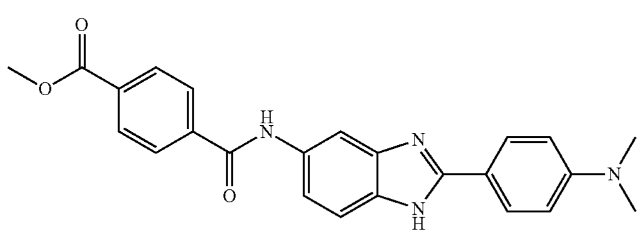 | Methyl 4-(2-(4-dimethylaminophenyl)-1H-benzimidazol-5-ylcarbamoyl)-benzoate |
| 1743 | 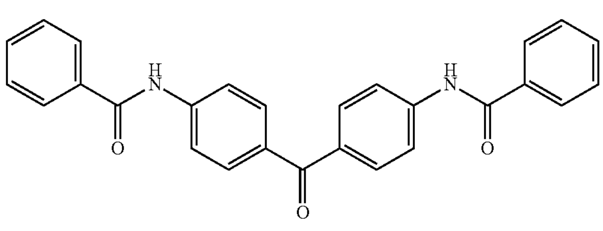 [SMILES: O=C(Nc1ccc(C(=O)c2ccc(NC(=O)c3ccccc3)cc2)cc1)c1ccccc1] | N,N'-(4,4'-Carbonylbis(4,1-phenylene))dibenzamide |

TABLE 1-continued

| Cpd # | Structure | Name |
|---|---|---|
| 1744 | (structure) | 4,4'-(5,5'-Bibenzimidazole-2,2'-diyl)bis(N,N-dimethylaniline) |
| 1745 | (structure) | 4,4'-(5,5'-Bibenzimidazole-2,2'-diyl)bis(anisole) |
| 1746 | (structure) | 4-Amino-N-(4-(5-(4-aminobenzamido)-1H-benzimidazol-2-yl)phenyl)benzamide |
| 1747 | (structure) | N-Phenyl-4-(5-benzamido-1H-benzimidazol-2-yl)benzamide |

Example 972

Cell Proliferation Assay

The primary testing for the exemplified compounds was performed in UT7/EPO Cell line. UT7/EPO is human leukemia cell line, obtained from Dr. Norio Komatsu (*Blood*, Vol 82 (2), pp 456-464, 1993). These cells express endogenous EPO receptor and are dependant upon EPO for growth and proliferation. Briefly, the cells were starved of EPO overnight and plated in 96 or 384 well plates. The compounds were added to the cells at 10 uM concentration. The plates were then incubated at 37° C. for 72 hours. The proliferative effect of the compounds was measured by a commercially available kit from Lonza (ViaLight Plus). The activities of the selected compounds are listed in the following table.

TABLE 2

| Compound | Activity (%) | Compound | Activity (%) | Compound | Activity (%) |
|---|---|---|---|---|---|
| 103 | 16 | 106 | 14 | 107 | 17 |
| 113 | 17 | 115 | 22 | 125 | 15 |
| 128 | 20 | 135 | 16 | 141 | 19 |
| 146 | 19 | 149 | 22 | 151 | 20 |
| 156 | 21 | 160 | 22 | 165 | 19 |
| 172 | 12 | 177 | 15 | 181 | 20 |
| 186 | 15 | 191 | 18 | 197 | 20 |
| 202 | 17 | 206 | 18 | 210 | 17 |
| 215 | 16 | 220 | 19 | 225 | 20 |
| 230 | 21 | 235 | 15 | 240 | 15 |
| 246 | 21 | 251 | 14 | 256 | 12 |
| 262 | 20 | 268 | 15 | 273 | 16 |
| 278 | 23 | 283 | 19 | 288 | 17 |
| 294 | 11 | 299 | 15 | 305 | 18 |
| 310 | 22 | 315 | 16 | 322 | 20 |
| 327 | 17 | 332 | 18 | 338 | 19 |
| 345 | 19 | 349 | 11 | 354 | 20 |
| 359 | 19 | 364 | 16 | 370 | 18 |
| 375 | 11 | 381 | 15 | 384 | 11 |
| 392 | 16 | 404 | 14 | 408 | 13 |
| 413 | 19 | 418 | 11 | 423 | 15 |
| 427 | 15 | 434 | 15 | 439 | 18 |
| 444 | 19 | 449 | 16 | 454 | 16 |
| 458 | 10 | 465 | 18 | 473 | 11 |
| 479 | 15 | 484 | 16 | 490 | 15 |
| 500 | 19 | 510 | 17 | 520 | 13 |
| 530 | 11 | 540 | 17 | 550 | 9 |
| 560 | 14 | 570 | 11 | 580 | 16 |
| 590 | 12 | 600 | 11 | 610 | 14 |
| 620 | 18 | 639 | 15 | 650 | 13 |
| 660 | 14 | 670 | 8 | 680 | 10 |
| 690 | 16 | 700 | 14 | 720 | 16 |
| 730 | 18 | 745 | 17 | 760 | 21 |
| 775 | 22 | 790 | 18 | 800 | 23 |
| 815 | 17 | 830 | 15 | 845 | 18 |
| 860 | 17 | 885 | 21 | 900 | 24 |
| 915 | 17 | 930 | 12 | 945 | 10 |
| 960 | 17 | 975 | 17 | 990 | 10 |
| 1005 | 13 | 1030 | 10 | 1045 | 15 |
| 1060 | 18 | 1070 | 15 | 1700 | 17 |
| 1705 | 12 | 1710 | 11 | 1715 | 10 |
| 1719 | 17 | 1724 | 13 | 1729 | 14 |
| 1734 | 20 | 1739 | 19 | 1744 | 11 |
| 1747 | 19 | | | | |

What is claimed is:

1. A compound of formula VIIIb:

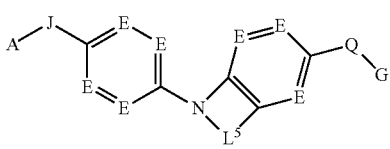

and pharmaceutically acceptable salts thereof, wherein:

A-J is

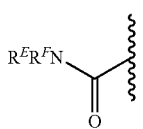

and Q-G is

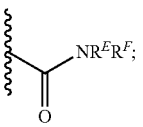

or A-J is

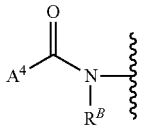

and Q-G is

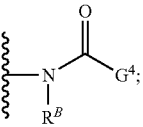

or A-J is

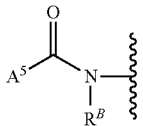

and Q-G is

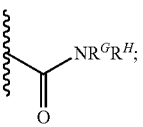

or A-J is

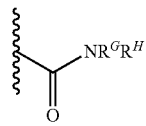

and Q-G is

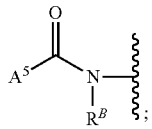

each E is separately selected from the group consisting of —$CR^{10a}$— and N (nitrogen);

each $R^{10a}$ is separately selected from the group consisting of H (hydrogen), halogen, cyano, $C_1$-$C_6$ alkyl optionally substituted with up to five fluoro, $C_1$-$C_6$ alkoxy optionally substituted with up to five fluoro, $C_2$-$C_6$ alkenyl optionally substituted with up to five fluoro, $C_2$-$C_6$ alkynyl optionally substituted with up to five fluoro, $C_3$-$C_7$ cycloalkyl optionally substituted with up to five fluoro, and $C_3$-$C_7$ cycloalkenyl optionally substituted with up to five fluoro;

$A^4$ is selected from the group consisting of $C_3$-$C_7$ cycloalkenyl, $C_3$-$C_7$ cycloalkyl, $C_1$-$C_6$ alkyl, $C_1$-$C_6$ heteroalkyl, $C_2$-$C_6$ alkenyl, $C_1$-$C_6$ alkoxy, —$(CH_2)_m$N-$R^P R^L$, heterocycle, polycyclic heterocyclyl, aryl, and heteroaryl, said $C_3$-$C_7$ cycloalkenyl, $C_3$-$C_7$ cycloalkyl, $C_1$-$C_6$ alkyl, $C_1$-$C_6$ heteroalkyl, $C_2$-$C_6$ alkenyl, heterocycle, polycyclic heterocyclyl, aryl, and heteroaryl, each optionally substituted with one or more substituents selected from the group consisting of $R^1$, $R^2$, and $R^3$;

$G^4$ is selected from the group consisting of polycyclic heterocyclyl, aryl, and heteroaryl, each optionally substituted with one or more substituents selected from the group consisting of $R^4$, $R^5$, and $R^6$;

$A^5$ is selected from the group consisting of polycyclic heterocyclyl, aryl and heteroaryl, each optionally substituted with one or more substituents selected from the group consisting of $R^1$, $R^2$, and $R^3$;

each $R^B$ is separately selected from the group consisting of hydrogen, an optionally substituted $C_1$-$C_6$ alkyl, an optionally substituted $C_2$-$C_6$ alkenyl, and an optionally substituted $C_3$-$C_7$ cycloalkyl;

each —$NR^E R^F$ is separately selected, wherein each $R^E$ is independently selected from the group consisting of hydrogen and an optionally $C_1$-$C_6$ alkyl, and each $R^F$ is independently selected from the group consisting of aryl and heteroaryl, said aryl and heteroaryl in the definition of $R^F$ are each optionally substituted with halogen, cyano, $C_1$-$C_6$ alkyl, $C_1$-$C_6$ alkoxy, $C_3$-$C_7$ cycloalkyl, $C_3$-$C_7$ cycloalkenyl, —$C(=O)NR^N R^O$, —$OC(=O)NR^N R^O$, —$NHC(=O)NR^N R^O$, —$O(CH_2)_q NR^N R^O$, —$NH(CH_2)_q NR^N R^O$ —$(CH_2)_p$N-$R^N R^O$, an optionally substituted aryl and an optionally substituted heteroaryl, and said aryl and heteroaryl in the definition of $R^F$ are each further optionally fused with an optionally substituted nonaromatic heterocycle or an optionally substituted nonaromatic carbocycle;

$R^G$ is selected from the group consisting of $C_1$-$C_6$ alkyl, $C_3$-$C_6$ cycloalkyl, $C_3$-$C_8$ cycloalkenyl, $C_1$-$C_6$ heteroalkyl, $C_2$-$C_6$ heteroalkenyl, $C_2$-$C_6$ heteroalkynyl, heterocycle, aryl, and heteroaryl, each optionally substituted with one or more substituents selected from the group consisting of $R^4$, $R^5$, and $R^6$, said aryl and heteroaryl in the definition of $R^G$ are each further optionally fused with an optionally substituted nonaromatic heterocycle or an optionally substituted nonaromatic carbocycle, or $R^G$ is —$OR^L$ or —$NR^PR^L$;

$R^H$ is selected from the group consisting of hydrogen, $C_1$-$C_6$ alkyl, $C_2$-$C_6$ alkenyl, $C_3$-$C_7$ cycloalkyl, and $C_1$-$C_3$ haloalkyl, or —$NR^GR^H$ is an optionally substituted non-aromatic heterocycle linked through a ring nitrogen atom;

each $R^1$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, optionally substituted $C_3$-$C_7$ cycloalkenyl, an optionally substituted $C_1$-$C_6$ haloalkyl, an optionally substituted $C_1$-$C_6$ heteroalkyl, an optionally substituted aryl, and an optionally substituted heteroaryl;

each $R^2$ is separately selected from the group consisting of halogen, —$O(CH_2)_mOR^I$, —$(CH_2)_mOR^I$, —$NR^JR^K$, —$(CH_2)_mSR^I$, —$C(=O)R^L$, —$(CH_2)_mR^L$, an optionally substituted $C_1$-$C_6$ alkyl, an optionally substituted $C_1$-$C_6$ alkoxy, an optionally substituted $C_2$-$C_6$ alkenyl, an optionally substituted $C_1$-$C_6$ haloalkyl, an optionally substituted $C_1$-$C_6$ heteroalkyl, and an optionally substituted $C_3$-$C_7$ cycloalkyl where said $C_3$-$C_7$ cycloalkyl is further optionally fused with aryl or heteroaryl;

each $R^3$ is separately selected from the group consisting of halogen, —$(CH_2)_mOR^G$, —$NR^LC(=O)R^M$, —$NR^LC(=O)OR^M$, —$NR^LC(=O)NR^NR^O$, —$NR^NR^O$, —$(CH_2)_mS(O)_{0-2}R^M$, —$(CH_2)_mNHS(O)_{0-2}R^M$, —$(CH_2)_mNO_2$, —$(CH_2)_mCN$, —$(CH_2)_mR^P$, $C_1$-$C_6$ alkyl $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —$C(=O)OR^M$, or —$NR^JR^K$;

each $R^4$ is separately selected from the group consisting of halogen, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, an optionally substituted $C_1$-$C_6$ heteroalkyl, an optionally substituted aryl, and an optionally substituted heteroaryl;

each $R^5$ is separately selected from the group consisting of halogen, —$O(CH_2)_mOR^I$, —$(CH_2)_mOR^I$, —$NR^JR^K$, —$(CH_2)_mSR^I$, —$(CH_2)_mC(=O)R^L$, —$(CH_2)_mR^L$, an optionally substituted $C_1$-$C_6$ alkyl, an optionally substituted $C_1$-$C_6$ alkoxy, an optionally substituted $C_2$-$C_6$ alkenyl, an optionally substituted $C_3$-$C_7$ cycloalkyl, an optionally substituted $C_1$-$C_6$ haloalkyl, and an optionally substituted $C_1$-$C_6$ heteroalkyl;

each $R^6$ is separately selected from the group consisting of halogen, —$(CH_2)_mOR^G$, —$NR^LC(=O)R^M$, —$NR^LC(=O)OR^M$, —$NR^LC(=O)NR^NR^O$, —$NR^NR^O$, —$(CH_2)_mS(O)_{0-2}R^M$, —$(CH_2)_mNHS(O)_{0-2}R^M$, —$(CH_2)_mNO_2$, —$(CH_2)_mCN$, —$(CH_2)_mR^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, $C_1$-$C_6$ heteroalkyl, heterocycle, aryl, polycyclic heterocyclyl, and heteroaryl, said heterocycle, aryl, polycyclic heterocyclyl, and heteroaryl in the definition of $R^6$ are each optionally substituted with halogen, cyano, $C_1$-$C_6$ alkyl, $C_1$-$C_6$ haloalkyl, $C_1$-$C_6$ alkoxy, —$C(=O)OR^M$, or —$NR^JR^K$;

each $R^I$ is separately selected from the group consisting of hydrogen, $C_1$-$C_6$ alkyl, $C_2$-$C_4$ alkenyl, $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl;

each —$NR^JR^K$ is separately selected, wherein $R^J$ and $R^K$ are each independently selected from the group consisting of hydrogen, $C_1$-$C_6$ alkyl optionally substituted with up to 5 fluoro, —$(CH_2)_mOR^{JA}$, —$(CH_2)_mNR^{JB}R^{JC}$, —$(CH_2)_mR^R$, $C_3$-$C_7$ cycloalkyl, heterocycle, aryl and heteroaryl, said $C_3$-$C_7$ cycloalkyl, heterocycle, aryl and heteroaryl in the definition of $R^J$ and $R^K$ are each independently optionally substituted with one or more substituents selected from the group consisting of halo, $C_1$-$C_6$ alkyl, $C_1$-$C_6$ haloalkyl, $C_1$-$C_6$ alkoxy, aryl and heteroaryl, said aryl and heteroaryl substituent off of $R^J$ and $R^K$ are each optionally substituted with one or more halo, $C_1$-$C_6$ alkyl, $C_1$-$C_6$ haloalkyl, $C_1$-$C_6$ alkoxy, or —$(CH_2)_mNR^{KA}R^{KB}$; or —$NR^JR^K$ is an optionally substituted non-aromatic heterocycle linked through a ring nitrogen atom;

each $R^{JA}$ is independently selected from the group consisting of hydrogen, $C_1$-$C_6$ alkyl, and $C_1$-$C_6$ haloalkyl;

each —$NR^{JB}R^{JC}$ is separately selected, wherein $R^{JB}$ and $R^{JC}$ are each independently selected from the group consisting of hydrogen, $C_1$-$C_6$ alkyl, and $C_1$-$C_6$ haloalkyl;

each —$NR^{KA}R^{KB}$ is separately selected, wherein $R^{KA}$ and $R^{KB}$ are each independently selected from the group consisting of hydrogen, $C_1$-$C_6$ alkyl, and $C_1$-$C_6$ haloalkyl;

each $R^M$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_3$-$C_7$ cycloalkenyl, and —$(CH_2)_mR^P$;

each —$NR^NR^O$ is separately selected, wherein $R^N$ and $R^O$ are each independently selected from the group consisting of hydrogen, —$(CH_2)_mNR^{NA}R^{NB}$, aryl and heteroaryl, said aryl and heteroaryl in the definition of $R^N$ and $R^O$ are each independently optionally substituted with one or more substituents selected from the group consisting of —$(CH_2)_mNR^{OA}R^{OB}$, halo, $C_1$-$C_6$ alkyl, $C_1$-$C_6$ haloalkyl, $C_1$-$C_6$ alkoxy, aryl and heteroaryl, said aryl and heteroaryl substituent off of $R^N$ and $R^O$ are each optionally substituted with one or more halo, $C_1$-$C_6$ alkyl, $C_1$-$C_6$ haloalkyl, $C_1$-$C_6$ alkoxy, or —$NR^{NA}R^{NB}$;

each —$NR^{NA}R^{NB}$ is separately selected, wherein $R^{NA}$ and $R^{NB}$ are each independently selected from the group consisting of hydrogen, $C_1$-$C_6$ alkyl, and $C_1$-$C_6$ haloalkyl;

each —$NR^{OA}R^{OB}$ is separately selected, wherein $R^{OA}$ and $R^{OB}$ are each independently selected from the group consisting of hydrogen, $C_1$-$C_6$ alkyl, and $C_1$-$C_6$ haloalkyl;

each $R^P$ is independently selected from the group consisting of hydrogen and $C_1$-$C_6$ alkyl;

each $R^L$ is independently selected from the group consisting of $C_3$-$C_7$ cycloalkyl, optionally substituted $C_1$-$C_6$ alkyl, optionally substituted $C_1$-$C_6$ alkoxy, —(CH$_2$)$_m$OR$^{LA}$, —(CH$_2$)$_m$NR$^{LB}$R$^{LC}$, aryl and heteroaryl, said aryl and heteroaryl in the definition of $R^L$ are each independently optionally substituted with one or more substituents selected from the group consisting of halo, $C_1$-$C_6$ alkyl, $C_1$-$C_6$ haloalkyl, $C_1$-$C_6$ alkoxy, —(CH$_2$)$_m$NR$^{LD}$R$^{LE}$, aryl and heteroaryl, said aryl and heteroaryl substituent off of $R^L$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{LF}$R$^{LG}$;

each $R^{LA}$ is independently selected from the group consisting of hydrogen, $C_1$-$C_6$ alkyl, and $C_1$-$C_6$ haloalkyl;

$R^{LB}$ and $R^{LC}$ are each independently selected from the group consisting of hydrogen, $C_1$-$C_6$ alkyl, $C_1$-$C_6$ haloalkyl, and $C_2$-$C_6$ heteroalkenyl, said $C_1$-$C_6$ alkyl, $C_1$-$C_6$ haloalkyl, and $C_2$-$C_6$ heteroalkenyl each optionally substituted with one or more halogen, cyano, or —(CH$_2$)$_m$C(=O)OH; or —NR$^{LB}$R$^{LC}$ is an optionally substituted non-aromatic heterocycle linked through a ring nitrogen atom;

each —NR$^{LD}$R$^{LE}$ is separately selected, wherein $R^{LD}$ and $R^{LE}$ are each independently selected from the group consisting of hydrogen, aryl, heteroaryl, and optionally substituted $C_1$-$C_6$ alkyl, said aryl and heteroaryl in the definition of $R^{LD}$ and $R^{LE}$ are each optionally substituted with $C_1$-$C_6$ alkyl or $C_1$-$C_6$ alkoxy; or —NR$^{LD}$R$^{LE}$ is an optionally substituted non-aromatic heterocycle linked through a ring nitrogen atom;

each —NR$^{LF}$R$^{LG}$ is separately selected, wherein $R^{LF}$ and $R^{LG}$ are each independently selected from the group consisting of hydrogen, and $C_1$-$C_6$ alkyl; or —NR$^{LF}$R$^{LG}$ is an optionally substituted non-aromatic heterocycle linked through a ring nitrogen atom;

$R^R$ is selected from the group consisting of $C_1$-$C_6$ alkyl, an optionally substituted aryl, and an optionally substituted heteroaryl;

each m is independently 0, 1, 2, or 3;

each p is independently 0, 1, 2, 3, 4, 5, or 6; and each q is independently 1, 2, 3, 4, 5, or 6;

$L^5$ is $E^1$=$E^1$ or $E^2$-$E^2$;

each $E^1$ is separately selected from the group consisting of —CR$^{10dd}$— and N (nitrogen);

each $R^{10dd}$ is separately selected from the group consisting of H (hydrogen), halogen, cyano, $C_1$-$C_6$ alkyl optionally substituted with up to five fluoro, $C_1$-$C_6$ alkoxy optionally substituted with up to five fluoro, $C_1$-$C_6$ alkylC(=O)— and $C_3$-$C_7$ cycloalkylC(=O)—;

each $E^2$ is separately selected from the group consisting of —CR$^7$R$^8$— and NR$^9$;

$R^7$ and $R^8$ are each independently selected from the group consisting of hydrogen, —OH, and $C_1$-$C_6$ alkyl optionally substituted with up to five fluoro, or optionally CR$^7$R$^8$ is —C(=O)—; and, $R^9$ is selected from the group consisting of hydrogen, $C_3$-$C_7$cycloalkylC(O)— and $C_1$-$C_6$ alkylC(O)—, and $C_1$-$C_6$ alkyl optionally substituted with up to five fluoro.

2. The compound of claim 1, having the formula VIIIbb:

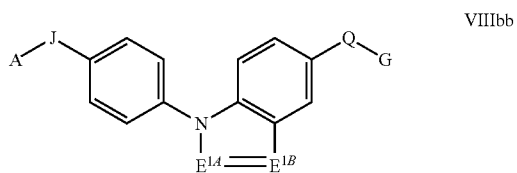

VIIIbb and pharmaceutically acceptable salts thereof, wherein:

$E^{1A}$ is N (nitrogen) and $E^{1B}$ is —CH—, or $E^{1A}$ is —CH— and $E^{1B}$ is —CH—, or $E^{1A}$ is —CH— and $E^{1B}$ is N (nitrogen); and A-J is

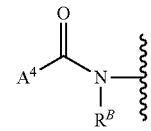

and Q-G is

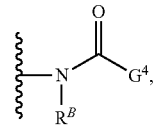

or A-J is

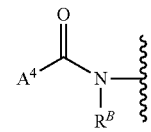

and Q-G is

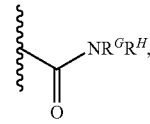

or A-J is

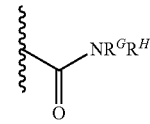

and Q-G is

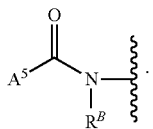

3. The compound of claim 2, having the formula VIIIbbb:

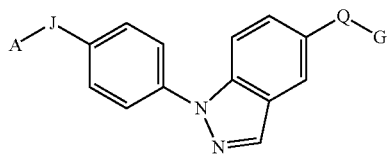

VIIIbbb and pharmaceutically acceptable salts thereof, wherein:

A-J is

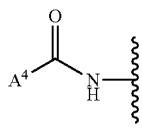

and Q-G is

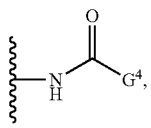

or A-J is

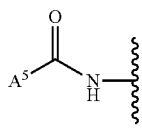

and Q-G is

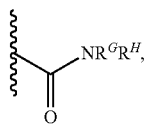

or A-J is

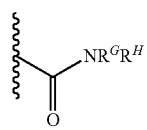

and Q-G is

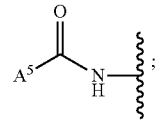

$A^4$ is selected from the group consisting of $C_5$-$C_7$ cycloalkenyl, $C_3$-$C_6$ cycloalkyl, $C_1$-$C_6$ alkyl, $C_1$-$C_6$ heteroalkyl, $C_2$-$C_6$ alkenyl, —$NR^PR^L$, heterocycle, aryl, and heteroaryl, said $C_5$-$C_7$ cycloalkenyl, $C_3$-$C_6$ cycloalkyl, $C_1$-$C_6$ alkyl, $C_1$-$C_6$ heteroalkyl, $C_2$-$C_6$ alkenyl, heterocycle, aryl, and heteroaryl, each optionally substituted with one or more substituents selected from the group consisting of $R^1$, $R^2$, and $R^3$;

each $R^1$ is separately selected from the group consisting of halogen, cyano, an optionally substituted $C_1$-$C_6$ alkyl, an optionally substituted $C_1$-$C_6$ alkoxy, an optionally substituted $C_1$-$C_6$ heteroalkyl, an optionally substituted aryl, and an optionally substituted heteroaryl;

each $R^2$ is separately selected from the group consisting of —$O(CH_2)_mOR^I$, —$(CH_2)_mOR^I$, —$NR^JR^K$, —$(CH_2)_mSR^I$, —$C(=O)R^L$, and —$(CH_2)_mR^L$;

each $R^3$ is separately selected from the group consisting of —$(CH_2)_mOR^G$, —$NR^LC(=O)R^M$, —$NR^LC(=O)OR^M$, —$NR^LC(=O)NR^NR^O$, —$NR^NR^O$, —$(CH_2)_mS(O)_{0-2}R^M$, —$(CH_2)_mNHS(O)_{0-2}R^M$, —$(CH_2)_mNO_2$, —$(CH_2)_mCN$, —$(CH_2)_mR^P$, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —$C(=O)OR^M$, or —$NR^JR^K$;

$G^4$ is selected from the group consisting of aryl, and heteroaryl, each optionally substituted with one or more substituents selected from the group consisting of $R^4$, $R^5$, and $R^6$;

each $R^4$ is separately selected from the group consisting of halogen, cyano, an optionally substituted $C_1$-$C_6$ alkyl, and an optionally substituted $C_1$-$C_6$ heteroalkyl;

each $R^5$ is separately selected from the group consisting of halogen, —$(CH_2)_mOH$, —$NR^JR^K$, and —$(CH_2)_mC(=O)R^L$;

each $R^L$ is independently selected from the group consisting of —OH, $C_1$-$C_6$ alkyl, and $C_1$-$C_6$ alkoxy;

each $R^6$ is separately selected from the group consisting of —$NR^LC(=O)R^M$, —$NR^LC(=O)OR^M$, —$NR^LC(=O)NR^NR^O$, —$NR^NR^O$, —$(CH_2)_mR^P$, heterocycle, aryl, polycyclic heterocyclyl, and heteroaryl, said heterocycle, aryl, polycyclic heterocyclyl, and heteroaryl in the definition of $R^6$ are each optionally substituted with halogen, cyano, $C_1$-$C_6$ alkyl, $C_1$-$C_6$ haloalkyl, $C_1$-$C_6$ alkoxy, —$C(=O)OR^M$, or —$NR^JR^K$;

$R^G$ within the definition of —$NR^GR^H$ is heteroaryl optionally substituted with one or more substituents selected from the group consisting of $R^4$, $R^5$, and $R^6$; and, $R^H$ within the definition of —$NR^GR^H$ is hydrogen.

4. A compound of Formula IX:

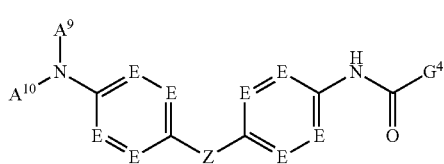

(IX)

and pharmaceutically acceptable salts thereof;
wherein:
Z is

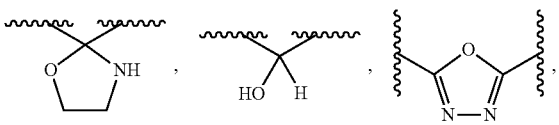

or —C(=E³)-;
each E is separately selected from the group consisting of —CR$^{10a}$— and N (nitrogen);
each R$^{10a}$ is separately selected from the group consisting of H (hydrogen), halogen, C$_1$-C$_6$ alkyl optionally substituted with up to five fluoro, and C$_1$-C$_6$ alkoxy optionally substituted with up to five fluoro;
E³ is O (oxygen), N—NHR$^Q$ or N—OR$^Q$ where R$^Q$ in the definition of E³ is selected from the group consisting of hydrogen, C$_1$-C$_6$ alkyl, C$_2$-C$_6$ alkenyl, —(CH$_2$)$_m$R$^{RA}$, and —C(=O)(CH$_2$)$_m$R$^{RA}$;
R$^{RA}$ is selected from the group consisting of C$_1$-C$_6$ alkyl, aryl, and heteroaryl;
A⁹ is hydrogen or C$_1$-C$_6$ alkyl;
A¹⁰ is selected from the group consisting of C$_1$-C$_6$ alkyl, C$_2$-C$_6$ alkenyl, —C(=O)R$^A$, —C(=O)C(=O)R$^A$, —(CH$_2$)R$^B$, —(CH$_2$)OR$^B$;
R$^A$ is selected from the group consisting of C$_1$-C$_6$ alkyl, C$_3$-C$_7$ cycloalkyl, heterocycle, polycyclic heterocyclyl, aryl and heteroaryl, each optionally substituted with one or more substituents selected from the group consisting of R¹, R², and R³;
R$^B$ is selected from the group consisting of hydrogen, C$_1$-C$_6$ alkyl, C$_1$-C$_6$ alkoxy, C$_2$-C$_6$ alkenyl, C$_3$-C$_7$ cycloalkyl, and heteroaryl;
G⁴ is selected from the group consisting of polycyclic heterocyclyl, phenyl, and heteroaryl, each optionally substituted with one or more substituents selected from the group consisting of R⁴, R⁵, and R⁶;
each R¹ is separately selected from the group consisting of halogen, cyano, C$_1$-C$_6$ heteroalkyl, an optionally substituted C$_1$-C$_6$ alkyl, an optionally substituted C$_1$-C$_6$ alkoxy, an optionally substituted C$_2$-C$_6$ alkenyl, an optionally substituted C$_2$-C$_6$ alkynyl, an optionally substituted C$_3$-C$_7$ cycloalkyl, optionally substituted C$_3$-C$_7$ cycloalkenyl, an optionally substituted C$_1$-C$_6$ haloalkyl, an optionally substituted aryl, and an optionally substituted heteroaryl;
each R² is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —C(=O)R$^L$, —(CH$_2$)$_m$R$^L$, C$_1$-C$_6$ heteroalkyl, an optionally substituted C$_1$-C$_6$ alkyl, an optionally substituted C$_1$-C$_6$ alkoxy, an optionally substituted C$_2$-C$_6$ alkenyl, an optionally substituted C$_1$-C$_6$ haloalkyl, and an optionally substituted C$_3$-C$_7$ cycloalkyl where said C$_3$-C$_7$ cycloalkyl is further optionally fused with aryl or heteroaryl;
each R³ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$CN, —(CH$_2$)$_m$R$^P$, C$_1$-C$_6$ alkyl, C$_1$-C$_6$ alkoxy, C$_2$-C$_6$ alkenyl, C$_2$-C$_6$ alkynyl, C$_3$-C$_7$ cycloalkyl, C$_1$-C$_6$ haloalkyl, heterocycle, aryl, polycyclic heterocyclyl, and heteroaryl, said heterocycle, aryl polycyclic heterocyclyl, and heteroaryl in the definition of R³ are each optionally substituted with halogen, hydroxy, cyano, C$_1$-C$_6$ alkyl, C$_1$-C$_6$ haloalkyl, C$_1$-C$_6$ alkoxy, —C(=O)OR$^M$, or —NR$^J$R$^K$;
each R⁴ is separately selected from the group consisting of halogen, cyano, C$_1$-C$_6$ heteroalkyl, an optionally substituted C$_1$-C$_6$ alkyl, an optionally substituted C$_1$-C$_6$ alkoxy, an optionally substituted C$_2$-C$_6$ alkenyl, an optionally substituted C$_2$-C$_6$ alkynyl, an optionally substituted C$_3$-C$_7$ cycloalkyl, an optionally substituted C$_1$-C$_6$ haloalkyl, an optionally substituted aryl, and an optionally substituted heteroaryl;
each R⁵ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —(CH$_2$)$_m$C(=O)R$^L$, —(CH$_2$)$_m$R$^L$, C$_1$-C$_6$ heteroalkyl, an optionally substituted C$_1$-C$_6$ alkyl, an optionally substituted C$_1$-C$_6$ alkoxy, an optionally substituted C$_2$-C$_6$ alkenyl, an optionally substituted C$_3$-C$_7$ cycloalkyl, and an optionally substituted C$_1$-C$_6$ haloalkyl;
each R⁶ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$CN, —(CH$_2$)$_m$R$^P$, C$_1$-C$_6$ alkyl, C$_1$-C$_6$ alkoxy, C$_2$-C$_6$ alkenyl, C$_2$-C$_6$ alkynyl, C$_3$-C$_7$ cycloalkyl, C$_1$-C$_6$ haloalkyl, C$_1$-C$_6$ heteroalkyl, heterocycle, aryl, polycyclic heterocyclyl, and heteroaryl, said heterocycle, aryl, polycyclic heterocyclyl, and heteroaryl in the definition of R⁶ are each optionally substituted with halogen, cyano, C$_1$-C$_6$ alkyl, C$_1$-C$_6$ haloalkyl, C$_1$-C$_6$ alkoxy, —C(=O)OR$^M$, or —NR$^J$R$^K$;
R$^G$ is selected from the group consisting of C$_1$-C$_6$ alkyl, C$_3$-C$_6$ cycloalkyl, C$_3$-C$_8$ cycloalkenyl, C$_1$-C$_6$ heteroalkyl, C$_2$-C$_6$ heteroalkenyl, C$_2$-C$_6$ heteroalkynyl, heterocycle, aryl, and heteroaryl, each optionally substituted with one or more substituents selected from the group consisting of R⁴, R⁵, and R⁶, said aryl and heteroaryl in the definition of R$^G$ are each further optionally fused with an optionally substituted nonaromatic heterocycle or an optionally substituted nonaromatic carbocycle, or R$^G$ is —OR$^L$ or —NR$^P$R$^L$;
each R$^I$ is separately selected from the group consisting of hydrogen, C$_1$-C$_6$ alkyl, C$_2$-C$_4$ alkenyl, C$_2$-C$_4$ alkynyl, C$_3$-C$_7$ cycloalkyl, C$_1$-C$_6$ haloalkyl, C$_1$-C$_6$ heteroalkyl, and C$_1$-C$_6$ heterohaloalkyl;
each —NR$^J$R$^K$ is separately selected, wherein R$^J$ and R$^K$ are each independently selected from the group consisting of hydrogen, C$_1$-C$_6$ alkyl optionally substituted with up to 5 fluoro, —(CH$_2$)$_m$OR$^{JA}$, —(CH$_2$)$_m$N-R$^{JB}$R$^{JC}$, —(CH$_2$)$_m$R$^R$, C$_3$-C$_7$ cycloalkyl, heterocycle, aryl and heteroaryl, said C$_3$-C$_7$ cycloalkyl, heterocycle, aryl and heteroaryl in the definition of R$^J$ and R$^K$ are each independently optionally substituted with one or more substituents selected from the group consisting of halo, C$_1$-C$_6$ alkyl, C$_1$-C$_6$ haloalkyl, C$_1$-C$_6$ alkoxy, aryl and heteroaryl, said aryl and heteroaryl substituent off of $R^J$ and $R^K$ are each optionally substituted with one or more halo, $C_1$-$C_6$ alkyl, $C_1$-$C_6$ haloalkyl, $C_1$-$C_6$ alkoxy, or —$(CH_2)_mNR^{KA}R^{KB}$; or —$NR^JR^K$ is an optionally substituted non-aromatic heterocycle linked through a ring nitrogen atom;

each $R^{JA}$ is independently selected from the group consisting of hydrogen, $C_1$-$C_6$ alkyl, and $C_1$-$C_6$ haloalkyl;

each —$NR^{JB}R^{JC}$ is separately selected, wherein $R^{JB}$ and $R^{JC}$ are each independently selected from the group consisting of hydrogen, $C_1$-$C_6$ alkyl, and $C_1$-$C_6$ haloalkyl;

each —$NR^{KA}R^{KB}$ is separately selected, wherein $R^{KA}$ and $R^{KB}$ are each independently selected from the group consisting of hydrogen, $C_1$-$C_6$ alkyl, and $C_1$-$C_6$ haloalkyl;

each $R^M$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_3$-$C_7$ cycloalkenyl, and —$(CH_2)_mR^P$;

each —$NR^NR^O$ is separately selected, wherein $R^N$ and $R^O$ are each independently selected from the group consisting of hydrogen, —$(CH_2)_mNR^{NA}R^{NB}$, aryl and heteroaryl, said aryl and heteroaryl in the definition of $R^N$ and $R^O$ are each independently optionally substituted with one or more substituents selected from the group consisting of —$(CH_2)_mNR^{OA}R^{OB}$, halo, $C_1$-$C_6$ alkyl, $C_1$-$C_6$ haloalkyl, $C_1$-$C_6$ alkoxy, aryl and heteroaryl, said aryl and heteroaryl substituent off of $R^N$ and $R^O$ are each optionally substituted with one or more halo, $C_1$-$C_6$ alkyl, $C_1$-$C_6$ haloalkyl, $C_1$-$C_6$ alkoxy, or —$NR^{NA}R^{NB}$;

each —$NR^{NA}R^{NB}$ is separately selected, wherein $R^{NA}$ and $R^{NB}$ are each independently selected from the group consisting of hydrogen, $C_1$-$C_6$ alkyl, and $C_1$-$C_6$ haloalkyl;

each —$NR^{OA}R^{OB}$ is separately selected, wherein $R^{OA}$ and $R^{OB}$ are each independently selected from the group consisting of hydrogen, $C_1$-$C_6$ alkyl, and $C_1$-$C_6$ haloalkyl;

$R^P$ is selected from the group consisting of hydrogen and $C_1$-$C_6$ alkyl;

each $R^L$ is independently selected from the group consisting of $C_3$-$C_7$ cycloalkyl, optionally substituted $C_1$-$C_6$ alkyl, optionally substituted $C_1$-$C_6$ alkoxy, —$(CH_2)_mOR^{LA}$, —$(CH_2)_mNR^{LB}R^{LC}$, aryl and heteroaryl, said aryl and heteroaryl in the definition of $R^L$ are each independently optionally substituted with one or more substituents selected from the group consisting of halo, $C_1$-$C_6$ alkyl, $C_1$-$C_6$ haloalkyl, $C_1$-$C_6$ alkoxy, —$(CH_2)_mNR^{LD}R^{LE}$, aryl and heteroaryl, said aryl and heteroaryl substituent off of $R^L$ are each optionally substituted with one or more halo, $C_1$-$C_6$ alkyl, $C_1$-$C_6$ haloalkyl, $C_1$-$C_6$ alkoxy, or —$(CH_2)_mNR^{LE}R^{LG}$;

each $R^{LA}$ is independently selected from the group consisting of hydrogen, $C_1$-$C_6$ alkyl, and $C_1$-$C_6$ haloalkyl;

$R^{LB}$ and $R^{LC}$ are each independently selected from the group consisting of hydrogen, $C_1$-$C_6$ alkyl, $C_1$-$C_6$ haloalkyl, and $C_1$-$C_6$ heteroalkenyl, said $C_1$-$C_6$ alkyl, $C_1$-$C_6$ haloalkyl, and $C_1$-$C_6$ heteroalkenyl each optionally substituted with one or more halogen, cyano, or —$(CH_2)_mC(=O)OH$; or —$NR^{LB}R^{LC}$ is an optionally substituted non-aromatic heterocycle linked through a ring nitrogen atom;

each —$NR^{LD}R^{LE}$ is separately selected, wherein $R^{LD}$ and $R^{LE}$ are each independently selected from the group consisting of hydrogen, aryl, heteroaryl, and optionally substituted $C_1$-$C_6$ alkyl, said aryl and heteroaryl in the definition of $R^{LD}$ and $R^{LE}$ are each optionally substituted with $C_1$-$C_6$ alkyl or $C_1$-$C_6$ alkoxy; or —$NR^{LD}R^{LE}$ is an optionally substituted non-aromatic heterocycle linked through a ring nitrogen atom;

each —$NR^{LF}R^{LG}$ is separately selected, wherein $R^{LF}$ and $R^{LG}$ are each independently selected from the group consisting of hydrogen, and $C_1$-$C_6$ alkyl; or —$NR^{LF}R^{LG}$ is an optionally substituted non-aromatic heterocycle linked through a ring nitrogen atom;

$R^R$ is selected from the group consisting of $C_1$-$C_6$ alkyl, an optionally substituted aryl, and an optionally substituted heteroaryl; and each m is independently 0, 1, 2, or 3, having the proviso that a compound of Formula IX is not selected from the group consisting of:

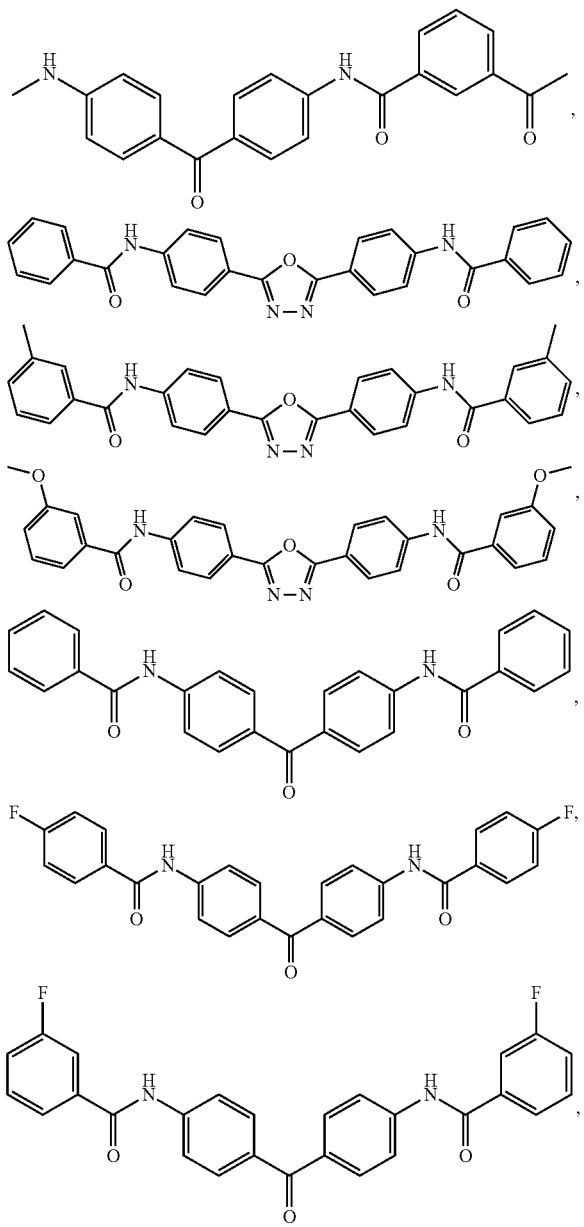

-continued

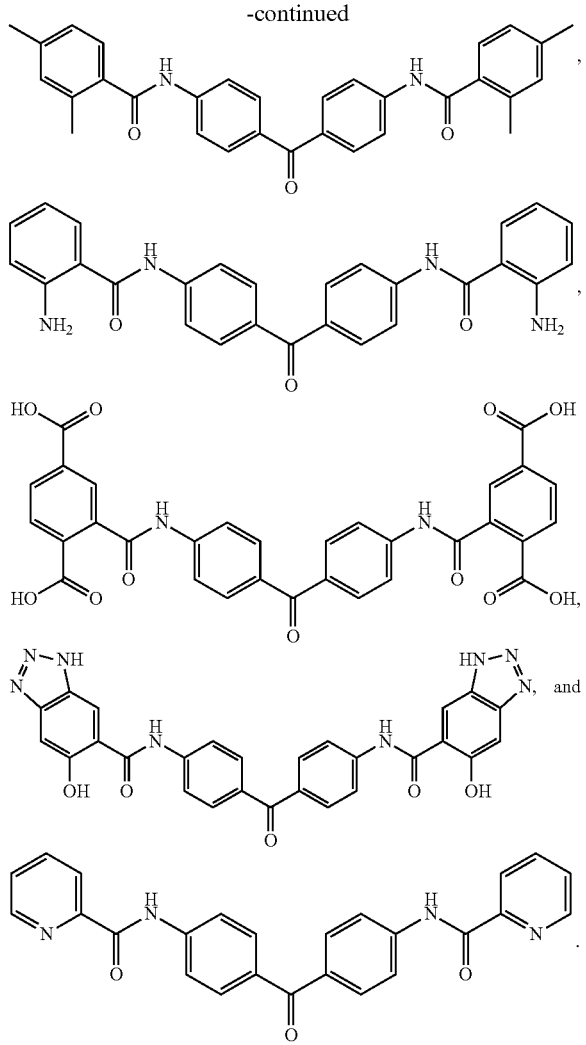

5. The compound of claim 4, having the formula IXa:

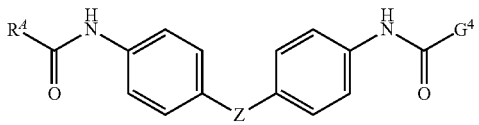

and pharmaceutically acceptable salts thereof,
wherein:
Z is

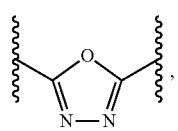 [SMILES: *c1nnc(*)o1]

or —C(=O)—;
$R^A$ is selected from the group consisting of heterocycle, polycyclic heterocyclyl, aryl and heteroaryl, each substituted with one or more substituents selected from the group consisting of $R^1$, $R^2$, and $R^3$;

each $R^1$ is separately selected from the group consisting of chloro, cyano, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_3$-$C_7$ cycloalkenyl, and $C_1$-$C_6$ haloalkyl;

each $R^2$ is separately selected from the group consisting of —O(CH$_2$)$_m$OR$^I$, —(CH$_2$)$_m$OR$^I$, —NR$^J$R$^K$, —(CH$_2$)$_m$SR$^I$, —C(=O)R$^L$, and —(CH$_2$)$_m$R$^L$; and each $R^3$ is separately selected from the group consisting of —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$CN, —(CH$_2$)$_m$R$^P$, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$.

6. A compound of formula IXaa:

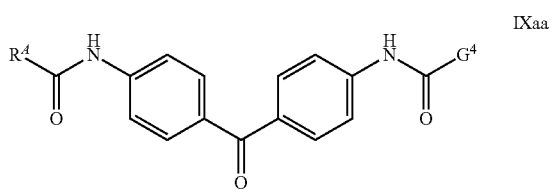

and pharmaceutically acceptable salts thereof,
wherein:
$R^A$ is selected from the group consisting of $C_1$-$C_6$ alkyl, $C_3$-$C_7$ cycloalkyl, heterocycle, polycyclic heterocyclyl, aryl and heteroaryl, each optionally substituted with one or more substituents selected from the group consisting of $R^1$, $R^2$, and $R^3$;

each $R^1$ is separately selected from the group consisting of halogen, cyano, $C_1$-$C_6$ heteroalkyl, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, optionally substituted $C_3$-$C_7$ cycloalkenyl, an optionally substituted $C_1$-$C_6$ haloalkyl, an optionally substituted aryl, and an optionally substituted heteroaryl;

each $R^2$ is separately selected from the group consisting of halogen, —O(CH$_2$)$_m$OR$^I$, —(CH$_2$)$_m$OR$^I$, —NR$^J$R$^K$, —(CH$_2$)$_m$SR$^I$, —C(=O)R$^L$, —(CH$_2$)$_m$R$^L$, $C_1$-$C_6$ heteroalkyl, an optionally substituted $C_1$-$C_6$ alkyl, an optionally substituted $C_1$-$C_6$ alkoxy, an optionally substituted $C_2$-$C_6$ alkenyl, an optionally substituted $C_1$-$C_6$ haloalkyl, and an optionally substituted $C_3$-$C_7$ cycloalkyl where said $C_3$-$C_7$ cycloalkyl is further optionally fused with aryl or heteroaryl;

each $R^3$ is separately selected from the group consisting of halogen, —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$CN, —(CH$_2$)$_m$R$^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, heterocycle, aryl, polycyclic heterocyclyl, and heteroaryl, said heterocycle, aryl polycyclic heterocyclyl, and heteroaryl in the definition of $R^3$ are each optionally substituted with halogen, hydroxy, cyano, $C_1$-$C_6$ alkyl, $C_1$-$C_6$ haloalkyl, $C_1$-$C_6$ alkoxy, —C(=O)OR$^M$, or —NR$^J$R$^K$;

$G^4$ is selected from the group consisting of polycyclic heterocyclyl, aryl, and heteroaryl, each substituted with one or more substituents selected from the group consisting of $R^4$, $R^5$, and $R^6$;

each $R^4$ is separately selected from the group consisting of chloro, cyano, an optionally substituted $C_1$-$C_6$ alkyl, an optionally substituted $C_1$-$C_6$ alkoxy, an optionally substituted $C_2$-$C_6$ alkenyl, an optionally substituted $C_2$-$C_6$ alkynyl, an optionally substituted $C_3$-$C_7$ cycloalkyl, an optionally substituted $C_1$-$C_6$ haloalkyl, an optionally substituted $C_1$-$C_6$ heteroalkyl, an optionally substituted aryl, and an optionally substituted heteroaryl;

each $R^5$ is separately selected from the group consisting of —O(CH$_2$)$_m$OR$^I$, —(CH$_2$)$_m$OR$^I$, —NR$^J$R$^K$, —(CH$_2$)$_m$SR$^I$, —(CH$_2$)$_m$C(=O)R$^L$, —(CH$_2$)$_m$R$^L$, an optionally substituted $C_1$-$C_6$ alkyl, an optionally substituted $C_1$-$C_6$ alkoxy, an optionally substituted $C_2$-$C_6$ alkenyl, an optionally substituted $C_3$-$C_7$ cycloalkyl, an optionally substituted $C_1$-$C_6$ haloalkyl, and an optionally substituted $C_1$-$C_6$ heteroalkyl;

each $R^6$ is separately selected from the group consisting of —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$NO$_2$, —(CH$_2$)$_m$CN, (CH$_2$)$_m$R$^P$, $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ haloalkyl, $C_1$-$C_6$ heteroalkyl, heterocycle, aryl, polycyclic heterocyclyl, and heteroaryl, said heterocycle, aryl, polycyclic heterocyclyl, and heteroaryl in the definition of $R^6$ are each optionally substituted with halogen, cyano, $C_1$-$C_6$ alkyl, $C_1$-$C_6$ haloalkyl, $C_1$-$C_6$ alkoxy, —C(=O)OR$^M$, or —NR$^J$R$^K$;

$R^G$ is selected from the group consisting of $C_1$-$C_6$ alkyl, $C_3$-$C_6$ cycloalkyl, $C_3$-$C_8$ cycloalkenyl, $C_1$-$C_6$ heteroalkyl, $C_2$-$C_6$ heteroalkenyl, $C_2$-$C_6$ heteroalkynyl, heterocycle, aryl, and heteroaryl, each optionally substituted with one or more substituents selected from the group consisting of $R^4$, $R^5$, and $R^6$, said aryl and heteroaryl in the definition of $R^G$ are each further optionally fused with an optionally substituted nonaromatic heterocycle or an optionally substituted nonaromatic carbocycle, or $R^G$ is —OR$^L$ or —NR$^P$R$^L$;

each $R^I$ is separately selected from the group consisting of hydrogen, $C_1$-$C_6$ alkyl, $C_2$-$C_4$ alkenyl, $C_2$-$C_4$ alkynyl, $C_3$-$C_7$ cycloalkyl, $C_1$-$C_6$ haloalkyl, $C_1$-$C_6$ heteroalkyl, and $C_1$-$C_6$ heterohaloalkyl;

each —NR$^J$R$^K$ is separately selected, wherein R$^J$ and R$^K$ are each independently selected from the group consisting of hydrogen, $C_1$-$C_6$ alkyl optionally substituted with up to 5 fluoro, —(CH$_2$)$_m$OR$^{JA}$, —(CH$_2$)$_m$NR$^{JB}$R$^{JC}$, —(CH$_2$)$_m$R$^R$, $C_3$-$C_7$ cycloalkyl, heterocycle, aryl and heteroaryl, said $C_3$-$C_7$ cycloalkyl, heterocycle, aryl and heteroaryl in the definition of R$^J$ and R$^K$ are each independently optionally substituted with one or more substituents selected from the group consisting of halo, $C_1$-$C_6$ alkyl, $C_1$-$C_6$ haloalkyl, $C_1$-$C_6$ alkoxy, aryl and heteroaryl, said aryl and heteroaryl substituent off of R$^J$ and R$^K$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{KA}$R$^{KB}$, or —NR$^J$R$^K$ is an optionally substituted non-aromatic heterocycle linked through a ring nitrogen atom;

each R$^{JA}$ is independently selected from the group consisting of hydrogen, $C_1$-$C_6$ alkyl, and $C_1$-$C_6$ haloalkyl;

each —NR$^{JB}$R$^{JC}$ is separately selected, wherein R$^{JB}$ and R$^{JC}$ are each independently selected from the group consisting of hydrogen, $C_1$-$C_6$ alkyl, and $C_1$-$C_6$ haloalkyl;

each —NR$^{KA}$R$^{KB}$ is separately selected, wherein R$^{KA}$ and R$^{KB}$ are each independently selected from the group consisting of hydrogen, $C_1$-$C_6$ alkyl, and $C_1$-$C_6$ haloalkyl;

each R$^M$ is independently selected from the group consisting of hydrogen, an optionally substituted $C_1$-$C_6$ alkyl, an optionally substituted $C_2$-$C_4$ alkenyl, an optionally substituted $C_2$-$C_4$ alkynyl, an optionally substituted $C_3$-$C_7$ cycloalkyl, an optionally substituted $C_3$-$C_7$ cycloalkenyl, and —(CH$_2$)$_m$R$^P$;

each —NR$^N$R$^O$ is separately selected, wherein R$^N$ and R$^O$ are each independently selected from the group consisting of hydrogen, —(CH$_2$)$_m$NR$^{NA}$R$^{NB}$, aryl and heteroaryl, said and heteroaryl in the definition of R$^N$ and R$^O$ are each independently optionally substituted with one or more substituents selected from the group consisting of —(CH$_2$)$_m$NR$^{OA}$R$^{OB}$, halo, $C_1$-$C_6$ alkyl, $C_1$-$C_6$ haloalkyl, $C_1$-$C_6$ alkoxy, aryl and heteroaryl, said aryl and heteroaryl substituent off of R$^N$ and R$^O$ are each optionally substituted with one or more halo, $C_1$-$C_6$ alkyl, $C_1$-$C_6$ haloalkyl, $C_1$-$C_6$ alkoxy, or —NR$^{NA}$R$^{NB}$;

each —NR$^{NA}$R$^{NB}$ is separately selected, wherein R$^{NA}$ and R$^{NB}$ are each independently selected from the group consisting of hydrogen, $C_1$-$C_6$ alkyl, and $C_1$-$C_6$ haloalkyl;

each —NR$^{OA}$R$^{OB}$ is separately selected, wherein R$^{OA}$ and R$^{OB}$ are each independently selected from the group consisting of hydrogen, $C_1$-$C_6$ alkyl, and $C_1$-$C_6$ haloalkyl;

$R^P$ is selected from the group consisting of hydrogen and $C_1$-$C_6$ alkyl;

each $R^L$ is independently selected from the group consisting of $C_3$-$C_7$ cycloalkyl, optionally substituted $C_1$-$C_6$ alkyl, optionally substituted $C_1$-$C_6$ alkoxy, —(CH$_2$)$_m$OR$^{LA}$, —(CH$_2$)$_m$NR$^{LB}$R$^{LC}$, aryl and heteroaryl, said aryl and heteroaryl in the definition of R$^L$ are each independently optionally substituted with one or more substituents selected from the group consisting of halo, $C_1$-$C_6$ alkyl, $C_1$-$C_6$ haloalkyl, $C_1$-$C_6$ alkoxy, —(CH$_2$)$_m$NR$^{LD}$R$^{LE}$, aryl and heteroaryl, said aryl and heteroaryl substituent off of R$^L$ are each optionally substituted with one or more halo, $C_1$-$C_6$ alkyl, $C_1$-$C_6$ haloalkyl, $C_1$-$C_6$ alkoxy, or —(CH$_2$)$_m$NR$^{LF}$R$^{LG}$;

each R$^{LA}$ is independently selected from the group consisting of hydrogen, $C_1$-$C_6$ alkyl, and $C_1$-$C_6$ haloalkyl;

R$^{LD}$ and R$^{LC}$ are each independently selected from the group consisting of hydrogen, $C_1$-$C_6$ alkyl, $C_1$-$C_6$ haloalkyl, and $C_1$-$C_6$ heteroalkenyl, said $C_1$-$C_6$ alkyl, $C_1$-$C_6$ haloalkyl, and $C_1$-$C_6$ heteroalkenyl each optionally substituted with one or more halogen, cyano, or —(CH$_2$)$_m$C(=O)OH; or —NR$^{LD}$R$^{LC}$ is an optionally substituted non-aromatic heterocycle linked through a ring nitrogen atom;

each —NR$^{LD}$R$^{LE}$ is separately selected, wherein R$^{LD}$ and R$^{LE}$ are each independently selected from the group consisting of hydrogen, aryl, heteroaryl, and optionally substituted $C_1$-$C_6$ alkyl, said aryl and heteroaryl in the definition of R$^{LD}$ and R$^{LE}$ are each optionally substituted with $C_1$-$C_6$ alkyl or $C_1$-$C_6$ alkoxy; or —NR$^{LD}$R$^{LE}$ is an optionally substituted non-aromatic heterocycle linked through a ring nitrogen atom;

each —NR$^{LF}$R$^{LG}$ is separately selected, wherein R$^{LF}$ and R$^{LG}$ are each independently selected from the group consisting of hydrogen, and C$_1$-C$_6$ alkyl; or —NR$^{LF}$R$^{LG}$ is an optionally substituted non-aromatic heterocycle linked through a ring nitrogen atom;
R$^R$ is selected from the group consisting of C$_1$-C$_6$ alkyl, an optionally substituted aryl, and an optionally substituted heteroaryl; and
each m is independently 0, 1, 2, or 3, having the proviso that the compound of Formula IXaa is not selected from the group consisting of:

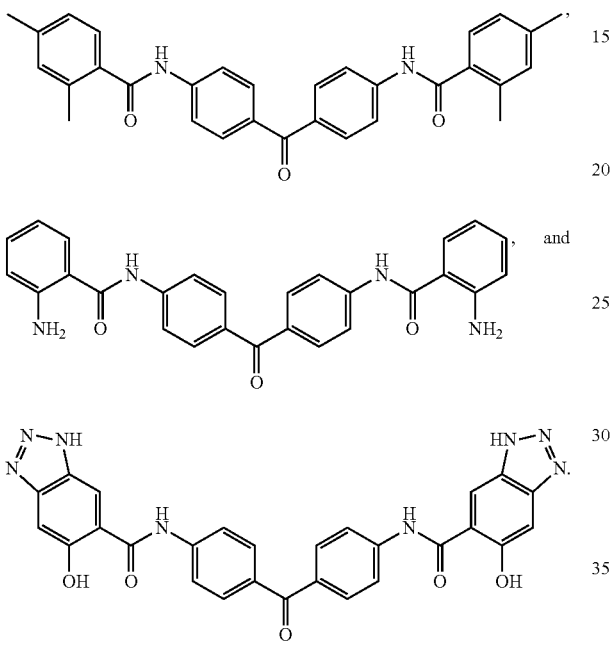

7. The compound of claim 5, wherein:
each R$^1$ is separately selected from the group consisting of cyano, an optionally substituted C$_1$-C$_6$ alkyl, an optionally substituted C$_1$-C$_6$ alkoxy, an optionally substituted C$_1$-C$_6$ heteroalkyl, an optionally substituted aryl, and an optionally substituted heteroaryl;
each R$^2$ is separately selected from the group consisting of —O(CH$_2$)$_m$OR$^I$, —(CH$_2$)$_m$OR$^I$, —NR$^J$R$^K$, —(CH$_2$)$_m$SR$^I$, —C(=O)R$^L$, and —(CH$_2$)$_m$R$^L$;
each R$^3$ is separately selected from the group consisting of —(CH$_2$)$_m$OR$^G$, —NR$^L$C(=O)R$^M$, —NR$^L$C(=O)OR$^M$, —NR$^L$C(=O)NR$^N$R$^O$, —NR$^N$R$^O$, —(CH$_2$)$_m$S(O)$_{0-2}$R$^M$, —(CH$_2$)$_m$NHS(O)$_{0-2}$R$^M$, —(CH$_2$)$_m$NO$_2$, —(CH$_2$)$_m$CN, —(CH$_2$)$_m$R$^P$, heterocycle, aryl, polycyclic heterocyclyl, and heteroaryl, said heterocycle, aryl polycyclic heterocyclyl, and heteroaryl in the definition of R$^3$ are each optionally substituted with halogen, hydroxy, cyano, C$_1$-C$_6$ alkyl, C$_1$-C$_6$ haloalkyl, C$_1$-C$_6$ alkoxy, —C(=O)OR$^M$, or —NR$^J$R$^K$;
each R$^4$ is separately selected from the group consisting of cyano, an optionally substituted C$_1$-C$_6$ alkyl, and an optionally substituted C$_1$-C$_6$ heteroalkyl;
each R$^5$ is separately selected from the group consisting of —(CH$_2$)$_m$OH, —NR$^J$R$^K$, and —(CH$_2$)$_m$C(=O)R$^L$;
each R$^L$ is independently selected from the group consisting of —OH, C$_1$-C$_6$ alkyl, and C$_1$-C$_6$ alkoxy; and
each R$^6$ is separately selected from the group consisting of —NR$^L$C(=O)R$^M$, —NR$^L$C(=O)OR$^M$, —NR$^L$C(=O)NR$^N$R$^O$, —NR$^N$R$^O$, —(CH$_2$)$_m$R$^P$, heterocycle, aryl, polycyclic heterocyclyl, and heteroaryl, said heterocycle, aryl, polycyclic heterocyclyl, and heteroaryl in the definition of R$^6$ are each optionally substituted with halogen, cyano, C$_1$-C$_6$ alkyl, C$_1$-C$_6$ haloalkyl, C$_1$-C$_6$ alkoxy, —C(=O)OR$^M$, or —NR$^J$R$^K$.

8. A compound of claim 1 that is an HGF mimetic, an HGF receptor agonist or an HGF receptor antagonist.

9. A compound of claim 1 that is a hematopoietic growth factor mimetic, a hematopoietic growth factor receptor agonist or a hematopoietic growth factor receptor antagonist.

10. A compound of claim 1 that is an EPO mimic.

11. A compound of claim 1 that is a selective EPO receptor agonist.

12. A compound of claim 1 to that is a selective EPO receptor partial agonist.

13. A compound of claim 1 that is a selective EPO receptor antagonist.

14. A compound of claim 1 that is a selective EPO receptor binding compound.

15. A method for modulating an EPO activity in a cell comprising contacting a cell with a compound of claim 1.

16. A method for identifying a compound that modulates an EPO activity, comprising contacting a cell that expresses an EPO receptor with a compound of claim 1; and monitoring an effect of the compound on the cell.

17. A method of treating thrombocytopenia in a patient, comprising administering to the patient a therapeutically effective amount of a compound of claim 1.

18. The method of claim 17, wherein the thrombocytopenia results from radiation or chemotherapy.

19. The method of claim 18, further comprising harvesting cells from the patient.

20. A method of treating a patient suffering from an anemia, a neutropenia, a cardiovascular disorder, an immune/autoimmune disorder, or a neurologic disorder, comprising administering to the patient a therapeutically effective amount of a compound of claim 1.

21. A pharmaceutical composition comprising a physiologically acceptable carrier, diluent, or excipient; and a compound of claim 1.

22. A compound of claim 1 selected from the group consisting of

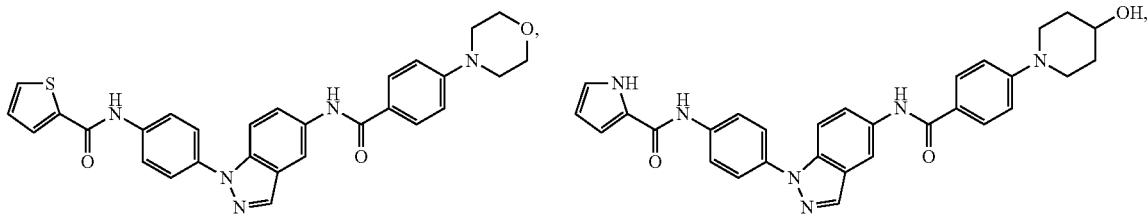

-continued
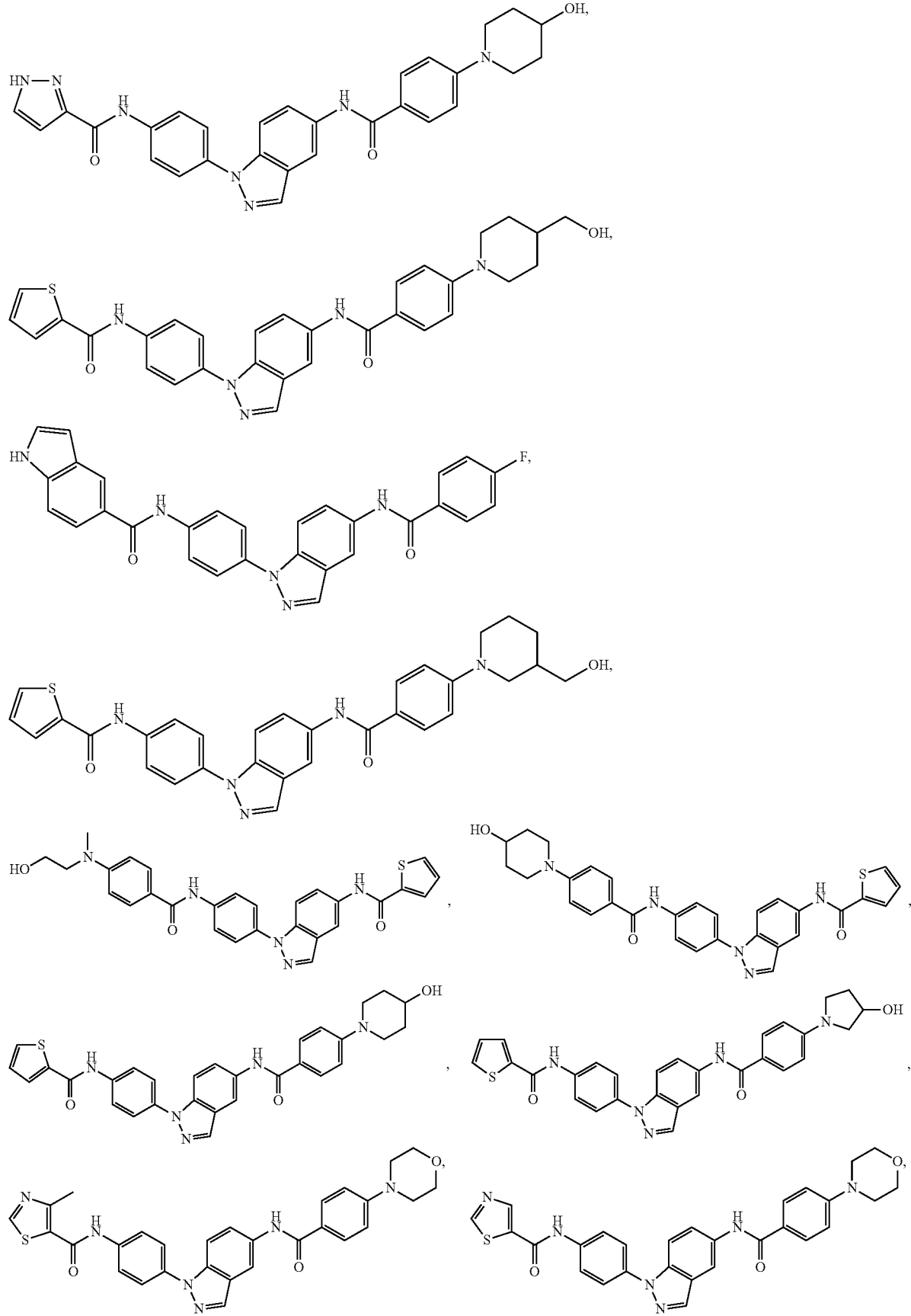

683 684
-continued
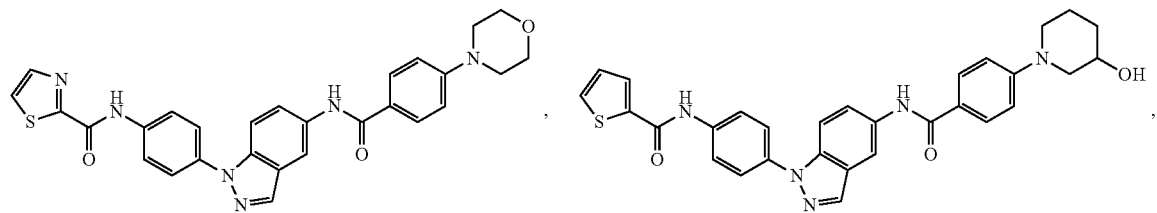
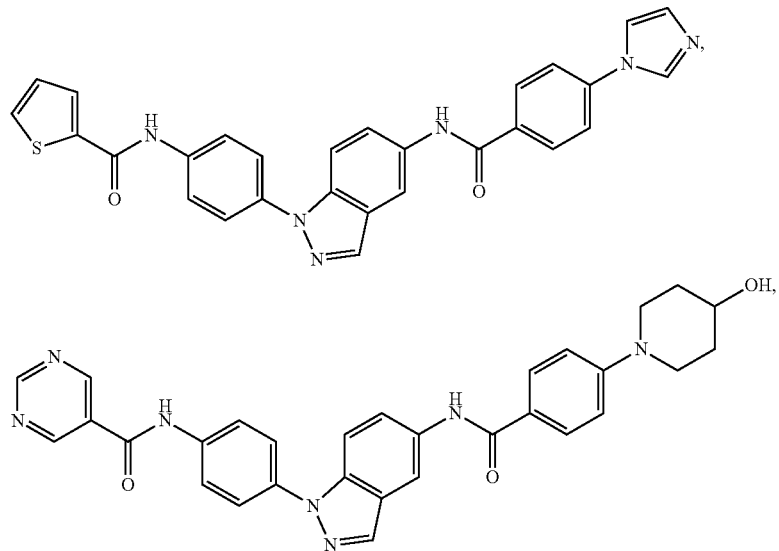
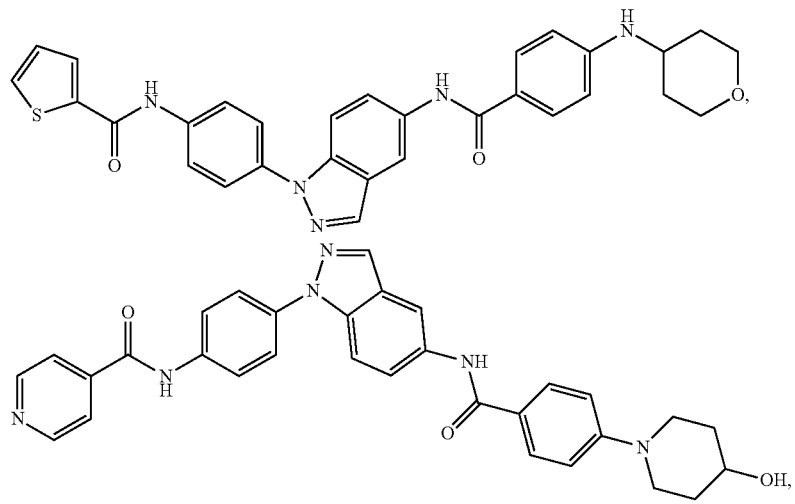
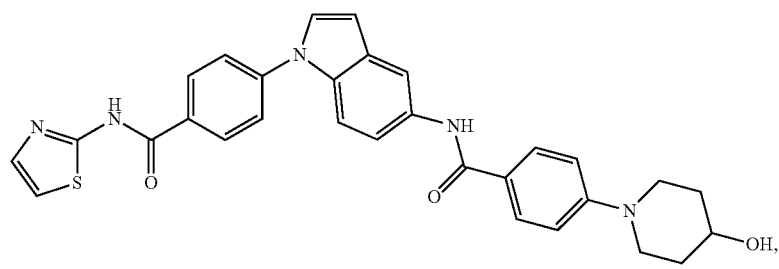

-continued
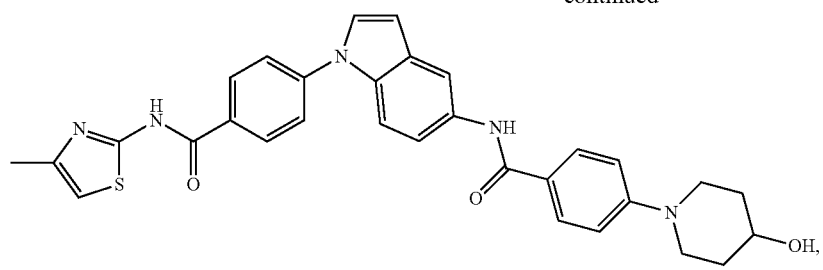
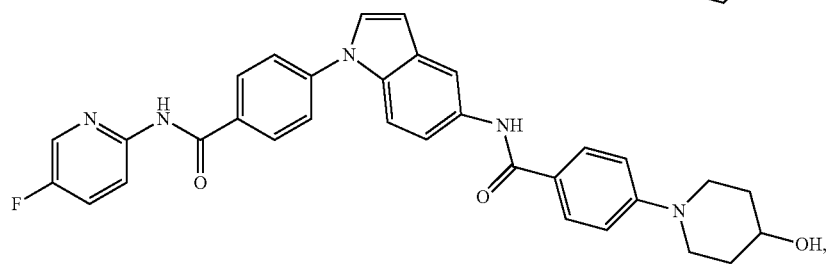
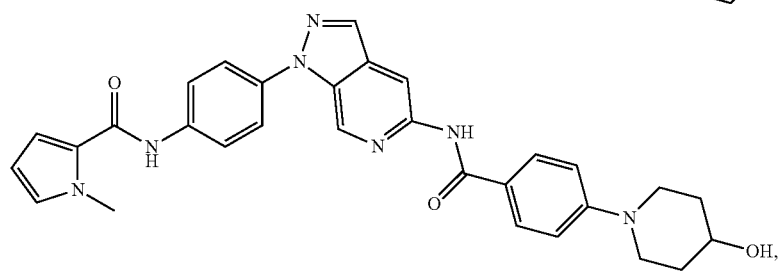
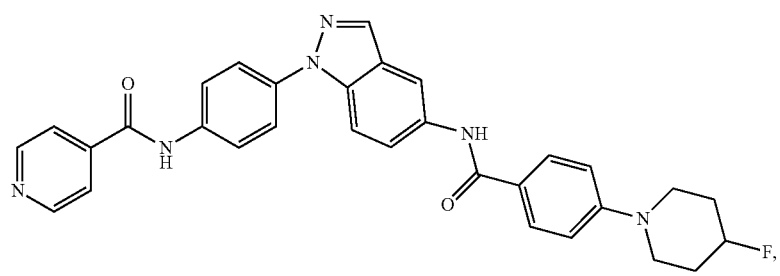
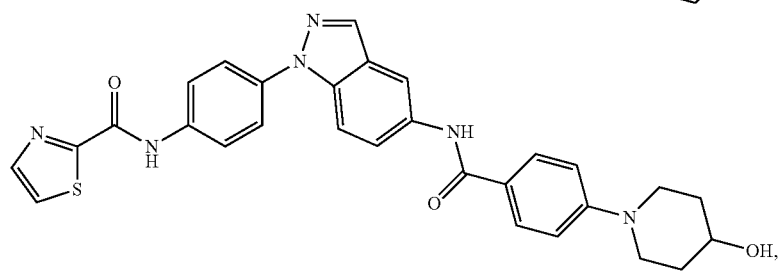
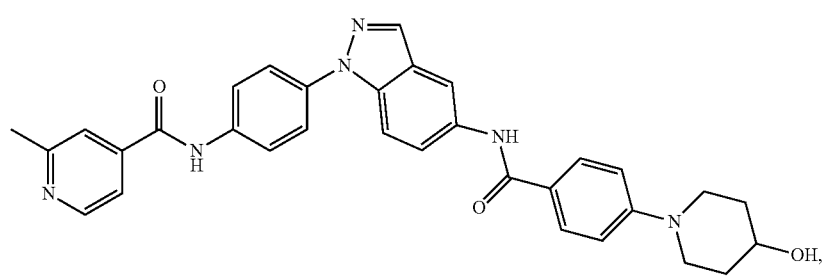

-continued
687
688
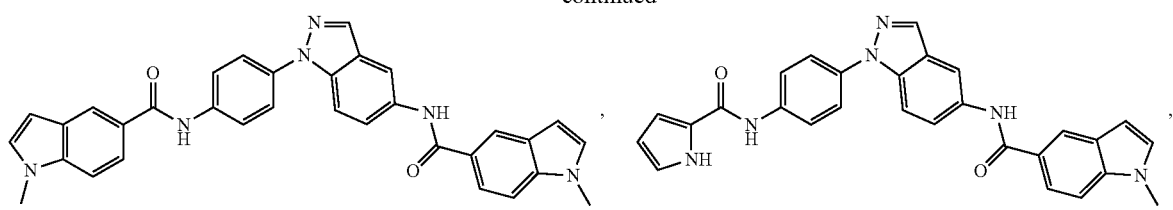
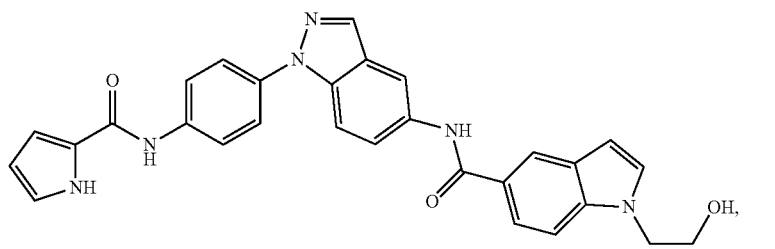
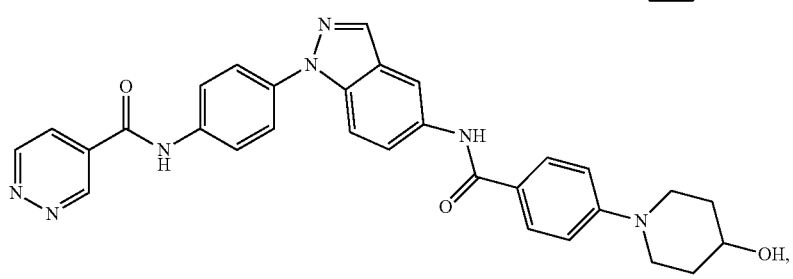
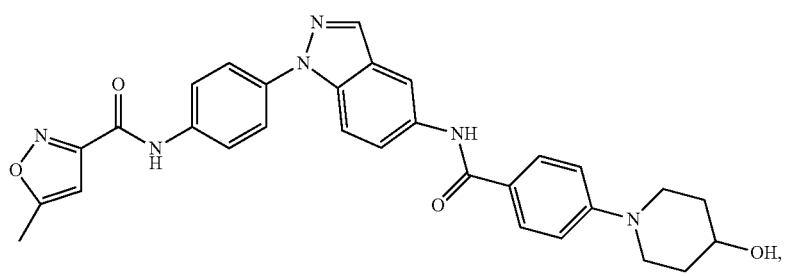
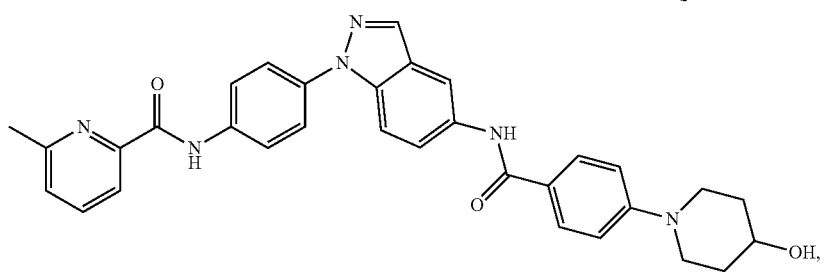
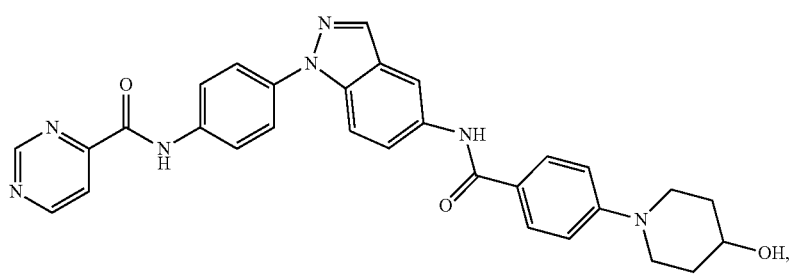

-continued
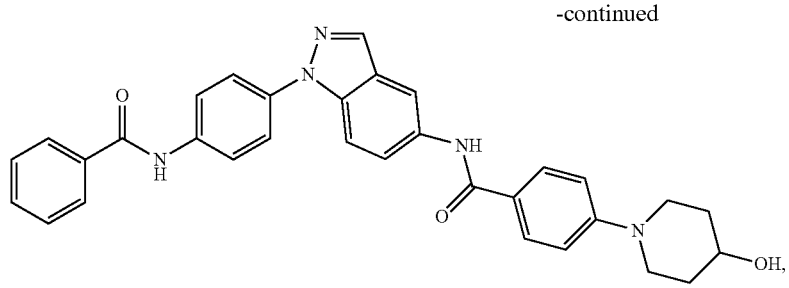
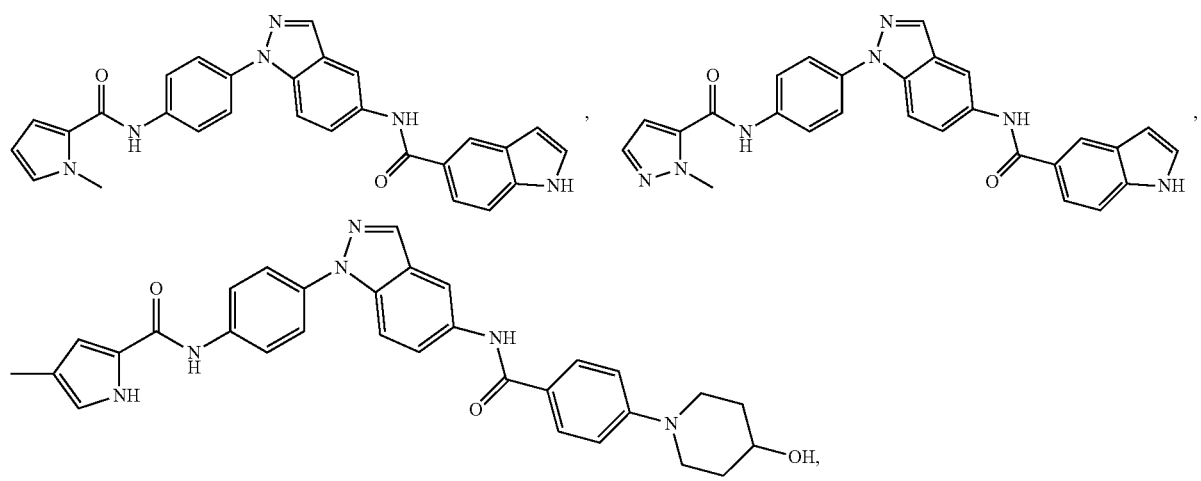
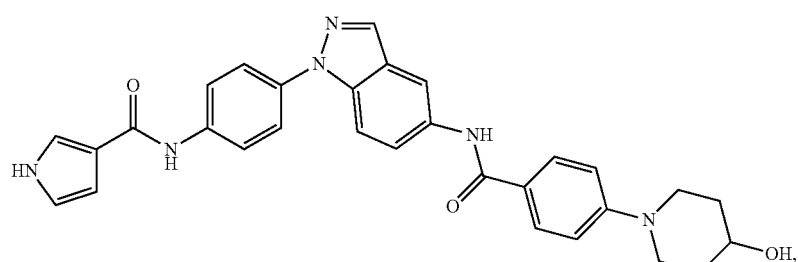
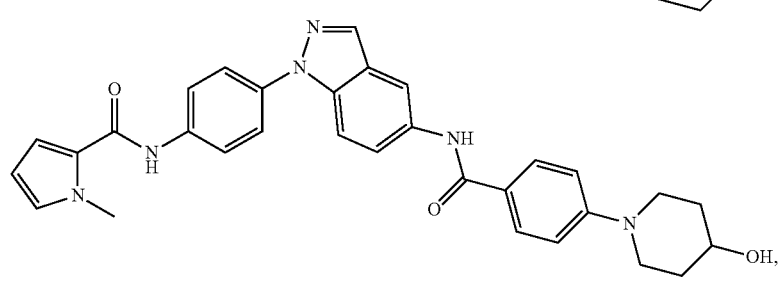
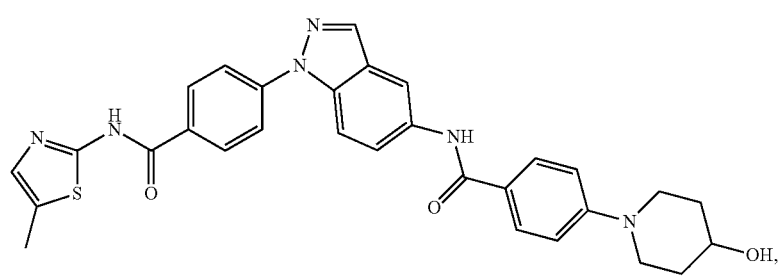

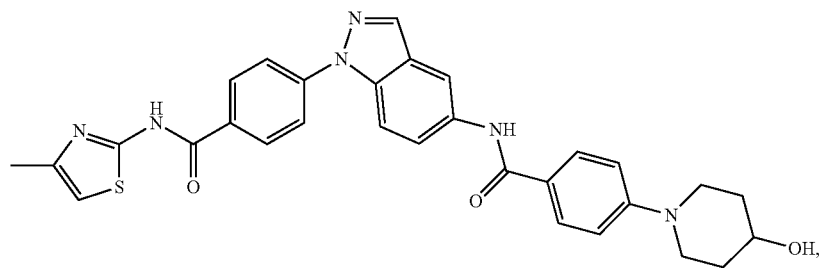
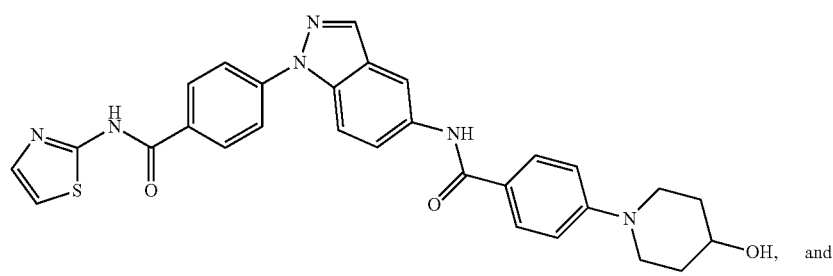
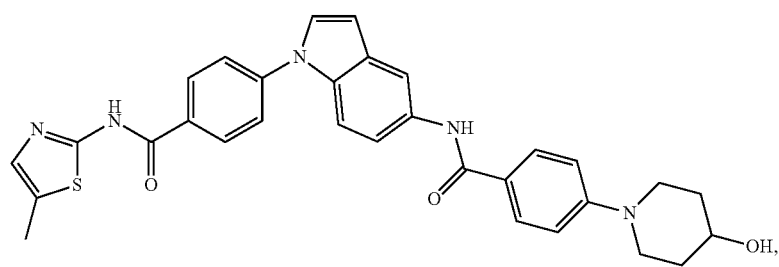
or a pharmaceutically acceptable salt thereof.
23. A compound of claim 4 selected from the group consisting of
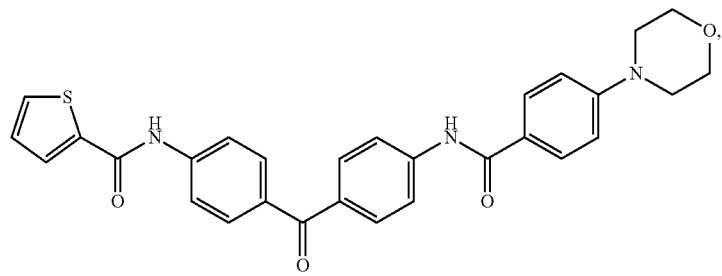
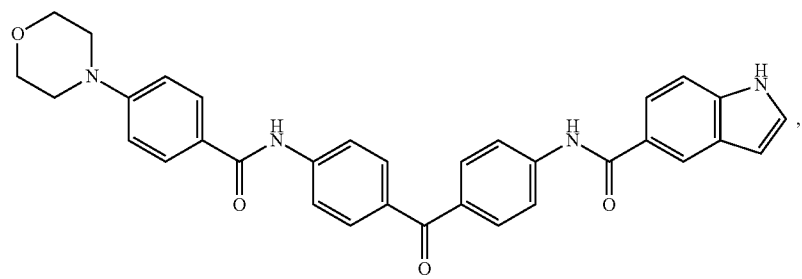

693 694
-continued
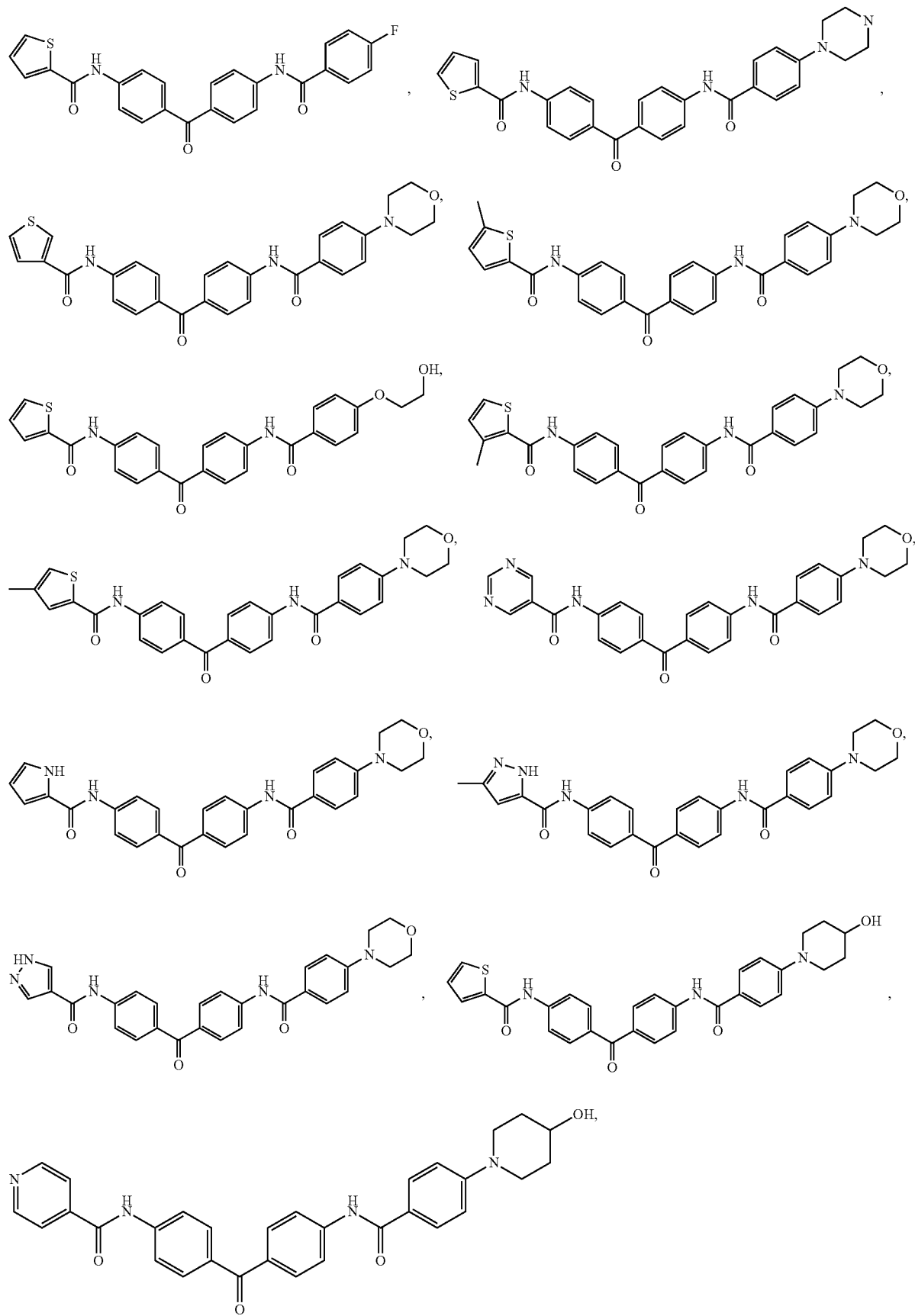

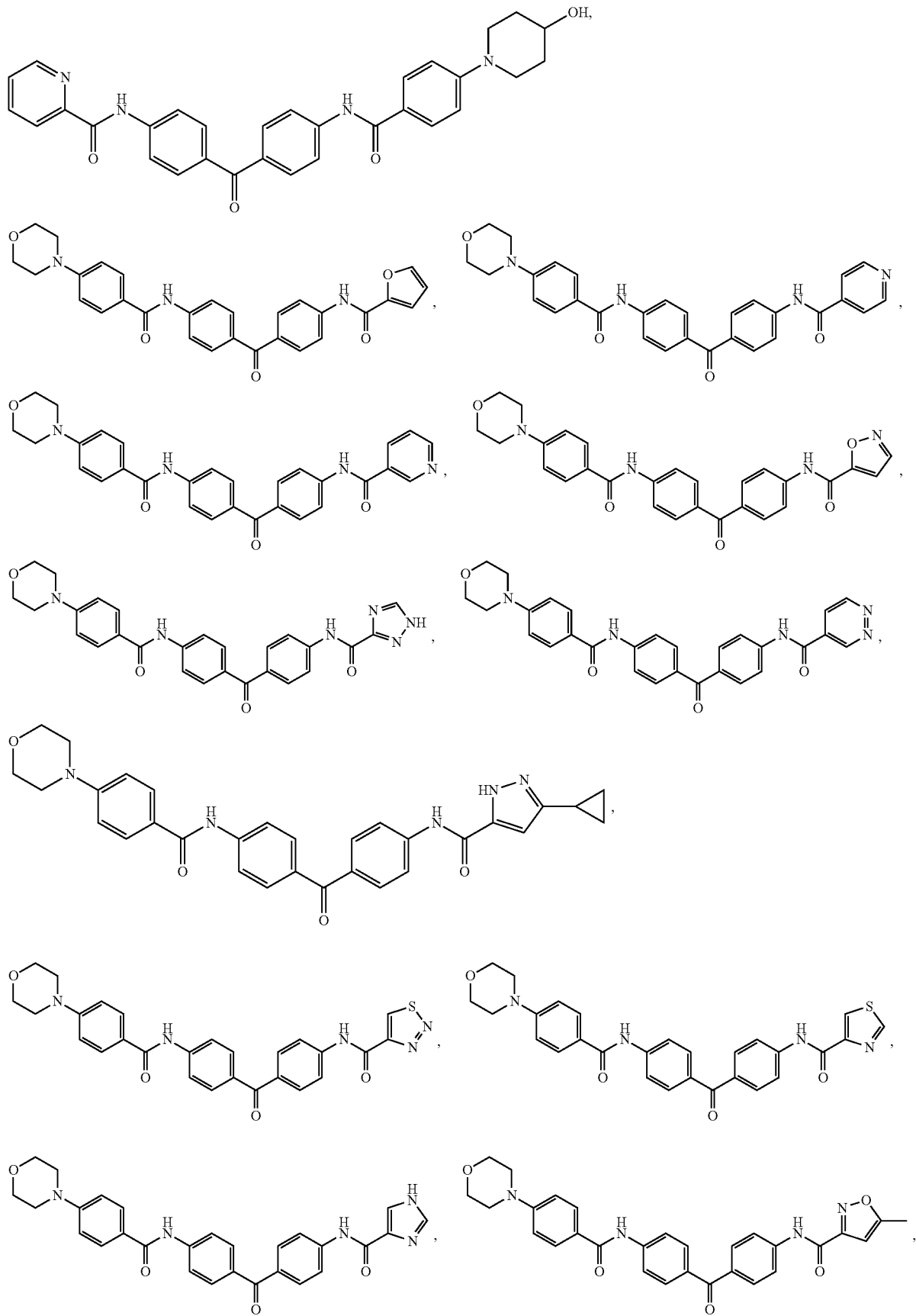

697 698
-continued
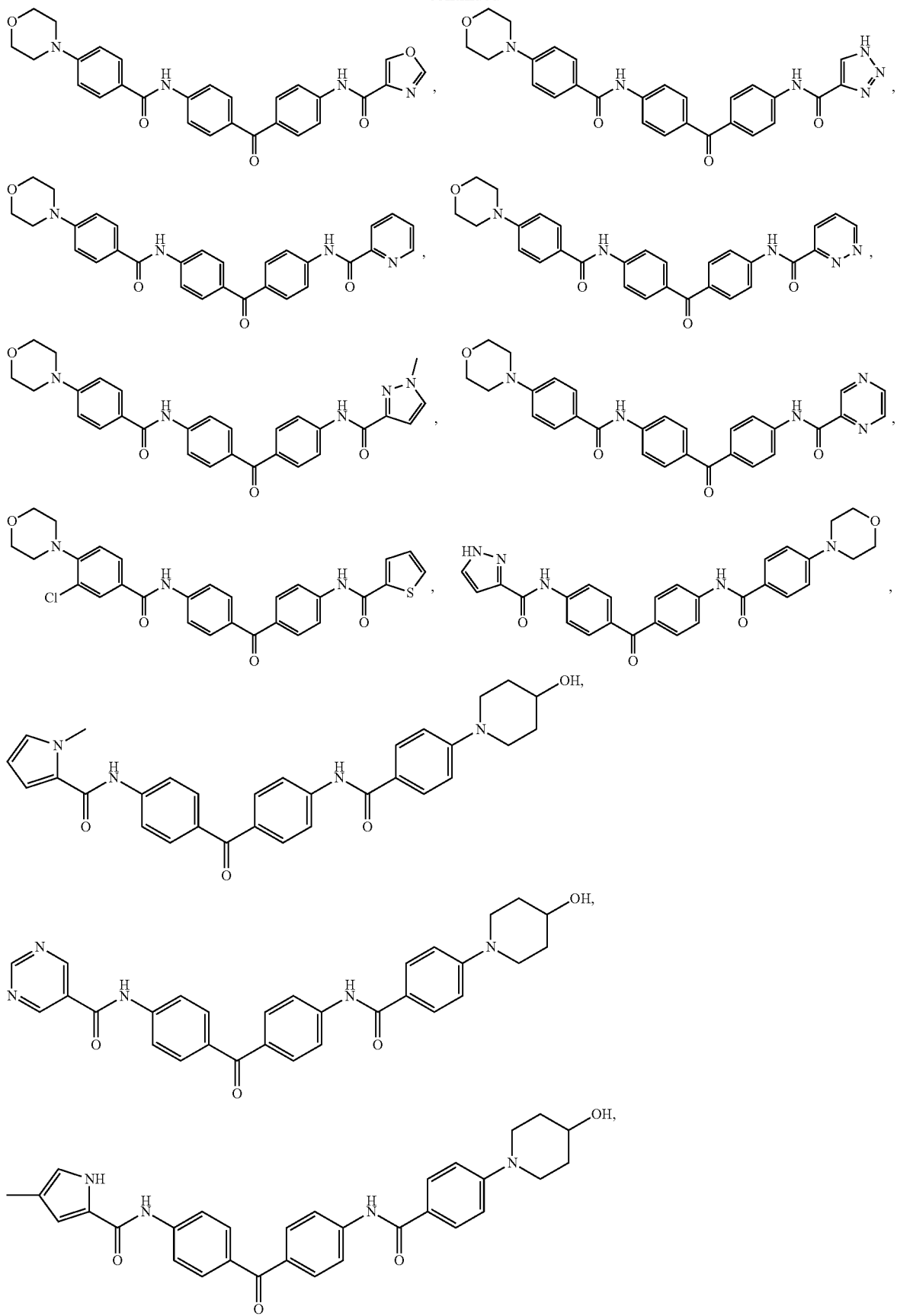

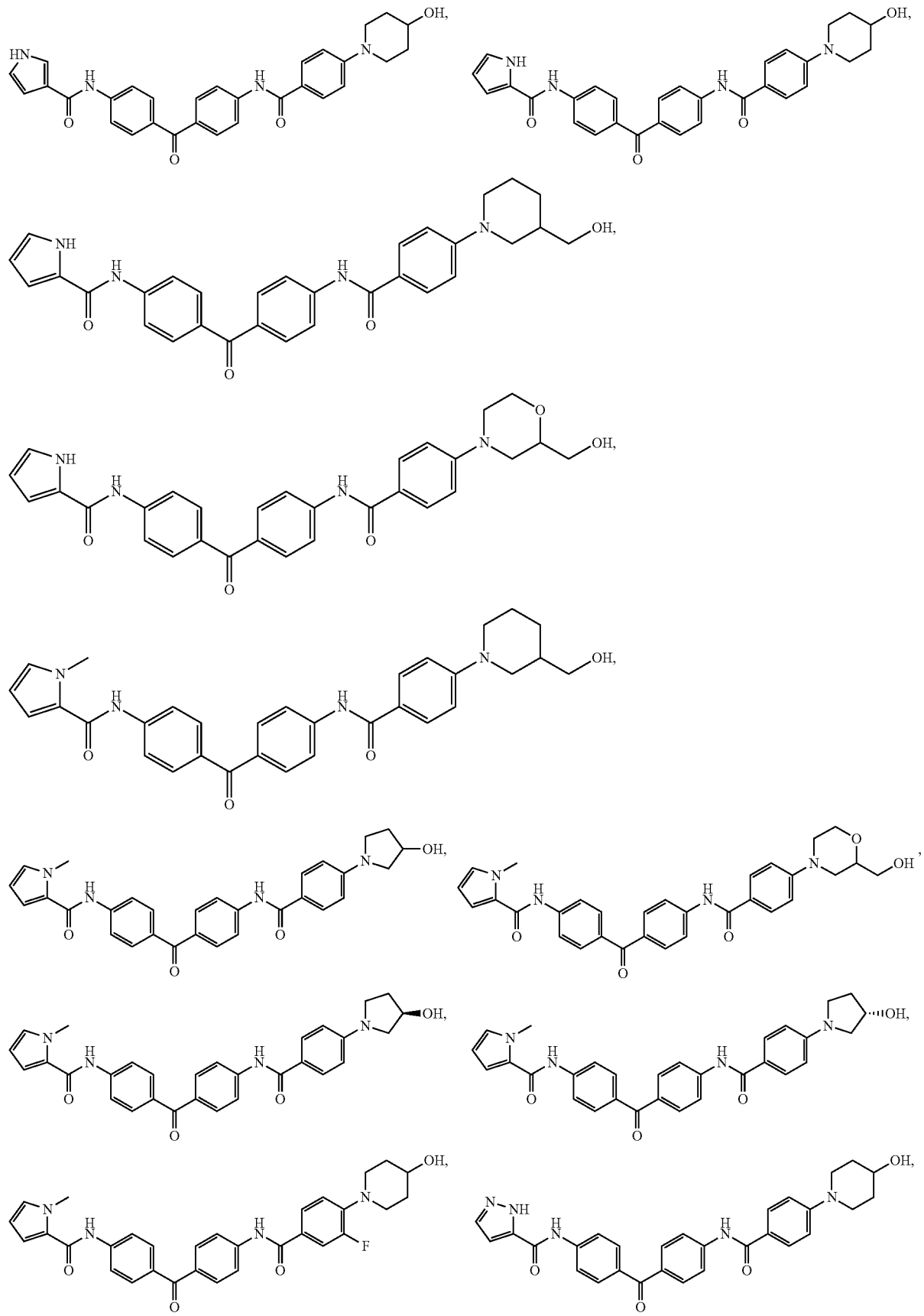

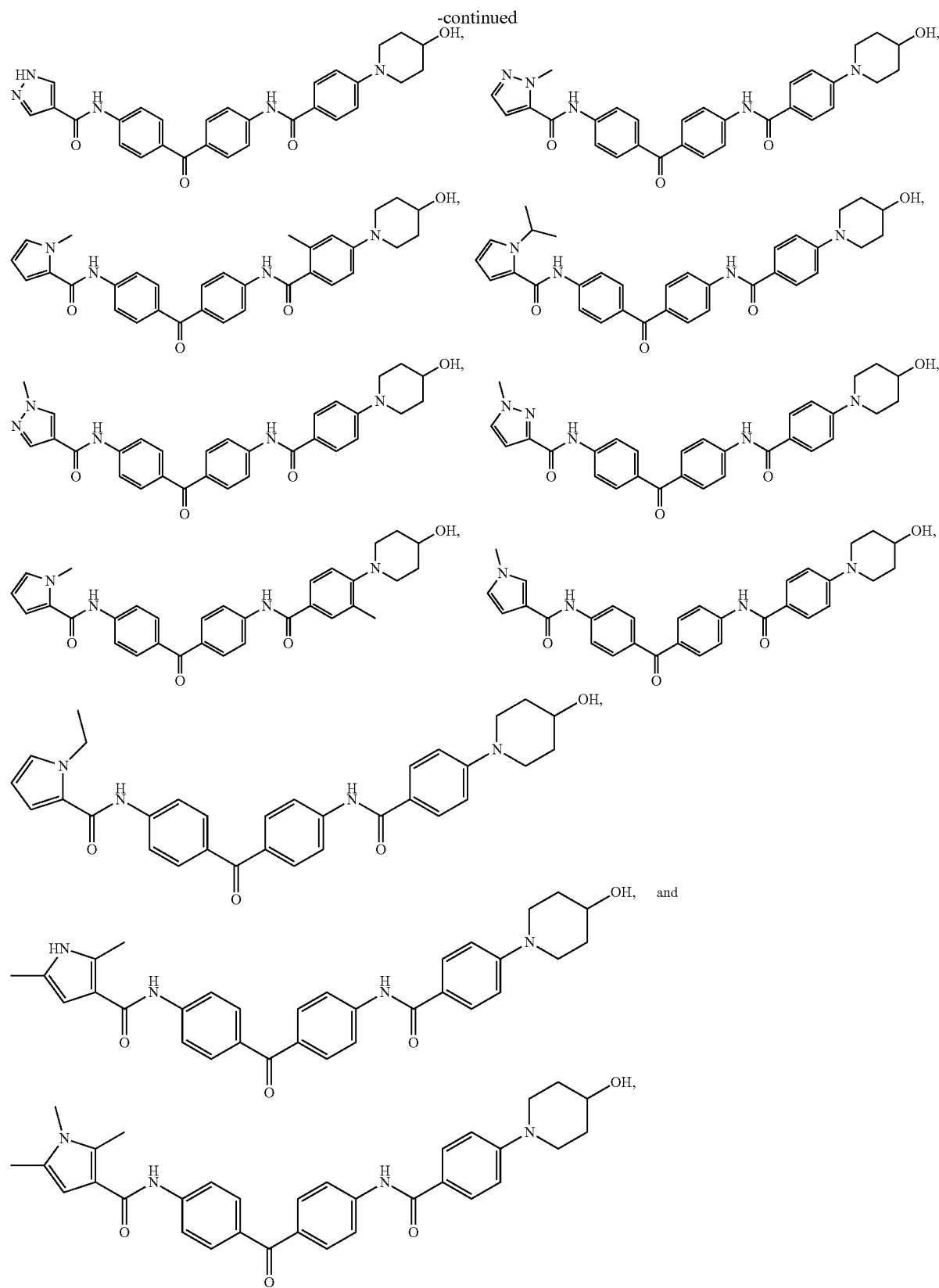
or a pharmaceutically acceptable salt thereof.